(12) United States Patent
Nadzan et al.

(10) Patent No.: US 10,815,494 B2
(45) Date of Patent: Oct. 27, 2020

(54) NUCLEOTIDE SEQUENCES AND CORRESPONDING POLYPEPTIDES CONFERRING MODIFIED PHENOTYPE CHARACTERISTICS IN PLANTS

(71) Applicant: Ceres, Inc., Thousand Oaks, CA (US)

(72) Inventors: Gregory Nadzan, Woodland Hills, CA (US); Richard Schneeberger, Carlsbad, CA (US); Han Suk Kim, Camarillo, CA (US); David Van-dinh Dang, San Diego, CA (US); Kenneth A. Feldmann, Tucson, AZ (US); Roger Pennell, Malibu, CA (US); Shing Kwok, Woodland Hills, CA (US); Hongyu Zhang, Thousand Oaks, CA (US); Cory Christensen, Sherwood, OR (US); Jack Okamuro, Oak Park, CA (US); Fasong Zhou, Oxnard, CA (US); Wuyi Wang, Newbury Park, CA (US); Emilio Margolles-Clark, Miami, FL (US); Gerard Magpantay, Calabasas, CA (US); Julissa Sosa, Northridge, CA (US); Nestor Apuya, Culver City, CA (US); Kerstin Piccolo, Woodland Hills, CA (US); Bonnie Hund, Denver, CO (US); Nickolai Alexandrov, Thousand Oaks, CA (US); Vyacheslav Brover, Simi Valley, CA (US); Peter Mascia, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 15/689,941

(22) Filed: Aug. 29, 2017

(65) Prior Publication Data
US 2018/0105829 A1 Apr. 19, 2018

Related U.S. Application Data

(60) Division of application No. 13/644,359, filed on Oct. 4, 2012, now Pat. No. 9,777,287, which is a continuation-in-part of application No. 13/465,846, filed on May 7, 2012, now abandoned, which is a division of application No. 10/572,827, filed as application No. PCT/US03/25997 on Aug. 18, 2003, now Pat. No. 8,193,409, said application No. 13/644,359 is a continuation-in-part of application No. 11/779,266, filed on Jul. 17, 2007, now abandoned, which is a continuation-in-part of application No. 11/778,060, filed on Jul. 15, 2007, now abandoned, said application No. 11/248,547 is a continuation-in-part of application No. 13/644,359, filed on Oct. 4, 2012, said application No. PCT/US2007/085007 is a continuation-in-part of application No. 13/644,359, filed on Oct. 4, 2012, said application No. 13/644,359 is a continuation-in-part of application No. 12/515,707, filed on Dec. 16, 2009, said application No. 13/644,359 is a continuation-in-part of application No. 12/615,920, filed on Nov. 10, 2009, now Pat. No. 8,471,099, which is a continuation of application No. 11/114,963, filed on Apr. 25, 2005, now Pat. No. 7,696,409, said application No. 13/644,359 is a continuation-in-part of application No. 12/605,261, filed on Oct. 23, 2009, now abandoned, which is a division of application No. 11/298,391, filed on Dec. 8, 2005, now Pat. No. 7,663,027, said application No. 13/644,359 is a continuation-in-part of application (Continued)

(51) Int. Cl.
C12N 15/82 (2006.01)
C07K 14/415 (2006.01)

(52) U.S. Cl.
CPC ........ *C12N 15/8271* (2013.01); *C07K 14/415* (2013.01); *C12N 15/8201* (2013.01); *C12N 15/8241* (2013.01); *C12N 15/8261* (2013.01); *C12N 15/8269* (2013.01); *Y02A 40/146* (2018.01)

(58) Field of Classification Search
None
See application file for complete search history.

(56) References Cited

U.S. PATENT DOCUMENTS

| | | |
|---|---|---|
| 2011/0061124 A1 | 3/2011 | Nadzan et al. |
| 2020/0048653 A1 | 2/2020 | Nadzan et al. |
| 2020/0056199 A1 | 2/2020 | Nadzan et al. |

FOREIGN PATENT DOCUMENTS

| | | |
|---|---|---|
| WO | WO 2009/105612 | 8/2009 |

OTHER PUBLICATIONS

Bowie et al, (1990, "Deciphering the Message in Protein Sequences: Tolerance to Amino Acid Substitutions", Science 247:1306-1310).*

(Continued)

*Primary Examiner* — Stuart F Baum
(74) *Attorney, Agent, or Firm* — Dentons US LLP

(57) ABSTRACT

Methods and materials for modulating low-nitrogen tolerance levels in plants are disclosed. For example, nucleic acids encoding low nitrogen tolerance-modulating polypeptides are disclosed as well as methods for using such nucleic acids to transform plant cells. Also disclosed are plants having increased$_{[RCL2]}$ low-nitrogen tolerance levels and plant products produced from plants having increased low-nitrogen tolerance levels.

11 Claims, 165 Drawing Sheets

Specification includes a Sequence Listing.

Related U.S. Application Data

No. 12/377,106, filed as application No. PCT/US2007/075747 on Aug. 10, 2007, now abandoned, said application No. 13/644,359 is a continuation-in-part of application No. 12/541,607, filed on Aug. 14, 2009, now abandoned, which is a continuation of application No. 11/140,347, filed on May 27, 2005, now Pat. No. 7,576,260, said application No. 13/644,359 is a continuation-in-part of application No. 13/184,361, filed on Jul. 15, 2011, now Pat. No. 8,962,921, which is a division of application No. 11/140,450, filed on May 27, 2005, now Pat. No. 8,022,273, said application No. 13/644,359 is a continuation-in-part of application No. 11/654,357, filed on Jan. 16, 2007, now abandoned, said application No. 13/644,359 is a continuation-in-part of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007, said application No. 13/644,359 is a continuation-in-part of application No. 12/922,143, filed as application No. PCT/US2009/037025 on Mar. 12, 2009, now abandoned, said application No. 13/644,359 is a continuation-in-part of application No. 11/241,685, filed on Sep. 30, 2005, now Pat. No. 8,481,814, said application No. 13/644,359 is a continuation-in-part of application No. 12/863,773, filed as application No. PCT/US2009/031609 on Jan. 21, 2009, now abandoned, said application No. 13/644,359 is a continuation-in-part of application No. 12/282,342, filed as application No. PCT/US2007/006544 on Mar. 14, 2007, now Pat. No. 8,324,454, said application No. 13/644,359 is a continuation-in-part of application No. 12/911,698, filed on Oct. 25, 2010, now Pat. No. 9,914,935, which is a division of application No. 11/324,098, filed on Dec. 29, 2005, now Pat. No. 7,884,261, which is a continuation-in-part of application No. 11/172,740, filed on Jun. 30, 2005, now Pat. No. 7,396,979, said application No. 13/644,359 is a continuation-in-part of application No. 13/609,176, filed on Sep. 10, 2012, now abandoned, which is a division of application No. 12/139,269, filed on Jun. 13, 2008, now abandoned, which is a division of application No. 11/172,740, filed on Jun. 30, 2005, now Pat. No. 7,396,979, said application No. 13/644,359 is a continuation-in-part of application No. 12/918,609, filed as application No. PCT/US2009/034638 on Feb. 20, 2009, now abandoned, said application No. 13/644,359 is a continuation-in-part of application No. 12/776,319, filed on May 7, 2010, now abandoned, which is a division of application No. 11/324,093, filed on Dec. 29, 2005, now Pat. No. 7,803,983, which is a continuation-in-part of application No. 11/172,740, filed on Jun. 30, 2005, now Pat. No. 7,396,979.

(60) Provisional application No. 60/859,467, filed on Nov. 16, 2006, provisional application No. 60/851,585, filed on Oct. 12, 2006, provisional application No. 60/860,296, filed on Nov. 21, 2006, provisional application No. 60/564,659, filed on Apr. 23, 2004, provisional application No. 60/635,140, filed on Dec. 8, 2004, provisional application No. 60/635,115, filed on Dec. 8, 2004, provisional application No. 60/837,434, filed on Aug. 11, 2006, provisional application No. 60/575,309, filed on May 27, 2004, provisional application No. 60/575,253, filed on May 27, 2004, provisional application No. 60/778,568, filed on Mar. 1, 2006, provisional application No. 60/758,831, filed on Jan. 13, 2006, provisional application No. 60/782,735, filed on Mar. 14, 2006, provisional application No. 61/036,396, filed on Mar. 13, 2008, provisional application No. 60/615,080, filed on Sep. 3, 2004, provisional application No. 61/022,786, filed on Jan. 22, 2008, provisional application No. 60/782,735, filed on Mar. 14, 2006, provisional application No. 61/030,142, filed on Feb. 20, 2008, provisional application No. 60/583,621, filed on Jun. 30, 2004, provisional application No. 60/584,829, filed on Jun. 30, 2004, provisional application No. 60/584,800, filed on Jun. 30, 2004.

(56) References Cited

OTHER PUBLICATIONS

McConnell et al, (2001, "Radial Patterning of *Arabidopsis* Shoots by Class III HD-ZIP and KANADI Genes", Nature 411 (6838):709-713).*

Kano-Murakami et al (1993, "A Rice Homeotic Gene, OSH1, Causes Unusual Phenotypes in Transgenic Tobacco", FEBS 334 (3): 365-368).*

Forde, "Local and long-range signaling pathways regulating plant responses to nitrate," Annu Rev Plant Biol, 53:203-224, 2002.

Gazzarrini et al., "Three functional transporters for constitutive, diurnally regulated, and starvation-induced uptake of ammonium into *Arabidopsis* roots," Plant Cell, 11:937-948, 1999.

GenBank Gene ID: 4914437, CD630_27000 sigma-54 dependent transcriptional regulator [Clostridioides difficile 630], Available at https://www.ncbi.nlm.nih.gov/gene/?term=4914437, Retrieved Jan. 12, 2017.

GenBank Gene ID: 7981380, DMR_t00510 [Desulfovibrio magneticus RS-1], Available at https://www.ncbi.nlm.nih.gov/gene/7981380, Retrieved Jan. 12, 2017.

Huber et al., "Regulation of maize leaf nitrate reductase activity involves both gene expression and protein phosphorylation," Plant Physiol, 106:1667-1674, 1994.

Hwang et al., "Sequences necessary for nitrate-dependent transcription of *Arabidopsis* nitrate reductase genes," Plant Physiol, 113:853-862, 1997.

Okamoto et al., "Regulation of NRT1 and NRT2 gene families of *Arabidopsis thaliana*: responses to nitrate provision," Plant Cell Physiol, 44:304-317, 2003.

Redinbaugh et al., "Higher plant responses to environmental nitrate," Physiol Plant, 82:640-650, 1991.

Good et al., "Can less yield more? Is reducing nutrient input into the environment compatible with maintaining crop production?," TRENDS in Plant Science 9(12):597-605, 2004.

Guerois et al., "Predicting Changes in the Stability of Proteins and Protein Complexes: A Study of More Than 1000 Mutations," *J. Mol. Biol.* 320:369-387, 2002.

Kumar et al., "Predicting the effects of coding non-synonymous variants on protein function using the SIFT algorithm," Nature Protocols 4(8):1073-1082, 2009.

Ng et al., "Predicting the Effects of Amino Acid Substitutions on Protein Function," *Annu. Rev. Genom. Hum. Genet.* 7:61-80, 2006.

Reva et al., "Predicting the functional impact of protein mutations: application to cancer genomics," *Nucleic Acids Research* 39(17):e118, 2011.

Sandhya et al., "CUSP: an algorithm to distinguish structurally conserved and unconserved regions in protein domain alignments and its application in the study of large length variations," BMS Structural Biology; 14 pages; May 31, 2008.

(56) References Cited

OTHER PUBLICATIONS

Bowie et al., Science 247:1306-1310, 1990.
McConnell et al., Nature 411 (6838): 709-713, 2001.
Kano-Murakami et al., (1993, FEBS 334:365-368).
Eddy, 2004, Nature Biotechnology 22(10):1315-1316.
U.S. Appl. No. 16/991,897, filed Aug. 12, 2020, Nadzan et al.
U.S. Appl. No. 16/991,904, filed Aug. 12, 2020, Nadzan et al.

* cited by examiner

FIG. 1

| SEQ_ID_NO_21 | ----------- | --- MTNLYLT | ---------- | ---------- | ---------- | ---------- | 8 |
|---|---|---|---|---|---|---|---|
| SEQ_ID_NO_36 | ----------- | --- MNPLA-- | ---------- | ---------- | ---------- | ---------- | 5 |
| SEQ_ID_NO_47 | ----------- | --- MGLWM V | F--------- | ---------- | ---------- | ---------- | 8 |
| SEQ_ID_NO_4 | -----MENRR | SGGGSGWWVC | VLP------ | L FTKDGPAYF | HSSSDDVSAW | ---------- | 39 |
| SEQ_ID_NO_46 | ---------- | ---------- | ---------- | ---------- | ---------- | ---------- | 0 |
| SEQ_ID_NO_39 | --MDSSPSTD | DCGGWLLYVS | LAAKC---G | GDPCRVVGFV | ---------- | ---------- | 34 |
| SEQ_ID_NO_40 | MDMDSSPSTD | DCGGWLLYVS | LAAKC---G | GDPCRVVGFV | ---------- | ---------- | 36 |
| SEQ_ID_NO_27 | -----MAPSE | KC-GWLLYVS | LAAKCCGNGD | GKPYRVVGFV | ---------- | ---------- | 34 |
| SEQ_ID_NO_29 | -----MAPPT | DC-GWLLYLS | LAAKC---- | GDPQRLLGFA | ---------- | ---------- | 30 |
| SEQ_ID_NO_38 | -----MAPSE | DC-GWLLYLS | LAAKC---- | GDPHRLLGFA | ---------- | ---------- | 29 |
| SEQ_ID_NO_3 | -------MAI | KLDTSSLLLA | LSKC--SL | LTQTNLALSL | ---------- | ---------- | 30 |
| SEQ_ID_NO_25 | -------MST | NI-DNLWM FA | LASKC---- | -TQENLAYSL | ---------- | ---------- | 26 |
| SEQ_ID_NO_22 | -------MTS | HIDDNLWM A | LTSKC---- | -TQENLAWWL | ---------- | ---------- | 27 |
| SEQ_ID_NO_6 | -------MGS | DI-ESVMLFA | LASKC--KA | FSQQNTAWP | ---------- | ---------- | 29 |
| SEQ_ID_NO_10 | -------MRT | DI-DSFWM FA | LASKC--RA | FTQENLAWSL | ---------- | ---------- | 29 |

| SEQ_ID_NO_21 | ------LLPT | FIFLIVLVLS | ---------- | ---------- | ----RRRNNR | 28 |
|---|---|---|---|---|---|---|
| SEQ_ID_NO_36 | ------LIFC | TALFCILLYH | FL-------- | ---------- | ----TRRSVR | 27 |
| SEQ_ID_NO_47 | ------VTLV | AAICINRLLN | LI-------- | ---------- | ----KKPTLP | 30 |
| SEQ_ID_NO_4 | RQWPLYALL | IYAVCAVLVS | NLSPGGCAWA | GRH------- | ----KRGRVA | 78 |
| SEQ_ID_NO_46 | ---------- | ---------- | ---------- | ---------- | ---------- | 0 |
| SEQ_ID_NO_39 | ------AVAV | VAFAVTSLLH | NLSPGGPAWG | RYWW------ | ---NRRGGLG | 69 |
| SEQ_ID_NO_40 | ------AVAV | VAFAVTSLLH | NLSPGGPAWG | RYWW------ | ---NRRGGLG | 71 |
| SEQ_ID_NO_27 | ------YVLL | AAFVVTSLLH | NASQGGAAWG | RYWW------ | ----RRKGLG | 68 |
| SEQ_ID_NO_29 | ------AVFV | AACVVTSLLH | NASPGGPAWG | WYWW------ | ----TRRAGLG | 65 |
| SEQ_ID_NO_38 | ------AVLA | TAFVVTALLH | NASPGGPAWG | RYWW------ | ----TRRAGLG | 64 |
| SEQ_ID_NO_3 | ------LVAS | LASLALSLFF | NSHPGGPAWG | KYFL------ | ----HRRRQTT | 65 |
| SEQ_ID_NO_25 | ------LIMA | LLWITMIFFY | NSHPGGPAWG | KYYYSSNYST | TKTNNKNNLN | 70 |
| SEQ_ID_NO_22 | ------LIMG | SLMLTMTFYY | NGHPGGPAWG | KYYT------ | ----YSPPLS | 61 |
| SEQ_ID_NO_6 | ------LITA | LAWLVMTIVY | NVHPGGPAWG | KYRF------ | ----KKCAIT | 63 |
| SEQ_ID_NO_10 | ------LIIG | LAWIVVTLIY | NAYPGGPAWG | KYKL------ | ----KNTSLT | 63 |

FIG. 1 (Continued)

| | | | | | | | |
|---|---|---|---|---|---|---|---|
| SEQ_ID_NO_21 | L--------- | ----PPGPNP | API I GNLPHM | -GPKPHQTLA | AMVTT---YG | | 61 |
| SEQ_ID_NO_36 | L--------- | ----PPGPKP | API VGNLPHL | -GPVPHRSLA | ALAKT---YG | | 60 |
| SEQ_ID_NO_47 | L--------- | ----PPGPSP | API VGNLPHM | -GPVPHHALA | ALALK---HG | | 63 |
| SEQ_ID_NO_4 | ---------- | ----PGPKG | API I GSLMDM | SVGLPHRKLE | QLARL-HGAK | | 113 |
| SEQ_ID_NO_46 | ---------- | ---------- | | | | | 0 |
| SEQ_ID_NO_39 | AAA------ | ----PGPRG | LPVLGSMSLM | -AGLAHRKLA | AAGGSPARR | | 108 |
| SEQ_ID_NO_40 | AAA------ | ----PGPRG | LPVLGSMSLM | -AGLAHRKLA | AAGGSPARR | | 110 |
| SEQ_ID_NO_27 | GEAR----- | ----PGPRG | FPVIGSMGLM | -TGLAHRKLA | AAAGNVRRR | | 108 |
| SEQ_ID_NO_29 | VRAA----- | ----PGPRG | LPVVGSMGLM | -TGLAHRKLS | AASERQASRH | | 105 |
| SEQ_ID_NO_38 | GAA------ | ----PGPRG | LPVLGSMGLM | -TGLAHRKLA | AANGK--ARR | | 101 |
| SEQ_ID_NO_3 | V-------- | ----PGPRG | LPFVGSMSLM | SNTLAHRC A | ATAEK-FRAE | | 101 |
| SEQ_ID_NO_25 | SGTKPSTTTS | SSI F PGPKG | YPLFGSMNLM | SSSLAHHRI A | SITAKT-CKAT | | 119 |
| SEQ_ID_NO_22 | L--------- | ----PGPKG | FPLIGSMGLM | -TGLAHHRI A | AAAT-CRAK | | 96 |
| SEQ_ID_NO_6 | TINKP----- | ----PGPRG | LPLIGSMNMV | ANSLAHHLA | TIAKT-CKAK | | 103 |
| SEQ_ID_NO_10 | SNP------ | ----PGPRG | FFITGSMKLM | -TGLAHHKI A | AADA-CKAR | | 101 |

| | | | | | | | |
|---|---|---|---|---|---|---|---|
| SEQ_ID_NO_21 | PLLHLRLGFA | DYVVAASKSV | AEQFLKVHDA | NFASRPPNSG | AKHMAYNYQD | | 111 |
| SEQ_ID_NO_36 | PLMHLRMCFV | DYVVASASV | ADFLKTHDA | NFSNRPPNSG | AKHIAYNYQD | | 110 |
| SEQ_ID_NO_47 | PLMHLQLGFV | DVI VASASV | AEQFLKVHDA | NFSSRPPNSG | AKYIAYNYQD | | 113 |
| SEQ_ID_NO_4 | QLMSFGLQCT | PAVITSDPEV | ARELLL-TSP | HFANRPLKQS | AQQLLFG-RA | | 160 |
| SEQ_ID_NO_46 | --MAFSVGLT | RFIVSSHPKT | AKEILL-SSP | AFADRPIKES | AYELLFN-RA | | 45 |
| SEQ_ID_NO_39 | RLMASLGET | RVVVTADPGV | ARELLL-ASA | AFADRPVKES | AYGMLFH-RA | | 155 |
| SEQ_ID_NO_40 | RLMASLGET | RVVVTADPGV | ARELLL-ASA | AFADRPVKES | AYGMLFH-RA | | 157 |
| SEQ_ID_NO_27 | RLMSFSMGET | RYVVTADPDV | ARELLL-ASP | AFADRPYKES | AYGLMFH-RA | | 155 |
| SEQ_ID_NO_29 | RLMAFSLGET | RVVVTADLDV | ARELLL-ASA | AFADRPVKES | AYGLLFH-RA | | 152 |
| SEQ_ID_NO_38 | RLMAFSLGET | RVVVTADPDV | ARELLL-ASA | TFADRPVKES | AYGLLFH-RA | | 148 |
| SEQ_ID_NO_3 | RLMAFSLGET | RVI VTCNPDV | AKEILL-NSP | VFADRPVKES | AYGLMFN-RA | | 148 |
| SEQ_ID_NO_25 | RLMAFSLGDT | RAMVTCNPDV | AKEILL-HSS | VFADRPIKES | AYSLMFN-RA | | 166 |
| SEQ_ID_NO_22 | RLMAFSLGDT | RVI VTCHPDV | AKEILL-NSS | VFADRPVKES | AYSLMFN-RA | | 143 |
| SEQ_ID_NO_6 | RLMAFSLGDT | RVI VTCNPEV | AKEILL-NSS | VFADRPVKES | AYSLMFN-RA | | 150 |
| SEQ_ID_NO_10 | RLMAFSLGDT | RVI VTCNPDV | AKEILL-NSS | VFADRPVKES | AYSLMFN-RA | | 148 |

FIG. 1 (Continued)

| | | | | | | | |
|---|---|---|---|---|---|---|---|
| SEQ_ID_NO_21 | LVFAPYGDRM | RMLRKISSVH | LFSAKALEDF | KHVRDEEVGT | LMRE--LARA | | 159 |
| SEQ_ID_NO_36 | LVFAPYGPRM | RMLRKICSVH | LFSGDALDDF | RHIRDEEVLA | LMRA--LARE | | 158 |
| SEQ_ID_NO_47 | LVFAPYGPRM | RLLRKISYVH | MFSSKALDDF | RHIRDDEVAR | LIRN--LSNS | | 161 |
| SEQ_ID_NO_4 | GFAPNGGYW | RLLRRIASAH | LFAPRRIARH | EAGRDADVVA | MLDD--QKE | | 208 |
| SEQ_ID_NO_46 | MGFAPFGDYW | RNLRRISSTY | LFSPRRVSGE | EKDRSEIGEG | MVRD--MKRM | | 93 |
| SEQ_ID_NO_39 | GFAPYGIYW | RALRRVASTH | LFSPRQVSAS | AAQRAVIARD | MVEAMRSAAA | | 205 |
| SEQ_ID_NO_40 | GFAPYGIYW | RALRRVASTH | LFSPRQVSAS | AAQRAVIARD | MVEAMRSAAA | | 207 |
| SEQ_ID_NO_27 | GFAPYGAYW | RTLRRVSSSH | LFSPRQYAAS | AAQRAVIAHQ | MVDA--MRPV | | 203 |
| SEQ_ID_NO_29 | GFAPHGAYW | RALRRVASAH | LFSPRQIAAS | AAQRAAIARD | MVDA--TTTA | | 200 |
| SEQ_ID_NO_38 | GFAPHGAYW | RALRRVASAH | LFSPRQIAAS | AAQRAVIARD | MVDAMMMEQG | | 198 |
| SEQ_ID_NO_3 | GFAPYGVYW | QTLRKIASNH | LFSPKQIKRS | ETQRSVIAND | VKC--LTKQ | | 196 |
| SEQ_ID_NO_25 | GFAPYGVYW | RTLRKISTNH | LFSPMQIKSS | GPDRSEIAID | MIDL--FRNR | | 214 |
| SEQ_ID_NO_22 | GFASYGVYW | RSLRRIASNH | LFCPRQIKAS | ELDRSDIAAD | MVHI--LNNK | | 191 |
| SEQ_ID_NO_6 | GFAPYGVYW | RELRRIAATH | LFCPKQIKNS | EEDRRFIADE | MVNL--FGRH | | 198 |
| SEQ_ID_NO_10 | GFAPYGVYW | RTLRKIASTH | LFCPKQIKAA | ESQRLQLASD | MYST--FNDR | | 196 |

| | | | | | | | |
|---|---|---|---|---|---|---|---|
| SEQ_ID_NO_21 | NTKP---WNL | GQLVNMCVLN | ALDREMIGRR | LFGAD----- | ADKAEEFRS | | 201 |
| SEQ_ID_NO_36 | GQTP---VKL | GDLLNVCITN | ALGRVMLGRR | VFGDGSGG-- | EDPKADEFKE | | 203 |
| SEQ_ID_NO_47 | GSKA---ANL | GQMLNVCITN | ALARVMLGRH | VFNEGNGGCE | CDPRADEFKS | | 208 |
| SEQ_ID_NO_4 | YHGK-GVRV | RRILQDAALN | NIMGSVFGRR | FDMSH----- | ENEEVKKLRE | | 252 |
| SEQ_ID_NO_46 | MERN-GVMEV | RRMLHYGGLN | NIMLTVFGKK | FDF------- | AKDEGLELEL | | 135 |
| SEQ_ID_NO_39 | AAAG-GGVAA | RPFLKRASLH | NVMASVFGRK | YELAAP---- | ESEETAELRS | | 250 |
| SEQ_ID_NO_40 | AAAG-GGVAA | RPFLKRASLH | NVMASVFGRK | YELAAP---- | ESEETAELRS | | 252 |
| SEQ_ID_NO_27 | GGAGVKHVEA | RRFLKRASLH | NVMASVFGRR | YELDEA---- | GGEAAELKS | | 249 |
| SEQ_ID_NO_29 | AAHA-PVVVA | RRFLKRASLH | NVMASVFGRR | YDLMA----- | DSREAEELKA | | 244 |
| SEQ_ID_NO_38 | AASP-GVVTA | RRFLKRASLH | SVMASVFGRR | YELQAAD-- | GGEEAAELQS | | 245 |
| SEQ_ID_NO_3 | GNIK-GLCFA | RDLIKIASLN | NMMCSVFGKE | YELEE----- | EHEEVSELRE | | 240 |
| SEQ_ID_NO_25 | HLHG-GFC-V | RDVLKKASLN | NMMCSVFGQR | FKIDE----- | VNERMMELSG | | 257 |
| SEQ_ID_NO_22 | RHRS---LRV | RQVLKKASLS | NMMCSVFGCE | YKLHD----- | PNGGMEDLGI | | 233 |
| SEQ_ID_NO_6 | GHER--SFIV | REVVKRASLN | NMMVSIFGRK | YKLDC----- | ONNEVDELRG | | 241 |
| SEQ_ID_NO_10 | EKSS---FSV | REVLKRASLN | NMMCSVFGRE | YKLDS----- | FNNEVEELRA | | 238 |

| | | | | | | | |
|---|---|---|---|---|---|---|---|
| SEQ_ID_NO_21 | LLLNMFTAGT | DTSAGTVDWA | AELIRHFEI | MRKAQEELDS | VV | GRGRPIN | 341 |
| SEQ_ID_NO_36 | LLLNLFTAGT | DTSSGTVEWA | AELIRHPEM | MAQAQQELDA | VV | GRGRLVT | 342 |
| SEQ_ID_NO_47 | LLLNMFTAGT | DTSGSTTEWA | AELIKNPRL | MIRIQNELDT | VV | GRDRLVT | 344 |
| SEQ_ID_NO_4 | VLWEMIFRGT | DTTALLTEWI | MAELVLHPEA | DKKAQAELDA | VV | GHDRSVK | 387 |
| SEQ_ID_NO_46 | VLWEMIFRGT | DTVAILLEYI | LARMVLHPDI | DSKADVEIDS | VV | DSSRPVL | 272 |
| SEQ_ID_NO_39 | VLWEMIFRGT | DTVAVLIEWV | AARLVLHQDV | DARVHDELDR | VV | GSDRAVT | 384 |
| SEQ_ID_NO_40 | VLWEMIFRGT | DTVAVLIEWV | AARLVLHQDV | DARVHDELDR | VV | GSDRAVT | 386 |
| SEQ_ID_NO_27 | VLWEMIFRGT | DTVAVVIEWV | LARLMLHQDV | DARVHEELDR | VV | GPNRAVT | 383 |
| SEQ_ID_NO_29 | VLWEMIFRGT | DTVAVLIEWV | LARLVLHQDV | DSKVQEELDR | VV | GLGQAVT | 379 |
| SEQ_ID_NO_38 | VLWEMIFRGT | DTVAVLMEWV | LARLVLHQDV | DRRVQEELDR | VV | GPGRAVT | 383 |
| SEQ_ID_NO_3 | VLWEMIFRGT | DTVAVLIEWI | LARMVLHPDI | DSTVHNELDQ | IV | GRSRAVE | 371 |
| SEQ_ID_NO_25 | VLWEMIFRGT | DTVAVLIEWI | LARLVIHPDV | DKKVQIELDE | VASGESCAIT | | 389 |
| SEQ_ID_NO_22 | VLWEMIFRGT | DTVAVLIEWI | LARMALHPHV | DSKVQEELDA | VV | GKARAVA | 364 |
| SEQ_ID_NO_6 | VLWEMIFRGT | DTVAVLIEWI | LARIVVHPDV | DSRVHDELDK | VV | GKSKAVY | 372 |
| SEQ_ID_NO_10 | VLWEMIFRGT | DTVAVLIEWI | LARMVLHPDV | DSKVHDELYK | VV | GRSRAVA | 359 |

| | | | | | | |
|---|---|---|---|---|---|---|
| SEQ_ID_NO_21 | ESDLSDIPYL | DAVIKENFRL | HPPTPLLSLP | HIASESCEI | NGYHIPKGST | 359 |
| SEQ_ID_NO_36 | DLDLPKLTYL | DAIVKEIFRL | HPSTPLLSLP | RMAAESCEI | NGYHIPKNAT | 390 |
| SEQ_ID_NO_47 | EDDLTHLPYL | EAVIKEIFRL | HPSTPLLSLP | RVATNSCEI | FNYHIPKGAT | 392 |
| SEQ_ID_NO_4 | DSDIPKLPYI | DAVVKEALRM | HPPGPLLSWA | RLSTEDVNMG | DGMCVPAGTT | 437 |
| SEQ_ID_NO_46 | DSDIQRLPYL | DSIVKETLRM | HPPGPLLSWA | RLAIHDVPV | DGHMVPAGTT | 321 |
| SEQ_ID_NO_39 | ESDASKLVYL | DAVIKEVLRL | HPPGPLLSWA | RLATSDVHV | GGFLVPSGTT | 433 |
| SEQ_ID_NO_40 | ESDASKLVYL | DAVIKEVLRL | HPPGPLLSWA | RLATSDVHV | GGFLVPSGTT | 435 |
| SEQ_ID_NO_27 | ESDHASLVFL | DAVVKEVLRL | HPPGPLLSWA | RLATSDVHV | DGLHVPAGTT | 432 |
| SEQ_ID_NO_29 | ESDTASLPYL | DAVIKEVLRL | HPPGPLLSWA | RLATSDVYV | SGYLVPAGTT | 428 |
| SEQ_ID_NO_38 | EFDGASLAYL | HAVIREVLRL | HPPGPLLSWA | RLATSDVHV | GGYLVPAGTT | 432 |
| SEQ_ID_NO_3 | ESDVSLVYL | TAVVKEVLRL | HPPGPLLSWA | RLAITDTII | DGRRVPAGTT | 420 |
| SEQ_ID_NO_25 | EEDVANMYL | PAVIKEVLRL | HPPGPLLSWA | RLAITDTTI | DGYHVPAGTT | 439 |
| SEQ_ID_NO_22 | EDDVANMTYL | PAVVKEVLRL | HPPGPLLSWA | RLSINDTTI | DGYHVPAGTT | 413 |
| SEQ_ID_NO_6 | ESDVMNLTYL | MAVIKEVLRL | HPPGPLLSWA | RLAITDTTV | DGYHVPKGTM | 421 |
| SEQ_ID_NO_10 | ESDITAMVYL | DAVVKEVLRL | HPPGPLLSWA | RLAITDTTI | DGYHVPKGTT | 418 |

FIG. 1 (Continued)

| | | | | | | |
|---|---|---|---|---|---|---|
| SEQ_ID_NO_21 | LLKNIWAIAR | DPDQMSDPLT | FRPERFLPGG | EKA-G----- | VDVKGNDFEL | 433 |
| SEQ_ID_NO_36 | LLVNVWAIAR | DPEVWEEPLE | FRPNRFLPGG | ERP-N----- | ADVRGNDFEV | 434 |
| SEQ_ID_NO_47 | LLVNVWAISR | DPKEMTNPLE | FKPERFLPGG | EKF-D----- | VDIRGNDFEV | 436 |
| SEQ_ID_NO_4 | AMVNMWSITH | DPNIWESPYE | FRPERFVFE | GGE-E----- | VDVRGNDLRL | 481 |
| SEQ_ID_NO_46 | AMVNMWAITH | DECNMAEPNK | FNPDRFIDED | ---------- | VNILGSDLRL | 361 |
| SEQ_ID_NO_39 | AMVNMWAITH | DPAVWPDPNE | FKPERFVAGP | SSDQA---AE | FPIMGSDLRL | 480 |
| SEQ_ID_NO_40 | AMVNMWAITH | DPAVWPDPNE | FKPERFVAGP | SSDQA---TE | FPIMGSDLRL | 482 |
| SEQ_ID_NO_27 | AMVNMWAITH | DPTVWKPAF | FKPERFLGGS | SSDHAAAGAE | FSVTGSDLRL | 482 |
| SEQ_ID_NO_29 | AMVNMWAITH | DPSLWPEPHE | FRPERFMGPA | AED------- | VPIMGSDLRL | 471 |
| SEQ_ID_NO_38 | AMVNMWAITH | DPAVWPDPAE | FKPERFAAGS | PGDEA----- | FPVMGSDLRL | 477 |
| SEQ_ID_NO_3 | AMVNMWAIAH | DPHVWENPLE | FKPERFVAKE | GEV-E----- | FSVLGSDLRL | 464 |
| SEQ_ID_NO_25 | AMVNMWAISR | DPDVWRNPLE | FNPERFVSEG | AE-------- | FSVLGSDLRL | 480 |
| SEQ_ID_NO_22 | AMVNIWAICR | DPHVWKDPLE | FMPERFVTAG | GDA-E----- | FSILGSDPRL | 457 |
| SEQ_ID_NO_6 | AVVNMWAIAR | DPQENADPIT | FVPDRFVAKT | GEV-E----- | FSVLGSDLRL | 465 |
| SEQ_ID_NO_10 | AMVNMWAISR | DPEFREDPLE | EMPERFVWTK | EDVLE----- | FSYLGSDLRL | 463 |
| | | | | | | |
| SEQ_ID_NO_21 | IPFGAGRRIC | AGLSLGLRFT | QLLTATLVHG | FEWELAGGVT | -PEKLNMEET | 482 |
| SEQ_ID_NO_36 | IPFGAGRRIC | AGMSLGLRMV | HLLTATLVHA | FNWELPEGDV | -AEKLNMDEA | 483 |
| SEQ_ID_NO_47 | IPFGAGRRIC | AGMSLGLRMV | QLLTATLAHA | YDWELENGLS | -PEKLNMDFA | 485 |
| SEQ_ID_NO_4 | APFGAGRRVC | PGKALGLATV | NLWAKLLHH | FEWLPHAF | --HPVDLSEV | 527 |
| SEQ_ID_NO_46 | APFGSGKRVC | PGKTMALAAV | HLMLADLLKS | FKLLPSR-- | --NSVDLSEC | 406 |
| SEQ_ID_NO_39 | APFGSGRRSC | PGKSLAIATV | GFWATLLHE | FDWLPLSDK | -SRGVDLSEV | 528 |
| SEQ_ID_NO_40 | APFGSGRRSC | PGKSLAIATV | GFWATLLHE | FDWLPLSDK | -SRGVDLSEV | 530 |
| SEQ_ID_NO_27 | APFGSGRRSC | PGKSLAIATV | GFWATLLHE | FEWIPPSSDG | -SGGVDLSEV | 531 |
| SEQ_ID_NO_29 | APFGSGRRSC | PGKSLAVATV | GFWATLLYE | FKWLPPSDEP | RGGGVDLSEV | 521 |
| SEQ_ID_NO_38 | APFGSGRRVC | PGKSLAMATV | AFWATLLHE | FEWLPASSDE | PPRGVDLSEV | 527 |
| SEQ_ID_NO_3 | APFGSGRRVC | PGKNLGLITV | TFWTATLLHE | FEWLTPSDE | --KITVGLSEK | 511 |
| SEQ_ID_NO_25 | APFGSGRRSC | PGKNLGLATV | TFWAKLLHE | FEWLPLDE | -VNGVDLTEV | 527 |
| SEQ_ID_NO_22 | APFGSGRRAC | PGKTLGMATV | NFWASLLHE | FEWVPSDE | --KGVDLTEV | 503 |
| SEQ_ID_NO_6 | APFGSGRRTC | PGKNLGLITV | SFWATLLHE | FEWLPSDQ | --NSVDLSEV | 511 |
| SEQ_ID_NO_10 | APFGSGRRTC | PGKTLGITTV | TFWASLLHE | YEWVPSEE | --NNVDLSEV | 509 |

FIG. 1 (Continued)

| | | | | |
|---|---|---|---|---|
| SEQ_ID_NO_21 | YGLTLDRAVP | LVVHPKLRLD | MSAYGLGSA | 511 |
| SEQ_ID_NO_36 | YGLTLDRAAP | LMVHPRPRLS | PQVFGK--- | 509 |
| SEQ_ID_NO_47 | YGLTLDRAVP | LAHPRPRLS | PHLYL---- | 510 |
| SEQ_ID_NO_4 | LKLSCEMARP | LHCVPVTRVP | FAKFSD--- | 553 |
| SEQ_ID_NO_46 | LKMSLEMKNP | LVCVAVPRFE | --------- | 426 |
| SEQ_ID_NO_39 | LKLSCEMATP | LEARLRPRRK | VMSV----- | 552 |
| SEQ_ID_NO_40 | LKLSCEMATP | LEARLRPRRK | V-------- | 551 |
| SEQ_ID_NO_27 | LRLSCEMAAP | LEARLRPRRA | V-------- | 552 |
| SEQ_ID_NO_29 | LRLSCEMARP | LEARVVPRHA | VC------- | 543 |
| SEQ_ID_NO_38 | LRLSCEMAAP | LEARLVPRRA | V-------- | 548 |
| SEQ_ID_NO_3 | LRLSCEMANP | LAAKLRPRRS | FSV------ | 534 |
| SEQ_ID_NO_25 | LRLSCEMANP | LTVGVRPRR | --------- | 546 |
| SEQ_ID_NO_22 | LKLSSEMANP | LTVKVRPRRG | --------- | 523 |
| SEQ_ID_NO_6 | LKLSCEMANP | LKVRIRPRRK | LT------- | 533 |
| SEQ_ID_NO_10 | LRLSCEMANP | LTVKVRPRRS | SQSPLY--- | 535 |

Figure 2

| | | | | | | |
|---|---|---|---|---|---|---|
| SEQ_ID_NO_67 | ---------- | MQLQPAVAN- | ---------P | NTPSGAA--- | ---------- | 17 |
| SEQ_ID_NO_65 | MDTSHWPQGI | GLVKAVEPS- | -----KPVPT | ERKPRPQ--- | ----KEQ--- | 34 |
| SEQ_ID_NO_63 | MGMDSSSGQQ | QQMSNQSLES | MLTCSKGE-Q | DKKPKPP--- | ----QPE--- | 39 |
| SEQ_ID_NO_73 | -----MDQQQ | QEMSSQTLES | MLVCTKPDQD | QKKPRPA--- | ----EQQ--- | 35 |
| SEQ_ID_NO_69 | -------MQEE | PGRRPVPPF- | -----AGVDL | RRPKGYP--- | -VAVAKEERP | 34 |
| SEQ_ID_NO_70 | --------MQE | AGRRPAPQF- | -----AGVDL | RRPKGYPAAA | QLTPAAEEAA | 37 |
| SEQ_ID_NO_71 | --------MQE | AGRRPAPQF- | -----AGVDL | RRPKGYPAAA | QLTPAAEEAA | 37 |
| SEQ_ID_NO_64 | -----MPSSD | SGESRRSK- | ---------P | QNRPGAP--- | --APEQE--- | 27 |
| SEQ_ID_NO_75 | --------MEA | GQVPDGRAL- | -----MAAVT | TTGGGGR--- | ----EPE--- | 27 |
| SEQ_ID_NO_51 | --------MQD | ----PTGFH- | ---------Q | MKAPAFQ--- | ----EQEQQ- | 21 |
| SEQ_ID_NO_53 | --------MQD | ----PSTAF- | ---------H | TIKPQFP--- | ----EQE--- | 19 |
| SEQ_ID_NO_60 | --------MQD | ----PLTLF- | ---------Q | PMKPHFP--- | ----EQE--- | 18 |
| SEQ_ID_NO_58 | --------MQE | DLTSAAAYYH | HQSMI MTAKQ | QQQPELP--- | ----EQE--- | 33 |
| SEQ_ID_NO_49 | --------MQD | ----PAAYY- | -QTMMAKQQQ | QQQPQFA--- | ----EQE--- | 27 |

| | | | | | | |
|---|---|---|---|---|---|---|
| SEQ_ID_NO_67 | ---REQCPRC | ASHDTKFCYY | NNYNISQPRH | FCRACRRYWT | LGGSLRNVPI | 64 |
| SEQ_ID_NO_65 | ---ALNCPRC | NSTNTKFCYY | NNYSLSQPRY | FCKTCRRYWT | EGGSLRNVPV | 61 |
| SEQ_ID_NO_63 | ---ALKCPRC | DSNNTKFCYY | NNYSLSQPRY | FCKSCRRYWT | KGGTLRNVPV | 86 |
| SEQ_ID_NO_73 | ---PQKCPRC | DSANTKFCYY | NNYSLTQPRY | FCKSCRRYWT | KGGTLRNVPV | 62 |
| SEQ_ID_NO_69 | APGGDPCPRC | GSRDTKFCYY | NNYNISQPRH | LCKSCRRYWT | KGGSLRNVPV | 84 |
| SEQ_ID_NO_70 | AGVGDPCPRC | ESRDTKFCYY | NNYNISQPRH | FCKSCRRYWT | KGGSLRNVPV | 87 |
| SEQ_ID_NO_71 | AGVGDPCPRC | ESRDTKFCYY | NNYNISQPRH | FCKSCRRYWT | KGGSLRNVPV | 87 |
| SEQ_ID_NO_64 | ---NLPCPRC | DSTNTKFCYY | NNYNYSQPRH | LCKACRRYWT | HGGTLRDIPV | 74 |
| SEQ_ID_NO_75 | ---GLPCPRC | ESVNTKFCYY | NNYNLSQPRY | FCKTCRRYWT | RGGALRNVPV | 74 |
| SEQ_ID_NO_51 | ---QLKCPRC | DSTNTKFCYY | NNYNLSQPRH | FCKNCRRYWT | KGGALRNIPV | 68 |
| SEQ_ID_NO_53 | ---QLKCPRC | DSNNTKFCYY | NNYNLSQPRH | FCKNCRRYWT | KGGALRNIPV | 66 |
| SEQ_ID_NO_60 | ---QLKCPRC | DSTNTKFCYY | NNYNLSQPRH | FCKNCRRYWT | KGGALRNIPV | 65 |
| SEQ_ID_NO_58 | ---QLNCPRC | ASPNTKFCYY | NNYNLSQPRH | FCKNCRRYWT | KGGSLRNIPV | 80 |
| SEQ_ID_NO_49 | ---QLKCPRC | DSPNTKFCYY | NNYNLSQPRH | FCKSCRRYWT | KGGALRNVPV | 74 |

Figure 2 (continued)

| | | | | | | | |
|---|---|---|---|---|---|---|---|
| SEQ_ID_NO_67 | GGSTRKRLRP | APQQTMRRPP | VHFGAP- -P | PPPMPA- - - | - - - - - - - - - - | | 97 |
| SEQ_ID_NO_65 | GGGSRKNKRS | SSSSNNSSSS | - - -TSS- - -S | YKKIPDLT- - | - - - - - - - - - - | | 113 |
| SEQ_ID_NO_63 | GGGCRKNKRS | SSASSKRSQD | - - - -QPFQTN | PNPLTCFPSL | SYDSNDLTLA | | 132 |
| SEQ_ID_NO_73 | GGGCRKNKKL | SSTTSAKRSS | QDNISPNISN | PIPSYDSSTD | LSLAFARLQK | | 132 |
| SEQ_ID_NO_69 | GGGTRKSSSS | SSSSSAAAAA | - - - -TTTTTS | TSPGAAPK- - | -ATKRSKNSK | | 127 |
| SEQ_ID_NO_70 | GGGSRKSSTS | SSSSSSAAAA | - - - -SS- - -S | SSPSSPAK- - | -SPKRSKNSK | | 127 |
| SEQ_ID_NO_71 | GGGSRKSSTS | SSSAAAAAAS | - - - - - -S- - -S | SSPSSPAK- - | -SPKRSKNSK | | 126 |
| SEQ_ID_NO_64 | GGGTRKNAKR | SRTHHVAVTS | - - - -SS- - -S | SSAVT- - - - | - - - - - - - - - - | | 102 |
| SEQ_ID_NO_75 | GGNTRKATPA | TGRRKRSTPA | - - - - -P- - -V | NVTVPAP- - - | - - - - - - - - - - | | 103 |
| SEQ_ID_NO_51 | GCGTRKGTKR | SSSSTNKPKR | - - - -QP- - -N | PSPDPTPNQK | -IPDPSPPPP | | 110 |
| SEQ_ID_NO_53 | GGGSRKNTKR | SSNTKRANPD | - - - - -P- - -N | PDPVKPTR- - | - - - - - - - - - - | | 96 |
| SEQ_ID_NO_60 | GGGSRKNTKR | SSSSNNNTKR | - - - - - - - - - - | ASPSPPVS- - | - - - - - - - - - - | | 93 |
| SEQ_ID_NO_58 | GGGTRKNSSK | RSSVGSSSSA | - - - -PS- - -S | SSPKSKTV- - | - - - - - - - - - - | | 111 |
| SEQ_ID_NO_49 | GGGSRKNATK | RSTSSSSSAS | - - - -SP- - -S | NSSQNKKT- - | - - - - - - - - - - | | 105 |

| | | | | | | | |
|---|---|---|---|---|---|---|---|
| SEQ_ID_NO_67 | -QSHSQQAPQ | GGLLSSLFAF | GAAPLFEGRV | GE- - - -D- - | LGLGLPGLSQ | | 139 |
| SEQ_ID_NO_65 | -IPTSSQNPK | IINEPHDLNL | AFNPSATSNF | SNISEFMA- - | LPLMNPNSTT | | 160 |
| SEQ_ID_NO_63 | LARLQKGHLG | FDHEHDFSIL | GNQTNTSCG | LNN- - - - - - | HGMNHSSNNQ | | 175 |
| SEQ_ID_NO_73 | QTNAHLEIDQ | EHDNNNMSMM | YNTGNNCTST | TELDALRGG- | FLENAPNHPG | | 181 |
| SEQ_ID_NO_69 | RRRVAPAPDP | AAPGTDASTA | DVASTAPSTV | - - - - - - - - - - | AASEKPSATE | | 167 |
| SEQ_ID_NO_70 | RRRVSPPPPQ | PAP- - - - - - - | APPPPTTADA | - - - - - - - - - - | ADVAAPTAPE | | 160 |
| SEQ_ID_NO_71 | RRRVSPPPPQ | PVP- - - - - - - | APPPPTTADA | - - - - - - - - - - | ADVAAPTAPE | | 159 |
| SEQ_ID_NO_64 | -SAPEQNYP- | - - - - - - - - - - | SMTPIQGGSF | PY- - - - - - - | GGVDGEGKQN | | 132 |
| SEQ_ID_NO_75 | -ATASPPPPP | ALHGGSLLRP | YGGGGGSGLL | SFAAPALASP | LAAADPDRRL | | 152 |
| SEQ_ID_NO_51 | KSSSSSMFPQ | QIVLNSGAQN | SDSDIDSTRM | -Y- - - -L- - | LPVDHQDGKM | | 152 |
| SEQ_ID_NO_53 | -RVADSSSSS | ATSSTSGQQL | AGNGNQDPTR | VY- - - - - - - | GVEADPDRKI | | 137 |
| SEQ_ID_NO_60 | -SAPAPEPDP | TRI- - - - - - - | - - - - - - - - - - | - - - - - - - - - - | GPTPVVG- - - | | 112 |
| SEQ_ID_NO_58 | -AVSDQESRT | TGN- - - - - - - | SGQEMDPTRM | LY- - - -G- - | LPVGDPS- - - | | 143 |
| SEQ_ID_NO_49 | -KNPDPDPDP | RNS- - - - - - - | QKPDLDPTRM | LY- - - -G- - | FPLSDQDVKG | | 140 |

Figure 2 (continued)

| | | | | | | | | |
|---|---|---|---|---|---|---|---|---|
| SEQ_ID_NO_67 | VGLGGGAG- - | - - E - - - - - - - | - - FGLHSLGL | RGGHAGT - - - | - - - - - SA - - - | | | 165 |
| SEQ_ID_NO_65 | SFMSSIMP- - | - - QLSDSNNI | M- YSSSSTGL | PNLHDLK- - - | - - - - - PTLNF | | | 197 |
| SEQ_ID_NO_63 | GFFEALMG- - | - - SDNNVQNL | YYMGEVDNGN | ANGNGNGEMM | LPYDHEMSI A | | | 221 |
| SEQ_ID_NO_73 | LFHHNMYNYA | NMGQLVENGE | MGMSYQQDQM | SIGTSTTMMT | TIVKQEMCNM | | | 231 |
| SEQ_ID_NO_69 | HAAAAVAT- - | - - EKPPAAPP | VSVGAFADTS | PAPDAGS- - - | - - - - - - - - - - | | | 200 |
| SEQ_ID_NO_70 | DTTKKAPE- - | - - DLTAAAAT | QPAVALGLGV | ADGGGGG- - - | - - - - - K- - - - | | | 194 |
| SEQ_ID_NO_71 | ATTKKAPE- - | - - DLTAAAAT | QPAVALGLGV | ADGGGGG- - - | - - - - - - - - - - | | | 192 |
| SEQ_ID_NO_64 | MSVCGSFT- - | - - SLLNNNPQ | QNSGFLALGG | FGLGLGH- - - | - - - - - GL- - - | | | 167 |
| SEQ_ID_NO_75 | LDFGGSFT- - | - - SLIAPGVA | DVGVHFSAGF | LMGGLAP- - - | - - - - - AALPR | | | 190 |
| SEQ_ID_NO_51 | MDIGGSFS- - | - - SLLASTGQ | - - FGNLLEGF | NSNGSGL- - - | - - - - - KT- - L | | | 186 |
| SEQ_ID_NO_53 | LDMGGSFS- - | - - SLLASSGQ | - - FGSIFEGL | DSGGSGL- - - | - - - - - KMVRM | | | 173 |
| SEQ_ID_NO_60 | - - - GGSFS- - | - - SLLASSGH | LGLGNLLEGL | NSSGSNL- - - | - - - - - KTVQM | | | 147 |
| SEQ_ID_NO_58 | - - - GGRFS- - | - - SLLVSNMQ | QIRGVNYET - | - - - GSG- - - - | - - - - - - - - - - | | | 168 |
| SEQ_ID_NO_49 | MEIGGSFS- - | - - SLLANNMQ | - - LGLGGGGI | MLDGSG- - - - | - - - - - - - - - - | | | 170 |

| | | | | | | | | |
|---|---|---|---|---|---|---|---|---|
| SEQ_ID_NO_67 | - - - - - - - - - - | - - - - - - - - - - | PMLH PTAFL | D- - - - - - - - - | - NGNVDTMKV | | | 184 |
| SEQ_ID_NO_65 | SL- - DGFDNN | - - - - - NGYGS | LQGE- TAGKK | LFFPLDDLKN | VSTPNDDHEF | | | 239 |
| SEQ_ID_NO_63 | TTQAVTVTTM | KQEMCNVREQ | NENRVLLGFP | WQFNNGDTNM | AEMDII- - - - - | | | 266 |
| SEQ_ID_NO_73 | ARSTEGHDLN | - - - - NSNNN | NKV- - LCGFP | WQQMNGDHHV | NNMNTNDFEY | | | 274 |
| SEQ_ID_NO_69 | - - - - GGVREL | - - - - - LPHPS | RFEM PSGCN | LG- - - - - - - - | - - - - - - - - - - | | | 222 |
| SEQ_ID_NO_70 | - - - - EHLDTS | - - - - - P- - - - | - FEM PSGCD | L- - - - - - - - - | - - - - - - - - - - | | | 210 |
| SEQ_ID_NO_71 | - - - KEHLDTS | - - - - - P- - - - | - FEM PSGCD | L- - - - - - - - - | - - - - - - - - - - | | | 209 |
| SEQ_ID_NO_64 | - - - - GDMGFG | - - - - - IGR- - | - - EMSFPGMM | DGSNMGVPVV | SSGIGNSMQL | | | 204 |
| SEQ_ID_NO_75 | AP- - GSVAAL | - - - - - PPPPP | QQQP- TVSQA | L- - - - - - - - - | - - - - - - - - - - | | | 213 |
| SEQ_ID_NO_51 | NHFGGNFDSG | - - - - - CEMDQ | NSGR- DPLFG | E- - - - - - - - - | SSKNGESYLD | | | 221 |
| SEQ_ID_NO_53 | GGFGEDLNAG | - - - - - PSR- - | - - - - - NPGLD | LQGSSNNNTT | NDGGGESY- - | | | 209 |
| SEQ_ID_NO_60 | EEFGENVSSG | - - - - - PVADP | DSGR- NPGLE | MD- - - - - - - - | SNGNAENFLS | | | 183 |
| SEQ_ID_NO_58 | - - - - - - - - - - | - - - - - - - - - - | - - - M YPGME | LG- - - - - - - - | - - - - - - - - - - | | | 176 |
| SEQ_ID_NO_49 | - - - - - - - - - - | - - - - - - - - - - | - - - MDHPGMG | LGL- - - - - - - | - - - - - - - - - - | | | 180 |

Figure 2 (continued)

| | | | | | | |
|---|---|---|---|---|---|---|
| SEQ_ID_NO_67 | ----SGGGA A | AMWAPEFSPA | PTVADVGGNG | MFHGGAQI MG QL | | 222 |
| SEQ_ID_NO_65 | D------EQN | RGQAAESHGF | WNG------ | M_GGGS---- -- | | 262 |
| SEQ_ID_NO_63 | ------LGR | AGWNGLTSSW | GHGL------ | LNSPLM--- -- | | 289 |
| SEQ_ID_NO_73 | STN----KQS | WNGFGGSSNW | HGL------- | NSPLM---- -- | | 299 |
| SEQ_ID_NO_69 | -------PPY | WGWGTSVFAD | TDPA------ | LFLNLP---- -- | | 245 |
| SEQ_ID_NO_70 | ---------G | PYWPTGVFAD | TDPS------ | LFLNLP---- -- | | 231 |
| SEQ_ID_NO_71 | ---------G | PYWPTGVFAD | TDPS------ | LFLNLP---- -- | | 230 |
| SEQ_ID_NO_64 | EGGE---TGF | VGGGGDCFSW | PGLA------ | STPGNGLK- -- | | 234 |
| SEQ_ID_NO_75 | ------PEG | MVW---SNGW | PDLS------ | L--------- | | 228 |
| SEQ_ID_NO_51 | V---QGGRDT | SCWSGDSNGW | PDLS------ | YTPGSSLRR -- | | 252 |
| SEQ_ID_NO_53 | ------LQG | GEWGNSNNGW | PGLA------ | YTPGSSFQ- -- | | 235 |
| SEQ_ID_NO_60 | LQN----GDS | SCW-NGTSGW | SHLA------ | FTPGSSFQ- -- | | 211 |
| SEQ_ID_NO_58 | -------LGS | GI RRNDDAAL | TDLA------ | MNRVEKN--- -- | | 200 |
| SEQ_ID_NO_49 | ------RRT | EPGNNNNNPW | TDLA------ | MNRAEKN--- -- | | 204 |

Figure 3

| | | |
|---|---|---|
| SEQ_ID_NO_88 | MAST- - - - - - - - - - - - - - - - - - - - - - RRVQ C- -LMRRFYR - - -QSRTFGV | 23 |
| SEQ_ID_NO_95 | MTSL- - - - - - - - - QSFLAI KPAAAGWAAG ARPAAAPDSR RARVSACLAA | 40 |
| SEQ_ID_NO_90 | MNSL- - - - - - - - - QSFLAV APVK- -PAAA A- -ARLPSSR RARVSACLAT | 36 |
| SEQ_ID_NO_93 | MNSL- - - - - - - - - QSFLAL NPPAAAAALG G- -ARLRPSR - - -VTACLAT | 35 |
| SEQ_ID_NO_80 | MGSL- - - - - - - - - KLFPSF SLSV- -SPAT N- -LRRPLNN GR-VNASLNM | 35 |
| SEQ_ID_NO_87 | MGAVYFSQSC YKPRQI FNLE REBTLVGRCP V- -VQI RCRR V- -VSACLNV | 46 |
| SEQ_ID_NO_77 | MASL- - - - - - - - - GQI TLPR APS- - -SEI G L- -LRRRFER PI - IRTRI GF | 35 |
| SEQ_ID_NO_92 | MASL- - - - - - - - - GQI TLPR APS- - -LQKG L- -LRRP- - - - - IRTPI RF | 30 |
| SEQ_ID_NO_78 | MTSL- - - - - - - - - QYFSLN RPV- - -FPAT H- -LHRPGI R HLQVSACANV | 35 |
| SEQ_ID_NO_82 | MGSL- - - - - - - - - QHFLNG PISVPFSPNL N- -HRRSFF- - - -LRACLNL | 34 |

| | | |
|---|---|---|
| SEQ_ID_NO_88 | ATQPNA- - - - - - - - - - - - - - - - SSGSQT I IDKEFQHSA HNYHPLPIVF | 55 |
| SEQ_ID_NO_95 | PPPPPT- - - -TAASAVGPA RRELSAASRA VMDDEARYLV GTYKRSRVVF | 85 |
| SEQ_ID_NO_90 | PAPAPT- - - - - - - -APAAA RRELSAASRA VMADEAKYIV GTYKRAQVVF | 77 |
| SEQ_ID_NO_93 | PTPTPPPPTS APLAPAAAAA RRELSAASRA VVEDEARYI V GTYNRSRVVL | 85 |
| SEQ_ID_NO_80 | DVEAPN- - - - - - - - - - - -P LKLKSNGSNE VI EKDAKFI V GTYARAPVVL | 72 |
| SEQ_ID_NO_87 | DVDAPN- - - - - - - - -TGN TTSEKKKTKD VI EMEGMYLV GTYARTPVVL | 85 |
| SEQ_ID_NO_77 | NGRI AS- - - -VLTNAGDQA VSVKASVSQK VI EEEAKVI V GTYARAPVVL | 80 |
| SEQ_ID_NO_92 | NGRI AS- - - -VLTNAG- - - -SVKASVSQK VI EEEAKVLV GTYARAPVVL | 71 |
| SEQ_ID_NO_78 | EVQAPS- - - - - - - - - - - - SVKKDGVSKE VMEAAGRVLV GTYARVPVVL | 71 |
| SEQ_ID_NO_82 | DVHAPD- - - - - - - - - -SV KPKTHLKSRE VMEMEGKVLV GTYARNPVVI | 72 |

| | | |
|---|---|---|
| SEQ_ID_NO_88 | AHAKGSAVWD PEGNKYI DFL SGYSAVNQGH CHPKI LKALK NQAGRLTVSS | 105 |
| SEQ_ID_NO_95 | EYGRGCKLYD VDGREYLDMS AGI AVTALGH ADPDVCATI A EQSGKI VHVS | 135 |
| SEQ_ID_NO_90 | VAGRGCKLYD I DGREYLDMA AGI AVNALGH GDPDVDAAAA DQRGRLVHAS | 127 |
| SEQ_ID_NO_93 | VAGRGCKLYD ADGREYLDMA AGI AVNALGH ADPDWAAVS AQAATLVHAS | 135 |
| SEQ_ID_NO_80 | SSGKGCKLYD PEGREFLDCA AGI AVNALGH GDPDWLRAVT EQASI LTHVS | 122 |
| SEQ_ID_NO_87 | ERGEGCKLYD VEGNEYLDLS AGI AVNALGH GDADWLKAVV EQAGTLTHTS | 135 |
| SEQ_ID_NO_77 | SSGKGCKLFD PEGKEYLDCA SGI AVNALGH GDPDWLRAVT EQAGVLAHVS | 130 |
| SEQ_ID_NO_92 | SSGKGCKLMD AEGKEYLDCA SGI AVNALGH GDPDWLQAVT DQASVLSHVS | 121 |
| SEQ_ID_NO_78 | SRGKGCKLYD PEGREYLDLS AGI AVNVLGH ADSDWLRAVT EQAATLTHVS | 121 |
| SEQ_ID_NO_82 | SSGKGCKLYD PEGREYLDCT SGI AVNALGH GDPDWKAVV EQANLLTHVS | 122 |

Figure 3 (continued)

| | | | | | | | |
|---|---|---|---|---|---|---|---|
| SEQ_ID_NO_88 | RAFYNDRFPV | FAEYSTALFG | YDMVLPINTG | AEGVETALKL | ARKAGYDKKK | | 155 |
| SEQ_ID_NO_95 | NVFYTTPQVE | LAKRLVEVSF | ADRAFFASTC | TEANEAAIKF | SRK--FQRVA | | 183 |
| SEQ_ID_NO_90 | NVGYTVPQVE | LAKRLVEASF | ADRAFFANSG | TEANEAAIKF | ARK--YQRVA | | 175 |
| SEQ_ID_NO_93 | NVQYTVPQVA | LAKRLVEASF | ADRVFFANTG | TEANEAAIKF | ARK--FQRVA | | 183 |
| SEQ_ID_NO_80 | NAYYSIPQ-  | ---------- | ---------- | ---------- | ---------- | | 130 |
| SEQ_ID_NO_87 | NIFHTIPQVE | LAKRLVASSF | ADRVFFANSG | TEANEAAIKF | ARK--YQRHT | | 183 |
| SEQ_ID_NO_77 | NVYYTIPQIE | LAKRLVASSF | ADRVFFCNSG | TEANEAAIKF | SRK--FQRFT | | 178 |
| SEQ_ID_NO_92 | NVYYTIPQIE | LAKRLVASSF | ADRVFFCNSG | TEANEAAIKF | SRK--FQRFT | | 169 |
| SEQ_ID_NO_78 | NVFYSIPQVE | LAKRLVASSF | ADRVFFSNSG | TEANEAAIKF | ARK--FQRFT | | 169 |
| SEQ_ID_NO_82 | NVFYSVPQVE | LAKRLVACSF | ADRVFFTNSG | TEANEAAIKF | ARK--YQRFT | | 170 |
| | | | | | | | |
| SEQ_ID_NO_88 | IPNDEAL--- | IVSCCGCFNG | RTLGVI3MSC | DNEATRGFGP | LIPGHLKVDF | | 202 |
| SEQ_ID_NO_95 | HPDSDDPPME | FLAFSSSFHG | RTMGAVALTS | KSQYREPFAP | VMPGVTFVDY | | 233 |
| SEQ_ID_NO_90 | HPNGDAPLTE | FMSFTNCFHG | RTIGSLALTS | KVQYREPFEP | VMPGSTFVEY | | 224 |
| SEQ_ID_NO_93 | RPDGDAPLTE | FMSFTNCFHG | RTMGSLALTS | KVQYREPFAP | VMPGATFAEY | | 232 |
| SEQ_ID_NO_80 | ---------- | ---------- | ---------- | ---------- | ---------- | | 130 |
| SEQ_ID_NO_87 | TSNGKVPATE | FIAFSNCFHG | RTLGALALTS | KVQYRMPFEP | VMPGVTFLEY | | 233 |
| SEQ_ID_NO_77 | HPEDKEVATG | FIAFTNSFHG | RTLGALALTS | KEQYRTPFEP | IMPGVTFLEY | | 228 |
| SEQ_ID_NO_92 | HPEDKEVATS | FIAFTNSFHG | RTLGALALTS | KEQYRTPFEP | IMPGVTFLEY | | 219 |
| SEQ_ID_NO_78 | RPDEKQPATE | FVSFSNSFHG | RTMGSLALTS | KENYRSPFEP | VMPGVTFLEY | | 219 |
| SEQ_ID_NO_82 | NPEKQQA-TE | FISFSNSFHG | RTMGALALTS | KEQYRFPFEP | VMPGVNFLEY | | 219 |
| | | | | | | | |
| SEQ_ID_NO_88 | GDAEALEKIL | KEKGDAIAAF | ILEPIQGEAG | VKIPPDGYLK | AVRDLCSKYN | | 252 |
| SEQ_ID_NO_95 | GDLEAAKKF  | --QSGRVAAV | FVEPVQGEGG | HSATQEFLQ  | GLREACDEAG | | 281 |
| SEQ_ID_NO_90 | GNLEEAKKVI | --QSGKIAAV | FVEPVQGEGG | HSATNEFLQ  | GLRDACDEAG | | 272 |
| SEQ_ID_NO_93 | GNLEEAKKVI | --QSGKIAAV | FVEPVQGEGG | HSATKEFLQ  | GLRDACDEAG | | 280 |
| SEQ_ID_NO_80 | ---------- | ---------- | ---------- | ---------- | ---------- | | 130 |
| SEQ_ID_NO_87 | GNAQAAVELI | --KQGKIAAV | FVEPIQGEGG | YSATKEFLQ  | SLRNACDETG | | 281 |
| SEQ_ID_NO_77 | GNIQAATDLI | --RSGKIAAV | FVEPIQGEGG | YSATKEFLQ  | SLRSACDAAG | | 276 |
| SEQ_ID_NO_92 | GNTDAATDLI | --RSGKIAAV | FVEPIQGEGG | VYSATKEFLQ | SLRSACDAAG | | 267 |
| SEQ_ID_NO_78 | GNIEAATQLI | --QRRKIAAV | FVEPIQGEGG | VYSATKEFLY | ALRKACDDSG | | 267 |
| SEQ_ID_NO_82 | GDVQAATELI | --KSGRIAAV | FVEPIQGEGG | YSATKEFLQ  | SLRSACDDAG | | 267 |

Figure 3 (continued)

| SEQ_ID_NO_88 | VLMIADEIQT GLARTGKMLA CEWEEVRPDV VVLGKALGGG I PVSAVLAD | 302 |
|---|---|---|
| SEQ_ID_NO_95 | ALLVFDEVQC GFGRTGYLWA HEAYGVEPDI MTLAKPLANG - L PIGVVLVK | 330 |
| SEQ_ID_NO_90 | ALLVFDEVQC GLGRTGYLWA HEVYGVLPDI MTLAKPLANG - LPIGVALVT | 321 |
| SEQ_ID_NO_93 | ALLVFDEVQC GLGRTGYLWA YEAYGVLPDI MTLAKPLAGG - LPIGVVLVT | 329 |
| SEQ_ID_NO_80 | -------VQC GLGRTGYLWA HEAYGVFPDM MTLAKPLAGG - LPIGATLVS | 172 |
| SEQ_ID_NO_87 | ALLVFDEVQC GLGRSGFLWA HEAYGVFPDM MTLAKPLAGG - LPIGALLVT | 330 |
| SEQ_ID_NO_77 | SLLVFDEVQC GLGRTGLMWA YEAFGVTPDI MTVAKPLAGG - LPIGAVLVT | 325 |
| SEQ_ID_NO_92 | SLLVFDEVQC GLGRTGNLWA YEAFGVTPDI MTVAKPLAGG - LPIGAVLVT | 316 |
| SEQ_ID_NO_78 | TLLVFDEVQC GLGRTGYLWA HELYDVFPDI MTLAKPLAGG - LPIGAVLVT | 316 |
| SEQ_ID_NO_82 | SLLVFDEVQC GLGRTGYLWA HEAYGVVPDI MTLAKPLAGG - LPIGAALVS | 316 |

| SEQ_ID_NO_88 | KEVMLCIKPG QHGSTFGGNP LASAVAIABL EVIKEERLAE RSTKLGGELL | 352 |
|---|---|---|
| SEQ_ID_NO_95 | EKVAAAINYG DHGTTFGGGP LACQTAITVF DKIMKPGFLA EVSKKGENFK | 380 |
| SEQ_ID_NO_90 | EKVAAAIHYG DHGTTFGGGP FVCHAALATL DKIQKPGFLA EVTKKGEYFK | 371 |
| SEQ_ID_NO_93 | EKVASAINFG DHGTTFGGGP LVCQAALTTL DKIQKPGFLA EVAKKGENFK | 379 |
| SEQ_ID_NO_80 | ERVASAIAHG DHGSTFAGSP FVCSAAICVF NKISNPSFLS SVLKKGDYMK | 222 |
| SEQ_ID_NO_87 | ERVASAINYG DHGSTFAGSP LVCSAALAVL DKISKPDFLS SVSKKGLYFK | 380 |
| SEQ_ID_NO_77 | EKVAETINYG DHGSTFAGSP LVCSAAIAVM DKVSKPSFLS SVSNKGRYFR | 375 |
| SEQ_ID_NO_92 | EKVAETIKYG DHGSTFAGNP LVCSAAIAVF DKVSKSSFLA SVSSKGLYFK | 366 |
| SEQ_ID_NO_78 | ERVASAITYG DHGTTFAGGP LVCKAALTVL DKILRPGFLA SVSKKGHYFK | 366 |
| SEQ_ID_NO_82 | EKVAAAIKYG DHGSTFAGGP LVCNAAIAVL DKISKPGFLA SVSEKGQYFK | 366 |

| SEQ_ID_NO_88 | GLLEKIQKQY PDHVKEVRGR GLFIGVELNS ESLSPVSFFE LSEKLKDRGV | 402 |
|---|---|---|
| SEQ_ID_NO_95 | QLLRTKLSGN P-HVKEVRGV GLLYGIELDI -----VPAGP LVDACLDAGV | 423 |
| SEQ_ID_NO_90 | QLLKTKLGGN P-HVKEIRGA GLIVGIELDI -----VPAGP LVDACLDAGV | 414 |
| SEQ_ID_NO_93 | QLLSTKLSGN A-HVKEIRGI GLIVGIELDI -----VPAGP LVDACLDRGV | 422 |
| SEQ_ID_NO_80 | ELLNQKLGGN P-HVKEIRGW GLMIGIELDI -----VSASP LVDACRNSGL | 265 |
| SEQ_ID_NO_87 | ELLREKLGEN R-HVKEIRGV GLIIGIDLDI -----VPASP LVDACRSSGL | 423 |
| SEQ_ID_NO_77 | DLLVKKLGGN S-YVKEVRGE GLIIGVELDI -----VPASS LVDACRDSGL | 418 |
| SEQ_ID_NO_92 | DLLVKKLGGN L-HVKEVRGE GLIIGVELDI -----VPAGP LVDACRDSGL | 409 |
| SEQ_ID_NO_78 | EMLINKLGGN S-HVREVRGV GLIVGIELDI -----VSASP LVNACLNSGL | 409 |
| SEQ_ID_NO_82 | ELLIHKLGGN S-HVREVRGL GLIIGIELDI -----VSASP LVDACRDSSL | 409 |

Figure 3 (continued)

| | | | | | | |
|---|---|---|---|---|---|---|
| SEQ_ID_NO_88 | LAKST-HDT | RFTPPLCIS | ADEIQQGSKA | LADVLEIDLP | MLKKMKPKDA | 451 |
| SEQ_ID_NO_95 | LVLTAGKGNV | VRLVPPLIIS | EKELEHA--- | -ADVIRDCLP | VLDVAAA--- | 466 |
| SEQ_ID_NO_90 | FLLTAGKGNV | VRLVPALIVS | EKELEQA--- | -AEVIRECLP | ALEASTS--- | 457 |
| SEQ_ID_NO_93 | IVLTAGKGNV | VRLVPPLIIS | EKELEQA--- | -AEVIRDCLP | ALDASTS--- | 465 |
| SEQ_ID_NO_80 | LVLTAGKGNV | VRLVPPLIIS | EEELKHA--- | -AEILHECLP | ALDNSN---- | 307 |
| SEQ_ID_NO_87 | LVLTAGKGNV | VRLVPPLIIT | EKELEQA--- | -AEILCDTLP | VLDN------ | 463 |
| SEQ_ID_NO_77 | LILTAGKGNV | VRIVPPLVIS | EEEIERA--- | -VEIMADNLT | ALD------- | 457 |
| SEQ_ID_NO_92 | LILTAGKGNV | VRIVPPLIIS | EEEIERA--- | -VEIIFHDLT | ALD------- | 448 |
| SEQ_ID_NO_78 | LVLTAGKGNV | VRIVPPLIIT | EQELEKA--- | -AEILLQCLP | ALDRHG---- | 451 |
| SEQ_ID_NO_82 | LILTAGKGNV | VRLVPPLIIS | EQELERA--- | -AEILLECLP | ALDKTS---- | 451 |

| | | | |
|---|---|---|---|
| SEQ_ID_NO_88 | APPAGPSACD | RCGRVVYG | 469 |
| SEQ_ID_NO_95 | ---------- | -------- | 466 |
| SEQ_ID_NO_90 | ---------- | -------- | 457 |
| SEQ_ID_NO_93 | ---------- | -------- | 465 |
| SEQ_ID_NO_80 | ---------- | -------- | 307 |
| SEQ_ID_NO_87 | ---------- | -------- | 463 |
| SEQ_ID_NO_77 | ---------- | -------- | 457 |
| SEQ_ID_NO_92 | ---------- | -------- | 448 |
| SEQ_ID_NO_78 | ---------- | -------- | 451 |
| SEQ_ID_NO_82 | ---------- | -------- | 451 |

Figure 4

```
SEQ_ID_NO_101   -MSETEAAPV VA-------- -----PAAEA APAAEAPK-- AKAPKAKAPK   34
SEQ_ID_NO_102   --MATTEAVE EP-------- ----VPVEAT ANEDAKPTE- EKPAKEKKPK   35
SEQ_ID_NO_150   --MASTDPPA DT------V  PAEPVANEDV KAAEEKP--- VKAPKEKKVK   38
SEQ_ID_NO_118   --MALDTPVS AP-------- -----VVPEV TERKSKRG-- TKAAAVKVPK   32
SEQ_ID_NO_145   --MATTVAIE TP-------- --------AFT PVAVDPPA-- AKPAKAKKAK   31
SEQ_ID_NO_149   --MSAAVAIE TP-------- -----AFAPV PVARDEPV-- AKPGKVTKAK   33
SEQ_ID_NO_144   --MATDETTD PR-------- ---------- ------PV-- AKSKKAKAPK   22
SEQ_ID_NO_125   --MSTDVAAD VP----APEV EVAADPVVET TAEAAAGD-- AKPAKETKAK   42
SEQ_ID_NO_137   --MATEVAET PA-------- ---PLAEAVP ETPAEAPA-- APAAEANST-   34
SEQ_ID_NO_146   --MATDVAAT EP-------- -----EVAAE EAAAAAPETT ATAGDSKPAK   35
SEQ_ID_NO_147   --MATDVAAT EP-------- -----EVAAE EAAAAAPETT ATAGDSKPAK   35
SEQ_ID_NO_119   -MAAVEDPIV PM-----EGV EEEYPVTVTE APEEAAPP-- AEDPAPKKGK   42
SEQ_ID_NO_100   --MSIEEENV PT------T  VDSGAADTTV KSPEKKPA-- AKGGKSKKTT   39
SEQ_ID_NO_113   --MSTEEETK VV-------- --VESGDAEA TVTEKKPA-- AKGGAKAKKT   36
SEQ_ID_NO_104   --MATEEPAV VA-------- -DPAPETEED KTAETKAT-- SKSGRAKKTK   37
SEQ_ID_NO_108   --MSSDEPTV AV-------- -DGSTEPTSA EPADDKPA-- AKPSRAKKTK   37
SEQ_ID_NO_116   MTSSVEEPTV SAVEQTIVEE PAAVDPLPPV VNESDEPT-- AAKPKL----   43
SEQ_ID_NO_117   --MASEEPTT VAVEQPIVEE PEAVDTFPPV VNESEEPT-- AKPKKAPK-   44
SEQ_ID_NO_122   --MATEEPLV VT-----EIV TEAVVVEAEP AKEENSPA-- AEPDEPKKEK   41
SEQ_ID_NO_120   --MATEEPVI VN------E  VVEEQAAPET VKDEANPP-- AKSGKAKKET   39

SEQ_ID_NO_101   QPKAPKAPKE PKAPKEKKPK AAPTHPPYI  E MVKDAITTLK ERNGSSLPAL   84
SEQ_ID_NO_102   TP----KEKK PRAAKGS--K PPAHPPYVQ  MIAEAITALK ERGGSSPYAI   79
SEQ_ID_NO_150   TP----KEKK PKAAKGS--K PPPAHPPYFQ MISEAIVALK ERGGSSPYAI   82
SEQ_ID_NO_118   ------EKKK VIAAKKPKSK GTSSHPSFFE MISDAISTLK ERTGSSQYAI   76
SEQ_ID_NO_145   VP----KEKK ASVAKL---- -PALHPTYLE MISEAIASLK ERTGSSQIAI   71
SEQ_ID_NO_149   AP----KEKK ASVAKKP--- --ALHPTYLE MISEAIASLK ERTGSSQYAI   74
SEQ_ID_NO_144   EA----RAKK AAAPRKP--- --SAHPPYAE MIKEAITTLK ERTGSSPYAI   63
SEQ_ID_NO_125   AA----KAKK PSAPRKP--R ATPAHPTYAE MVSEAITALK ERTGSSQYAI   86
SEQ_ID_NO_137   ------KAKK ASAPKK---R ANPTHPPYAE MISEAVTSLK ERTGSSQYAI   75
SEQ_ID_NO_146   EA----KAKK AAAPRKA--R STATHPPYAE MISEAIATLK ERTGSSQYAI   79
SEQ_ID_NO_147   EA----KAKK AAAPRKA--R STATHPPYAE MISEAIATLK ERTGSSQYAI   79
SEQ_ID_NO_119   EL----KPKK AAAPRKP--R SAPAHPPYLE MITDAITSLK ERTGSSQAI    86
SEQ_ID_NO_100   TAKATKKPVK AAAPTKK--K TTSSHPTYEE MIKDAIVTLK ERTGSSQYAI   87
SEQ_ID_NO_113   PA----KKKP AAAPRK---R TTSSHPYEE  MIKDAIVTLK ERTGSSQYAI   79
SEQ_ID_NO_104   EP----KTKK AAAPRKP--R AAPTHPPYEE MIKDAIVTLK ERTGSSQYAI   81
SEQ_ID_NO_108   EP----KAKK APAPKKPRHR TPSSHPPYEE MIKDAIVTLK ERTGSSQYAI   83
SEQ_ID_NO_116   -----KAPK  EPKPRKPASK NTRTHPTYEE MVTDAIVTLK EKNGSSQYAL   87
SEQ_ID_NO_117   ------EPKA KKAPAKP--- -RTHPTYEE  MVKEAIVALK ERNGSSQYAI   83
SEQ_ID_NO_122   EI----EAKK PAAPRK---R NPPTHPSYFE MIKDAIVTLK DKTGSSQHAI   84
SEQ_ID_NO_120   ------KAKK PAAPRKR--S ATPTHPPYFE MIKDAIVTLK ERTGSSQHAI   81
```

Figure 4 (continued)

| SEQ_ID | Sequence | | | | | | Pos |
|---|---|---|---|---|---|---|---|
| SEQ_ID_NO_101 | KKFIENKYGK | DIHDKNFAKT | LSQVVKTFVK | GGKLVKVKGS | FKLSE | ---- | 129 |
| SEQ_ID_NO_102 | AKFLGDKYK | ADLPPNFKKQ | LNVQLKNLTK | SGKLTKVKAS | YKLTA | ---- | 123 |
| SEQ_ID_NO_150 | AKFLSEKYK | SDLPPVFKKK | LNVQLRNLTN | SGKLTKVKGS | YKLAE | ---- | 126 |
| SEQ_ID_NO_118 | NKFVEDKHK | Q-LPSNFRKL | LLFHLKKLVA | SGKLVKVKNS | FKLPS | ---- | 119 |
| SEQ_ID_NO_145 | SKFVENKHK | AHLPANFKKL | LLVQLRKLTA | AGKLTKVKNS | YKISA | ---- | 115 |
| SEQ_ID_NO_149 | AKFVEDKHK | SHLPANFKKL | LLVQLQKLTA | AGKLTKVKNS | YKISA | ---- | 118 |
| SEQ_ID_NO_144 | GKFIEDKHK | AHLPSNFRKI | LFLQLKKLAA | AGKLTKVKSS | YKLST | ---- | 107 |
| SEQ_ID_NO_125 | AKFVEDKHK | AHLPANFRKI | LSVQLKKLVA | SGKLTKVKAS | YKLSA | ---- | 130 |
| SEQ_ID_NO_137 | AKFVEDKHK | DKLPPNFRKL | LLGQLKKLVA | AGKLTKVKNS | YKLPA | ---- | 119 |
| SEQ_ID_NO_146 | GKFLEDKHK | DHLPSNFRKQ | LLVQIKKLVA | AGKLTKVKNS | YKLPP | ---- | 123 |
| SEQ_ID_NO_147 | GKFLEDKHK | DHLPSNFRKQ | LLVQIKKLVA | AGKLTKVKNS | YKLPP | ---- | 123 |
| SEQ_ID_NO_119 | QKFLEAKHK | D-LPAVFRKM | LSNNLKKLVA | AGKLVKVKAS | YKLPS | ---- | 129 |
| SEQ_ID_NO_100 | QKFIEEKHK | SLPPTFRKL | LLVNLKRLVA | SEKLVKVKAS | FKIPS | ---A- | 131 |
| SEQ_ID_NO_113 | QKFIEEKQ-K | SLPPTFRKL | LLVNLRRLVA | SGKLVKVKAS | FKIPS | ---- | 122 |
| SEQ_ID_NO_104 | AKFIEEKQ-K | N-LPGNFKKL | LLVHLKKLVA | AGKLVKVKAS | YKLPS | ---A- | 125 |
| SEQ_ID_NO_108 | TKFLEEKHK | Q-LPSNFKKL | LLFHLKKLVL | SDKIVKVKGS | FKLPS | ---- | 126 |
| SEQ_ID_NO_116 | AKFIEEKHK | N-LPANFKKI | LLVQIKKLVA | SGKLVKVKGS | YKLPA | --KS | 132 |
| SEQ_ID_NO_117 | AKFIEEKHK | Q-LPSNFKKL | LLYQIRKLVA | SGKLVKVKAS | YKLPA | ---- | 126 |
| SEQ_ID_NO_122 | TKFIEDKQ-K | N-LPSNFRKL | LLVQLKKLVA | SGKLVKVKSS | YKLPA | -AR- | 129 |
| SEQ_ID_NO_120 | TKFIEEKQ-K | SLPSNFKKL | LLTQLKKFVA | SEKLVKVKNS | YKLPS | GSKP- | 128 |

| SEQ_ID | Sequence | | | | | | Pos |
|---|---|---|---|---|---|---|---|
| SEQ_ID_NO_101 | ---ALKAKAK | KSTPKK-AKA | DG----EAKP | KK-SE-AKPK | ----KAEAVK | | 165 |
| SEQ_ID_NO_102 | -----PKAPA | APKPKK-EKK | TVAKKKAPKP | KV-PA-AKPK | -APAAKAAKP | | 164 |
| SEQ_ID_NO_150 | ----KEKKAD | APKPKT-EKK | PA----AKKP | KA-PA-AKAP | -AKAPSKAS | | 163 |
| SEQ_ID_NO_118 | --------ARA | APAPAL-AKK | PT----IPKP | KV-------- | --AAKPKTAK | | 147 |
| SEQ_ID_NO_145 | ----KPTTAT | KPKKTS-AKS | TT----VAKP | KS-AA-AKPK | --STAAKVKK | | 152 |
| SEQ_ID_NO_149 | ----KPTPAA | KPKSA----- | ------AVKP | KS-AA-TKLK | -SAAKKVKK | | 149 |
| SEQ_ID_NO_144 | ---IVHAAPA | EPKS------ | ------AAGP | KK-PA-AVQT | --KLKAKAKP | | 138 |
| SEQ_ID_NO_125 | --------AAA | KPKP------ | ------AAKK | KPAAK-KKAP | --AKKTATKT | | 158 |
| SEQ_ID_NO_137 | ----RAPAAA | KPKPKS-KTA | ------VKKP | KA-------- | --GAKKPKAA | | 148 |
| SEQ_ID_NO_146 | ---TRAPAAA | KPKAKP-AAA | A----KPKP | KPKAA-AKPK | --AAAKPKAK | | 161 |
| SEQ_ID_NO_147 | ---TRAPAAA | KPKAKP-AAA | A----KPKP | KPKAA-AKPK | --AAAKPKAK | | 161 |
| SEQ_ID_NO_119 | -AKSSAPAKK | KPAAAP-AKK | KA----AAAP | AKKKT-AAAP | --KKKAAAAP | | 170 |
| SEQ_ID_NO_100 | -RSAATPKPA | APVKKK-ATV | VA----KPKG | KV-AA-AVAP | --AKAKAAAK | | 171 |
| SEQ_ID_NO_113 | --AAKPAATT | KPVNKK-PAA | A-----VTKP | KG----KAP | --AKAKPAAK | | 157 |
| SEQ_ID_NO_104 | -RSSKTATAA | SAPAKK-KTA | TT----KSKS | KP--A-SKPK | --EGKSTKAT | | 164 |
| SEQ_ID_NO_108 | ---AKSSAPA | KPAASPAKK | KTATAAKPKA | KSKPAYSKAK | ETKSAKSTAK | | 173 |
| SEQ_ID_NO_116 | AAPAKKPAAA | KPKPKPKAKA | PVAKAPAAKS | KAKAA-PAKA | KAKAKAKAAP | | 181 |
| SEQ_ID_NO_117 | -KSSAAKPAK | KPAAAK-SKA | KPKAKAATKS | KAKPA-AKAK | --PAAKAKPA | | 171 |
| SEQ_ID_NO_122 | -SAAPKAAAT | APAKKK-PGA | KPKAT-KAKP | KPKPK-TVAP | --KAKTATKP | | 173 |
| SEQ_ID_NO_120 | -AAAAVPAKK | KPAAAK-SKP | AAKPKAAVKP | KAKPA-AKAK | --PAAKAKPA | | 173 |

Figure 4 (continued)

| SEQ_ID_NO_101 | KTKAPKEKVE | RPKKEKKEKV | EKKKATPKAE | KPKK----AA | TPKSAGKKK- | 210 |
|---|---|---|---|---|---|---|
| SEQ_ID_NO_102 | KAAKKAAPAK | PAAPAPP--- | ------KKEE | KPAA-AA-PK | KAAPAAKPKK | 203 |
| SEQ_ID_NO_150 | KPAAPKKAEK | PVAPKK---A | AAPKKAAKPA | APKAAAPKAK | KPAAAAKPL- | 208 |
| SEQ_ID_NO_118 | IGAKPKAKAK | VAAKTKA--T | TKTVA----- | ---------- | KKIPAAKPKA | 180 |
| SEQ_ID_NO_145 | A--------- | ---------A | VKPKPKSAAV | KPKAEPA-AP | KPKAVSKPKA | 183 |
| SEQ_ID_NO_149 | AAVKPKPKSA | ---------A | VKPKAPAVNM | KSKP-A-AL | KPNTVTKSKT | 187 |
| SEQ_ID_NO_144 | AAAASKTKAK | IATTAKA--K | SKHVASTVKP | KPKA-A-AA | KPRVAPKRKS | 183 |
| SEQ_ID_NO_125 | KAKAPAKKAL | ---------A | AKPKA-KAPA | KPKA----AA | KPKAAAKPKA | 193 |
| SEQ_ID_NO_137 | TKPKPKAKAK | SPAKAKP--A | AKPKA-AAKP | KPAA-----A | KPKAAAKPKA | 190 |
| SEQ_ID_NO_146 | APAKSKAAAK | PKAAAKP--A | AKPKAAAKPK | SPAK--P-AA | KPKAAPKAKA | 206 |
| SEQ_ID_NO_147 | APAKSKAAAK | PKAAAKP--A | AKPKAAAKPK | SPAK--P-AA | KPKAAPKAKA | 206 |
| SEQ_ID_NO_119 | KKKAPVAKAK | PAAKPKAKAV | VKPKA-KAAV | KPKA-KP-AA | KPAAKAKPA- | 216 |
| SEQ_ID_NO_100 | GTKKPAAKVV | AKAKV----T | AKPKAKVTAA | KPKS-----K | SVAAVSKTKA | 212 |
| SEQ_ID_NO_113 | GAKKPAAAAK | PKAKT----T | ATTKA-AAKP | KPKT-----K | SVAAVSKTKA | 197 |
| SEQ_ID_NO_104 | PKAKAKTKTT | SKAKSKP--A | AKPKA---TS | KAKAAPA-KT | KAVASVKPKT | 208 |
| SEQ_ID_NO_108 | SPAKSKAAAK | PKAKPKAA-A | AKPKV-TAKA | KPKA-AP-AK | AKTSVAKPKA | 219 |
| SEQ_ID_NO_116 | AKAKPAAKAK | PAAKAKP--A | AKAKP-VAKA | KPKAKAP-VA | KANAVPVA-- | 225 |
| SEQ_ID_NO_117 | AKAKPAAKAK | PAAKAKP--A | AKAKPAAKPV | KTAAAKP-AA | KAKPAAKPKA | 218 |
| SEQ_ID_NO_122 | KAKQRQVKAK | LVAKAKP--A | VKPKA----- | ------AA-VA | MPKAAEKPKL | 209 |
| SEQ_ID_NO_120 | AKAKPAAKAK | PAAKAKP--A | AKAKP-VAKA | KPKA-AA-AA | KPKAAVKPKA | 218 |

| SEQ_ID_NO_101 | -ATPKPKAAP | ---------- | ---------K | SPAKKDAKPK | KATPSKKAAP | 240 |
|---|---|---|---|---|---|---|
| SEQ_ID_NO_102 | -PAAKPKKAA | ---------- | ---------- | ---TPKKPAP | KPKPAKKAAT | 229 |
| SEQ_ID_NO_150 | -AAPKRSST- | ---------- | ---------- | ---RTAAKPA | APKAAKKPTP | 233 |
| SEQ_ID_NO_118 | KTAGKPKTVA | ---------- | ---------A | KPAKVAKTAA | VASPGKKKAV | 211 |
| SEQ_ID_NO_145 | -VAPKPKTAG | ---------- | ---------- | -PAKKAKTSA | KPSPSKKAAP | 211 |
| SEQ_ID_NO_149 | -VALKGKTAG | ---------- | ---------- | RPAKAAKTSV | KAAPGKKAAP | 216 |
| SEQ_ID_NO_144 | PVKPKPKPKP | ---------- | ---------- | RPTRAAKTAA | KDSPGKKAAK | 213 |
| SEQ_ID_NO_125 | KAAAKPKAAA | ---------- | -----KPKG | RPAKAAKTSA | KDAPGKKAPA | 227 |
| SEQ_ID_NO_137 | KPAAKAKPKA | ------VAA | KPKPAAKKAG | RPAKAAKTSA | KDTPGKKAAP | 233 |
| SEQ_ID_NO_146 | KPAAKPKAKA | APKPKAAVVT | KTKATSAPAR | RPAKAAKTSA | KDTPSKKAAP | 256 |
| SEQ_ID_NO_147 | KPAAKPKAKA | APKPKAAAVT | KTKATSAPAR | RPAKAAKTSA | KDTPSKKAAP | 256 |
| SEQ_ID_NO_119 | -AKAKPAAKP | ---------- | KAK-----A | KPAKVARTST | RTTPGKKAPA | 249 |
| SEQ_ID_NO_100 | -VAAKPKAKE | ---------- | ---------- | RPAKASRTST | RTSPGKKVAA | 241 |
| SEQ_ID_NO_113 | -VAAKPKAKE | ---------- | ---------- | RPVKASRTST | RTSPGKKAAA | 226 |
| SEQ_ID_NO_104 | TAATKPKAAA | ---------- | KPK-----D | KPVKASRTST | RTSPGKRAAA | 242 |
| SEQ_ID_NO_108 | -APAKPKAKE | ---------- | ---------- | RPAKASRTST | RTSPGKKAAA | 248 |
| SEQ_ID_NO_116 | -AKAKPAAKA | ---------- | KPAAKAKPAA | RPAKASRTST | RTSPGKRAAA | 264 |
| SEQ_ID_NO_117 | AAKAKPAAKA | ---------- | KPAAKAKPAA | KPAKAARTST | RTSPAAAAAA | 258 |
| SEQ_ID_NO_122 | -TPVKTKAAA | ---------- | KP--KAK--E | KPAKVARTAT | RSTPSRKAAP | 244 |
| SEQ_ID_NO_120 | -APAKTKAAV | ---------- | KPNLKAK--T | TTAKVAKTAT | RTTPSRKAAP | 255 |

Figure 4 (continued)

| | | | | | |
|---|---|---|---|---|---|
| SEQ_ID_NO_101 | - - KKAPAKKS | T- PKAKEA- - | - - - - - - - - - - - - - - | - - - - - - - - - - | - - - - KP- - | 255 |
| SEQ_ID_NO_102 | - - - - - - - - - - - - PKKKAG- - | - - - - - - - - - - - - - - | - - - - - - - - - - | - - - - RP- - | 237 |
| SEQ_ID_NO_150 | - - - - - - - - - - - - - - - - KKAG- - | - - - - - - - - - - - - - - | - - - - - - - - - - | - - - - GA- - - | 239 |
| SEQ_ID_NO_118 | - - - - - PVKKV | K- TVKSPA- - | - - - - - - - - - - - - - - | - - - - - - - - - - | - - - - - - - - - - | 223 |
| SEQ_ID_NO_145 | - - - - VASKKA | K- PVKKATA- | - - - - - - - - - - - - - - | - - - - - - - - - - | - - - - - - - - - - | 225 |
| SEQ_ID_NO_149 | - - - - VALKKA | K- AGKKVTT- | - - - - - - - - - - - - - - | - - - - - - - - - - | - - - - - - - - - - | 230 |
| SEQ_ID_NO_144 | - - - - RSSSRS | A- PTKKPK- - | - - - - - - - - - - - - - - | - - - - - - - - - - | - - - - PAVKKA | 232 |
| SEQ_ID_NO_125 | - - - - AAAPKK | A- AARKPPT- | - - - - - - - - - - | KRSTPVKKAA | PAKKAAPAKK | 261 |
| SEQ_ID_NO_137 | - - - - - AKKPA | A- AAKKAPA- | - - - - - - - - - - | KKAAPAKKA- | - - - - PTPSRK | 261 |
| SEQ_ID_NO_146 | - - - - AAKKPA | A- AAKKAPA- | - - - - - - - - - - | KKAAPAKKA- | - - - - AAPARK | 285 |
| SEQ_ID_NO_147 | - - - - AAKKPA | A- AAKKAPA- | - - - - - - - - - - | KKAAPAKKA- | - - - - AAPARK | 285 |
| SEQ_ID_NO_119 | KPAAAPVKKA | T- PVKKATAT | PVKKAAPVKK | AAPAKGKSV- | - - - - KTPVKR | 293 |
| SEQ_ID_NO_100 | - - - - - PAKKV | A- VTKKAP- - | - - - - - - - - - - - - - - | - - - AKSAKV- | - - - - KSPAKR | 265 |
| SEQ_ID_NO_113 | - - - - PAKKAA | AAATKKAP- - | - - - - - - - - - - - - - - | - - - AKSVKV- | - - - - KSPAKR | 252 |
| SEQ_ID_NO_104 | - - PKPAAKKA | P- AAKKAP- - | - - - - - - - - - - - - - - | AKSVKPKSV- | - - - - KSPAKK | 272 |
| SEQ_ID_NO_108 | - - TKVAPKKA | A- TPKKAP- - | - - - - - - - - - - - - - - | AKTVKLKSV- | - - - - KTPTKK | 278 |
| SEQ_ID_NO_116 | - - AKPAVKKA | ATPVKKAVPA | - - - - - - - - - - | KKAATPVKK- | - - - - AAPARK | 297 |
| SEQ_ID_NO_117 | - - PKPAAKKA | A- PVKKTPV- | - - - - - - - - - - | KAAAKAKTA- | - - - - KSPAKK | 289 |
| SEQ_ID_NO_122 | - - - KPVAKKV | P- VKKAAPA- | - - - - - - - - - - | AKSVKAKTA- | - - - - KSPAKR | 274 |
| SEQ_ID_NO_120 | - - KATPAKKE | - - PVKKAP- - | - - - - - - - - - - - - - - | - - - - - AKNV- | - - - - KSPAKK | 279 |

| | | |
|---|---|---|
| SEQ_ID_NO_101 | - - - KSKGKK | 261 |
| SEQ_ID_NO_102 | - - - AKKAKK | 243 |
| SEQ_ID_NO_150 | - - - AKKAKK | 245 |
| SEQ_ID_NO_118 | - - - GKRTRK | 229 |
| SEQ_ID_NO_145 | - - - PKKAKK | 231 |
| SEQ_ID_NO_149 | - - - PKKAKK | 236 |
| SEQ_ID_NO_144 | AAAAKKAKK | 241 |
| SEQ_ID_NO_125 | APAAKKAKK | 270 |
| SEQ_ID_NO_137 | VP- SRKAKK | 269 |
| SEQ_ID_NO_146 | VP- ARKAKK | 293 |
| SEQ_ID_NO_147 | VP- ARKAKK | 293 |
| SEQ_ID_NO_119 | TSARKAGKK | 302 |
| SEQ_ID_NO_100 | AS- TRKAKK | 273 |
| SEQ_ID_NO_113 | ASTRKK- - - | 258 |
| SEQ_ID_NO_104 | AT- SRRGKK | 280 |
| SEQ_ID_NO_108 | AA- VKKGKK | 286 |
| SEQ_ID_NO_116 | APAKRGGRK | 306 |
| SEQ_ID_NO_117 | AA- AKRGKK | 297 |
| SEQ_ID_NO_122 | AS- ARKGRK | 282 |
| SEQ_ID_NO_120 | AT- PKRGRK | 287 |

Figure 5

| | | | | | | | | |
|---|---|---|---|---|---|---|---|---|
| SEQ_ID_NO_164 | MENM----- | KMNNDERFA- | ------QKGV | PVHSQVMKIK | QESEKIVDWS | | | 37 |
| SEQ_ID_NO_158 | MENN----- | SSNDDSRGRN | GDGDHGYVGF | PIHSQVIKIR | QEFDKIKHPS | | | 44 |
| SEQ_ID_NO_154 | MEQKKISSSS | SSNNNAVIRD | EDE---YKGV | PIHSQVMKIK | QEFEKIKHPS | | | 47 |
| SEQ_ID_NO_152 | MENK----- | TDNGN----- | ------EDGP | IIHSQVEKIK | KEFEKIRQPS | | | 33 |
| SEQ_ID_NO_162 | MENK----- | TNNGN----- | ------EDG- | PKHSQVVKIK | REFEKISQPS | | | 32 |

| | | | | | | |
|---|---|---|---|---|---|---|
| SEQ_ID_NO_164 | PGKPEIRSVL | REISFRQLSR | SPLGISGDPI | SVGES | 71 |
| SEQ_ID_NO_158 | LQQLEVRGVV | KCRINRQRSR | SPLGLAERPI | SVGN- | 78 |
| SEQ_ID_NO_154 | LQQPDMRRVL | REITFRQRSR | SPLGLAERPI | SVGNS | 81 |
| SEQ_ID_NO_152 | LQQPEMRRVL | SEIKRRQRSR | SPLGLGERSI | SVGN- | 67 |
| SEQ_ID_NO_162 | LKQPEMRRVL | SEITRRQRSR | SPLGLGERSI | SVGH- | 66 |

Figure 6

| | | |
|---|---|---|
| SEQ_ID_NO_184 | ......... ......... .......MG L....... ......... | 3 |
| SEQ_ID_NO_168 | ......... ......... .......MS SPTQVLQG LLGEFHSRRL | 22 |
| SEQ_ID_NO_177 | ......... ......... .......ME YPRRTLLH-- ......... | 10 |
| SEQ_ID_NO_181 | ......... ......... .......MG TPLRMPHMST CSNVAPAP-- | 20 |
| SEQ_ID_NO_182 | ......... ......... .......MA MSPHDQHEHE PDHAHRSP-- | 20 |
| SEQ_ID_NO_183 | ......... ......... .......MA MSPHDQHEHE PDHAHRSP-- | 20 |
| SEQ_ID_NO_170 | ......... ......... .......MR PAPLEAEAAA ANISHLSP-- | 20 |
| SEQ_ID_NO_166 | ......... ......... .......MR LLVAEAA--- ......... | 9 |
| SEQ_ID_NO_174 | MWMMISQEGQ RSNPIIYHNN IHLLCEVDQK REKASVIVLK IQTKHPNPES | 50 |

| | | | | | |
|---|---|---|---|---|---|
| SEQ_ID_NO_184 | -----SSLP | GPSEGMLCVI | LVN------ | TALSISFKG | VRSVLHVLG | 40 |
| SEQ_ID_NO_168 | LLTP--TTAS | PPSSEHHNS | SDLYTRNNSF | DANIVMVLSV | LLCALICSLG | 70 |
| SEQ_ID_NO_177 | --TPFSGHPS | GPSQPIDGAT | A---TDGSNF | DANVVMILAV | LLCALICALG | 55 |
| SEQ_ID_NO_181 | --APEAPRAP | PSSP------ | ---------L | DYDVVVILAA | MLCALVCALG | 53 |
| SEQ_ID_NO_182 | ------SNGT | AATSTIATNR | NGPYSGAGDF | ASNMAVILAA | LLAALALALA | 64 |
| SEQ_ID_NO_183 | ------SNGT | AATSTIATNR | NGPYSGAGDF | ASNMAVILAA | LLAALALALA | 64 |
| SEQ_ID_NO_170 | --PPLHSRAP | SCDPQVHSCK | WAPYSNSNDF | GANTAMILII | LLCALICALV | 68 |
| SEQ_ID_NO_166 | --SPLSSFAA | TPTCNSHTCR | MKPYSNSTDF | TANASVLLIL | VISALICALS | 56 |
| SEQ_ID_NO_174 | FKTSLEP-SP | PLSPHSLCIR | MKPYSNSSEF | QANASVLLIL | FVSALICSLS | 99 |

| | | | | | |
|---|---|---|---|---|---|
| SEQ_ID_NO_184 | IRLSQSSSSP | SSVTASSEIP | ASEPFDFRVS | HPESFLEEFR | NKIPTLRYES | 90 |
| SEQ_ID_NO_168 | LNSIIRCALR | CSSLIASESG | ATTSSRLANK | ---GNKRKAL | KTFPTVNYS- | 116 |
| SEQ_ID_NO_177 | LNSIVRCALR | CSSRVVGPE | PNQVTRLVQS | ---GLRRKAL | RAMPVLVYS- | 101 |
| SEQ_ID_NO_181 | LNSMLOCVVR | CTRRAVADPV | GWAHRRASA | ---SLKREDV | VALPVVTYS- | 99 |
| SEQ_ID_NO_182 | LNAAVRYLLR | RHRRARQQPA | AAAAAAEDPE | KPPVQEADPP | PPPPALVYSA | 114 |
| SEQ_ID_NO_183 | LNAAVRYLLR | RHRRARQQPA | AAAAAAEDPE | KPPVQEADPP | PPPPALVYSA | 114 |
| SEQ_ID_NO_170 | LNTAIRMFLR | SNNNSSDRL | GELEEQRKPK | --DEADMATL | VLATTQVYS- | 115 |
| SEQ_ID_NO_166 | LYAAIRCFLR | -------PT | LETEDDHKPD | --PEAAASST | PTTPTLVYS- | 95 |
| SEQ_ID_NO_174 | LCAAIRCFLR | PN-----L | QTDDNEHKPD | --PEEDVSST | VPTPTLVYS- | 139 |

| | | | | | |
|---|---|---|---|---|---|
| SEQ_ID_NO_184 | LCRCKKHEDN | ECSVCLSKFE | EDSEINKLK- | -C----GHL | FHKTCLEKW- | 132 |
| SEQ_ID_NO_168 | ADLKLPGLDS | ECIICLSDFT | AGDRVRLLPK | -C----NHG | FHVRCIDKW- | 159 |
| SEQ_ID_NO_177 | PGLRINAANP | TCAICLSDFE | AGEHVRVLPK | -C----NHG | FHVRCIDRW- | 144 |
| SEQ_ID_NO_181 | -ASPPAAAAA | GCAICLSDFA | DGERMRVLPV | -C----GHR | FHVVCIDRW- | 141 |
| SEQ_ID_NO_182 | AGTKLAGA-A | ECAICLAEFV | DGDTVRVMPC | WCQEIPLESG | LRFAQIKVYQ | 163 |
| SEQ_ID_NO_183 | AGTKLAGA-A | ECAICLAEFV | DGDTVRVMPV | -C----GHG | FHARCIERW- | 156 |
| SEQ_ID_NO_170 | AGMKLGGVEA | DCAICLSEFV | EGEGRVLGR | -C----DHG | FHVLCIEKW- | 158 |
| SEQ_ID_NO_166 | SDLELAGAEA | ECAICLSEFE | QGESIQVLEK | -C----QHG | FHVKCIHKW- | 138 |
| SEQ_ID_NO_174 | SDLELAGAQA | ECAICLSEFE | PGESIHVLEK | -C----HHG | FHIKCIHKW- | 182 |

Figure 6 (continued)

```
SEQ_ID_NO_184              ........... .I- DYWN TC PL CRT- PLVV ........... ........V    150
SEQ_ID_NO_168              ........... .L- SAHSSC PKCRH- CLVD TCDKI VGCI- --QASSSEPP    192
SEQ_ID_NO_177              ........... .L- LARSTC PTCRD- SLFG VPQKASGCSE ASRAAEPEPA    180
SEQ_ID_NO_181              ........... .L- ASHKSC PTCRR- RLSS ........... ........ES   159
SEQ_ID_NO_182              TGPFNVEAAN LL- PTPGIC TTCRF- VYRG VVKHLHFL-- --YGDWRD L      206
SEQ_ID_NO_183              ........... .LAGGRRSSC PTCRA- PAAT ........... ........PP   176
SEQ_ID_NO_170              ........... .L- SSHSSC PTCRRSCLAS SPSSPEPDNC SAGNGHDSNS     195
SEQ_ID_NO_166              ........... .L- STRSSC PTCRT SIFS ........... ........     154
SEQ_ID_NO_174              ........... .I- SSRSSC PTCRT- SIFS ........ --QNTLDSAT      206

SEQ_ID_NO_184              AAAEDQKQLS SNVW- ..... ....    164
SEQ_ID_NO_168              PVQETILSII TPVDREGFIH SYR-     215
SEQ_ID_NO_177              PAPAPARSVL VPLRPEGLVT HYDF     204
SEQ_ID_NO_181              GGGHRHLQVL TAV- ...... ....    172
SEQ_ID_NO_182              ACFVKGKKNT NS- ....... ....    218
SEQ_ID_NO_183              GATATEPAAV APL- ...... ....    188
SEQ_ID_NO_170              SQSAEPERAA DNLSTNGNIP V---     216
SEQ_ID_NO_166              QHSETPSSHI NA- ....... ....    166
SEQ_ID_NO_174              SAVAPSTNEL NA- ....... ....    218
```

Figure 7

```
SEQ_ID_NO_194    MLKSKSCREE MRSSS AYK  YHCLTNGGTP EAVAAPSPTN PQLPVMLRSY   49
SEQ_ID_NO_199    -MAAADYDRA YRFYAPSSAA DYDRPYRNE- ---------- ------VPY    32
SEQ_ID_NO_204    -MAAADADYE YRAYG-APA- DHDRPYHG-- ---------- RE---VVPY    31
SEQ_ID_NO_186    ---MANYYE- -PPAS-GNRR DAVKGYNS-- -G-------- --------SF   25
SEQ_ID_NO_201    ---MD--RS- -KSYA-GGR  MQIEPYYD-- -G----GGAR PD---FRSY    30
SEQ_ID_NO_203    ---MDDFRS- -RSFN-DGK  MQLEVYGSRR SGAVPAPPVL HD---YRSY    39
SEQ_ID_NO_188    ---MEHFRS- -KSCR-EGR- IEMEGYDEDK AA----PTNM QD---LRSY    35
SEQ_ID_NO_196    ---MEEFRS- -KSYG-DGR- MQIEAYRG-- -------ANI QD---LRCY    30
SEQ_ID_NO_197    ---MEDYNKQ IRPYG-NSCM MQMEGYYG-- -A----TNPN YD---LRSY    35
SEQ_ID_NO_193    ---MEDYNRQ -RAYG-DTG- MQIQPYHG-- -G----GPGT GD---FRKY    33

SEQ_ID_NO_194    S-------- TSTYS----- ---------- ----PHKNPT TVRDNPNS-K   70
SEQ_ID_NO_199    G-------- DRRIDLVVKP PPP------- ----TRSPPP PLPVTKSG--   60
SEQ_ID_NO_204    G-------- DRRIDVVVKP PGTTTTTT-- ----TRSPPP PLPVTKVG-G   65
SEQ_ID_NO_186    D-------- DSSGDQSQ-- ---------- ----TNDYQL KIKKSKSVPN   50
SEQ_ID_NO_201    SYSAGGSGMG TSSYAYQYEY S--------- ----GAGAGE EMKRSKS---  64
SEQ_ID_NO_203    S-------- -ASYFYTYD- ---------- ----GSGVGY GDFKGKPDHG   64
SEQ_ID_NO_188    S-------- -VSYAVSVQP N--------- ----QSGKEG KMKKDKSN--   60
SEQ_ID_NO_196    S-------- -ASYASSVHP TTTTTTTTQT QMGGNNNNEA KFKKGKST--   68
SEQ_ID_NO_197    S-------- DFSYAQTQRG ---------- ----PNNKDL KLKKGKS-S    61
SEQ_ID_NO_193    S-------- -TSYA----- ---------- ----TENNIX NIKKEKS---   52

SEQ_ID_NO_194    SNGKVKKGL- --KEAEIQRK KRVAAYNVYG VEGKVKGSIR KNFKWEKETC   117
SEQ_ID_NO_199    GGGGIGSAWC F-SDPEVKRR RRVASYKAYS VEGKVKASFR RGFRWKDKC    109
SEQ_ID_NO_204    GGGGMGSAWC F-SDPEMKRR RRVASYKAYS VEGKVKSSLR RGFRWKAKC    114
SEQ_ID_NO_186    ADRAASRSWS F-SDPESRRK RRVAGYKVYS VEDKMKGSIR KSFKWFKD--   97
SEQ_ID_NO_201    -----KRRML ALADPDMERK RRVAAYKAVG VEGKMKGSFR KSFKWKDRY    109
SEQ_ID_NO_203    SSASNKGGRV F-KDPEFQRK RRVASYKAYA VEGKVKGSLR RSLRWFKDKY   113
SEQ_ID_NO_188    -LESSSKSWS F-NDPELQRK RRVANYKVYA IEGKMKGSLR KSFRWKDTC    108
SEQ_ID_NO_196    -NGSTSKSWS F-SDPELQRK KRVASYKVYA VEGKLKGSLR KSFKWLKDRC   116
SEQ_ID_NO_197    SRSSISKSWG FGDDPEFQRK KRVASYKMYS VEGKVKGSFR KSFKWLKNRY   111
SEQ_ID_NO_193    ---ARSKSWG I-TDPELQRK KRVASYKMYS VEGKVKGSFR KSFRWLKQRY   98
```

Figure 7 (continued)

| | | | |
|---|---|---|---|
| SEQ_ID_NO_194 | SNAVNGLW | | 125 |
| SEQ_ID_NO_199 | TGF HG | | 115 |
| SEQ_ID_NO_204 | SELIHGWYGS LLLPLSFSLD DFIITSKQAL S | | 145 |
| SEQ_ID_NO_186 | ---IGLS | | 102 |
| SEQ_ID_NO_201 | LNLVYGWS | | 117 |
| SEQ_ID_NO_203 | TRAVYGWW | | 121 |
| SEQ_ID_NO_188 | TQVVYGWR | | 116 |
| SEQ_ID_NO_196 | NRVVYG | | 122 |
| SEQ_ID_NO_197 | WHVVYSLW | | 119 |
| SEQ_ID_NO_193 | TQVVYGWW | | 106 |

Figure 8

```
SEQ_ID_NO_216    MGKGEAWVNG QRIGRYWPTY VASDASCTDS CNYRGPYSAS KCRKNCEKPS    50
SEQ_ID_NO_208    .......... .......... .....METLQ CRHQHVFIL. .........L    15
SEQ_ID_NO_214    .......... .......... ....MDTTHS CRRG--YIL. .........L    14

SEQ_ID_NO_216    QTLYHVPRSW LKPSGNILVL FFFRGGDPTQ ISIVTKQTES LCAHVSDSHP    100
SEQ_ID_NO_208    LVLFHS-SL. FMLASKIDVS DDARGIRIDG ---GQKRFLT NSPQHGKEHA    60
SEQ_ID_NO_214    LVLSYS-SV. FGLASNMSLS NDTSGNKTDS FFESQSTSTE WGTDMGDKY.    62

SEQ_ID_NO_216    PPVDLWNSET ESGRKVGPVL SLTCPHDNQV SBIKFASYG  TPLGTCGNFY    150
SEQ_ID_NO_208    .......ACT NEEPDLGPLT RISCNEPEYV LTKINFADYG NPTGTCGHFR    103
SEQ_ID_NO_214    .......MCT ESNMEIPWM- ISCKKSKEV  FTRINFADYG NPSGRCEHYR    103

SEQ_ID_NO_216    HGRCSSNKAL SIVQKACIGS SSCSVGVSBD TFGDP-CRGM AKSLAVEATC    199
SEQ_ID_NO_208    RDNCGARATM RIVKKNCLGK EKCHLLVTDE MFGPSKCKGA PM-LAVETTC    152
SEQ_ID_NO_214    HGNCGAKTTM EVAKKNCLGK HDCVFKVSDE MFGTSHCKKE AK-FFVQLTC    152

SEQ_ID_NO_216    A--         200
SEQ_ID_NO_208    TIA         155
SEQ_ID_NO_214    TKA         155
```

Figure 9

| | | | | | | | |
|---|---|---|---|---|---|---|---|
| SEQ_ID_NO_218 | ----MDEEAA | KPRDSTVNQQ | H--------- | ---------- | ----QYY | YGTFQGVANF | 30 |
| SEQ_ID_NO_225 | ----MDEEAA | KPRDTTINQQ | Q--------- | ---------- | ----QYY | YGTFQGVANY | 30 |
| SEQ_ID_NO_227 | -MGDGEEDKS | KGFADEADTH | H--------- | ---------- | -------Q | YGTFQGVSNY | 31 |
| SEQ_ID_NO_220 | ----MSGDEK | NPAVVDHQH | H--------- | ---------- | -------Q | YGTFQGVSNY | 28 |
| SEQ_ID_NO_222 | ----MSDQEK | NRGVVDHRH | HEDQPPPPP | -----PPDPQ | YGTFQGVANY | | 40 |
| SEQ_ID_NO_231 | MAGEMPDADG | KPRSASSDFQ | PSAPPQPQ-- | -----AQQYQ | YGTFGA---- | | 39 |
| SEQ_ID_NO_230 | -MGGGREEEA | ASK--VGYSS | GDLPPSAPPH | LQGQDPQQYQ | YGTFQ---- | | 42 |
| SEQ_ID_NO_229 | -MGGGDEQEA | DAGKSGGYSS | SGLPPSEP- | -----SQQYG | YGTFQG--- | | 38 |
| SEQ_ID_NO_1052 | -MGGRHEAEA | DGGKAGGYSS | SGLPPSEAPH | LQGQPSQEYG | YGTFQG--- | | 45 |

| | | | | | | | |
|---|---|---|---|---|---|---|---|
| SEQ_ID_NO_218 | PTPAPPPDFM | QPQHPITTF | ---PGHAY- | ---------Q | NLQGHG---- | | 61 |
| SEQ_ID_NO_225 | PPPAPPP--- | LPHQPIVTSP | LLPP------ | ---------- | ----------- | | 51 |
| SEQ_ID_NO_227 | PPPRP---- | QNSPPVTGFP | QPSAPPRY-- | --------Y | D-SAPP---- | | 60 |
| SEQ_ID_NO_220 | PPPPPP--- | QHHGPAIGFP | QPVPPPGL- | --------H | EPSAPP---- | | 59 |
| SEQ_ID_NO_222 | PPPS------ | --QSHVIGFP | QPVPPPGI-- | ---------- | --TAEP---- | | 64 |
| SEQ_ID_NO_231 | PSSAPG--- | EVPQPAVGFP | QPAPPPGL- | --------R | HYPQPPPPSY | | 74 |
| SEQ_ID_NO_230 | PPPHHHAASG | ELARPPVGFP | QPAPPPGFAG | ASGGGGHYHH | HHQQQP--- | | 89 |
| SEQ_ID_NO_229 | SRAGSG--- | EFRKPPVGFP | QPAPPPGF- | --GGGG---Y | HNQQQP--- | | 73 |
| SEQ_ID_NO_1052 | P-------- | --RQPPVGFP | QPAPPPGF- | --GGGG---Y | HNQQKP--- | | 73 |

| | | | | | | | |
|---|---|---|---|---|---|---|---|
| SEQ_ID_NO_218 | ---------- | ---GGVNYAQ | GFPVVVPDYT | -VVEVRP- | -M | IEHELPCCGL | 95 |
| SEQ_ID_NO_225 | ---------- | -------VH | GYQ-TLQEYT | -VVEVRP- | -V | REHDVPCCGF | 79 |
| SEQ_ID_NO_227 | ---------- | -----HYAH | GYQ-TVPVHG | -IAEGRPVHV | | RQRRLPCCGI | 92 |
| SEQ_ID_NO_220 | ---------- | ----PQYYPQ | GYQ-TVPGYA | -VAEGRP- | -V | RERRLPCCGI | 91 |
| SEQ_ID_NO_222 | ---------- | -------YAQ | GYQ-TVPGYA | -VAEGRP- | -V | RQRRLPCCGC | 93 |
| SEQ_ID_NO_231 | AVYPPLPPQT | YPAAAPYYAL | GYQ-AVQGYL | PVVEGRP- | -V | RMRRLPFCGL | 121 |
| SEQ_ID_NO_230 | ---------- | YAPAEPYYAQ | GYQ-TSPGYG | SIAEGRP- | -V | RMRRLPCCGL | 125 |
| SEQ_ID_NO_229 | ---------- | YTPEEPYYAQ | GYQ-AVPGYG | QVAEGRP- | -V | RMRRLPCCGL | 110 |
| SEQ_ID_NO_1052 | ---------- | YAPAEPYYAQ | GYQ-AVPGYG | PVAEGRP- | -V | RMRRLPCCGL | 110 |

| | | | | | | | |
|---|---|---|---|---|---|---|---|
| SEQ_ID_NO_218 | GMGWFLFIMG | FLFGGIPWYL | GAFIVLVT-S | VDHREKAGYV | ACSIA---- | | 139 |
| SEQ_ID_NO_225 | GMGWFLFIMG | FLFGGIPWYL | GAMIILFT-S | VDHREKAGYV | ACSVA---- | | 123 |
| SEQ_ID_NO_227 | GLGWFLFIVG | FFLGAIPWYV | GMFIMIVGRR | IDHREKPGYI | ACTIA---- | | 137 |
| SEQ_ID_NO_220 | GFGWFLFIIG | FFLGAIPWYI | GLFVLLCA-R | IDYREKPGYI | ACTIA---- | | 135 |
| SEQ_ID_NO_222 | GVGWFLFIIG | FFLGAIPWYI | GLFIIACM-R | DPREKPGYV | ACTIALRKHL | | 142 |
| SEQ_ID_NO_231 | GMGWFLFIIG | FFLAAIPWYI | GAFVLICVRV | HDYREKPGYV | ACTIA---- | | 166 |
| SEQ_ID_NO_230 | GLGWLLFIAG | FFLAAIPWYV | GAFILICVRV | HDYREKPGYV | ACTVA---- | | 170 |
| SEQ_ID_NO_229 | GLGWCLFITG | FFLAAIPWYI | GAFIMICVRV | HDHREKPGYV | ACTIAVSS-- | | 158 |
| SEQ_ID_NO_1052 | GLGWCLFITG | FFLAAIPWYI | GAFILICVRV | HDQREKPGYV | ACTIA---- | | 155 |

Figure 9 (continued)

| | | | |
|---|---|---|---|
| SEQ_ID_NO_218 | ---------- ---------- S | VVYLIAVMLG MTGDI N I W | 158 |
| SEQ_ID_NO_225 | ---------- ---------- S | VVYLIAVMLG MAGN NI W | 143 |
| SEQ_ID_NO_227 | ---------- ---------- A | ILATIAVILG VTKGAE DW | 156 |
| SEQ_ID_NO_220 | ---------- ---------- A | VLATIAIILG VTKGID DF | 153 |
| SEQ_ID_NO_222 | VEHECHIEIR CLLHNLCVK A | LLATIAIILG ATKGAD EW | 180 |
| SEQ_ID_NO_231 | ---------- ---------- A | SLAAIAILLG VTRGEE I W | 185 |
| SEQ_ID_NO_230 | ---------- ---------- A | VIAAIM PLG LTKGAH VW | 189 |
| SEQ_ID_NO_229 | ---------- ---------- F | LL QCNL TVY FTSGI --- | 174 |
| SEQ_ID_NO_1052 | ---------- ---------- A | VVAAVAILLG VTKGTH VW | 174 |

Figure 10

```
SEQ_ID_NO_244    MEYQRTNNLS LAFQFFRKAF EMCDSDPLLF NEYGVLRYRQ G-NYEEAVEN    49
SEQ_ID_NO_234    MEYMRTHSYK LADQFFMQAK AICPSDPLVY NELGVVAYHM KEYGKAVRW     49
SEQ_ID_NO_236    MEYMRTHSYK LAEQFFMQAK TICPSDPLVY NELGVVAYNM KEYNKAVLA     49
SEQ_ID_NO_241    MQYVRMHNFK LAEQFFTQAK SICPSDPLIH NELGVVAYNM KEEYQKAVSY    50
SEQ_ID_NO_242    MQYLRMHNFK LAEQFFTQAK SICPSDPLIY NEMGVVAYNM KEYQKAVQW     49

SEQ_ID_NO_244    FERALDLAPK PVGSRWESLI VNLAQAFRKI GRYDEAIATF QSALLISPRN    99
SEQ_ID_NO_234    FEKTLAHIPS ALTESWEPTV VNLAHAYRKL RKDREAISYY ERALTLSTKS    99
SEQ_ID_NO_236    FEKTLKHIPS -LSQLWEPTV INLAHAYRKL KIYHEAISCY ERALALSTRS    98
SEQ_ID_NO_241    YAKNLTFPTK SLSL----AF AGLAYIYHLM DDFEAAINYY HKALWLKPDD    95
SEQ_ID_NO_242    FELTLEHTSS SLNEMWEPTL VNLGHALRKL KKYQKAISYY EKALTFQTKS    99

SEQ_ID_NO_244    ASTYAALAFT YQMKSRCSEP VSLGLAIEYY HKALSLRADD AFSQHHLELA    149
SEQ_ID_NO_234    LSTYSGLAYT YHLQGNFS-- ----AAISYY HKALWLKPDD QFCTEMLNVA    143
SEQ_ID_NO_236    LSTYAGLAYT YHLQDNFT-- ----AAITCY HKALWLKPDD QFCTEMLSLA    142
SEQ_ID_NO_241    QFCTDMLTYA LESICQIT-- ---------- ---------- ---------A    114
SEQ_ID_NO_242    LSAFAGLAYT YHLMAMYH-- ----V----- HRA------- ----EVLQL     127

SEQ_ID_NO_244    LIDQSAITIP RHQQVEWDTM FPKVEDINAV TPTFGIASSP QGGILFPTPS    199
SEQ_ID_NO_234    LMDE------ ---------- ---------- ---------- ----------    147
SEQ_ID_NO_236    LVDE------ ---------- ---------- ---------- ----------    146
SEQ_ID_NO_241    RRKP------ ---------- ---------- ---------- ----------    118
SEQ_ID_NO_242    TKEP------ ---------- ---------- ---------- ----------    131

SEQ_ID_NO_244    PHSFQGTPTF GQTPFSARVD RMDESVDMDQ SVDMDESE              237
SEQ_ID_NO_234    ---------- CQNGVDSKV- ---------- ----ELC               159
SEQ_ID_NO_236    ---------- GRRGIDPKI- ---------- ----EFR               158
SEQ_ID_NO_241    ---------- GRGLLTATGG ---------- ----VTC               131
SEQ_ID_NO_242    ---------- GR-------- ---------- --------              133
```

Figure 11

| | | | | | | |
|---|---|---|---|---|---|---|
| SEQ_ID_NO_268 | ---MEEQCAA | AAGGG---GG | GEGASMCANG | CGFFGSEATK | KLCSKCYRDQ | 44 |
| SEQ_ID_NO_226 | ---MAER-QE | VSG------ | GMAAPMCANR | CGFFGSAATK | NLCSKCYK- | 37 |
| SEQ_ID_NO_260 | ---MSBEQNN | STSFP---- | PTEPKLCDNG | CGFFGSPSNM | NLCSKCYR- | 40 |
| SEQ_ID_NO_249 | ---MAEE-HR | CQA------ | P---DLCANN | CGFFGSPTTC | NLCSECYR- | 34 |
| SEQ_ID_NO_255 | ---MAEEQHR | CQE------ | P---RLCVNN | CGFFGSPATC | NLCSKCYG- | 36 |
| SEQ_ID_NO_265 | ---MAEE-HR | CQA------ | --ADRLCANN | CGFFGSPAMG | DLCSKCYR- | 36 |
| SEQ_ID_NO_262 | ---MAEE-HR | CQA------ | PEGHRLCSNN | CGFFGSPATM | NLCSKCYR- | 37 |
| SEQ_ID_NO_251 | ---MAEE-HR | CQA------ | PEGHRLCVNN | CGFFGSSATM | NLCSKCYR- | 37 |
| SEQ_ID_NO_248 | ---MAEE-HR | CET------ | PEGHRLCVNN | CGFFGSSATM | NLCSNCYG- | 37 |
| SEQ_ID_NO_274 | ---MAEE-HP | CQT------ | PEGHRLCVNN | CGFFGSSATM | NLCSNCYG- | 37 |
| SEQ_ID_NO_243 | MAQRDKEETE | MKV------ | SEBLBLCINN | CGFSGNPATK | NMCDSCYK- | 41 |
| SEQ_ID_NO_279 | ---MAQESWK | QESEETRVHA | PEAPILCINN | CGFFGSSMTN | NMCSKCYR- | 45 |
| SEQ_ID_NO_266 | ---MAQESWK | QESHA----- | PEAPILCINN | CGFFGSSMTN | NMCSKCYR- | 40 |
| SEQ_ID_NO_270 | ---MQHDKTG | CQSP----- | PEGPKLCINN | CGFFGSAATM | NMCSKCHK- | 39 |
| SEQ_ID_NO_267 | ---MEQNETG | CQVP----- | PDAPML CVNN | CGFFGSAATM | NPCSKCHK- | 39 |
| SEQ_ID_NO_277 | ---MEHEETG | CQPH----- | PEGPILCVNN | CGFFGSMATR | NMCSKCHK- | 39 |
| SEQ_ID_NO_286 | ---MEHKETG | CQQ------ | PKGPILCINN | CGFFGSAATM | NMCSKCHK- | 38 |
| SEQ_ID_NO_290 | ---MEHKETG | CQQ------ | PEGPILCINN | CGFFGSAATM | NMCSKCHK- | 38 |

| | | | | | | |
|---|---|---|---|---|---|---|
| SEQ_ID_NO_268 | LKAAPSSPPA | APDLVANEEE | EASTAAAAAN | DELALCSSG | CGFFGSKETN | 94 |
| SEQ_ID_NO_226 | ---------- | --EHLIKTAK | DEASAAVVIG | GAIVKCAADE | CGFFGSSATN | 75 |
| SEQ_ID_NO_260 | ---------- | --SLRAEEDQ | TAVAKAAVEK | SLKLPSCSL | TAPAPKD PL | 77 |
| SEQ_ID_NO_249 | ---------- | --GLQLKEQQ | SSAKQAFNH | TLVPSSSSLP | --------SS | 64 |
| SEQ_ID_NO_255 | ---------- | --DLRDSCPL | NCLLAPSSSA | SVSSFSSPL- | ---------- | 61 |
| SEQ_ID_NO_265 | ---------- | --DLQMKEQR | SSAKLVLNQ | TLIPDCSNSS | SLDTS HP | 72 |
| SEQ_ID_NO_262 | ---------- | --DIRLKEEE | DAKTKSTIET | ALSGSSSATV | ---------T | 66 |
| SEQ_ID_NO_251 | ---------- | --DLCLKEQE | ASSKSALSS | SPSSSSTVV | ---------- | 64 |
| SEQ_ID_NO_248 | ---------- | --DLCLKQQQ | DASMKSTVES | SLSPVIAPV | ---------- | 64 |
| SEQ_ID_NO_274 | ---------- | --DLCLKMQQ | DASMKSTVES | SLSAASPPS | ---------- | 64 |
| SEQ_ID_NO_243 | ---------- | ------STGI | MTQPALTFSG | KEKARSSFLR | --------LP | 68 |
| SEQ_ID_NO_279 | ---------- | --DFI----- | KLMEAPVVEK | KVTTSASSS | ---------- | 67 |
| SEQ_ID_NO_266 | ---------- | --DFV---KL | MEMDAPVVDK | KLITTASS- | ---------- | 63 |
| SEQ_ID_NO_270 | ---------- | --TLFDQEQ | GAKLASAVSG | SPSNLKET | --------TA | 69 |
| SEQ_ID_NO_267 | ---------- | --DLMLKQQQ | TELAASSIGS | ANGGSGPS | KEPDSALT-- | 75 |
| SEQ_ID_NO_277 | ---------- | --DMMLKEEQ | AKLAASSFGN | VNGTSNSNG | NEPV----VA | 73 |
| SEQ_ID_NO_286 | ---------- | --EMINKQEQ | AKLAASSIDS | VNGGDSGKE | PIIAG---HA | 73 |
| SEQ_ID_NO_290 | ---------- | --EMINKQEQ | AKLAASSIDS | VNGGDSGKE | PIIAG---HA | 73 |

Figure 11 (continued)

| | | | | | | |
|---|---|---|---|---|---|---|
| SEQ_ID_NO_269 | NMCSKCYRDH | LKRTSPLFSS | SSSPRTASTT | DITVPIAPAT | TAPTPSLKGK | 144 |
| SEQ_ID_NO_278 | NMCSGCYMDF | LKDAH----- | ----ASPAVA | DKVVLAAEK | DPAAAQISAA | 116 |
| SEQ_ID_NO_260 | E--------- | ---------- | ----TKPASV | ETVVAETSS | VPPVATGCDE | 104 |
| SEQ_ID_NO_249 | S--------- | ---------- | ----SARGSF | SASLPAKEEP | SAGTKEFKVV | 91 |
| SEQ_ID_NO_255 | ---------- | ---------- | ----TVDVIK | NCIAPVLVVE | GDEKGEFKAE | 67 |
| SEQ_ID_NO_265 | S--------- | ---------- | ----STSPSV | MVSSSTPTV | ELVAAAGPS | 99 |
| SEQ_ID_NO_262 | A--------- | ---------- | ----TAVVAS | GVESPSAPVE | SLPPPVLIS | 93 |
| SEQ_ID_NO_251 | ---------- | ---------- | ----ESGQV | PLLALHEVNR | ESAVPEIASA | 90 |
| SEQ_ID_NO_246 | ---------- | ---------- | ----LENYAA | ELEPTTKKT | EEKKPQIPT | 90 |
| SEQ_ID_NO_274 | ---------- | ---------- | ----SPEDS | IETST APVV | DIYAAEIQE | 90 |
| SEQ_ID_NO_248 | E--------- | ---------- | ----RSDYCR | --RDLITQDD | KKGDDDAK | 93 |
| SEQ_ID_NO_279 | ---------- | ---------- | ----TAPLET | KRDDAPAAAA | TEAVAEKQAE | 93 |
| SEQ_ID_NO_268 | ---------- | ---------- | ----STVPFE | TAKQDDTVPD | AAAMDDKQPA | 69 |
| SEQ_ID_NO_270 | D--------- | ---------- | ----LVDAGT | KSIEPVAVSV | DAVAEVVAPE | 96 |
| SEQ_ID_NO_267 | ---------- | ---------- | ----TVHVDA | GESDSMVSM | DASHESLLNE | 101 |
| SEQ_ID_NO_277 | A--------- | ---------- | ----GVDVQA | HLVEPKTSL | DPSFSFSGS | 100 |
| SEQ_ID_NO_258 | E--------- | ---------- | ----VAVAQV | EVKTLVAQPA | EIAGPSEGVT | 100 |
| SEQ_ID_NO_250 | E--------- | ---------- | ----VAVAQV | EVKTLVAQPA | EIAGPSEGVT | 100 |

| | | | | | | |
|---|---|---|---|---|---|---|
| SEQ_ID_NO_269 | EEEATAAASS | SAAAAAKPNR | CVACRKKVGL | GFECRCGGT | FCSTHRHADK | 194 |
| SEQ_ID_NO_278 | TSSTAPAA- | -VKAAAKPNR | CASCRKKVGL | GFPCRCGGT | FCALHRYAEK | 163 |
| SEQ_ID_NO_260 | GEP------ | --GKPARPNR | CFSCNKKVGV | NGFKCKCGST | FCGSHRYPEK | 145 |
| SEQ_ID_NO_249 | EEE------ | --EVGVFPNR | CLSCKKRVGL | TGFKCRCGMV | FCGHRYPGT | 132 |
| SEQ_ID_NO_255 | PTV------ | --VVPCQKPNR | CLTCRRVGL | TGFNCRCGMV | FCGTHRYPEQ | 129 |
| SEQ_ID_NO_265 | EAE------ | --PPKVQPNR | CGTCRRRVGL | TGFKCRCGLT | LCGTHRYPEQ | 140 |
| SEQ_ID_NO_262 | PDI------ | --AAPVQRNR | CGACRKRVGL | TGFKCRCGTT | FCGSHRYPEK | 134 |
| SEQ_ID_NO_251 | AED------ | --RSQQPNR | CMVCRKRVGL | TGFRCKCGVT | FCGSHRYPEN | 131 |
| SEQ_ID_NO_246 | EQP------ | --SPPQRPNR | CTVCRKRVGL | TGFMCRCGTT | FCGSHRYPEV | 131 |
| SEQ_ID_NO_274 | KQI------ | ---QQQRPNR | CTVCRKRVGL | TGFMCRCGTT | FCGTHRYPEV | 130 |
| SEQ_ID_NO_248 | NDSTTKI-- | -VEKKQEVNR | CSGCRRKVGL | TGFRCRCGDM | FCSEHRYSDR | 140 |
| SEQ_ID_NO_279 | QEP------ | ---PKPPSNR | CLTCRKKVGL | TGFDCRCGDT | FCSTHRYTDS | 133 |
| SEQ_ID_NO_268 | QEP------ | ---PKPPSNR | CSTCRKKVGL | TGFQCRCGGT | FCSLHRYTDS | 129 |
| SEQ_ID_NO_270 | EAR------ | --AKPKEGPSR | CTTCNKRVGL | TGFKCRCGDL | FCGTHRYADV | 136 |
| SEQ_ID_NO_267 | NHV------ | --LVKEVPPNR | CSACRKRVGL | TGFNCRCGNL | FCAVHRYSDK | 143 |
| SEQ_ID_NO_277 | GGS------ | -GEAKPEGPKR | CGTCNKRVGL | TGFNCRCGHL | FCAVHRYSDK | 143 |
| SEQ_ID_NO_258 | VNP------ | ---KGREGPNR | CSTCRKRVGL | TGFNCRCGNL | YCAMHRYSDK | 141 |
| SEQ_ID_NO_250 | VNP------ | ---KGREGPNR | CSTCRKRVGL | TGFNCRCGNL | YCAMHRYSDK | 141 |

Figure 11 (continued)

| | | | | |
|---|---|---|---|---|
| SEQ_ID_NO_268 | HACTFDFKKS | DREKIAKENP | LIVAPK TKF | 224 |
| SEQ_ID_NO_298 | HACDFDFKAA | GREKIAKNNP | LVVAAK NKI | 193 |
| SEQ_ID_NO_280 | HECSFDFKEV | GRSAIAKANP | VVKADKVQRI | 175 |
| SEQ_ID_NO_249 | TCLCF.... | .......... | | 137 |
| SEQ_ID_NO_255 | HDCEFDFKSL | GKEQIAKANP | VVKGEKLQRI | 159 |
| SEQ_ID_NO_265 | HGCGFDFKGM | GREEIKKANP | VVKGEKLNKI | 170 |
| SEQ_ID_NO_262 | HACGFDFKAV | GREEIARANP | VIKGEKLRRI | 164 |
| SEQ_ID_NO_251 | HGCTFDFKKV | GREEIARANP | LVKAEKLEKI | 161 |
| SEQ_ID_NO_246 | HGCTFDFKSA | GREEIAKANP | LVIAAKLQKI | 161 |
| SEQ_ID_NO_274 | HGCTFDFKSA | GREEIAKANP | LVVAAKLQKI | 160 |
| SEQ_ID_NO_248 | HDCSFDYKAA | GREEARQNP | VVKAAK RL | 170 |
| SEQ_ID_NO_279 | HQCTFDYKKV | AREQIAKQNP | VVMAEK NKI | 163 |
| SEQ_ID_NO_296 | HECTFDYKKV | AREQIAKQNP | VV AEK NKI | 159 |
| SEQ_ID_NO_270 | HNCSFDYHVA | AQEAIAKANP | VVKADKLDKI | 168 |
| SEQ_ID_NO_267 | HDCPFDYRSA | AQDAIAKANP | VVKAEKLDKL | 173 |
| SEQ_ID_NO_277 | HDCPYDYHTA | ARDVAKANP | VVKADKLEKI | 173 |
| SEQ_ID_NO_288 | HDCQFDYRTA | ARDAIAKANP | VVKAEKLDKI | 171 |
| SEQ_ID_NO_290 | HDCQFDYRTA | ARDAIAKANP | VVKAEKLDKI | 171 |

Figure 12

| | | | | | | | |
|---|---|---|---|---|---|---|---|
| SEQ_ID_NO_310 | ·······MAE | AKGAAAPL- | ···LAREDGRR | RGGAGGATWA | G--TLGNVVV | | 37 |
| SEQ_ID_NO_316 | MGFGMG-NDG | ASSSSSRLDP | APLLPHHGSA | GGEIG--LSS | QPKTFANVFI | | 47 |
| SEQ_ID_NO_325 | MGFGMGNNNG | ASSSSSRLDP | APLLPHHGSG | SREVG--LSS | QPKTFANVFI | | 48 |
| SEQ_ID_NO_312 | MGF----DKE | ASSSSSRLDA | APLLPQHG-- | GGGAGGH-SS | QPKTFANVFI | | 44 |
| SEQ_ID_NO_319 | MGL----HKE | ASSSSSRLDA | APLLPHHGHG | GGGAGHH-SS | QPKTFANVFI | | 46 |
| SEQ_ID_NO_321 | MGL----HKE | ASSSSSRLDA | APLLPHHGHG | GGGAGHH-SS | QPKTFANVFI | | 46 |
| SEQ_ID_NO_300 | MGF----QNE | ASSSSYTLKI | PPPAREDTPL | LGK-GPPLSS | QFKTFANVFI | | 45 |
| SEQ_ID_NO_302 | MGFG---RKK | ASSSAKTF-- | --PPREDTPL | IAK-STPLSS | QSKTFANVFI | | 42 |

| | | | | | | | |
|---|---|---|---|---|---|---|---|
| SEQ_ID_NO_310 | SIVGTGVLGL | PYAFRAAGWV | AGSLGMAAAG | FATLYCMLLL | VDCKDKLQEE | | 87 |
| SEQ_ID_NO_316 | AVVGAGVLGL | PYTFSHTGWA | AGSLLLFAVA | VLTFYCMMLL | VACRRRLAD- | | 96 |
| SEQ_ID_NO_325 | AVVGAGVLGL | PYTFSHTGWA | AGTLLLFSVA | ALTFYCMMLL | VACRRRLAD- | | 97 |
| SEQ_ID_NO_312 | AVVGSGVLGL | PYTFSRTGWA | AGTLLLLAVA | ALTFHCMMLL | VAARRRIAD- | | 93 |
| SEQ_ID_NO_319 | AVVGSGVLGL | PYTFSRTGWV | AGSVLLLAVA | ALTFHCMMLL | VACRRRLAY- | | 95 |
| SEQ_ID_NO_321 | AVVGSGVLGL | PYTFSRTGWV | AGSVLLLAVA | ALTFHCMMLL | VACRRRLAY- | | 95 |
| SEQ_ID_NO_300 | AVVGAGVLGL | PYAFKRTGWL | MGVLLLVSVS | VLTHHCMMLL | VYTRRKLDSF | | 95 |
| SEQ_ID_NO_302 | AIVGAGVLGL | PYAFKHTGWL | MSLIMLFSVA | GLTHYCMMLL | VNTRGKLQSF | | 92 |

| | | | | | | | |
|---|---|---|---|---|---|---|---|
| SEQ_ID_NO_310 | ETDEPKNYTY | GDFGEKCFGT | IGRCLTEILI | LISQAGGSMA | YLVFIGENLH | | 137 |
| SEQ_ID_NO_316 | --ERPKIASF | GDLGDAVFGA | HGRFAVDVML | VLSQASFCIG | YLIFISNTMA | | 144 |
| SEQ_ID_NO_325 | --EHPKIASF | GDLGDAVFGA | HGRFAVDVML | VLSQVSFCVG | YLIFISNTMA | | 145 |
| SEQ_ID_NO_312 | --AHPKIASF | GDLGHAIYGA | PGRHAVDAML | VLSQASFCVG | YLIFISNTMA | | 141 |
| SEQ_ID_NO_319 | --DHPKIASF | GDLGAAVCGP | AGRHVVDAML | VLSQASFCVG | YLIFISNTMA | | 143 |
| SEQ_ID_NO_321 | --DHPKIASF | GDLGAAVCGP | AGRHVVDAML | VLSQASFCVG | YLIFISNTMA | | 143 |
| SEQ_ID_NO_300 | NAGISKIGSF | GDLGFAVCGS | LGRIVVDLFI | ILSQAGFCVG | YLIFIGTTLA | | 145 |
| SEQ_ID_NO_302 | SGGFSKITSF | GDVGFTVCGS | IGRFVVDVMI | VLSQAGFCIG | YLIFIANTLA | | 142 |

| | | | | | | | |
|---|---|---|---|---|---|---|---|
| SEQ_ID_NO_310 | SVFS------ | ---------- | -----QSMS | PAGFIFAVLL | PVQIALSFL | | 165 |
| SEQ_ID_NO_316 | HLYP----IF | APSSS----- | ------ALLS | PKALFIWAML | PFQLGLNSIK | | 179 |
| SEQ_ID_NO_325 | HLYP----IT | APSSS----- | ------ALLS | PKALVIWAML | PFQLGLNSIK | | 180 |
| SEQ_ID_NO_312 | HLYPAIGAQ | SPAS------ | ------PLLT | AKALFIWAML | PFQLGLNSIR | | 179 |
| SEQ_ID_NO_319 | HLYP--VGDS | SPSS------ | ------PLLT | AKAIFIWVML | PFQLGLNSIK | | 179 |
| SEQ_ID_NO_321 | HLYP--VGDS | SPSS------ | ------PLLT | AKAIFIWVML | PFQLGLNSIK | | 179 |
| SEQ_ID_NO_300 | NLSD----PE | SPTSLRHQFT | RLGSEFLGVS | SKSLYIWGCF | PFQLGLNSIK | | 191 |
| SEQ_ID_NO_302 | NLFN----SP | SPNGLASQIL | A-----LSMS | AKSAYMWGCF | PFQLGLNSIA | | 183 |

Figure 12 (continued)

| | | | | | | | |
|---|---|---|---|---|---|---|---|
| SEQ_ID_NO_310 | SLSBLSPESI | FADVCNVLAA | AVVIRKDLQL | IDHPFANRSA | FNGVLAIPFA | | 215 |
| SEQ_ID_NO_316 | TLTLLAPLSI | FADVVDLGAM | GVVLGQDVAA | M.AMPPPVVA | FGGPAALLYG | | 229 |
| SEQ_ID_NO_325 | TLTLLAPLSI | FADVVDLGAM | GVVLGQDVAA | WAKPVPVAA | FGGPAALLYG | | 230 |
| SEQ_ID_NO_312 | TLTLLAPLSI | FADVVDLGAM | GVVLGQDASV | M.ADRPPVFA | FAGPAQLLYG | | 229 |
| SEQ_ID_NO_319 | TLTLLAPLSI | FADVVDLGAM | GVVLGQDVST | M.ANKPPVFA | SAGPTELLYG | | 229 |
| SEQ_ID_NO_321 | TLTLLAPLSI | FADVVDLGAM | GVVLGQDVST | M.ANKPPVFA | SAGPTELLYG | | 229 |
| SEQ_ID_NO_300 | TLTHLAPLSI | FADIVDLGAM | AVVIVEDSM | ILKQRPDVVA | FGGMSLFLYG | | 241 |
| SEQ_ID_NO_302 | TLTHLAPLSI | FADVVDLAAM | GVVIVKDVF | MENRAEVRA | FGGLSVFFYG | | 233 |

| | | | | | | | |
|---|---|---|---|---|---|---|---|
| SEQ_ID_NO_310 | FGVAVFCFEG | FSMTLALESB | MAERRKFRW | LSDAVVGILV | VYACFGVCGY | | 265 |
| SEQ_ID_NO_316 | LGVSVYAFEG | VGMVLPLEAE | AANKRKFGVT | LGLSMAFIAV | MYGLFGVMGY | | 279 |
| SEQ_ID_NO_325 | LGVSVYAFEG | VGMVLPLEAE | AANKKKFGVT | LGLSMAFIAV | MYGLFGVMGY | | 280 |
| SEQ_ID_NO_312 | LGVAVYAFEG | IGMVLPLEAE | AADKRRFGAT | LALSMAFIAV | MYGLFGAMGY | | 279 |
| SEQ_ID_NO_319 | LGVAVYAFEG | IGMVLPLEAE | AADKRKFGGT | LALSMAFIAV | MYGLFGAMGY | | 279 |
| SEQ_ID_NO_321 | LGVAVYAFEG | IGMVLPLEAE | AADKRKFGGT | LALSMAFIAV | MYGLFGAMGY | | 279 |
| SEQ_ID_NO_300 | MGVAVYSFEG | VGMVLPLESE | MKDKDKFGKV | LALGNGFISL | IYLAFGILGY | | 291 |
| SEQ_ID_NO_302 | MGVAVYAFEG | IGMVLPIESE | MREREKFGRI | LGLSMGLLSV | IYGAFGVLGY | | 283 |

| | | | | | | | |
|---|---|---|---|---|---|---|---|
| SEQ_ID_NO_310 | LAYGEATKDI | TLNLPNSNS | SAAVKVGLCI | ALAFTEPVMM | HPIHEIVETR | | 315 |
| SEQ_ID_NO_316 | VAFGDATRDI | TTNLGAGWL | SAAVQLGLCI | NLFFTMPVMM | NPVYEVAERL | | 329 |
| SEQ_ID_NO_325 | VAFGDATRDI | TTNLGAGWL | SAAVQLGLCI | NLFFTMPVMM | NPVYEVAERL | | 330 |
| SEQ_ID_NO_312 | LAFGAATRDI | TTNLGTGWL | SVLVQLGLCI | NLFFTMPVMM | NPVYEVAERL | | 329 |
| SEQ_ID_NO_319 | LAFGAATRDI | TTNLGTGWL | SVAVQLGLCI | NLFFTMPVMM | NPVYEVAERL | | 329 |
| SEQ_ID_NO_321 | LAFGAATRDI | TTNLGTGWL | SVTVQLGLCI | NLFFTMPVMM | NPVYEVAERL | | 329 |
| SEQ_ID_NO_300 | LAFGEDTMDI | TANLGAGLV | STVVQLGLCI | NLFFTFPLMM | NPVFEIVERR | | 341 |
| SEQ_ID_NO_302 | FAFGNDTQDI | TANLGPGL | SLLVQLGLCI | NLFFTFPLMM | NPVYEILERR | | 333 |

| | | | | | | | |
|---|---|---|---|---|---|---|---|
| SEQ_ID_NO_310 | LRSSGCFQKL | SHGVPGAEWL | GLHSSRLMV | TLLTVMASCI | PAFGSFVSFV | | 365 |
| SEQ_ID_NO_316 | L-------- | -HGKRYCWWL | -----RWLLV | VVVGLAAMYV | PNFTDFLALV | | 364 |
| SEQ_ID_NO_325 | L-------- | -HGKRYCWWL | -----RWLLV | IVVGLAAMYV | PNFTDFLALV | | 365 |
| SEQ_ID_NO_312 | L-------- | -CGKRYAWWL | -----RWILV | VLVGLLAMLV | PNFADFLSLV | | 364 |
| SEQ_ID_NO_319 | L-------- | -CRKRYAWWL | -----RWLLV | MVVGLMAMLV | PNFADFLSLV | | 364 |
| SEQ_ID_NO_321 | L-------- | -CRKRYAWWL | -----RWLLV | MVVGLMAMLV | PNFADFLSLV | | 364 |
| SEQ_ID_NO_300 | F-------- | -SRGMYSAWL | -----RWLV | LAVTLVALFV | PNFADFLSLV | | 376 |
| SEQ_ID_NO_302 | F-------- | -WGGRYCLWL | -----RWSV | LLVTLVALMV | PNFADFMSLV | | 368 |

Figure 12 (continued)

| | | | | | | | |
|---|---|---|---|---|---|---|---|
| SEQ_ID_NO_310 | GCTVCALLSF | VLPTFFHLN | VGSSMSLWRR | VLDYGFLLFG | LGFAGYGLFT | | 415 |
| SEQ_ID_NO_316 | GSSVCVLLGF | VLPASFHLKV | FGAEMAWPGV | LSDALLVVLG | LALAVFGTYT | | 414 |
| SEQ_ID_NO_325 | GSSVCVLLGF | VLPASFHLKV | FGEMEWPGV | VSDVLVVIG | LSLAVFGTYT | | 415 |
| SEQ_ID_NO_312 | GSSVCVVLGF | VLPAVFHLKV | FGTEIGWAGL | VADVAIIVTG | LALAVSGTWT | | 414 |
| SEQ_ID_NO_319 | GSSVCVLLGF | VLPAAFHLKV | FGAEVGWPGL | AGDVAVIVVG | TALAVSGTWT | | 414 |
| SEQ_ID_NO_321 | GSSVCVLLGF | VLPAAFHLKV | FGAEVGWPGL | AGDVAVIVVG | TALAVSGTWT | | 414 |
| SEQ_ID_NO_300 | GSSTCCVLGF | VLPALFHLLV | FKEEMGWLQW | SSDTAIVYLG | VVLAVSGTWS | | 426 |
| SEQ_ID_NO_302 | GSSVCCGLGF | VLPALFHLLV | FKEEMSWKGW | SIDVGIVALG | LVLAVSGTWY | | 418 |

| | | |
|---|---|---|
| SEQ_ID_NO_310 | ALSSH----- - | 420 |
| SEQ_ID_NO_316 | SLLQIFHSSS A | 425 |
| SEQ_ID_NO_325 | SLLQIFHSSS A | 426 |
| SEQ_ID_NO_312 | SLVQIFSSSD L | 425 |
| SEQ_ID_NO_319 | SLAQIFSSSD V | 425 |
| SEQ_ID_NO_321 | SLAQIFSSSD V | 425 |
| SEQ_ID_NO_300 | SLSEIFSVKV - | 436 |
| SEQ_ID_NO_302 | ALMEIFAVKV - | 428 |

Figure 13

| | | | | | | | |
|---|---|---|---|---|---|---|---|
| SEQ_ID_NO_368 | ----- | NEAEM | LYSALALTFA | L MVHRILSN | SQNK | ----- | RSLINLPPSP | 39 |
| SEQ_ID_NO_348 | ----- | NEAEM | LYSALALTFA | FMVYRILSN | SQDK | ----- | RSLTKLPPSP | 39 |
| SEQ_ID_NO_365 | ----- | NEAEM | LYSALALTFA | FMVYRILSN | SCEK | ----- | SSLIKLPPSP | 39 |
| SEQ_ID_NO_346 | -------- | MV | LLSELAAATL | FLTTH FIS | TLLS | -----I | TNGRRLPPGP | 37 |
| SEQ_ID_NO_2546 | --- | MAPKKSK | TAMKPCTVS | PPYLSKK DR | NLKCSYSLKS | KKIHLPPSP | 47 |
| SEQ_ID_NO_332 | ---------- | --------- | ---------- | ---------- | ------ | ---------- | 0 |
| SEQ_ID_NO_329 | --- | MEA MNV | DFDNCLILIL | LCLLSFLCVS | FFFK | ---KP | KDGNLPPSP | 43 |
| SEQ_ID_NO_341 | ---------- | MEMI | VFLFL | LLISLLSS | SENN | ----- | SLQLPKGP | 32 |
| SEQ_ID_NO_2548 | ----- | NGTFT | DLQKYTIFFI | LEFISTLLLR | SFLN | TTP | TRLRLPPSP | 44 |
| SEQ_ID_NO_2544 | -------- | MLL | E ALGLLVLG | LFLHLRPTPS | AKSK | ----A | RHLPNPPSP | 38 |
| SEQ_ID_NO_2541 | -------- | MLL | ELALGLLVLA | LFLHLRPTPT | AKSK | ----A | RHLPNPPSP | 38 |
| SEQ_ID_NO_358 | -------- | MLL | ELALGLLVLA | LFLHLRPTPT | AKSK | ----A | RHLPNPPSP | 38 |
| SEQ_ID_NO_360 | -------- | MLL | ELALGLLVLA | LFLHLRPTPT | AKSK | ----A | RHLPNPPSP | 38 |
| SEQ_ID_NO_339 | ------ | MRLV | E AVTLVLIA | LFIHFRPTPT | AKSK | ----A | RHLPNPPSP | 39 |
| SEQ_ID_NO_2550 | -------- | MLV | ELALALLAIA | LFLHLRPTPT | AKSK | ----A | RHLPNPPSP | 38 |
| SEQ_ID_NO_2543 | -------- | ML | E QGYVVLFL | LWFISS FIR | SLFK | ----K | SVCYKLPPGP | 37 |
| SEQ_ID_NO_2551 | -------- | ML | D QGYLVLFL | LWFISTLIR | SIFK | ----K | SQCYKLPPGP | 37 |
| SEQ_ID_NO_2549 | MEVATSRELI | NPFAFPILVL | VAGLTTVFYV | LRRR | ---CSG | NGGLRLPPSP | 47 |
| SEQ_ID_NO_353 | ----- | NDHQL | VARGLFKPLL | LFVAGLIVLY | ALRR | RRHRR | SSDLRLPPSP | 44 |
| SEQ_ID_NO_354 | ----- | NDHQL | VARGLFKPLL | LFVAGLIVLY | ALRRR | RRHRR | SSGLRLPPSP | 45 |
| SEQ_ID_NO_334 | -------- | MA | D QGYIILFL | LWLLSTILVR | AILN | ----KF | RAKPRLPPSP | 38 |
| SEQ_ID_NO_356 | ----- | MEPCLV | AVSVLVSALI | CYFFFRPYFH | RYGK | ------ | ----NLPPSP | 36 |
| SEQ_ID_NO_349 | ----- | MNIFEV | FQSVSPAIIA | FFISSLFIY | LVL | ----RH | QKSLSPPSP | 42 |
| SEQ_ID_NO_351 | ------ | MNT | QLFLLFFFP | TLLFLYCLPY | KRNQ | ----- | NHRRLPPSP | 37 |
| SEQ_ID_NO_2553 | ----- | MNIFVL | FQSLSPAVIA | AVVLPSLFLY | LLSK | ----S | KQNHRLPPSP | 41 |
| SEQ_ID_NO_364 | ---------- | ---MALYAA | LFLLSAAVVR | SVLD | ---RK | RGRPPYPPGP | 32 |
| SEQ_ID_NO_347 | ---------- | --MSTLVYST | LFILSTLLLT | LLTR | ----- | TRRKTRPPGP | 32 |
| SEQ_ID_NO_359 | --------- | M DTVLITLYTA | LFVITTFLF | LLRR | ----- | RGPPSPPGP | 34 |

Figure 13 (continued)

| | | | | | | | |
|---|---|---|---|---|---|---|---|
| SEQ_ID_NO_366 | PGWLPIIGH | -LHLIK NPL | HRTLYDCSQK | LGSIFSVWFG | --SRLVVVVS | 84 |
| SEQ_ID_NO_349 | PGWLPVIGH | -AHLMK NLL | HRTLYDFSQK | LGPIFSIRFG | --SRLVVVVS | 84 |
| SEQ_ID_NO_365 | PGWLPVIGH | -VHLMK NLL | HRTLYDFSQK | LGPIFSLRFG | --TRLVVVVS | 84 |
| SEQ_ID_NO_346 | -RSWPVIGA- | -LPLLG AMP | HVSLAKMAKK | YGA MYLKVG | --TCGMVVAS | 61 |
| SEQ_ID_NO_2548 | -PALPFIGH | -LHILG ELV | HQSFQKLALR | YGPFMLIHAE | --ASTSYVVS | 91 |
| SEQ_ID_NO_332 | ........... | ........... | ........... | ........... | ........... | 0 |
| SEQ_ID_NO_338 | -PSLPIIGH | -LHHLLSLFM | HRSLQKLSSK | YGPLLYLHVF | --NVP LLVS | 88 |
| SEQ_ID_NO_341 | -PSIPLLGH | -LHHLT-PSL | YKSLYTLSSK | HGPLLLLRLG | PSRRLLLLVS | 78 |
| SEQ_ID_NO_2549 | -PALPIIGHL | RLHFLS-SSI | YKSFHSLSTC | YGPLLYLHFG | --ASRCLLVS | 90 |
| SEQ_ID_NO_2544 | KPRLPLIGH | -HLLKDQLL | HHSLIDLSKR | YGPLYSLYFG | --SMPTVVAS | 84 |
| SEQ_ID_NO_2541 | KPRLPFIGH | -LHLLKDKLL | HYALIDLSKK | HGPLFSLYFG | --SMPTVVAS | 84 |
| SEQ_ID_NO_359 | KPRLPFIGH | -LHLLKDKLL | HYALIDLSKK | HGPLFSLYFG | --SMPTVVAS | 84 |
| SEQ_ID_NO_360 | KPRLPFIGH | -LHLLKDKLL | HYALIDLSKK | HGPLFSLYFG | --SMPTVVAS | 84 |
| SEQ_ID_NO_339 | KPRLPFVGH | -LHLLDHPLL | HQSLIRLGER | YGPLYSLYFG | --SMPTIVAS | 85 |
| SEQ_ID_NO_2550 | KPRLPFVGH | -LHLLDDPLL | HHSLIKLGER | YGPLYSLYFG | --SMPTVVAS | 84 |
| SEQ_ID_NO_2543 | PISFPILGH | -APYLR SLL | HKSLYKLSNR | YGPLMHIMLG | --SQHVVVAS | 82 |
| SEQ_ID_NO_2551 | PISLPLIGH | -APYLR SLL | HQALYKLSTR | YGPLMHVLIG | --SQHVIVAS | 82 |
| SEQ_ID_NO_2548 | -LALPVLGH | -FHLLA PLP | HQALHRLASR | HGPLLYLRLG | --SMPAAACC | 91 |
| SEQ_ID_NO_353 | -FGLPILGH | -LHLLA PLP | HQALHRLAAR | HGPLLFLRLG | --SVPCVAAC | 88 |
| SEQ_ID_NO_354 | -FGLPILGH | -LHLLA PLP | HQALHRLAAR | HGPLLFLRLG | --SVPCVAAC | 88 |
| SEQ_ID_NO_334 | -LALPIIGH | -LHLLA PIP | HQALHKLSTR | YGPLIHLFLG | --SVPCVVAS | 82 |
| SEQ_ID_NO_352 | FFRLPIIGH | -MHMLG PLL | HQSFHNLSHR | YGPLFSLNFG | --SVLCVVAS | 81 |
| SEQ_ID_NO_349 | -PALPIIGH | -LHHLG PLI | HHSFHDLSTR | YGPLIHLRLG | --SVPCVVAS | 88 |
| SEQ_ID_NO_351 | -PSFPIIGH | -LHHLG PLI | HQSFHALSTR | YGSLIHLRLG | --SVPCVVYS | 81 |
| SEQ_ID_NO_2553 | -PSLPIIGH | -LHHLG PLI | HQSFHNLSTR | YGPLIHLRLG | --SVPCVVAS | 85 |
| SEQ_ID_NO_364 | -FPLPIIGH | -LHLLG PRL | HQTFHDLSQR | YGPLMQLRLG | --SIRCVIAA | 78 |
| SEQ_ID_NO_347 | -LALPLIGH | -LHLLG PKL | HHTFHQFSQR | YGPLIQLYLG | --SVPCVVAS | 78 |
| SEQ_ID_NO_359 | -LSLPIIGH | -LHLLG PRL | HHTFHEFSLK | YGPLIQLKLG | --SIPCVVAS | 78 |

Figure 13 (continued)

| | | | | | | | |
|---|---|---|---|---|---|---|---|
| SEQ_ID_NO_368 | SSSLVEECFT | KYD | IVLANR | PDLHLDLRSL | GNSTLSVIGA | PYGDHWRNLR | 133 |
| SEQ_ID_NO_349 | SSSLVEECFT | KYD | IVLANR | PCAEVDRRSL | GFSTTSVIGA | PYGDHWRNLR | 133 |
| SEQ_ID_NO_365 | SSSLVEECFT | KYD | IVLANR | PQPSVDRRSL | GFSTTSVIGA | PYGDHWRNLR | 133 |
| SEQ_ID_NO_346 | TPDAAKAFLK | TLD | LNFSNR | PPNAEATHFL | AYGAQDMVFA | HYGPRMKLR | 129 |
| SEQ_ID_NO_2548 | NGAIAKEVFK | TND | INFANR | PEFGSSEY-Q | IYNDIMFSIM | DYNKLMFLK | 139 |
| SEQ_ID_NO_332 | .......... | ... | ...... | .......... | .......... | ......... | 0 |
| SEQ_ID_NO_339 | SPSIAVEIFR | TDD | VNVSSR | DFPTNEGS-L | LFGSFSFSTA | PYGEYWKFMK | 136 |
| SEQ_ID_NO_341 | SAAVAIDVFK | THD | LAFSSR | PHFAFAERL | PFGTSGFVTA | PYGPYWRFMK | 126 |
| SEQ_ID_NO_2542 | SAAMAAEIFK | TND | LAFASR | PRLAFADKL | PYGTSSFITA | EYGDYWRFMK | 138 |
| SEQ_ID_NO_2544 | TPELFKLFLQ | THEAASFNTR | FQTSAIKR | L | TYDNSLVAMV | PFGPYWKFIR | 132 |
| SEQ_ID_NO_2541 | TPELFKLFLQ | THEATSFNTR | FQTSAIRR | L | TYDSSLVAMV | PFGPYWKFVR | 132 |
| SEQ_ID_NO_358 | TPELFKLFLQ | THEATSFNTR | FQTSAIRR | L | TYDSSLVAMV | PGPYWKFVR | 132 |
| SEQ_ID_NO_370 | TPELFKLFLQ | THEATSFNTR | FQTSAIRR | L | TYDSSLVAMV | PFGPYWKFVR | 132 |
| SEQ_ID_NO_337 | TPDLFKLFLQ | THEAVSFNTR | FQTSAIRR | L | TYDNSLVAMV | PFAPYWKFIR | 133 |
| SEQ_ID_NO_2550 | TPELFKLFLQ | THEASSFNTR | FQTSAIRR | L | TYDNSLVAMV | PFAPYWKFIR | 132 |
| SEQ_ID_NO_2543 | TAESAKQILK | TQEIESFTNR | PIMIASEN | L | TYGAADYFFI | PYGNYWRFLK | 130 |
| SEQ_ID_NO_2551 | SAEMAKQILK | TYEIESFCNR | PIMIASEN | L | TYGAADYFFI | PYGTYWRFLK | 130 |
| SEQ_ID_NO_2549 | SPDAAREVLK | THEIAAFLDR | AMPTAVHR | L | MYGGQDFIFS | AYGPYWRFMK | 139 |
| SEQ_ID_NO_353 | SPDAAREVLK | THEIAAFLDR | PKPAAVHR | L | TYGGQDFSFS | AYGPYWRFMK | 136 |
| SEQ_ID_NO_354 | SPDAAREVLK | THEIAAFLDR | PKPAAVHR | L | TYGGQDFSFS | AYGPYWRFMK | 137 |
| SEQ_ID_NO_334 | TPEIAKEFLK | THEINSFCDR | PKSTAVDF- | L | TYGSADFSFA | PYGPYWKFMK | 130 |
| SEQ_ID_NO_355 | TPHFAKQLLQ | TNEILAFNCR | IESTAVKK | L | TYESSLLAFA | PYGDYWRFIK | 128 |
| SEQ_ID_NO_342 | TPDLARDFLK | TNEILAFSSR | KHSLAIDH | M | TYGVSLFAFA | PYGPYWKFIK | 133 |
| SEQ_ID_NO_351 | TPDLAKDFLK | TNEILAFSSR | KHSLAIDH | I | TYGVALFAFA | PYGTYWKFIK | 128 |
| SEQ_ID_NO_2553 | TPDLARDFLK | TNEILAFSSR | KHSLAIDH | I | TYGVALFAFA | PYGPYWKFIK | 132 |
| SEQ_ID_NO_364 | SPELAKECLK | THEILVFSSR | KHSTAIDI | M | TYDSSLFAFS | PYGPYWKFIK | 123 |
| SEQ_ID_NO_347 | TPELAREFLK | THEILDFSSR | KHSTAIDI | M | TYDSSLFAFA | PYGPYWKFIK | 123 |
| SEQ_ID_NO_359 | TPELAREFLK | TNEILAFSSR | KHSTAIDI | M | TYDSSLFAFS | PYGPYWKYIK | 125 |

Figure 13 (continued)

| | | | | | | | |
|---|---|---|---|---|---|---|---|
| SEQ_ID_NO_366 | KLCDLEVFAP | TRLASFLSIR | RDERDRMISG | LYKSSAGLA | KVNLEAKIAE | 183 |
| SEQ_ID_NO_348 | KLCDLEVFAP | TRLASFLSIR | LDERDRMISA | LYKSSAGFA | KVNLEAKIVE | 183 |
| SEQ_ID_NO_365 | KLCDLEVFAP | TRLASFLSIR | LDERDRMISS | LYKSSAGFA | KVNLETKIVE | 183 |
| SEQ_ID_NO_346 | KLSNLHMLGG | KALENWANVR | ANELSHMLKS | MFDMGREGE | RVWAEMLTF | 178 |
| SEQ_ID_NO_2548 | KICMTEILSA | QQISKFAPVR | KEEMKVLQF | F-LKCSEQGD | AFDVGQLMD | 188 |
| SEQ_ID_NO_332 | .......... | .......... | .......... | .......... | ........MK | 2 |
| SEQ_ID_NO_338 | KLIVTKFLGP | QALERSQKVR | ....RSYYLN | L-DKAVKKE | SVEIAEEAMK | 181 |
| SEQ_ID_NO_341 | KLCVTELLST | RQLERSRSIR | REEILRSKR | V-IDNAREIV | ALDLGSEFTK | 175 |
| SEQ_ID_NO_2549 | KLCVTELLGV | KQLERSRMVR | REELDCFLKK | L-VESGENGE | AVDVRAEVMK | 187 |
| SEQ_ID_NO_2544 | KLIMNDLLNA | TTVNKLRPLR | SHEIRKVLRV | L-AQSAEAQC | PLNVTEELLK | 181 |
| SEQ_ID_NO_2541 | KLIMNDLFNA | TTVNKLRPLR | TQQIRKFLRV | M-AQGAEAQK | PLDLTEELLK | 181 |
| SEQ_ID_NO_359 | KLIMNDLLNA | TTVNKLRPLR | TQQIRKFLRV | M-AQGAEAQK | PLDLTEELLK | 181 |
| SEQ_ID_NO_360 | KLIMNDLLNA | TTVNKLRPLR | TQQIRKFLRV | M-AQGAEAQK | PLDLTEELLK | 181 |
| SEQ_ID_NO_339 | KLIMNDLLNA | TTVNKLRPLR | SQEIRKVLNM | M-AKSAQTQE | PLNVTEELLK | 182 |
| SEQ_ID_NO_2550 | KIIMNDLLNA | TTVNKLRPLR | SQEIRKVLKA | K-AHSAESQC | PLNVTEELLK | 181 |
| SEQ_ID_NO_2543 | KLCMTELLSG | KTLEHFVHIR | EDEIKCFMGT | L-LEISKNGK | PIEMRHELIR | 179 |
| SEQ_ID_NO_2551 | KLCMTELLSG | KTLEHFVNIR | EDEIQCFLRN | V-LEISKTGK | GVEMRQELIR | 179 |
| SEQ_ID_NO_2545 | RACVHELLDS | RTLERLRHVR | REEVSRLVRS | L-RSAGDESA | AVDVDAMLMG | 189 |
| SEQ_ID_NO_353 | RACVHELLAG | RTLDRLRHVR | REEVARLVGS | L-RASADGGE | RVDVDAALMG | 185 |
| SEQ_ID_NO_354 | RACVHELLAG | RTLDRLRHVR | REEVARLVGS | L-RASADGGE | RVDVDAALMG | 186 |
| SEQ_ID_NO_334 | KICMTELLGG | RMDQLLPVK | HEEIRQFLQF | L-LKKANARE | SIDVGSQLIR | 179 |
| SEQ_ID_NO_358 | KLSMNELLGS | RSINNFQHLR | AQETHQLLRL | L-SNRARAFE | AVHITEELLK | 177 |
| SEQ_ID_NO_349 | KTSIVELLGN | QNLSNFLPIR | TQEVHELLQT | L-MVKSKKNE | SVHLSEELLK | 182 |
| SEQ_ID_NO_351 | KLFTVELLGT | QNLSHFLPIR | THEIRELLRT | L-MVKSRAKE | RVNLTEELLK | 177 |
| SEQ_ID_NO_2553 | KLSTVELLGN | QNLGHFLPIR | TQEIHELLHT | L-MEKSKRKE | SVNLTEELLK | 181 |
| SEQ_ID_NO_364 | KLCTYELLGA | RNLAHFQPIR | TLEVKSFLQI | L-MRKGESGE | SFNVTEELVK | 172 |
| SEQ_ID_NO_347 | KLCTYELLGA | RNLSHFQPIR | ALEVMSFLRI | L-YEKFEQKC | SVNVTEELVK | 172 |
| SEQ_ID_NO_350 | KLCTYELLGA | RNLGHFQPIR | NLEVRSFLQL | L-MHKSFKGE | SVNVTDELVR | 174 |

Figure 13 (continued)

| | | | | | | |
|---|---|---|---|---|---|---|
| SEQ_ID_NO_368 | LTFNNLMRML | AGKYYGEEA | EDEEEAKRFR | DMTKEALELM | NTFNLAEIFP | 233 |
| SEQ_ID_NO_348 | LTFNNIMRMV | AAKRYYGEEA | EDDEEAKRFR | DLTKEALELT | SASNPGEIFP | 233 |
| SEQ_ID_NO_365 | LTFNNIMRMV | AGKRYYGEEA | EDDEEAKRFR | DLTKEALELT | SASNPGEIFP | 233 |
| SEQ_ID_NO_346 | ANANMISQVI | LSKRVFVN-- | KSV-EVNEFK | DMVVELMTTA | GVFNIGDFIP | 225 |
| SEQ_ID_NO_2546 | MTNNLICRLI | MSTRTSEN-- | VN-ESAEIR | EIAKSVLLA | GQLSGEIFG | 234 |
| SEQ_ID_NO_332 | LVNNTVCQMI | MGRSCSEE-- | HG-EAERVR | GLVTKTDALT | KKFILAGILR | 48 |
| SEQ_ID_NO_329 | LVNNTVCQMI | MGRSCSEE-- | HG-EAERVR | GLVTKTDALT | KKFILAGILR | 227 |
| SEQ_ID_NO_341 | FTNNVTCRTA | MSTSCAEK-- | CE-DAERIR | KLVKESFELA | AKLCFGDVLG | 221 |
| SEQ_ID_NO_2542 | LTNHSTCRVI | LSARCSED-- | ND-EAERLL | EMVTEWELA | VKMSFGDVFG | 233 |
| SEQ_ID_NO_2544 | WTNNTISMLM | LG------ | ----EAEEVR | DLARETVKIF | GEYSLTDFIW | 219 |
| SEQ_ID_NO_2541 | WTNSTISMMM | LG------ | ----EAEEIR | DIAREVLKIF | GEYSLTDFIW | 218 |
| SEQ_ID_NO_358 | WTNSTISMMM | LG------ | ----EAEEIR | DIAREVLKIF | GEYSLTDFIW | 219 |
| SEQ_ID_NO_360 | WTNSTISMMM | LG------ | ----EAEEIR | DIAREVLKIF | GEYSLTDFIW | 219 |
| SEQ_ID_NO_339 | WTNSTISRMM | LG------ | ----EAEEIR | DIARDVLKIF | GEYSLTDFIW | 220 |
| SEQ_ID_NO_2550 | WTNNTISRMM | LG------ | ----EAEEVR | DIAREVLKIF | GEYSLTDFIW | 219 |
| SEQ_ID_NO_2543 | HTNNIISRMT | MGKKSSGM-- | ND-EVGQLR | KVVREIGELL | GAFNLGDIIG | 225 |
| SEQ_ID_NO_2551 | HTNNIISRMT | MGKKSNGT-- | ND-EVGQVR | KLVREIGELL | GAFNLGDIIG | 225 |
| SEQ_ID_NO_2549 | VTGDIVSRMV | MSRRWTGD-- | DSATDTEEMR | GVIAETAVLT | GTFNLQDYIG | 237 |
| SEQ_ID_NO_353 | LTGDIVSRMV | MGRRWTGD-- | DN-DAEEMR | GVVAETAELT | GTFNLQDYIG | 231 |
| SEQ_ID_NO_354 | LTGDIVSRMV | MGRRWTGD-- | DN-DAEEMR | GVVAETAELT | GTFNLQDYIG | 232 |
| SEQ_ID_NO_324 | LTNNVISRMA | MSQRCSDH-- | DD-EADEVR | NLVREVADLT | GKFNLSDFIW | 225 |
| SEQ_ID_NO_355 | LTNNVISIMM | VG------ | ----EAEEAR | DVVRDVTEIF | GEFNVSDFIW | 215 |
| SEQ_ID_NO_349 | LTNNVICQMM | MSIRCSGT-- | IN-EADEAK | NLVREVTKIF | GEFNISDFIC | 228 |
| SEQ_ID_NO_351 | LTNNVISQMM | MSIRCSGT-- | NS-EADEAK | NLVREVTKIF | GQFNVSDFIW | 223 |
| SEQ_ID_NO_2553 | LTNNVICQMM | MSIRCSGT-- | NS-EADEAK | NLVREVTTIF | GQFNVSDFIW | 227 |
| SEQ_ID_NO_364 | LTSNVISHMM | LSIRCSET-- | ES-EAEAAR | TVIREVTQIF | GEFDVSDIIW | 218 |
| SEQ_ID_NO_347 | LTSNVISNMM | LGIRCSGT-- | EG-EAEVAR | TVIREVTQIF | GEFDVSEIVW | 218 |
| SEQ_ID_NO_352 | LTSNVISHMM | LSIRCSED-- | EG-DAEAAR | TVIREVTQIF | GEFDVTDIIW | 220 |

Figure 13 (continued)

| SEQ_ID_NO | | | | | | | |
|---|---|---|---|---|---|---|---|
| SEQ_ID_NO_366 | -LRWIGCNG | FEKQLPVHSR | KTDEIMQGLL | DEHR | ..... | .......... | 266 |
| SEQ_ID_NO_346 | -LRWLGCNG | LEKKLAVHSR | KTDEFMQGLL | DEHR | ..... | .......... | 266 |
| SEQ_ID_NO_365 | -LRWLGFNG | LEKKLAVHAR | KTDEFMQGLL | DEHR | ..... | .......... | 266 |
| SEQ_ID_NO_346 | -CLSMMDLQG | EKEMKRLHK | KFDALLTKMF | DEHK | ..... | ......ATSV | 262 |
| SEQ_ID_NO_2546 | -PLKKFDLLG | AGRKAKALLL | KFDKLMDGIT | KKHE | ..DER R | ........V | 272 |
| SEQ_ID_NO_332 | KPLQKIGISL | FKKELMDASC | KFNEVLEKIL | VEYK | ..... | ......EKVE | 66 |
| SEQ_ID_NO_338 | KPLQKIGISL | FKKELMDASC | KFNEVLEKIL | VEYK | ..... | ......EKVE | 265 |
| SEQ_ID_NO_341 | -PFKELEFVW | YGKKADMST | RYDELLEEVL | KEHE | ..HKR L | ....SRAN | 262 |
| SEQ_ID_NO_2549 | -PLKRLGFVW | YGRKAVELTL | RYDEILEKML | KEHE | ..ER | .......... | 266 |
| SEQ_ID_NO_2544 | -PLKKLKFGK | YEKRIDEIFN | KFDPVIEKVI | KKRQEIVRRR | KN | ...GEVV | 264 |
| SEQ_ID_NO_2541 | -PLKHLKVGK | YEKRIDDILN | KFDPVVERVI | KKRREIVRRR | KN | ...GEVV | 264 |
| SEQ_ID_NO_359 | -PLKHLKVGK | YEKRIDDILN | KFDPVVERVI | KKRREIVRRR | KN | ...GEVD | 264 |
| SEQ_ID_NO_360 | -PLKHLKVGK | YEKRIDDILN | KFDPVVERVI | KKRREIVRRR | KN | ...GEVV | 264 |
| SEQ_ID_NO_339 | -PLKKLKVGK | YEKKIEEIFN | RFDPVIEKVI | KKRQDVRRRR | KERN | .GELE | 267 |
| SEQ_ID_NO_2550 | -PLKKLKVGD | YEKRIDEIFN | KFDPVIEKVI | KKRQEITKRR | KERD | .GELE | 266 |
| SEQ_ID_NO_2543 | -FMRPLDLQG | FGKRNKDTHH | KMDVMMEKVL | KEHE | ..EAR | AL....KEGA | 266 |
| SEQ_ID_NO_2551 | -FMRPFDLQG | FGKKNRDAHH | MMDVMMEKVL | KEHE | ..EAR | AKE..KGGA | 266 |
| SEQ_ID_NO_2545 | -VFKYWDMQG | LGKRIDAVHR | KFDAMMERIL | TARDA.RRRR | RKEP | ..ADGA | 264 |
| SEQ_ID_NO_353 | -VFKYWDVQG | LGKRIDAVHR | KFDAMMERIL | TEREAKRKLR | RQ | ...AAAD | 276 |
| SEQ_ID_NO_354 | -VFKYWDVQG | LGKRIDAVHR | KFDAMMERIL | TAREAKRKLR | RQ | ...AAAD | 277 |
| SEQ_ID_NO_334 | -FCKNLDLQG | FGKRLKEVRK | RFDTMTERII | VEHE | ..EAR | KKK..KETG | 266 |
| SEQ_ID_NO_355 | -LFKKMDLQG | FGKRIEDLFQ | RFDTLVERII | SKREQTRKDR | RRNGKKGEGG | | 264 |
| SEQ_ID_NO_349 | -LFKNIDLQG | FKKRYVDTHT | RYNALLEKMI | FERE | ..EKR | KQ...KKSE | 270 |
| SEQ_ID_NO_351 | -FCKNIDLQG | FKKRYEGTHR | RYDALLERII | MERE | ..ENR | RR...GKLK | 265 |
| SEQ_ID_NO_2553 | -FCKNLDLQG | FKKRYEDTHR | RYDALLEKII | SERE | ..EKR | RK...GGKR | 269 |
| SEQ_ID_NO_354 | -LCKNFDFQG | IRKRSEDIQR | RYDALLEKII | TORE | ..KQR | RTH..GGGG | 261 |
| SEQ_ID_NO_347 | -FCKNLDLQG | IRKRSEDIRR | RYDALLEKII | SDRE | ..RLR | RG...GGGG | 261 |
| SEQ_ID_NO_359 | -FCKKFDLQG | IKKRSEDIQR | RYDALLEKII | SDRE | ..RSR | RQNRDKHGGG | 266 |

Figure 13 (continued)

| | | | | | | | |
|---|---|---|---|---|---|---|---|
| SEQ_ID_NO_368 | RGERQNTMVG | HLLSL--QE | SQPDYYTDEI | TGLIISLII | AGTDASVVTT | 313 |
| SEQ_ID_NO_345 | RGERQNTMVD | HLLSL--QE | SQPEYYTDEI | TGLIVALII | AGTDASVVTT | 313 |
| SEQ_ID_NO_365 | RGERQNTMVD | HLLSL--QE | SQPEYYTDEI | TGLIVALII | AGTDASVVTT | 313 |
| SEQ_ID_NO_346 | ERKGKPDFLD | CVMENRD-NS | ECELRLSTTN | KALLLNLFT | AGTDTSSSAI | 310 |
| SEQ_ID_NO_2546 | GGKERRDMMD | ILLEIAD-DE | HAEMKLTRNG | KGLFLDLFL | GGTDTTSVAL | 321 |
| SEQ_ID_NO_332 | EHHQGTDMMD | KLLEVYG-DE | KAEYKITRDH | KSLFVDLFF | AGTDTSTHAI | 135 |
| SEQ_ID_NO_338 | EHHQGTDMMD | KLLEVYG-DE | KAEYKITRDH | KSLFVDLFF | AGTDTVTHAI | 314 |
| SEQ_ID_NO_341 | GDCSERDLMD | ILLDVYH-DR | HAEFKITMAH | KAFFMDLFI | AGTHTSAEAT | 311 |
| SEQ_ID_NO_2542 | GKREDKDLMD | VLLEVYQ-DD | KAGNKLTRTH | KAFILDLFM | AGTNTSAESM | 317 |
| SEQ_ID_NO_2544 | EGEQSGIFLD | TLLEFAE-DE | TMEIKITKEC | KGLVVDFFS | AGTDSTAVAT | 313 |
| SEQ_ID_NO_2541 | EGEVSGVFLD | TLLEFAE-DE | TMEIKITKDH | KGLVVDFFS | AGTDSTPVAT | 313 |
| SEQ_ID_NO_358 | EGEVSGVFLD | TLLEFAE-DE | TTEIKITKDH | KGLVVDFFS | AGTDSTAVAT | 313 |
| SEQ_ID_NO_360 | EGEVSGVFLD | TLLEFAE-DE | TMEIKITKDH | KGLVVDFFS | AGTDSTAEAT | 313 |
| SEQ_ID_NO_339 | EGEQSVVFLD | TLLDFAE-DE | TMEIKITKEC | KGLVVDFFS | AGTDSTAVAT | 316 |
| SEQ_ID_NO_2550 | EGEQSVVFLD | TLLEFAE-DE | TMEIKITKEC | KGLVVDFFS | AGTDSTAVAT | 315 |
| SEQ_ID_NO_2543 | GSDRKKDLFD | ILLNLIEADD | GAESKLTRGS | AKAFALDMFI | AGTNGPASVL | 316 |
| SEQ_ID_NO_2551 | ESDRKKDLFD | ILLNLIE-AD | GADNKLTRES | AKAFALDMFI | AGTNGPASVL | 317 |
| SEQ_ID_NO_2545 | GEGAKKDLLD | MLFDMHE-DE | AAEMRLTRDN | KAFMLDIFS | AGTDTTAITL | 333 |
| SEQ_ID_NO_353 | GEDDEKDLLD | MLFDMHE-DE | AAEMRLTRDN | KAFMLDIFA | AGTDTTTITL | 325 |
| SEQ_ID_NO_354 | GEDDEKDLLD | MLFDMHE-DE | AAEMRLTRDN | KAFMLDIFA | AGTDTTTITL | 328 |
| SEQ_ID_NO_334 | EGDPVKDLLD | ILLDISE-DD | SSEMKLTREN | KAFILDIFA | AGTDTSAVTM | 317 |
| SEQ_ID_NO_356 | SSDGIRDFLD | ILLDCTE-DE | NSEIKIDRVH | KALIMDFFT | AGTDTTAIST | 313 |
| SEQ_ID_NO_349 | DGIKGKDFLD | ILLDVLE-DE | HAEIKITRDH | KALILDFFT | AATDTTAISI | 318 |
| SEQ_ID_NO_351 | DGIEGKDFLD | MLLDVLE-DG | KAEIKITRDH | KALILDFLT | AGTDTTAIAI | 313 |
| SEQ_ID_NO_2553 | DDVKGTDFLD | MLLDVLE-DG | KAEIKITRDH | KALILDFFT | AATDTTAIAV | 318 |
| SEQ_ID_NO_364 | GGGEAKDFLD | MFLDIME-SG | KAEVKFTREH | LKALILDFFT | AGTDTTAIVC | 310 |
| SEQ_ID_NO_347 | GGGEVKDFLD | MLLDVME-SE | KSEVEFTREH | LKALILDFFT | AGTDTTAITT | 310 |
| SEQ_ID_NO_352 | NNEEAKDFLD | MLLDVME-SG | DTEVKFTREH | LKALILDFFT | AGTDTTAIAT | 315 |

Figure 13 (continued)

| | | | | | | | |
|---|---|---|---|---|---|---|---|
| SEQ_ID_NO_368 | EWAMSLLLNH | PKVLEKARQE | MDTLVGHERM | VEEDDLPKLR | YLHV ILETL | 363 |
| SEQ_ID_NO_346 | EWAMSLLLNH | PKVLEKARKE | LDTLVGHERM | VDEHDLPKLR | YLHCI VLETL | 363 |
| SEQ_ID_NO_365 | EWAMSLI LNH | PQVLEKARKE | LDTLVGHERM | VDEHDLPKLR | YLHCI VLETL | 363 |
| SEQ_ID_NO_348 | EWALAEMMKN | FA LKKAGGE | MDQVI GNNRR | LLESDI PNLP | YLRAI CKETF | 360 |
| SEQ_ID_NO_2546 | QWE AEVLNH | PKALKKLQEE | DRVVGPNRL | VDDSDI PNLP | YLQAVVKETL | 371 |
| SEQ_ID_NO_332 | QWMAEI I NN | SYI LERLREE | DSVVGKTRL | QETDLPNLP | CLQATVKEGL | 185 |
| SEQ_ID_NO_339 | QWMAEI I NN | SYI LERLREE | DSVVGKTRL | QETDLPNLP | CLQATVKEGL | 364 |
| SEQ_ID_NO_341 | QWAMAELLNH | PEAFQKVRKE | ELVFGNVRL | VDESDI TNLP | YLQAVVKETL | 361 |
| SEQ_ID_NO_2549 | QWT I AELI NH | PDVFKKVREE | DLAVGRTRL | VEESDI PNLP | YLQAVVKETL | 367 |
| SEQ_ID_NO_2544 | EWALAELI NN | PRVLQKAREE | VYSVVGKDRL | VDEVDTQNLP | YI RAI VKETF | 363 |
| SEQ_ID_NO_2541 | EWALAELI NN | PKVLEKAREE | VYSVVGKDRL | VDEVDTPNLP | YI GAI VKETF | 363 |
| SEQ_ID_NO_359 | EWALAELI NN | PKVLEKAREE | VYSVVGKDRL | VDEVDTQNLP | YI RAI VKETF | 363 |
| SEQ_ID_NO_370 | EWALAELI NN | PKVLEKAREE | VYSVVGKDRL | VDEVDTQNLP | YI RAI VKETF | 363 |
| SEQ_ID_NO_339 | DWE SELI NN | PRVMKKAREE | VDSVVGKDRL | VDESDI QNLP | YI RAVVKETF | 366 |
| SEQ_ID_NO_2550 | DWALSELI NN | PRVLKKAREE | VESVVGKDRL | VDEADI QNLP | YI RAI VKETF | 365 |
| SEQ_ID_NO_2543 | EWALAELI RN | PHVFKKAREE | DSTVGKERL | FKESDI PNLP | YLQAVVKETL | 366 |
| SEQ_ID_NO_2551 | EWSLAELI RN | PQVFKKAREE | DSVVGKERL | VKESDI PNLP | YLQAVVKETL | 367 |
| SEQ_ID_NO_2548 | EWALSELI NN | PDI LRRAQAE | LDAI VGASRL | ADESDI PRLP | YLQAI AKETL | 363 |
| SEQ_ID_NO_353 | EWALSELI NN | PPVLRKLQAE | LDAVVGGARL | ADESDI PSLP | YLQAVAKETL | 375 |
| SEQ_ID_NO_354 | EWALSELI NN | PPVLRKLQAE | LDAVVGGARL | ADESDI PSLP | YLQAVAKETL | 376 |
| SEQ_ID_NO_334 | EWALAELI NN | PNI LERAREE | DSVVGQSRL | VQESDI ANLP | YVQAI LKETL | 367 |
| SEQ_ID_NO_355 | EWALVELVKK | PSVLQKVREE | DNVVGKDRL | VEESDCPNLP | YLQAI LKETF | 363 |
| SEQ_ID_NO_349 | EWTLVELTNN | PKVLENARKE | AEVVGDERL | VQESDI PNLP | YI QAI I KETL | 368 |
| SEQ_ID_NO_351 | EWALVELI NN | PNALEKARQE | DQVI GOERL | VQESDTPNLP | YI QAI I KEAL | 363 |
| SEQ_ID_NO_2553 | EWTMVELI NN | PKVLEKAKKE | VDNVI GNSRL | VOESDAPNLP | YI QAI I KETL | 368 |
| SEQ_ID_NO_364 | EWAI AEVI NN | PNVLKKAQEE | I ANI VGFDRI | LQESDAPNLP | YLQALI KETF | 360 |
| SEQ_ID_NO_347 | EWAI AELI SN | PNVLKKAQEE | MDKVI GSQRL | LQESDAPNLP | YLNAI I KETF | 360 |
| SEQ_ID_NO_359 | EWAI AELI NN | PNVLKKAQEE | SRI I GTKRI | VQESDAPDLP | YLQAI I KETF | 365 |

Figure 13 (continued)

| SEQ_ID_NO | | | | | | | |
|---|---|---|---|---|---|---|---|
| SEQ_ID_NO_366 | RLFPSVPTLV | PHEPSEDCN | GGYNVPKGTM | LVNAWAIHR | DPKVV | DDPM | 412 |
| SEQ_ID_NO_348 | RLFPSVPTLV | PHEPSEDCKI | GGYNVPKGTM | VLVNAWAIHR | DPKVV | DDPL | 412 |
| SEQ_ID_NO_365 | RLFPSVPTLV | PHEPSEDCKI | GGYNVPKGTM | LVNAWAIHR | DPKVV | DDPL | 412 |
| SEQ_ID_NO_346 | RKHPSTPLNL | PRSNEPCIV | DGYYIPKNTR | LSVNIWAIGR | DPEVV | ENPL | 409 |
| SEQ_ID_NO_2546 | RVHPSLPLEI | FRKCREDCVV | NGYTIPKNSR | LVLNIYAINR | DPHEH | RDAD | 419 |
| SEQ_ID_NO_332 | RLHPPVPLV | LRTFKEGCTI | GGFYVPEKTT | LVVHGYAMMR | DPEYV | EDPQ | 233 |
| SEQ_ID_NO_338 | RLHPPVPLLV | LRTFKEGCTI | GGFYVPEKTT | LVVNGYAMMR | DPEYV | EDPQ | 412 |
| SEQ_ID_NO_341 | RLYPPAPLT | TRECROHCKI | NBFDVPPKTA | VAINLYAIMR | DPDSI | DNPN | 409 |
| SEQ_ID_NO_2542 | RLHPPAPLVA | TRECRKNCKI | GGFNIPEKTA | VAINLYAIMR | DPEIV | DDPT | 415 |
| SEQ_ID_NO_2544 | RMHPPLPLVV | KRKCVEECEI | EGCVIPEGAL | LFNVWAVGR | DPKYV | DRPS | 411 |
| SEQ_ID_NO_2541 | RMHPPLPLVV | KRKCTEECEI | NGYVIPEGAL | LFNVWQVGR | DPKYV | DRPS | 411 |
| SEQ_ID_NO_358 | RMHPPLPLVV | KRKCTEECEI | NGYVIPEGAL | LFNVWQVGR | DPKYV | DRPS | 411 |
| SEQ_ID_NO_360 | RMHPPLPLVV | KRKCTEECEI | NGYVIPEGAL | LFNVWQVGR | DPKYV | DRPS | 411 |
| SEQ_ID_NO_339 | RMHPPLPLVV | KRKCTEECEI | NGYVIPEGAL | VLFNVWAVGR | DPKYV | DRPL | 414 |
| SEQ_ID_NO_2550 | RMHPPLPLVV | KRKCVQECEL | NGYVIPEGAL | LFNVWAVDR | DPKYV | EBPS | 413 |
| SEQ_ID_NO_2543 | RMHPPTPLF | AREATRSCQV | DGYDVPAFSK | FINAWAIGR | DPHYV | DNPL | 414 |
| SEQ_ID_NO_2551 | RMHPPTPLF | AREAIRGCQV | DGYDIPANSK | FINAWAIGR | DPKYV | DNPQ | 415 |
| SEQ_ID_NO_2549 | RLHPAFPLV | VRRSTEPCKV | SGYDVPAGST | VFNVWAIGR | DPACWA | PDPL | 432 |
| SEQ_ID_NO_353 | RLHPTGPLV | VRRSLERATV | AGYDVPAGAT | VFYNVWAIGR | DAAWV | PEPT | 423 |
| SEQ_ID_NO_354 | RLHPTGPLV | VRRSLERATV | AGYDVPAGAT | VFYNVWAIGR | DAAWV | PEPT | 424 |
| SEQ_ID_NO_334 | RLHPTGPLI | LRESSESCTI | NGYEIPARTR | LFVNVWAINR | DPNYV | ENPL | 415 |
| SEQ_ID_NO_358 | RLHPPVPLMV | TRRCVAECTV | ENYVIPEDGL | LFVNVWSIGR | NPKFV | DNPL | 411 |
| SEQ_ID_NO_349 | RMHPPIPLMV | RKSIDNVTV | DGYDIRAGTM | LFVNIWSIGR | NPLYV | ESPL | 416 |
| SEQ_ID_NO_351 | RLHPPIPLML | IRKSTEHVIV | DGYDIPAGTL | LFVNIWSIGR | NPQCV | ETPL | 411 |
| SEQ_ID_NO_2553 | RLHPPIPLML | RKSIEKVTV | DGYEIPAGTM | LFVNIWSIGR | NAQYV | ESPL | 416 |
| SEQ_ID_NO_364 | RLHPPIPLML | ARKSISDCVI | DGYNPANTL | LFVNLWSMGR | NPKIV | DVPT | 408 |
| SEQ_ID_NO_347 | RLHPPIPLML | TRKSISDVVV | NGYTIPAKTL | LFVNLWSMGR | NPHYV | ENPM | 408 |
| SEQ_ID_NO_359 | RLHPPIPLML | SRKSTSDCTV | NGYKQAKSL | LFVNIWSIGR | NPHYV | ESPM | 413 |

Figure 13 (continued)

| SEQ_ID_NO_368 | SFKPDRFET | ......... | ........ | LE | VETHKLLPFG | MGRRGCPGAG | 443 |
|---|---|---|---|---|---|---|---|
| SEQ_ID_NO_348 | SFKPDRFET | ......... | ........ | ME | VETHKLLPFG | MGRRACPGAG | 443 |
| SEQ_ID_NO_365 | SFKPDRFET | ......... | ........ | ME | VETHKLLPFG | MGRRACPGAG | 443 |
| SEQ_ID_NO_346 | EFYPERFLS | ...SRNSKI | .D.... | PR | SNDFELIPFG | AGRR CASTR | 447 |
| SEQ_ID_NO_2545 | EFLPERYLVN | SGGGEENQLA | EPDELEAMK | | SQNFQYVPFG | GGRRGCPGAG | 469 |
| SEQ_ID_NO_332 | EFKPERFLAS | SRSSQND... | .E.... | R | DELLKYLPFG | NGRRACPGAN | 273 |
| SEQ_ID_NO_338 | EFKPERFLAS | SRSSQND... | .E.... | R | DELLKYLPFG | NGRRACPGAN | 452 |
| SEQ_ID_NO_341 | EFPERFLQE | CDHEDLSD. | .D.... | GK | RMKFNFVPFG | GGRRGCPGTA | 450 |
| SEQ_ID_NO_2542 | EFRPERFLVP | SKEDVDLD. | .Q.... | TK | GQNFNFVPFG | GGRRGCPGTL | 468 |
| SEQ_ID_NO_2544 | EFRPERFLEN | GGEGAVGPI | .D.... | LR | GQHFQLLPFG | SGRRMCPGVN | 463 |
| SEQ_ID_NO_2541 | EFRPERFLET | GAEGEAGPL | .D.... | LR | GQHFQLLPFG | SGRRMCPGVN | 463 |
| SEQ_ID_NO_355 | EFRPERFLET | GAEGEARPL | .D.... | LR | GQHFQLLPFG | SGRRMCPGVN | 463 |
| SEQ_ID_NO_360 | EFRPERFLET | GAEGEARPL | .D.... | LR | GQHFQLLPFG | SGRRMCPGVN | 453 |
| SEQ_ID_NO_339 | EFRPERFLEN | AGEGDAGSI | .D.... | LR | GQHFQLLPFG | SGRRMCPGVN | 458 |
| SEQ_ID_NO_2550 | EFRPERFLT | .AEGGATSI | .D.... | LR | GQNFELLPFG | SGRRMCPGVN | 463 |
| SEQ_ID_NO_2543 | VFNPERFLQ | SDDPSKSKI | .D.... | VR | GQYYQLLPFG | SGRRSCPGSS | 455 |
| SEQ_ID_NO_2551 | VYPERFLI | TDEPGKSKI | .D.... | VR | GQYYQLLPFG | SGRRSCPGSS | 458 |
| SEQ_ID_NO_2548 | AFRPERFLE | GGEGRGDSAG | LD.... | VR | GQHFHLLPFG | SGRRICPGAS | 475 |
| SEQ_ID_NO_353 | AFRPERFVS | SGGGGGTAA | .D.... | VR | GQHFHLLPFG | SGRRICPGAS | 464 |
| SEQ_ID_NO_354 | AFRPERFVS | SGGGGGTAA | .D.... | VR | GQHFHLLPFG | SGRRICPGAS | 465 |
| SEQ_ID_NO_334 | EFEPERFLC- | AGEIGKSQL | .D.... | VR | GQHFHFLPFG | SGRRGCPGTT | 458 |
| SEQ_ID_NO_356 | EFRPERFLK | LEDDSSDVV | .D.... | VR | GSHFQLLPFG | SGRRMCPGVS | 452 |
| SEQ_ID_NO_349 | EFKPHRFLD | ...HARNL | .D.... | VK | GCCFQLLPFG | TGRRGCPGIS | 454 |
| SEQ_ID_NO_351 | EFKPHRFLD | .GGDLKSSL | .D.... | K | GHNFQLLPFG | TGRRGCPGVN | 451 |
| SEQ_ID_NO_2553 | EFEPDRFFE | .GDFLKSSL | .D.... | K | GCSFQLLPFG | TGRRGCPGIN | 456 |
| SEQ_ID_NO_364 | AFQPERFLE | ...KEKAAI | .D.... | VK | GQHFELLPFG | TGRRGCPGML | 446 |
| SEQ_ID_NO_347 | EFRPERFLEK | GTSSI.... | .D.... | VK | GQHFELLPFG | TGRRGCPGML | 446 |
| SEQ_ID_NO_359 | EFRPERFLEK | GRESI.... | .D.... | VK | GQHFELLPFG | TGRRGCPGML | 451 |

Figure 13 (continued)

| | | | | | | | |
|---|---|---|---|---|---|---|---|
| SEQ_ID_NO_368 | LAKKFVGLAL | ASLIQCFDWE | R | SA-EKI | ·······DLK | EGAI RI | TLPK | 483 |
| SEQ_ID_NO_349 | LAQKFVGLAL | GSLIQCFDWE | R | TSP-EKI | ·······DLN | EGSG | TLPK | 482 |
| SEQ_ID_NO_365 | LAQKFVGLAL | GSLIQCFEWE | R | MSA-EKI | ·······DLN | EGSG | TLPK | 482 |
| SEQ_ID_NO_346 | MGI VMVEYI L | GTLV HSFDWK | L | PSEV ELL | ·······NME | EAFG | LALQK | 487 |
| SEQ_ID_NO_2548 | LARAVLHRTL | GVLIQCFDWK | | KGAF-EKL | ·······NME | QGVG | FSEAM | 508 |
| SEQ_ID_NO_332 | LAYI SVGTAI | GVMVQCFDWE | | ···KGDKI | ·······NMD | EAPGKI | TLTM | 312 |
| SEQ_ID_NO_339 | LAYI SVGTAI | GVMVQCFDWE | | ···KGDKI | ·······NMD | EAPGKI | TLTM | 491 |
| SEQ_ID_NO_341 | LAFSL NNTAV | AAMVQCFDWK | | GKDGKGEKV | ·······DME | SGSG | NSLSM | 492 |
| SEQ_ID_NO_2549 | LAFAMNNTTV | AAIVQCFDWK | L | GSDGDGSKV | ·······DMQ | SGPG | LTLSM | 498 |
| SEQ_ID_NO_2544 | LSTSGMATLL | ASVIQCFDLQ | V | LDPQGHVL | KGDDAKVSME | ERAG | LTVPR | 501 |
| SEQ_ID_NO_2541 | LATSGMATLL | ASLIQCFDLQ | V | LGPQGQIL | KGGDAKVSME | ERAG | LTVPR | 501 |
| SEQ_ID_NO_358 | LATSGMATLL | ASLIQCFDLQ | V | LGPQGQIL | KGGDAKVSME | ERAG | LTVPR | 501 |
| SEQ_ID_NO_360 | LATSGMATLL | ASLIQCFDLQ | V | LGPQGQIL | KGGDAKVSME | ERAG | LTVPR | 501 |
| SEQ_ID_NO_329 | LATAGMATLL | SSVLQCFELQ | V | AGPNGQIL | KGADAKVSMD | ERPG | LTVPR | 504 |
| SEQ_ID_NO_2550 | LATAGMATLL | ASVIQCFDLQ | V | VGLKGKLL | KGSDAKVSME | ESPG | LTVPR | 501 |
| SEQ_ID_NO_2543 | LALLVI QATL | ASLIQCFDWW | V | NDGKSHD | ·······DMS | EVGR | VTVFL | 496 |
| SEQ_ID_NO_2551 | LALLVI QATL | ASLVQCFDWW | V | NDGKNSEI | ·······DMS | EEGR | VTVFL | 497 |
| SEQ_ID_NO_2548 | LAMLVVQAAL | AAMLQCFEVA | P | VGG-ATM | ·······DME | EGPG | TLPR | 514 |
| SEQ_ID_NO_353 | LAMLVVQAAL | AAMVQCFEWS | P | VGG-APV | ·······DME | EGPG | LTLPR | 503 |
| SEQ_ID_NO_354 | LAMLVVQAAL | AAMVQCFEWS | P | VGG-APV | ·······DME | EGPG | LTLPR | 504 |
| SEQ_ID_NO_324 | LALQMVQTGL | AAMIQCFDWK | V | NGFM··· | ·······DMQ | EGTG | TLPR | 493 |
| SEQ_ID_NO_352 | LAMQEVPALL | GAIIQCFDFH | V | VGPKGEIL | KGDD VI NVD | ERPG | TAPR | 500 |
| SEQ_ID_NO_349 | LAMRELPVVI | AGLIQCFEWN | A- | NDK-EVL | ·······GMD | ERAG | TAPR | 493 |
| SEQ_ID_NO_351 | LAMRELSVVI | ANLIQCFDWD | V | VGE-RLL | ·······NTD | ERAG | TAPR | 490 |
| SEQ_ID_NO_2553 | LAMRELPVVI | AGLIQCFEWD | V | NNK-ERL | ·······ITD | ERAG | TAPR | 485 |
| SEQ_ID_NO_364 | LAI QEVVII I | GTMIQCFDWK | L | PDGSGHV | ·······DMA | ERPG | LTAPR | 466 |
| SEQ_ID_NO_347 | LGMQELFSI I | GAMVQCFDWK | L | PDGV-KSM | ·······DMT | ERPG | LTAPR | 488 |
| SEQ_ID_NO_359 | LAI QEVVSI I | GTMVQCFDWK | L | ADGSGNNV | ·······DMT | ERSG | LTAPR | 492 |

Figure 13 (continued)

| SEQ_ID_NO | Sequence | | | | Number |
|---|---|---|---|---|---|
| SEQ_ID_NO_368 | ATTLEAMCKP | RHVMEKVLRQ | VSNV | | 507 |
| SEQ_ID_NO_348 | AKTLEAMCKP | RHVMEKVLRQ | VSNV | | 506 |
| SEQ_ID_NO_365 | AKTLEAMCKP | RHIMERVLRQ | VSNV | | 506 |
| SEQ_ID_NO_346 | AVPLEAMVTP | RLP DVYAPL | A | | 506 |
| SEQ_ID_NO_2546 | VHPLICYPVV | R----VNPL | ETAN | | 527 |
| SEQ_ID_NO_332 | AHPLNCTLVP | RTLIPVTSTV | DIPSS | | 337 |
| SEQ_ID_NO_338 | AHPLNCTLVP | RTLIPVTSTV | DIPSS | | 516 |
| SEQ_ID_NO_341 | VHPLICVPVV | H----FIPY | D | | 509 |
| SEQ_ID_NO_2549 | LHPLKCHPIV | H----FNPF | EG | | 515 |
| SEQ_ID_NO_2544 | KHNLVCLPLA | K-TTLAAKL | LSP | | 522 |
| SEQ_ID_NO_2541 | AHSLVCVPLA | R-IGVASKL | LS | | 521 |
| SEQ_ID_NO_359 | AHSLVCVPLA | R-IGVASKL | LS | | 521 |
| SEQ_ID_NO_360 | AHSLVCVPLA | R-IGVASKL | LS | | 521 |
| SEQ_ID_NO_339 | AHNLVCVPLA | R-PGAAAKL | LSS | | 525 |
| SEQ_ID_NO_2550 | AHNLMCVPLA | R-TNVTSE | LSS | | 522 |
| SEQ_ID_NO_2543 | AKPLKCKPVP | H----FVPF | SSA | | 514 |
| SEQ_ID_NO_2551 | AKPLKCKPVP | R----FVPF | SA | | 514 |
| SEQ_ID_NO_2548 | KRPLVCTVKA | R----LHPV | PVPTAAAADN | GVDGTLHCA | 546 |
| SEQ_ID_NO_353 | KRPLVCTVSP | R----HPL | PAAASASLT | | 527 |
| SEQ_ID_NO_354 | KRPLVCTVSP | R----HPL | PAAASASLT | | 528 |
| SEQ_ID_NO_334 | AHPLICVPVA | R----LNPF | PSF | | 511 |
| SEQ_ID_NO_356 | AHNLVCVPVD | RTSGGGPLKI | EC | | 523 |
| SEQ_ID_NO_349 | AVDLEFVPLM | R-CNCPNIF | VSA | | 514 |
| SEQ_ID_NO_351 | AVDFVCVPLE | R-GNTLKI | LGSN | | 511 |
| SEQ_ID_NO_2553 | AVDFVCVPSM | R-ENCPKVF | | | 513 |
| SEQ_ID_NO_364 | ETDLFCRVVP | R----VDPL | VVSTD | | 506 |
| SEQ_ID_NO_347 | ANDLVCQLVP | R----DPV | VVSGP | | 506 |
| SEQ_ID_NO_359 | AFDLVCRLYP | R----VDPA | TSGA | | 512 |

Figure 14

| SEQ_ID | Sequence | # |
|---|---|---|
| SEQ_ID_NO_475 | ----------MSS-------------------RL------YVGN | 9 |
| SEQ_ID_NO_436 | MAFCNKLGNL LRQGATQS-- -----SHAP VSSMLNYLRH MSSSKLFIGG | 42 |
| SEQ_ID_NO_420 | MAFLSKVGKI FRQTSAHVTA SNSMLQSI-- --------RC MSSSKIFVGG | 40 |
| SEQ_ID_NO_473 | ----------MAASDV-------EF---------RC------FVGG | 14 |
| SEQ_ID_NO_369 | ----------MAGGE--------EF---------RC------FVGG | 13 |
| SEQ_ID_NO_371 | ----------MASADV-------EF---------RC------FVGG | 14 |
| SEQ_ID_NO_372 | ----------MASADV-------EF---------RC------FVGG | 14 |
| SEQ_ID_NO_373 | ------------MAEV-------EY---------RC------FVGG | 12 |
| SEQ_ID_NO_458 | ------------MADV-------EY---------RC------FVGG | 12 |
| SEQ_ID_NO_597 | ------------MADV-------EY---------RC------FVGG | 12 |
| SEQ_ID_NO_455 | ----------MAAADV-------EY---------RC------FVGG | 14 |
| SEQ_ID_NO_477 | ----------MAAADV-------EY---------RC------FVGG | 14 |
| SEQ_ID_NO_465 | ----------MAASDV-------EY---------RC------FVGG | 14 |
| SEQ_ID_NO_488 | ----------MAAPDV-------EY---------RC------FVGG | 14 |
| SEQ_ID_NO_494 | ----------MAAPDV-------EY---------RC------FVGG | 14 |
| SEQ_ID_NO_374 | -----------MDAEV-------EY---------RC------FVGG | 13 |
| SEQ_ID_NO_441 | ------------MAEV-------EY---------RC------FVGG | 12 |
| SEQ_ID_NO_444 | ----------MASADV-------EY---------RC------FVGG | 14 |
| SEQ_ID_NO_451 | ------------MGDV-------EY---------RC------FVGG | 12 |
| SEQ_ID_NO_505 | ------------MAEV-------EY---------RC------FVGG | 12 |
| SEQ_ID_NO_474 | ------------MAEV-------EY---------RC------FVGG | 12 |
| SEQ_ID_NO_447 | ------------MAEV-------EY---------SC------FVGG | 12 |
| SEQ_ID_NO_450 | -----------MAAEV-------EY---------SC------FVGG | 13 |
| SEQ_ID_NO_434 | ----------MGSSDV-------EY---------RC------FVGG | 14 |
| SEQ_ID_NO_437 | ----------MAAADI-------EY---------RC------FVGG | 14 |
| SEQ_ID_NO_438 | -----------MSADI-------EY---------RC------FVGG | 13 |
| SEQ_ID_NO_454 | -------------MAE-------EY---------RC------FVGG | 11 |
| SEQ_ID_NO_392 | -----------MSAEV-------EY---------RC------FVGG | 13 |
| SEQ_ID_NO_425 | ----------MASAEV-------EF---------RC------FVGG | 14 |
| SEQ_ID_NO_504 | ----------MASAEI-------EF---------RC------FVGG | 14 |
| SEQ_ID_NO_368 | ----------MASGDV-------EY---------RC------FVGG | 14 |
| SEQ_ID_NO_422 | ----------MASPDV-------EY---------RC------FVGG | 14 |
| SEQ_ID_NO_596 | ----------MASADV-------EF---------RC------FVGG | 14 |
| SEQ_ID_NO_433 | -----------M-ADV-------ED---------RC------FVGG | 12 |
| SEQ_ID_NO_376 | ----------MASADV-------EY---------RC------FVGG | 14 |
| SEQ_ID_NO_440 | ----------MASADV-------EY---------RC------FVGG | 14 |

Figure 14 (continued)

| | | | | | | | |
|---|---|---|---|---|---|---|---|
| SEQ_ID_NO_475 | LSWNAKEEDL | RTYFGKFGEV | EEASIALDRE | SGRSRGFGFV | TLPADVALKD | 58 |
| SEQ_ID_NO_436 | LSYGVDDQSL | KDAFASYGEV | VEARVITDRD | TGRSRGFGFV | NFTSDESATS | 92 |
| SEQ_ID_NO_420 | ISYSTDEFGL | REAFSKYGEV | VDAKIIVDRE | TGRSRGFAFV | TFTSTEEASN | 90 |
| SEQ_ID_NO_473 | LAWATDDASL | ERAFSTYGDI | VESKIINDRE | TGRSRGFGFV | TFRDEQSMRD | 64 |
| SEQ_ID_NO_369 | LAWATTDGRL | EGAFRPFGEV | VQSKVISDRE | TGRSRGFGFV | TFADENSMNA | 63 |
| SEQ_ID_NO_371 | LAWSTDDRSL | QEAFSPYGEV | VESKIISDRE | TGRSRGFGFV | TFNDEQSMRD | 64 |
| SEQ_ID_NO_372 | LSWSTDDRSL | KDAFTAFGEV | MDSKVVSDRE | TGRSRGFGFV | TFMDEQSMRD | 64 |
| SEQ_ID_NO_373 | LSWGTDDRSL | AFAFNKFGEV | TDSKIINDRE | TGRSRGFGFV | TFANEQSMRD | 62 |
| SEQ_ID_NO_458 | LAWATDDQSL | DNAFSKYGDV | FDSKIITDRE | TGRSRGFGFV | TFASDEAMRD | 62 |
| SEQ_ID_NO_507 | LRWATDDQSL | QNAFSKYGDV | IDSKIITDRE | TGRSRGFGFV | TFASDEAMRD | 62 |
| SEQ_ID_NO_455 | LAWATNNETL | EQAFANFGQV | IDSKVITDRE | TGRSRGFGFV | TFSSEQSMLD | 64 |
| SEQ_ID_NO_477 | LAWATDNASL | QQAFASYGDV | LDSKVITDRE | TGRSRGFGFV | TFSSEQSMLD | 64 |
| SEQ_ID_NO_465 | LAWATDDHSL | HNAFSTYGEV | LESKIILDRE | TDRSRGFGFV | TFSTEEAMRN | 64 |
| SEQ_ID_NO_488 | LAWATDDRSL | FAAFSTYGEI | LDSKIINDRE | TGRSRGFGFV | TFSSEQSMRD | 64 |
| SEQ_ID_NO_494 | LAWATDDRSL | EAAFSTYGEI | LDSKIINDRE | TGRSRGFGFV | TFSSEQSMRD | 64 |
| SEQ_ID_NO_374 | LAWATDDQSL | ERAFSNYGQV | LESKIINDRE | TGRSRGFGFV | TFSSEQAMRD | 63 |
| SEQ_ID_NO_441 | LAWATNDESL | EQAFSQFGDI | TDSKIINDRE | TGRSRGFGFV | TFKDEKSMRD | 62 |
| SEQ_ID_NO_444 | LAWATTDQSL | SEAFSQYGEI | LESKIINDRE | TGRSRGFGFV | TFKDEQSMRD | 64 |
| SEQ_ID_NO_451 | LAWATTDNTL | SEAFSQYGEV | VESKIINDRE | TGRSRGFGFV | TFKDEQAMRD | 62 |
| SEQ_ID_NO_505 | LAWATTDQTL | GDAFSQFGEI | LDSKIINDRE | TGRSRGFGFV | TFKDEKAMRD | 62 |
| SEQ_ID_NO_474 | LAWATTDQTL | GDAFSQYGEI | LDSKIINDRE | TGRSRGFGFV | TFKDEQAMRD | 62 |
| SEQ_ID_NO_447 | LAWATTDRTL | ADAFGTYGEV | LDSKIINDRE | TGRSRGFGFV | TFKDEKCMRD | 62 |
| SEQ_ID_NO_450 | LAWATTDRTL | SDAFSTYGEV | VDSKIINDRE | TGRSRGFGFV | TFKDEKSMKE | 63 |
| SEQ_ID_NO_434 | LAWATDSDAL | EQAFSKFGEI | TDSKVINDRE | TGRSRGFGFV | TFAEEKSMRD | 64 |
| SEQ_ID_NO_437 | LAWATSDKAL | EEAFSAYGEV | LESKIINDRE | TGRSRGFGFV | TFNNEKSMRD | 64 |
| SEQ_ID_NO_438 | LAWATTDQSL | QEAFSPYGEI | LDSKIINDRE | TGRSRGFGFV | TFNNEKSMRD | 63 |
| SEQ_ID_NO_454 | LAWATNDQSL | EQAFSQFGEI | TDCKIINDRE | TGRSRGFGFV | TFSSSESMKN | 61 |
| SEQ_ID_NO_392 | LAWATTDQVL | QEAFSQYGEI | FDSKIINDRE | TGRSRGFGFV | TFGNEKAMRD | 63 |
| SEQ_ID_NO_425 | LAWATDHDAL | EKAFSQFGEI | VESKVINDRE | TGRSRGFGFV | TFATEQAMRD | 64 |
| SEQ_ID_NO_504 | LAWATDNDAL | ERAFSPFGEI | IESKIINDRE | TGRSRGFGFV | TFSNEKAMRD | 64 |
| SEQ_ID_NO_368 | LAWATDDRAL | ETAFAQYGDV | IDSKIINDRE | TGRSRGFGFV | TFKDEKAMKD | 64 |
| SEQ_ID_NO_422 | LAWATDDRAL | ETAFSQYGEV | LDSKIINDRE | TGRSRGFGFV | TFKDEKSMKD | 64 |
| SEQ_ID_NO_506 | LAWATTDSSL | HEAFSAYGDI | LESKIINDRE | TGRSRGFGFV | TFRDEKSMRD | 64 |
| SEQ_ID_NO_433 | LAWATDNDAL | EKAFSQYGEI | VDSKIINDRE | TGRSRGFGFV | TFANEKSMND | 62 |
| SEQ_ID_NO_376 | LAWATDDRAL | EEAFSVYGEI | VESKIINDRE | SGRSRGFGFV | TFRDEKSMRD | 64 |
| SEQ_ID_NO_440 | LAWATDDHAL | EQAFSQYGEV | VESKIINDRE | TGRSRGFGFV | TFSNEKSMND | 64 |

Figure 14 (continued)

| SEQ_ID_NO_475 | AI EKTNGAEF | MGRNI KVNEA | SPPGER- PPR | TNN- · · · · · Y | GGGYGDFN- - | 99 |
|---|---|---|---|---|---|---|
| SEQ_ID_NO_436 | ALSAMDGQDL | NGRNI RVSYA | NDRPSA- · · · | · · · · · · · · · · · · | · · · · P- · · · | 119 |
| SEQ_ID_NO_420 | AMQ- LDGQDL | HGRRI RVNYA | TERGSGFGGR | G- · · · · · · · F | GGP- · · · · · · · | 124 |
| SEQ_ID_NO_473 | AI KGMNGQTL | DGRNI TVNEA | EVFAAA- YAA | · · · · · · · · · G | TAAAAEVAVT | 104 |
| SEQ_ID_NO_369 | AI KEMNGQEL | DGRNI TVNQA | QSRGGG- GGG | GG- · · · · · · G | GGGYGR- · · · | 101 |
| SEQ_ID_NO_371 | AI DAMNGKML | DGRSI TVNPA | QSRGNG- GGG | GGG- · · · · · G | SRGYR- · · · · | 102 |
| SEQ_ID_NO_372 | AI EGMNGRDL | DGRNI TVNRA | QARGGG- GGG | GG- · · · · · · G | GGGYRG- · · · | 102 |
| SEQ_ID_NO_373 | AI DEMNGKEL | DGRSI TVNEA | QSRGSG- GGG | · · · · · · · · · G | GGGYRS- · · · | 98 |
| SEQ_ID_NO_458 | AI EAMNGQDL | DGRNI TVNEA | HSRRBG- GGG | GGFSGG- · · G | GGGYGGQRRE | 108 |
| SEQ_ID_NO_507 | AI EAMNGQDL | DGRNI TVNEA | QSRRSD- GGG | GFGG- · · · · G | GGGYGGQRRE | 106 |
| SEQ_ID_NO_455 | AI ENMNGKEL | DGRNI TVNQA | QSRGGG- GGG | GGYGG- · · · G | GGGY- · · · · · | 103 |
| SEQ_ID_NO_477 | AI EAMNGKDL | DGRNI TVNQA | QSRGGG- · · · | · · · · · · · · · G | GGGY- · · · · · | 95 |
| SEQ_ID_NO_465 | AI EGMNGKEL | DGRNI TVNEA | QSRGGR- GG- | · · · · · · · · · G | GGGYG- · · · · | 98 |
| SEQ_ID_NO_488 | AI EGMNGKEL | DGRNI TVNEA | QSRRBG- GGG | · · · · · · · · · G | GGGY- · · · · · | 98 |
| SEQ_ID_NO_494 | AI EGMNGKEL | DGRNI TVNEA | QSRRBG- GGG | GGYGG- · · · G | GGGY- · · · · · | 103 |
| SEQ_ID_NO_374 | AI EGMNGQDL | DGRNI TVNEA | QSRGSG- GGG | GGYRGG- · · G | GGGY- · · · · · | 103 |
| SEQ_ID_NO_441 | AI EGMNGQEL | DGRNI TVNEA | QSRGSG- GGG | GRREG- · · · G | GGGY- · · · · · | 101 |
| SEQ_ID_NO_444 | AI EGMNGQTL | DGRNI TVNEA | QSRGSG- GN- | · · · · · · · · · G | GGGFRGPRRD | 103 |
| SEQ_ID_NO_451 | AI EGMNGQDL | DGRNI TVNEA | QSRGGG- GGG | GGR- · · · · · G | GGGYGGGRRE | 105 |
| SEQ_ID_NO_505 | AI EGMKGQDL | DGRNI TVNEA | QSRGSG- GGG | · · · · · · · · · G | GGGYR- · · · · | 97 |
| SEQ_ID_NO_474 | AI EGMNGQDL | DGRNI TVNEA | QSRGSG- GGG | GG- · · · · · · Y | RGG- - R- · · · | 98 |
| SEQ_ID_NO_447 | AI EGMNGQEL | DGRSI TVNEA | QARGSG- GGG | GG- · · · · · · Y | GGGRRE- · · · | 100 |
| SEQ_ID_NO_450 | AI SGMNGSEL | DGRNI TVNEA | QARGSG- GGG | G- · · · · · · · G | GGGFGGGRRR | 104 |
| SEQ_ID_NO_434 | AI EEMNGQDI | DGRNI TVNEA | QSRGSG- GGG | RGGGGGGYGG | GGGYGG- · · · | 109 |
| SEQ_ID_NO_437 | AI EGMNGQNL | DGRNI TVNEA | QSRGGG- GG- | · · · · · · · · · G | GGGYR- · · · · | 98 |
| SEQ_ID_NO_438 | AI QGMNSQEL | DGRNI TVNEA | QSRGSG- GGG | · · · · · · · · · G | GGGYSR- · · · | 99 |
| SEQ_ID_NO_454 | AI EGMNGQDL | DGRNI TVNEA | QSRSGG- · · · | · · · · · · · · · G | GGGY- · · · · · | 92 |
| SEQ_ID_NO_392 | AI DGMNGQDL | DGRNI TVNEA | QSRGSG- GGG | G- · · · · · · · G | GGGYNR- · · · | 100 |
| SEQ_ID_NO_425 | AI EGMNGQNL | DGRNI TVNEA | QSRGKGGGGG | GGGYGG- · · G | GGGY- · · · · · | 105 |
| SEQ_ID_NO_504 | AI EGMNGQNL | DGRNI TVNEA | QSRGSG- GGG | GG- · · · · · · N | GGGYSR- · · · | 102 |
| SEQ_ID_NO_368 | AI EGMNGQDL | DGRSI TVNEA | QSRGSG- GGG | GHRGG- · · · G | GGGY- R- · · · | 104 |
| SEQ_ID_NO_422 | AI EGMNGQDL | DGRSI TVNEA | QSRGSG- GGG | GGRG- · · · · G | GGGYR- · · · · | 103 |
| SEQ_ID_NO_506 | AI EGMNGQNL | DGRNI TVNEA | QSRGSG- GGG | GGGYGSR- - G | GGGY- · · · · · | 105 |
| SEQ_ID_NO_433 | VI EAMNGQDL | DGRNI TVNQA | QSRGSG- GGG | GGR- · · · · · G | GGGY- · · · · · | 99 |
| SEQ_ID_NO_376 | AI EGMNGQNL | DGRNI TVNEA | QSRRBG- GGG | GEGYGG- · · G | SGGYKR- · · · | 106 |
| SEQ_ID_NO_440 | AI EGMNGQNL | DGRNI TVNEA | QSRGSG- GGG | GRREGG- · · G | GGGYGR- · · · | 106 |

Figure 14 (continued)

| SEQ_ID_NO_475 | GNGGGRDYG | ---------- | RGGYGRG- | ------NGGY | GGRNAG- YGG | 128 |
|---|---|---|---|---|---|---|
| SEQ_ID_NO_436 | RGGG- GGY- | ---------- | -GGGY- --- | ---------- | ------G- DGF | 134 |
| SEQ_ID_NO_420 | GGGNAGGYGA | P--------- | -SGGYGGG- | ------GGY | -----G- GGA | 149 |
| SEQ_ID_NO_473 | EVVG- ---- | ---------- | -TAATAGTA- | ---------- | -----V- DRR | 120 |
| SEQ_ID_NO_369 | REQGGGGY- | ---------- | -GGGYGGSR- | ------GGG- | -----D- REG | 124 |
| SEQ_ID_NO_371 | GGGG- ---- | ---------- | -GGGYGGSRD | RG----DRGY | -----G- GGG | 125 |
| SEQ_ID_NO_372 | GGGG- ---- | ---------- | -SGGYGGGG- | ------SGGY | ESRRSG- GGG | 127 |
| SEQ_ID_NO_373 | GGGG- ---- | ---------- | -GGGYGGG- | ------GGGY | GGRREG- GGG | 122 |
| SEQ_ID_NO_458 | GGGGGGGY- | ---------- | -GGGRSGG- | ------GGY | GS---R- EGG | 133 |
| SEQ_ID_NO_507 | GGGG- -GYGG | G--------- | -GGGYGGG-R | ---------- | -----S- GGG | 127 |
| SEQ_ID_NO_455 | GGREGGGYGG | G--------- | -GGGYGGRRE | G-----GGGY | GGGGYG- GGG | 137 |
| SEQ_ID_NO_477 | GGGRQGGYGG | G--------- | -GGGYGGGGG | ------GGGY | GG---G- RRE | 125 |
| SEQ_ID_NO_465 | GGRGGGGYGG | GGRRDG---- | -GGGYGGG- | ------GGGY | --------GGG | 128 |
| SEQ_ID_NO_488 | GGGG- GGYGG | GRG------- | -GGGYGGGG- | ------GGGY | GRREGGY GGG | 132 |
| SEQ_ID_NO_494 | GGGGGGGYGR | R--------- | -EGGYGGG- | ---------- | -----G- GYG | 125 |
| SEQ_ID_NO_374 | GGRREGGYNR | GG-------- | -GGGYGGG- | ------GGGY | -----G- GGG | 130 |
| SEQ_ID_NO_441 | -GGG- GGYGG | RREGGG---- | -GGGYGGRR- | ---------- | -----E- GGG | 127 |
| SEQ_ID_NO_444 | GGGG- GGYGG | GRR------- | -DGGYGGN- | ------GGY | GG---G- RRE | 131 |
| SEQ_ID_NO_451 | GGGG- -GYGG | ---------- | -GGGYGGRR | E--------- | -----G- GGG | 127 |
| SEQ_ID_NO_505 | GGGG- GGYGG | GGRR------ | -EGGYGGG- | ------GGY | GG---G- RRE | 126 |
| SEQ_ID_NO_474 | GGGG- GGYGG | GGRR------ | -EGGYGGG- | ------GGGY | GG---G- RRE | 128 |
| SEQ_ID_NO_447 | GGGG- -GYGG | G--------- | -GGGYGGGRR | ---------- | -----E- GGG | 122 |
| SEQ_ID_NO_450 | EGGG- GGYGG | ---------- | -GGGYRGGG- | ------GGGY | -------GGG | 128 |
| SEQ_ID_NO_434 | GGGCYGGGGC | RRDGGYSRSG | GGGGYGGGG- | ------DRGY | G---G- GGG | 147 |
| SEQ_ID_NO_437 | NGGG- GGYGG | GRR------- | -EGGYGGG- | ------GGY | -----S- RGG | 124 |
| SEQ_ID_NO_438 | GGGG- GGYGG | GGRR------ | -EGGYGGG- | ------GGGY | NSRS-S- GGG | 131 |
| SEQ_ID_NO_454 | SRGG- ---- | ---------- | ---------- | ---------- | ------------ | 96 |
| SEQ_ID_NO_392 | NSGG- GGYGG | GGRREG---- | -GGGYSRG- | ------GGGY | GG---G- GGG | 132 |
| SEQ_ID_NO_425 | GGGG- -GYSR | G--------- | -GGGYGGGGG | RR----EGGY | NR---N- GGG | 135 |
| SEQ_ID_NO_504 | GGGG- GGYGG | ---------- | -GGGYGGGGR | R-----EGCG | GGYSRG- GGG | 134 |
| SEQ_ID_NO_368 | SGGG- GGYSG | --G------- | -GGSYGGGG- | ---------- | ------------ | 122 |
| SEQ_ID_NO_422 | SGGG- GGYGG | G--------- | -GGGYGGGGR | ------EGGY | -----S- GGG | 130 |
| SEQ_ID_NO_506 | GGGGRRESGG | ---------- | -GGGYGGSR- | --------GY | -----G- GGG | 129 |
| SEQ_ID_NO_433 | GGGG- ---- | ---------- | ---------- | ---------- | ------------ | 103 |
| SEQ_ID_NO_376 | SGGG- GGYGR | --R------- | -EGGYGGGRR | EGVFWNGGGY | DG---G- GGG | 141 |
| SEQ_ID_NO_440 | REGG- GGYSR | GGG------- | -GGGYGGG- | ------GGGY | G---G- GNG | 134 |

Figure 14 (continued)

| | | | | | | | |
|---|---|---|---|---|---|---|---|
| SEQ_ID_NO_475 | RGNFG- -GQG | ----- | GYGD | NRFGNDNFGG | SYGGRGGYRG | -PRGPSAEEN | 169 |
| SEQ_ID_NO_436 | SNRGG- -GGG | ----- | ----- | ----- | ----- | ----- | 142 |
| SEQ_ID_NO_420 | GGYGA- -PGG | ----- | GYGX | ---WWWL-RR | RCWWLRC--- | ----- | 174 |
| SEQ_ID_NO_473 | MGTGG- ---- | ----- | ----- | ----- -AK | AVVRLPR--- | ----- | 134 |
| SEQ_ID_NO_369 | SGYGG- -SRG | G----- | GYG- | ----- -GG | GGGGYGG- -R | -GG------ | 148 |
| SEQ_ID_NO_371 | GGYGG- -GGG | ----- | GYG- | ----- -GG | GGSRYGG- -- | -GG------ | 147 |
| SEQ_ID_NO_372 | SGGGGYSGGG | RERSERGYGG | GSRN---- | -GG | GYGGYSG- GG | -GGGSRYGGG | 171 |
| SEQ_ID_NO_373 | GGYGG- -GSG | G----- | GYGG | ---RRE- -GG | GGGGYGG- -G | -GGGGYRG-- | 155 |
| SEQ_ID_NO_458 | GGYGG- -GGG | ----- | GYGG | SRGGS--- -GG | GGGGYGGSRG | -G------ | 163 |
| SEQ_ID_NO_507 | GGYGSRDGGG | G----- | GYL- | ----- -GG | GGGGYGG- -S | RGG------ | 153 |
| SEQ_ID_NO_455 | GGYGGREGGG | ----- | GYGG | ----- -GG | GYGGNRG--- | ----- | 160 |
| SEQ_ID_NO_477 | GGYGG- -GGG | GGRREGGYG- | ----- | -GG | GYGSRG--- | ----- | 150 |
| SEQ_ID_NO_465 | GGYGG- -GGG | ----- | GYGG | ----- -GN | RGGGYGN--- | ----- | 149 |
| SEQ_ID_NO_488 | GGYGGGRGGG | G----- | GYG- | ----- -GS | RGGGYGG--- | ----- | 155 |
| SEQ_ID_NO_494 | GGGRGG- -GGG | ----- | GYG- | ----- -GS | RGGGYGG--- | ----- | 145 |
| SEQ_ID_NO_374 | GGYGG- -GGG | ----- | GYCG | ----- -GR | REGGYGG- -G | -GGDRYARG- | 160 |
| SEQ_ID_NO_441 | GGYGG- -GGG | ----- | GYGG | RR----- -EG | GDGGYGG--- | ----- | 150 |
| SEQ_ID_NO_444 | GGYGG- -GDR | ----- | GYG- | ----- -GG | GGGGSRYSRG | -GG------ | 156 |
| SEQ_ID_NO_451 | GGYSG- -GGG | ----- | GYGG | GRREGGY- -GG | GGGGYGGGDR | YSDRSSRGGG | 168 |
| SEQ_ID_NO_505 | GGYGG- -GGG | G----- | GYCG | ----- -GR | REGGYGG--- | ----- | 148 |
| SEQ_ID_NO_474 | GGYGG- -GGG | ----- | YGG | ----- -GR | REGGYGG--- | ----- | 148 |
| SEQ_ID_NO_447 | GGYGG- -GRR | ----- | ----- | ----- -EG | GGGGYGG--- | ----- | 139 |
| SEQ_ID_NO_450 | RREGG- -GGG | ----- | GYGG | GRRE---- -GG | GGGGYGG--- | ----- | 153 |
| SEQ_ID_NO_434 | GGYGG- -GRD | R----- | GYGG | ----- -GG | GDRGYGG- GG | -GGDRYSRGG | 180 |
| SEQ_ID_NO_437 | GGYGG- -GGG | ----- | GYG- | ----- -GG | RDRGYGGGGD | -GGSRYSRGG | 156 |
| SEQ_ID_NO_438 | GGYGG- -GRD | Q----- | GYGG | ----- -GG | GGSRYSR- -G | -GG------ | 156 |
| SEQ_ID_NO_454 | ----- -GGG | ----- | ----- | ----- | ----- | ----- | 99 |
| SEQ_ID_NO_392 | YGSGG- -GGG | ----- | GYG- | ----- -GG | RDRGYGD--- | -GGSRYSSR | 160 |
| SEQ_ID_NO_425 | GGYGG- -GGG | GYGGGGGYGG | ----- | -GG | RDRGYGG- -D | -GGSRYSRGG | 172 |
| SEQ_ID_NO_504 | GGYGS- -GGG | ----- | GYGG | G----- -GR | REGGYGGGEG | -GGARYSRGS | 168 |
| SEQ_ID_NO_368 | -GRRE- -GGG | ----- | GYG- | ----- -GG | EGGGYGG- -S | -GG------ | 144 |
| SEQ_ID_NO_422 | GGYSSRGGGG | G----- | GYGG | GGRRD--- -GG | EGGGYGG- -S | -GG------ | 162 |
| SEQ_ID_NO_506 | GGYGGRREGG | YSRDG- GYG- | ----- | -GD | GGSRYSR- -S | -GA------ | 159 |
| SEQ_ID_NO_433 | ----- ----- | ----- | ----- | ----- | ----- | ----- | 103 |
| SEQ_ID_NO_376 | GGYGG- -GGG | ----- | GYG- | ----- -GG | GGGGY----- | ----- | 159 |
| SEQ_ID_NO_440 | GGYGG- -GRE | QR----- | GYGD | ----- -SG | GGSRYSR--- | ----- | 157 |

Figure 14 (continued)

| SEQ_ID | Sequence | # |
|---|---|---|
| SEQ_ID_NO_475 | NSNNYGGY- | 177 |
| SEQ_ID_NO_436 | ----GGGW- | 146 |
| SEQ_ID_NO_420 | --SSWWLWRR WLQCSRWWLR RWLILWWKCC WWRLWR | 208 |
| SEQ_ID_NO_473 | ----SEGWAS | 140 |
| SEQ_ID_NO_369 | --PSSGNWRN DRQPEY---- | 162 |
| SEQ_ID_NO_371 | --SEGGSWRR | 155 |
| SEQ_ID_NO_372 | GVSDDGGWRS | 181 |
| SEQ_ID_NO_373 | --NSDGNWRN | 163 |
| SEQ_ID_NO_458 | --SGGNWRE | 171 |
| SEQ_ID_NO_507 | --SGGGNWRE | 181 |
| SEQ_ID_NO_455 | --DSGGNWRN | 168 |
| SEQ_ID_NO_477 | --DSGGNWRN | 158 |
| SEQ_ID_NO_465 | ---SDGNWRN | 156 |
| SEQ_ID_NO_488 | --DSGGNWRN | 163 |
| SEQ_ID_NO_494 | --DSGGNWRN | 153 |
| SEQ_ID_NO_374 | --NSDSDWRN | 168 |
| SEQ_ID_NO_441 | ----GGGGSR W- | 157 |
| SEQ_ID_NO_444 | --ASDGNWRN | 164 |
| SEQ_ID_NO_451 | GGSSDGNWRN | 178 |
| SEQ_ID_NO_505 | --GSEG---- | 152 |
| SEQ_ID_NO_474 | --GSEGNWRN | 156 |
| SEQ_ID_NO_447 | --GGYGGGGR Y- | 148 |
| SEQ_ID_NO_450 | --GGYGGGDR Y- | 162 |
| SEQ_ID_NO_434 | GADSGGNWRD | 190 |
| SEQ_ID_NO_437 | G-ASEGNWRS | 165 |
| SEQ_ID_NO_438 | --ESDGNWKN | 164 |
| SEQ_ID_NO_454 | --DSGGNWRN | 107 |
| SEQ_ID_NO_392 | GESEGGSWRS | 170 |
| SEQ_ID_NO_425 | GCSDGGSWRN | 162 |
| SEQ_ID_NO_504 | GCSEGGSWRS | 178 |
| SEQ_ID_NO_366 | ----GGGW- | 148 |
| SEQ_ID_NO_422 | ----GGGW- | 166 |
| SEQ_ID_NO_506 | --SDGGSWRN | 167 |
| SEQ_ID_NO_433 | ----GG--- | 105 |
| SEQ_ID_NO_376 | ----GG--- | 161 |
| SEQ_ID_NO_440 | -DSDGGNWRS | 166 |

Figure 15

| | | | | | | | |
|---|---|---|---|---|---|---|---|
| SEQ_ID_NO_527 | ---MAGI SV | VVVVAF LHI | LAF VLAI GAE | NRRST---- | ---------- | | 32 |
| SEQ_ID_NO_529 | MGDVGRSSL | VHI LVI AL CL | AAFGFAI AAE | RRRST---- | ---------- | | 35 |
| SEQ_ID_NO_530 | MGDTERSSL | VHI LVI AL CL | TAFGFAI AAE | RRRSTVKSTY | LRYI LNFVFE | | 50 |
| SEQ_ID_NO_531 | MGDTERSSL | VHI LVI AL CL | TAFGFAI AAE | RRRST---- | ---------- | | 35 |
| SEQ_ID_NO_510 | MGE-GKASTL | VFI LVV AL SL | VAFGFSI AAE | RRRSI---- | ---------- | | 34 |
| SEQ_ID_NO_525 | MGE-GKGSTL | VFI LVI AL CL | VAFGFSI AAE | RRRSI---- | ---------- | | 34 |
| SEQ_ID_NO_521 | MAE-GRGSTL | VHLLVV VL CL | VAFGFAI AAE | RRRSV---- | ---------- | | 34 |
| SEQ_ID_NO_513 | MGE-GKGSTL | VHLLVV VL SL | VAFGFAI AAE | RRRSV---- | ---------- | | 34 |
| SEQ_ID_NO_517 | MEE-GKGSTL | VHLLVV VL SL | VAFGFAI AAE | RRRS----- | ---------- | | 33 |
| SEQ_ID_NO_511 | ----MASKL | LLI AVFVL DL | I AFGL AVAAE | QRRST---- | ---------- | | 30 |
| SEQ_ID_NO_523 | -----MASI L | VQVSAL L NL | AFGL AVAAE | QRRSK---- | ---------- | | 30 |

| | | | | | | | |
|---|---|---|---|---|---|---|---|
| SEQ_ID_NO_527 | ---------- | ---GK VVPDE | YDERTFCAYD | SDASTAVGLS | AFGL LL SQA | | 69 |
| SEQ_ID_NO_529 | ---------- | ---GSI VTDS | S-NTTFCVYD | SDI ATGYGVG | AFLFLLSGHS | | 71 |
| SEQ_ID_NO_530 | FMDGVFFTI Y | I VQGSI VTDS | F-NSTFCVYD | SDI ATGYGVG | AFLFLLSGQS | | 99 |
| SEQ_ID_NO_531 | ---------- | ---GSI VTDS | F-NSTFCVYD | SDI ATGYGVG | AFLFLLSGQS | | 71 |
| SEQ_ID_NO_510 | ---------- | ---GKSI QDP | I TNTTFCVYD | SDVATGYGVG | AFLFLLSSES | | 71 |
| SEQ_ID_NO_525 | ---------- | ---GKSI QDP | I TNATYCVYS | SDVATGYGVG | AFLFLLSSES | | 71 |
| SEQ_ID_NO_521 | ---------- | ---GTMHKI E | GTNETFCSYS | SDVATGYGVG | AFLFLLSXES | | 71 |
| SEQ_ID_NO_513 | ---------- | ---GTVVKDD | I TNSTYCVYN | SDVATGYGVG | AFLFLLSGES | | 71 |
| SEQ_ID_NO_517 | ---------- | ---------- | ---------- | ------YGVG | AFLFLLSSES | | 47 |
| SEQ_ID_NO_511 | ---------- | ---AK VQDS | EVNYNYCVYD | SY STGYGVG | AFLFLMVSQA | | 67 |
| SEQ_ID_NO_523 | ---------- | ---ATVTPDL | AKEYDYCVYD | SDVATGYGVG | AL LL VAAQA | | 67 |

| | | | | | | | |
|---|---|---|---|---|---|---|---|
| SEQ_ID_NO_527 | VMSAATRCLC | FGRGL SAGGP | RTCAI ASFVV | SWI SFLVAEN | CLLAGSARNA | | 119 |
| SEQ_ID_NO_529 | LLMGLTKCMC | FGAPLAPGGS | RAWSI I YFAS | SWVTFAI AEA | CLI AGATKNA | | 121 |
| SEQ_ID_NO_530 | LLMVVTKCMC | FGKPLAPGGS | RAWSI I YFAS | SWVTFMI AES | CLI AGATKNA | | 149 |
| SEQ_ID_NO_531 | LLMVVTKCMC | FGKPLAPGGS | RAWSI I YFAS | SWVTFMI AES | CLI AGATKNA | | 121 |
| SEQ_ID_NO_510 | LLMSVTKCMC | FGRPLAPGSD | RAWSI I YFI S | SWMTFLVAEA | CVI AGATKNA | | 121 |
| SEQ_ID_NO_525 | LLMGVTKCMC | FGRPLSPGSD | RAWSI I YFI S | SWMTFLVAEA | CLI AGATKNA | | 121 |
| SEQ_ID_NO_521 | LXMGVTKCMC | FGRPLTPGVN | RAXSI XYFLS | SWVTFXVAEA | CLI AGATKNA | | 121 |
| SEQ_ID_NO_513 | LLMGVTKCMC | FGRPLAPGSD | RAWSI I YFVS | SWLTFLVAEA | CLI AGATRNA | | 121 |
| SEQ_ID_NO_517 | LLMGI TKCMC | FGRSLAPGGD | RAWAI I YFVS | SWATFLVAEG | CLI AGAKKNA | | 97 |
| SEQ_ID_NO_511 | LI MAASKCFC | CGKGLNPSGS | RAWAVI LFI V | CMLEFLI AEI | CLLAGSVRNA | | 117 |
| SEQ_ID_NO_523 | VVML ASRCFC | CGRGLKPGGS | RACALMLFLF | SWLTFLVAAA | CLLAGSVRNA | | 117 |

Figure 15 (continued)

| | | | | | | | |
|---|---|---|---|---|---|---|---|
| SEQ_ID_NO_527 | YHTKYVGYYA | KKDLSSCTAL | RKGVFAAGAT | FVLLSMISSL | LYYMSYSKA- | 168 |
| SEQ_ID_NO_529 | YHTKYRDMVY | AGNW-TCQSL | RKGVFIAGAV | FVVFTMILDV | YFYMYYAKA- | 169 |
| SEQ_ID_NO_530 | YHTRYRHMVY | VGSW-TCESL | RKGVFIAGAV | FVVFTMILNV | YFYMYYTKS- | 197 |
| SEQ_ID_NO_531 | YHTRYRHMVY | VGSW-TCESL | RKGVFIAGAV | FVVFTMILNV | YFYMYYTKS- | 169 |
| SEQ_ID_NO_510 | YHTKY---LS | SGTF-SCASL | RKGIFIAGAV | FIVATMVLNV | YYYMYFTKSV | 167 |
| SEQ_ID_NO_525 | YHTKY---LS | AGAF-SCESL | RKGIFIAGAV | FTVATMILNV | YYYFHFTKFV | 167 |
| SEQ_ID_NO_521 | YHTKYRGMIY | AHNF-SCEAL | RKGXFIAGAV | FVVATMILNV | YYYMYFTKAM | 170 |
| SEQ_ID_NO_513 | YHTKYRGMIY | AGNF-SCETL | RKGVFIAGAV | FVVATMILNV | YYYMYFAKAT | 170 |
| SEQ_ID_NO_517 | YHTKYRGMIY | AGNF-TCETL | RKGVFIAGAV | FVVATMILNV | YYYMYFSKAT | 146 |
| SEQ_ID_NO_511 | YHTKYRTIFS | EQPP-SCETV | RKGVFGAGAA | FIFLNAIVNK | FYYICYSSA- | 185 |
| SEQ_ID_NO_523 | YHTRYRGIFN | GDPL-SCETL | RKGVFAAGAA | FTFFTALLSE | FYYISYSKS- | 185 |

| | | | | |
|---|---|---|---|---|
| SEQ_ID_NO_527 | -DMGGWKHQ | NEGGVGMAEF | GPEKRGLGNT NG | 199 |
| SEQ_ID_NO_529 | TSQAAKKISK | TTPSVGMIGY | A- ........ .. | 190 |
| SEQ_ID_NO_530 | TSQAAKKLNK | TTPNVGMIGY | A- ........ .. | 218 |
| SEQ_ID_NO_531 | TSQAAKKLNK | TTPNVGMIGY | A- ........ .. | 190 |
| SEQ_ID_NO_510 | SSPPAHKANR | SSSNIGMAGY | A- ........ .. | 188 |
| SEQ_ID_NO_525 | FFPPTHKANR | SGSNIGMAGY | A- ........ .. | 188 |
| SEQ_ID_NO_521 | TXPVXHKANR | VSSTVGMAGY | A- ........ .. | 191 |
| SEQ_ID_NO_513 | TTMPAHKANR | TNSTVGMIGY | A- ........ .. | 191 |
| SEQ_ID_NO_517 | ASKAAHKTNR | TSS-VGMIGN | P- ........ .. | 166 |
| SEQ_ID_NO_511 | -RDKSFQAYG | GETGVGMGTY | K- ........ .. | 185 |
| SEQ_ID_NO_523 | -RDAAGGAPY | GGSSIGMGPY | T- ........ .. | 185 |

Figure 16

| | | | | | | | |
|---|---|---|---|---|---|---|---|
| SEQ_ID_NO_546 | ---- MSSSLE | RKKGKTVI-- | ---------- | M | LRSCSQCGSN | GHN------ | 28 |
| SEQ_ID_NO_542 | ---------- | ---------- | ---------- | M | GRKCSHCGNI | GHN------ | 14 |
| SEQ_ID_NO_547 | ---------- | ---------- | ---------- | M | TRRCSHCSTN | GHN------ | 14 |
| SEQ_ID_NO_533 | ---- MESVVA | T--------- | ---------- | W | SREEEKAFEN | AI ALHCV--- | 25 |
| SEQ_ID_NO_539 | ---- MSSGGT | I--------- | ---------- | W | SYDEEKAFEN | AI AMHM --- | 25 |
| SEQ_ID_NO_535 | ---- MAGSVS | ---------- | ---------- | W | SREEEKAFEN | AI AMHM --- | 24 |
| SEQ_ID_NO_538 | ---- MASVGT | ---------- | ---------- | W | TRDEEKTFEN | AI AMHM --- | 24 |
| SEQ_ID_NO_553 | ---- MTSQAA | TTTTTAAAAA | A--------- | W | TREDDKAFEN | ALAACAAPPP | 38 |
| SEQ_ID_NO_550 | ---- MAAEEA | SSSGGGEEGS | GAGAGG---- | W | TREQEKAFEN | ALATV----- | 38 |
| SEQ_ID_NO_552 | ---- MAVNEA | SSSGGGEEGC | GS-------- | W | TREQEKAFEN | AVATMGG--- | 36 |
| SEQ_ID_NO_536 | ---- METLYP | SSHLSSSAWF | VLDNPS- TKW | TKEENKMFES | ALAIY ---- | 40 |
| SEQ_ID_NO_543 | MDRGEILSP | ASYLQNSNWL | FPETRA- TKW | TPEENKFEN | ALALY ----- | 44 |
| SEQ_ID_NO_548 | ---- MEILAP | SSYFSSSSWF | LEESRSTTRW | TAAENKAFEN | ALAVF ---- | 41 |

| | | | | | | | |
|---|---|---|---|---|---|---|---|
| SEQ_ID_NO_546 | -- SRTCGESS | SAAGNGASDG | EFMLFGVRVK | VDPMRKSVSM | NDLSD- YELP | 75 |
| SEQ_ID_NO_542 | ---------- | SR- TCNSLRG | SGBFVGVRLF | GVOLDLSSSC | VSMKKSFSMD | 53 |
| SEQ_ID_NO_547 | -- SRTCPNRG | VK- LFGVRLT | - DGL RKSAS | MGNLTHFASG | SGGGS- TPLN | 59 |
| SEQ_ID_NO_533 | - EEEI TEDQW | NK- MSSMVPS | - KAL EEVKKH | YQLLEDVKA | ENGQ- VPLP | 71 |
| SEQ_ID_NO_539 | -- EESSKEQW | EK- I ASAVPS | - KSMEEVKQH | YQVLVEDVSA | EAGH- I SFP | 70 |
| SEQ_ID_NO_535 | - DKEECEEQW | EK- I ASTVPT | - KSLEELKLH | YELLVEDVTA | EAGH- VPLP | 70 |
| SEQ_ID_NO_538 | -- DEDSNEQW | EK- I ASMVPS | - KSLEELKLH | YKILVEDVCA | EAGN- VPIP | 69 |
| SEQ_ID_NO_553 | ADGGAPDDDW | FAALAASVPG | ARSAEEVRRH | YEALVEDVAA | DAGR- VPLP | 87 |
| SEQ_ID_NO_550 | - DEEEGEAMW | DK- I ADAVEG | - KTPEEVRRH | YELLVEDVDG | EAGR- VPLL | 84 |
| SEQ_ID_NO_552 | -- EEDGDARW | EK- LAEAVEG | - KTPEEVRRH | YELLVEDVDG | ESGR- VPLP | 81 |
| SEQ_ID_NO_536 | -- DKETPDRW | FK- VAALI PG | - KTVSDVI KQ | YKELEEDVCE | EAGR- FPVP | 85 |
| SEQ_ID_NO_543 | -- DKDEPDRW | DK- VAAVI PG | - KTVGDVI KQ | YRELEEDVSD | EAGL- I PI P | 89 |
| SEQ_ID_NO_548 | -- DENTPNRW | ER- VAERVPG | - KTVGDVMRQ | YKELEDDVSS | EAGF- VPVP | 86 |

Figure 16 (continued)

```
SEQ_ID_NO_546   SNVN------ QNGVDNSKNS NDSDKVVADD VVTAGAGYV- ---------S  109
SEQ_ID_NO_542   SFPT------ ---SSSSPTS SFSSSRLTID DRASIGYLSD GL--------  86
SEQ_ID_NO_547   GVVH------ DSPGDTPDHP A-VGGGSADS YASEDFVAG- ----------  91
SEQ_ID_NO_533   RYHHRKGLIV DEAAAAATSP ANRDSHSSGS SEKKPNPGTS GIS------S  115
SEQ_ID_NO_539   NYAS------ DETTSSNKD- FHGSSKATSS DKRSNCNYSS GFSGLGLDST  113
SEQ_ID_NO_535   CYKG------ EEPSSSAKDY FHGPSMAPNS DRRSNSGYGN GFSGLTLDST  114
SEQ_ID_NO_538   NYEG------ EEAASSTKD- LHGLSGTMTT VKKLNCGYSS GFVGLGHESS  112
SEQ_ID_NO_553   RYAG------ EESAAPPDGA GAAAASKDS GHRRDERKGG G-------G  123
SEQ_ID_NO_550   VYAG------ DGDEGGSGGG AGGSGGGGGG GGKKSGGGG ---------G  118
SEQ_ID_NO_552   AYAA------ ---------- -DGAAEEGGG GGKKGSGGG ---------G  104
SEQ_ID_NO_536   GYDL------ ----ASSFSF EFVDDRNFDV YRRKSSVG-- ----------  113
SEQ_ID_NO_543   GYSS------ ---SDAFTLE WFNNNQGYDG FRHYYTPGG ----------  119
SEQ_ID_NO_548   GYST------ ----SSPFTL EWGSGHGFDG FKQSYGTGG ----------  115

SEQ_ID_NO_546   ADDAVQHQ-- STGGRERKRG IPWTEEEHKL FLLGLQKVGK GDWRGI SRNF  157
SEQ_ID_NO_542   ---------- IVRTQERKKG VPWTEEEHRK FLVGLEKLGK GDWRGI SRNY  126
SEQ_ID_NO_547   ---------- SSSSRERKKG VPWTEEEHRM FLLGLQKLGK GDWRGI ARNY  131
SEQ_ID_NO_533   SNGGRSGG-- SRAEQERRKG IPWTEEEHRL FLLGLDKFGK GDWRSI SRNF  163
SEQ_ID_NO_539   THSSGKGGLS RSSEQERRKG IPWTEEEHRL FLLGLDKFGK GDWRSI SRNF  163
SEQ_ID_NO_535   GHGGKQS--- SRSDQERRKG IPWTEEEHRL FLLGLDKFGK GDWRSI SRNF  161
SEQ_ID_NO_538   GHGGKGA--- SRSEQERKKG IPWTEEEHRL FLLGLDKFGK GDWRSI SRNF  159
SEQ_ID_NO_553   GYDGGKSC-- SKAEQERRKG IPWTEEEHRL FLLGLDKFGK GDWRSI SRNF  171
SEQ_ID_NO_550   GHGEKGSS-- KSAEQERRKG AWTEDEHRL FLLGLEKYGK GDWRSI SRNF  166
SEQ_ID_NO_552   THGDKRSA-- KSAEQERRKG AWTEDEHRL FLLGLEKYGK GDWRSI SRNF  152
SEQ_ID_NO_536   ---------- RGSEHERKKG VPWTEEEHKQ FLRGLLKYGK GDWRNI SRNF  153
SEQ_ID_NO_543   ----KRTTAA RSSEQERRKG VPWTEEEHRQ FLMGLQKYGK GDWRNI SRNF  165
SEQ_ID_NO_548   ----RKSSSG RPSEQERKKG VPWTEEEHKL FLMGLKKYGK GDWRNI SRNF  161
```

Figure 16 (continued)

| | | | | | | | |
|---|---|---|---|---|---|---|---|
| SEQ_ID_NO_546 | VKTRTPTQVA | SHAQKYYLRK | NNLNRRRRRS | SLFDITTDSV | PGGLPMDDVK | | 207 |
| SEQ_ID_NO_542 | VTTRTPTQVA | SHAQKYFIRL | ATLNKKKRRS | SLFDMVGSGK | TN-KTVD--- | | 172 |
| SEQ_ID_NO_547 | VISRTPTQVA | SHAQKYFIRQ | SNMSRRKRRS | SLFDIVADES | GDTPMVSR-- | | 179 |
| SEQ_ID_NO_533 | VISRTPTQVA | SHAQKYFIRL | NSMNRDRRRS | SIHDITTVNN | QA-------- | | 205 |
| SEQ_ID_NO_539 | VISRTPTQVA | SHAQKYFIRL | NSMNRDRRRS | SIHDITSVNN | GD-------- | | 205 |
| SEQ_ID_NO_535 | VISRTPTQVA | SHAQKYFIRL | NSMNRDRRRS | SIHDITSVNN | GD-------- | | 203 |
| SEQ_ID_NO_538 | VISRTPTQVA | SHAQKYFIRL | NSMNRDRRRS | SIHDITSLNN | GD-------- | | 201 |
| SEQ_ID_NO_553 | VISRTPTQVA | SHAQKYFIRL | NSMNRDRRRS | SIHDITSVTA | GDQV------ | | 215 |
| SEQ_ID_NO_550 | VISRTPTQVA | SHAQKYFIRL | NSMNRERRRS | SIHDITSVNL | GE-------- | | 207 |
| SEQ_ID_NO_552 | VISRTPTQVA | SHAQKYFIRL | NSMNRERRRS | SIHDITSVNN | GD-------- | | 194 |
| SEQ_ID_NO_536 | VNSKTPTQVA | SHAQKYFMRQ | LSGGKDKRRP | SIHDITTVNL | TE-------- | | 195 |
| SEQ_ID_NO_543 | VTTRTPTQVA | SHAQKYFIRQ | STGGKDERRS | SIHDITTVNL | PDTKS----- | | 210 |
| SEQ_ID_NO_548 | VITRTPTQVA | SHAQKYFIRQ | LSGGKDKRRA | SIHDITTVNL | SDNQTPS--- | | 208 |

| | | | | | | | |
|---|---|---|---|---|---|---|---|
| SEQ_ID_NO_546 | NHQDKSVPKV | LQHSQVPHAE | KPNMNGYTIA | PFPLAVGPIL | LPVQVHNPME | | 257 |
| SEQ_ID_NO_542 | ---------- | -----PNNS | SKSKSGDSVC | RHDHEVEKDA | TLSL---LIN | | 203 |
| SEQ_ID_NO_547 | ---------- | -----DFLA | DDPAQAEMQS | ----NNLLPP | TPAVDEECES | | 209 |
| SEQ_ID_NO_533 | ---------- | -----PAVT | GGGQQPQVVK | ----HRPAQP | QPQP---Q-- | | 230 |
| SEQ_ID_NO_539 | ---------- | -----VASS | QAPITGLHSS | -----TISSN | TMGV------ | | 228 |
| SEQ_ID_NO_535 | ---------- | -----TSH | QAPITGQQAN | --------TN | SPGA---AVM | | 225 |
| SEQ_ID_NO_538 | ---------- | -----VSSH | QAPITGQQAN | ----TSPAGP | APAM------ | | 225 |
| SEQ_ID_NO_553 | ---------- | -----AAQQ | GAPITGHQAT | ----GNPAAA | ALGP---PGM | | 242 |
| SEQ_ID_NO_550 | ---------- | -----ASAA | QGPITG---- | ----TNGQAA | VPGK---S-- | | 228 |
| SEQ_ID_NO_552 | ---------- | -----PSTA | QGPITGQ--- | ----TNGQAA | NPGK---P-- | | 216 |
| SEQ_ID_NO_536 | ---------- | -----PTAS | ENEKLSSMDQ | ---FSKLPSL | QKSP---CYQ | | 223 |
| SEQ_ID_NO_543 | ---------- | -----PSPD | EKKSSPDHST | TSLQSQPQQK | MVGM---A-- | | 239 |
| SEQ_ID_NO_548 | ---------- | -----PDNK | KPPSSPDHSM | ----AQQQTS | STSI---H-- | | 233 |

Figure 16 (continued)

| | | | | | | | |
|---|---|---|---|---|---|---|---|
| SEQ_ID_NO_546 | NKAFHWGDHQ | L-QNGPGMLL | RTVPFIPVAN | S---------- | ------SSAR | | 292 |
| SEQ_ID_NO_542 | SLQQQTKSDD | Y-DMQKIEDD | SEEAEHKDVP | D---------- | ------WLHPL | | 238 |
| SEQ_ID_NO_547 | MGSAASANSI | DGEHALPIPE | SSQYQHPLVY | PAYVAPFYPM | PYPCWPGYTA | | 259 |
| SEQ_ID_NO_533 | POPQQHHPPT | --MAGLGMYG | GAPVGQPIIA | P---------- | ------PDHMG | | 264 |
| SEQ_ID_NO_539 | GQSLKHRVQG | HIPPGLGMYG | TLPVGHPVAA | P---------- | ------PGHMA | | 263 |
| SEQ_ID_NO_535 | GQSVKHRAQP | H-LPGLGMYG | ALPVGRPIAA | A---------- | ------PGHIG | | 259 |
| SEQ_ID_NO_538 | GPPVKHRTQA | H-MPGLAMYG | P-PLGHPVAP | P---------- | ------PGHMA | | 259 |
| SEQ_ID_NO_553 | KHHHHHHPGG | A-PPPMPMYS | AAPMGHPVA- | ---------- | ------GHMV | | 274 |
| SEQ_ID_NO_550 | PKQSPHQPGN | L-PPGVDAFG | TLTLGQPVGG | P---------- | ------LV--- | | 259 |
| SEQ_ID_NO_552 | SKQSP-QPAN | T-PPGVDAYG | TLTLGQPVGG | P---------- | ------LV--- | | 246 |
| SEQ_ID_NO_536 | KLLFDWNRSS | --NGGLLGLG | SLNYGDRLMS | F---------- | ------PSGIA | | 256 |
| SEQ_ID_NO_543 | KGLIDWKPQN | EGGGAAGVFS | Q-ANGNLLMA | P---------- | ------LCGL- | | 273 |
| SEQ_ID_NO_546 | KLPFQWDQTS | N-ETIMGFAS | SGHHGNMFQS | N---------- | ------PFGM- | | 267 |

| | | | | | | |
|---|---|---|---|---|---|---|
| SEQ_ID_NO_546 | DLNLN-QRVL | ----EGEPSS | P---------- | ----------LS | LKLSLSSSDN | 319 |
| SEQ_ID_NO_542 | TKSLN-MTLV | LPNSSNVAP | P---------- | ----------DL | ELTLAGSKSN | 269 |
| SEQ_ID_NO_547 | EPAIAETHEM | LKPIAVHSKS | PINVDELVGM | SKLSLGESIG | DAAKPPSLSL | 309 |
| SEQ_ID_NO_533 | -SAVGLTPVM | LPPPMGTHHH | H---------- | ----------HH | HHLGVAPYAV | 295 |
| SEQ_ID_NO_539 | -SAVGLTPVM | LPPGPHPHPH | P---------- | ----------HH | HAHPHPPYVL | 294 |
| SEQ_ID_NO_535 | -SAVGLTPVM | LPPAHHPHS | P---------- | ----------- | ----PPYIV | 282 |
| SEQ_ID_NO_538 | -SAVGLTPVM | LPPPGHHPH- | ---------- | ----------- | ----PPYVV | 281 |
| SEQ_ID_NO_553 | PAAVGLTPVV | F-PPGH---- | ---------- | ----------- | ----APYVV | 293 |
| SEQ_ID_NO_550 | -SAVGLTPVT | LPVAAPPHM | G---------- | ----------YA | MHAPVPGTVV | 289 |
| SEQ_ID_NO_552 | -SAVGLTPVT | LPVSAPPHL | A---------- | ----------YG | MRAPVPGAVV | 276 |
| SEQ_ID_NO_536 | ANGLK-N--- | --EQDQELNS | A---------- | ----------YY | GTYSKPHKSI | 283 |
| SEQ_ID_NO_543 | -SSYGLQRL- | --QEQNLLRG | T---------- | ----------LP | GYQFAPYNLI | 301 |
| SEQ_ID_NO_546 | -NSYGLFKM- | --QGQQMQRG | G---------- | ----------FC | DTYLGSQNMA | 295 |

Figure 16 (continued)

| | | | | |
|---|---|---|---|---|
| SEQ_ID_NO_546 | SQSSSTRHST | GFQAMAATSF | SKGGDSIISV A-- | 350 |
| SEQ_ID_NO_542 | NMEQDKTSSS | SFLIGPISVT | ........... ... | 289 |
| SEQ_ID_NO_547 | KLVEGSSRQS | AFHANPSSGS | SGMNSSHNPI HAV | 342 |
| SEQ_ID_NO_533 | PA-------- | -YPVPPLPQQ | HPAPSTMH-- --- | 314 |
| SEQ_ID_NO_539 | PLA------- | -YPMAPPTMH | Q--------- --- | 307 |
| SEQ_ID_NO_535 | PVA------- | -YPMAPPPMH | Q--------- --- | 295 |
| SEQ_ID_NO_538 | PVA------- | -YPTAPPKTA | ---------- --- | 293 |
| SEQ_ID_NO_553 | PVG------- | -YPAPPAKMH | Q--------- --- | 306 |
| SEQ_ID_NO_550 | PRAPM----- | -YPMPPPPSR | ---------- --- | 303 |
| SEQ_ID_NO_552 | PGAPVNIAPM | PYPMPPPPSH | G--------- --- | 297 |
| SEQ_ID_NO_536 | ---------- | -FQFEPSRYQ | IYG------- --- | 295 |
| SEQ_ID_NO_543 | ---------- | -FQMQPMQRQ | ---------- --- | 310 |
| SEQ_ID_NO_548 | ---------- | -FQMQSGLHF | PNA------- --- | 307 |

| SEQ_ID | Sequence (block 1) | Len |
|---|---|---|
| SEQ_ID_NO_559 | PSA I LPGSK EELSNTI RC RKGSWT RLR SGGHSYEGLS YTS - - - DTP | 116 |
| SEQ_ID_NO_586 | PSM I LPQSK EELAASVVCS NRGLWT RLR SGGHSYEGLS YVA - - - DTP | 112 |
| SEQ_ID_NO_591 | PRV I LPESM DQLANVI SCC TRGSWT RLR SGGHSYEGLS HI A - - - DNP | 113 |
| SEQ_ID_NO_581 | PLG I AATEH AHADTTVRCG RRHGVRVRVR SGGHDYEGLS YASVHLHNRN | 130 |
| SEQ_ID_NO_588 | PLA VAATEP AHAQAAVRCG RRHGVRVRTR SGGHDYEGLS YASL - - - DPR | 125 |
| SEQ_ID_NO_589 | PLY VTPTDV KHIQVAVSCG RRHNVRI RVR SGGHDYEGLS YRS - - - E P | 124 |
| SEQ_ID_NO_590 | PLY VTPTDV KHIQVAVSCG RRHNVRI RVR SGGHDYEGLS YRS - - - E P | 129 |
| SEQ_ID_NO_584 | PLY I TPTNV SHI OSAVVCG RRHSVRI RVR SGGHDYEGLS YRS - - - LQP | 123 |
| SEQ_ID_NO_583 | PVY I TPTEA AHI OATVACG RXHGLRVRVR SGGHDYEGLS YRS - - - AKP | 128 |
| SEQ_ID_NO_585 | PLY I TPTNA SHI OAAVVCG RRHGMRI RVR SGGHDYEGLS YRS - - - EKP | 125 |
| SEQ_ID_NO_560 | PLV VTPSNV SHI OASI LCS KKVGLQI RTR SGGHDAEGLS YI S - - - QVP | 126 |
| SEQ_ID_NO_577 | PLV VTPQVV SHI OATI KCS QRHGLQI RTR SGGHDYEGLS YVA - - - RVP | 121 |
| SEQ_ID_NO_569 | PL I I TPLDE SHVSAAVI CS QKLGFDLKI R SGGHDYEGLS YVF - - - DNP | 124 |
| SEQ_ID_NO_575 | PLL VTPLSE NQVQATYVCA KSI GLQLKI R SGGHDFEGVS YI S - - - QVP | 128 |
| SEQ_ID_NO_576 | PLA I TAKDD SHI OETI KCA KSNN QI RLR SGGHDYEGFS YVS - - - DVP | 119 |
| SEQ_ID_NO_578 | PEL I TAEHV SHI OAAVVCG KQNRLLLKTR SGGHDYEGLS YLT - - - NTN | 129 |
| SEQ_ID_NO_579 | PI L I TALHP SHI OAAVVCA KTHRLLMKTR SGGHDYEGLS YVT - - - NSN | 128 |
| SEQ_ID_NO_558 | PVA VAAADV THI OATI TCA KKLGLQLRI R SGGHDYDGMS YLS - - - TI D | 126 |
| SEQ_ID_NO_571 | PLA I AAKHE SHVQATI CS KKLGLQI RI R SGGHDYDGLS YVS - - - DVA | 119 |

| SEQ_ID | Sequence (block 2) | Len |
|---|---|---|
| SEQ_ID_NO_559 | - - FI LI DLMN LNRVSI DLES ETAWESGST LGELYYA TE SSSKL GFTA | 163 |
| SEQ_ID_NO_586 | - - FVVI DLMN LNRI SI DLES KTAWESGAT LGEI YCA SE ASDTL GFSG | 159 |
| SEQ_ID_NO_591 | - - FVI I DLMN LNG SI DLDT QTAWESGAT LGEI YHA GK SSGTM AFSA | 160 |
| SEQ_ID_NO_581 | EPFAVLDLAA LRAI HVDAAR AEAWVESGAT VGELYYANGA ASRSL GFPA | 179 |
| SEQ_ID_NO_588 | ESFAVLDLAA FREVRVDAAR AEAWAGSGAT LGEVYYANGA ASRAL AFPA | 174 |
| SEQ_ID_NO_589 | EPFAI VDLVN MRNVTVDGKA RTAWESGAQ GELYYGI SK ASPTL AFPA | 173 |
| SEQ_ID_NO_590 | EPFAI VDLVN MRNVTVDGKA RTAWESGAQ GELYYGI SK ASPTL AFPA | 178 |
| SEQ_ID_NO_584 | ETFAVVDLNK MRAVMVDGKA RTAWWDSGAQ LGELYYA YK ASPTL AFPA | 172 |
| SEQ_ID_NO_583 | ETFAVVDLSM MRQVRI DGKA ATAWDSGAQ LGELYYAVAK MTPSL GFPA | 177 |
| SEQ_ID_NO_585 | EPFAVVDMNK MRAVSI DSKA ATAWDSGAQ LGDLYYG AK ASPKL GFPA | 174 |
| SEQ_ID_NO_560 | - - FAI VDLRN MHTVKVDI HS QTAWVEAGAT LGEVYYM NE MNENF SFPG | 173 |
| SEQ_ID_NO_577 | - - FVI LDLLN FREI KVDVEN RTAWQVGAT LGELYYT SQ ASKTL GFPA | 168 |
| SEQ_ID_NO_569 | - - FFVLDMFN LRSI TVNMAD ETAWGAGAT LGELYYN MK NSKVH GFPA | 171 |
| SEQ_ID_NO_575 | - - FI I LDMFN FQDVTVDVQN ETAV QAGAS GQVYYR WE KSKVH GFPA | 175 |
| SEQ_ID_NO_576 | - - FI I LDMFH LNSVDI NLGE STAWESGAT LGKI YYN AN KSNKL AFPS | 166 |
| SEQ_ID_NO_578 | QPFFI VDMFN LRSI NVDI ED ETAWQAGAT LGEVYYR AE KSNKH GFPA | 176 |
| SEQ_ID_NO_579 | QPFFVVDMFN LRSI NVS ED ETAWQAGAT LGEVYYR AE KSNSH AFPA | 177 |
| SEQ_ID_NO_558 | - - FVVLDMFN LRSI NI DPKL DTAWQSGAT LGEI YYGVAN KSNDLRGFPA | 174 |
| SEQ_ID_NO_571 | - - FI I LDMFN LRSI NI DI ED ESAWQAGAT LGEVYYR AE KSNVH GFPA | 166 |

Figure 17 (continued)

| SEQ_ID_NO_559 | GWCPTVGTGG | HISGGGFGMM | SRKYGLAADN | VVDALIDAN | GALDRQAMG | 213 |
| SEQ_ID_NO_586 | GYCPTVGSGG | HISGGGFGMM | SRKYGLAADN | VIDALIVDAN | GAVLDRSSMG | 209 |
| SEQ_ID_NO_591 | GYCPTGSSGG | HIAPGGFGMM | SRKYGLAADN | VVDALLVDAN | GVVLDRESMG | 210 |
| SEQ_ID_NO_581 | GSCPTMGVGG | HLSGGGFGSL | ARKYGLSADN | VLDAVVVDAD | GRLVNRSTMG | 229 |
| SEQ_ID_NO_588 | GVCPTVGVGG | HLGGGGFGTL | MRRYGLAADN | VLDAVLVDAD | GRLLNRTTMG | 224 |
| SEQ_ID_NO_589 | GVCPTIGVGG | HFSGGGFGML | LRKFGLASDN | VLDVKVVDAN | GKVQDRKSMG | 223 |
| SEQ_ID_NO_590 | GVCPTIGVGG | HFSGGGFGML | LRKFGLASDN | VLDVKVVDAN | GKVQDRKSMG | 228 |
| SEQ_ID_NO_584 | GVCPTIGVGG | NFAGGGFGML | LRKYGIAAEN | VIDVKLVDAN | GKLHDKKSMG | 222 |
| SEQ_ID_NO_583 | GVCATIGVGG | HFSGGGFGML | LRKYGTAGDN | VIDAKVVDAN | GTLLDRKSMG | 227 |
| SEQ_ID_NO_585 | GVCITIGVGG | HFSGGGFGML | LRKYGTAADN | VIDAKVVDAQ | GRLLDRKAMG | 224 |
| SEQ_ID_NO_560 | GYCPTVGVGG | HFSGGGYGAL | MRNYGLAADN | IDAHLVNVD | GKVLDRKSMG | 223 |
| SEQ_ID_NO_577 | GVCYSVGAGG | HISGGGYGFL | MRKYGLAADN | VIDAHIDVN | GNLLDRKAMG | 218 |
| SEQ_ID_NO_569 | GVCPTVGVGG | HLSGAGYGTL | IRKYGLSVDH | VVDAKLVDVN | GKILDRKTMG | 221 |
| SEQ_ID_NO_575 | GACPTVGVGG | HLSGGGYGNM | IRKYGLSVDH | VVDAKIVDVK | GRILDKESMG | 225 |
| SEQ_ID_NO_576 | GVCFTLGAGG | HFSGGGYGNL | MRKFGLSVDN | IDAKMVDVK | GNLLDRKSMG | 216 |
| SEQ_ID_NO_578 | GVCPTVGVGG | HFSGGGYGNL | MRKYGLSVDN | VDAQIIDVN | GKLLDRKSMG | 228 |
| SEQ_ID_NO_579 | GVCPTVGVGG | HFSGGGYGNL | MGKYGLSVDN | VDAQLIDVN | GKLLNRKSMG | 227 |
| SEQ_ID_NO_558 | GICPGLGAGG | HFSGGGYGNM | MRKYGLSIDN | IDAKIVDAK | GKVLDRSSMG | 224 |
| SEQ_ID_NO_571 | GVCPTLGVGG | HFSGGGYGNM | MRKYGLSVDN | VDAQIIDVR | GRILDRKSMG | 216 |

| SEQ_ID_NO_559 | EDVFWAIRGG | GGGVWGAIYA | WKIKLLPVPE | KNTVFRVTKN | VAIDE--ATS | 261 |
| SEQ_ID_NO_586 | EDVFWAIRGG | GGGVWGAIYA | WKLQLLPVPK | QVTVFKLVKN | FDNIE-EASK | 258 |
| SEQ_ID_NO_591 | EDVFWAIRGG | GGGVWGAVYA | WKLQLVPVPK | NVTIFRLVKH | SEVED--ASK | 258 |
| SEQ_ID_NO_581 | EDHFWALCGG | GGESFGVVLS | WKVRLVPVPE | TVTVFSIVRS | RSDS---AVE | 276 |
| SEQ_ID_NO_588 | EDLFWAIRGG | GGESFGVVLS | WKLRLVPVPE | TVTVFTVRRS | RNQS---ASE | 271 |
| SEQ_ID_NO_589 | EDYLWAVRGG | GGSSFGIVVS | WKLRLLPVPA | TVTVLQMPKM | VNEG---AVD | 270 |
| SEQ_ID_NO_590 | EDYLWAVRGG | GGSSFGIVVS | WKLRLLPVPA | TVTVLQMPKM | VNEG---AVD | 275 |
| SEQ_ID_NO_584 | DDHFWAVRGG | GGESFGVVVA | WQVKLLPVPP | TVTIFKISKT | VSEG---AVD | 269 |
| SEQ_ID_NO_583 | EDYFWAIRGG | GGESFGIMVS | WQVQLVPVPP | KVTVFQIHRG | VKDG---AID | 274 |
| SEQ_ID_NO_585 | EDHFWAIRGG | GGESFGIVAS | WQVKLLPVPP | KVTVFQVHKG | IKES---AID | 271 |
| SEQ_ID_NO_560 | EDLFWAIRGG | GGENFGIIAA | WKIKLVVNPS | KAFIFSVKKN | MELHG--LVK | 271 |
| SEQ_ID_NO_577 | EDLFWAIRGG | GGASFGIVVS | WKIKLVPVPS | TVTVFNVERI | LEEN---ATE | 265 |
| SEQ_ID_NO_569 | EDLFWAIRGG | GAASFGVVLS | YKIKLVPVPE | TVTVFRIERL | LTEN---ATD | 268 |
| SEQ_ID_NO_575 | EDLFWAIRGG | GGASFGVILS | YILVKLVPVPE | NVTVFQIDKT | LEEN---ATD | 272 |
| SEQ_ID_NO_576 | EDLFWAIRGG | GGASFGVILS | WKLQLVPVTP | QVLVFDVKRN | VSEG---ATD | 263 |
| SEQ_ID_NO_578 | EDLFWAITGG | GGVSFGVVLA | YKIKLVRVPE | VVTVFTIERR | EEQN---LST | 275 |
| SEQ_ID_NO_579 | EDLFWAITGG | GGVSFGVVVA | YKIKLVRVPT | TVTVFNVQRT | SEQN---LST | 274 |
| SEQ_ID_NO_558 | EDLFWALRGG | GAASFCVVLA | WKIKLVPVPA | KVTVFNIETF | GNTGSVNTTE | 274 |
| SEQ_ID_NO_571 | EDLFWAIRGG | GAASFGVILS | WKIKLVPVPE | IVTVFSVDRT | LEEG---VSD | 263 |

Figure 17 (continued)

| | | | | | | |
|---|---|---|---|---|---|---|
| SEQ_ID_NO_559 | LLHKWQFV-A | EELEEDFTLG | VLGGADEK-- | -------QVW | LTMLGFHFGL | 301 |
| SEQ_ID_NO_586 | MLHKWQVV-A | PALEDDFTLS | VLAGADTN-- | -------G W | FSFLGLYLGP | 298 |
| SEQ_ID_NO_591 | LLHKWQLV-A | PKLEDDFSLA | VLAGTNKDS- | -------SIW | LTFLGLYLGP | 299 |
| SEQ_ID_NO_581 | LITKWQEM-A | PASPQELYLR | VLVL------ | -------NDQ | ANFQALFLGR | 312 |
| SEQ_ID_NO_588 | LITKWQE--A | PALPRDLLR | VVVQ------ | -------GRH | AQFEALFLGR | 307 |
| SEQ_ID_NO_589 | LLTKWQSL-A | PTFPFDLMR | VMAQ------ | -------ADK | ANFEGLYLGT | 308 |
| SEQ_ID_NO_590 | LLTKWQSL-A | PTFPEDLMR | VMAQ------ | -------ADK | ANFEGLYLGT | 311 |
| SEQ_ID_NO_584 | INKWQVV-A | PQLPADLMR | IAQ------- | -------GPK | ATFEAMYLGT | 305 |
| SEQ_ID_NO_583 | LINKWQQV-A | PSLPDDLMR | MAM------- | -------EQD | AMFEALYLGT | 310 |
| SEQ_ID_NO_585 | LVTKWQT-V-A | PALPDDLMR | MAM------- | -------GQG | AMFEALYLGT | 307 |
| SEQ_ID_NO_560 | LFNKWQN--A | YKYDKDLMLT | THFRTRNITD | NHGKNKTTVH | GYFSSIFLGG | 320 |
| SEQ_ID_NO_577 | IEKWQLV-A | NKLDERFLR | MDLARANSS- | QHGKL--ALQ | ANFVAMFQGG | 311 |
| SEQ_ID_NO_569 | TFKWQT--A | PTTDENLFMR | MLQPVTRN-- | --KKK--TAR | ISVIALYLGD | 312 |
| SEQ_ID_NO_575 | LVVQWQKV-A | PHTDDRLYLR | LVLQPVSSNF | VKGKK--TIR | ASVEALFLGE | 319 |
| SEQ_ID_NO_576 | VVYKWQL-A | PKLHKDLFIR | AQPNVVQIG- | QEGKK--VVQ | ISFIGQFLGK | 309 |
| SEQ_ID_NO_578 | AERWQV-A | DKLDRDLFLR | MTFSVINDT- | NGG-K--TVR | AIFPTLYLGN | 320 |
| SEQ_ID_NO_579 | AHRWIQV-A | DKLDNDLFLR | MTFNVINNT- | NGE-K--TIR | GLFPTLYLGN | 319 |
| SEQ_ID_NO_558 | LVAKWQE--A | DKIDNDLFIR | LTLGSSNK-- | -------TVK | ASFMGMYLGN | 314 |
| SEQ_ID_NO_571 | LAWKWQQ-AA | DKLDNDLFIR | LMLQPVNGT- | QEGKK--TIQ | ASFVAMFLGR | 310 |

| | | | | | | |
|---|---|---|---|---|---|---|
| SEQ_ID_NO_559 | KTYAKSTFDL | LFPELGLVEE | DYLEMSWGES | FAMLAGLE-- | -----TVSQL | 344 |
| SEQ_ID_NO_586 | KELASSVDQ | NFPELNLVME | DCKEMSWVES | FAHLAGLN-- | -----SVEEM | 341 |
| SEQ_ID_NO_591 | KELASSSMHK | KFPELNLLE | DCMEMSWVEA | TAELAGLK-- | -----SVSEL | 342 |
| SEQ_ID_NO_581 | CGGLHRLMQD | RFPELGMTEQ | DCEEVSWVQS | TAFFGFSTTS | V----PPEQL | 358 |
| SEQ_ID_NO_588 | CSRVLEHMRA | HFPELGVARA | DCEEISWIQS | TVYFAFYSSS | K----PPELL | 353 |
| SEQ_ID_NO_589 | CDALLPLVTS | RFPELGVNRS | HCNEMSWVQS | IAFIHLGKNA | T----VKDI | 351 |
| SEQ_ID_NO_590 | CDALLPLVTS | RFPELGVNRS | HCNEMSWVQS | IAFIHLGKNA | T----VKDI | 356 |
| SEQ_ID_NO_584 | CKTLTPLMSG | KFPELGMNPD | HCNEMSWIQS | IPFVHLGHRD | A----LEDDL | 351 |
| SEQ_ID_NO_583 | CKDLLPLMAS | RFPELGVKQE | DCNEMPWIQS | VAFIPMGKSA | T----VMDL | 355 |
| SEQ_ID_NO_585 | CKDLVLLMTA | RFPELGMNAT | HCKEMTWIES | VPYLPMGPKG | T----VRDL | 352 |
| SEQ_ID_NO_560 | VDSLVDLMNK | SFPELGIKKT | DCKELSWIDT | TIFYSGVVNY | NTANFKKEL | 370 |
| SEQ_ID_NO_577 | VEELIPLMQK | NFPELGLKRK | DCFETSWIGS | AVFTNGALIG | SSGHEAPEVL | 361 |
| SEQ_ID_NO_569 | SDSLVSLLQK | DFPELSIGKS | NCNETTWIDS | VLWWANFNLG | T----PPTAL | 358 |
| SEQ_ID_NO_575 | ADELVKLLGD | EFPLLGLKKE | LCHEMRWIDS | VVWWANYNDG | S----SVNAL | 365 |
| SEQ_ID_NO_576 | IERLLTLMNK | EFPELGLNKS | DCFSMPWINS | TLFWYGEPIG | T----PLEVL | 355 |
| SEQ_ID_NO_578 | SRNLVTLLNK | DFPELGLQES | DCTEMSWVES | VLYYTGFPSG | T----PTTAL | 366 |
| SEQ_ID_NO_579 | STALVALLNK | DFPELGVEIS | DCIEMSWIES | VLFYTNFPIG | T----PTTAL | 365 |
| SEQ_ID_NO_558 | SSNLLEIMNA | KFPELGLKR | ECIEMKWIES | VLFWLGIPPG | TA---PTTSM | 361 |
| SEQ_ID_NO_571 | AERLLSVMNE | SFPELGLQAK | DCAEMRWIES | VLSWGMPKG | T----PLEVL | 356 |

Figure 17 (continued)

| | | | | | | | |
|---|---|---|---|---|---|---|---|
| SEQ_ID_NO_559 | NNRF LKFDER | AFK TKVDL TK | EPL PSK AF YG | LL - ERL SK - | EPNGF I AL NG | 391 |
| SEQ_ID_NO_586 | NNRF LKYDDR | AFK TKVDF VK | EPI PL EGI KG | AL - TML TK - | EL RGF MAF NG | 388 |
| SEQ_ID_NO_591 | KDRF LRYDDR | AFK TKVDF PK | EA PL EGI QG | AL - EI LKK - | EQRGF MVMNG | 389 |
| SEQ_ID_NO_581 | LNR SSNPSY | YLK AKSDHVQ | EPI PRDVMES | WTT WL EK - | PEAA LL ML DP | 405 |
| SEQ_ID_NO_588 | LDR I GETGR | YVK AKSDYYQ | EPI PRHAMES | TM SWL EK - | PEAGLLI LDP | 399 |
| SEQ_ID_NO_589 | LNR TSSI RA | FGK YKSDYYT | DPL SK ATMDT | YKDWF SK - | PGSGI MI MDP | 398 |
| SEQ_ID_NO_590 | LNR TSSI RA | FGK YKSDYYT | DPL SK ATMDT | YKDWF SK - | PGSGI MI MDP | 403 |
| SEQ_ID_NO_584 | LNR NNSFKP | FAE YKSDYVY | DPF PK TVMEQ | LNTWL VK - | PGAGI MI FDP | 398 |
| SEQ_ID_NO_583 | LNR TSNI KA | FGK YKSDYVK | DPI PRDVMEK | YL TWL AK - | PGAGVMI MDP | 401 |
| SEQ_ID_NO_585 | LNR TSNI KA | FGK YKSDYVL | EPI PKSDMEK | FL TWL VK - | PGAGVMI MDP | 398 |
| SEQ_ID_NO_560 | LDR SAGKKT | AFSI KL DYVK | KL PETAMVK | L - EKL YEEE | VGVGMYVL YP | 418 |
| SEQ_ID_NO_577 | LNR TQI RSG | KYK GKSDYVR | KPI PVDGLRG | LW RWL NDDK | VQYSQL QF AP | 409 |
| SEQ_ID_NO_569 | LDR DLNDAG | FLK RKSDYYQ | TPI PKSGLES | LW QKM E - | LGKVGMVF NA | 404 |
| SEQ_ID_NO_575 | LDR NHYSVH | SNK RKSDYYQ | TPI SKDGF TW | WL KKM E - | LGKYSI VF NP | 411 |
| SEQ_ID_NO_576 | LDE PKDPQPL | YQK NKSDYVK | KPI PREALES | WL KLM E - | GENFL MQMNP | 402 |
| SEQ_ID_NO_578 | LSR TPQRLN | PFK I KSDYVQ | NPI SKRQF EF | FL ERMKE - | LENQML AF NP | 412 |
| SEQ_ID_NO_579 | LSR TPQRLN | PFK I KSDYVK | NTI SKQGF ES | FL ERMKE - | LENQML AF NP | 411 |
| SEQ_ID_NO_558 | RNR I PQKQI | YLK RKSDYVQ | KPI SRT GLES | FL K MT E - | NENV TMAF NP | 407 |
| SEQ_ID_NO_571 | LDR I PKGVS | YLK RKSDYVK | EPI SKEGLES | WL KVMT E - | VGEVAML WNP | 402 |

| | | | | | | | |
|---|---|---|---|---|---|---|---|
| SEQ_ID_NO_559 | FGGQMSKI SS | DF TPFPHRSG | TRLMVEYI VA | RNQSEQKKKT | EFL DWL EKVY | 441 |
| SEQ_ID_NO_586 | QGGL MSRI SS | DSTPFPHRKG | TL MMMEYI VA | MDRDEDAKSV | EFI GML HGF Y | 438 |
| SEQ_ID_NO_591 | QGGMMDRI ST | DASPFPHRSG | TL SMVEYI VA | MDKHEDL HSN | EFI HWL HQL F | 439 |
| SEQ_ID_NO_581 | YGGVMSSI PP | SETPFPHRQG | NL YQL QYYSF | WYENGT AAAE | KRMSWVRGL Y | 455 |
| SEQ_ID_NO_588 | YGGRMASI SP | BATPFPHRKG | NL YNL QYYSF | WF ENGT AAME | KRMNWVRGL Y | 449 |
| SEQ_ID_NO_589 | YGATI SKPGE | ADTPFPHRKG | MLYN QYI TF | WF GEGAPAEA | - PI KM RDF Y | 447 |
| SEQ_ID_NO_590 | YGATI SKPGE | ADTPFPHRKG | MLYN QYI TF | WF GEGAPAEA | - PI KM RDF Y | 452 |
| SEQ_ID_NO_584 | YGATI SATPE | SATPFPHRKG | VLFNI QYVNY | MF APGAAAAL | - PL SWSKDI Y | 446 |
| SEQ_ID_NO_583 | YGARI SSI PQ | DATPFPHRQG | VLFNI QYVBY | MF GEGDGAAL | - PTQMSRDMY | 449 |
| SEQ_ID_NO_585 | YGGG ASVPE | SATPFPRRSG | VLFNI QYVVY | MF GEGAAAL - | - PTQWTRDI Y | 446 |
| SEQ_ID_NO_560 | YGGL MDEI SE | SAT PFPHRAG | I MYEL MYT AT | MEKQEDNEK - | - HI NWVRSVY | 466 |
| SEQ_ID_NO_577 | YGGKMDN SE | SEI PFAHRSG | YI FHI HYVVV | MQEEGDEAT Q | RHVNM RRL Y | 459 |
| SEQ_ID_NO_569 | YGGRMDQI KP | DETPFPHRAG | NL YKI QYSVN | MDQPGSEADK | NF I TQAKL L H | 454 |
| SEQ_ID_NO_575 | YGGKMNEVPS | DATPFPHRAG | NL YKI QYT VS | MQEPGAAVEK | SFL SDI RVL H | 461 |
| SEQ_ID_NO_576 | YGGRMEEI LP | SETPFSHRAG | NLFL J QYLNI | MSNESSEVSE | RHVNFSRSFF | 452 |
| SEQ_ID_NO_578 | YGGRMSEI SE | FAKPFPHRSG | NI AKI QYEVN | MEDL SDEAEN | RYL NFI TRL MY | 462 |
| SEQ_ID_NO_579 | YGGRMSEI SE | FAKPFPHRSG | NI AKI QYEVN | MDEL GVEAAN | RYL NFI TRVMY | 461 |
| SEQ_ID_NO_558 | YGGRMSEI PS | TETAFPHRAG | NMFKI QYAAN | MF VPGEAVAK | DCL SQTERL F | 457 |
| SEQ_ID_NO_571 | YGGKMSEI SE | TETAFPHRAG | NI FKI QYSVN | MKQEGI DT TN | HYVNL TRT LF | 452 |

Figure 17 (continued)

| | | | | | | | |
|---|---|---|---|---|---|---|---|
| SEQ_ID_NO_559 | EFMKPFVSKN | PRLGYVNHID | LDLGGIDW-- | -GNKTVVNN- | AIEISRS- | WG | 486 |
| SEQ_ID_NO_586 | NYMGQFLPSD | PRIAYVNHVD | LDLGRLDW-- | -TNSTIASN- | AIEIART- | WG | 483 |
| SEQ_ID_NO_591 | DYMGKFVSNN | PRVGYVNHVD | LDLGRIDW-- | -VNKTISSGR | AIEIART- | WG | 485 |
| SEQ_ID_NO_581 | KEMEPYVSKN | PRAVYVNYRD | LDLGTNELD- | -GDVT---- | SYEKARVS | WG | 498 |
| SEQ_ID_NO_588 | REMEPYVSKN | PRTGYVNYRD | LDLGTNELE- | -GNVT---- | SYAKARI- | WG | 491 |
| SEQ_ID_NO_589 | AFMEPYVTKN | PRQAYVNYRD | LDLGVNAVEA | GANVS---- | CYQVGKV- | WG | 491 |
| SEQ_ID_NO_590 | AFMEPYVTKN | PRQAYVNYRD | LDLGVNAVEA | GANVS---- | CYQVGKV- | WG | 496 |
| SEQ_ID_NO_584 | NYMEPYVSKN | PRQAYANYRD | IDLGRNEVV- | -NDVS---- | TYASGKV- | WG | 488 |
| SEQ_ID_NO_583 | AFMEPYVSKN | PRQAYANYRD | LDLGVNEVV- | -GDVS---- | TYDSGRV- | WG | 491 |
| SEQ_ID_NO_585 | DFMTPYVSKN | PRQAYVNYRD | LDLGVNQVV- | -GNVS---- | TYASGKV- | WG | 488 |
| SEQ_ID_NO_580 | NFTTPYVSQN | PRLAYLNYRD | LDLGKTNP-- | -ESPN---- | NYTQARI- | WG | 507 |
| SEQ_ID_NO_577 | KYMEPYVSNS | PRAAYVNYRD | LDIGVNN--- | -NGYT---- | SYHQAS- | WG | 499 |
| SEQ_ID_NO_569 | DFMTPFVSKN | PRSAYFNYRD | DVG--S--- | -TKKW---- | SYEEGKV- | YG | 492 |
| SEQ_ID_NO_575 | NYMTPFVSKN | PRSAYFNYRD | LDIGINS--- | -HGKD---- | NFEDGKV- | YG | 501 |
| SEQ_ID_NO_576 | EFMTPYVSTS | PREAFLNYRD | ADIGANHP-- | -SNVT---- | RFDIAKT- | YG | 493 |
| SEQ_ID_NO_578 | DYMTPFVSKN | PREAFLNYRD | LDIGINS--- | -HGRN---- | AYTEGMV- | YG | 502 |
| SEQ_ID_NO_579 | DYMTPFVSKN | PREAFLNYRD | LDIGVNS--- | -HGKN---- | AYGEGMV- | YG | 501 |
| SEQ_ID_NO_558 | EAMSPYVSKN | PREAFLNYRD | VDIGK----- | -SLNS---- | TYEEGKV- | YG | 495 |
| SEQ_ID_NO_571 | EAMTPYVSKN | PREAFLNYRD | DIGSIGS-- | -HGNG---- | TFQEASV- | YG | 493 |

| | | | | | | |
|---|---|---|---|---|---|---|
| SEQ_ID_NO_559 | ESYFLS-NYE | RLIRAKTLID | PNNVFNHPQS | PPMANFDYL EKTLGSDGGE | | 535 |
| SEQ_ID_NO_586 | EKYFLS-NYE | RLVRAKTLID | PKNVFHHPQS | PPMPQDDLR PNGIWRTEEM | | 532 |
| SEQ_ID_NO_591 | EKYFMS-NYD | RLVRAKTMID | PKNVFNHPQS | PPLLEIMLD NVKENDVIYK | | 534 |
| SEQ_ID_NO_581 | DKYFKG-NFK | RLAAVKTMVD | PHDFFRNEQS | PPLPTAKMM IDSI------ | | 541 |
| SEQ_ID_NO_588 | EKYFRG-NFE | RLAAVKAMVD | PDDFFRNEQS | PPLPAAKGW SSI------- | | 533 |
| SEQ_ID_NO_589 | EKYFKG-NFE | RLARTKAKVD | PTDFFRNEQS | PPLLA---- ---------- | | 526 |
| SEQ_ID_NO_590 | EKYFKG-NFE | RLARTKAKVD | PTDFFRNEQS | PPLLA---- ---------- | | 531 |
| SEQ_ID_NO_584 | QKYFKG-NFE | RLAITKGKVD | PTDYFRNEQS | PPLIKKY-- ---------- | | 525 |
| SEQ_ID_NO_583 | EKYYNG-NFE | RLARTKAKVD | PCDYFRNEQS | PPLLK---- ---------- | | 526 |
| SEQ_ID_NO_585 | EKYFKG-NFE | RLARTKGKID | PEDYFRNEQS | PPLL----- ---------- | | 522 |
| SEQ_ID_NO_580 | EKYFGK-NFN | RLVKVKTKAD | PNNFFRNEQS | PPLPPHHH- ---------- | | 545 |
| SEQ_ID_NO_577 | LKYFSN-NFK | RLATVKTKVD | PHNFFRNEQS | PTLSKE--- ---------- | | 535 |
| SEQ_ID_NO_569 | ESYFNG-NYE | RLVDVKTAVD | ANNFFRNEQS | PPRSSKI-- ---------- | | 529 |
| SEQ_ID_NO_575 | IKYFNK-NFE | RLVKVKSAID | PENFFMNEQS | PTYPRSNA- ---------- | | 539 |
| SEQ_ID_NO_576 | SKFFKG-NFE | RLVSVKTKVD | PQNFFRYEQS | PTRSL---- ---------- | | 528 |
| SEQ_ID_NO_578 | HKYFKETNYK | RLVSVKTKVD | PDNFFRNEQS | PTLSS---- ---------- | | 538 |
| SEQ_ID_NO_579 | HKYFKETNYK | RLTMVKTRVD | PSNFFRNEQS | PTLSSSWK- ---------- | | 540 |
| SEQ_ID_NO_558 | FKYFKD-NFE | KLVKIKSRVD | PDNFFRYEQS | PVLSSH--- ---------- | | 531 |
| SEQ_ID_NO_571 | HKYFKD-NFD | RLVQIKTRVD | PDNFFGYEQS | PTQSSSYRP DLCAWQQPRK | | 542 |

Figure 17 (continued)

| SEQ_ID_NO_559 | VVI | 538 |
| --- | --- | --- |
| SEQ_ID_NO_586 | FFLE | 536 |
| SEQ_ID_NO_591 | L | 535 |
| SEQ_ID_NO_581 | | 541 |
| SEQ_ID_NO_588 | | 533 |
| SEQ_ID_NO_589 | | 526 |
| SEQ_ID_NO_590 | | 531 |
| SEQ_ID_NO_584 | | 525 |
| SEQ_ID_NO_583 | | 526 |
| SEQ_ID_NO_585 | | 522 |
| SEQ_ID_NO_560 | | 545 |
| SEQ_ID_NO_577 | | 535 |
| SEQ_ID_NO_569 | | 529 |
| SEQ_ID_NO_575 | | 539 |
| SEQ_ID_NO_576 | | 528 |
| SEQ_ID_NO_578 | | 538 |
| SEQ_ID_NO_579 | | 540 |
| SEQ_ID_NO_558 | | 531 |
| SEQ_ID_NO_571 | RTLGARTSER AWQQHQAADT WRRAVMPYGL GKLARLAKHP KRRFTGPPAW | 592 |

| SEQ_ID_NO_559 | | 538 |
| --- | --- | --- |
| SEQ_ID_NO_586 | | 536 |
| SEQ_ID_NO_591 | | 535 |
| SEQ_ID_NO_581 | | 541 |
| SEQ_ID_NO_588 | | 533 |
| SEQ_ID_NO_589 | | 526 |
| SEQ_ID_NO_590 | | 531 |
| SEQ_ID_NO_584 | | 525 |
| SEQ_ID_NO_583 | | 526 |
| SEQ_ID_NO_585 | | 522 |
| SEQ_ID_NO_560 | | 545 |
| SEQ_ID_NO_577 | | 535 |
| SEQ_ID_NO_569 | | 529 |
| SEQ_ID_NO_575 | | 539 |
| SEQ_ID_NO_576 | | 528 |
| SEQ_ID_NO_578 | | 538 |
| SEQ_ID_NO_579 | | 540 |
| SEQ_ID_NO_558 | | 531 |
| SEQ_ID_NO_571 | VCRHVLWQT PTSGSAATRA WGMCPALLTL QTWALGADSH ARVNCDPHLS | 642 |

Figure 17 (continued)

| | | |
|---|---|---|
| SEQ_ID_NO_559 | .......... .......... .......... .......... .......... | 538 |
| SEQ_ID_NO_586 | .......... .......... .......... .......... .......... | 536 |
| SEQ_ID_NO_591 | .......... .......... .......... .......... .......... | 535 |
| SEQ_ID_NO_581 | .......... .......... .......... .......... .......... | 541 |
| SEQ_ID_NO_588 | .......... .......... .......... .......... .......... | 533 |
| SEQ_ID_NO_589 | .......... .......... .......... .......... .......... | 526 |
| SEQ_ID_NO_590 | .......... .......... .......... .......... .......... | 531 |
| SEQ_ID_NO_584 | .......... .......... .......... .......... .......... | 525 |
| SEQ_ID_NO_583 | .......... .......... .......... .......... .......... | 526 |
| SEQ_ID_NO_585 | .......... .......... .......... .......... .......... | 522 |
| SEQ_ID_NO_560 | .......... .......... .......... .......... .......... | 545 |
| SEQ_ID_NO_577 | .......... .......... .......... .......... .......... | 535 |
| SEQ_ID_NO_569 | .......... .......... .......... .......... .......... | 529 |
| SEQ_ID_NO_575 | .......... .......... .......... .......... .......... | 539 |
| SEQ_ID_NO_576 | .......... .......... .......... .......... .......... | 528 |
| SEQ_ID_NO_578 | .......... .......... .......... .......... .......... | 538 |
| SEQ_ID_NO_579 | .......... .......... .......... .......... .......... | 540 |
| SEQ_ID_NO_558 | .......... .......... .......... .......... .......... | 531 |
| SEQ_ID_NO_571 | RTQEEYIKLG PAQQDPFKLG SALEGPKIAR LDPLALALVA LMGPVLSKTH | 692 |

| | | |
|---|---|---|
| SEQ_ID_NO_559 | .......... . | 538 |
| SEQ_ID_NO_586 | .......... . | 536 |
| SEQ_ID_NO_591 | .......... . | 535 |
| SEQ_ID_NO_581 | .......... . | 541 |
| SEQ_ID_NO_588 | .......... . | 533 |
| SEQ_ID_NO_589 | .......... . | 526 |
| SEQ_ID_NO_590 | .......... . | 531 |
| SEQ_ID_NO_584 | .......... . | 525 |
| SEQ_ID_NO_583 | .......... . | 526 |
| SEQ_ID_NO_585 | .......... . | 522 |
| SEQ_ID_NO_560 | .......... . | 545 |
| SEQ_ID_NO_577 | .......... . | 535 |
| SEQ_ID_NO_569 | .......... . | 529 |
| SEQ_ID_NO_575 | .......... . | 539 |
| SEQ_ID_NO_576 | .......... . | 528 |
| SEQ_ID_NO_578 | .......... . | 538 |
| SEQ_ID_NO_579 | .......... . | 540 |
| SEQ_ID_NO_558 | .......... . | 531 |
| SEQ_ID_NO_571 | QRSLKKKISL M | 703 |

Figure 18

| | | | | | | |
|---|---|---|---|---|---|---|
| SEQ_ID_NO_603 | MAAAT--SSS AVAVSTPQGV | AERRGI PAAS | FVEDVETYLR | QAGLEVNSAL | | 48 |
| SEQ_ID_NO_605 | MAAAA------SASTPQGV | AERRGI PAAA | FVEDVEAYLR | QAGLDVNSAL | | 43 |
| SEQ_ID_NO_610 | MAAAAASSSS SSAAATPQGV | TERRGI PAAS | FVEDVETYLR | QAGLDVNSGL | | 50 |
| SEQ_ID_NO_593 | MSSSS------PSGSGSDL | TERRGI PAAK | FIQDVETYLS | QSGLDPNSAL | | 43 |
| SEQ_ID_NO_595 | MASSS----S TAVATAYETT | TERRGI PGAQ | FVEDVETYLN | QSGLDVNSAL | | 46 |
| SEQ_ID_NO_599 | MASSS---------SESAV | SERRGI PGAQ | FVEDVQTYLT | QSGLDVGSAL | | 40 |

| | | | | | | |
|---|---|---|---|---|---|---|
| SEQ_ID_NO_603 | AFLQERLQQY | KMVEMKLLAQ | QRELQAKI PD | EKCLDI VAT | LKAKKALGEA | 98 |
| SEQ_ID_NO_605 | AFLQERLQQY | KIVEMKLLAQ | QRDLQAKI PD | EKCLDI VST | LQAKKDLGEA | 93 |
| SEQ_ID_NO_610 | AFLQERLQQY | KIVEMKLLAQ | QRDLQAKI PD | EKCLDI VAT | LQAKKALGEA | 100 |
| SEQ_ID_NO_593 | AFHQERLQQY | KVVEMKLLAQ | QRDLQAKI PD | EKCLEVVAT | LEAKKGTGEA | 93 |
| SEQ_ID_NO_595 | SFLQERLQQY | KLVEMKLLAQ | QRDLQAKI PD | EKCLDVVAT | LQAKKGTGEP | 96 |
| SEQ_ID_NO_599 | AFLQERLQQY | KVVEMKLLAQ | QRDLQAKI PD | EKCLDVVAT | LKAKKGTGEE | 90 |

| | | | | | | |
|---|---|---|---|---|---|---|
| SEQ_ID_NO_603 | LIADFELSEG | YSRAKI EDS | DSVCLWLGAN | VMLEYSCDEA | NELLKSNLEN | 148 |
| SEQ_ID_NO_605 | LIADFELSEG | YSCAKI EDT | DSVCLWLGAN | VMLEYSCDEA | NALLKKNLEN | 143 |
| SEQ_ID_NO_610 | LTADFELSEG | YSRAKI EDT | DSVCLWLGAN | VMLEYSCDEA | NALLKKNLEN | 150 |
| SEQ_ID_NO_593 | LLADFEVSEG | YSRACI EDT | DSVCLWLGAN | VMLEYSCEEA | SALLKNNLEN | 143 |
| SEQ_ID_NO_595 | LIADFEVSEG | YSQARI EDA | ESVCLWLGAN | VMLEYSCEEA | NDLLQKNLDN | 146 |
| SEQ_ID_NO_599 | LIADFEVSEG | YSRARI EET | NSVCLWLGAN | VMLEYSLEEA | TGLLQKNLDN | 140 |

| | | | | | | |
|---|---|---|---|---|---|---|
| SEQ_ID_NO_603 | ARASLEVLVG | DLHFLRDQQT | ITQVTI ARI F | NWDVHQ-RRS | KQ----SVM | 192 |
| SEQ_ID_NO_605 | AKASLEVLVA | DLQFLRDQQT | ITQVTI ARVF | NWDVHH-RRS | KQ-----AV | 186 |
| SEQ_ID_NO_610 | AKASLEVLVA | DLQFLRDQQT | ITQVTI ARVF | NWDVHQ-RRS | KQ-----AI | 193 |
| SEQ_ID_NO_593 | AKASLEVLVA | DLQFLRDQVT | VTQVTI ARVY | NWDVHQ-RRV | KQVTPTALAV | 192 |
| SEQ_ID_NO_595 | AKASLEVLVA | DLLFLRDQVT | ITQVTI ARVY | NWDVHQKRRM | RE---AVTAE | 193 |
| SEQ_ID_NO_599 | ARASLEVLIA | DLQFLRDQVT | ITQVTI ARVY | NWDVHQ-RRV | QQ---AVATT | 186 |

| | | |
|---|---|---|
| SEQ_ID_NO_603 | KET | 195 |
| SEQ_ID_NO_605 | KEP | 189 |
| SEQ_ID_NO_610 | KET | 196 |
| SEQ_ID_NO_593 | ADS | 195 |
| SEQ_ID_NO_595 | KDS | 196 |
| SEQ_ID_NO_599 | AQD | 189 |

Figure 19

| | | | | | | | |
|---|---|---|---|---|---|---|---|
| SEQ_ID_NO_622 | ----MAFSNA | LRSAAKLVAS | SESSLSNSVS | RGFHSTGMKR | M-GGGHGHDE | 45 |
| SEQ_ID_NO_613 | ----MALSTS | RSVSKIISS | SEASVSRSVT | RSFHSTGVKK | MSGGHGGYD | 46 |
| SEQ_ID_NO_620 | ----MALNTG | RSISKIIAF | SEASVSRSVS | RSFHSTGAKK | M-SGGHGHDE | 45 |
| SEQ_ID_NO_626 | ----MALNTG | RSVSRLIAS | SESSVSRSVS | RSFHSTGAKK | M-SGGHGHDE | 45 |
| SEQ_ID_NO_643 | ----MAAAAA | --------AA | GEEE--GEAS | RGFHATGVKR | M--GGHGHDE | 34 |
| SEQ_ID_NO_644 | MATATALNRG | LRSGIRLLAT | GAEA-SKTDS | RGFHATGVKR | M--GGHGHDE | 47 |
| SEQ_ID_NO_624 | --MATALNRG | LRSGIRLLAT | GAEA-SKPAS | RGFHATGVKR | M--SGHGHDE | 45 |
| SEQ_ID_NO_638 | --MATALNRG | LRSGIRLLAA | GAEA-SKPAS | RGFHATGVKR | M--GGHGHDE | 45 |
| SEQ_ID_NO_634 | ----MALSRG | IRSGLKLLSH | SEAALPRSVT | HEFHATSMKR | M--GGHGHDE | 44 |
| SEQ_ID_NO_615 | ----MAMIRG | ISSGIKLLTS | SEAALFRSVT | REFHATGMKR | M--GGHGHDE | 44 |

| | | | | | | | |
|---|---|---|---|---|---|---|---|
| SEQ_ID_NO_622 | PYYLHAKHMY | NLDRMKHQGL | KMSLAVFTAF | SIGVAPVYA | VIFQQKKTAS | 95 |
| SEQ_ID_NO_613 | EYYLHAKHMY | NLDRMKYQAL | KMSLGVFTAF | SIGVGVPIFA | VVFQQRKTQS | 96 |
| SEQ_ID_NO_620 | PYYLHAKHMY | NLDRMKYQGL | KMSLGVFTAF | SIGVGVPIFA | VVFQQRKTAS | 95 |
| SEQ_ID_NO_626 | PYYLHAKHMY | NLDRMKFQGL | KMSLAVFTAF | SIGVGVPIFA | VVFQQRKTAS | 95 |
| SEQ_ID_NO_643 | PYYLHAKHMY | NLHRMKHQKP | KVYLSVLGAV | GIGIAVPVYA | VVFQQKKTAS | 84 |
| SEQ_ID_NO_644 | PYYLHAKHMY | NLHRMKHQKP | KVYLSVLGAV | GIGIAVPVYA | VVFQQKKTAS | 97 |
| SEQ_ID_NO_624 | PYYLHAKHMY | NLHRMKHQKL | TAWTSVLGAV | SIGIGVPVFA | VVFQQKKTSS | 95 |
| SEQ_ID_NO_638 | PYYLHAKHMY | NLHRMKHQGL | KVTLSVLGAV | SIGVGVPVYA | VIFQQKKTAS | 95 |
| SEQ_ID_NO_634 | PFYIHAKHMY | NLDRMKHQKL | KVTLGVLSAF | SIGVVPIYA | VIFQQKKAAS | 94 |
| SEQ_ID_NO_615 | PYYLHAKHMY | NLDQMKHQKL | KVALSVWSAF | GIGMAVPVYA | VMFQQKKAAS | 94 |

| | | |
|---|---|---|
| SEQ_ID_NO_622 | S | 96 |
| SEQ_ID_NO_613 | G | 97 |
| SEQ_ID_NO_620 | G | 96 |
| SEQ_ID_NO_626 | G | 96 |
| SEQ_ID_NO_643 | G | 85 |
| SEQ_ID_NO_644 | G | 98 |
| SEQ_ID_NO_624 | G | 96 |
| SEQ_ID_NO_638 | G | 96 |
| SEQ_ID_NO_634 | G | 95 |
| SEQ_ID_NO_615 | A | 95 |

Figure 20

| | | | | | | | |
|---|---|---|---|---|---|---|---|
| SEQ_ID_NO_685 | MGFISFVGRV | LFASLFLLSA | YQEFLEFGND | GGPAAKTLKP | KFNLFVKLVS | 50 |
| SEQ_ID_NO_679 | MGFVSFAGRV | LFASVFLLSA | YQEFSEFGAD | GGPAAKALRP | KYNVFTKNIS | 50 |
| SEQ_ID_NO_681 | MGFVSFAGRV | LFASVFLLSA | YQEFSEFGAD | GGPAAKALRP | KYNVFTKNIS | 50 |
| SEQ_ID_NO_668 | MGFVSFVGRV | LFMAAFLLSA | YQEFNEFGAD | GGPAAKALRP | KFNVFVKNVS | 50 |
| SEQ_ID_NO_676 | MGFVSFVGRV | LFMAAFLLSA | YQEFNEFGTD | GGPAAKALQP | KFNVFVKNIS | 50 |
| SEQ_ID_NO_646 | MELASFLGRA | LFVSVFLLSA | WQEFNDFGED | GGRSAKSLKP | KFNAFVNHVT | 50 |
| SEQ_ID_NO_648 | MALVSFVGRV | LFASVFILSA | WQEFNEFGVD | GGPAAKALKP | KFNVFSKTVT | 50 |
| SEQ_ID_NO_656 | MAFTSFLGRV | LFASVFILSA | YQEFNEFGVD | GGPAAKALKP | KFGVFTSHVD | 50 |
| SEQ_ID_NO_660 | MAFASFLGRV | LFASVFILSA | YQEFNEFGVD | GGPAAKALRP | KFDAFTHRVH | 50 |

| | | | | | | | |
|---|---|---|---|---|---|---|---|
| SEQ_ID_NO_685 | KNTGLGVPHI | DIKIVIAATM | FLKGFGGLLF | ESSSFGAFL | LLIYLAFMTP | 100 |
| SEQ_ID_NO_679 | AHLGVAVPHV | ELKHIVAATI | GLKGLGGLLF | LSSSFGAYL | LLIYLAFITP | 100 |
| SEQ_ID_NO_681 | AHLGVAVPHV | ELKHIVAATI | GLKGLGGLLF | LSSSFGAYL | LLIYLAFITP | 100 |
| SEQ_ID_NO_668 | AHLGVAVPHI | ELKHVIAATI | GLKGLGSLLF | LSSSLGAYL | LLLYLALITP | 100 |
| SEQ_ID_NO_676 | SHLGVAVPHI | ELKHVIAATI | ALKGLGGLLF | LSCSLGAYL | LLLYLAIVTP | 100 |
| SEQ_ID_NO_646 | THTGQQLPPV | DMKILVAAAI | ALKGIGGLLF | VFGSSLGAYL | LLHQAVATP | 100 |
| SEQ_ID_NO_648 | AHTGVEVPEF | DIKVLVAAAV | AFKGVGGILF | FGSTIGAYL | ALQOVVTT | 100 |
| SEQ_ID_NO_656 | SHAGIQVPEI | EIKHLVSAAI | FLKGIGGILF | IGSSLGAYL | LIHQLAIP | 100 |
| SEQ_ID_NO_660 | SDVGFQLPEI | DLKFLIAGAI | ALKGLGGVLF | FGSSFGALL | LLHQLATP | 100 |

| | | | | | | | |
|---|---|---|---|---|---|---|---|
| SEQ_ID_NO_685 | VYDFYNYEM | ESEQFVQLFF | KFTQNLAFIG | ALLFFLGMKN | SIPRRRSK | 148 |
| SEQ_ID_NO_679 | VVYDFYNYNM | EKSEFVQLFM | KFTQNLALFG | ALLFFLGMKN | SIPKRQAK | 148 |
| SEQ_ID_NO_681 | VVYDFYNYDM | EKSEFVQLFM | KFTQNLALFG | ALLFFLGMKN | SIPKRQAK | 148 |
| SEQ_ID_NO_668 | IHDFYNYDM | EKAEFAGLFA | KFTQDLALIG | ALLFFLGMKN | SIPKROGGK | 149 |
| SEQ_ID_NO_676 | IVHDFYNYDM | EKAEFAQIFG | KFTQDLALIG | ALLFFLGMKN | SIPKRQSK | 148 |
| SEQ_ID_NO_646 | LYDFYNYDV | DRKEFGQLFS | KFTQSLALLG | GLLFFIGMKN | SRKHGRQLR | 149 |
| SEQ_ID_NO_648 | LYDFYNYDT | EKKEFGLLFS | KFSQNLALLG | ALLFFIGMKN | SIPS-RQLK | 148 |
| SEQ_ID_NO_656 | LYDFYNYDS | EEKEFNQLFI | KFTQNMALYG | ALLFFIGMKN | SFPRRQHK | 148 |
| SEQ_ID_NO_660 | HYDFYNYDS | EDKEFTQLFI | KFTQNMALFG | ALLFFIGMKN | SIPRR-VP | 147 |

| | | |
|---|---|---|
| SEQ_ID_NO_685 | GRTTKTKTN | 157 |
| SEQ_ID_NO_679 | KKAPKSKTN | 157 |
| SEQ_ID_NO_681 | KKAPKSKTN | 157 |
| SEQ_ID_NO_668 | KKAPKAKTN | 158 |
| SEQ_ID_NO_676 | KKAPKAKTN | 157 |
| SEQ_ID_NO_646 | KKAPKAKAN | 158 |
| SEQ_ID_NO_648 | KKAPKTKTV | 157 |
| SEQ_ID_NO_656 | KKVPKTKTG | 157 |
| SEQ_ID_NO_660 | KKAPKTKTY | 156 |

Figure 21

| | | | | | | |
|---|---|---|---|---|---|---|
| SEQ_ID_NO_708 | MDEI MNKMGS | YWL GQRANKE | MSSAGDDI ES | LSTSVGDGAK | MLVNKLKGKM | 50 |
| SEQ_ID_NO_728 | MDQI FNKVGS | YWL GQKANKE | FNSVGDDI NS | VGSSI GDGTK | MLVNKLKGKM | 50 |
| SEQ_ID_NO_718 | MDQI LNKVGS | YWM NKRANKE | LSSVGDDLNS | LSSSI EGGAK | MLVNKLKGKM | 50 |
| SEQ_ID_NO_687 | MDQI FNKVGS | YWL GQKANKQ | FDSVGNDLNS | VSTSI EGGTK | MLVNKI KGKM | 50 |
| SEQ_ID_NO_699 | MDQVF XKVGS | YWL GQKANKQ | FDSVGKDVSS | LSTSI EGGTK | MLVNKFKGTM | 50 |
| SEQ_ID_NO_689 | MDQI LNKVGS | YWL GQKANKE | LDSVGDDLNS | LSTSI EGGAK | MLVNKI KGKM | 50 |
| SEQ_ID_NO_691 | MDAVLNKVGS | YWL GQKASKE | FNSVGDDI NS | LSTSI EGGTK | MLVNKLKGKM | 50 |
| SEQ_ID_NO_703 | MDQI FNKVGS | YWF NQKASSD | LNSVGDDI NS | MTNSI XGGTK | MLVNKI KGKM | 50 |
| SEQ_ID_NO_706 | MDQVFNKVGS | YWF NQKASKE | LNSVGDEI NS | LSNSI EGGTK | MLVNKVKGKM | 50 |
| SEQ_ID_NO_721 | MDQI MGKVGS | YWF KQNAGKE | LNNI GDDI NS | LSSSI GDGAK | MMVNKI KGKM | 50 |
| SEQ_ID_NO_712 | MDQVLNKVGS | YWF SKRASKE | LDSI GDDLNS | VSSSI GGGAK | MMVNKI KGKL | 50 |
| SEQ_ID_NO_724 | MDQVLNKVGS | YWF SKRASKE | LDSI GDDI SS | LSTSI GTGAK | MMVNKI KGKM | 50 |
| | | | | | | |
| SEQ_ID_NO_708 | QKPLAELLQE | HDLPAGLFPR | EATNYEFEPE | TRRLTVHI PA | VCEVGYRDGS | 100 |
| SEQ_ID_NO_728 | QKPLPELLKD | YDLAVGI FPR | DATHYEFDER | QGKLTVYVPQ | I CEVGYKDSS | 100 |
| SEQ_ID_NO_718 | QKSLPELLRE | YDMPI GLFPQ | DATHYEFNEE | TGKLTVFI PS | I CEVGYRDSS | 100 |
| SEQ_ID_NO_687 | QKPLPELLKE | YDLPI GI FPG | DATNYEFDEE | TKKLTVLI PS | I CEVGYKDSS | 100 |
| SEQ_ID_NO_699 | QKPLAELLKD | YDLPVGI FPR | DATNYEFDEQ | TKKLTVLI PS | VCEVGYKDSS | 100 |
| SEQ_ID_NO_689 | QKPLPELLRE | YNLPI GI FPR | DATNYEFNEE | TGKLTVFI PA | I CEVGYKDSS | 100 |
| SEQ_ID_NO_691 | QKPLPDLLKE | YDLPI GI FPR | DATNYEFNEE | TRKLTVFI PS | I CEVGYKDSS | 100 |
| SEQ_ID_NO_703 | QKALPELLKE | YDLPI GI FPR | DATNYEFNEE | TGKLMVYI PD | VCEVGYKDSS | 100 |
| SEQ_ID_NO_706 | QKPLPELLKE | YDLPI GI FPR | DATNYEFNEE | TGKLEVFI PQ | VCEVGYKDSS | 100 |
| SEQ_ID_NO_721 | QKPLPEFLKE | YDLPVGLFPQ | DATNYEFNEE | TKKLTVYI SS | VCEVGYKDSS | 100 |
| SEQ_ID_NO_712 | QKALPDLLKE | YDMPAGLFPR | DTTNYEFNEE | TKKLTVYI PS | ACDVGYKDSS | 100 |
| SEQ_ID_NO_724 | QKALPDLLKE | YDMPAGLFPR | DATNYEFNEE | TKKLTVYI PS | ACDVGYKDSS | 100 |
| | | | | | | |
| SEQ_ID_NO_708 | ELRFDTTVTG | TLDKGSLTGV | EGLKAKVLVW | ARVTAVKADA | AKVYFAVGI K | 150 |
| SEQ_ID_NO_728 | VLRFFATVTG | YLEKGKLADI | EGLKTKI I I W | VKVTAI TSEG | SKLHFTAGVK | 150 |
| SEQ_ID_NO_718 | VLRFLNI VTG | YLEKGKLVDI | EGI KTKVLI W | SKVTRI STEG | SKI HFTTGVK | 150 |
| SEQ_ID_NO_687 | VLKFI TTVTG | HLEKGKLTDV | EGI KTKVMI W | VKVTSI STDA | SKVYFTAGMK | 150 |
| SEQ_ID_NO_699 | VLKFI TTVTG | RLEKGKLGDL | EGMKTKVMI W | VKVTSI SADS | SKVYFTAGVK | 150 |
| SEQ_ID_NO_689 | F-----CASS | PL-------- | ---------- | ---------- | ---------- | 107 |
| SEQ_ID_NO_691 | VVRFLTTVTG | YLEKGKI ADI | EGMKTKVMI W | VKVTCI ASTS | SKLNFTAGMK | 150 |
| SEQ_ID_NO_703 | VLRFXTTVTG | YLEKGKLADI | EGMKTKVLI W | VKVTTLSKS | XKKYVTAGKK | 150 |
| SEQ_ID_NO_706 | VLRFFTTVTG | YLEKGKLADI | EGMKTKVI I W | VKVTTFSEG | SKLYVTAGMK | 150 |
| SEQ_ID_NO_721 | VLRFSTTVTG | YLENGKLSEV | EGLKTKI LI W | TKVTAVRTEA | TKVHFAAGMN | 150 |
| SEQ_ID_NO_712 | VVRFFTCVTG | YLEKGKLSDI | EGMKTKVLVW | TKVTSI KTEG | SKVHFTAGMK | 150 |
| SEQ_ID_NO_724 | VLRFFTCVTG | YLEKGKLSDI | EGLKTKVLVW | TKVTAI KTEG | SKVHFTAGVK | 150 |

Figure 21 (continued)

| | | | |
|---|---|---|---|
| SEQ_ID_NO_708 | KSRSREAYEV VRGAITVDEF | 170 |
| SEQ_ID_NO_728 | KTRSREAYQV LRDGVLVDKF | 170 |
| SEQ_ID_NO_718 | KTRSRDAYQV LRAGITVDKF | 170 |
| SEQ_ID_NO_687 | KSRSRDAYEV QRNGLRVDKF | 170 |
| SEQ_ID_NO_699 | KSRNRDAYEV LRDGVRADKF | 170 |
| SEQ_ID_NO_689 | .......... .......... | 107 |
| SEQ_ID_NO_691 | KTRDRGAYEV LRDGVGIDKF | 170 |
| SEQ_ID_NO_703 | KTRSREAYEV TRXGVCIDKF | 170 |
| SEQ_ID_NO_706 | KTRSREAYDV TRDGVPVDKF | 170 |
| SEQ_ID_NO_721 | KARNRDAYEV VRDGVGIDKF | 170 |
| SEQ_ID_NO_712 | KTRSRDAYEV VRDGIIDKF | 170 |
| SEQ_ID_NO_724 | KTRSRDAYEV VRDGIPIDKF | 170 |

Figure 22

| | | | | | | | |
|---|---|---|---|---|---|---|---|
| SEQ_ID_NO_737 | ‑‑MDEL GGGG | G‑‑‑‑ KKGKA | WPWWL GASAA | QI TGAL VWFR | RGKGG SDMTM | 44 |
| SEQ_ID_NO_738 | ‑‑‑MEE GGGG | E‑‑‑‑‑ EAER | WPWWA GASAA | QVAAG VAWFR | RGRGG AAFAM | 42 |
| SEQ_ID_NO_742 | ‑‑MDDR GGGG | G‑‑‑‑ GEAER | WPWWA AASAA | QAAAG VAWFR | RGRGG TAVAM | 44 |
| SEQ_ID_NO_735 | MKMEE AAGSG | N‑‑‑‑ SDGGN | KWWWG VASAA | QMGLG I RTFA | KGHGG DSRLM | 46 |
| SEQ_ID_NO_730 | MEEQN AGTGA | GESSL LDGSG | HWWWA LGSGA | QI MWGI RLIR | RGYAG DVRLM | 50 |
| SEQ_ID_NO_732 | ‑‑‑MEN GDGG | G‑‑‑‑ I ETQW | WWWWA MASMA | KFGWGI SAYK | RGFAG DSRLM | 43 |

| | | | | | | | |
|---|---|---|---|---|---|---|---|
| SEQ_ID_NO_737 | PFRAFAVASL | FVGAGATTVT | AGVSAAGVGS | VEEMKGLGAR | RKWSRVPPR | 94 |
| SEQ_ID_NO_738 | PFKAFAI ATL | FVGAGATAVT | AGVLAAGVGS | VDEMKGVGAS | RRWMGAPPR | 92 |
| SEQ_ID_NO_742 | PFKAFAI ASL | FVGAGATAVS | AGVLAAGVGS | VEEMKGVGAS | RRWMGAPPR | 94 |
| SEQ_ID_NO_735 | PFKAFVVASL | FVSSAASASV | LLLQANGI HR | VEDLMKAGAN | LRAKLGLRPR | 96 |
| SEQ_ID_NO_730 | PLKAFGVASL | FVGSLATSSV | ALVRATGI HT | VQDAI DLGAN | RTNLGVTPQ | 100 |
| SEQ_ID_NO_732 | PLKAFAVASL | FVGSAASASI | ASLQASGI HK | VQDLI ELGAN | RTGLGVPPR | 93 |

| | | |
|---|---|---|
| SEQ_ID_NO_737 | RVEGGE‑‑‑‑‑ | 100 |
| SEQ_ID_NO_738 | RRVEGGGDP‑‑ | 101 |
| SEQ_ID_NO_742 | RAGGSD‑‑‑‑‑ | 100 |
| SEQ_ID_NO_735 | TQNKNMDDS‑‑ | 105 |
| SEQ_ID_NO_730 | I PDKQI TERD G | 111 |
| SEQ_ID_NO_732 | VAKE‑‑‑‑‑‑ | 97 |

Figure 23

| | | | | | | | |
|---|---|---|---|---|---|---|---|
| SEQ_ID_NO_765 | MSPMSNPSFD | HSY---E--L | PLRRNLLLL | DLLGRLRFIA | EVLLDRLGVA | | 45 |
| SEQ_ID_NO_763 | MMLSSAYSTP | AADELGGPPP | LPPPPGADVS | VIVGALTGVL | LGLFLFL--- | | 47 |
| SEQ_ID_NO_758 | ------MGFP | VGY--PE--V | SVPNFLYTL | SLLSFLRSLT | ISFLBLLHLS | | 40 |
| SEQ_ID_NO_761 | ------MGFP | VGY--SE--L | LLPRLLLQVL | LLLGHLHRFL | LAAFHAVGLG | | 40 |
| SEQ_ID_NO_762 | ------MGFP | VGY--SE--L | LLPRLLLQVL | LLLGHLHRFL | LAAFHAVGLG | | 40 |
| SEQ_ID_NO_755 | ------MGFY | AEDPLSG--L | TIGQAI YEVA | LMIAVLRWVL | CLIFRV--- | | 39 |
| SEQ_ID_NO_748 | ------MGFF | VEE--SG--L | VFHLLYKAA | LVLAVLRWAL | AWALRFK--- | | 37 |
| SEQ_ID_NO_746 | ------MTFF | IED--TS--L | ISHVLYKTA | LIITVLRWIF | AWLRYR--- | | 37 |
| SEQ_ID_NO_751 | ------MTFF | IED--TS--L | IBHVLYKTA | LIITVLRWIF | AWLRYR--- | | 37 |
| SEQ_ID_NO_753 | ------MSFF | IQD--SG--L | VFQLLYQMA | VFTLLRWI | SWLRYR--- | | 37 |
| SEQ_ID_NO_760 | ------MSFF | LED--SG--L | VFQLLYQMA | VLITLLRWIF | TWLRYR--- | | 37 |
| | | | | | | | |
| SEQ_ID_NO_765 | SW-----QG | EVHLPGQLWG | WGGEHASDAT | LEHFLEARLW | ETGTRSPLTT | | 89 |
| SEQ_ID_NO_763 | ---------- | --IYAKHCRQ | RGRGGARGAA | GGLGLGFRAS | STCDRCRSGV | | 85 |
| SEQ_ID_NO_758 | DL-------- | ---------- | ---------L | DTDFSTTTLP | DSHIHRPTLS | | 63 |
| SEQ_ID_NO_761 | DLIDNPPGLA | ATEQDMMLQG | RGGGMAEGWA | SSSALQHRRP | EFRAIPPM- | | 88 |
| SEQ_ID_NO_762 | DLIDNPPGLA | ATEQDLMLQG | RGGGMAEGWA | SSSALQHRRP | EFRAIPPM- | | 88 |
| SEQ_ID_NO_755 | ---------- | ---------- | ---------- | NDRRTCSDE | TPTPEPCSQM | | 59 |
| SEQ_ID_NO_748 | ---------- | ---------- | ---------N | RTHLASPSND | SLRRSHPVPS | | 58 |
| SEQ_ID_NO_746 | ---------- | ---------- | ---------- | SRSSSSSSS | SQSSSSPSIS | | 57 |
| SEQ_ID_NO_751 | ---------- | ---------- | ---------- | --SRSSSSSS | SQSSSSPSIS | | 55 |
| SEQ_ID_NO_753 | ---------- | ---------- | ---------- | ------SKS | RTSSAPPVLS | | 49 |
| SEQ_ID_NO_760 | ---------- | ---------- | ---------- | ----SRSTSS | SSSSTPPILS | | 52 |
| | | | | | | | |
| SEQ_ID_NO_765 | TRYRRRRVAL | AQPADGKLAA | EGDAEGAA-- | AVCAICVAGL | ESGDLEIVVE | | 137 |
| SEQ_ID_NO_763 | SLSVVDALPV | VRFGD---MG | GARAAAQP-- | -ECAVCLGTF | DPAADELLRV | | 129 |
| SEQ_ID_NO_758 | ALLRQFLPI | ITFND---LA | EGDSSPPV-- | -GCAVCLNEF | --AGEEEIRC | | 105 |
| SEQ_ID_NO_761 | --AIEEALPV | VRFDE---LV | ASAPAAVCGG | GDCAVCLSGI | --CGRDEVRR | | 131 |
| SEQ_ID_NO_762 | --AIEEALPV | VRFDE---LV | ASAPAAVCGG | GDCAVCLSGI | --CGRDEVRR | | 131 |
| SEQ_ID_NO_755 | TRDKDSILLL | TTFGE---IK | ERLPETE--- | ETCAVCLSQL | --SVEDEVRE | | 101 |
| SEQ_ID_NO_748 | SQQRDGLIL | TTFGD---VT | ERMPLGVC-- | DTCAVCLSQL | --RDQDEVRE | | 100 |
| SEQ_ID_NO_746 | SQTIKESLAV | FAFRD---AV | ERSPAAIN-- | DMCAVCLGDL | --EDEDEIRE | | 100 |
| SEQ_ID_NO_751 | SQTIKESLAV | SAFRD---AV | ERSPAAIN-- | DMCAVCLGDL | --EDEDEIRE | | 98 |
| SEQ_ID_NO_753 | SQAIKESLSV | TTFHD---AL | ERKPELIS-- | DTCAVCLGDL | --EDGDEVRE | | 92 |
| SEQ_ID_NO_760 | SQTIKESLAV | TTFRD---AA | DRSPELIS-- | DTCAVCLGDL | --EDGDEVRE | | 95 |

Figure 23 (continued)

| | | | | | | |
|---|---|---|---|---|---|---|
| SEQ_ID_NO_765 | LCSCSHAFHD | ACIDAWRSG | D---------- | -DDAATCPLC | RAPCCPRRG- | 176 |
| SEQ_ID_NO_763 | LPKCRHAFHA | DCVDTMLEA- | ---------- | ---HSTCPVC | RRRVGKEDA- | 164 |
| SEQ_ID_NO_758 | MANCRHMFHR | TCVDRWIDHD | ---------- | ---QKTCPLC | RTHFVPYHK- | 141 |
| SEQ_ID_NO_761 | LSNCRHVFHR | GCLDRWMAHE | ---------- | ---QRTCPLC | RAPLIPDELL | 168 |
| SEQ_ID_NO_762 | LSNCRHVFHR | GCLDRWMAHE | ---------- | ---QRTCPLC | RAPLIPDELL | 168 |
| SEQ_ID_NO_755 | LMNCYHVFHR | ECIDRWLEHE | HE-------- | -NHSATCPIC | RAPLLSSSC- | 141 |
| SEQ_ID_NO_748 | LRNCCHVFHR | DCIDRWVDHD | HEHD------ | -ENHNTCPLC | RAPLLTTSQ- | 142 |
| SEQ_ID_NO_746 | LRNCTHVFHR | DCIDRWLDYE | CCGGDD---- | -DNHRTCPLC | RTPLLPSFT- | 144 |
| SEQ_ID_NO_751 | LRNCTHVFHR | DCIDRWLDYE | CCGGDD---- | -DNHRTCPLC | RTPLLPSFT- | 142 |
| SEQ_ID_NO_753 | LRNCSHVFHR | ECIDRWLDYE | CCGGDGNEGE | EDNHRTCPLC | RTPLLAADT- | 141 |
| SEQ_ID_NO_760 | LRNCSHVFHR | ECIDRWLDYE | CCGGDDNDGE | EDNHRTCPLC | RTPLLAANT- | 144 |

| | | | | | | |
|---|---|---|---|---|---|---|
| SEQ_ID_NO_765 | ---------- | ---------- | TTTGGEQSLS | R----VLKGV | CVSVP | 197 |
| SEQ_ID_NO_763 | ---------- | -----FAVIP | ELEAADADMY | PAREAEMQIV | VRRPA | 194 |
| SEQ_ID_NO_758 | -----MEDYN | QRLWNDAASE | DDIDDDVSLF | SHRHDYYYIA | NASL- | 180 |
| SEQ_ID_NO_761 | PAASGLPDPS | DYDLSYYPSP | LPLAPTPTLL | RPHELLLNGL | GGFQ- | 212 |
| SEQ_ID_NO_762 | PAASGLPDPS | DYDLSYYPSP | LPLAPTPTLL | RPHELLLNGL | GGFQ- | 212 |
| SEQ_ID_NO_755 | ---------- | ----HHSSAT | CLPPPDPSWA | VERLLYLFGD | DLLPC | 172 |
| SEQ_ID_NO_748 | ---------- | --------SL | ARTRAEPSWA | VERILYLFGD | DLVM- | 168 |
| SEQ_ID_NO_746 | ---------- | ---------D | YSTVTQTSWA | VERLLYLFGD | DLLP- | 169 |
| SEQ_ID_NO_751 | ---------- | ---------D | YSTVTQTSWA | VERLLYLFGD | DLLP- | 167 |
| SEQ_ID_NO_753 | ---------- | -----SSCGD | WPVKTEPSWA | VERLLYLFGD | DLLV- | 170 |
| SEQ_ID_NO_760 | ---------- | -----SSCAD | WPVKNEPSWA | VERLLYLFGD | DLLV- | 173 |

Figure 24

```
SEQ_ID_NO_779    MVLESIL SS S--KSPSF------RRQF AKHELGSWST LKRHRFLLF       39
SEQ_ID_NO_783    MVLDSILSSS PCLKSPSF------SRQF ARHELGSWST LVKRHCFLLS       42
SEQ_ID_NO_769    MVLDGLV SS PSRRQCL------KKQW --DELGSWST LIQRHQYLLT       39
SEQ_ID_NO_777    MVLDGIV SS PLRRHQSL------KKQW --EDLGSCST VVNRHRYLLT       39
SEQ_ID_NO_773    MVLDSMI TS PHRRSPSF------RKPF PRDELGSWST LLRRHRFLLT       41
SEQ_ID_NO_771    MVLDGIV SS PLRRSAST------RRQS SRDEFGSWST LVERHRFLLT       41
SEQ_ID_NO_789    MVLDSL--SS PHRRSQNTVF LASPSKKQQS GFNEPGSWST IYERHRFLLT       48
SEQ_ID_NO_785    MVLDSL--SS PHRRSQNTFF VSSA-KKPQS SRDD--SWSA LVERHRFLLT       45
SEQ_ID_NO_790    MVLDSL--SS PHRRSQNTFF LSSP-KKLQS SKDDVGSWSA LVERHRFLLT       47

SEQ_ID_NO_779    ALALLTVLCT YLYFAVTFA AN--DSCSGL NGPLKDSCHM EHVKASVAKS       87
SEQ_ID_NO_783    ALALLTVLCT IYLYFAVTFA AN--DSCSGL SGSLRDSCHM EHVMDSEAKS       90
SEQ_ID_NO_769    ALALLAFLCT VYLYFAVTLG ARH-SSCYGL TGKDKAMCQL -QLVQALSKG       87
SEQ_ID_NO_777    ALLLGFLCT VYLYFAVTLD ARHNSSCYGL AGKEKAMC- ----QAISKG        83
SEQ_ID_NO_773    AFALLAFLCT IYLYFAVTLG AT--ESCSGL TGTKKTLCRL ELAKDSVGNG       89
SEQ_ID_NO_771    ALGLLAFLCT IYLYFAVTLG AT--DTCSGL KGTEKATCNL QHVSSTLSHG       89
SEQ_ID_NO_789    MLALLAFLCT IYLYFAVTLG AT--GSCSGM SGAEKALC- -QAKSSLHKG       93
SEQ_ID_NO_785    TLLVLAFLCT VYLYFAVTLG AS--DACTGL TGAEREC- -QARSVLQHG       90
SEQ_ID_NO_790    TLVLVFLCT IYLYFAVTLG AP--DACSGL AGTEKAVC- -RAKSALRHG       92

SEQ_ID_NO_779    KLKGLRHF      95
SEQ_ID_NO_783    KLKGLRHL      98
SEQ_ID_NO_769    KLK---FF      92
SEQ_ID_NO_777    KLK---LF      88
SEQ_ID_NO_773    KLK---FF      94
SEQ_ID_NO_771    KLK---FL      94
SEQ_ID_NO_789    KLK---FF      98
SEQ_ID_NO_785    KLK---FR      95
SEQ_ID_NO_790    KLK---FF      97
```

Figure 25

```
SEQ_ID_NO_799    - - MI AE - SM LLNPTSHI ST N-DSLDDPSP A- - - - - - - -  - - - - - - - - - -   26
SEQ_ID_NO_819    MMMMGE- - -  - - -GVSSVPP W- - - -SHLPV SGMDVLGGGG G- - - - - - -GG    32
SEQ_ID_NO_821    MMMMGE- - -  - - -GVSSVPP W- - - -SHLPV SGMDVLGGGG G- - - - - - -GG    32
SEQ_ID_NO_810    MMMMGE- - -  - - - -RAHAPP W- - - -QHSPA A- - - - - -SGV T- - - - - - -DA   25
SEQ_ID_NO_816    MMMMGE- - -  - - - -GAHAPP WQQQQQQPAA S- - - - - -AGM V- - - - - - -DG   29
SEQ_ID_NO_801    - MMI GELSHH RSNPTVQI PQ WDPYEEQTTT SPSLSPI PTS P- - - - - - - -F       41
SEQ_ID_NO_792    - MMI GE- SHR GFNPTVHI PP W-PLSEDLIV SDI YGSPDGG S- - - - - - - - -      38
SEQ_ID_NO_794    - MML GE- THR P-NPTVHVPP W-PDLDDDQT DVVYSPI HYN ATDNNLSSNG      46
SEQ_ID_NO_808    - MML GEPPHR T-NPTVHVPP W-PTLNNPTA E- I FSPLTSN D- - - - - - -DY       39
SEQ_ID_NO_805    - MML GE- THR P-NPTVHVPP W- - - - - - - -A PELFSPYTGN A- - - - - - -DY    32

SEQ_ID_NO_799    - - - - - I SGYF GTAHVSPLDS PTAALMDFDS SLWEDPDLPA PVDAYSCDQF   71
SEQ_ID_NO_819    DEMTPY- VI A ALRDYLPAND VGVGA-DEEE EAAAMAA- - -  AVDAYACDEF    77
SEQ_ID_NO_821    DEMTPY- VI A ALRDYLPAND VGVGA-DEEE EAAAMAA- - -  AVDAYACDEF    77
SEQ_ID_NO_810    DDASPYALLA ALQHYLPSNE V- -AAFDEDD EEAALAAATA AVDAYACDEF   73
SEQ_ID_NO_816    DDASPYSLLV ALRHFLPSNE AAAAAYDEDD EL- - - -EALA AVDAYACDEF    74
SEQ_ID_NO_801    TNFNALDSLT SLHRYLPSNE PDP- - -TFED ELDL- - - - - -  PVDAFSCDHF   82
SEQ_ID_NO_792    - - -SMMEALA ELQRYLPSNE PDP- - -DSDP DLSGPDS- - -  PI DAYTCDHF    79
SEQ_ID_NO_794    NPFYLHEALS ALQRYLPSNG PDV- - - -ELDS EFPGLDGPDS PVDAYSCDHF   93
SEQ_ID_NO_808    SQFYMQEALS AFQHYVNENN DS- - - -DSDS EI FPTHE- - -  SVDSYSNDHF   82
SEQ_ID_NO_805    SPYSMQEALS ALQHYESTDA - - - - - -ESDS EVPSREP- EV PVDAYSCDHF   75

SEQ_ID_NO_799    RMYEFKVRSC ARGRSHDWTK CPYAHTGEKA RRRDPRKFNY SGAECPDLRH   121
SEQ_ID_NO_819    RMYEFKVRRC ARGRSHDWTE CPFAHPGEKA RRRDPRKYHY SGTACPDFRK   127
SEQ_ID_NO_821    RMYEFKVRRC ARGRSHDWTE CPFAHPGEKA RRRDPRKYHY SGTACPDFRK   127
SEQ_ID_NO_810    RMYEFKVRRC GRGRNHDWTA CPYAHPGEKA RRRDPRRYHY SGAACPDFRK   123
SEQ_ID_NO_816    RMYEFKVRRC GRGRSHDWTD CPYAHPGEKA RRRDPRRYHY SGTACPDYRK   124
SEQ_ID_NO_801    RMYEFKVKRC ARGRSHDWTE CPYAHPGEKA RRRDPRRYHY SGTACPEFRK   132
SEQ_ID_NO_792    RMYEFKVRRC ARGRSHDWTE CPYAHPGEKA RRRDPRKFHY SGTACPEFRK   129
SEQ_ID_NO_794    RMYEFKI RRC ARGRSHDWTE CPYAHPGEKA RRRDPRKYHY SGTACPDFRK   143
SEQ_ID_NO_808    RMFEFKI RRC ARGRSHDWTE CPFSHPGEKA RRRDPRKYNY SGTSCPDFRK   132
SEQ_ID_NO_805    RMFEFKVRRC ARCRSHDWTD CPYAHPGEKA RRRDPRKYHY SGTACPDFRK   125
```

Figure 25 (continued)

| | | | | | | | |
|---|---|---|---|---|---|---|---|
| SEQ_ID_NO_799 | GCCKKGDACE | YAHGTFEL KL | HPDRYRTQPC | RDGTGCRRRV | CFFAHTSEQL | 171 |
| SEQ_ID_NO_819 | GGCKRGDACE | YAHGVFECWL | HPARYRTQPC | KDGTACRRRV | CFFAHTPDQL | 177 |
| SEQ_ID_NO_821 | GGCKRGDACE | YAHGVFECWL | HPARYRTQPC | KDGTACRRRV | CFFAHTPDQL | 177 |
| SEQ_ID_NO_810 | GGCKRGDACE | LAHGVFECWL | HPSRYRTQPC | KDGTGCRRRV | CFFAHTPDQL | 173 |
| SEQ_ID_NO_816 | GGCKRGDACE | FAHGVFECWL | HPSRYRTQPC | KDGTACRRRV | CFFAHTPDXL | 174 |
| SEQ_ID_NO_801 | GGCKKGDACE | FAHGVFECWL | HPARYRTQPC | KDGPACRRRV | CFFAHTPEQL | 182 |
| SEQ_ID_NO_792 | GCCKRGDACE | FSHGYFECWL | HPARYRTQPC | KDGGNCRRRV | CFFAHSPDQI | 179 |
| SEQ_ID_NO_794 | GNCRKGDSCE | FAHGVFECWL | HPARYRTQPC | KDGSGCRRRV | CFFAHTPDQL | 193 |
| SEQ_ID_NO_808 | GSCKKGDSCE | FAHGVFECWL | HPSRYRTQPC | KDGTSCRRPV | CFFAHTTEQL | 182 |
| SEQ_ID_NO_805 | GSCKKGDACE | YAHGVFECWL | HPARYRTQPC | KDGTSCRRRV | CFFAHTPDQL | 175 |

| | | | | | | | |
|---|---|---|---|---|---|---|---|
| SEQ_ID_NO_799 | RI PGKQSVR | SPRAREM--- | ---------- | ---------- | ---AI PAVSS | 194 |
| SEQ_ID_NO_819 | RVLPAQQS- | SPRSVAS- S | PLAESYD GS | PLRRQAFESY | LTKTI MSSS | 221 |
| SEQ_ID_NO_821 | RVLPAQQS- | SPRSVAS- S | PLAESYD GS | PLRRQAFESY | LTKTI MSSS | 221 |
| SEQ_ID_NO_810 | RVPPPRQS- | SPRGAAAA S | PLAESYD GS | PLRRQAFESY | LTKSGI VSSP | 219 |
| SEQ_ID_NO_816 | RVLPPQQSSA | SPRGAGAAPS | PLAESYD GS | PLRRQAFESY | LTKTGI MSSS | 223 |
| SEQ_ID_NO_801 | RLLPQQ--- | SPKGNGSGSG | LGGGEYDFGS | PVI HPFDSY | MTKAGI FVSS | 227 |
| SEQ_ID_NO_792 | RVLPNQ--- | SPDR------ | --VDSFDVLS | PTI RRAFQ - | ------FS S | 209 |
| SEQ_ID_NO_794 | RLVSS----- | ---------- | --TDTYD GS | PL-------- | CGKTLTFASS | 216 |
| SEQ_ID_NO_808 | RAPTQQ--- | SPRSVPS--- | --VDSYD GS | PL RLAFESS | CVKTLDFMSS | 221 |
| SEQ_ID_NO_805 | RVLPQQ--- | SPRS------ | --ADSYD GS | PL RHAESS | CAKSHPFVAS | 211 |

| | | | | | | | |
|---|---|---|---|---|---|---|---|
| SEQ_ID_NO_799 | PTSLLSPSS | -------DSP | PLSPL SP--V | SGG------ | ESLSRLVALM | 229 |
| SEQ_ID_NO_819 | PTSTLMSPPK | SPPS---ESP | PLSPDGAA-A | RRGSAPGVG | SPVNDYLASF | 267 |
| SEQ_ID_NO_821 | PTSTLMSPPK | SPPS---ESP | PLSPDGAA-A | RRGSAPGVG | SPVNDYLASF | 267 |
| SEQ_ID_NO_810 | PTSTLVSPPR | SPPS---ESP | PMSPDAAA-A | LRRGSAPGVG | SPVNEVLASM | 265 |
| SEQ_ID_NO_816 | PTSTLVSPPR | SPPS---ESP | PMSPDAAAGA | LRRGSAPGVG | SPVNEVVASL | 270 |
| SEQ_ID_NO_801 | PTSLTSPPV | SPPS---DSP | PMSPGSP--Q | VI GGSGPGSL | NSMSALLASM | 272 |
| SEQ_ID_NO_792 | PSSN--SPPV | SPRG------ | --DSDSSCSL | SRLGSNLG | ---NDVVASL | 246 |
| SEQ_ID_NO_794 | PGSS-SPPV | SPRAESCSSP | PVSPMAQ--S | LSRSLGSASI | NEM---VTSL | 259 |
| SEQ_ID_NO_808 | PGSV--SPPV | -------ESP | PMSPMTR--S | LGRSVGS--- | SSVNEMVASL | 257 |
| SEQ_ID_NO_805 | PGSA--SSPV | -------ESP | PMSPMT---- | ---------- | VSVNEMVASL | 238 |

Figure 25 (continued)

| | | | | | | |
|---|---|---|---|---|---|---|
| SEQ_ID_NO_799 | HSLRLDELK | ·········· | ·········· | ·········· | TNPGVSSF-- | 246 |
| SEQ_ID_NO_819 | RQLRLNKVK | -SSPSGGWSY | PSSS------ | AVYGSPKAA | --TGLYSLPT | 306 |
| SEQ_ID_NO_821 | RQLRLNKVK | -SSPSGGWSY | PSSS------ | AVYGSPKAA | --TGLYSLPT | 306 |
| SEQ_ID_NO_810 | RQLRLGGGS- | PRSAPSGGSF | LGGG------ | YPFGSPKSP- | --AGLYSLPS | 305 |
| SEQ_ID_NO_816 | RQLRLGGGGS | PRSAPSGGSF | LVG------- | YPFGSPKSP- | --AALYSLPS | 310 |
| SEQ_ID_NO_801 | RGLQVGKAK | MGSPVGSWGV | QSG------- | FRFGSPRGSS | LRPGFCSLPS | 314 |
| SEQ_ID_NO_792 | RNLQLNKVK | -SSLSSSYNN | QFGGYG---- | SGFGSPRGSV | LGPGFRSLPT | 290 |
| SEQ_ID_NO_794 | RNLQLGKGK | ------SWKT | QVGCCSPSSP | SSFGSPRAAM | RPGFCSLPS | 302 |
| SEQ_ID_NO_808 | RNLQLGTMK | --SLPSSWNV | QMGS------ | PRFGSPRGPV | RPGFCSLPS | 298 |
| SEQ_ID_NO_805 | RNLQLGKVK | --SLPSSWNV | -MGS------ | SGFGSPRGPM | RPGFFSLPT | 278 |
| | | | | | | |
| SEQ_ID_NO_799 | SPNL------ | -RRSSGAAF- | -DLWDRGL-N | EEEPAMERVE | SGRNLRAQMY | 285 |
| SEQ_ID_NO_819 | TPLASTATVT | TASSFMPNL | -EPLDLGLG | DEEPVLDRVE | SGRALREKVF | 353 |
| SEQ_ID_NO_821 | TPLASTATVT | TASSFMPNL | -EPLDLGLG | DEEPVLDRVE | SGRALREKVF | 353 |
| SEQ_ID_NO_810 | TPTRPSPVTV | TTASGATVLT | VERLNLGLG | DEEPVMERVE | SGRALREKVF | 355 |
| SEQ_ID_NO_816 | TPTRPAAVTV | TTPSGATVMT | VERLNLGLG | DEEPVMERVE | SGRALREMVF | 360 |
| SEQ_ID_NO_801 | TPTR----TM | ASRSGLSQL | -DIMGDGVTC | EEEPAMERVE | SGRDLRAKIY | 358 |
| SEQ_ID_NO_792 | TPTRP----- | ------GFM | -NIMENG--L | EEEPAMERVE | SGRELRAQLF | 325 |
| SEQ_ID_NO_794 | TPTR----NL | -TRPGISYP- | -DSMDKA--C | EEEPVMERVE | SGRDLRAKMF | 343 |
| SEQ_ID_NO_808 | TPTQ----V | PSRGRVNHF- | -DLMDQS--C | EEEPVMERVE | SGRDIRVKMF | 339 |
| SEQ_ID_NO_805 | TPTQ----A | PTRGGVNYF- | -DDMDQS-CC | EEEPVMERVE | SGRSLRARMF | 320 |
| | | | | | | |
| SEQ_ID_NO_799 | AKLMRENSVD | RVRPMISA- | ---------- | QSLN----- | ---------- | 307 |
| SEQ_ID_NO_819 | ERLSRDGAIY | GDATAFATAG | -----VGLDV | DWSDLIN- | ---------- | 386 |
| SEQ_ID_NO_821 | ERLSRDGAIS | GDATAFATAG | -----VGLDV | DWSDLIN- | ---------- | 386 |
| SEQ_ID_NO_810 | ERLSKEATYP | SDTAASANVE | GAA--PAPDV | GWSDLIN- | ---------- | 391 |
| SEQ_ID_NO_816 | ERLSKEATYP | NDAAASANAE | GAAPAAAPDV | GWSDLIN- | ---------- | 398 |
| SEQ_ID_NO_801 | AKLSKENSVD | RDRGDSGVSG | ------PDV | GWSELYK-- | ---------- | 389 |
| SEQ_ID_NO_792 | EKLSKENQMG | RIEPDPDQGA | G----DTPDV | GWSDLVM-- | ---------- | 359 |
| SEQ_ID_NO_794 | EKLSKENSLE | RVNPDQSSGG | -------PDL | NWSDLGKQA | MGIIVMVDIV | 386 |
| SEQ_ID_NO_808 | EKLSKENSFN | GSGMGSGSGL | GEVV-EDPDV | GWSELVSPF | LGD------- | 381 |
| SEQ_ID_NO_805 | EKLSKENHLD | GSGSGSSQIS | ------VPDV | GWSELVSR- | ---------- | 353 |

Figure 25 (continued)

| | | |
|---|---|---|
| SEQ_ID_NO_799 | - - - - - - | 307 |
| SEQ_ID_NO_819 | - - - - - - | 386 |
| SEQ_ID_NO_821 | - - - - - - | 386 |
| SEQ_ID_NO_810 | - - - - - - | 391 |
| SEQ_ID_NO_816 | - - - - - - | 398 |
| SEQ_ID_NO_801 | - - - - - - | 389 |
| SEQ_ID_NO_792 | - - - - - - | 359 |
| SEQ_ID_NO_794 | L F I K Y F | 392 |
| SEQ_ID_NO_808 | - - - - - - | 381 |
| SEQ_ID_NO_805 | - - - - - - | 353 |

Figure 26

```
SEQ_ID_NO_1705    MA PPLSSWP WASLG YKYF LLGPLVWKVA QEWAE -QGG AP -LGSRWL   45
SEQ_ID_NO_826     MA APLSSWP WTBLCDYKYA LLGPLAWKVV QEWREDGDGA LPLVLGSWWL   49
SEQ_ID_NO_1713    MA PPLSSWP WASLGQYKYV LFGALVWKVV QEWRE -QGG LP -LGSWWL   45
SEQ_ID_NO_824     MAPPPLSSWP WASLGQYKYV LLGPLVWKVL QEWRE -QAG LP -LGSWWL   48

SEQ_ID_NO_1705    HLLLLFSARG LTYQFWFSYS NMLFLTRRRR VVPDGVDFRC VDHEWDW-- 92
SEQ_ID_NO_826     HLLLLFVVRG LTYQFWFTYG NMLFFTRRRR VVADGVDFRC DAEWDW-- 96
SEQ_ID_NO_1713    HLLVLFAVRG LTYQFWFTYG NMLFFTRRRR VVADGVDFRC DAEWDW-- 92
SEQ_ID_NO_824     HLLLLFAARG LTYQFWFSYG NMLFFTRRRR VVADGVDFRC DAEWDWKKI 96

SEQ_ID_NO_1705    .......... .......... .......... ..........              92
SEQ_ID_NO_826     .......... .......... .......... ..........              96
SEQ_ID_NO_1713    .......... .......... .......... ..........              92
SEQ_ID_NO_824     LWI PPPNNQP WSPSDTGNAQ AHLAGI GRLF FLRLVPAFG             136
```

Figure 27

```
SEQ_ID_NO_828    ---MGRKP-- DAVAKSYHSG GGGAAASS-- ---------- --PRAARKAS  31
SEQ_ID_NO_845    ---MGRKP-- DPSKPHY--- GGGAS----- ---------- --PRAARRTQ  25
SEQ_ID_NO_847    ---MGRKP-- DPSKPHY--- GGGAS----- ---------- --PRAARRTO  25
SEQ_ID_NO_832    -MLSLLSE-- KPNLALYNQS NGKHYQYHQN IYNDWRWWRS SATQQHRRKV  47
SEQ_ID_NO_837    --MGVVAEVW RSSVRLLTNS PQLNGGSHKS ALWKWRFF-- ---SAQPKRTV  44
SEQ_ID_NO_840    --MKRRKQ-- RSHEKLFLVL QIILHTLIF- ---------- --KRRRRIHH  33
SEQ_ID_NO_842    ---MVLPR-- RRGGHNHH-- ---------- ---------- --PCPRRAVL  21
SEQ_ID_NO_844    ---MGSRR-- RRHHHHHG-- ---------- ---------- --PMLVPAVA  21
SEQ_ID_NO_839    MFMAPRRGLL DGGEDRYGLM SFGTKDI--- ---------- --FTMRRKIR  35
SEQ_ID_NO_850    ---MSEAEKF IYHRKLMEVK GISVGESKAE KLRSY----- --LVSRSRMK  40

SEQ_ID_NO_828    PSP------- VFLGTALFVL GFVSLFTGHV VTDADW---- ARIRSRWRPK  70
SEQ_ID_NO_845    PSP------- VFLGTALFVL GFVSLFTGHI VTDADW---- SRIRSRWRSK  64
SEQ_ID_NO_847    PSP------- VFLGTALFVL GFVSLFTGHI VTDADW---- SRIRSRWRSK  64
SEQ_ID_NO_832    PWS------- LVCGLMLFGL GLVSLFTGHV ASDLEW---- YSQRLVKRSL  66
SEQ_ID_NO_837    MWT------- WVCGFMLFSL GVISLFTGHV VSHLEW---- YSQQLSKRSL  63
SEQ_ID_NO_840    LLP------- LAALTGGIL  FFFVLFSPPI TSQHH----- HLNPIWFNN  71
SEQ_ID_NO_842    PAA------- ALLLL--FLL AAVTLLYVSP PPLSDHPALA YSRRRSPHAL  62
SEQ_ID_NO_844    PAA------- AAFAAAGLLL VVWAFHCFLS PPLGDGGGGA RVVRRPNPPF  64
SEQ_ID_NO_839    YWQKQFKQRH LFGGLMVLLL MCVITKFILW NMFSDQ---- LDLDTAIPSN  81
SEQ_ID_NO_850    LWM------- IRAVTILLLW SCVV----HL MALGEFWG-- PRLLKGWPSC  77

SEQ_ID_NO_828    -----DHRNY EP-------- --------D  WESKYSSMY YGCSERSASF  99
SEQ_ID_NO_845    -----DVRNN EP-------- --------N  WKSRYSNLY YGCSRRSVNF  93
SEQ_ID_NO_847    -----DVRNN EP-------- --------N  WKSRYSNLY YGCSRRSVNF  93
SEQ_ID_NO_832    FYSRLEGRRR EA-------- --------D  WKSKYSNLF YGCSERGRNF 120
SEQ_ID_NO_837    ----LDMSRR EP-------- --------D  VWKSKYSKFF YGCSERGRNF 113
SEQ_ID_NO_840    GTELQMNLQK EH----VFRV PMGGGSLSGD WTSKQSILY HGCSNSSYKF 117
SEQ_ID_NO_842    LNSSGGGSLV EPGRREISRV PKGGWSATDG LWGSKLASKF YGCSNSSSKF 112
SEQ_ID_NO_844    LLKKPAEVAR SVIGAVDFTV PSGGSKHGQE LWESKATGNF FGCSNATKHF 114
SEQ_ID_NO_839    VVQDEPSPNN WP-------- -------TLE LWKHPNSDNY ENCMGRAK-- 114
SEQ_ID_NO_850    ---------- ---------- --------FN HHDLPVAAET ASLPMKIA-- 97
```

Figure 27 (continued)

| | | | | | | | |
|---|---|---|---|---|---|---|---|
| SEQ_ID_NO_828 | RSAVPENSST | GYLLIATSGG | LNQQRIGITD | AVVVAMLNA | TLVVPELDHH | | 149 |
| SEQ_ID_NO_845 | RSAVPENSST | GYLLIGTSGG | LNQQRIGITD | AVVVARILNA | TLVVPELDHH | | 143 |
| SEQ_ID_NO_847 | RSAVPENSST | GYLLIGTSGG | LNQQRLGITD | AVVVARILNA | TLVVPELDHH | | 143 |
| SEQ_ID_NO_832 | PPAVRERASN | GYLLIAASGG | LNQQRTGITD | AVVVARILNA | TLVVPELDHH | | 170 |
| SEQ_ID_NO_837 | LPAVQEQSSN | GYLLIAASGG | LNQQRTGITD | AVVVARILNA | TLVVPELDHH | | 163 |
| SEQ_ID_NO_840 | PSADVNTHPN | RYLMIATSGG | LNQQRTGIVD | AVVAAHILNA | VLVVPKLDQK | | 167 |
| SEQ_ID_NO_842 | LDSGVMTHPD | RYLMIVTSGG | LNQQRTGIID | AVVAARILNA | TLVVPKLDQT | | 162 |
| SEQ_ID_NO_844 | AOAKAVTKLD | RYLMIATSGG | LNQQRTGILD | AVVAARILNA | TLVIPKLDEE | | 164 |
| SEQ_ID_NO_839 | KDIRQGNNTN | GYLLVHANGG | LNQMKTGISD | MVAIAKIMNA | TLVFPTLDHN | | 164 |
| SEQ_ID_NO_850 | LPPKRVYKNN | GYLMVSCNGG | LNQMRAALCD | MVTLARYMNV | TLIVPELDKT | | 147 |

| | | | | | | | |
|---|---|---|---|---|---|---|---|
| SEQ_ID_NO_828 | SFWKDDSDFS | DIFDVEWFIS | HLSKDVTIVK | RIPYEVMLSM | DKLPWTMRAP | | 199 |
| SEQ_ID_NO_845 | SFWKDDSDFS | DIFDVDWFIS | YLSKDVTIVK | RIPYEVMMSM | DKLPWTMRAP | | 193 |
| SEQ_ID_NO_847 | SFWKDDSDFS | DIFDVDWFIS | YLSKDVTIVK | RIPYEVMMSM | DKLPWTMRAP | | 193 |
| SEQ_ID_NO_832 | SYWKDDSDFV | NIFDVDWFIS | YLAKDVTIVK | RVPDKVMRSM | EKPPYTMRVP | | 220 |
| SEQ_ID_NO_837 | SYWKDDSDFS | DIFDVNWFIS | SLAKDVTIVK | RVPDRVMRAM | EKPPYTTRVP | | 213 |
| SEQ_ID_NO_840 | SYWKDSSNFS | EIFDVDRFIS | HLSKDVKIIR | DIPR--IGDK | VITPYTTRVP | | 215 |
| SEQ_ID_NO_842 | SFWKDASDFA | EIFNADWFIS | FLSKDVRIVK | ELPK--IGGK | LWAPHRMRVP | | 210 |
| SEQ_ID_NO_844 | SFWNDASDFA | QIFDVDSFIY | SLSNDVKVIR | QLPD--MNGK | KLSPYKMRIP | | 212 |
| SEQ_ID_NO_839 | SFWTDPSDFK | EIFNMKNFVE | VLNEDVCVVE | SLPPELAAIK | P----ALKAP | | 210 |
| SEQ_ID_NO_850 | SFWSDPSEFD | DIFDVDHFIT | SLRDEVRILK | ELPPRLKRRF | ELGMYYSFPP | | 197 |

| | | | | | | | |
|---|---|---|---|---|---|---|---|
| SEQ_ID_NO_828 | RK-SVPEFYI | DEVLPILMRR | RALQLTKFDY | RLTSD-LDED | LQKLRCRVNF | | 247 |
| SEQ_ID_NO_845 | RK-SMPDFYI | DEVLPILMRR | RALQLTKFDY | RLTNE-LDEE | LQKLRCRVNF | | 241 |
| SEQ_ID_NO_847 | RK-SMPDFYI | DEVLPILMRR | RALQLTKFDY | RLTNE-LDEE | LQKLRCRVNF | | 241 |
| SEQ_ID_NO_832 | RK-SPPEYYL | DQVLPILLRR | RVVQLTKFDY | RLASN-LDEE | LQKLRCRANY | | 268 |
| SEQ_ID_NO_837 | RK-STLEYYL | DQVLPILTRR | HVLQLTKFDY | RLAND-LDED | MQKLRCRVNY | | 261 |
| SEQ_ID_NO_840 | RK-CNAKCYQ | TRILPILKKK | HAVQLTKFDY | RLSNR-LDFD | MQKLRCRVNF | | 263 |
| SEQ_ID_NO_842 | RK-CTQRCYL | NRVLPALVKK | HVVRLTKFDY | RLANR-LDSD | LQKLRCRVNY | | 258 |
| SEQ_ID_NO_844 | RK-CTPKCYE | NRVLPALLKK | HVVQLTKFDY | RVSNR-LETD | LQKLRCRVNY | | 260 |
| SEQ_ID_NO_839 | VSWSKASYYR | TDMLQLLKKH | KVIKFTHTDS | RLVNNGLASS | IQRVRCRAMV | | 260 |
| SEQ_ID_NO_850 | ISWSDISYYB | NQILPLVKKY | KVVHLNKTDT | RLANNGLSLD | LQKLRCRVNF | | 247 |

Figure 27 (continued)

```
SEQ_ID_NO_828    HALKFTSSI H AMGQKLVQKL RLMNTRYVAI HLRFEPDMLA FSGCYYGGGE  297
SEQ_ID_NO_845    HALRFTNSI Q TLGEKLVRKL RSMSSRYVAV HLRFEPDMLA FSGCYYGGGD  291
SEQ_ID_NO_847    HALRFTNSI Q TLGEKLVRKL RSMSSRYVAV HLRFEPDMLA FSGCYYGGGD  291
SEQ_ID_NO_832    HALRFTKPI Q EIGERLVTKM RKMAKRYIAI HLRFEPDMLA FSGCYFGGGE  318
SEQ_ID_NO_837    HALRFTKRI Q SVGMKVYKRM RKMAKRFIAV HLRFEPDMLA FSGCDFGGGE  311
SEQ_ID_NO_840    HALKFTDPI I EMGRKLVERI RMKSKHFVAL HLRFEPDMLA FSGCYYGGGD  313
SEQ_ID_NO_842    HALRFTDPI Q EMGEKIIQRV RERSTYFIAL HLRFEPDMLA FSGCYYGGGE  308
SEQ_ID_NO_844    HALQFTDPI L RMGELLVQRM KEKSGRFIAL HLRFEPDMLA FSGCYYGGGD  310
SEQ_ID_NO_839    EALRFAVPI E ELGKKLVNRL RENNTPYIAL HLRYEKDMLA FTGCSHNLTK  310
SEQ_ID_NO_850    NALRFTPQ E ELGRRVVRI L REK-GPFLVL HLRYEMDMLA FSGCSHGCNP  296

SEQ_ID_NO_828    KERKELGEIR ---KRWDTLP ELSAEDERSR GKCPLTPHEV GLMLRALGFG  344
SEQ_ID_NO_845    KERRELGEIR ---KRWDTLP ELSAEDERSR GKCPLTPQEI GLMLRALGFS  338
SEQ_ID_NO_847    KERRELGEIR ---KRWDTLP ELSAEDERSR GKCPLTPQEI GLMLRALGFS  338
SEQ_ID_NO_832    KERFELGEIR ---KRWAILP DLSPDGERER GKCPLTPHEV GLMLRALGFA  365
SEQ_ID_NO_837    KERAELAEIR ---KRWDTLP DLDPLEERKR GKCPLTPHEV GLMLRALGFT  358
SEQ_ID_NO_840    KETKELGKIR ---KRWKTLH ATNPDKERRH GKCPLTPEEI GLMLRALGFG  360
SEQ_ID_NO_842    KEKRELGVIR ---KRWKTLH ASNPEKERRH GRCPLTPEEV GLMLRALGYR  355
SEQ_ID_NO_844    IERRELGEIR ---KRWKTLH ASNPDRERRH GKCPLTPEEV GLMLRALGFG  357
SEQ_ID_NO_839    EETQELKKMR YSVKHAKE-K EIDSKSKRLKI GSCPNTPREV AVFLEALGYP  359
SEQ_ID_NO_850    DEEEELTRMR YAYPWAKE-K VINSELKRKD GLCPLTPEET ALALNALGID  345

SEQ_ID_NO_828    NDTLLYVASG EIYGGDSTLQ PLRGLFPNFY TKEKLAG-DD LNPFLPFSSR  393
SEQ_ID_NO_845    NDTYLYVASG EIYGGEETLQ PLRDLFPNYY TKEMLAG-ND LKLFLPFSSR  387
SEQ_ID_NO_847    NDTYLYVASG EIYGGEETLQ PLRDLFPNYY TKEMLAG-ND LKPFLPFSSR  387
SEQ_ID_NO_832    NDTYLYVASG EIYGGEETLR PLRELFPNFY TKEMLAL-EE LKSFFPFSSR  414
SEQ_ID_NO_837    NDTYIYVASG EIYGGEKTLK PLRELFPNFY TKEMLAN-DE LKPLLPYSSR  407
SEQ_ID_NO_840    NDVHIYVASG EIYGGEETLA PLKALFPNFY SKETIASKEE LAPFSSFSSR  410
SEQ_ID_NO_842    KNVHIYVASG DIYGGAKTLA PLKALFPNLH TKETVTSKDE LAPFSKYSSR  405
SEQ_ID_NO_844    KDVHLYVASG DVYGGEETLA PLKALFPNFH SKETLASKEE LAPFLPYSSR  407
SEQ_ID_NO_839    VDTKIYVAAG VIYGSEG-MK PLQKKFPNLL WHSSLATKEE LQPFEGHLNQ  408
SEQ_ID_NO_850    RNVQIYIAAG EIYGGERRMK ALAEAFPNVV RKETLLEPSD LKFFQNHSSQ  395
```

Figure 27 (continued)

| | | |
|---|---|---|
| SEQ_ID_NO_828 | LAAIDFIVCD ESDVFVTNNN GNMAKVLAGR RRYMGHKRTI RPNAKKLNVL | 443 |
| SEQ_ID_NO_845 | LAAIDFIVCD GSDVFVTNNN GNMAKVLAGR RRYMGHKRTI RPNAKKLNLL | 437 |
| SEQ_ID_NO_847 | LAAIDFIVCD GSDVFVTNNN GNMAKVLAGR RRYMGHKRTI RPNAKKLNLL | 437 |
| SEQ_ID_NO_832 | MAAIDYIVCD ESDVFVTNNN GNMAKILAGR RRYAGHKRTI RPNAKKLSAL | 464 |
| SEQ_ID_NO_837 | LAAIDYIVSD ESDVFITNNN GNMAKILAGR RRYMGHKRTI RPNAKKLSAL | 457 |
| SEQ_ID_NO_840 | MAALDFMVCD ESDVFVSNNN GNMARMLAGR RRYFGHKPTI RPNAKKLYKL | 460 |
| SEQ_ID_NO_842 | MAALDFIVCD GSDAFVTNNN GNMAKILAGR RRYLGHKRTI RPNARKLYSL | 455 |
| SEQ_ID_NO_844 | MAALDFIVCD RSDVFVTNNN GNMARMLAGR RRYFGHRRTI RPNAKKLYSL | 457 |
| SEQ_ID_NO_839 | LAALDYYTV ESDVFVYSYD GNMAKAARGH RKFDGFKKTI SPDKDRFVRL | 458 |
| SEQ_ID_NO_850 | MAALDYLVSL ESDIFVPTYD GNMAKVVEGH RRFLGFKKTI LLDRKLLVNL | 445 |

| | | |
|---|---|---|
| SEQ_ID_NO_828 | FQTRNQ-LS WDTFSRKVQR VQRGLMGEPD DI----RPK QDD-FHEFP- | 484 |
| SEQ_ID_NO_845 | FKRRKQ-MG WDIFSQKVKK VQRGLMGEPD DI----RPG RDD-FNEFP- | 478 |
| SEQ_ID_NO_847 | FKRRKQ-MG WDIFSQKVKK VQRGLMGEPD DI----RPG RDD-FNEFP- | 478 |
| SEQ_ID_NO_832 | FKARDR-MD WDTFAKKVKA SQRGFMGEPD EV----RPG RGD-FHEYP- | 505 |
| SEQ_ID_NO_837 | FMDREK-ME WQTFAKKVKS CQRGFMGDPD EF----KPG RGE-FHEYP- | 498 |
| SEQ_ID_NO_840 | FLSRNN--MT WEEFASQVRT SQI GFMGEPM EV----KPG RGE-FHENP- | 501 |
| SEQ_ID_NO_842 | FLSRGN--MS WDAFSSKVHM AQKGFMGEPK EL----RPG RGE-FHENP- | 496 |
| SEQ_ID_NO_844 | FLNRTS--MS WDTFASKVLT FQKGFMGEPN EI----KPG RGE-FHEHP- | 498 |
| SEQ_ID_NO_839 | IDQLDNGLIS WNDFSTKVKS HAKKKGAPQ AR-KIHRHPK FEE-TFYANPF | 507 |
| SEQ_ID_NO_850 | IDQYTEGLLS WDEFSSTVKE VHEDRMGSPK KRLVIPDKPK EEDYFYANP- | 494 |

| | | |
|---|---|---|
| SEQ_ID_NO_828 | SSCICSRK-- .......... .......... .......... | 492 |
| SEQ_ID_NO_845 | SSCICQR -- .......... .......... .......... | 486 |
| SEQ_ID_NO_847 | SSCICQR -- .......... .......... .......... | 486 |
| SEQ_ID_NO_832 | -SCICEKPFT DDENRKGEDL LSDRIHMNLK ENVDSKYVGE NQGDKSLQRL | 554 |
| SEQ_ID_NO_837 | QSCICQRP-- .......... .......... ......FSYD | 510 |
| SEQ_ID_NO_840 | SACICADS-- .......... .......... .......... | 509 |
| SEQ_ID_NO_842 | TTCICENT-- --------D PKTPTKPNPR SEQGLINGTE GRKAITEPTV | 535 |
| SEQ_ID_NO_844 | MDCICAKA-- .......... .......... -NGKIGQSRH HQIKRAGKGA | 525 |
| SEQ_ID_NO_839 | PGCICQK--- .......... .......... .......... | 514 |
| SEQ_ID_NO_850 | HECLQLL--- .......... .......... .......... | 501 |

Figure 27 (continued)

| | | |
|---|---|---|
| SEQ_ID_NO_828 | .......... .......... .......... .......... .......... | 492 |
| SEQ_ID_NO_845 | .......... .......... .......... .......... .......... | 486 |
| SEQ_ID_NO_847 | .......... .......... .......... .......... .......... | 486 |
| SEQ_ID_NO_832 | KKRSIEEPIS LRENKDVTVI GSANELGLCT GDRYVKVNGT CLVASTKSDL | 604 |
| SEQ_ID_NO_837 | KTSTDDEEED MSEENHNSTS PGHVHLSS.. .......... .......... | 538 |
| SEQ_ID_NO_840 | DANDREDASL FGTHSIISEI DTGSSTNSAR RDMVEVTDGQ ASEEEQEWS- | 558 |
| SEQ_ID_NO_842 | ANHTNEELVG SSAEEDDASV EKEDDTSAEK EDDTSEEKEE IADPEAEDDA | 585 |
| SEQ_ID_NO_844 | ENHSSDGDLD WRDLDYGEHT PLGRDSSNES ESDDIRVGGS .......... | 565 |
| SEQ_ID_NO_839 | .......... .......... .......... .......... .......... | 514 |
| SEQ_ID_NO_850 | .......... .......... .......... .......... .......... | 501 |

| | | |
|---|---|---|
| SEQ_ID_NO_828 | .......PG NISATT.... . | 500 |
| SEQ_ID_NO_845 | .......PV NRSVTARAEN L | 499 |
| SEQ_ID_NO_847 | .......PV NRSVTARAEN L | 499 |
| SEQ_ID_NO_832 | LCHHVLSFST PFLDETGSGM L | 625 |
| SEQ_ID_NO_837 | .......AD NERDEVFPD- | 549 |
| SEQ_ID_NO_840 | .......DT EYMETELEI-- | 569 |
| SEQ_ID_NO_842 | LVRP....DD PELEEVLSD- | 600 |
| SEQ_ID_NO_844 | .......DI PELEDMMSD- | 576 |
| SEQ_ID_NO_839 | .......PT HLMAETNHES L | 527 |
| SEQ_ID_NO_850 | .......DE PLRTTRLSMF L | 514 |

Figure 28

```
SEQ_ID_NO_876    ----MGPVVL TQLATGLSML AGAALVKSVM DQN--TMMGP GSD---RF--  39
SEQ_ID_NO_855    ----MSPIVI TQLATGISVL AGAVFIKSVM DQK-----P MAG---QF--  35
SEQ_ID_NO_862    ----MGPIVL TQLATGLSVL AGAVLVKSVM DQK-----P MAG------  33
SEQ_ID_NO_858    ----MVPIVL TQMATGLGVL AGAVFVKSVM DQK-----P MAG---PF--  35
SEQ_ID_NO_856    ----MFPAVL TQVATGLSVL AGAVLVKSVM DQK-----P MAG---PF--  35
SEQ_ID_NO_885    MVVVVAPIAV A--SAGLGML AGVAMASRSS NSSSSSGRTS SPAALLRWGA  48
SEQ_ID_NO_868    ---MVSPVVI A--SAGLGML AGVALASRGT GDG-----LP ASS---RWDA  37
SEQ_ID_NO_886    ---MVGPIVI A--SAGLGML AGVAMANRTM GGGGDGRQLP AAS---RWDA  42
SEQ_ID_NO_870    ---MVAPVVI A--SAGLGML AGVAMANRSL GNG-----LP AAS---RWDA  37
SEQ_ID_NO_878    ---MVAPVYI T--SAGLGML AGLAMANRSL GDG-----LP AAS---RWDA  37

SEQ_ID_NO_876    ----PRCSRC NGTGRVSC-L CNRWSD--GD -RGCRTCAGS GRMVCSSCGG  81
SEQ_ID_NO_855    ----PRCPTC NGTGRVTC-F CSRWSD--GD -VGCRRCSGS GRAACSNCGG  77
SEQ_ID_NO_862    ----PLCPSC NGTGRVAC-L CSRWSD--GD -AGCRACSGS GRMACSSCGG  75
SEQ_ID_NO_858    ----QRCPTC NGTGRVSC-L CSRWSD--GD -VGCRTCSGS GRRACSSCGG  77
SEQ_ID_NO_856    ----QRCPTC NGTGRITC-L CTRWSD--GD -IGCRTCAGS GRMACSSCGG  77
SEQ_ID_NO_885    PEPAPRCAAC GGTGREECRL CARWSDARGD CSGCRACAGT RRAPCRSCGG  98
SEQ_ID_NO_868    R---PRCSTC SGTGREEC-L CSRWSD--GD -VGCGTCSGS GRKRCRSCGG  80
SEQ_ID_NO_886    R---PRCATC GGSGRVDC-L CNRWSD--GD -SGCRTCAGS GRMPCRSCGG  85
SEQ_ID_NO_870    R---PRCATC GGSGRVEC-L CNRWSD--GD -SGCRTCAGS GRMPCRSCGG  80
SEQ_ID_NO_878    R---PRCATC GGSGRVEC-L CNRWSD--GD -SGCRTCAGS GRMPCRSCGG  80

SEQ_ID_NO_876    TGTGRPLPVQ SVR------ ---PPNQS-- ---Y-       101
SEQ_ID_NO_855    SGTGRPLPAQ TVQ------ ---PPNRP- ---Y-        97
SEQ_ID_NO_862    TGTGRPIPVQ SMR------ ---SPNRP- ---PS        96
SEQ_ID_NO_858    SGTGRPIPVQ LIVR------ ---QPTNR-- ---SF       98
SEQ_ID_NO_856    SGTGRPIPVQ SVR------ ---QPTNR-- ---NS        98
SEQ_ID_NO_885    SGTGRRAPVR VSSS------ ---APPSR-- ------      117
SEQ_ID_NO_868    SGTGRPLPAR LIVQ------ EQKLPTAPGR RGDYN        109
SEQ_ID_NO_886    SGTGRPLPAR LLARGHHHHH NPPPSSAPGR GGDYS        120
SEQ_ID_NO_870    SGTGRPLPAR LTVQ---HQ KPPPPPPG- ---YN        107
SEQ_ID_NO_878    SGTGRPLPAR LTVQ---HH K--PPPPAG- ---YN        105
```

| SEQ_ID | Sequence Block 1 | Sequence Block 2 | Sequence Block 3 | Sequence Block 4 | Sequence Block 5 | Sequence Block 6 | # |
|---|---|---|---|---|---|---|---|
| SEQ_ID_NO_907 | IKALQFSVFS | AVSGAYLMNP | ARRLGAGGQL | --PTADDLTS | PPAGFPPSSS | | 179 |
| SEQ_ID_NO_912 | ARAAHFSVFT | AVTSAYLTVP | ARRRLHHGAA | SCPTVDDLAT | APVGFPPSSS | | 187 |
| SEQ_ID_NO_911 | VKAALFSVFA | AVSGAYVMAP | ARRRLPGPWR | --PTVDDLAS | APEGFPPSSP | | 195 |
| SEQ_ID_NO_898 | IKSVHFSVYS | AISDAYITVP | SRFADVEGRN | --ITFEDLKK | PPPGYPQNSN | | 177 |
| SEQ_ID_NO_913 | IKTIYFSVYM | ----ANIVMP | STSKLTGNKP | --STVEDIK- | ----ALQQSDG | | 175 |
| SEQ_ID_NO_901 | IKTVYYSVVV | ALSTAFLTCP | ARVLE-PKKY | --PSLEDMKK | PPLGFPQTSV | | 182 |
| SEQ_ID_NO_915 | IKTVFYSVFV | ALSTAFLTCP | ARVTE-PKKY | --PTLEDMKK | PPLGFPHTSI | | 180 |
| SEQ_ID_NO_904 | IKSVFYSTIS | PLMHGFALSP | ERRVA--GKQ | --LTEADMMK | APASFPDPSI | | 176 |
| SEQ_ID_NO_905 | IKSVFYSTIS | PLMHGYALSP | ERRVV-GKQ | --LTEADMMK | APASFPDPSI | | 176 |
| SEQ_ID_NO_908 | IKSVFYSTIS | PLMHGYALSP | ERRVV-GKQ | --LTEADMMK | APASFPDPSI | | 176 |
| SEQ_ID_NO_891 | IKSVSYMVS | ATTIAYTFAP | G-------- | -----GVLGV | PPPGYPSSKV | | 163 |
| SEQ_ID_NO_893 | IKTIKYSVVS | AAAIAIVLVP | ARNVV-EGKA | --ITAAELSV | PPTGYPSTSV | | 180 |

| SEQ_ID | | | | | | | # |
|---|---|---|---|---|---|---|---|
| SEQ_ID_NO_907 | ITVPAYQAA | DFSYVFTSFH | GEP-CVYDRV | LAGVQASDAL | VIKTCFEMEG | | 228 |
| SEQ_ID_NO_912 | LATVPTYQAA | DFTYVFTSFH | GMP-SAYDRV | AACDKASDVL | VFKTCAEMEG | | 236 |
| SEQ_ID_NO_911 | LATVPAYQAA | DFSYVFESFH | GMP-CVYDRV | AACHNACDAL | VIKTCAEMEG | | 245 |
| SEQ_ID_NO_898 | I-SLKAFEAM | DFMFLFTRFG | EKNLTGYERV | LQSLGECSFI | VFKTCKEIEG | | 226 |
| SEQ_ID_NO_913 | L-PVKTFEAI | SLMNVFKSFH | -------DIM | DKCINGCNLM | LIKSCREMEG | | 217 |
| SEQ_ID_NO_901 | T-SVRTFEAR | DFLYVFKSFH | NGP-TLYDRI | QSGLRGCSAI | LAKTCSQMEG | | 230 |
| SEQ_ID_NO_915 | T-SVKTFEAQ | DFLYIFKSFN | NRP-TVYDRV | LSGLKGCSAI | LAKTCSQMEG | | 228 |
| SEQ_ID_NO_904 | K--LHAHEAR | GFTARTVMKF | GGDITFFDRI | FTAVSESDGL | AYSTCREIEG | | 224 |
| SEQ_ID_NO_905 | K--LHAHEAR | GFTARTVMKF | GGDITFFDRI | FTAVSESDGL | AYSTCREIEG | | 224 |
| SEQ_ID_NO_908 | K--LHAHEAR | GFTARTVMKF | GGDITFFDRI | FTAVSESDGL | AYSTCREIEG | | 224 |
| SEQ_ID_NO_891 | L--YRENDAH | ALATLSIFYK | ----RLYHDI | TTGFKSCDI | ALRTCNEIEG | | 207 |
| SEQ_ID_NO_893 | V--LRGHEVR | SLLFVSQPYG | EGT-TFYERA | CTGMKGCDAI | AIRSCYEMEE | | 227 |

| SEQ_ID | | | | | | | # |
|---|---|---|---|---|---|---|---|
| SEQ_ID_NO_907 | PYINYLTAQH | GKPVLVTGPV | VPEPPQGE-L | EERWARMLSS | FPDNAVVFAS | | 277 |
| SEQ_ID_NO_912 | PYIEYVATQY | DKPILVTGPL | VPEPPHGE-L | EERWETMLSS | FPDNAVVFAS | | 285 |
| SEQ_ID_NO_911 | PYIDYIAAEH | GKPVLVTGPI | VPEPPRGE-L | EERWATMLSS | FPDNSVVFAS | | 294 |
| SEQ_ID_NO_898 | PYLDYIETQF | RKPVLLSGPL | VPEPSTDV-L | EEKWSKMLDG | FPAKSVILCS | | 275 |
| SEQ_ID_NO_913 | SRIDDYTKQS | TRPVFLTGPV | VPEPHSGE-L | DETWANMLNR | FPAKSVIYCS | | 266 |
| SEQ_ID_NO_901 | PYIKYVEAQF | NKPVFLIGPV | VPDPPSGK-L | EEKWATMLNK | FEGGTVIYCS | | 279 |
| SEQ_ID_NO_915 | PYIEYVKSQF | KKPVLLVGPV | VPDPPSGK-L | EEKWDAMLNK | FEAGTVIYCS | | 277 |
| SEQ_ID_NO_904 | QFCDYIETQF | KKPVLLAGPA | LPVPSKST-M | EQKWSDMLGK | FKEGSVIYCA | | 273 |
| SEQ_ID_NO_905 | QFCDYIETQF | QKPVLLAGPA | LPVPSKST-M | EQKWSDMLGK | FKEGSVIYCA | | 273 |
| SEQ_ID_NO_908 | QFCDYIETQF | QKPVLLAGPA | LPVPSKST-M | EQKWSDMLGK | FKEGSVIYCA | | 273 |
| SEQ_ID_NO_891 | KFCDYISSQY | HKKVLLTGPM | LPEDDTSKPL | EEQLSHFLSR | FPPRSVVFCA | | 257 |
| SEQ_ID_NO_893 | KLCDYIGRQY | GKPVFLTGPV | LPESARTP-L | EDRWAQMLNR | FEAGSVVFCS | | 276 |

Figure 29 (continued)

| | | | | | | |
|---|---|---|---|---|---|---|
| SEQ_ID_NO_907 | FGSETFLPAA | AATELLLGLE | STNRPFFVYL | NFPKGTDTEA | ELAKCTPPGF | 327 |
| SEQ_ID_NO_912 | FGSETFLPTA | AATELLLGLE | ATGQPFVAVL | NFPRSVDAEA | EVKKCMAPGF | 335 |
| SEQ_ID_NO_911 | FGSETFLLHA | AATELLLGLE | ATALPFLAVL | NFPKGTDAEA | ELRKLTPPGL | 344 |
| SEQ_ID_NO_898 | FGSETFLSDY | QIKELASGLE | LTGLPFILVL | NFPSNLSAKA | ELERALPKGY | 325 |
| SEQ_ID_NO_913 | FGSETFLTDD | QIRELALGLE | LTGLPFFLVL | NFPANVDKSA | ELKRTLPDGF | 316 |
| SEQ_ID_NO_901 | FGSETFLTDD | QVKELALGLE | QTGLPFFLVL | NFPANVDVSA | ELNRALPEGF | 329 |
| SEQ_ID_NO_915 | FGSETFLKDD | QIKELALGLE | QTGLPFFLVL | NFPANVDASA | ELNRGLPEGF | 327 |
| SEQ_ID_NO_904 | FGSECTLRKE | QFQELLMGLE | LTGMPFFAAL | KAPFGTDS-- | -IEAAIPEEL | 320 |
| SEQ_ID_NO_905 | FGSECTLRKD | KFQELLMGLE | LTGMPFFAAL | KPPFETES-- | -VEAAIPEEL | 320 |
| SEQ_ID_NO_908 | FGSECTLRKD | KFQELLMGLE | LTGMPFFAAL | KPPFEAES-- | -IEAAIPEEL | 320 |
| SEQ_ID_NO_891 | LGSQIVLEKD | QFQELCLGME | LTGLPFLIAV | KPPRGSST-- | -VEEGLPEGF | 304 |
| SEQ_ID_NO_893 | FGSQLILEKE | QLQELVLGFE | STGLPFLVVL | KPPVGSST-- | -IEEALPEGF | 323 |

| | | | | | | |
|---|---|---|---|---|---|---|
| SEQ_ID_NO_907 | AERTKGRGVV | HTGWVQQQHI | LRIHRGVGCFV | NHAGLSSVVE | GLVAGCRLVL | 377 |
| SEQ_ID_NO_912 | EERVKGRGVV | HSGWVQQQHI | LRHRGVGCYV | NHAGFSSVVE | GLVAGCRLVL | 385 |
| SEQ_ID_NO_911 | EERVKGRGIL | HTGWVQQQHI | LRHRGVGCFV | NHSGLSSVVE | GLIAGCRLVL | 394 |
| SEQ_ID_NO_898 | LERVKNRGVV | HSGWFQQQLV | LKHSGVGCYV | CHGGFSSVIE | AMVNECQLVL | 375 |
| SEQ_ID_NO_913 | LERVKDKGIV | HSGWVQQRHI | LAHDGVGCYV | FHAGYGSVIE | GLVNDCQLVM | 366 |
| SEQ_ID_NO_901 | LERVKDKGII | HSGWVQQQNI | LAHSGVGCYV | CHAGFSSVIE | ALVNDCQVVM | 379 |
| SEQ_ID_NO_915 | RERVKEKGVI | HSGWVQQQHI | LAHTGVGCYV | CHAGFSSVIE | AFMNDCQVVM | 377 |
| SEQ_ID_NO_904 | REKIHGKGIV | HGGWVQQQLF | LQHPGVGCFV | SHCGWASLSE | ALVNDCQIVL | 370 |
| SEQ_ID_NO_905 | KEKIQGRGIV | HGEWVQQQLF | LQHPGVGCFV | SHCGWASLSE | ALVNDCQIVL | 370 |
| SEQ_ID_NO_908 | KEKIQGRGIV | HGEWVQQQLF | LQHPGVGCFV | SHCGWASLSE | ALVNDCQIVL | 370 |
| SEQ_ID_NO_891 | QERVKGRGVV | WGGWVQQPLI | LDHPSIGCFV | NHCGPGTIVE | CLMTDCQMVL | 354 |
| SEQ_ID_NO_893 | EERVKGRGVV | WGGWVQQLEI | LDHPSIGCFV | NTCGFGSMVE | SLMSDCQIVL | 373 |

| | | | | | | |
|---|---|---|---|---|---|---|
| SEQ_ID_NO_907 | LPMKGDQYLN | AALFARDLRV | GAEVARRDGD | GWFGRGDVSD | AVDTAMAD-- | 425 |
| SEQ_ID_NO_912 | LPMKSDQFFN | AALLARELRV | GTEVARRDGD | GWFGHDAVRD | AVNAAVAD-- | 433 |
| SEQ_ID_NO_911 | LPMKGDQYLN | AALFARELRV | GTEVARRARD | GWFGREDVRD | ALAAAFAG-- | 442 |
| SEQ_ID_NO_898 | LPFKGDQFFN | SKLIANDLKA | GVEVNRSDED | GFFHKEDILE | ALKTVMLEDN | 425 |
| SEQ_ID_NO_913 | LPMKVDQFTN | SKVIALELKA | GVEVNRRDED | GYFGKDDVFE | AVESVMNDTE | 416 |
| SEQ_ID_NO_901 | LPQKGDQILN | AKLVSGDMEA | GVEINRRDED | GYFSKEDIKE | AVEKVMVDVE | 429 |
| SEQ_ID_NO_915 | LPQKGDQLLN | AKLVSGDMKA | GVEVNRRDED | GYFSKDDIEE | AVEKVMVEL- | 425 |
| SEQ_ID_NO_904 | LPQVGDQIIN | ARIMSVSLKV | GVEVEKGEED | GVFSRESVCK | AVKAVM-DEK | 419 |
| SEQ_ID_NO_905 | LPQVGDQIIN | ARIMSVSLKV | GVEVEKGEED | GVFSRESVCK | AVKAVM-DEK | 419 |
| SEQ_ID_NO_908 | LPQVGDQIIN | ARIMSVSLKV | GVEVEKGEED | GVFSRESVCK | AVKAVM-DEK | 419 |
| SEQ_ID_NO_891 | LPFLGDQVLF | TRLMTEEFKV | SVEVSR-EKT | GWFSKEBLSD | AIKSVM-DKD | 402 |
| SEQ_ID_NO_893 | VPHLGDQILN | TRLMAEELKV | AVEVER-DEK | GWFTKENLSN | AIKCVM-DKD | 421 |

Figure 29 (continued)

| | | | | | | |
|---|---|---|---|---|---|---|
| SEQ_ID_NO_907 | ···GMEGDG· | ·IKWRDFLMD | DAVQKRLADD | FVRDFKKFVR | A··· | 461 |
| SEQ_ID_NO_912 | ···AGGGDDD | ERKWREFLTD | DAVQRRFVEE | FVRELRKLVL | ···· | 470 |
| SEQ_ID_NO_911 | ···GEDGGGE | EKKWREFLMD | DAVQRRFVRE | FVAGLRRLKG | ···· | 479 |
| SEQ_ID_NO_898 | KEQGKQIREN | HMQWSKFLSN | KEIQNKFITD | LVAQLKSMA- | ···· | 464 |
| SEQ_ID_NO_913 | NEPAKSIREN | HRKLKEFLQN | DEIQKKYIAD | FVENLKAL- | ···· | 454 |
| SEQ_ID_NO_901 | KDPGKLIREN | QKKWKEFLLN | KDIQSKYIGN | LVNEMTAMAK | VSTT | 473 |
| SEQ_ID_NO_915 | ····KVIREN | QKKWKEFLLN | KDTHSKFVED | LVHDMMAMAK | LSTT | 465 |
| SEQ_ID_NO_904 | SEIGREVRGN | HDKLRGFLLN | ADLDSKYMDS | FNQKLQDLLG | ···· | 459 |
| SEQ_ID_NO_905 | SEIGREVRGN | HDKLRGFLMN | ADLDSKYMDS | FNQKLQDLLG | ···· | 459 |
| SEQ_ID_NO_908 | SEIGREVRGN | HDKLRGFLLN | ADLDSKYMDS | FNQKLQDLLG | ···· | 459 |
| SEQ_ID_NO_891 | SDLGKLVRSN | HAKLKETLGS | HGLLTGYVDK | FVEELQEYI | ···· | 442 |
| SEQ_ID_NO_893 | SEVGSMKKN | HTEWRKLLRS | EGFMSSYFDK | FFQNMQELVD | HK-- | 463 |

Figure 30

```
SEQ_ID_NO_935   MAY--DRRRS -SLFDAFTLS PLPYPVLLIL LMVFLLLSLS WFFDHESFME   47
SEQ_ID_NO_917   MSYYGDRRAE SSIVEAFTLS PLPYPVILVL LMVTLLLGAS WFFTYDDFIE   50
SEQ_ID_NO_925   MSYY-DRRGE SSVLEAFTLS PLPYPVILIL MMVTLLLGAS WFFSYEDFME   49
SEQ_ID_NO_940   MAY--QRGET SSVVEAFTLS PLPYPVILIL LMVMLLGVS  WFFTYEDFME   48
SEQ_ID_NO_937   MAYYGDRRPE SSIVEAFTLS PLPYPVILIL LMVSLLGVS  WFFTYEDFIE   50
SEQ_ID_NO_921   MAY--EERRS -SILDSFSLS PLPYPVLLIL AVASVFLSS  WYFSLEEAAE   47
SEQ_ID_NO_919   MHY--YRRRS DSIFDAFTLN PLPYPVLLIL AVLSIFLGMS WFFSYEDMVE   48
SEQ_ID_NO_923   MGY--GRSRA SSVLDGFSLN PVPYPVLLIL SLILFLGIS  WYLSYEEVVE   48

SEQ_ID_NO_935   ETEEQMSWVL ITLPVVLILV RWLSSIERL  DDTLMGLFRY DRRRPSVYGY   97
SEQ_ID_NO_917   EASQQLSWAL LGVPIALVLL RWISSVDSF  EGYLGFYPR  ESRWKGRYE-   98
SEQ_ID_NO_925   EASEQFSWFL LGVPIALVLL RWISSVDTF  EGYFGFYPT  ESRWRG-YP-   96
SEQ_ID_NO_940   EAAEQLSWAL LLVPVALVLL RWISSVDTF  DGYFSFYPT  ERRWNRVDP-   96
SEQ_ID_NO_937   EAAEQFSWAL LVVPIALVLL RWISSVDSF  DGYFEGFYPS ERRWRPGVG-   99
SEQ_ID_NO_921   SAEEQINFAL LLIPLFLIVL VRWLSSMENP DAL-LGMFSS SRRTTYVSPG   96
SEQ_ID_NO_919   TTEEQMGWML LVVPLVLIVI VRWLSSMENP DMI-FVMSPW DKRRRTHHR-   96
SEQ_ID_NO_923   AAEEQLGWML LATPVVLILV VRWLSSVDTS EMFFFNSSPW ERRRRTHHF-   97

SEQ_ID_NO_935   SDPQEGSSPW GIAAVLVLLL VMVYF----- ----------                122
SEQ_ID_NO_917   RGPAEGSSPW GVALLVLLLL VLARAGCGKV VYGNPGRLGR KRRGGDKVKE  148
SEQ_ID_NO_925   AAPSEGSSPW GVAMVVVLLL LLASF----- ----------                121
SEQ_ID_NO_940   -GPAEGSSPW GVAMVVLLLL VLASF----- ----------                120
SEQ_ID_NO_937   SAPAEGSSPW GVAMLVLLLI VLASF----- ----------                124
SEQ_ID_NO_921   AGGDQGSSPW GVAALIVLLL VLLQY----- ----------                121
SEQ_ID_NO_919   --PSEGSSPW GVAAFIVLLL VLVKF----- ----------                119
SEQ_ID_NO_923   --PSEGSSPW GVAALILLVL VLLHY----- ----------                120

SEQ_ID_NO_935   ---HSSIQDM AGP------- ----------                             132
SEQ_ID_NO_917   QAGDEAAKFP ASGMRLATEK RRRVRRSPSK KGIVLKQKSR KVSLQHRSKK  198
SEQ_ID_NO_925   ---HSTFQDM AKP------- ----------                             131
SEQ_ID_NO_940   ---HSTFQDM AKP------- ----------                             130
SEQ_ID_NO_937   ---HETIRDM ARP------- ----------                             134
SEQ_ID_NO_921   ---QSSFLEM ASG------- ----------                             131
SEQ_ID_NO_919   ---QSTFLDS ALV------- ----------                             129
SEQ_ID_NO_923   ---HSTFLDA AFV------- ----------                             130
```

Figure 30 (continued)

| | | |
|---|---|---|
| SEQ_ID_NO_935 | - - - | 132 |
| SEQ_ID_NO_917 | L K A | 201 |
| SEQ_ID_NO_925 | - - - | 131 |
| SEQ_ID_NO_940 | - - - | 130 |
| SEQ_ID_NO_937 | - - - | 134 |
| SEQ_ID_NO_921 | - - - | 131 |
| SEQ_ID_NO_919 | - - - | 129 |
| SEQ_ID_NO_923 | - - - | 130 |

Figure 31

| | | | | | | | |
|---|---|---|---|---|---|---|---|
| SEQ_ID_NO_947 | MGI KFSQGPS | NTTI HNRS-- | -HQDGEDQRN | ETATKLNHDK | PQNQSS--SF | | 45 |
| SEQ_ID_NO_972 | MGSL-GPSTI | SSMNMAKAAS | VVGGKTGVVA | VADQQKEVPP | KTMNCSSYAF | | 49 |
| SEQ_ID_NO_967 | MGSL-GPAVV | VSASAAKM-- | ---AGGGQQP | STERKETSSA | FGGGCCGGGF | | 44 |
| SEQ_ID_NO_964 | MGSLLGPTVT | VNVSMTKPDA | AAAGGGQQPP | --ERKEGGGR | CGVLGC--GF | | 46 |
| SEQ_ID_NO_944 | MGSL-GPTVS | LSI-MARP-- | ----GGQQPA | EMERKKDSGV | FFGGC--GF | | 40 |
| SEQ_ID_NO_946 | ---MSGVSCP | SSVSSAMP-- | -----KDLRP | NGYNQHDASK | RGTCSC---F | | 37 |
| SEQ_ID_NO_962 | MGSISQPVAN | LSLAASAQ-- | ---------- | --AKQQQRDL | H----C---F | | 29 |
| SEQ_ID_NO_950 | MESVTTRPSP | NVVGVANS-- | ---------- | --------K | HGVEWCG-HF | | 28 |

| | | | | | | | |
|---|---|---|---|---|---|---|---|
| SEQ_ID_NO_947 | QI PLHYPKYT | KSDYEKMPEW | QLDRLLREYG | LPVLGDSYEK | RKFAIGAFLW | | 95 |
| SEQ_ID_NO_972 | QMPLHYPRYK | KADYESMPEW | RVDCLLREYG | LPADGDLDSK | RKFAMGAFLW | | 99 |
| SEQ_ID_NO_967 | QMPLHYPRYK | KADYEAMPEW | RVDCLLREYG | LPVDGGVEEK | RRFAMGAFLW | | 94 |
| SEQ_ID_NO_964 | RMPLHYPRYK | KEDYEGMPEW | RVDSLLREYG | LPADGDLDSK | RRFAMGAFLW | | 96 |
| SEQ_ID_NO_944 | RMPLHYPRYK | KADYESMPEW | RVDCLLREYG | LPADGDVDSK | RRFAMGAFLW | | 90 |
| SEQ_ID_NO_946 | QMPLHYPRYK | KSDYETMPEW | RLDCLLKEYG | LPAIGDANQK | RKFAMGAFLW | | 87 |
| SEQ_ID_NO_962 | RMPLHYPRYT | RADYESMPEW | KLDCLLREYG | LPVTGDVDHK | RSFAMGAFLW | | 79 |
| SEQ_ID_NO_950 | QMPLHYPRYT | QADYEAMPEW | RLDCLLKEYG | LPIFGDVESK | RKFAMGAFLW | | 78 |

| | | |
|---|---|---|
| SEQ_ID_NO_947 | SSENEH | 101 |
| SEQ_ID_NO_972 | PDQY- | 103 |
| SEQ_ID_NO_967 | PDQY- | 98 |
| SEQ_ID_NO_964 | PDQY- | 100 |
| SEQ_ID_NO_944 | PDQY- | 94 |
| SEQ_ID_NO_946 | PSENE- | 92 |
| SEQ_ID_NO_962 | PAH--- | 82 |
| SEQ_ID_NO_950 | IK---- | 80 |

Figure 32

```
SEQ_ID_NO_976   ------MALH LNTVIDLTVD NVVLFRIPPI TLDFLNKLPQ QSEAPTPASA    44
SEQ_ID_NO_980   MAPSTIYQYH MRQDFSTNVD SN---NSTAP TTDAIIHLQ  FSHVLELCYP    47
SEQ_ID_NO_978   ---------- ---------- ---------- MARLLFRLLQ ETNSPTPATP    20

SEQ_ID_NO_976   VTAQLTRRFT CSTGDFL-VL YRQPQRVEEM VTAAGLPLEC APSVAEFISL    92
SEQ_ID_NO_980   ETIQIPLNTT NESHLFPRCL FSSHVNRESI VKEILSSMGC SSDFIESAAP    97
SEQ_ID_NO_978   SP-------- -------- AL YSDLVF--VV LAALLCALIC VLGLLAVSL-    49

SEQ_ID_NO_976   SVRSNSYRK- ---------- --PVVMTVEV GAPVDEDEDE DELL------   123
SEQ_ID_NO_980   DISSFALDMV TNPCNASSSE VLTMVLAIHV TTPYDEREEI DRALSESLMQ   147
SEQ_ID_NO_978   --RCVWLRRI ANR------- ---------- SATNSDQPPA NKGLKKKVLK    60

SEQ_ID_NO_976   ---------- ---------- -PPGAVFEEC AICYKEYLVG GATSVKLACS   152
SEQ_ID_NO_980   EASRFKPASK SCIDGLKRMS LEGSCSMKEC MVCLEEFLMG SEVLVCLPCG   196
SEQ_ID_NO_978   SLPKLTYSPD S--------- -PPAEKFAEC AICLMEFAAG DELRVLSQCG   120

SEQ_ID_NO_976   HTFHRKCLDR ATAVNRTCPY CRAPVPVEQD YWDDEDACDN SESESDDIPS   202
SEQ_ID_NO_980   HIFHGDCIVR MLETSHLCPL CRFAMP---- ---------- -BARCQKCGG   222
SEQ_ID_NO_978   HGFHVSCIDT MLGSHSSCPS CRDILV---- ---------- SIARCQKCGG   156

SEQ_ID_NO_976   EEGDDEESEY DDIPSEGGDD EETEHDDIPS EEGDDVESEY EDVPNEEDDG   252
SEQ_ID_NO_980   ---------- ---------- ---------- ---------- ----------   222
SEQ_ID_NO_978   LPGSSSSGPE PDTRIKQDDP NSNNNDNXSX LN-------- ----------   188

SEQ_ID_NO_976   SSPAPDGSSQ EITAASPEFV SSVRDLSLSC LRLD        286
SEQ_ID_NO_980   ---------- ---------- ---------- ----        222
SEQ_ID_NO_978   ---------- ---------- ---------- ----        188
```

Figure 33

| SEQ_ID_NO_991 | -MAMGMLEVH LISGKGLRAH DPLN- ------ ------KPID PYVEINYKGD | 37 |
| SEQ_ID_NO_1032 | -MAMGMLEVH LISGKGLQAH DPLN- ------ ------KPID PYVEINYKGD | 37 |
| SEQ_ID_NO_985 | -MGMGMLEVH LISGKGLQAH DPLN- ------ ------KPID PYVDINYKGD | 37 |
| SEQ_ID_NO_992 | -MAMGMLEVH LISGKGLQAH DPLN- ------ ------KPID PYVEINYKGD | 37 |
| SEQ_ID_NO_1008 | MAGSGVLEVH LVDAKGLTGN DFL- ------ ------GKID PYVVVQYRSQ | 37 |
| SEQ_ID_NO_1001 | -MPRGTLEVV LISAKGLEDN DFL- ------ ------SSID PYVILSYRAQ | 36 |
| SEQ_ID_NO_1003 | -MAQGTLEVL LVGAKGLENT DYL- ------ ------CNMD PYAVLKCTSQ | 36 |
| SEQ_ID_NO_1028 | -MVQGTLEVL LVGAKGLENT DYL- ------ ------CNMD PYAVLKCRSQ | 36 |
| SEQ_ID_NO_984 | -MPQGKLQVV LVSAKGLENT DFL- ------ ------CNMD PYVLLTCRTQ | 36 |
| SEQ_ID_NO_995 | -MPEGTIQVV LVGAKGLENT DFFNYRVPCN DVKTYPSNID PYVLLTCRSQ | 49 |
| SEQ_ID_NO_982 | -MPHGTLEVV LVSAKGLEDS DFL- ------ ------NSMD PYVLLTCRTQ | 36 |
| SEQ_ID_NO_996 | -MPHGTLEVV LVSAKGLEDA DFL- ------ ------NNMD PYVQLTCRTQ | 36 |
| SEQ_ID_NO_1011 | -MVRGKLEVL LVSAKGLDDS DFF- ------ ------NSMD PYVILTCRSH | 36 |
| SEQ_ID_NO_1023 | -MVHGKLEVL LVSAKGLEDT DFL- ------ ------NNMD PYVILTCRTQ | 36 |
| SEQ_ID_NO_1026 | .......... .......... .......... ........MD PYVILTCRTQ | 12 |

| SEQ_ID_NO_991 | ERMSKVAKNA GPDPVWNEKF KFLAEYPGSG GDFLILFKVM DHDVIDGDDY | 87 |
| SEQ_ID_NO_1032 | ERMSKVAKNA GPDPVWNEKF KFLAEYPGSG GDFLILFKVM DHDVIDGDDY | 87 |
| SEQ_ID_NO_985 | ERMSGVAKNG GPNPLWDEKF KFLAEYPGSG GDFHILFKVM DHDAIDGDDY | 87 |
| SEQ_ID_NO_992 | ERMSKVAKNA GPDPLWDEKF KFLAEYPGSG GDFHVLFKVM DHDAIDGDDY | 87 |
| SEQ_ID_NO_1008 | ERKSSVARDQ GKNPSWNEVF KFDINSTAAT GDHKLFLRLM DHDTFSRDDF | 87 |
| SEQ_ID_NO_1001 | EHKSTVQEGA GSNPQWNETF LFTV---SD SASELNLRIM EKDNFNNDDN | 82 |
| SEQ_ID_NO_1003 | EQKSTVASGK GSDPEWNETF VFTV---SE NATELVIKLL DSDGGTDDDS | 82 |
| SEQ_ID_NO_1028 | EQKSSVASGK GSDPEWNETF MFSV---TH NATELIIKLM DSDSGTDDDF | 82 |
| SEQ_ID_NO_984 | EQKSSVASGK GSEPEWNEDF FNI---SE GASELAKIM DSDAGSQDDF | 82 |
| SEQ_ID_NO_995 | EQRSSVASGQ GSEPEWNETF VFTI---SE GTSELVLKIV DHDTITDDDY | 95 |
| SEQ_ID_NO_982 | DQKSNVASGQ GTTPEWNETF FNV---SE GTTELKAKIF DTDVGIEDDP | 82 |
| SEQ_ID_NO_996 | DQKSNVAEGM GTTPEWNETF FTV---SE GTTELKAKIF DKDVGTEDDA | 82 |
| SEQ_ID_NO_1011 | EQKSTVASGA GSEPEWNETF FFAV---SS DSPELRVKIM DSDALSADDL | 82 |
| SEQ_ID_NO_1023 | EQKSSVANGE GSEPEWNETF FTV---SD DTPQLNLKIM DSDFVTNDDF | 81 |
| SEQ_ID_NO_1026 | EQKSSVAKGA GSEPEWNETF VFTV---SD DVPQLNVKIM DSDAFSADDF | 58 |

Figure 33 (continued)

| | | | | | | | |
|---|---|---|---|---|---|---|---|
| SEQ_ID_NO_991 | GDVSIDVKD | LLVEGVRKGW | SELPPRMYQV | AHKLYFKGE | EVGVSFKRQ | 137 |
| SEQ_ID_NO_1032 | GDVSIDVKD | LLVEGVRKGW | SELPPRMYQV | AHKLYFKGE | EVGVSFKRQ | 137 |
| SEQ_ID_NO_985 | GDVKIDVKD | LLAEGVRKGW | SELPPRMYHV | AHKIHFKGE | EVGVSFKLQ | 137 |
| SEQ_ID_NO_992 | GDVKIDVKD | LLAEGVRKGW | SEIRPRMYHV | AHKIHFKGE | EVGVSFKLQ | 137 |
| SEQ_ID_NO_1008 | LGEATINNTD | LISLGMEHGT | WEMSESKHRV | VLADKIVHGE | RVSLTFTAS | 137 |
| SEQ_ID_NO_1001 | LGEAIPLEA | VFEEG----- | -SLAENAYKL | VLKEQEYCGE | KVALTFTPE | 125 |
| SEQ_ID_NO_1003 | VGEATIPLDG | VYTEG----- | -SIPPTVYNV | VLKDEEYRGE | KIGLTFTPE | 125 |
| SEQ_ID_NO_1028 | VGEATISLEA | IYTEG----- | -SIPPTVYNV | VLKEEEYRGE | KVGLTFTPE | 125 |
| SEQ_ID_NO_984 | VEEVAIPLEP | VFIER----- | -NIPLTPYIV | VLKDGEYRGE | KFGLTFTPE | 125 |
| SEQ_ID_NO_995 | LGKASIPLEP | LFIEG----- | -NLPITAYNV | VLKDEEYRGE | RVGLSFTPE | 138 |
| SEQ_ID_NO_982 | LGEATIPLEA | VFLEG----- | -DIPPAAYNV | VLKDEEFKGE | IAALSFKPS | 125 |
| SEQ_ID_NO_996 | VGEATIPLEP | VFNEG----- | -SIPPTAYNV | VLKDEEYKGE | IWALSFKPS | 125 |
| SEQ_ID_NO_1011 | VGEACIPLEA | VLCEG----- | -SLPPAVHRV | VLKDEEYRGE | KIALTFTPA | 125 |
| SEQ_ID_NO_1023 | VGEASIPLEA | VFCEG----- | -SLPPTVHPV | VLKEEKYCGE | KLALTFTPA | 124 |
| SEQ_ID_NO_1026 | VGEANIPLEP | VFLEG----- | -SLPPAVHRV | VLKEEKYCGE | KVALTFTPA | 101 |

| | | | | | | |
|---|---|---|---|---|---|---|
| SEQ_ID_NO_991 | ---------- | ---------- | ---------- | ---------- | ---------- | 137 |
| SEQ_ID_NO_1032 | ---------- | ---------- | ---------- | ---------- | ---------- | 137 |
| SEQ_ID_NO_985 | ---------- | ---------- | ---------- | ---------- | --GGGGCGGC | 145 |
| SEQ_ID_NO_992 | ---------- | ---------- | ---------- | ---------- | --GGGGCAGC | 145 |
| SEQ_ID_NO_1008 | ---------- | ---------- | ---------- | ---------- | AKAQDHAEQV | 147 |
| SEQ_ID_NO_1001 | ---------- | ---------- | ---------- | ---------- | --RNDEEETC | 133 |
| SEQ_ID_NO_1003 | --E------- | ---------- | ---------- | ---------A | RDEDQPEENY | 137 |
| SEQ_ID_NO_1028 | --D------- | ---------- | ---------- | ---------D | RDRGLSEEDI | 137 |
| SEQ_ID_NO_984 | ERE------- | ---------- | ---------- | ---------S | RDFEV-EESF | 138 |
| SEQ_ID_NO_995 | RRT------- | ---------- | ---------- | ---------S | RTFDAGEESY | 152 |
| SEQ_ID_NO_982 | --E------- | ---------- | ---------- | ---------N | RSRGFEEESY | 137 |
| SEQ_ID_NO_996 | --E------- | ---------- | ---------- | ---------N | RSRGMDEESY | 137 |
| SEQ_ID_NO_1011 | ---------- | ---------- | ---------- | ---------- | -EENEEEESY | 134 |
| SEQ_ID_NO_1023 | -VE------- | ---------- | ---------- | ---------T | RRPDNEEGTY | 137 |
| SEQ_ID_NO_1026 | AVKTLTSVSC | NIDGVVAIVS | EHLVGVCDAN | VLDTRISSGN | SPSSQPRERG | 151 |

Figure 33 (continued)

| | | |
|---|---|---|
| SEQ_ID_NO_991 | -G-------- -- | 138 |
| SEQ_ID_NO_1032 | -G-------- -- | 138 |
| SEQ_ID_NO_985 | NPWEN----- -- | 150 |
| SEQ_ID_NO_992 | YPWEN----- -- | 150 |
| SEQ_ID_NO_1008 | GGWAHSFRQ- -- | 156 |
| SEQ_ID_NO_1001 | GGWKESTRDF -- | 143 |
| SEQ_ID_NO_1003 | GGWNQSS--- -- | 144 |
| SEQ_ID_NO_1028 | GGWKQSS--- -- | 144 |
| SEQ_ID_NO_984 | GGWKQSSYTD -- | 148 |
| SEQ_ID_NO_995 | GGWKESAYTD -- | 162 |
| SEQ_ID_NO_982 | GGWKNSEASY -- | 147 |
| SEQ_ID_NO_996 | GGWKNSEASY -- | 147 |
| SEQ_ID_NO_1011 | GGWNQST--- -- | 141 |
| SEQ_ID_NO_1023 | SSW-N----- -- | 141 |
| SEQ_ID_NO_1026 | GGLQQLELIA CY | 163 |

Figure 34

```
SEQ_ID_NO_1058    MHRFASGLAS ---------- ------KARL ARKGANQIAS RSSMSRN---   31
SEQ_ID_NO_1077    ---MASTFAG MSSAGPLAAP STSSNKLSSM ANISSTSFGS KRNVALRKSR   47
SEQ_ID_NO_1078    ---MASTFAG MSSAGPLAAP STGSNKLSSM ANISSTSFGS KRNVALRKSR   47
SEQ_ID_NO_1075    ---MNTQIHP --HTSLLFFP PN---RFNF ISSFSSF--- -----RRRNP   33
SEQ_ID_NO_1095    ---MTTARGL ---------- ------SART TRGA------ -----SNRRV   20
SEQ_ID_NO_1055    ---MAQSQLA ---------- ------KGSR QTTGRPFQNK P----ARAAR   27
SEQ_ID_NO_1060    ---MATIPTT --GSASLLRG SA---ALQRD GRSTRPSSAA RPLPGRRARS   42
SEQ_ID_NO_1086    ---MATMPST CASSSSLFLL LR----KDRR SSRSASL--- -----PGPAR   35
SEQ_ID_NO_1085    ---MATIPTT --DSALLLGS SA---LHRA RRASAARLPG A----NRRRP   37
SEQ_ID_NO_1097    ---MATIPTT --DSGLLLGS ------SALL RRTRRAASSA RLPAAARRRP   39
SEQ_ID_NO_1054    ---MASANAI --STASPFRP LS----QGRL ---------- -----ATRSD   25
SEQ_ID_NO_1088    ---MASANAI --STASLLRS FS---SQGRV RRAK------ -----NGRAQ   31
SEQ_ID_NO_1068    ---MASANAL --SSASVLCS SR---QSKL G-GGNQQQGQ RVSYNKRTIR   40
SEQ_ID_NO_1072    ---MATANAL --SSPSVLCS SR---QCKL S-GGSQQKGQ RVSY-RKANR   39
SEQ_ID_NO_1057    ---MASANAL --SSASILCS PN---KGSL RRKGNQRQNQ RVNY-RQGNN   40
SEQ_ID_NO_1061    ---MATSNAL --STASILCS PK---QGGL RRRGNQQNNS RLNY-GLSSR   40
SEQ_ID_NO_1076    ---MASTNAL --SSTSILRS PTN--QADT SLSKKVKQHG RVNF-RQKPN   41
SEQ_ID_NO_1092    ---MASTNAL --SSTSILRS PTNN-QADT SLSKKAKQHG RVNY-RQNPN   42
SEQ_ID_NO_1074    ---MASTNAL --SSASILRS PN---RQSL TRRANH--NG RVNY-RKPNN   38
SEQ_ID_NO_1083    ---MASTNAL --SSASILRS PN---HQSL SRRANQ--NG RVNY-RQPNH   38

SEQ_ID_NO_1058    ------YAAK DVKFGVEARG --LMLKGVED LADAVKVTMG PKGRNVVIEQ   73
SEQ_ID_NO_1077    RLTIL-AAAK ELFFNKDGSA IKKLQNGVNK LADLVGVTLG PKGRNVVLES   96
SEQ_ID_NO_1078    RPTIL-AAAK ELFFNKDGSA IKKLQNGVNK LADLVGVTLG PKGRNVVLES   96
SEQ_ID_NO_1075    QFAVRF-ASPK KISFGKECRE --NLQVGIDK LADAVSLTVG PKGRNVILSE   80
SEQ_ID_NO_1095    QVQVRF-AEAK KLTFDMASRR --KIQAGIDK LADAVGVTLG PRGRNVVLEE   67
SEQ_ID_NO_1055    RLVIRAADAK EIVFDQESRR --RLQAGINK VADAVGVTLG PRGRNVVLEQ   75
SEQ_ID_NO_1060    LSVVRF-ASAK DIAFDQASRS --ALQAGVEK LAAAVGVTLG PRGRNVVLDE   89
SEQ_ID_NO_1086    RLGVVRASAK EIAFDQGSRS --SLQAGVEK LAAAVAVTLG PRGRNVVLDE   83
SEQ_ID_NO_1085    QALVRF-ASAK EIAFDQGARA --SLQAGVEK LAAAVGVTLG PRGRNVVLDE   84
SEQ_ID_NO_1097    QLLVRF-ASAK EIAFDQGBRA --SLQAGVEK LAAAVGVTLG PRGRNVVLDE   86
SEQ_ID_NO_1054    RFVVRF-ANAK DIAFDQKSRA --ALQAGVEK LANAVGVTLG PRGRNVVLDE   72
SEQ_ID_NO_1088    RLVVRF-ADAK DIAFDQKSRA --ALQAGVEK LANAVGVTLG PRGRNVVLDE   78
SEQ_ID_NO_1068    RFSVRF-ANVK EIAFDQHSRA --ALQAGIDK LADCVGLTLG PRGRNVVLDE   87
SEQ_ID_NO_1072    RFSLRF-ANVK EIAFDQSSRA --ALQAGIDK LADAVGLTLG PRGRNVVLDE   86
SEQ_ID_NO_1057    RFGVKF-ACAK EIAFDQSSRA --AMQAGIDK LADAVGLTLG PRGRNVVLDE   87
SEQ_ID_NO_1061    RFSVRF-ANAK DIAFDQKSRA --ALQSGIDK LADAVGLTLG PRGRNVVLDE   87
SEQ_ID_NO_1076    RFVVKF-AAAK DIAFDQHSRS --AMQAGIDK LADAVGLTLG PRGRNVVLDE   88
SEQ_ID_NO_1092    RFMVKF-AAAK DIAFDQHSRR --AMQAGIDK LADAVGLTLG PRGRNVVLDE   89
SEQ_ID_NO_1074    RFSVKF-ASAK EIAFDQHSRS --AMQAGIDK LADAVGLTLG PRGRNVVLDE   85
SEQ_ID_NO_1083    RFAVKF-ASAK EIAFDQSSRA --AIQAGIDK LADAVGLTLG PRGRNVVLDE   85
```

Figure 34 (continued)

| | | | | | | |
|---|---|---|---|---|---|---|
| SEQ_ID_NO_1058 | SYGAPKVTKD | GVTVAKSIEF | KDKVKNVGAS | LVKQVANATN | DVAGDGTTCA | 123 |
| SEQ_ID_NO_1077 | KYGAPKIVND | GVTVAREVEL | EDPVKNIGAK | LVRQAAAKTN | DLAGDGTTTS | 146 |
| SEQ_ID_NO_1078 | KYGAPKIVND | GVTVAREVEL | EDPVENIGAK | LVRQAAAKTN | DLAGDGTTTS | 146 |
| SEQ_ID_NO_1075 | -SGKLKVIND | GVTIARSIEL | SDAIENAGAM | LIQEVASKMN | DLAGDGTSTA | 129 |
| SEQ_ID_NO_1095 | KFGMPQVIND | GVTIARAIEL | PDPVENAGAQ | LIKEVAGRTN | DSAGDGTTTA | 117 |
| SEQ_ID_NO_1055 | KFGVPQVIND | GVSIRRAIEL | KDPVENAGAQ | LIKEVAGRTN | DAAGDGTTTA | 125 |
| SEQ_ID_NO_1080 | -FGSPKVVND | GVTIARAIEL | ADPMENAGAA | LIREVASKTN | DSAGDGTTTA | 138 |
| SEQ_ID_NO_1086 | -FGSPKVVND | GVTIARAIEL | ADPMENAGAA | LIREVASKTN | DSAGDGTTTA | 132 |
| SEQ_ID_NO_1085 | -FGTPKVVND | GVTIARAIEL | ADPMENAGAS | LIREVASKTN | DSAGDGTTTA | 133 |
| SEQ_ID_NO_1097 | -FGTPKVVND | GVTIARAIEL | ADPMENAGAA | LIREVASKTN | DSAGDGTTTA | 135 |
| SEQ_ID_NO_1054 | -YGNPKVVND | GVTIARAIEL | YDPMENAGAA | LIREVASKTN | DSAGDGTTTA | 121 |
| SEQ_ID_NO_1088 | -YGSPKVVND | GVTIARAIEL | YDPMENAGAA | LIREVASKTN | DSAGDGTTTA | 127 |
| SEQ_ID_NO_1068 | -FGSPKVVND | GVTIARAIEL | PNAMENAGAA | LIREVASKTN | DSAGDGTTTA | 136 |
| SEQ_ID_NO_1072 | -FGSPKVVND | GVTIARAIEL | PDAMENAGAA | LIREVASKTN | DSAGDGTTTA | 135 |
| SEQ_ID_NO_1057 | -FGSPKVVND | GVTIARAIEL | PNAMENAGAA | LIREVASKTN | DSAGDGTTTA | 136 |
| SEQ_ID_NO_1061 | -FGSPKVVND | GVTIARAIEL | PDPMENAGAA | LIREVASKTN | DSAGDGTTTA | 136 |
| SEQ_ID_NO_1076 | -FGSPKVVND | GVTIARAIEL | PDPMENAGAA | LIREVASKTN | DSAGDGTTTA | 137 |
| SEQ_ID_NO_1092 | -FGSPKVVND | GVTIARAIEL | PDPMENAGAA | LIREVASKTN | DSAGDGTTTA | 138 |
| SEQ_ID_NO_1074 | -FGSPKVVND | GVTIARAIEL | PDPMENAGAA | LIREVASKTN | DSAGDGTTTA | 134 |
| SEQ_ID_NO_1083 | -FGSPKVVND | GVTIARAIEL | PDAMENAGAA | LIREVASKTN | DSAGDGTTTA | 134 |

| | | | | | | |
|---|---|---|---|---|---|---|
| SEQ_ID_NO_1058 | TILTRAFTE | GCKSVAAGMN | AMDLRRGISM | AVDSVVTNLK | SRARMSTSE | 173 |
| SEQ_ID_NO_1077 | VVLAQGLIAE | GVKVVAAGAN | PVLITRGIEK | TAKALVAELK | NMSKEVEDS- | 195 |
| SEQ_ID_NO_1078 | VVLAQGLIAE | GVKVVAAGAN | PVLITRGIEK | TAKALVAELK | NMSKEVEDS- | 195 |
| SEQ_ID_NO_1075 | IILARAMIKG | GLSAVAFGAN | PISLKKGMEK | TVKDLVKFLK | KRSIPVEGRD | 179 |
| SEQ_ID_NO_1095 | SVLAREMIKY | GLQSVAAGAN | PVTVKRGMDK | TSEFCRKKLD | ELTIPVRNAA | 167 |
| SEQ_ID_NO_1055 | SVLAREMIHY | GLQSVTAGAN | PIAVKRGLDK | TAEYLVAKLK | EHAKPVKGRD | 175 |
| SEQ_ID_NO_1080 | SVLAREIIKL | GLLSVTSGAN | PVSIKKGIDK | TVQSLVEELE | KKSRPVKGSG | 188 |
| SEQ_ID_NO_1086 | SVLAREIIKL | GLLSVTSGAN | PVSIKKGIDK | TVHSLVEELE | KKSRPVKGSG | 182 |
| SEQ_ID_NO_1085 | SVLAREIIKL | GMLSVTSGAN | PVSIKKGIDK | TVQKLVEELE | KKSRPVKGGG | 183 |
| SEQ_ID_NO_1097 | SVLAREIIKL | GMLSITSGAN | PVSVKKGIDK | TVCKLVEELE | KKSRPVKGSG | 185 |
| SEQ_ID_NO_1054 | CVLAREIIKL | GLLSVTSGAN | PVSLKKGIDK | TVQGLIQELE | NKSRPIKGGG | 171 |
| SEQ_ID_NO_1088 | SVLAREIIKL | GLLSVTSGAN | PVSLKKGIDK | TVHGLIEELE | KKARPVKGSG | 177 |
| SEQ_ID_NO_1068 | SILAREIIKH | GLLSVTSGAN | PVSLKRGIDK | TVQGLIEELQ | KKARPVKGRD | 186 |
| SEQ_ID_NO_1072 | SVLAREIIKH | GLLSVTSGAN | PVSLKRGIDK | TVQALIEELE | KRSRPVKGGR | 185 |
| SEQ_ID_NO_1057 | SVLAREIIKL | GLLTVTSGAN | PVSVKRGIDK | TVQSLIEELE | KKARPVKGRD | 186 |
| SEQ_ID_NO_1061 | SVLAREIIKL | GLLSVTSGAN | PVSIKRGIDK | TVQGLVEELE | KKARPVKGRD | 186 |
| SEQ_ID_NO_1076 | SILAREIIKL | GLLNVTSGAN | PVSIKKGIDK | TVAALVEELE | KLARPVKGGD | 187 |
| SEQ_ID_NO_1092 | SILAREIIKL | GLLSVTSGAN | PVSIKKGIDK | TVAGLIEELE | KLARPVKGGD | 188 |
| SEQ_ID_NO_1074 | SVLAREIIKL | GLLSVTSGAN | PVSLKRGIDK | TVQGLVEELE | KKARPVKGGD | 184 |
| SEQ_ID_NO_1083 | SVLAREIIKL | GLLSVTSGAN | PVSLKRGIDK | TVQGLVEELE | KRARPVKGGD | 184 |

Figure 34 (continued)

```
SEQ_ID_NO_1058  EIAQVGTISA NGEREGELI  AKAMEKVGKE GVITISDGKT LFNELEVVEG  223
SEQ_ID_NO_1077  ELPDVAAVSA GNNLEVGSMI AEPMSTVGRK GVVTLEEGKS AENSLRVVEG  245
SEQ_ID_NO_1078  ELADVAAVSA GNNLEVGSMI AEAMSKVGRK GVVTLEEGKS AENSLRVVEG  245
SEQ_ID_NO_1075  HIKAVASISA GNDEYVGNLI AEAIEKIGFD GVITIESSRS SETSVVIEEG  229
SEQ_ID_NO_1095  DIRAVASISA GNNEEGNMI  AEAIEKVGPD GVLSIETGSG LETVVEVEEG  217
SEQ_ID_NO_1055  DIKNVASISA GNDNAGEMI  ADALDKVGSN GVLSIETSNS TETVVEVQEG  225
SEQ_ID_NO_1080  DIKAIAAISA GNDDFGTMI  AEAINKVGPD GVLSIESSSS FETTVEVEEG  238
SEQ_ID_NO_1086  DIKAVAAISA GNDDFVGTMI AEAIDKVGPD GVLSIESSSS FETTVEVEEG  232
SEQ_ID_NO_1085  DIKAVAAISA GNDEFVGTMI AEAIDKVGPD GVLSIESSSS FETTVEVEEG  233
SEQ_ID_NO_1097  DIKAVAAISA GNDEFVGTMI AEAIDKVGPD GVLSIESSSS FETTVEVEEG  235
SEQ_ID_NO_1054  DIKAVASISA GNDEFGSMI  AEAIDKVGPD GVLSIESSSS FETTVEVEEG  221
SEQ_ID_NO_1088  DIKAVASISA GNDELGSMI  ADAIDKVGPD GVLSIESSSS FETTVDVEEG  227
SEQ_ID_NO_1068  DIRAVASISA GNDDLGSMI  ADAIDKVGPD GVLSIESSSS FETTVEVEEG  236
SEQ_ID_NO_1072  DIKAVATISA GNDELGAMI  ADAIDKVGPD GVSPESSSS  FETTVEVEEG  235
SEQ_ID_NO_1057  DIKAVASISA GNDDLGTMV  ADAIDKVGPD GVLSIESSSS FETTVDVEEG  236
SEQ_ID_NO_1061  DIKAVASISA GNDELGTMI  ADAIDKVGPD GVLSIESSSS FETVVEVEEG  236
SEQ_ID_NO_1076  DIKAVATISA GNDELGKMI  AEAIDKVGPD GVLSIESSNS FETTVEVEEG  237
SEQ_ID_NO_1092  DIKAVASISA GNDELGKMI  AEAIDKVGPD GVLSIESSSS FETTVEVEEG  238
SEQ_ID_NO_1074  DIKAVASISA GNDELGQMI  AEAIDKVGPD GVLSIESSSS FETTVEVEEG  234
SEQ_ID_NO_1083  DIKAVASISA GNDELGKMI  AEAIDKVGPD GVLSIESSSS FETTVEVEEG  234

SEQ_ID_NO_1058  MKLDRGYISP YFITNQKNQK CELDDPLILI HEKKISSINS VVKVLELALK  273
SEQ_ID_NO_1077  MQFDRGYFAP YFVTDSEKMS VEYDNCKLLL VDKKITNAKD LVNVLKDAIR  295
SEQ_ID_NO_1078  MQFDRGYVSP YFVTDSEKMS VEYENCKLLL VDKKITNARD LVNVLEDAIR  295
SEQ_ID_NO_1075  MKIDRGYMSP HFITNQEKSI VEFDNAKVLV TDQKISSVRE IVPLLEKAMQ  279
SEQ_ID_NO_1095  MEIDRGYISP QFVNDNERLM VEYEGCRILI TDEKIEQVQM LVPLLEEVSQ  267
SEQ_ID_NO_1055  MEIDRGYISP QFVTNQERLL VEYDNCRVLV TDQKIDAIRD IIPILEQVTR  275
SEQ_ID_NO_1080  MEIDRGYISP QFVTNSEKSV VEFENARVLV TDQKISSIKE ILPLLEQTTQ  288
SEQ_ID_NO_1086  MEIDRGYISP QFVTNPEKSL VEFENARILV TDQKISSIKE IIPLLEQTTQ  282
SEQ_ID_NO_1085  MELDRGYISP QFVTNPEKST VEFENARILV TDQKISSIKE ILPLLEQTTQ  283
SEQ_ID_NO_1097  MELDRGYISP QFVTNPEKST VEFENARILV TDQKISSIKE IIPLLEQTTQ  285
SEQ_ID_NO_1054  MEIDRGYISP QFVTNLEKSI VEFENCKYLI TDQKITSIKE ILPILEKTTQ  271
SEQ_ID_NO_1088  MEIDRGYISP QFVTNLEKSI VEFENAKVLI TDQKITSIKE ILPILEKTTQ  277
SEQ_ID_NO_1068  MEIDRGYISP QFVTNPEKLL AEFENARVLI TDQKITAIKD IIPILEKTTQ  286
SEQ_ID_NO_1072  MEIDRGYISP QFVTNPEKLL VEFENARVLI TDQKITAIKD IIPILEKTTQ  285
SEQ_ID_NO_1057  MEIDRGYISP QFVTNPEKLI CEFENARVLV TDQKITAIKD IPLLEKTTQ   286
SEQ_ID_NO_1061  MEIDRGYISP QFVTNPEKLI CEFENARVLI TDQKITAIKD IIPLLEKTTQ  286
SEQ_ID_NO_1076  MEIDRGYISP QFVTNPEKSI VEFENARVLI TDQKISAIKD IIPLLEKTTQ  287
SEQ_ID_NO_1092  MEIDRGYISP QFVTNLEKSI VEFENARVLI TDQKISAIKD IPLLEKTTQ   288
SEQ_ID_NO_1074  MEIDRGYISP QFVTNPEKLI VEFENARVLI TDQKISAIKD IIPLLEKTTQ  284
SEQ_ID_NO_1083  IEIDRGYISG -FVTNLEKSI VEFENARVLV TDQKISAIKD IIPLLEKTTQ  283
```

Figure 34 (continued)

| | | | | | | | |
|---|---|---|---|---|---|---|---|
| SEQ_ID_NO_1058 | RQ- RPLLIVS | EDVESDALAT | LILNKLRAG | KVCAIKAPGF | GENRKAGLHD | 322 |
| SEQ_ID_NO_1077 | NG- SPTLIIA | ENIDQEALAT | LVVNKLRGAL | KVAALKAPGF | GERKSQYLDD | 344 |
| SEQ_ID_NO_1078 | NG- YPILIIA | EDIEQEALAT | LVVNKLRGAL | KVAALKAPGF | GERKSQYLDD | 344 |
| SEQ_ID_NO_1075 | LS- APLLIIA | EDVTAQVLET | LIVNKMQGLL | RVAAVKCPGL | GDGKKALLQD | 328 |
| SEQ_ID_NO_1095 | AGSPPLLIIA | EDITGEALAT | LVVNKMRGVL | KVAAIKAPGF | GERRKALLQD | 317 |
| SEQ_ID_NO_1055 | LN- APLLIIA | EDVSGEALAT | LVVNKLRGVL | NVCAIKAPGF | GERRKSLLQD | 324 |
| SEQ_ID_NO_1080 | LR- APLLIIA | EDVSGEALAT | LVVNKLRGIL | NVAAIKAPGF | GERRKALLQD | 337 |
| SEQ_ID_NO_1086 | LR- APLLIIA | EDVAGEALAT | LVVNKLRGIL | NVAAIKAPGF | GERRKALLQD | 331 |
| SEQ_ID_NO_1085 | LR- APLLIIA | EDVSGEALAT | LVVNKLRGIL | NVAAIKAPGF | GERRKALLQD | 332 |
| SEQ_ID_NO_1097 | LR- APLLIIA | EDVSGEALAT | LVVNKLRGIL | NVAAIKAPGF | GERRKALLQD | 334 |
| SEQ_ID_NO_1054 | LR- APLFIA | EDITGEALAT | LVVNKLRGIL | NVAAIKAPSF | GERRKAVLQD | 320 |
| SEQ_ID_NO_1088 | LR- APLFIA | EDITGEALAT | LVVNKLRGIL | NVAAIKAPSF | GERRKAVLQD | 326 |
| SEQ_ID_NO_1068 | LR- APLLIIA | EDVTGEALAT | LVVNKLRGVL | NVVAVKAPGF | GERRKAMLQD | 335 |
| SEQ_ID_NO_1072 | LR- APLLIIA | EDVTGEALAT | LVVNKLRGVL | NVVAVKAPGF | GERRKAMLQD | 334 |
| SEQ_ID_NO_1057 | LR- APLLIIA | EDVTGEALAT | LVVNKLRGIL | NVAAIKAPSF | GERRKAVLQD | 335 |
| SEQ_ID_NO_1061 | LR- APLLIIA | EDVTGEALAT | LVVNKLRGVL | NVAAIKAPGF | GERRKAMLQD | 335 |
| SEQ_ID_NO_1076 | LR- APLLIIS | EDITGEALAT | LVVNKLRGIL | NVAAIKAPGF | GERRKALLQD | 336 |
| SEQ_ID_NO_1092 | LR- APLFIA | EDITGEALAT | LVVNKLRGIL | NVAAIKAPGF | GERRKALLQD | 337 |
| SEQ_ID_NO_1074 | LR- APLLIIA | EDVTGEALAT | LVVNKLRGIL | NVAAIKAPGF | GERRKALLQD | 333 |
| SEQ_ID_NO_1083 | LR- APLIIIA | EDVTGEALAT | LVVNKLRGIL | NVAAIKAPSF | GERRKAVLQD | 332 |

| | | | | | | | |
|---|---|---|---|---|---|---|---|
| SEQ_ID_NO_1058 | LAVLTGGQLI | TEELGMNLEK | VDLDMLGSCK | KITISKDDTV | ILDGAGDKKS | 372 |
| SEQ_ID_NO_1077 | ATLTGGTVI | REELGLTLDK | ADKEVLGHAA | KVMLTKDATT | VGDGSTQEA | 394 |
| SEQ_ID_NO_1078 | ATLTGGTVI | REELGLTLDK | ADKEVLGHAA | KVMLTKDATT | VGDGSTQEA | 394 |
| SEQ_ID_NO_1075 | ALMIGADFL | CGDLGLTLEG | TTSDQLGSAL | KVKITSNATT | FADPNTKAE | 378 |
| SEQ_ID_NO_1095 | AIVTGAQYI | AKDLGLSVQR | AIMDSLGYAR | KVSIAQTTTT | LIADGASKED | 367 |
| SEQ_ID_NO_1055 | AIVTGAEFL | AKDLGMKVEQ | AVVEQLGVAR | KVTVANNTTT | LIADAASKDE | 374 |
| SEQ_ID_NO_1080 | AIVTGAEFQ | AKDLGQLIEQ | TTVEQLGIAR | KVTISGSSTT | IADVATKDE | 387 |
| SEQ_ID_NO_1086 | AIVTGAEFQ | AKDLGLLVES | TTVEQLGIAR | KVTISQSSTT | IADVATKDE | 381 |
| SEQ_ID_NO_1085 | AIVTGAEYQ | SKDLGLLVEK | TTVEQLGIAR | KVTISSSSTT | IADAASKDD | 392 |
| SEQ_ID_NO_1097 | AIVTGAEYQ | SKDLGLLVEN | TTVEQLGIAR | KVTISSSSTT | IADAASKDD | 394 |
| SEQ_ID_NO_1054 | AIVTGAEFL | AKDLGLLVEN | ATEEQLGTAR | KVTIHQTTTT | LIADAASKDE | 370 |
| SEQ_ID_NO_1088 | AIVTGAEFL | AKDLGLLVEN | ATEEQLGTAR | KVTIHQTTTT | LIADAASKDE | 376 |
| SEQ_ID_NO_1068 | AILTGAEYL | AMDMSLVEN | ATIDQLGIAR | KVTISKDSTT | LIADAASKDE | 385 |
| SEQ_ID_NO_1072 | AILTEPS-T | ALDMGLLVEN | TTIDQLGIAR | KVTISKDSTT | LIADAASKAE | 383 |
| SEQ_ID_NO_1057 | AILTGAEFQ | ANDLGLLIEN | TSVEQLGIAR | KVTKDSTD | IADAASKDE | 385 |
| SEQ_ID_NO_1061 | AILTGAEFQ | ASDLGLSEN | TSIEQLGLAR | KVTISKDSTT | IADAASKDE | 385 |
| SEQ_ID_NO_1076 | AILTGAEFQ | ASDLGLLVEN | TTIEQLGLAR | KVTISKDSTT | IADAASKDE | 386 |
| SEQ_ID_NO_1092 | AILTGAEYQ | ASDLGLLVEN | TSIEQLGLAR | KVTISKDSTT | IADAASKDE | 387 |
| SEQ_ID_NO_1074 | AILTGAEFQ | ASDLGLLVEN | TSVEQLGLAR | KITISKDSTT | VIADAATKDE | 383 |
| SEQ_ID_NO_1083 | AILTGAEFQ | ASDLGLLVEN | TSIEQLGLAR | KVTISKDSTT | IADAASKDE | 382 |

Figure 34 (continued)

| | | | | | | | |
|---|---|---|---|---|---|---|---|
| SEQ_ID_NO_1058 | EERCEQIRS | AIELSTSDYD | KEKLQERLAK | LSGGVAVLKI | GGASEAEVGE | 422 |
| SEQ_ID_NO_1077 | VNKRVAQIKN | LIEAADQDYE | KEKLNERIAK | LSGGVAVIQV | GAQTETELKE | 444 |
| SEQ_ID_NO_1078 | VNKRVAQIKN | LIEAADQDYE | KEKLNERIAK | LSGGVAVIQV | GAQTETELKE | 444 |
| SEQ_ID_NO_1075 | IQARILQIKK | DLIETDNANH | SRKLSERIAK | LTGGIAVIKV | GAHITELELED | 428 |
| SEQ_ID_NO_1095 | DMRVAQLKQ | ELAETDSVYD | TEKLSERIAK | LAGGVAVIKV | GAATETEMEE | 417 |
| SEQ_ID_NO_1055 | EMRIAQLKK | ELAETDSVYD | TEKLSERIAK | LSGGVAVIKV | GAATEAELED | 424 |
| SEQ_ID_NO_1080 | IQARIAQLKR | ELSQTDSTYD | SEKLAERIAK | LSGGVAVIKV | GAATETELED | 437 |
| SEQ_ID_NO_1086 | IQARIAQLKR | ELSQTDSAYD | SEKLAERIAK | LSGGVAVIKV | GAATETELED | 431 |
| SEQ_ID_NO_1085 | IQARIAQLKR | ELSQTDSTYD | SEKLAERIAK | LSGGVAVIKV | GASTEAELED | 432 |
| SEQ_ID_NO_1097 | IQARIAQLKR | ELSQTDSAYD | SEKLAERIAK | LSGGVAVIKV | GASTEAELED | 434 |
| SEQ_ID_NO_1054 | IQARIAQLKK | ELAETDSVYD | TEKLAERIAK | LAGGVAVIKV | GAATETELED | 420 |
| SEQ_ID_NO_1088 | IQARVAQLKK | ELSETDSIYD | TEKLAERIAK | LSGGVAVIKV | GAATETELED | 426 |
| SEQ_ID_NO_1068 | LQARIAQLKK | ELFETDSVYD | SEKLAERIAK | LSGGVAVIKV | GAATETELED | 435 |
| SEQ_ID_NO_1072 | LQARISQLKK | ESFETDSVYD | SEKLAERIAK | LSGGVAVIKV | GAATETELED | 433 |
| SEQ_ID_NO_1057 | IQARVQQLKK | ELAETDSVYD | TEKLAERIAK | LSGGVAVIKV | GAATETELED | 435 |
| SEQ_ID_NO_1061 | LQARIAQLKK | ELSETDSVYD | SEKLAERIAK | LSGGVAVIKV | GAATETELED | 435 |
| SEQ_ID_NO_1076 | LQSRVAQLKK | ELSETDSIYD | SEKLAERIAK | LSGGVAVIKV | GAATETELED | 436 |
| SEQ_ID_NO_1092 | LQSRVAQLKK | ELSETDSVYD | SEKLAERIAK | LSGGVAVIKV | GAATETELED | 437 |
| SEQ_ID_NO_1074 | LQARVAQLKK | ELSQTDSVYD | TEKLAERIAK | LSGGVAVIKV | GAATETELED | 433 |
| SEQ_ID_NO_1083 | LQARVAQLKK | ELAETDAVYD | SMKLAERITK | LSGGVAVIKV | GAATETELED | 432 |

| | | | | | | | |
|---|---|---|---|---|---|---|---|
| SEQ_ID_NO_1058 | KKDRVTDALN | ATKAAVEEGI | VPGGGVALLY | ASKELDKLL- | STANFDQKIG | 470 |
| SEQ_ID_NO_1077 | KKLRVEDALN | ATKAAVERGI | VVGGGCTLLR | LAAKVDAIKG | TLANDEEKVG | 494 |
| SEQ_ID_NO_1078 | KKLRVEDALN | ATKAAVERGI | VVGGGCTLLR | LAAKVDAIKG | TLANDEEKVG | 494 |
| SEQ_ID_NO_1075 | RKLRIEDAKN | ATFAAINEGL | VPGGGATYVH | LDLIPAIKN | SMEDLDEQIG | 478 |
| SEQ_ID_NO_1095 | RKLRIEDAKN | ATFAAVEEGI | VPGGGAALVH | LSKMDEFIP | TLTSAEERLG | 467 |
| SEQ_ID_NO_1055 | RKLRIEDAKN | ATFAAVEEGI | VPGGGAALLH | LSELVPAFKE | TLTDKEEKLG | 474 |
| SEQ_ID_NO_1080 | RKLRIEDAKN | ATFAAIEEGI | VPGGGAAYVH | LSTFVPAIKE | KLDDPEERLG | 487 |
| SEQ_ID_NO_1086 | RKLRIEDAKN | ATFAAIEEGI | VPGGGAAYVH | LSKFVPAIKE | KLDDPEERLG | 481 |
| SEQ_ID_NO_1085 | RKLRIENAKN | ATFAAIEEGI | VPGGGAAYVH | LSTFVPAIKE | KLDDPEERLG | 482 |
| SEQ_ID_NO_1097 | RKLRIEDAKN | ATFAAIEEGI | VPGGGAAYVH | LSTFVPAIKE | TLDDPEERLG | 484 |
| SEQ_ID_NO_1054 | RQLRIEDAKN | ATFAAIEEGI | VPGGGAAYVH | LSTVVPKIKE | AIEDPDERLG | 470 |
| SEQ_ID_NO_1088 | RQLRIEDAKN | ATFAAIEEGI | VPGGGTAYVH | LSTTVPAIKE | TIEDHDERLG | 476 |
| SEQ_ID_NO_1068 | RKLRIEDAKN | ATFAAIEEGI | VPGGGAALVH | LSTVIPAIKE | TFEDADERLG | 485 |
| SEQ_ID_NO_1072 | RKLRIEDAKN | ATFAAIEEGI | VPGGGATLVH | LSTVIPAIKE | TFEDADVRLG | 483 |
| SEQ_ID_NO_1057 | RKLRIEDAKN | ATFAAIEEGI | VPGGGAALVH | LSTCVPAIKD | KLEDPEERIG | 485 |
| SEQ_ID_NO_1061 | RKLRIEDAKN | ATFAAIEEGI | VPGGGAALVH | LSTCVPAIKD | KIEDADERLG | 485 |
| SEQ_ID_NO_1076 | RKLRIEDAKN | ATFAAIEEGI | VPGGGTALVH | LSGYVPAIKE | KLEDADERLG | 486 |
| SEQ_ID_NO_1092 | RKLRIEDAKN | ATFAAIEEGI | VPGGGTALVH | LSAYVPAIKE | KLEDADERLG | 487 |
| SEQ_ID_NO_1074 | RKLRIEDAKN | ATFAAIEEGI | VPGGGTALVH | LSTHVPAIKD | KLEDADERLG | 483 |
| SEQ_ID_NO_1083 | RKLRIEDAKN | ATFFAIEVGI | VL-VDTALLH | LSTHVPAIKD | KLEDADERLG | 480 |

Figure 34 (continued)

| | | | | | | | |
|---|---|---|---|---|---|---|---|
| SEQ_ID_NO_1058 | VQIQNALKT | PVHTIASNAG | VEGAVVVGKL | LEDDNPDLGY | DAAKGEYVDM | 520 |
| SEQ_ID_NO_1077 | ADIVQRALSY | PLKLIAKNAG | VNGSVVSEKV | LSSDDPKFGY | NAATGNYEDL | 544 |
| SEQ_ID_NO_1078 | ADIVKRALSY | PLKLIAKNAG | VNGSVVSEKV | LSSDDPKFGY | NAATGNYEDL | 544 |
| SEQ_ID_NO_1075 | ADIVAKALVE | PAKSIAANAG | VDGDVVVEKT | RTFID-WRIGY | NAMTGTYEDL | 527 |
| SEQ_ID_NO_1095 | AEIVQKALLA | PCRLIGNNAG | VEGDVIVQHV | MEGD-FNYGY | DAMVGEYGDL | 516 |
| SEQ_ID_NO_1055 | ADIVMKSLRA | PCRLIADNAG | VEGEVIVQRL | LGKP-FEVGY | NAMDKVENL | 523 |
| SEQ_ID_NO_1080 | ADIIQKALVA | PASLIAHNAG | VEGEVIVEKI | KDSE-WEFGY | NAMTDKHENL | 536 |
| SEQ_ID_NO_1086 | ADIIQKALVA | PAALIAHNAG | VEGEVIVEKI | KESE-WEVGY | NAMADRHENL | 530 |
| SEQ_ID_NO_1085 | ADIIQKALVA | PAALIAHNAG | VEGEVIVDKI | KESE-WEYGY | NAMADKHENL | 531 |
| SEQ_ID_NO_1097 | ADIIQKALVA | PAALIAHNAG | VEGEVIVDKI | RESE-WEFGY | NAMADKHENL | 533 |
| SEQ_ID_NO_1054 | ADIIQKALVA | PASLIAHNAG | VEGEVVVEKI | KOSD-WEVGY | NAMTDKYENL | 519 |
| SEQ_ID_NO_1088 | ADIIQKALVA | PASLIAHNAG | VEGEVVVEKI | KDGE-WEVGY | NAMNDKYENL | 525 |
| SEQ_ID_NO_1069 | ADIVQKALLS | PAALIAQNAG | VEGEVVVEKI | MFSD-WENGY | NAMTDTYENL | 534 |
| SEQ_ID_NO_1072 | ADIVQKALVA | Q-SLIAQNAG | IEGEVVVEKI | MFSE-WELGY | NAMTDTYENL | 531 |
| SEQ_ID_NO_1057 | ADIVQKALVA | PASLIAQNAG | MEGEVVVEKV | KNSE-WEIGY | NAMTDTYENL | 534 |
| SEQ_ID_NO_1061 | ADIVQKALYS | PASLIAQNAG | IEGEVVVEKL | KASE-WEIGY | NAMTDKYENL | 534 |
| SEQ_ID_NO_1076 | ADIVQKALVA | PAALIAQNAG | IEGEVVVEKI | KNGE-WEVGY | NAMTDTYENL | 535 |
| SEQ_ID_NO_1092 | ADIVQKALVA | PASLIAQNAG | IEGEVVVEKI | RNGE-WEVGY | NAMTDTYENL | 536 |
| SEQ_ID_NO_1074 | ADIVQKALIA | PAALIAQNAG | IEGEVVVEKI | KSGE-WEVGY | NAMADRYENL | 532 |
| SEQ_ID_NO_1083 | ADIVQKALIA | PASLIAQNAG | IEGEVVVEKV | KNGE-WEVGY | NAMTDRYENL | 529 |

| | | | | | | | |
|---|---|---|---|---|---|---|---|
| SEQ_ID_NO_1058 | -IKAGIIDPL | KVIRTALVDA | ASVSSLMTTT | EAIVVELPKD | E---KEVPA | 565 |
| SEQ_ID_NO_1077 | IMAAGIIDPT | KVWRCCLEHA | ASVAKTFLMS | DCVVVEIKEP | E---AAVAG | 590 |
| SEQ_ID_NO_1078 | -MAAGIIDPT | KVWRCCLEHA | ASVAKTFLMS | DCVVVEIKEP | E---AAVAG | 589 |
| SEQ_ID_NO_1075 | -LNAGVADPS | RVARCALQSA | VSIAGVVLTT | QAILVDKYL- | -----GSN-K | 569 |
| SEQ_ID_NO_1095 | -IEKGVIDPK | KVTRSGVQNS | CSIAGMVLTT | QAVITE-PKK | KRAIGANAGP | 565 |
| SEQ_ID_NO_1055 | -LDAGVIDPA | KVTRNGLLNS | VSIAGIMLTT | QAVMVEKHKP | SEIPGGMT-A | 571 |
| SEQ_ID_NO_1080 | -VEAGVIDPA | KVTRCALQNA | ASVAGMVLTT | QAIVVEKPSK | K---APA-P | 580 |
| SEQ_ID_NO_1086 | -VQAGVIDPA | KVTRCALQNA | ASVAGMVLTT | QAIVVEKPKK | K---ASA-A | 574 |
| SEQ_ID_NO_1085 | -VEAGVIDPA | KVTRCALQNA | ASVAGMVLTT | QAIVVEKPKK | K---APA-A | 575 |
| SEQ_ID_NO_1097 | -VEAGVIDPA | KVTRCALQNA | ASVAGMVLTT | QAIVVEKPQK | -----APA-A | 576 |
| SEQ_ID_NO_1054 | -MEAGVIDPA | KVTRCALQNA | ASVAGMVLTT | QAIVVEKPKP | K---PQV-A | 563 |
| SEQ_ID_NO_1088 | -IEAGVIDPA | KVTRCALQNA | ASVAGMVLTT | QAIVVEKPKP | K---APV-A | 569 |
| SEQ_ID_NO_1069 | -FEAGVIDPA | KVTRCALQNA | ASVAGMVLTT | QAIVVDKPKP | K---APA-A | 578 |
| SEQ_ID_NO_1072 | -LEAGVIDPA | KVTRCALQNA | ASVAGMVLTT | QAIVVDKPKP | K---APA-A | 575 |
| SEQ_ID_NO_1057 | -LAAGVIDPA | KVTRCALQNA | ASVAGMVLTT | QAIVVEKAKP | K---APA-A | 578 |
| SEQ_ID_NO_1061 | -MEAGVIDPA | KVTRCALQNS | ASVAGMVLTT | QAIVVEKPKP | K---TPA-A | 578 |
| SEQ_ID_NO_1076 | -VESGVIDPA | KVTRCALQNA | ASVAGMVLTT | QAIVVEKPKP | K---AAV-A | 579 |
| SEQ_ID_NO_1092 | -IESGVIDPA | KVTRCALQNA | ASVAGMVLTT | QAIVVEKPKP | R---APV-P | 580 |
| SEQ_ID_NO_1074 | -VEAGVIDPA | KVTRCALQNA | ASVAGMVLTT | QAIVVEKPKP | K---APV-A | 576 |
| SEQ_ID_NO_1083 | -VEAGVIDPA | KVTRCALQNA | ASVAGMVLTT | QAIVVEKPKP | K---APT-A | 573 |

Figure 34 (continued)

| | | | | |
|---|---|---|---|---|
| SEQ_ID_NO_1058 | MGGGMGGMDY | - - - - - - - - - - | - - - - - - | 575 |
| SEQ_ID_NO_1077 | NPMDNSGYGY | - - - - - - - - - - | - - - - - - | 600 |
| SEQ_ID_NO_1078 | NPMDNSGYGY | - - - - - - - - - - | - - - - - - | 599 |
| SEQ_ID_NO_1075 | NALTNGKVTV | AVSYSWGMMK | PMYYKA | 595 |
| SEQ_ID_NO_1095 | MADEEGNFSL | - - - - - - - - - - | - - - - - - | 575 |
| SEQ_ID_NO_1055 | SGMPSG-MTI | - - - - - - - - - - | - - - - - - | 580 |
| SEQ_ID_NO_1080 | AGMPQGMM- | - - - - - - - - - - | - - - - - - | 588 |
| SEQ_ID_NO_1086 | SGAPEGSLAM | - - - - - - - - - - | - - - - - - | 584 |
| SEQ_ID_NO_1085 | AGAPEGSFAM | - - - - - - - - - - | - - - - - - | 585 |
| SEQ_ID_NO_1097 | AAAP- - - - - | - - - - - - - - - - | - - - - - - | 580 |
| SEQ_ID_NO_1054 | -EPPEGALTV | - - - - - - - - - - | - - - - - - | 572 |
| SEQ_ID_NO_1088 | -EPAEGTLTV | - - - - - - - - - - | - - - - - - | 578 |
| SEQ_ID_NO_1068 | -AAPEG-LMV | - - - - - - - - - - | - - - - - - | 586 |
| SEQ_ID_NO_1072 | -AAPEG-LMV | - - - - - - - - - - | - - - - - - | 583 |
| SEQ_ID_NO_1057 | -AAPEG-LTI | - - - - - - - - - - | - - - - - - | 586 |
| SEQ_ID_NO_1061 | -AATQGQYAV | - - - - - - - - - - | - - - - - - | 587 |
| SEQ_ID_NO_1076 | -AAPQG-LTI | - - - - - - - - - - | - - - - - - | 587 |
| SEQ_ID_NO_1092 | -GAPQG-LTV | - - - - - - - - - - | - - - - - - | 588 |
| SEQ_ID_NO_1074 | -GAPQG-LTV | - - - - - - - - - - | - - - - - - | 584 |
| SEQ_ID_NO_1083 | -AAPQG-LTI | - - - - - - - - - - | - - - - - - | 581 |

Figure 35

```
SEQ_ID_NO_1106    MAELNVAPSP PPSTILTLED MLRKLPLPSD ETIRSPATTK MCKIVSHRSS    50
SEQ_ID_NO_1105    ---------- ---------- ---------- ---------- ---------M    1
SEQ_ID_NO_1108    ---------- ---------- ---------- ---------- ------MREY    4
SEQ_ID_NO_1109    --MAAVAPIA MPARVHHHHH HHRRALAASP AALAAAGNGL SATRRVRRSP    48
SEQ_ID_NO_1101    ---------- ------MPFA SSSSLIKRRP LL-------- ------RHHN    20
SEQ_ID_NO_1099    ---------- ---------- MTRHVILTSE E--------- ------RNSP    15
SEQ_ID_NO_1103    ---------- ---------- MTRHVILKSP LLVSSEESTM ------RNSP    24

SEQ_ID_NO_1106    PRHPTTKANK G------FQC AEVAGGTTAG CAALVCC-PC GVGLLVLAT    93
SEQ_ID_NO_1105    TRQNQLQNRR R------SV GEVAGNALAE CAAICCCVPC AVVDMVALAT    44
SEQ_ID_NO_1108    GRGHEEEEGE E--HEPQPGC GEGAGDAAAN CAAVCCCCPL ALLDVLLLVT    52
SEQ_ID_NO_1109    AVEMRRERER RRAREQQPRC GEVAGGTAAE CAAVFCCFPE AVVELVVLAA    98
SEQ_ID_NO_1101    SSGSSCCSGR F--------- GEIAGGTTAE CAAICCCCPC GLVNLLVLTI    61
SEQ_ID_NO_1099    PTTMIKHAER R------KV GEVAGGAAAE CAAVMCCGPC AVVNLVVLAV    58
SEQ_ID_NO_1103    PSTTSLSKER R------KV GEVAGGAAAE CAAVMCCCPC AVVNLMVLAV    67

SEQ_ID_NO_1106    VKLPAGLCRR ALSQKRRKRV KKR------- -----STTL RSRAMSFVSD    130
SEQ_ID_NO_1105    YKVPASLMKK AAINNRKKRL LKQ------- ---------- MKKDMKNFLE    77
SEQ_ID_NO_1108    VKLPAGVMRR VRRRRRHRD RVS-----RK KRSAAAAVE PASPSGSSGK    97
SEQ_ID_NO_1109    VRAPAALCRR AVRGGRRRRV RST-----KP KETGAMDIAS PRSLAAAAAK    143
SEQ_ID_NO_1101    YKIPAGICRR ALKRKQRKKL IKKGLFPPRG RGYGCGSCDD PELHIHPMAR    111
SEQ_ID_NO_1099    YRVPAAVCKK AMRQTKRQRF MRR----RH GLLASAAA-- -ESTVHARLK    100
SEQ_ID_NO_1103    YKVPAAVCKK AMRRSKRRRF TRK----RH GLLASATAEG SESTVHARLN    112

SEQ_ID_NO_1106    DEDFGVPSFV PRTPETWPSK SPSVEVAEK- EEEMW-AEFY SAGFWRSPSQ    178
SEQ_ID_NO_1105    HEKPGGP--G PETVVVGPTM EELLAQEELP EEDLW-ARFS VNGFWRSSSS    124
SEQ_ID_NO_1108    AMIGAAP--S PLEAEEEEAR GEAAAAAEL- EREIMSSRFY GAGFWRSVSS    144
SEQ_ID_NO_1109    ARKVDAD--F PAT---PKA EHLVDM--- EKEVW-ASFY GGGFWRSPSQ    182
SEQ_ID_NO_1101    VEDSLRE--F DGE-E-AVKK EEL-AMLRL- EKEMW-ETFY GTGFWRSPSQ    153
SEQ_ID_NO_1099    EEDPTAE--I VFE-E-NVVN VELNDVVVL- EDEMF-ERFY GAGFWRSPSQ    144
SEQ_ID_NO_1103    EEDLTAE--I VFE-ECHVSG GELNDVVRL- ENEML-DRFY GAGFWRSPSQ    157
```

Figure 35 (continued)

| | | | | | |
|---|---|---|---|---|---|
| SEQ_ID_NO_1106 | ---------- | KESN- ---- | ---------- | ---------- | --- | 182 |
| SEQ_ID_NO_1105 | -----QKHEP | DELQTGEN-- | ---------- | ---------- | -NR | 139 |
| SEQ_ID_NO_1108 | ---------- | GCSSSASMRY | Q--------- | ---------- | --- | 155 |
| SEQ_ID_NO_1109 | REDRRCI AAG | DGAAAAALFF | FSFTTVVGFL | AFLLPFLGKR | EDR | 225 |
| SEQ_ID_NO_1101 | RELPAKRSSP | RETPNARL-- | ---------- | ---------- | --- | 171 |
| SEQ_ID_NO_1099 | ---------- | RDTSSGSI-- | ---------- | ---------- | --- | 152 |
| SEQ_ID_NO_1103 | ---------- | KDTSSGSL-- | ---------- | ---------- | --- | 165 |

Figure 36

| | | | | | | | |
|---|---|---|---|---|---|---|---|
| SEQ_ID_NO_1112 | MAQNKMVMV | LLSTFLVVA | RSLWPEEPS | NADD-RGAC | IEECTKE-NK | | 48 |
| SEQ_ID_NO_1113 | MAQNKTIAVA | LLATLVAV- | ----MGKEPE | TLEETLRAGC | KEECSEQKKK | | 45 |
| SEQ_ID_NO_1114 | MAQNKTIAVA | LLATLVAV- | ----MGKEPE | TLEEAVRAGC | KEECSEQKKK | | 45 |
| | | | | | | | |
| SEQ_ID_NO_1112 | APGDKKTCEV | LC-------- | ---------- | ---------- | --------T | | 61 |
| SEQ_ID_NO_1113 | APIDEKQCED | FCFIKTKSIF | EAHKGVKDLK | ADRFIDFCNN | ECNAVYKEDP | | 95 |
| SEQ_ID_NO_1114 | APIDEKQCED | FCFIKTKSIF | EAHKGVKDLK | ADRFIDFCNN | ECNAVYKEDP | | 95 |
| | | | | | | | |
| SEQ_ID_NO_1112 | KLTKKPSEEG | KHD------- | ---------- | ---- | 74 | | |
| SEQ_ID_NO_1113 | ATSKKCAESC | EADAKEAEVF | LDKVVAYMQT | MKQA | 129 | | |
| SEQ_ID_NO_1114 | ATSKKCAESC | EADAKEAEVF | LDKVVAYIQT | TKQA | 129 | | |

Figure 37

```
SEQ_ID_NO_1138    M---KRSREA EEEEEQAA-- --GAELLLLL SLSRGDKPA- ----------    32
SEQ_ID_NO_1141    M------TKH PRDGEVIS-- --LSLSLTLG AAADSGERK- ----------    29
SEQ_ID_NO_1143    -MAMKR-MRS EDIVGDKDSL DDMAKCLMLL S--HGGGLT- ----------    35
SEQ_ID_NO_1120    MLLSKVGQAD HEILTNYR-- --SAAAAAAA A--TAGA---  ----------    31
SEQ_ID_NO_1147    MAKRERAAWE VEAGAAAD-- --TARLLMLL A--QAQQQHL LQQHAHHHHH    44
SEQ_ID_NO_1132    -----MAMKR QRSNEGID-- --YANCLMLL S--CPQQ---  ----------    26
SEQ_ID_NO_1134    MSAMKR-SRE DRQVEAAA-- --MANCLMLL S--KLNDKS-  ----------    32
SEQ_ID_NO_1136    ---------- ---------- --MARILLLF SGHHQHHAH-  ----------    17
SEQ_ID_NO_1145    ---------- ---------- --MPMPMPVA A--RGHR---  ----------    13
SEQ_ID_NO_1144    MVAI---SEI KSTVETTA-- --AANCLMLL S--RVGQEN-  ----------    30
SEQ_ID_NO_1116    MVAI---SEI NPTVEAT--- --AANCLMLL S--RVGQK--  ----------    28
SEQ_ID_NO_1123    MVAI---SEI KSTVDVT--- --AANCLMLL S--RVGQEN-  ----------    29
SEQ_ID_NO_1140    -MTIKRSWED DREVENLA-- --MANCLMLL S--RVGQS--  ----------    31
SEQ_ID_NO_1133    MVMINIPMKR TREANDFDSI TTMANCLMLL SQNRSGEFI-  ----------    39
SEQ_ID_NO_1118    -------MKR GRDIDAMD-- --MADCLMLL S--RVGET--  ----------    25
SEQ_ID_NO_1129    -------MKR GREESKLD-- --MANCLMLL T--KVGES--  ----------    25

SEQ_ID_NO_1138    ------TVRK K---VRAAEG ---VFECKIC SRQFPTFQAL GGHRISHNRP    70
SEQ_ID_NO_1141    ------KPRR GSSPAASGSG ---DFVCKTC SRAFPSFQAL GGHRTSHLRG    70
SEQ_ID_NO_1143    ------TDTK ----PKTCPH PVDVFECKTC NRQFSSFQAL GGHRASHKRP    75
SEQ_ID_NO_1120    ---------- ----GAGAGR ---SFSCKTC NKNFPSFQAL GGHRASHKKP    64
SEQ_ID_NO_1147    HHHGVGVPPF PAGRAAVHGR ---VFECKTC SRQFPTFQAL GGHRASHKRP    91
SEQ_ID_NO_1132    ---------- ----KSYENG ---EYECKTC NKKFSSFQAL GGHRASHKRM    59
SEQ_ID_NO_1134    ------TSTT TT--NQDHHN ---DFECKTC NKRFSSFQAL GGHRASHKRP    71
SEQ_ID_NO_1136    ------YG-- -----PSSPER ---VFECKTC NRRFPSFQAL GGHRASHKKP    52
SEQ_ID_NO_1145    ---------- ------APER ---VFVCKTC DRVFPSFQAL GGHRASHKKP    44
SEQ_ID_NO_1144    ------VD-- ----GGSAKR ---VFTCKTC LKEFHSFQAL GGHRASHKKP    65
SEQ_ID_NO_1116    ---------- ----GGDQKR ---VFTCKTC LKEFHSFQAL GGHRASHKKP    61
SEQ_ID_NO_1123    ------VD-- ----GGDQKR ---VFTCKTC LKQFHSFQAL GGHRASHKKP    64
SEQ_ID_NO_1140    ---------- ----GSTPDR ---VFHCKTC DKEFKSFQAL GGHRASHKRP    64
SEQ_ID_NO_1133    ------DSTT SNSSNLNSNR ---VFECKTC NRQFPSFQAL GGHRASHKRP    80
SEQ_ID_NO_1118    ---------- ----DRVAGR ---VFACKTC NKKFSSFQAL GGHRASHKKP    58
SEQ_ID_NO_1129    ------ETNY PISKGSDIG- ---DFKCKTC NRRFSSFQAL GGHRASHKKP    65
```

Figure 37 (continued)

| | | | | | | |
|---|---|---|---|---|---|---|
| SEQ_ID_NO_1138 | RVDRS----- | -----TS--- | ---------- | ---------- | --RRSVHQCS | 85 |
| SEQ_ID_NO_1141 | RHGLA----L | GLAAATAKET | TKKVQEKPA- | ---------- | --AAATHECH | 103 |
| SEQ_ID_NO_1143 | RLMGE----- | -----EHKVD | RTKLCSSGN- | ---------- | --KPKMHECS | 102 |
| SEQ_ID_NO_1120 | KLKES----- | -----T---- | -GNLKLPNS  | PS-------- | --KPKTHQCS | 89 |
| SEQ_ID_NO_1147 | RVLQQQQLQQ | QQTVVADHAG | QLCLGRQPLQ | LPLPTTTTPQ | QAKPRVHECP | 141 |
| SEQ_ID_NO_1132 | KLAEG----- | ---------- | -EELKEQAKS | LSLWN----- | --KPKMHECS | 86 |
| SEQ_ID_NO_1134 | KLLIG----- | -----A---- | -GEFLVQPS- | ---------- | --SKKMHECS | 93 |
| SEQ_ID_NO_1136 | RLADG----- | ---------- | --AGAEPP-- | ---------- | --KPKVHGCS | 71 |
| SEQ_ID_NO_1145 | RLDDG----- | ---------- | -GDL------ | ---------- | --KPKLHGCS | 60 |
| SEQ_ID_NO_1144 | NNENL----- | -----S---- | -GLMKKTK-- | ---------- | --ASSSHPCP | 88 |
| SEQ_ID_NO_1116 | NNNES----- | --------L  | SGLVKKAK-- | ---------- | --APSSHPCP | 93 |
| SEQ_ID_NO_1123 | NNDAL----- | -----SS--- | -GLMKKV--- | ---------- | --KTSSHPCP | 85 |
| SEQ_ID_NO_1140 | KTSDG----- | ---------- | -SEARTPP-- | ---------- | --KPKTHECP | 84 |
| SEQ_ID_NO_1133 | RLGGD----- | ---------- | -LTLSQIPVA | AA-------- | --KPKTHECS | 104 |
| SEQ_ID_NO_1118 | KLTVG----- | -----DN--- | -EGLAVSP-- | ----K----- | --KPKTHECS | 61 |
| SEQ_ID_NO_1129 | KLMVT----- | -----DL--- | -SCHQELPNP | TMKQ------ | --QPRMHPCP | 93 |

| | | | | | | |
|---|---|---|---|---|---|---|
| SEQ_ID_NO_1138 | CGVEFAMGQ | ALGGHMRRHK | PMAEDSKRSD | PKK------- | ---------- | 118 |
| SEQ_ID_NO_1141 | CGQGFEMGQ | ALGGHMRRHR | EEAAAAAAV  | H--------- | ---------- | 134 |
| SEQ_ID_NO_1143 | LCGQKFSMGQ | ALGGHMRRHR | AL-NEGLSSI | MNPLDHA--- | ------KVPM | 141 |
| SEQ_ID_NO_1120 | CGLEFPLGQ | ALGGHMRRHR | APNNVDTTST | SSKDHELAVT | QPPFLPAVPV | 139 |
| SEQ_ID_NO_1147 | VCGLEFAVGQ | ALGGHMRRHR | AEAEAEATEA | PSKVMMR--- | --------PA | 180 |
| SEQ_ID_NO_1132 | CGMGFSLGQ | ALGGHMRKHR | AVINEGVSSI | NQIIEKF--- | --------PV | 125 |
| SEQ_ID_NO_1134 | CGMEFSLGQ | ALGGHMRRHR | AAIDEKSKAA | TKAMMIP--- | ---------V | 131 |
| SEQ_ID_NO_1136 | CGLEFAVGQ | ALGGHMRRHR | AVAAAGPGVG | LGLSLGL--- | --GLGPNEDG | 116 |
| SEQ_ID_NO_1145 | VCGLEFAIGQ | ALGGHMRRHR | AMAAGGGGGM | MPMTPPT--- | -----AAALKE | 103 |
| SEQ_ID_NO_1144 | CGVEFPMGQ | ALGGHMRRHR | NEGG-GAGAL | VTRELLP--- | -----EAALMT | 128 |
| SEQ_ID_NO_1116 | CGVEFPMGQ | ALGGHMRRHR | NEIG-GGAAL | VTRALLP--- | -----EPTMTT | 125 |
| SEQ_ID_NO_1123 | CGVEFPMGQ | ALGGHMRRHR | NESGAAGGAL | VTRALLP--- | -----EPTVTT | 128 |
| SEQ_ID_NO_1140 | VCGLEFAIGQ | ALGGHMRRHR | DVGNEK--GG | RPVAARP--- | ---------- | 119 |
| SEQ_ID_NO_1133 | ICGLEFAIGQ | ALGGHMRRHR | AAMSDSASGN | SASPPRDDRT | VVVKKSNIV- | 153 |
| SEQ_ID_NO_1118 | ICGLEFAIGQ | ALGGHMRRHR | AALNDG---L | VTRDLLP--- | ---------E | 116 |
| SEQ_ID_NO_1129 | ICGLEFAIGQ | ALGGHMRKHR | TAINDGLLCG | KPSSSLS--- | ------ILKE | 134 |

Figure 37 (continued)

| SEQ_ID_NO_1138 | ·········· ········· M DLTMADPEF · ········· G DLHRVR ··· | 135 |
|---|---|---|
| SEQ_ID_NO_1141 | ·········· ········· ····APPV ·········· ·········· | 138 |
| SEQ_ID_NO_1143 | LMKRSNS··· ···TRVVCSL DLN·LTPL ·········· E N·DLK·LF | 170 |
| SEQ_ID_NO_1120 | LKRSNSS··· ···KRVLC·L DLS·ALPMY ·········· Q NDSELQ·LEK | 171 |
| SEQ_ID_NO_1147 | HDKTCDV··· ···AGGIC·L DLN·LTPS· ·········· E NCAKCRSVW | 211 |
| SEQ_ID_NO_1132 | LKRLNS···· ···KRIMG·L DLN·LTPL ·········· E ND·DLM·FGI | 153 |
| SEQ_ID_NO_1134 | LKKSNSS··· ···KRIFC·L DLN·LTPR ·········· N EDVDLK·LWP | 161 |
| SEQ_ID_NO_1136 | NKKAAA···· ···AAELA·L DLN·EPAL ·········· E EEPADR·AML | 145 |
| SEQ_ID_NO_1145 | HGESGDDDAV VGMKRGLW·L DLN·HPPCD EYGAGSESDD ECGHVD·AAA | 149 |
| SEQ_ID_NO_1144 | LKKSSS···· ···GRLAC·L DLS·LGMV ·········· E NL·NLK·LEL | 156 |
| SEQ_ID_NO_1116 | LKKSSSG··· ···KRVAC·L DLS·LGMV ·········· E NL·NLK·LEL | 154 |
| SEQ_ID_NO_1123 | LKKSSSG··· ···KRVAC·L DLS·LGMV ·········· D NL·NLK·LEL | 157 |
| SEQ_ID_NO_1140 | ···ESVT··· ···KRGLF·M DLN·LTPL ·········· E N·DLK·LWS | 144 |
| SEQ_ID_NO_1133 | ···DDDND·· ···RRVAG·L DLN·LTPF ·········· E N·HLE·FQL | 179 |
| SEQ_ID_NO_1118 | MNKSTGD··· ···GRDPS· DLG·LTSW ·········· G VDLELK·L· | 144 |
| SEQ_ID_NO_1129 | SSKDGDQ··· ···KLNLR·L DLN·LTPL ·········· E ED·DLK·LNL | 163 |

| SEQ_ID_NO_1138 | ·······RTG SHCQL·QLFV | 148 |
|---|---|---|
| SEQ_ID_NO_1141 | ·········· ····LLELFV | 144 |
| SEQ_ID_NO_1143 | ·······GKM APKVDLRLM | 183 |
| SEQ_ID_NO_1120 | ·········· VARPMLRCFI | 181 |
| SEQ_ID_NO_1147 | LGAAAGQGVH KTLAMLDCSL | 231 |
| SEQ_ID_NO_1132 | ·······KSP PTPIPLSLF | 165 |
| SEQ_ID_NO_1134 | ·······TAP ISSPVLRIFI | 174 |
| SEQ_ID_NO_1136 | ·······GLA VGFRPRGG·· | 156 |
| SEQ_ID_NO_1145 | AGYTFHQFMD TGTMAVDCV· | 168 |
| SEQ_ID_NO_1144 | ·······GRP VC······· | 161 |
| SEQ_ID_NO_1116 | ·······GRT VC······· | 159 |
| SEQ_ID_NO_1123 | ·······GRT VY······· | 162 |
| SEQ_ID_NO_1140 | ·······NTV NTALAM··· | 153 |
| SEQ_ID_NO_1133 | ·······GKI APT··VDCFL | 190 |
| SEQ_ID_NO_1118 | ·······GKV TPTPVHCFI | 157 |
| SEQ_ID_NO_1129 | ·········· ·RTPVLNCFI | 172 |

Figure 38

| | | | | | | | |
|---|---|---|---|---|---|---|---|
| SEQ_ID_NO_1162 | MATKIFALLV | LLALSASATT | AVIIPQCSLA | PTAAIIPRFL | PPVSAIGFEH | | 50 |
| SEQ_ID_NO_1163 | MATKIFVLLA | LLALSVSTTT | AVIIPQCSLA | PNAFLISQFL | PPLTLVGFEH | | 49 |
| SEQ_ID_NO_1161 | MAAKIFAILA | LLALSASVAT | ATIIPQCSQF | ------ | QYLSPVTAARFEY | | 42 |
| SEQ_ID_NO_1159 | MATKIFSLLM | LLALSACVAN | ATIFPQCSQA | PIASLLPPYL | PSMIASVCEN | | 50 |
| SEQ_ID_NO_1164 | MAAKIFCFLM | LLGLSASVAT | ATIFPQCSQA | PIASLLPPYL | SPAVSSMCEN | | 50 |

| | | | | | | | |
|---|---|---|---|---|---|---|---|
| SEQ_ID_NO_1162 | PAVQAYRLQQ | ALAASIL-- | ----QQPLAQ | LQQQSSAHLT | IQTIAAQQIQ | | 92 |
| SEQ_ID_NO_1163 | PALQAYRLQQ | ALANSIL-- | ----QQPFPQ | LQQQSSAHLT | VQTIAAQQQQ | | 92 |
| SEQ_ID_NO_1161 | PTIQSYRLQE | AIAASILRSL | ALTVQQPYAL | LQQPSLMNLY | LQRIAAQQLQ | | 92 |
| SEQ_ID_NO_1159 | PALQPYRLQQ | AIAASNPLS | PLLFQQSPAL | ----SLVQSL | VQTIRAQQLQ | | 96 |
| SEQ_ID_NO_1164 | PIVQPYRIQQ | AIATGLPLS | PLFLQQPSAL | QQLPLVHLV | AQNIRAQQLQ | | 100 |

| | | | | | | | |
|---|---|---|---|---|---|---|---|
| SEQ_ID_NO_1162 | QQFLPSLSQL | AAANPTAYLQ | QQLLASNPLA | VANAIAYQHQ | QQLQQLLPAL | | 142 |
| SEQ_ID_NO_1163 | QQFLPALSQL | ALANPVAYLQ | QQLLASNPLA | LVNNAAYQ-Q | QQLQQVLPVI | | 141 |
| SEQ_ID_NO_1161 | QQLLPTINQV | VAANLAAYLQ | Q--------- | ---------- | ---QQFLPFF | | 119 |
| SEQ_ID_NO_1159 | QLVLPVINQV | ALANLSPYSQ | Q--------- | ---------- | ---QQFLPFF | | 123 |
| SEQ_ID_NO_1164 | -------QL | VLANLAAYSQ | Q--------- | ---------- | ---HQFLPFF | | 119 |

| | | | | | | | |
|---|---|---|---|---|---|---|---|
| SEQ_ID_NO_1162 | SQLAVANPAA | YLQ-SQLFPS | NPLV-ANAAA | YLQQQQLQQI | LPVLSQLAVA | | 190 |
| SEQ_ID_NO_1163 | SQVAMANPAA | YLQ-QQQLAY | NPLVAANAAA | YLQQQQLQQI | LPALSQLALV | | 190 |
| SEQ_ID_NO_1161 | NQLAGVNPAA | YLQAQQLLPF | NQLV-RSPAA | FLLQQQL--- | LPFHLQVMA | | 164 |
| SEQ_ID_NO_1159 | NQLSTLNPAA | YLQ-QQLLPF | SQLA----TA | YSQQQQL--- | LPFNQLAAL | | 164 |
| SEQ_ID_NO_1164 | NQLAALNSAA | YLQ-QQFLPF | SQLV----AA | YP--RQF--- | LPFNQLAAL | | 157 |

| | | | | | | | |
|---|---|---|---|---|---|---|---|
| SEQ_ID_NO_1162 | DPNSYL-QQQ | QLLPFNQVAV | ANNAVYEQQH | QLLQVNPLA- | -----AAFLQ | | 233 |
| SEQ_ID_NO_1163 | NPAAYL-QQQ | QLLPFNQLAV | TNTAAYLQQQ | QLLRVNPVVA | ANPLAAAFLQ | | 239 |
| SEQ_ID_NO_1161 | NIAAFLQQQQ | QLLPFYPQVV | GNINAFLQQQ | QLLPFYPQDV | ANN--VAFLQ | | 212 |
| SEQ_ID_NO_1159 | NPAAYL-QQQ | ILLPFSQLAA | ANRASFLTQQ | QLLPFYQQFA | ANP--ATLLQ | | 211 |
| SEQ_ID_NO_1164 | NSAAYL-QQQ | QLLPFSQLAD | VSPAAFLTQQ | QLLPFYLHAM | PNA--GTLLQ | | 204 |

| | | | | | | |
|---|---|---|---|---|---|---|
| SEQ_ID_NO_1162 | QQQRQLLPFN | QMSLMNPALS | VQQPIVGGVG | FI | | | 264 |
| SEQ_ID_NO_1163 | QQ--QLLPFN | DISLMNPAFS | VQQPIVGSAI | FI | | | 268 |
| SEQ_ID_NO_1161 | QQ--QLLPFN | QLALTNPTTL | LQQPTIGGAI | FI | | | 241 |
| SEQ_ID_NO_1159 | LQ--QLLPFV | QLALTDRAAS | YQQHIGGAL | FI | | | 240 |
| SEQ_ID_NO_1164 | LQ--QLLPFN | QLALTNSTVF | YQQPIIGGAL | FD | | | 234 |

Figure 39

| | | | | | | | |
|---|---|---|---|---|---|---|---|
| SEQ_ID_NO_1167 | MAK------ | -NGI NNSVAV | GI AVQSDWDN | RHFSSSLSLN | VRRLFEFLLQ | | 42 |
| SEQ_ID_NO_1182 | MGR----GG | --GMGNPVNV | GI AVQADWGN | REFI SNI SLN | VRRLFDFLLR | | 43 |
| SEQ_ID_NO_1166 | MGR----GG | --GMGNPVNV | GI AVQADWEN | REFI SNI SLN | VRRLFDFLLR | | 43 |
| SEQ_ID_NO_1183 | MAR----AG | GHGMGNPVNV | GI AVQADWEN | REFI SNI SLN | VRRLFDFLLR | | 45 |
| SEQ_ID_NO_1173 | MARAGGGGGG | GGGI TNAVNV | GI AVQADWEN | REFI SHI SLN | I RRLFDFLIQ | | 50 |
| SEQ_ID_NO_1169 | MSR----GG | GVGI TNAVNV | GI AVQADWEN | REFI SNI SI N | VRRLFDFLIN | | 45 |
| SEQ_ID_NO_1177 | MAR----AG | --GI TNAVNV | GI AVQADWEN | REFI SHI SLN | VRRLFDFLVQ | | 43 |
| SEQ_ID_NO_1180 | MAR----AG | --GI TNAVNV | GI AVQADWEN | REFI SHI SLN | VRRLFDFLVQ | | 43 |
| SEQ_ID_NO_1171 | MAR----AG | --GI TNAVNV | GI AVQADWEN | REFI SHI SLN | VRRLFEFLLQ | | 43 |
| SEQ_ID_NO_1175 | MAK----AG | --GI TNAVNV | GI AVQADWEN | REFI SHI SLN | VRRLFEFLVQ | | 43 |

| | | | | | | |
|---|---|---|---|---|---|---|
| SEQ_ID_NO_1167 | FESSTRSKLA | TLNEKLTVLE | RQLEFLEADF | STALINPV-- | -------- | 79 |
| SEQ_ID_NO_1182 | FEATTKSKLA | SLNEKLDI LE | RKLEVLEVQV | SSATTNPSVF | N------- | 84 |
| SEQ_ID_NO_1166 | FEATTKSKLA | SLNEKLDI LE | RKLEVLEVQV | GSATTNPSVF | N------- | 84 |
| SEQ_ID_NO_1183 | FEATTKSKLA | SLNEKLDI LE | RKLEVLEVQV | SSATTNPSVF | N------- | 86 |
| SEQ_ID_NO_1173 | FESTTKSKLS | SLNLKLDFLE | RRLQLLELQV | STATSNPSLF | TSTTTTTA | 98 |
| SEQ_ID_NO_1169 | FEATTKSKLA | SLNEKLDTLE | RRLELLEVQV | GTASANPSLF | T------- | 86 |
| SEQ_ID_NO_1177 | FEATTKSKLA | SLNEKLDVLE | RRLELLEVQV | GNASANPSLF | AT------ | 85 |
| SEQ_ID_NO_1180 | FEATTKSKLA | SLNEKLDVLE | RRLELLEVQV | GNASANPSLF | AT------ | 85 |
| SEQ_ID_NO_1171 | FEATTKSKLA | SLNEKLDTLE | RRLELLEVQV | GTASANPSLF | ST------ | 85 |
| SEQ_ID_NO_1175 | FESTTKSKLA | SLNEKLDLLE | RRLEMLEVQV | STATANPSLF | AT------ | 85 |

Figure 40

| | | | | | | |
|---|---|---|---|---|---|---|
| SEQ_ID_NO_1187 | MFSWLRGCR | DECSATDQLK | Q- - - - - - - - - - - - - - - - - -A | RDVFVAKEAV | | 32 |
| SEQ_ID_NO_1185 | MFAWLRGCR | DECSASDQLK | Q- - - - - - - - - - - - - - - - - -A | HDVFKAKEVV | | 32 |
| SEQ_ID_NO_1189 | MFSWLRGCR | DECSASDQLK | Q- - - - - - - - - - - - - - - - - -A | RDVFMAKEAV | | 32 |
| SEQ_ID_NO_1190 | MFAWLLRGCR | DECSASDQLK | QGVVKEKNRC | WFWGAFSVNA | RDVFVAKEAV | 50 |
| SEQ_ID_NO_1191 | MFAWLLRGCR | DECSASDQLK | Q- - - - - - - - - - - - - - - - - -A | RDVFVAKEAV | | 32 |

| | | | | | | |
|---|---|---|---|---|---|---|
| SEQ_ID_NO_1187 | LQKKISQEME | RAKEFKKSGN | KQAAMQCLKR | KRYYESQMNQ | VGSVRLRIDT | 82 |
| SEQ_ID_NO_1185 | LQKKISQEVE | RAKEFTKSGN | KQAAMQCLKR | KRYYESQMNQ | VGSVQLRINT | 82 |
| SEQ_ID_NO_1189 | LQKKISQEME | RAKEFTKSGN | KQAAMQCLKR | KKYYESQMSQ | VGSVQLRINT | 82 |
| SEQ_ID_NO_1190 | LQKKISQEME | RAKEFTKSGN | KQAAMQCLKR | KKYYESQMNQ | VGSVQLRINT | 100 |
| SEQ_ID_NO_1191 | LQKKISQEME | RAKEFTKSGN | KQAAMQCLKR | KKYYESQMNQ | VGSVQLRINT | 82 |

| | | | |
|---|---|---|---|
| SEQ_ID_NO_1187 | KEKMIADNMV | N- - K | 94 |
| SEQ_ID_NO_1185 | KERMIADHTG | N- - K | 94 |
| SEQ_ID_NO_1189 | KEKMIADHMG | N- - K | 94 |
| SEQ_ID_NO_1190 | KEKMIADHSG | NKEDK | 115 |
| SEQ_ID_NO_1191 | KEKMIADHSG | NKEDK | 97 |

Figure 41

| | | | | | | | |
|---|---|---|---|---|---|---|---|
| SEQ_ID_NO_1204 | ........MVK | TRAAATPR.. | ........... | ..... | PSGGG | GAGAADI TAG | 26 |
| SEQ_ID_NO_1203 | MGEQSLSDPK | PQPLSPFPSP | PASAAL---- | ----- | PPPAS | ASASASASAA | 41 |
| SEQ_ID_NO_1205 | MESPNPQQVN | SMGDQSPLSP | NLHPLS---- | ----- | PSPSA | AAAAAA---- | 37 |
| SEQ_ID_NO_1196 | MGEDTPSQPQ | PQVQSQPPND | SSTTTQAQVQ | NQSGDP | SNTS | TAAVSTVTTA | 50 |
| SEQ_ID_NO_1202 | MGEQTLGQAQ | SLIEPQPL.. | ........... | ..... | PAPSS | TAVPDGATVD | 33 |
| SEQ_ID_NO_1194 | ---MSLRKTL | TAVNQSSL.. | ........... | ..... | PPDSL | ISAGNLTVSE | 30 |
| SEQ_ID_NO_1200 | MGKPVTRSHS | LLLHEPSS.. | ........... | ..... | PPLS | .......... | 22 |

| | | | | | | | |
|---|---|---|---|---|---|---|---|
| SEQ_ID_NO_1204 | .......... | .......... | ....KISFRS | RKIVKSTPAK | GKSVATTTTA | 52 |
| SEQ_ID_NO_1203 | .......... | .......... | ....STSRTTSAAAS | RPKKKVTN-P | SPDRNPAKKP | 71 |
| SEQ_ID_NO_1205 | .......... | .......... | ....TPTPAAAASS | RSSRSKKPPH | SSDPNQSKKP | 68 |
| SEQ_ID_NO_1196 | CTAI VACGPT | ELVNVPLPTS | SPPSKIPSRP | RKIRKLSPDL | SFDPNASQQA | 100 |
| SEQ_ID_NO_1202 | ........S | ELNNVPRPTT | SPATKIPLRP | RKIRKVSPDP | STSESQTETP | 74 |
| SEQ_ID_NO_1194 | .......... | ........VS | GSSSRIRFRP | RKIRKVSSDP | SPRIIIASP | 62 |
| SEQ_ID_NO_1200 | .......... | .......... | ....TTTSSKISFQS | RKIRKLSTNK | TTTTTTAITS | 53 |

| | | | | | | | |
|---|---|---|---|---|---|---|---|
| SEQ_ID_NO_1204 | .......... | .VLS...... | .......... | ---PP....P | LSSPGELAAA | 68 |
| SEQ_ID_NO_1203 | .......... | .RLT...... | .......... | ---FSIPGRP | LSAVGEVGVA | 91 |
| SEQ_ID_NO_1205 | .......... | .RLT...... | .......... | ---LTVPGRP | LSADGEVAAA | 88 |
| SEQ_ID_NO_1196 | TTSSSTSLTE | QRKTVGRTSK | TKLSQHRALA | VVAPRIIARS | LSDEGEVETA | 150 |
| SEQ_ID_NO_1202 | .......... | .KPAKTGGRN | TTKAAPPRAL | TVVPRIVARS | LSDDGEVEIA | 113 |
| SEQ_ID_NO_1194 | .......... | .......... | .......... | .........P | LSTKSTVDIA | 73 |
| SEQ_ID_NO_1200 | .......... | .TSI...... | .......... | ---PPL-KP | LSHKGEIELA | 71 |

| | | | | | | | |
|---|---|---|---|---|---|---|---|
| SEQ_ID_NO_1204 | LSHLRTADPL | LSEVIASTGA | PAFISSPSRP | AFHSLAHSIL | HQQLAPSAAA | 118 |
| SEQ_ID_NO_1203 | IRYLRAADPA | LAAVIDAH-E | PPVFQCPHRP | -FHSLVRSIL | YQQLAFKAAA | 139 |
| SEQ_ID_NO_1205 | IQHLRAADPA | LATVIDAH-D | PPAFQCPHRP | -FHSLVRSIL | YQQLAFKAAA | 136 |
| SEQ_ID_NO_1196 | IRHLRDADPL | LASLIDLH-P | PPTFDTFHAP | -FLALTRSIL | YQQLAFKAGT | 198 |
| SEQ_ID_NO_1202 | LRYLRNADPV | LSPLIDH-Q | PPTFDNFHTP | -FLALTRSIL | YQQLAYKAGT | 161 |
| SEQ_ID_NO_1194 | LRHLQSSDE | LGALITTHND | PPVFDSSNTP | -FLSLARSIL | YQQLATKAAK | 122 |
| SEQ_ID_NO_1200 | LDHLSKSDPL | LAPLLNSH-E | PPALNPCTSP | -FLSLTKSIL | FQQLATNAAK | 119 |

Figure 41 (continued)

```
SEQ_ID_NO_1204    AI YARFLAL  PAAADPDAAV  VNPAAVLALS  AADLRAI GVS  ARKAAYLHDL   168
SEQ_ID_NO_1203    SVYSRFLALL  ----G-GESC  VAPDAVLALT  PHQLRQI GVS  PRKASYLHDL   184
SEQ_ID_NO_1205    SVYSRFLSLL  ----G-GEHN  VLPEAVLALT  TQDLRQI GVS  PRKASYLHDL   181
SEQ_ID_NO_1196    SI YTRFI SLC  ----G-GENG  VVPETVLSLT  SQQLRQI GVS  GRKASYLHDL   243
SEQ_ID_NO_1202    SI YTRFI ALC  ----G-GENG  VVPETVLALT  PQQLRQI GVS  GRKASYLHDL   206
SEQ_ID_NO_1194    CYDRFI SLF  ----NGGEAG  VFPESVI SLS  AVDLRKI GVS  GRKASYLHDL   168
SEQ_ID_NO_1200    SI YTRFLTLC  ----D-GESQ  VNPDTVLSLS  APKLREI GVS  GRKASYLHDL   164

SEQ_ID_NO_1204    AGRFAAGELS  ESAVAAMDEA  ALLAELTKVK  GVGEWTVHMF  MI FSLHRPDV   218
SEQ_ID_NO_1203    ARKYASGI LS  DAAI VNMDDR  SLAAMLTMVK  GI GSWSVHMF  MI FSLARPDV   234
SEQ_ID_NO_1205    ARKYASGI LS  DAAVVNMDDR  SLAAMLTMVK  GI GAWSVHMF  MI FSLNRPDV   231
SEQ_ID_NO_1196    ARKYQTGI LS  DSAI VNMDDK  SLFTMLTMVN  GI GSWSVHMF  MI FSLHRPDV   293
SEQ_ID_NO_1202    ARKYQNGI LS  DSAI VNMDDK  SLLTMLTMVN  GI GSWSVHMF  MI FSLHRPDV   256
SEQ_ID_NO_1194    ADKYNNGVLS  DELI LKMSDE  ELI DRLTLVK  GI GVWTVHMF  MI FSLHRPDV   218
SEQ_ID_NO_1200    AEKYRNGSLS  DSSI LEMNDD  MLLNRLTEVK  GI GVWSVHMF  MLFSLHRPDV   214

SEQ_ID_NO_1204    LPSGDLGVRK  GVQELYGLPA  LPKPEEMAAL  CERWRPYRSV  GAWYMWRLME   268
SEQ_ID_NO_1203    LPSADLGVRK  GVQMLYALED  VPRPSQMDKL  CERWRPYRSV  GAWYMWRLI E   284
SEQ_ID_NO_1205    LPAADLGVRK  GVQHLYGLDA  VPRPSQMEKL  CEQWRPYRSV  GAWYMWRLI E   281
SEQ_ID_NO_1196    LPI NDLGVRK  GVCLLYNLEE  LPRPSQMDQL  CEKWRPYRSV  ASWYLWRYVE   343
SEQ_ID_NO_1202    LPI NDLGVRK  GVQLLYNLED  LPRPSQMDQL  CDKWRPYRSV  ASWYMWREVE   306
SEQ_ID_NO_1194    LPVGDLGVRK  GVKDLYGLKN  LPGPLQMEQL  CEKWRPYRSV  GSWYMWRLI E   268
SEQ_ID_NO_1200    LPVGDLGVRK  GVQSLYGLKD  LPQALEMEQI  CEKWKPYRSV  GSWYMWRLME   264

SEQ_ID_NO_1204    SKGAAAKKAK  SNAI AFLPS-  --------SC-  ----------  ----------   289
SEQ_ID_NO_1203    SKVPQPAPAI  PVGSLAFPS-  ---------P  DGQSMLQQDE  QQQQQTVI QM   324
SEQ_ID_NO_1205    SKAPPPPPAI  PVGPPALTE-  -------HGD  ELMLQQQQHQ  QQQQSVI QM   323
SEQ_ID_NO_1196    AKGAPSSAAA  VAAGASLPP-  ----------  ----LQQQEE  PQQHQQQPPL   378
SEQ_ID_NO_1202    AKGTPSSAVA  VATGAGLQQQ  QHHQHHHQHQ  QQEQQQQQQQ  QQQHPPQPQL   356
SEQ_ID_NO_1194    SRKTK-----  ----------  ----------  ----------  ----------   273
SEQ_ID_NO_1200    AKALANKAAK  KA--------  ----------  ----------  ----------   276
```

Figure 41 (continued)

| | | | |
|---|---|---|---|
| SEQ_ID_NO_1204 | - - - - - - - - - - | - - - - - - - - | 289 |
| SEQ_ID_NO_1203 | I DPL QML PGM | G - - - - - - | 335 |
| SEQ_ID_NO_1205 | I DPL QML PGM | G - - - - - - | 334 |
| SEQ_ID_NO_1196 | MDPI NSI LNL | G-ACAWGQ | 395 |
| SEQ_ID_NO_1202 | LDPI NSMFNL | GAACAWGQ | 374 |
| SEQ_ID_NO_1194 | - - - - - - - - - - | - - - - - - - - | 273 |
| SEQ_ID_NO_1200 | - - - - - - - - - - | - - - - - - - - | 276 |

Figure 42

| | | | | | | | |
|---|---|---|---|---|---|---|---|
| SEQ_ID_NO_1241 | | MFLVDWFYGV | LASLGLWQKD | AKILFLGLDN | AGKTTLLHML | KDERLVQHQP | 50 |
| SEQ_ID_NO_1229 | | MFVLDWFYGV | LASLGLWQKE | AKILFLGLDN | AGKTTLLHML | KDERLVQHQP | 50 |
| SEQ_ID_NO_1249 | | MFLWDWFYGV | LASLGLWQKE | AKILFLGLDN | AGKTTLLHML | KDERLVQHQP | 50 |
| SEQ_ID_NO_1264 | --- | MGIVFTR | LFSSVFGNRE | ARILVLGLDN | AGKTTILYRL | QMGEVVSTIP | 47 |
| SEQ_ID_NO_1251 | --- | MGIVFTR | LFSSVFGNRE | ARILVLGLDN | AGKTTILYRL | QMGEVVSTIP | 47 |
| SEQ_ID_NO_1265 | --- | MGIVFTR | LFSSVFGNRE | ARILVLGLDN | AGKTTILYRL | QMGEVVSTIP | 47 |
| SEQ_ID_NO_1253 | --- | MGIVFTK | LFSSVFGNKE | ARILVLGLDN | AGKTTILYRL | QMGEVVSTIP | 47 |
| SEQ_ID_NO_1210 | --- | MGILFTR | MFSSVFGNKE | ARILVLGLDN | AGKTTILYRL | QMGEVVSTIP | 47 |
| SEQ_ID_NO_1267 | --- | MGILFTR | MFSSVFGNKE | ARILVLGLDN | AGKTTILYRL | QMGEVVSTIP | 47 |
| SEQ_ID_NO_1213 | --- | MGILFTK | MFSNLFGNRE | ARILVLGLDN | AGKTTILYRL | QMGEVVSTIP | 47 |
| SEQ_ID_NO_1218 | --- | MGILFSK | MFSSVFGNKE | ARILVLGLDN | AGKTTILYRL | QMGEVVSTIP | 47 |
| SEQ_ID_NO_1232 | --- | MGLVFTK | LFSSLFGNKE | ARILVLGLDN | AGKTTILYRL | QMGEVVSTIP | 47 |
| SEQ_ID_NO_1234 | --- | MGLVFTR | LFSSVFGNKE | ARILVLGLDN | AGKTTILYRL | QMGEVVSTIP | 47 |
| SEQ_ID_NO_1272 | --- | MGLSFTK | LFSRLFAKKE | MRILMVGLDA | AGKTTILYKL | KLGEIVTTIP | 47 |
| SEQ_ID_NO_1268 | --- | MGITFAK | LFQRLFSKKE | MRILMVGLDA | AGKTTILYKL | KLGEIVTTIP | 47 |
| SEQ_ID_NO_1211 | --- | MGLRFTK | ALSRLFSKKE | MRILMVGLDA | AGKTTILYKL | KLGEIVTTIP | 47 |
| SEQ_ID_NO_1216 | --- | MGLSFTK | LLGRLFSEKE | MRILMVGLDA | AGKTTILYKL | KLGEIVTTIP | 47 |
| SEQ_ID_NO_1269 | --- | MGLSFTK | LLGRLFSKKE | MRILMVGLDA | AGKTTILYKL | KLGEIVTTIP | 47 |
| SEQ_ID_NO_1239 | --- | MGLSFTK | LFSRLFAKKE | MRILMVGLDA | AGKTTILYQL | KLGEIVTTIP | 47 |
| SEQ_ID_NO_1259 | --- | MGLTFTK | LFSRLFAKKE | MRILMVGLDA | AGKTTILYKL | KLGEIVTTIP | 47 |
| SEQ_ID_NO_1233 | --- | MGLTFTK | LFSRLFAKKE | MRILMVGLDA | AGKTTILYKL | KLGEIVTTIP | 47 |
| SEQ_ID_NO_1235 | --- | MGLSFTK | LFSRLFAKKE | MRILMVGLDA | AGKTTILYKL | KLGEIVTTIP | 47 |
| SEQ_ID_NO_1243 | --- | MGLSFTK | LFSRLFAKKE | MRILMVGLDA | AGKTTILYKL | KLGEIVTTIP | 47 |
| SEQ_ID_NO_1270 | --- | MGLSFTK | LFSRLFAKKE | MRILMVGLDA | AGKTTILYKL | KLGEIVTTIP | 47 |
| SEQ_ID_NO_1242 | --- | MGLSFGK | LFSRLFAKKE | MRILMVGLDA | AGKTTILYKL | KLGEIVTTIP | 47 |
| SEQ_ID_NO_1238 | --- | MGLSFTK | LFSRLFAKKE | MRILMVGLDA | AGKTTILYKL | KLGEIVTTIP | 47 |
| SEQ_ID_NO_1236 | --- | MGLSFTK | LFSRLFAKKE | MRILMVGLDA | AGKTTILYKL | KLGEIVTTIP | 47 |
| SEQ_ID_NO_1240 | --- | MGLSFGK | LFSRLFAKKE | MRILMVGLDA | AGKTTILYKL | KLGEIVTTIP | 47 |

Figure 42 (continued)

| SEQ_ID | Sequence | Length |
|---|---|---|
| SEQ_ID_NO_1241 | T--------- -----QYPT SEELSI GNIK FKAFDLGGHQ IARRVWRDYY | 85 |
| SEQ_ID_NO_1229 | T--------- -----QHPT SEELSI GKIK FKAFDLGGHQ IARRVWKDYY | 85 |
| SEQ_ID_NO_1249 | T--------- -----QHPT SEELSI GKIK FKAFDLGGHQ IARRVWKDYY | 85 |
| SEQ_ID_NO_1264 | SGFPAPDSLI FFLPFA GFN VETVQYNNIK FQVWDLGGQT SI RPYWRCYF | 97 |
| SEQ_ID_NO_1251 | T--------- ------I GFN VETVQYNNIK FQVWDLGGQT SI RPYWRCYF | 82 |
| SEQ_ID_NO_1265 | T--------- ------I GFN VETVQYNNIK FQVWDLGGQT SI RPYWRCYF | 82 |
| SEQ_ID_NO_1253 | T--------- ------I GFN VETVQYNNIK FQVWDLGGQT SI RPYWRCYF | 82 |
| SEQ_ID_NO_1210 | T--------- ------I GFN VETVQYNNIK FQVWDLGGQT SI RPYWRCYF | 82 |
| SEQ_ID_NO_1267 | T--------- ------I GFN VETVQYNNIK FQVWDLGGQT SI RPYWRCYF | 82 |
| SEQ_ID_NO_1213 | T--------- ------I GFN VETVQYNNIK FQVWDLGGQT SI RPYWRCYF | 82 |
| SEQ_ID_NO_1218 | T--------- ------I GFN VETVQYNNIK FQVWDLGGQT SI RPYWRCYF | 82 |
| SEQ_ID_NO_1232 | T--------- ------I GFN VETVQYNNIK FQVWDLGGQT SI RPYWRCYF | 82 |
| SEQ_ID_NO_1234 | T--------- ------I GFN VETVQYNNIK FQVWDLGGQT SI RPYWRCYF | 82 |
| SEQ_ID_NO_1272 | T--------- ------I GFN VETVEYKNI S FTVWDVGGQD KI RPLWRHYF | 82 |
| SEQ_ID_NO_1268 | T--------- ------I GFN VETVEYKNI S FTVWDVGGQD KI RPLWRHYF | 82 |
| SEQ_ID_NO_1211 | T--------- ------I GFN VETVEYKNI S FTVWDVGGQD KI RPLWRHYF | 82 |
| SEQ_ID_NO_1216 | T--------- ------I GFN VETVEYKNI S FTVWDVGGQD KI RPLWRHYF | 82 |
| SEQ_ID_NO_1269 | T--------- ------I GFN VETVEYKNI S FTVWDVGGQD KI RPLWRHYF | 82 |
| SEQ_ID_NO_1239 | T--------- ------I GFN VETVEYQY S FTVWDVGGQD KI RPLWRHYF | 82 |
| SEQ_ID_NO_1259 | T--------- ------I GFN VETVEYKNI S FTVWDVGGQD KI RPLWRHYF | 82 |
| SEQ_ID_NO_1233 | T--------- ------I GFN VETVEYKNI S FTVWDVGGQD KI RPLWRHYF | 82 |
| SEQ_ID_NO_1235 | T--------- ------I GFN VETVEYKNI S FTVWDVGGQD KI RPLWRHYF | 82 |
| SEQ_ID_NO_1243 | T--------- ------I GFN VETVEYKNI S FTVWDVGGQD KI RPLWRHYF | 82 |
| SEQ_ID_NO_1270 | T--------- ------I GFN VETVEYKNI S FTVWDVGGQD KI RPLWRHYF | 82 |
| SEQ_ID_NO_1242 | T--------- ------I GFN VETVEYKNI S FTVWDVGGQD KI RPLWRHYF | 82 |
| SEQ_ID_NO_1238 | T--------- ------I GFN VETVEYKNI S FTVWDVGGQD KI RPLWRHYF | 82 |
| SEQ_ID_NO_1236 | T--------- ------I GFN VETVEYKNI S FTVWDVGGQD KI RPLWRHYF | 82 |
| SEQ_ID_NO_1240 | T--------- ------I GFN VETVEYKNI S FTVWDVGGQD KI RPLWRHYF | 82 |

Figure 42 (continued)

| | | | | | | | |
|---|---|---|---|---|---|---|---|
| SEQ_ID_NO_1241 | AKVDAVVYLV | DANDRERFPE | AKKELDGLLS | DESLTNVPFL | LGNKI DI PY | 135 |
| SEQ_ID_NO_1229 | AKVDAVVYLV | DAYDKERFAE | SKKELDALLS | DESLATVPFL | LGNKI DI PY | 135 |
| SEQ_ID_NO_1249 | AKVDAVVYLV | DAYDKERFAE | SKKELDALLS | DDSLANVPFL | LGNKI DI PY | 135 |
| SEQ_ID_NO_1264 | PNTQAI YVV | DSSDTDRLVT | AKEEFHAI LE | EDELKGAVVL | VYANKQDLPG | 147 |
| SEQ_ID_NO_1251 | PNTQAI YVV | DSSDTDRLVT | AKEEFHSI LE | EDELKGAVVL | VYANKQDLPG | 132 |
| SEQ_ID_NO_1265 | PNTQAI YVV | DSSDTDRLVT | AKEEFHAI LE | EDELKGAVVL | VYANKQDLPG | 132 |
| SEQ_ID_NO_1253 | PNTQAVI YVV | DSSDTDRI GV | AKEEFHAI LE | EEELKGAMVL | I FANKQDLPG | 132 |
| SEQ_ID_NO_1210 | PNTQAVI YVV | DSSDTDRI GV | AKEEFHAI LE | EDELKGAVVL | FANKQDLPG | 132 |
| SEQ_ID_NO_1267 | PNTQAVI YVV | DSSDTDRI GV | AKEEFHAI LE | EEELKGAVVL | FANKQDLPG | 132 |
| SEQ_ID_NO_1213 | PNTQAI YVV | DSSDTDRLV | AKEEFHAI LE | EEELRGAAVL | FANKQDLPG | 132 |
| SEQ_ID_NO_1218 | PNTQAI YVV | DSSDVDRLV | AKDEFHAI LE | EEELRGAI VL | FANKQDLPG | 132 |
| SEQ_ID_NO_1232 | PNTQAI YVV | DSSDVDRLV | AKEEFHAI LE | EEELKGAVVL | FANKQDLPG | 132 |
| SEQ_ID_NO_1234 | PNTQAI YVV | DSSDTDRLV | AREEFHAI LE | EEELKGAVVL | FANKQDLPG | 132 |
| SEQ_ID_NO_1272 | QNTQGLI FVV | DSNDRDRVVE | ARDELHRMLN | EDELRDAVLL | VFANKQDLPN | 132 |
| SEQ_ID_NO_1268 | QNTQGLI FVV | DSNDRDRVSE | ARDELHRMLN | EDELRDAVLL | VFANKQDLPN | 132 |
| SEQ_ID_NO_1211 | QNTQGLI FVV | DSNDRERVVE | ARDELHRMLN | EDELRDAVLL | VFANKQDLPN | 132 |
| SEQ_ID_NO_1216 | QNTQGLI FVV | DSNDRDRVGE | AREELHRMLN | EDELRDAVLL | VFANKQDLPN | 132 |
| SEQ_ID_NO_1269 | QNTQGLI FVV | DSNDRDRVGE | ARDELHRMLN | EDELRDAVLL | VFANKQDLPN | 132 |
| SEQ_ID_NO_1239 | QNTQGLI FVV | DSNDRDRVVE | ARDELHRMLN | EDELRDAVLL | VFANKQDLPN | 132 |
| SEQ_ID_NO_1259 | QNTQGLI FVV | DSNDRDRI VE | AKDELHRMLN | EDELRDAVLL | VFANKQDLPN | 132 |
| SEQ_ID_NO_1233 | QNTQGLI FVV | DSNDRDRVVE | ARDELHRMLN | EDELRDAVLL | VFANKQDLPN | 132 |
| SEQ_ID_NO_1235 | QNTQGLI FVV | DSNDRDRVVE | ARDELHRMLN | EDELRDAVLL | VFANKQDLPN | 132 |
| SEQ_ID_NO_1243 | QNTQGLI FVV | DSNDRDRVVE | ARDELHRMLN | EDELREAVLL | VFANKQDLPN | 132 |
| SEQ_ID_NO_1270 | QNTQGLI FVV | DSNDRDRVVE | ARDELHRMLN | EDELRDAVLL | VFANKQDLPN | 132 |
| SEQ_ID_NO_1242 | QNTQGLI FVV | DSNDRDRVVE | ARDELHRMLN | EDELREAVLL | VFANKQDLPN | 132 |
| SEQ_ID_NO_1238 | QNTQGLI FVV | DSNDRDRVVE | AKDELHRMLN | GDELRDAVLL | VFANKQDLPN | 132 |
| SEQ_ID_NO_1236 | QNTQGLI FVV | DSNDRDRVVE | ARDELHRMLN | EDELRDAVLL | VFANKQDLPN | 132 |
| SEQ_ID_NO_1240 | QNTQGLI FVV | DSNDRDRVVE | ARDELHRMLN | EDELRDAVLL | VFANKQDLPN | 132 |

Figure 42 (continued)

| | | | | | | | |
|---|---|---|---|---|---|---|---|
| SEQ_ID_NO_1241 | AASEDELRYH | LGLTGVTTGK | GNINLAGTNV | RP--IEVFMC | SIVRK--MGY | | 181 |
| SEQ_ID_NO_1229 | AASEDELRYH | LGLSNFTTGK | GKVDLVGSNV | RP--LEVFMC | SIVRK--MGY | | 181 |
| SEQ_ID_NO_1249 | AASEEELRYH | LGLSSFTTGK | GKVSLCDSNV | RP--LEVFMC | SVVRK--MGY | | 181 |
| SEQ_ID_NO_1264 | ALDDAAITES | LELHKIKS-- | ---------- | RQ--WAFKT | SAIKG--EGL | | 181 |
| SEQ_ID_NO_1251 | ALDDAAITES | LELHKIKS-- | ---------- | RQ--WAFKT | SAIKG--EGL | | 166 |
| SEQ_ID_NO_1265 | ALDDAAITES | LELHKIKS-- | ---------- | RQ--WAFKT | SAIKG--EGL | | 166 |
| SEQ_ID_NO_1253 | ALDDAAVTEA | LELHKIKS-- | ---------- | RQ--WAFKT | CAVKG--EGL | | 166 |
| SEQ_ID_NO_1210 | ALDDAAVTEA | LELHKIKS-- | ---------- | RQ--WAFKT | CAVKG--EGL | | 166 |
| SEQ_ID_NO_1267 | ALDDAAVTEA | LELHKIKS-- | ---------- | RQ--WAFKT | CAVKG--EGL | | 166 |
| SEQ_ID_NO_1213 | ALDDAAVTES | LELHKIKN-- | ---------- | RQ--WAFKT | SAIKG--EGL | | 166 |
| SEQ_ID_NO_1218 | ALDDAAVTEA | LELHKIKN-- | ---------- | RQ--WAFKT | SAIKG--EGL | | 166 |
| SEQ_ID_NO_1232 | ALDDAAVTEA | LELHKIKN-- | ---------- | RQ--WAFKT | SAIKG--EGL | | 166 |
| SEQ_ID_NO_1234 | ALDDAAVTES | LELHKIKN-- | ---------- | RQ--WAFKT | SAIKG--EGL | | 166 |
| SEQ_ID_NO_1272 | AMNAAEITDK | LGLHSLRQ- | ---------- | RPNLWGLNS | PKEVPLVANL | | 170 |
| SEQ_ID_NO_1268 | AMSAAEITDK | LGLHSLRQ- | ---------- | RH--WFIQST | CATSG--EGL | | 166 |
| SEQ_ID_NO_1211 | AMNAAEITDK | LGLHSLRQ- | ---------- | RH--WYIQST | CATSG--EGL | | 166 |
| SEQ_ID_NO_1216 | AMNAAEITDK | LGLHSLRQ- | ---------- | RH--WYIQST | CATSG--EGL | | 166 |
| SEQ_ID_NO_1269 | AMNAAEITDK | LGLHSLRQ- | ---------- | RH--WYIQST | CATSG--EGL | | 166 |
| SEQ_ID_NO_1239 | AMNAAEITDK | HGLHSLRQ- | ---------- | RH--WYIQST | CATSG--EGL | | 166 |
| SEQ_ID_NO_1259 | AMNAAEITDK | LGLHSLRQ- | ---------- | RH--WYIQST | CATSG--EGL | | 166 |
| SEQ_ID_NO_1233 | AMNAAEITDK | LGLHSLRQ- | ---------- | RH--WYIQST | CATSG--EGL | | 166 |
| SEQ_ID_NO_1235 | AMNAAEITDK | LGLHSLRQ- | ---------- | RH--WYIQST | CATSG--EGL | | 166 |
| SEQ_ID_NO_1243 | AMNAAEITDK | LGLHSLRQ- | ---------- | RH--WYIQST | CATSG--EGL | | 166 |
| SEQ_ID_NO_1270 | AMNAAEITDK | LGLHSLRQ- | ---------- | RH--WYIQST | CATSG--EGL | | 166 |
| SEQ_ID_NO_1242 | AMNAAEITDK | LGLHSLRQ- | ---------- | RH--WYIQST | CATSG--EGL | | 166 |
| SEQ_ID_NO_1238 | AMNAAEITDK | LGLHSLRQ- | ---------- | RH--WYIQST | CATSG--EGL | | 166 |
| SEQ_ID_NO_1236 | AMNAAEITDK | LGLHSLRQ- | ---------- | RH--WYIQST | CATSG--EGL | | 166 |
| SEQ_ID_NO_1240 | AMNAAEITDK | LGLHSLRQ- | ---------- | RH--WYIQST | CATSG--EGL | | 166 |

Figure 42 (continued)

| SEQ ID | Sequence | # |
|---|---|---|
| SEQ_ID_NO_1241 | GEGFK---- ........... ........... ......WMSQY K-------- | 193 |
| SEQ_ID_NO_1229 | GEGFK---- ........... ........... ......WLSQY K-------- | 193 |
| SEQ_ID_NO_1249 | GDGFK---- ........... ........... ......WVSQY N-------- | 193 |
| SEQ_ID_NO_1264 | FEGLDCSVLQ HIILQFLPDE CIWEYLMELT YKSLMYLHIE KNRFVENDE | 231 |
| SEQ_ID_NO_1251 | FEGLN---- ........... ........... ......MLSNA KSGGS---- | 182 |
| SEQ_ID_NO_1265 | FEGLD---- ........... ........... ......MLSNA KSKSS---- | 182 |
| SEQ_ID_NO_1253 | FEGLD---- ........... ........... ......MLSNT KSGTG---- | 182 |
| SEQ_ID_NO_1210 | FEGLD---- ........... ........... ......MLSNT KSGSG---- | 182 |
| SEQ_ID_NO_1267 | FEGLD---- ........... ........... ......MLSNT KSGSG---- | 182 |
| SEQ_ID_NO_1213 | FEGLD---- ........... ........... ......MLSNT KSGSG---- | 182 |
| SEQ_ID_NO_1218 | FEGLD---- ........... ........... ......MLSNT KSGGG---- | 182 |
| SEQ_ID_NO_1232 | FEGLD---- ........... ........... ......MLSNT KSGGG---- | 182 |
| SEQ_ID_NO_1234 | FEGLD---- ........... ........... ......MLSNT KSGGG---- | 182 |
| SEQ_ID_NO_1272 | FLG- ........... ........... ......AKGVL LGGGPKNLG | 188 |
| SEQ_ID_NO_1268 | YEGLD---- ........... ........... ......MLSSN SQRA---- | 181 |
| SEQ_ID_NO_1211 | YEGLD---- ........... ........... ......MLSNN ANKT---- | 181 |
| SEQ_ID_NO_1216 | YEGLD---- ........... ........... ......MLSNN ASKA---- | 181 |
| SEQ_ID_NO_1269 | YEGLD---- ........... ........... ......MLSNN SSKA---- | 181 |
| SEQ_ID_NO_1239 | YEGLD---- ........... ........... ......MLSNN ANKA---- | 181 |
| SEQ_ID_NO_1259 | YEGLD---- ........... ........... ......MLSNN ASKA---- | 181 |
| SEQ_ID_NO_1233 | YEGLD---- ........... ........... ......MLSNN ASKA---- | 181 |
| SEQ_ID_NO_1235 | YEGLE---- ........... ........... ......MLSNN ASKA---- | 181 |
| SEQ_ID_NO_1243 | YEGLD---- ........... ........... ......MLSNN ASKA---- | 181 |
| SEQ_ID_NO_1270 | YEGLD---- ........... ........... ......MLSNN ASKG---- | 181 |
| SEQ_ID_NO_1242 | YEGLD---- ........... ........... ......MLSNN SNKA---- | 181 |
| SEQ_ID_NO_1238 | YEGLD---- ........... ........... ......MLSNN ANKA---- | 181 |
| SEQ_ID_NO_1236 | YEGLD---- ........... ........... ......MLSNN ANKA---- | 181 |
| SEQ_ID_NO_1240 | YEGLD---- ........... ........... ......MLSNN ANKA---- | 181 |

Figure 42 (continued)

| | | |
|---|---|---|
| SEQ_ID_NO_1241 | - - - - - - - - - - - - - | 193 |
| SEQ_ID_NO_1229 | - - - - - - - - - - - - - | 193 |
| SEQ_ID_NO_1249 | - - - - - - - - - - - - - | 193 |
| SEQ_ID_NO_1264 | QTVRTLGHWW LYP | 244 |
| SEQ_ID_NO_1251 | - - - - - - - - - - - - - | 182 |
| SEQ_ID_NO_1265 | - - - - - - - - - - - - - | 182 |
| SEQ_ID_NO_1253 | - - - - - - - - - - - - - | 182 |
| SEQ_ID_NO_1210 | - - - - - - - - - - - - - | 182 |
| SEQ_ID_NO_1267 | - - - - - - - - - - - - - | 182 |
| SEQ_ID_NO_1213 | - - - - - - - - - - - - - | 182 |
| SEQ_ID_NO_1218 | - - - - - - - - - - - - - | 182 |
| SEQ_ID_NO_1232 | - - - - - - - - - - - - - | 182 |
| SEQ_ID_NO_1234 | - - - - - - - - - - - - - | 182 |
| SEQ_ID_NO_1272 | LLSPKPK- - - - - - | 195 |
| SEQ_ID_NO_1268 | - - - - - - - - - - - - - | 181 |
| SEQ_ID_NO_1211 | - - - - - - - - - - - - - | 181 |
| SEQ_ID_NO_1216 | - - - - - - - - - - - - - | 181 |
| SEQ_ID_NO_1269 | - - - - - - - - - - - - - | 181 |
| SEQ_ID_NO_1239 | - - - - - - - - - - - - - | 181 |
| SEQ_ID_NO_1259 | - - - - - - - - - - - - - | 181 |
| SEQ_ID_NO_1233 | - - - - - - - - - - - - - | 181 |
| SEQ_ID_NO_1235 | - - - - - - - - - - - - - | 181 |
| SEQ_ID_NO_1243 | - - - - - - - - - - - - - | 181 |
| SEQ_ID_NO_1270 | - - - - - - - - - - - - - | 181 |
| SEQ_ID_NO_1242 | - - - - - - - - - - - - - | 181 |
| SEQ_ID_NO_1238 | - - - - - - - - - - - - - | 181 |
| SEQ_ID_NO_1236 | - - - - - - - - - - - - - | 181 |
| SEQ_ID_NO_1240 | - - - - - - - - - - - - - | 181 |

Figure 43

| | | | | | | | |
|---|---|---|---|---|---|---|---|
| SEQ_ID_NO_1285 | | | | ----MVGNAF | VEQYYS LHR | DPDQVHRFYH | 26 |
| SEQ_ID_NO_1297 | MAVSDGVQTP | TP------- | ---DVVGNAF | VEQYYS LHQ | DPDQVHKFYH | | 39 |
| SEQ_ID_NO_1284 | MALQ-TATPP | TT-------- | PSAQVVGNAF | VEQYYHI LHH | SPGSVYRFYQ | | 41 |
| SEQ_ID_NO_1300 | MAAP-QPAAP | AP-----EAP | PSAQVVGNAF | VQQYYL VLHQ | SPDLVYRFYQ | | 44 |
| SEQ_ID_NO_1294 | MAAP-Q-ASP | S--------- | PSAQVVGNAF | VQQYYQ LHQ | SPDLVYRFYQ | | 39 |
| SEQ_ID_NO_1295 | MAAP-Q-ASP | S--------- | PSAQVVGNAF | VQQYYQ LHQ | SPDLVYRFYQ | | 39 |
| SEQ_ID_NO_1287 | MAAP-TPPPA | AAPAAAPGPT | PPAQVVGNAF | VQQYYNI LHQ | SPELVFRFYQ | | 49 |
| SEQ_ID_NO_1289 | -MAS-QPPPP | AA-AAASGAP | PPAQVVGNAF | VHQYYNI LHQ | SPELVYRFYQ | | 47 |
| SEQ_ID_NO_1291 | MASP-PPPPP | AG-AAAPGSP | PPAQVVGNAF | VNQYYNI LHQ | SPELVHRFYQ | | 48 |
| SEQ_ID_NO_1274 | MAML GAQQVP | AA-----ACT | PL-DMVGNAF | VPQYYHI LHQ | SPEHVHRFYQ | | 43 |
| SEQ_ID_NO_1276 | MASV-EQQVP | AG-----IAT | PTSDVVGNAF | VHQYYL LHQ | SPELVHRFYH | | 44 |
| SEQ_ID_NO_1280 | MAAP-VTQLP | V--------- | PTADVVGNAF | AHQYYHI LQQ | SPDLVHRFYQ | | 40 |

| | | | | | | |
|---|---|---|---|---|---|---|
| SEQ_ID_NO_1285 | DSSVMSRP-- | -EEDGTMTTV | TTTAEI DKKI | QSLEYTSFRV | EVLSADAQPS | 73 |
| SEQ_ID_NO_1297 | ESSVLSRP-- | -EEDGTMTTV | TTTAEI DKKI | QSFDYTSYRV | EVLSADAQPS | 86 |
| SEQ_ID_NO_1284 | DSSVI SRP-- | -DSSGVMTSV | TTMKG NEKI | LSLNFKEFKA | EI KTADAQKS | 88 |
| SEQ_ID_NO_1300 | DASRLARPAS | AAGAAGMDSV | TTMEAI SEKI | MEMDVS--KA | EI RTVDSQES | 92 |
| SEQ_ID_NO_1294 | DASRLGRP-P | ADRYGDMVSV | TTMEAI NEKI | MAMDMS--RA | EI KTVDSQES | 86 |
| SEQ_ID_NO_1295 | DASRLGRP-P | ADRYGDMVSV | TTMEAI NEKI | MAMDMS--RA | EI KTVDSQES | 86 |
| SEQ_ID_NO_1287 | EASRI GRPAT | TGADL-MDTV | TTMEAI NEKI | MSMDI A--RA | EI RGVDAQES | 95 |
| SEQ_ID_NO_1289 | EASQL GRPAG | TGADG-MDTV | TTMDAI NDKI | VSMGI D--RA | KI KAVDAQES | 94 |
| SEQ_ID_NO_1291 | DASRLGRPAG | AGADG-MDTV | TTMDAI SDKI | VSMGI T--RA | EI KAVDAQES | 95 |
| SEQ_ID_NO_1274 | EI SKLGRP-- | -EENGLMSI T | STLQAI DKKI | MALGYGVI SA | EI RTVDTQES | 90 |
| SEQ_ID_NO_1276 | DSSKLGRP-- | -EENGGMSI T | TTMQAI NEKI | LSLGYGEFTA | EI TTVDAQDS | 91 |
| SEQ_ID_NO_1280 | DGSKFGRP-- | -GEDGVMSTT | TTMNAI NEKI | LSLGYGQVRA | EI VTVDSQES | 87 |

| | | | | | | |
|---|---|---|---|---|---|---|
| SEQ_ID_NO_1285 | YNNGVMVVVT | GQLTGTDNI K | RKFAQSFFLA | PQDKGFYVLN | DVFRYVDAY- | 122 |
| SEQ_ID_NO_1297 | YNSGVVVVVT | GQLTGTDNVK | RKFAQSFFLA | PODKGFYVLN | DVFRYVDAY- | 135 |
| SEQ_ID_NO_1284 | YKEGVTVLVT | GQLTGKDNLR | RKFAQSFFLA | PODNGYFVLN | DVFRYYEDH- | 137 |
| SEQ_ID_NO_1300 | LGGGVTVLVT | GHLTGRDSVR | REFSQSFFLA | PQEKGYFVLN | DI FRFYGDL- | 141 |
| SEQ_ID_NO_1294 | LGGGVTVLVT | GHLTVRDGVC | REFSQSFFLA | PQEKGYFVLN | DMFRYVGDG- | 135 |
| SEQ_ID_NO_1295 | LGGGVTVLVT | GHLTVRDGVC | REFSQSFFLA | PQEKGYFVLN | DMFRYVGDG- | 135 |
| SEQ_ID_NO_1287 | LCGGVTVLVT | GHLTGKDDVC | REFAQSFFLA | PQEKGYFVLN | DI LRYVGQG- | 144 |
| SEQ_ID_NO_1289 | LCGGVSVLVM | GHLTGRNSVS | RQFVQSFFLA | PQEKGYFVLN | DI LRYVGEG- | 143 |
| SEQ_ID_NO_1291 | LGGGVTVLVM | GHLTGRTSVG | REFVQSFFLA | PQEKGYFVLN | DI LRYVGDGX | 145 |
| SEQ_ID_NO_1274 | HGGGYI VLVT | GYLTGKDSVR | RTFSQTFFLA | POETGYFVLN | DMFRFI DEG- | 139 |
| SEQ_ID_NO_1276 | HNGGVLVLVT | GYLTGKDKVK | RKFTQSFFLA | PQDKGYFVLN | DVFRFVDDT- | 140 |
| SEQ_ID_NO_1280 | YKGGVLVLVT | GYLNGNDNLR | QKFI QSFFLA | PODKGYFVLN | DVFRYYDDS- | 136 |

Figure 43 (continued)

```
SEQ_ID_NO_1285    ........KS IDIESVPAND ADESAPSEA  TPEPEPVHV PEVIPPTQTV   164
SEQ_ID_NO_1297    .........K SVDIETVPAN DADESAPSEA FTPDPEPIHV A.......ED   169
SEQ_ID_NO_1284    ........EP SELPPVTGDG DSAAVTVTPE LEPSHVAD.. ........SC   169
SEQ_ID_NO_1300    ........PA PTAVEAQPEA DAVVPPVAAP LANGTATPAV EPAIPDDHDA   183
SEQ_ID_NO_1294    .......PTP AAAAAAAVEV QPEADAVAPP LANGTATAPL QPAAPDY-DG   177
SEQ_ID_NO_1295    ..........P TPAAAAAAEV QPEADAVAPP LANGTATAPL QPAAPDY-DA   175
SEQ_ID_NO_1287    ..EADPSLPP PQQQPPAPEL DAVVAP-AAA LANGTVAP-- VETVPREQEA   189
SEQ_ID_NO_1289    ....GGDEGA EKOPAPEVAA DAEKTTSAPI LANGTVGGDA TTVPQ---DA   186
SEQ_ID_NO_1291    GEEGAGHPPP PPQQPVQETV TGAEAVPAPI LANGTVGG-D NETLPCEQDA   194
SEQ_ID_NO_1274    .......... ....TVVHGN QIPVNNVQAP VNTYQDTAAA KEIPDDFVQE   175
SEQ_ID_NO_1276    .......... ....KHQPGG QDPVNGFEAS LTHEQGHS-- ..........   164
SEQ_ID_NO_1280    .......... ....THQNGN QEPASNFEAP VAPDQDTP-- ..........   160

SEQ_ID_NO_1285    IPTAQTVPP TQTVIADTET IISKEVSLPL ENGKLSVT-- ..........   202
SEQ_ID_NO_1297    IPTIQPV AD TDTNISK-- ----EVSLPL ENGKLSVT-- ..........   200
SEQ_ID_NO_1284    APEPTNSHVN KGQTVAEL-- ----NAVELS NNHERQIPV- ..........   201
SEQ_ID_NO_1300    VPQQENHVVD RSPPQPEEED EA--EVYNPP PEEVV----- ..........   216
SEQ_ID_NO_1294    MPQEEPDVVE HAAVPPEEEE ----EVYNPP LEEVEGGAV- ..........   212
SEQ_ID_NO_1295    MPHEEPDVVE NVAVPPEEEE ----EVYNPP LEEVEGGAV- ..........   210
SEQ_ID_NO_1287    SPQPELDLSE SVPHTNEEED PKE-EVYNPP NDVEVPV--- ..........   225
SEQ_ID_NO_1289    SPQPECQVAE PALNPKEEVL NG--EVCNBL SDVEKPV--- ..........   221
SEQ_ID_NO_1291    SPQPEQPAAE SAPPTPEEED LYGEEVYNPP NDMEKPV--- ..........   231
SEQ_ID_NO_1274    KYVQENHAVK QTEVLSKSTN EPE-KVFTPS EDEQVSA--- ..........   211
SEQ_ID_NO_1276    -PVPENHIEQ PAA-LPEECN GP--EVYNSS ENGDGS E-- ..........   198
SEQ_ID_NO_1280    -HTQETHISE PTAALSEEVI GG--EVYNPS ESGDVSVEVE EEESGDVSFE   207

SEQ_ID_NO_1285    ENVIPVNHVK ESSHHVKEPE QPTS EKVAS NTQEDTPKKS FASIVNALKD   252
SEQ_ID_NO_1297    ENVIPVNHVK ESSHQEQMAS IEKV----PS NTQEDTPKKS FASIVSAYKD   246
SEQ_ID_NO_1284    ENFGNVESHF QSNGNDDSQA TELA----S SAQDDAPKKS YASIVKVQKG   246
SEQ_ID_NO_1300    DEEQPVPEVI NEVPNNVAPV AATT--VAP VLQEEAPKKS YASIVKVMKE   263
SEQ_ID_NO_1294    EEEQSVPEVI NEVPNNVVPV VAPA--AAP VSHEEAPKKS YASIVKVMKE   259
SEQ_ID_NO_1295    EEEQSVPEVI NEVPNNVVPV VAPA--DAP VSHEEAPKKS YASIVKVMKE   257
SEQ_ID_NO_1287    VEETLVPEVI DEVPNNVAAS IPVS--APP VPHEEAPKKS YASIVKVMKA   272
SEQ_ID_NO_1289    AEETPVPDVI NEVPNNVAVA PPIS--SPP VPLKEAPKKS YASIVKVMKE   268
SEQ_ID_NO_1291    VDETPVAEVI NEVPNNVAVA APSS--SPS LPIEEAPKKS YASIVKVMKE   278
SEQ_ID_NO_1274    AEEVLVTEIV NEAPIEVQKV GESD------ SRTGEPKRS YASIVKVMKE   255
SEQ_ID_NO_1276    EEESPVAEVV DEIPDDSKMV SDSK------ PEMEELPKKS YASILKVLKE   242
SEQ_ID_NO_1280    EEEEPMPEVV DEIPPDSQLV ADSDVVVESS AKIEDTPKKS YASVVKVQKE   257
```

Figure 43 (continued)

| | | | | | | | | |
|---|---|---|---|---|---|---|---|---|
| SEQ_ID_NO_1285 | NSAPFHL--- | -RASPAKPAV | HPP- | -RVHSV | PAPEAPTPNM | D-PLEKNN- | - | 294 |
| SEQ_ID_NO_1297 | NSAPFLS--- | -RTSPAKPAV | QPP- | -RVHSV | PAPEAPAPNM | D-PSEKNN- | - | 288 |
| SEQ_ID_NO_1284 | SSVPTKVYV- | -PTNTLKSGP | NKT- | -ESKVV | ES-VESTEVP | EAALESVSNP | | 291 |
| SEQ_ID_NO_1300 | VPLPA----- | -PAPPTRPAP | PKP- | -EKQS- | -PLPAPTPVT | DVPPFSSN- | P | 301 |
| SEQ_ID_NO_1294 | APVPAPIPAT | RPAPAARPAP | PKP- | -EKQSP | APLPAPAPVA | DATPFSSN- | A | 305 |
| SEQ_ID_NO_1295 | APVPAPIPAT | RPAPAARPAP | PKP- | -EKQSP | APLPAPAPVA | DATPFSSN- | A | 303 |
| SEQ_ID_NO_1287 | VLPPN----- | -STVPYRPAP | PKP- | -EKQA- | -PAPAQSVAV | DAPTFSPN- | P | 311 |
| SEQ_ID_NO_1289 | HRPLA----- | -PAVPSRPAP | PLT- | -EKQA- | -S-PAPTPVT | EAPAFSPN- | P | 306 |
| SEQ_ID_NO_1291 | YPPPA----- | -PAVPSRPAP | PKP- | -EKQA- | -PLPAPSLVA | DAPAFSPN- | T | 316 |
| SEQ_ID_NO_1274 | NAAPMSA--- | -SRTPTKVEP | KKD- | -EDDAV | HI-PLPTPLS | EKSDSGANVA | | 296 |
| SEQ_ID_NO_1276 | NAVPVSAP-- | -TQSPVKSAV | KSQGHPRI | AA | PPL-SAPMPAS | DADVSSNNVT | | 288 |
| SEQ_ID_NO_1280 | YTAPFSSP-- | -TPSPLRSAP | KIQ- | -EQVTA | AV-SQPLPAA | ESHVSSSNTF | | 300 |

| | | | | | | | |
|---|---|---|---|---|---|---|---|
| SEQ_ID_NO_1285 | ENAGR---- | --AHAIFVAN | LPMSATVEQL | DRAFKKFGPI | KRDGIQVRSN | | 337 |
| SEQ_ID_NO_1297 | ENGGR---- | --AHAIFVAN | LPMTATVEQL | DRVFKKFGTI | KRDGIQVRSN | | 331 |
| SEQ_ID_NO_1284 | ESSDAHELEV | EL-GHSIYIRN | LPLNVTVADL | ELFFKKFGPI | KPGGIQVRNN | | 339 |
| SEQ_ID_NO_1300 | DNSNIQEPEV | DL-AHAIYVRN | LPLNATETQL | EDEFKKFGTI | KQNGIQVRSN | | 350 |
| SEQ_ID_NO_1294 | ESSNTHEPEV | DL-AHAIYVRS | LPLNATITQL | EDEFKKFGTI | KPDGIQVRSH | | 354 |
| SEQ_ID_NO_1295 | ESSNTHEPEV | DL-AHAIYVRS | LPLNATITQL | EDEFKKFGTI | KPDGIQVRSH | | 352 |
| SEQ_ID_NO_1287 | ESSNIQDQEV | DL-ALAVYVKN | LPLHATPSQL | EEEFKRFGTI | KHDGIQVRSH | | 360 |
| SEQ_ID_NO_1289 | QSGGFQDPEV | DL-AHAIYVRS | LPLNATPQDL | EEEFKRFGTI | KHEGIQVRSN | | 355 |
| SEQ_ID_NO_1291 | QGGSFQDPEV | DL-AHAIYVRN | LPLNATPQDL | EEEFKRFGTI | KHEGIQVRSN | | 365 |
| SEQ_ID_NO_1274 | VNENNQENER | ALGPSIYLKG | LPLDATPALL | ENEFQKFGLI | RTNGIQVRSQ | | 348 |
| SEQ_ID_NO_1276 | ENGNNQDAEA | EL-GPSIYVKG | LPLNATPSML | EVEFKKFGPI | KSGGIQVRSQ | | 337 |
| SEQ_ID_NO_1280 | ENGNAQEBEL | EL-GPSIYVKG | LPLDATITLL | ENEFKKFGPI | RNGGVQVRFQ | | 348 |

| | | | | | | | |
|---|---|---|---|---|---|---|---|
| SEQ_ID_NO_1285 | KL-GSCFGFV | EFESAASMQS | ALEASPPVML | DNRRLSIEER | RGR------ | | 378 |
| SEQ_ID_NO_1297 | KL-GSCFGFV | EFESAASLQS | ALEASPPVML | DNRRLSIEER | RGR------ | | 372 |
| SEQ_ID_NO_1284 | KQQGYCFGFV | EFLSLNSMNS | AIQASLPVPI | GGRQAVVELK | RTTTRVGSGI | | 388 |
| SEQ_ID_NO_1300 | KIQGFCYGFV | EFEDSTSVQS | AIEASLPVTI | GGRQCYVEEK | RTP---GSR- | | 395 |
| SEQ_ID_NO_1294 | KIQGFCYGFV | EFEEATAVQS | AIEASLPVMI | GGRQCFVEEK | RTP---GSR- | | 399 |
| SEQ_ID_NO_1295 | KIQGFCYGFV | EFEEATAVQS | AIEASLPVMI | GGRQCFVEEK | RTP---GSR- | | 397 |
| SEQ_ID_NO_1287 | KIQGFCYGFI | EFEDASSVQS | ALAASLPVTI | DDRPCHVEEK | RTP---GS- | | 404 |
| SEQ_ID_NO_1289 | KIQGFCYGFV | EFEDASAVQA | AIEASLPVTI | GERQCFVEEK | RTT---GSRG | | 401 |
| SEQ_ID_NO_1291 | KIQGFCYGFV | EFEDANAVQT | AIEASLPVMI | SERQCYVEEK | RTT---GSR- | | 410 |
| SEQ_ID_NO_1274 | KL-GFCFGFV | EFESASSMQS | AIEASLPVML | NGHKVVEEK | RST---A--- | | 389 |
| SEQ_ID_NO_1276 | KL-GFCFGFV | EFEMASSVQS | AIEASLPIN | GGRKAVVEEK | RST---S--- | | 378 |
| SEQ_ID_NO_1280 | KL-GFCFGFV | EFEVASAVQS | ALELIYLFLF | T--------- | ---------- | | 377 |

Figure 43 (continued)

| | | | | | | | |
|---|---|---|---|---|---|---|---|
| SEQ_ID_NO_1285 | SGYR----- | ----NDRND | NFRGRGNFGG | GRGGGFNGRN | DF-ERRGGEF | | 416 |
| SEQ_ID_NO_1297 | GGYR----- | ----NDRND | NFRGRGNFGG | GRGGGFNGRN | DF-DRRG-EF | | 409 |
| SEQ_ID_NO_1284 | NGTGRPR-PS | GRG-GLRND | SFRGRGNYVG | GR-G--YGRN | DY-VSRG-GF | | 431 |
| SEQ_ID_NO_1300 | GSSRGGRFAP | GRGN-NFRSE | GTRGRGNYGG | GR-G--YGRG | EF-SYRS-DY | | 439 |
| SEQ_ID_NO_1294 | GSSRGGRFAP | GRGNNNFRAD | GMRGRGNYGG | GR-S--YGRG | DF-SYRS-DY | | 444 |
| SEQ_ID_NO_1295 | GSSRGGRFAP | GRGNNNFRAD | GMRGRGNYGG | GR-S--YGRG | DF-SYRS-DY | | 442 |
| SEQ_ID_NO_1287 | RGSSRGRFPP | GRGG-NFRGE | GMRGRGSYTG | GR-G--YGRG | EYNNYRS-DF | | 449 |
| SEQ_ID_NO_1289 | GGSRGGRFPP | GRGG-NFRGE | GIRGRGTYNG | GR-G--YGRG | EF-SYRS-DY | | 445 |
| SEQ_ID_NO_1291 | GSNRGGRFAP | GRGG-NFRGE | GLRGRGTYNG | GR-G--YGRG | EF-SYRS-DY | | 454 |
| SEQ_ID_NO_1274 | RGNYRGRSTF | GVNT-GYRNE | GGRGRGSFGG | GRGG--YGRT | DFNGYGN-- | | 433 |
| SEQ_ID_NO_1276 | RGN-KGKSSS | VSGA-GYRNE | GARGRGNYGG | GR-G--YSRG | EF------- | | 415 |
| SEQ_ID_NO_1280 | TGNNRGRFPS | GSGA-GYKSE | GMRGRGNL-G | GK-V--YGR- | EF-GIRT-EF | | 420 |

| | | | | | | | |
|---|---|---|---|---|---|---|---|
| SEQ_ID_NO_1285 | SGRSRGG-QN | AGR------- | ---------- | ---------- | ---------- | ·S | 429 |
| SEQ_ID_NO_1297 | SGRPRGG-NN | TGR------- | ---------- | ---------- | ---------- | ·S | 422 |
| SEQ_ID_NO_1284 | SGRGRGH--- | ---------- | ---------- | ---------- | ---------- | | 438 |
| SEQ_ID_NO_1300 | GGRSGGR-GG | PAR------- | ---------- | ---------- | ---------- | ·G | 452 |
| SEQ_ID_NO_1294 | GGRGGGR-GG | SAR------- | ---------- | ---------- | ---------- | ·G | 457 |
| SEQ_ID_NO_1295 | GGRGGGR-GG | SAR------- | ---------- | ---------- | ---------- | ·G | 455 |
| SEQ_ID_NO_1287 | GGRGGGR-GG | SGR------- | ---------- | ---------- | ---------- | ·G | 462 |
| SEQ_ID_NO_1289 | GGRGGGR-GG | SLH------- | ---------- | ---------- | ---------- | ·G | 458 |
| SEQ_ID_NO_1291 | GGRGGGR-GG | SSR------- | ---------- | ---------- | ---------- | ·G | 467 |
| SEQ_ID_NO_1274 | -NRGNNR-GG | YANRAN---- | ---------- | ---------- | ---------- | ·G | 448 |
| SEQ_ID_NO_1276 | GNRSSNR-GG | YSS------- | ---------- | ---------- | ---------- | ·R | 428 |
| SEQ_ID_NO_1280 | GNRGGSRGGG | YSNRGGDGYS | NRGGGGGGGG | DGYSNRGGGG | GGDGYSNRGG | | 470 |

| | | | | | | |
|---|---|---|---|---|---|---|
| SEQ_ID_NO_1285 | NGDAVPRSYQ | NG--GGKVAA | RQPPVKVQ-- | ---------- | ---- | 455 |
| SEQ_ID_NO_1297 | NGDAAPRSYQ | NG--GGKV-A | RQPPVKAQ-- | ---------- | ---- | 447 |
| SEQ_ID_NO_1284 | -GEGYHQG-- | ----RGRG-G | RSSGQKQNAV | SN-------- | ---- | 462 |
| SEQ_ID_NO_1300 | ADVGYQRVDH | AGYAGGRG-G | RTAAAGAPAK | ---------- | ---- | 481 |
| SEQ_ID_NO_1294 | PDVGYQRVD- | ----GGRG-G | RTSAGPGAPA | K--------- | ---- | 482 |
| SEQ_ID_NO_1295 | PDVGYQRVD- | ----GGRG-G | RTSAGPGAPA | K--------- | ---- | 480 |
| SEQ_ID_NO_1287 | GDVGYQRVDH | SGT-GGRGGA | RAAAK----- | ---------- | ---- | 486 |
| SEQ_ID_NO_1289 | GDVGYQRVDY | SGTSSGRG-A | RAPSAAAAMA | K--------- | ---- | 488 |
| SEQ_ID_NO_1291 | -EVGYQRVDH | SGTAGGRG-T | RPASAATAAK | ---------- | ---- | 495 |
| SEQ_ID_NO_1274 | DGGGFPRANG | N---NGRV-R | RGGIDANRA | TKPVDDAPHV | SVTA | 488 |
| SEQ_ID_NO_1276 | GGDGYQRGEH | MGGNGGRV-S | RSGEATFNAS | TKNV--APRV | SAPA | 469 |
| SEQ_ID_NO_1280 | GGDGYRRADK | MGNNGGRA-N | RSGGLGLNGT | AKTT--APRV | SATA | 511 |

Figure 44

| | | | | | | |
|---|---|---|---|---|---|---|
| SEQ_ID_NO_1327 | MVVTVAATG- | PDTAETLHST | TFASRYVRDQ | LPRYRMPENS | PKEAAYQII | 49 |
| SEQ_ID_NO_1333 | MVVSVAATGA | GTDAEPVTST | FFASRYVRDP | LRRYRMPERS | PREAAYQII | 50 |
| SEQ_ID_NO_1336 | MVVSVAATDS | DTAQPVQYST | FFASRYVRDP | LPRFRMPEQS | PREAAYQII | 50 |
| SEQ_ID_NO_1319 | MVLTTTS-- | RDSEESLHCT | -FASRYVQEP | LPKFKMPKKS | MPKEAAYQIV | 47 |
| SEQ_ID_NO_1302 | MVLATN--- | SDSDEHLHST | -FASRYVRAV | VPRFKMPDHC | MPKDAAYQVI | 45 |
| SEQ_ID_NO_1311 | MVISTAA-- | TDSDENLYST | -FASRYVRTA | LPRFKMPENS | MPKDAAYQVI | 46 |
| SEQ_ID_NO_1317 | MVLTSTATHP | DEQDQSLNYT | -FASRYVREP | PKFKMPEKS | PKDAAYQII | 49 |
| SEQ_ID_NO_1305 | MLAAT---- | NPTEEHVHST | -FASRYVRAP | VPRFKMPEKS | PKDAAYQVI | 44 |
| SEQ_ID_NO_1339 | MALSSA---- | TDSDGSIHST | -FASRYVQFS | LPRFQIPSRS | PKDAAYQII | 45 |
| SEQ_ID_NO_1318 | MVLSETA--- | THMDASVHST | -FASRYVRTS | LPRFKMGENS | PKEAAYQII | 46 |
| SEQ_ID_NO_1331 | MVLSNTASSG | SESDLSIHST | -FASRYVRTS | LPRFKMPQES | PKEAAYQII | 49 |
| SEQ_ID_NO_1313 | MVLSKTA-- | SESDVSIHST | -FASRYVRTS | LPRFEMPENS | PKEAAYQII | 46 |
| SEQ_ID_NO_1303 | MVLSKTE--- | SESDESIHST | -FASRYVRNS | LPRFTMPENS | PKEAAYQII | 46 |
| SEQ_ID_NO_1340 | MVLSKTA-- | SESDVSVHST | -FASRYVRAS | LPRFKMPENS | PKEAAFQII | 46 |
| SEQ_ID_NO_1320 | MVLSKTA-- | SESDVSIHST | -FASRYVRTS | LPRFKMPENS | PKEAAYQII | 46 |
| SEQ_ID_NO_1326 | MVLSKTV--- | SQSDVSIHST | -FASRYVRTS | LPRFKMPDNS | PKEAAYQII | 46 |
| SEQ_ID_NO_1334 | MVLSKAV--- | SESDMSVHST | -FASRYVRAS | LPRYRMPENS | PKEAAYQII | 46 |
| SEQ_ID_NO_1330 | MVLSHGV--- | GGSDESVHST | -FASRYVRTS | LPRYRMPEQS | PKEAAYQII | 46 |

| | | | | | | |
|---|---|---|---|---|---|---|
| SEQ_ID_NO_1327 | SDELMLDGNP | RLNLASFVTT | MMEPECGKLI | MDSVNKNYVD | MDEYPVTTEL | 99 |
| SEQ_ID_NO_1333 | NDELMLDGNP | RLNLASFVTT | MMEPECDKLI | MGSINKNYVD | MDEYPVTTEL | 100 |
| SEQ_ID_NO_1336 | NDELMLDGNP | RLNLASFVTT | MMEPECDKLI | MDSVNKNYVD | MDEYPVTTEL | 100 |
| SEQ_ID_NO_1319 | NDELMLDGNP | RLNLASFVST | MMEPECDKLI | MSSINKNYVD | MDEYPVTTEL | 97 |
| SEQ_ID_NO_1302 | NDELMLDGNP | RLNLASFVTT | MMEPECDKLI | MDSVNKNYVD | MDEYPVTTEL | 95 |
| SEQ_ID_NO_1311 | NDELMLDGNP | RLNLASFVTT | MMEPECNDLI | MASINKNYVD | MDEYPVTTEL | 96 |
| SEQ_ID_NO_1317 | NDELMLDGAP | RLNLASFVTT | MMEPECDKLI | MASLNKNYVD | MDEYPVTTEL | 99 |
| SEQ_ID_NO_1305 | HDELMLDGNP | RLNLASFVTT | MMEPECDKLM | MAAINKNYVD | MDEYPVTTEL | 94 |
| SEQ_ID_NO_1339 | SDELMLDGNP | RLNLASFVTT | MMEPECDKLI | MQAINKNYVD | MDEYPVTTEL | 95 |
| SEQ_ID_NO_1318 | NDELMLDGNP | RLNLASFVTT | MMEPECDKLI | MASINKNYVD | MDEYPVTTEL | 96 |
| SEQ_ID_NO_1331 | NDELMLDGNP | RLNLASFVTT | MMEPECDKLI | MASINKNYVD | MDEYPVTTEL | 99 |
| SEQ_ID_NO_1313 | NDELMLDGNP | RLNLASFVTT | MMEPECDKLM | MESINKNYVD | MDEYPVTTEL | 96 |
| SEQ_ID_NO_1303 | NDELMLDGNP | RLNLASFVTT | MMEPECDKLM | MAAINKNYVD | MDEYPVTTEL | 96 |
| SEQ_ID_NO_1340 | NDELMLDGNP | RLNLASFVTT | MMEPECDKLI | IASINKNYVD | MDEYPVTTEL | 96 |
| SEQ_ID_NO_1320 | NDELMLDGNP | RLNLASFVTT | MMEPECNKLM | MDSINKNYVD | MDEYPVTTEL | 96 |
| SEQ_ID_NO_1326 | NDELMLDGNP | RLNLASFVTT | MMEPECDKLM | MDSINKNYVD | MDEYPVTTEL | 96 |
| SEQ_ID_NO_1334 | NDELMLDGNP | RLNLASFVTT | MMEPECDKLI | MAAINKNYVD | MDEYPVTTEL | 96 |
| SEQ_ID_NO_1330 | NDELMLDGNP | RLNLASFVTT | MMEPECDKLI | GASVNKNYVD | MDEYPVTTEL | 96 |

Figure 44 (continued)

| | | | | | | | |
|---|---|---|---|---|---|---|---|
| SEQ_ID_NO_1327 | QDRCVNMIAH | LFNAPIGEDE | TAIGVSTVGS | SEAIMLAGLA | FKRKWANKMK | 149 |
| SEQ_ID_NO_1333 | QNRCVNMIAH | LFNAPIKEDE | TAVGVGTVGS | SEAIMLAGLA | FKRKWQNKRK | 150 |
| SEQ_ID_NO_1336 | QNRCVNMIAH | LFNAPIKEDE | TAIGVGTVGS | SEAIMLAGLA | FKRKWQNKRK | 150 |
| SEQ_ID_NO_1319 | QNRCVNMLAH | LFHAPVGDDE | TAVGVGTVGS | SEAIMLAGLA | FKRKWQSKRK | 147 |
| SEQ_ID_NO_1302 | QNRCVNMIAN | FFHAPVGEDE | AAIGCGTVGS | SEAIMLAGLA | FKRKWQHRRK | 145 |
| SEQ_ID_NO_1311 | QNRCVNIIAH | LFNAPVGEKE | TAVGVGTVGS | SEAIMLAGLA | FKRKWQNKRK | 146 |
| SEQ_ID_NO_1317 | QNRCVNIIAN | LFHAPISDDE | TAVGVGTVGS | SEAIMLAGLA | FKRKWQTKRK | 149 |
| SEQ_ID_NO_1305 | QNRCVNMIAN | LFHAPVGEEE | TAVGVGTVGS | SEAIMLAGLA | FKRRWQHKRK | 144 |
| SEQ_ID_NO_1339 | QNRCVNIIAN | LFNAPLGDGE | EAVGVGTVGS | SEAIMLAGLA | FKRKWQNKRK | 145 |
| SEQ_ID_NO_1318 | QNRCVNMIAH | LFNAPLEDSE | PAVGVGTVGS | SEAIMLAGLA | FKRKWQNRRK | 146 |
| SEQ_ID_NO_1331 | QNRCVNMIAH | LFNAPLGDSD | I--VGTVGS | SEAIMLAGLA | FKRTWQNRRK | 146 |
| SEQ_ID_NO_1313 | QNRCVNMIAR | LFNAPLGDGE | AAVGVGTVGS | SEAIMLAGLA | FKRQWQNKRK | 146 |
| SEQ_ID_NO_1303 | QNRCVNIIAR | LFNAPLEDSE | TAVGVGTVGS | SEAIMLAGLA | FKRKWQNKRK | 146 |
| SEQ_ID_NO_1340 | QNRCVNMIAH | LFNAPLGDSE | TAVGVGTVGS | SEAIMLAGLA | FKRKWQNKRK | 146 |
| SEQ_ID_NO_1320 | QNRCVNMIAH | LFNAPLGDGE | TAVGVGTVGS | SEAIMLAGLA | FKRKWQNKMK | 146 |
| SEQ_ID_NO_1326 | QNRCVNMIAH | LFNAPLEDGE | TAVGVGTVGS | SEAIMLAGLA | FKRKWQNKMK | 146 |
| SEQ_ID_NO_1334 | QNRCVNMIAH | LFHAPLGEDE | TAVGVGTVGS | SEAIMLAGLA | FKRRWQNKRK | 146 |
| SEQ_ID_NO_1330 | QNRCVNMIAH | LFNAPLGDAE | TAVGVGTVGS | SEAIMLAGLA | FKRRWQNKMK | 146 |

| | | | | | | | |
|---|---|---|---|---|---|---|---|
| SEQ_ID_NO_1327 | EQGKPCDKPN | VTGANVQVC | MEKFARYFEV | ELKEVKLTEG | YYVMDPKKAV | 199 |
| SEQ_ID_NO_1333 | EQGKPYDKPN | VTGANVQVC | MEKFARYFEV | ELKEVKLSEG | YYVMDPVKAV | 200 |
| SEQ_ID_NO_1336 | EQGKPCDKPN | VTGANVQVC | MEKFARYFEV | ELKEVKLSEG | YYVMDPVKAV | 200 |
| SEQ_ID_NO_1319 | AEGKPFDKPN | VTGANVQVC | MEKFARYFEV | ELKEVKLKEG | YYVMDPAKAV | 197 |
| SEQ_ID_NO_1302 | AQGLPIDKPN | VTGANVQVC | MEKFARYFEV | ELKEVKLSED | YYVMDPAKAV | 195 |
| SEQ_ID_NO_1311 | AEGKPYDKPN | VTGANVQVC | MEKFARYFEV | ELKEVKLTEG | YYVMDPVKAV | 198 |
| SEQ_ID_NO_1317 | AEGKPYDKPN | VTGANVQVC | MEKFARYFEV | ELKEVKLKEG | YYVMDPAKAV | 199 |
| SEQ_ID_NO_1305 | TEGKPIDNPN | VTGANVQVC | MEKFARYFEV | GLKEVKLKEG | YYVMDPEQAV | 194 |
| SEQ_ID_NO_1339 | AEGKPYDKPN | VTGANVQVC | MEKFARYFEV | ELKEVKLKKD | YYIMDPVKAV | 195 |
| SEQ_ID_NO_1318 | SEGKSCENPN | VTGANVQVC | MEKFARYFEV | ELKEVKLRDG | YYVMDPEKAA | 196 |
| SEQ_ID_NO_1331 | AEGKPHDKPN | VTGANVQVC | MEKFARYFEV | ELKEVKLSEG | YYVMDPQKAV | 196 |
| SEQ_ID_NO_1313 | AQGLPYDKPN | VTGANVQVC | MEKFARYFEV | ELKEVKLREG | YYVMDPEKAV | 196 |
| SEQ_ID_NO_1303 | AEGKPFDKPN | VTGANVQVC | MEKFARYFEV | ELKEVKLSEG | YYVMDPAKAV | 196 |
| SEQ_ID_NO_1340 | AEGKPYDKPN | VTGANVQVC | MEKFARYFEV | ELKEVKLSDG | YYVMDPEKAV | 196 |
| SEQ_ID_NO_1320 | AQGKPCDKPN | VTGANVQVC | MEKFARYFEV | ELKEVKLSDG | YYVMDPEKAV | 196 |
| SEQ_ID_NO_1326 | AQGKPCDKPN | VTGANVQVC | MEKFARYFEV | ELKEVKLSEG | YYVMDPEKAV | 196 |
| SEQ_ID_NO_1334 | AEGKPFDKPN | ITGANVQVC | MEKFARYFEV | ELKEVKLRDG | YYVMDPEKAV | 196 |
| SEQ_ID_NO_1330 | AAGKPCDKPN | VTGANVQVC | MEKFARYFEV | ELKEVKLSDG | YYVMDPQKAV | 196 |

Figure 44 (continued)

| SEQ_ID | Col1 | Col2 | Col3 | Col4 | Col5 | Col6 | Pos |
|---|---|---|---|---|---|---|---|
| SEQ_ID_NO_1327 | EMVDENTICV | AAILGSTLTG | EYEDVKLLND | LLVEKNKETG | MNVPIHVDAA | | 249 |
| SEQ_ID_NO_1333 | DMVDENTICV | AAILGSTLTG | EFEDVKQLND | LLTEKNKETG | MDVPIHVDAA | | 250 |
| SEQ_ID_NO_1336 | EMVDENTICV | AAILGSTLTG | EFEDVKLLNN | LLTEKNKETG | MDVPIHVDAA | | 250 |
| SEQ_ID_NO_1319 | EIVDENTICV | AAILGSTLTG | EFEDVKLLNE | LLTKKNKETG | METPIHVDAA | | 247 |
| SEQ_ID_NO_1302 | EMVDENTICV | AAILGSTLTG | EFEDVKQLND | LLAEKNAETG | METPIHVDAA | | 245 |
| SEQ_ID_NO_1311 | EMVDENTICV | AAILGSTLTG | EFEDVKLLND | LLSKKNKETG | MNTPIHVDAA | | 246 |
| SEQ_ID_NO_1317 | EMVDENTICV | AAILGSTMTG | EFEDVKLLDE | LLTKKNNETG | MDTPIHVDAA | | 249 |
| SEQ_ID_NO_1305 | ELVDENTICV | AAILGSTLTG | EFEDVKTLND | LLMKKNEETG | MGTPIHVDAA | | 244 |
| SEQ_ID_NO_1339 | EMVDENTICV | AAILGSTYNG | EFEDVKLVND | LLIQKNKETG | MDTPIHVDAA | | 245 |
| SEQ_ID_NO_1318 | EMVDENTICV | AAILGSTLNG | EFEDVKRLND | LLVEKNAETG | MDTPIHVDAA | | 246 |
| SEQ_ID_NO_1331 | DLVDENTICV | AAILGSTLNG | EFEDVKRLND | LLIEKNKETG | MDTPIHVDAA | | 246 |
| SEQ_ID_NO_1313 | EMVDENTICV | AAILGSTLTG | EFEDVKLLND | LLVEKNKQTG | MDTGHVDAA | | 246 |
| SEQ_ID_NO_1303 | EMVDENTICV | AAILGSTLNG | EFEDVKLLND | LLTEKNKETG | ADTPIHVDAA | | 246 |
| SEQ_ID_NO_1340 | QMVDENTICV | AAILGSTLNG | EFEDVKLLND | LLVEKNKSTG | MDTPIHVDAA | | 246 |
| SEQ_ID_NO_1320 | EMVDENTICV | AAILGSTLNG | EFEDVKRLND | LLIEKNKETG | MDTPIHVDAA | | 246 |
| SEQ_ID_NO_1326 | EMVDENTICV | AAILGSTLNG | EFEDVKRLND | LLVEKNKETG | MDTPIHVDAA | | 246 |
| SEQ_ID_NO_1334 | DMVDENTICV | AAILGSTLNG | EFEDVKLLND | LLDKKNKETG | METPIHVDAA | | 246 |
| SEQ_ID_NO_1330 | DMVDENTICV | AAILGSTLNG | EFEDVKLLND | LLTKKNAETG | MDTPIHVDAA | | 246 |

| SEQ_ID | Col1 | Col2 | Col3 | Col4 | Col5 | Pos |
|---|---|---|---|---|---|---|
| SEQ_ID_NO_1327 | SGGFIAPFLQ | PELEWDFRLP | LVKSINVSGH | KYGLVYPGVG | WIWRSKDDL | 299 |
| SEQ_ID_NO_1333 | SGGFIAPFLY | PELEWDFRLP | LVKSINVSGH | KYGLVYAGVG | WIWRSKKDL | 300 |
| SEQ_ID_NO_1336 | SGGFIAPFLY | PELEWDFRLP | LVKSINVSGH | KYGLVYPGVG | WIWRSKEDL | 300 |
| SEQ_ID_NO_1319 | SGGFIAPFLW | PDLEWDFRLP | LVKSINVSGH | KYGLVYAGVG | WIWRSKEDL | 297 |
| SEQ_ID_NO_1302 | SGGFIAPFLY | PDLEWDFRLP | WKSINVSGH | KYGLVYAGVG | WVWRTKDDL | 295 |
| SEQ_ID_NO_1311 | SGGFIAPFIW | PDLEWDFRLP | LVKSINVSGH | KYGLVYAGVG | WVWRTKEDL | 296 |
| SEQ_ID_NO_1317 | SGGFIAPFLY | PDLEWDFRLP | LVKSINVSCH | KYGLVYPGVG | WVWRSKDDL | 299 |
| SEQ_ID_NO_1305 | SGGFIAPFLY | PDLEWDFRLP | LVKSINVSGH | KYGLVYAGVG | WVWRNKEDL | 294 |
| SEQ_ID_NO_1339 | SGGFIAPFLY | PELEWDFRLP | LVKSINVSGH | KYGLVYAGIG | WIWRAKQDL | 295 |
| SEQ_ID_NO_1318 | SGGFIAPFLY | PELVMDFRLS | LVKSINVSGH | KYGLVYAGIG | MIWRSKEDL | 296 |
| SEQ_ID_NO_1331 | SGGFIAPFIY | PELEWDFRLP | LVKSINVSGH | KYGLVYAGIG | WIWRNKEDL | 296 |
| SEQ_ID_NO_1313 | SGGFIAPFLY | PELEWDFRLP | LVKSINVSGH | KYGLVYAGIG | WVWRTKSDL | 296 |
| SEQ_ID_NO_1303 | SGGFIAPFLY | PELEWDFRLP | LVKSINVSGH | KYGLVYAGIG | WVWRNKEDL | 296 |
| SEQ_ID_NO_1340 | SGGFIAPFIY | PELEWDFRLP | LVKSINVSGH | KYGLVYAGIG | WIWRNKEDL | 296 |
| SEQ_ID_NO_1320 | SGGFIAPFLY | PELEWDFRLP | LVKSINVSGH | KYGLVYAGIG | WAWRNKEDL | 296 |
| SEQ_ID_NO_1326 | SGGFIAPFIY | PELEWDFRLP | LVKSINVSGH | KYGLVYAGIG | WVWRNKDDL | 296 |
| SEQ_ID_NO_1334 | SGGFIAPFLY | PELEWDFRLP | WKSINVSGH | KYGLVYAGIG | WCWRNKEDL | 296 |
| SEQ_ID_NO_1330 | SGGFIAPFLY | PELEWDFRLP | LVKSINVSGH | KYGLVYAGIG | WCWRTKVDL | 296 |

Figure 44 (continued)

| SEQ_ID | col1 | col2 | col3 | col4 | col5 | col6 | num |
|---|---|---|---|---|---|---|---|
| SEQ_ID_NO_1327 | PEELIFHINY | LGADQPTFTL | NFSKGQ-QII | AQYYQLIRLG | FEGYKHIMEN | | 348 |
| SEQ_ID_NO_1333 | PEELIFHINY | LGTDQPTFTL | NFSKGSSQII | AQYYQLIRLG | FQGYKNIMEN | | 350 |
| SEQ_ID_NO_1336 | PEELIFHINY | LGTDQPTFTL | NFSKGSSQII | AQYYQLIRLG | FEGYKNIMQN | | 350 |
| SEQ_ID_NO_1319 | PDELVFHINY | LGSDQPTFTL | NFSKGSYQII | AQYYQLIRLG | FEGYKNVMKN | | 347 |
| SEQ_ID_NO_1302 | PEELVFHINY | LGADQPTFTL | NFSKGSSQII | AQYYQFIRLG | FEGYKNIMEN | | 345 |
| SEQ_ID_NO_1311 | PDELIFHINY | LGSDQPTFTL | NFSKGSGQII | AQYYQFIRLG | FEGYKRIMEN | | 346 |
| SEQ_ID_NO_1317 | PDELVFHINY | LGSDQPTFTL | NFSKGSSQII | AQYYQLIRLG | FEGYKNIMEN | | 349 |
| SEQ_ID_NO_1305 | PDDLVFHINY | LGSDQPTFTL | NFSKGSSQII | AQYYQFLRLG | FEGYKNIIEN | | 344 |
| SEQ_ID_NO_1339 | PEELIFHINY | LGADQPTFTL | NFSKGASQII | AQYYQLIRLG | FEGYRNIMGN | | 345 |
| SEQ_ID_NO_1318 | PEELIFHINY | LGADQPTFTL | NFSKGSSQVI | AQYYQLIRLG | YEGYRNVMEN | | 346 |
| SEQ_ID_NO_1331 | PEELIFHINY | LGADQPTFTL | NFSKGSSQII | AQYYQLIRLG | YEGYKHVMEN | | 346 |
| SEQ_ID_NO_1313 | PDELIFHINY | LGADQPTFTL | NFSKGSSQVI | AQYYQLIRLG | FEGYRNVMDN | | 346 |
| SEQ_ID_NO_1303 | PEELIFHINY | LGADQPTFTL | NFSKGSSQVI | AQYYQLIRLG | FEGYRNVMEN | | 346 |
| SEQ_ID_NO_1340 | PEELIFHINY | LGADQPTFTL | NFSKGSSQVI | AQYYQLIRLG | YEGYKNVMEN | | 346 |
| SEQ_ID_NO_1320 | PDELIFHINY | LGADQPTFTL | NFSKGSSQVI | AQYYQLIRLG | FEGYKNVMEN | | 346 |
| SEQ_ID_NO_1326 | PDELIFHINY | LGADQPTFTL | NFSKGSSQVI | AQYYQLIRLG | YEGYKNVMEN | | 346 |
| SEQ_ID_NO_1334 | PEELIFHINY | LGADQPTFTL | NFSKGSSQVI | AQYYQLIRHG | FEGYRNIMEN | | 346 |
| SEQ_ID_NO_1330 | PEELIFHINY | LGADQPTFTL | NFSKGSSQVI | AQYYQLIRLG | FEGYKNIMEN | | 346 |

| SEQ_ID | col1 | col2 | col3 | col4 | col5 | num |
|---|---|---|---|---|---|---|
| SEQ_ID_NO_1327 | CKLNAAVLKE | GIDATGRFDV | LSKADGVPLV | AIRLKDSTNF | SVFDISENLR | 398 |
| SEQ_ID_NO_1333 | CMENAAILRE | GIAATGRFDI | LSKDAGVPLV | AFSLKDSSRF | SVFDISENLR | 400 |
| SEQ_ID_NO_1336 | CMENTAILRE | GIEATGRFE | LSKEAGVPLV | AFSLKDSGRY | TVFDISEHLR | 400 |
| SEQ_ID_NO_1319 | CLSNAKVLTE | GIIKMGRFDI | VSKDVGVPVV | AFSLRDSSKY | TVFEVSEHLR | 397 |
| SEQ_ID_NO_1302 | CMDNARRLRE | GIEMTGKFNI | VSKDIGVPLV | AFSLKDSSKH | TVFEIAESLR | 395 |
| SEQ_ID_NO_1311 | CLENARVLRE | GLEKTGRFDI | VSKDKGVPLV | AFSLKDSSKH | TVFEIAESLR | 396 |
| SEQ_ID_NO_1317 | CMENARVLKE | GIERTGRFNI | ISKDIGVPLV | AFSLQDSSQH | TVFEIADHLR | 399 |
| SEQ_ID_NO_1305 | CMENMKVLKQ | GIENTGRFNI | LSKDIGVPLV | AFSLKDSSKH | TVFEIAENLR | 394 |
| SEQ_ID_NO_1339 | CAANAKALSD | GLVRTGRFNI | LSKEIGVPLV | AFSLKDSSRH | DEYEISDHLR | 395 |
| SEQ_ID_NO_1318 | CRDNMMVLKD | GLEKTERFE | VSKDEGVPLV | AFTLKDHNNF | NEFQISDMLK | 396 |
| SEQ_ID_NO_1331 | CRDNMLVLKE | GLQKTGRFE | VSKDNGVPLV | AFTLKDHTHY | NEFQISDSLL | 395 |
| SEQ_ID_NO_1313 | CRENMMVLRE | GLEKTGRFNI | VSKENGVPLV | AFSLKDSSRH | DEFEVAETLR | 396 |
| SEQ_ID_NO_1303 | CHENAMVLKE | GLEKTGRFNI | VSKDEGVPLV | AFSLKDNKRH | DEFEVAELLR | 396 |
| SEQ_ID_NO_1340 | CRDNMLVLKQ | GLEKTGKFNI | VSKDKGVPLV | AFSLKDNSLH | NEFEVSDMLR | 396 |
| SEQ_ID_NO_1320 | CQENARVLRE | GLEKSGRFNI | ISKEIGVPLV | AFSLKDNSQH | NEFEISETLR | 396 |
| SEQ_ID_NO_1326 | CQENASVLRE | GLEKTGRFNI | ISKEIGVPLV | AFSLKDNRQH | NEFEISETLR | 396 |
| SEQ_ID_NO_1334 | CHENAMVLKE | GLVKTGRFDI | VSKDEGVPLV | AFSLKDRSRH | DEFEISDMLR | 396 |
| SEQ_ID_NO_1330 | CQENAIVLKQ | GLEKTGKFNI | VSKDNGVPLV | AFSLKDSSRH | SEFEISDFLR | 396 |

Figure 44 (continued)

| | | | | | | |
|---|---|---|---|---|---|---|
| SEQ_ID_NO_1327 | RFGW VPAYT | MPADAEHVAV | LRIVI REDFN | RSLAQRLLAD | NKI I GELDA | 448 |
| SEQ_ID_NO_1333 | RFGW VPAYT | MPADAEHVAV | LRVVI REDFS | RTLLERLVGD | VLKI LRELDA | 450 |
| SEQ_ID_NO_1336 | RFGW VPAYT | MPANAEHVAV | LRVVI REDFS | RSLAERLVSD | VKI LHELDA | 450 |
| SEQ_ID_NO_1319 | RFGW VPAYT | MPPDAEHI AV | LRVVI REDFS | HSLAERLVSD | EKI LSELDT | 447 |
| SEQ_ID_NO_1302 | KFGW I PAYT | MPADAQHI AV | LRVVI REDFS | RGLADRLI TH | QVLKEI EG | 445 |
| SEQ_ID_NO_1311 | RFGW I PAYT | MPANAQHI AV | LRVVVREDFN | RSLAERLVSH | DQVMKETDS | 446 |
| SEQ_ID_NO_1317 | KFGW VPAYT | MPPDAQHI AV | LRVVI REDFS | RGLAERLAAD | EKVVKLLDT | 449 |
| SEQ_ID_NO_1305 | RFGW LPAYT | MPANAQHVAV | LRAVI REDFS | HGLAKRLVAH | EQVLKEMDG | 444 |
| SEQ_ID_NO_1339 | RFGW VPAYT | MAPDAQEVKL | LRVVVREDFN | RSLAERLVHD | EKVL HELDT | 445 |
| SEQ_ID_NO_1318 | RHGW I PAYT | MPPDAEHVTV | LRVVI REDFS | RTFAERLVI D | TRVI HELDL | 446 |
| SEQ_ID_NO_1331 | - - - - - - - - - - | - - - - - - - - - A | LRV- - - - - - | - - - - - - - - - - | - - - - - - - - DS | 401 |
| SEQ_ID_NO_1313 | RFGW VPAYT | MPADAQHVTV | LRVVI REDFS | RTLAERLVAD | FEKVL HELDT | 446 |
| SEQ_ID_NO_1303 | RFGW VPAYT | MPADAQHI TV | LRVVI REDFS | RTLAERLVLD | TKVL HELDS | 446 |
| SEQ_ID_NO_1340 | RFGW VPAYT | MPPDAQHVTV | LRVVI REDFS | RTLAERLVI D | GKVL HELET | 446 |
| SEQ_ID_NO_1320 | RFGW I PAYT | MPPNAQHVTV | LRVVI REDFS | RTLAERLVI D | EKVL HELDT | 446 |
| SEQ_ID_NO_1326 | RFGW VPAYT | MPPNAQHI TV | LRVVI REDFS | RTLAERLVRD | EKVL HELDT | 446 |
| SEQ_ID_NO_1334 | RFGW VPAYT | MPPDAQHVTV | LRVVI REEFS | RTLAERLVLD | EKVMYQLDA | 446 |
| SEQ_ID_NO_1330 | RFGW VPAYT | MPPDAQHVTV | LRVVI REDFS | RTLAERLVLD | EKVL HELDA | 446 |

| | | | | | | |
|---|---|---|---|---|---|---|
| SEQ_ID_NO_1327 | HAVHAI KLST | AAAGGDG- - - | - - - - - - - - - - | - - - - - - - - - A | SKSAVDAATE | 476 |
| SEQ_ID_NO_1333 | CATHAVRYAT | ATAAVQSGDG | GGVVARK- - - | - - - - - - - - - S | I LEI FREVAS | 489 |
| SEQ_ID_NO_1336 | HSAQVLKI SS | AI AKQQSGDD | GVVTKK- - - - | - - - - - - - - - S | VLETEREI FA | 487 |
| SEQ_ID_NO_1319 | QPPRLPTKAV | RVTAEEVRDD | KGDGLHHFHM | - - - - - - - - D | TVETQKDI K | 488 |
| SEQ_ID_NO_1302 | LPSRI AHLAA | AAAVSGDDEE | VKVK- - - - - | - - - - - - - - T | AKMSLEDI TK | 480 |
| SEQ_ID_NO_1311 | LPSRVAVQAS | RI VTVDETQD | NMDGKKTVKK | - - - - - - - - S | SREI DEFVTL | 487 |
| SEQ_ID_NO_1317 | LPSPLTTKAV | HI TAI TSETG | EKI KK- - - - - | - - - - - - - - A | AI ETQKEI AF | 485 |
| SEQ_ID_NO_1305 | LPSGI DHKK- | - - - - - - - - - - | - - - - - - - - - - | - - - - - - - - - A | ERETQEEVFR | 464 |
| SEQ_ID_NO_1339 | LPSKI AREVV | ASLYDGHPEL | KEVKDLGI DV | TQFKSSAVFN | EI VNSQKAVK | 495 |
| SEQ_ID_NO_1318 | VPSRVVSTNT | I TVTGGEEDA | DNDGTVTI AN | Q- - - - - - - S | VLETQRKI TT | 488 |
| SEQ_ID_NO_1331 | AGI QHAPKYS | A- - - - - - - - - | - - - - - - - - - - | - - - - - - - - - - | - - - - - - - - - - | 412 |
| SEQ_ID_NO_1313 | LPARVQAKMA | NGNANGVKK- | - - - - - - - - - - | - - - - - - - - - T | EEETTREYTA | 476 |
| SEQ_ID_NO_1303 | LPSKVLVPAS | EQNGRNGKK- | - - - - - - - - - - | - - - - - - - - - T | EI ETQREVTT | 476 |
| SEQ_ID_NO_1340 | LPSRI SAKI V | LANEEKDAVA | AGKEKK- - - - | - - - - - - - - D | VQNETREI T | 483 |
| SEQ_ID_NO_1320 | LPARVNAKLA | VAEANGSGVH | KK- - - - - - - - | - - - - - - - - T | DREVQLEI TT | 479 |
| SEQ_ID_NO_1326 | LPARVNAKLA | VAEEQAAANG | SEVHKK- - - - | - - - - - - - - T | DSEVQLEM T | 483 |
| SEQ_ID_NO_1334 | LPSRLMPPVP | PAPLLVVAKK | - - - - - - - - - - | - - - - - - - - S | ELETQRSVTE | 477 |
| SEQ_ID_NO_1330 | LPARVPSGDL | AALAAAESSE | - - - - - - - - - - | - - - - - - - - R | EMEKQRQVS | 477 |

Figure 44 (continued)

| | | |
|---|---|---|
| SEQ_ID_NO_1327 | AFKDLAGK- - -KKAGVC- | 490 |
| SEQ_ID_NO_1333 | RMRDAVSK- - -KKTGPC- | 502 |
| SEQ_ID_NO_1336 | YMRDQVKK- - -KDTGIC- | 501 |
| SEQ_ID_NO_1319 | HWRKIAGK- - -KTSGVC- | 502 |
| SEQ_ID_NO_1302 | YWKRLVEH- - -KRNIVC- | 494 |
| SEQ_ID_NO_1311 | YMRRLASE- - -KRTGAC- | 501 |
| SEQ_ID_NO_1317 | YWKRLVDG- - -KRLGAC- | 499 |
| SEQ_ID_NO_1305 | CWKRLVDR- - -KIAGVC- | 478 |
| SEQ_ID_NO_1339 | AWKKFVAQ- - -KANRVC- | 509 |
| SEQ_ID_NO_1318 | AWKKFVMNRK - -KTNGVC- | 504 |
| SEQ_ID_NO_1331 | - - - - - - - - - - - -RDRGPCSH | 420 |
| SEQ_ID_NO_1313 | YWKKFVEAKK -SNKNRIC- | 493 |
| SEQ_ID_NO_1303 | YMRKFVSERK ANNKNKIC- | 494 |
| SEQ_ID_NO_1340 | AMRKLVVQRK - -KLNGVC- | 499 |
| SEQ_ID_NO_1320 | AWKKFVADKK K-KTNGVC- | 496 |
| SEQ_ID_NO_1326 | AWKKFVEEKK K-KTNRVC- | 500 |
| SEQ_ID_NO_1334 | AWKKFVLAK- - -RTNGVC- | 492 |
| SEQ_ID_NO_1330 | LMKRAVLAKK - -KTNGVC- | 493 |

Figure 45

```
SEQ_ID_NO_1363   . . . . . . . . . .   . . . . . . . . . .   . . . . . . . . . .   . . . MSKTTNQ   NRRPSFTSST     17
SEQ_ID_NO_1373   . . . . . . . . . .   . . . . . . . . . .   . . . . . . . . . .   . . . . . . . . . .   . . . . . . . MVD      3
SEQ_ID_NO_1342   . . . . . . . . . .   . . . . . . . . . .   . . . . . . . . . .   . . . . . . . . . .   . . . . . . . . . .      0
SEQ_ID_NO_1381   . . . . . . . . . .   . . . . . . . . . .   . . . . . . . . . .   . . . . . . . . . .   . . . . . . . . . .      0
SEQ_ID_NO_1382   . . . . . . . . . .   . . . . . . . . . .   . . . . . . . . . .   . . . . . . . . . .   . . . . . . . . . .      0
SEQ_ID_NO_1371   . . . . . . . . . .   . . . . . . . . . .   . . . . . . . . . .   . . . . . . . . . .   . . . . . . . . . .      0
SEQ_ID_NO_1366   . . . . . . . . . .   . . . . . . . . . .   . . . . . . . . . .   . . . . . . . . . .   . . . . . . . . . M      1
SEQ_ID_NO_1370   . . . . . . . . . .   . . . . . . . . . .   . . . . . . . . . .   . . . . . . . . . .   . . . . . . . . . .      0
SEQ_ID_NO_1346   . . . . . . . . . .   . . . . . . . . . .   . . . . . . . . . .   . . . . . . . . . .   . . . . . . . . . .      0
SEQ_ID_NO_1372   . . . . . . . . . .   . . . . . . . . . .   . . . . . . . . . .   . . . . . . . . . .   . . . . . . . . . .      0
SEQ_ID_NO_1374   . . . . . . . . . .   . . . . . . . . . .   . . . . . . . . . .   . . . . . . . . . .   . . MKKQEKEA      8
SEQ_ID_NO_1355   . . . . . . . . . .   . . . . . . . . . .   . . . . . . . . . .   . . . . . . . . . .   . . . . . . . . . .      0
SEQ_ID_NO_1364   . . . . . . . . . .   . . . . . . . . . .   . . . . . . . . . .   . . . . . . . . . .   . . . . . . . . . .      0
SEQ_ID_NO_1378   MGSRHQVVQQ   QNRGDVVPGA   IKQKSMAVEK   KNRRALGDIG   NVV-TVRGVE    49
SEQ_ID_NO_1377   ---MNTNRAV   LVPHRGEVGG   KQKNGQADGR   NNRRVLGDIG   NLVTGAPYIE    47
SEQ_ID_NO_1379   MGSRAVVVPD   QQPRGR--GG   KQKNGQAEGR   -NRRVLRDIG   NLV-PVPTVE    46
SEQ_ID_NO_1380   . . . . . . . . . .   . . . . . . . . . .   . . . . . . . . . .   ---MAGADEN   HGAVKLANFR    17
SEQ_ID_NO_1383   . . . . . . . . . .   . . . . . . . . . .   . . . . . . . . . .   . . . . . . . . . .   . . . . . . . . . .      0

SEQ_ID_NO_1363   ESSMRKRHGP   SSSSSAVK-   PISNTAVMVA   KKRAPLGNIT   . . . . . . . . . .    55
SEQ_ID_NO_1373   EENKVPATAA   ASRGSNKR-   AFDSAITNE    NDPLQISERP   . . . . . . . . . .    41
SEQ_ID_NO_1342   . . . . . . . . . .   . . . . . . . . . .   . . . . . . . . . .   . . . . . . . . . .   . . . . . . . . . .      0
SEQ_ID_NO_1381   -MADKENSTP   ASAARLTRSS   AAAGAQAKRS   AAAGVADGGA   . . . . . . . . . .    39
SEQ_ID_NO_1382   -MADKENSTP   ASAARLTRSS   AAAGAQAKRS   AAAGVADGGA   . . . . . . . . . .    39
SEQ_ID_NO_1371   . . . . . . . . . .   . . . . . . . . . .   -APSMTTPE    . . . . . . . . . .   . . . . . . . . . .      8
SEQ_ID_NO_1366   ATSENNSSAR   PQREAKKR-   AAAISQIHG    N- - - - - - - -    . . . . . . . . . .    30
SEQ_ID_NO_1370   MADDDNSTRR   PQREAKKR-   AVAALCE- - -    . . . . . . . . . .   . . . . . . . . . .    25
SEQ_ID_NO_1346   -MAEQENCTR   VTRAAKKR-   AAALASTEDQ   . . . . . . . . . .   . . . . . . . . . .    27
SEQ_ID_NO_1372   -MADKENCIR   VTRLAKKR-   AVEAMAASEQ   Q- - - - - - - - -    . . . . . . . . . .    28
SEQ_ID_NO_1374   IMADLENCGR   VTRLAKKR-   AAEAMASHQQ   Q- - - - - - - - -    . . . . . . . . . .    37
SEQ_ID_NO_1355   MADEKENCVR   MTRAATKRKA   SMEAAIDKE    . . . . . . . . . .   . . . . . . . . . .    29
SEQ_ID_NO_1364   -MAENQNSTR   MTRAAAKR-   KASVTDEN- -    . . . . . . . . . .   . . . . . . . . . .    25
SEQ_ID_NO_1378   GKALPQVSRP   ITRGFCAQLI   ANAEANAAEN   NKNSLAVNAK   GADGALPIKR    99
SEQ_ID_NO_1377   GKPKAQISRP   ATRSFCAQLL   ANAQAEKNKV   KPLAEVVNKV   . . . . . . . . . .    87
SEQ_ID_NO_1379   EKPQNQISRP   VTRSLCVQ-   PAAAAEKKNK   KPLAEVVNGG   GEVKAAAAAH    94
SEQ_ID_NO_1380   ETTNRRALKD   IKNFVGAP--   SFPCAANKRQ   LKEVVCGNND   . . . . . . . . . .    55
SEQ_ID_NO_1383   -MITGAQGVR   QTRSKTTY--   EVPQQQQQQS   FEW- - - - -    . . . . . . . . . .    30
```

Figure 45 (continued)

| | | | | | |
|---|---|---|---|---|---|
| SEQ_ID_NO_1363 | -----NQRKD | SRIFPNSSSA | DSAHCPNKSA | KLKLAAPTQP | VCVNACETKS | 100 |
| SEQ_ID_NO_1373 | -----YPANK | KRVVLGELNN | LGNV------ | --IVSTQNSD | LTETHESKRK | 78 |
| SEQ_ID_NO_1342 | ------MGYL | WRVRLSSFAA | GAAT------ | --ASAAGFFL | LYKDHLLARA | 38 |
| SEQ_ID_NO_1381 | -----PPAKR | KRVALSDLPT | LSNA------ | --VVVAPRQP | HHPVVIKPSS | 76 |
| SEQ_ID_NO_1382 | -----PPAKR | KRVALSDLPT | LSNA------ | --VVVAPRQP | HHPVVIKPSS | 76 |
| SEQ_ID_NO_1371 | ------PASK | RRVVLGEISN | NSSA------ | --VSGNEDLL | CREFEVPKCV | 44 |
| SEQ_ID_NO_1366 | ------AAKK | KRVVLGDVTN | VSSS------ | ---------- | -----DVAVS | 53 |
| SEQ_ID_NO_1370 | ------QRKR | KRVALGDITN | DVVS------ | --ETEKLVSD | SHSHTQKKKK | 61 |
| SEQ_ID_NO_1346 | ------PLNK | KRVVLGELPN | LSNA------ | --IVSS---- | -NEPQKDKAK | 58 |
| SEQ_ID_NO_1372 | ------RPSK | KRVVLGELKN | LSSN------ | ---ISSIQTY | DFSSGPQKQQ | 63 |
| SEQ_ID_NO_1374 | ------HPSK | KRVVLGEIQN | FSNL------ | --GVSQIKGL | NTEPKKQPKS | 73 |
| SEQ_ID_NO_1355 | ------RINK | KRVVLGELPN | LSNI------ | ---------- | ----KKSRKA | 53 |
| SEQ_ID_NO_1364 | ------PVSK | KRVVLGELPN | NSNV------ | ----PAPLIP | LQERETQKPK | 59 |
| SEQ_ID_NO_1378 | AVAR--VPVQ | KKTVKSKPQE | IEISPDTEK | KKAPVLEKEI | TGEKSLKKKA | 147 |
| SEQ_ID_NO_1377 | ------PAKK | KASDKPAVQE | AVIVISPDEE | VKKKTIEKSP | LSKRKAKKTG | 131 |
| SEQ_ID_NO_1379 | KKHYDPPKPE | TVIVISSDEE | LESE------ | --EKKKPVAV | IARKSRVGSS | 136 |
| SEQ_ID_NO_1360 | -----SVIPR | RPITRQFAST | LASK------ | --SQQSHGET | SNKHGQITGN | 92 |
| SEQ_ID_NO_1383 | ------GRTS | QRTSHGKPRR | GSVM------ | -------GGT | MTTAGADVDM | 61 |

| | | | | | |
|---|---|---|---|---|---|
| SEQ_ID_NO_1363 | TCEEVVPIE | RKAFSNLCIT | PSSDTTTNVM | SETENKEEKF | MNDNKDDAD | 150 |
| SEQ_ID_NO_1373 | IKLRKTRNVV | KETVELKTSA | NSSPK----- | ---------- | --------DN | 105 |
| SEQ_ID_NO_1342 | ADAESNSASY | SPPLATADTA | FSAPP----- | ---------- | RAVAP---AD | 68 |
| SEQ_ID_NO_1381 | KQPEPAAEAA | APSGGGGGSP | VSSAST---- | ---------- | STASPSSGWD | 112 |
| SEQ_ID_NO_1382 | KQPEPAAEAA | APSGGGGGSP | VSSAST---- | ---------- | STASPSSGWD | 112 |
| SEQ_ID_NO_1371 | AQKKRKRGVK | EDVGVDFGEK | F--------- | ---------- | --------DD | 67 |
| SEQ_ID_NO_1366 | VSKKPVQTHK | NVKLEKPAAP | VAIPE----- | ---------- | ---KVEERHD | 85 |
| SEQ_ID_NO_1370 | RNIAKSPVPE | KL-------- | ---------- | ---------- | --------ED | 75 |
| SEQ_ID_NO_1346 | AKPKARKGAS | TKKEGVLKED | VDGNP----- | ---------- | --------ED | 85 |
| SEQ_ID_NO_1372 | KNKNKRKAKE | SLGFEVKEKK | VEEAG----- | ---------- | IDVFSQS-DD | 97 |
| SEQ_ID_NO_1374 | KQQQSKRKLK | RAVTSKIDKE | ELNVD----- | ---------- | -NVDANY-DD | 106 |
| SEQ_ID_NO_1355 | TTKQKKKSVS | IPTIETLNSD | IDTRS----- | ---------- | --------DD | 80 |
| SEQ_ID_NO_1364 | STLFAAKKQT | KTPPIPQTVD | FESGS----- | ---------- | ---------SD | 86 |
| SEQ_ID_NO_1378 | PTLTSTLTAR | SKAASVVRTK | PKEQI----- | ---------- | VDIDAADVNN | 182 |
| SEQ_ID_NO_1377 | KTLTSTLTAR | SKAACGLSNR | PKNEI----- | ---------- | DDIDAADAAN | 166 |
| SEQ_ID_NO_1379 | RIMTSILTAR | SKALCGPTTK | PKVPI----- | ---------- | ADIDAADVDN | 171 |
| SEQ_ID_NO_1380 | EKHNPIIIDE | DVPMVEESEE | MEECELVEEI | TMEDIVIDSA | QDIDIGDVGN | 142 |
| SEQ_ID_NO_1383 | RESYSTYLER | SSAADVMTDA | L--------- | ---------- | PDIDLYDHDN | 92 |

Figure 45 (continued)

| | | | | | | | |
|---|---|---|---|---|---|---|---|
| SEQ_ID_NO_1363 | PQLYATFACD | YNHLRAAE- | -AKKQPAVDY | METVQKDVNS | TMRGILVDWL | | 198 |
| SEQ_ID_NO_1373 | LDKCS-YGPL | YQHLHSLEV | EERRRPLSNY | MEKYQNNVIP | SMRTVLVDWL | | 154 |
| SEQ_ID_NO_1342 | LDLSGSYASD | YTYLRSLEV | DPQRRSRSDY | EAVQADVTA | HMRSILVDWL | | 118 |
| SEQ_ID_NO_1381 | PQ---YASD | YTYLRSMEV | EARRQSAADY | ESVQVDVTA | NMRAILVDWL | | 158 |
| SEQ_ID_NO_1382 | PQ---YASD | YTYLRSMEV | EARRQSAADY | EAVQVDVTA | NMRAILVDWL | | 158 |
| SEQ_ID_NO_1371 | PQMCSAYVSD | VYEYLKQMEM | ETKRRPMMNY | EQVQKDVTS | NMRGVLVDWL | | 117 |
| SEQ_ID_NO_1366 | PQLCGPYVSD | IYEYLRGMEV | DPSKRPLMDY | VQKIQRDVNA | NMRGVLVDWL | | 135 |
| SEQ_ID_NO_1370 | PQLCEPYVSD | HDYLRNLEV | DPSKRPLPDY | QKVQRDINA | NMRGVLVDWL | | 125 |
| SEQ_ID_NO_1346 | PQMCAPYASD | IYEYLHKMEV | DPKRRPLPDY | EKVQKDVSP | NMRGILVDWL | | 135 |
| SEQ_ID_NO_1372 | PQMCGAYVSD | IYEYLHKMEM | ETKRRPLPDY | LDKVQKDVTA | NMRGVLIDWL | | 147 |
| SEQ_ID_NO_1374 | PQMCSAYVSD | IYDYLRKMEI | EEKRRPLPDY | LEKVQKDLSP | NMRGVLVDWL | | 156 |
| SEQ_ID_NO_1355 | PQMCGPYVTS | IFEYLRQLE- | -VKSRPLVDY | EKIQKDVTS | NMRGVLVDWL | | 128 |
| SEQ_ID_NO_1364 | PQMCGPFVAD | ICAYLREMEG | KLKQRPLHDY | EKVQSDLTP | SMRGVLMDWL | | 136 |
| SEQ_ID_NO_1378 | DLAVVEYVED | MYKFYKSAE- | -NDSRPH-DY | MDFSQPEINE | KMRAILIDWL | | 228 |
| SEQ_ID_NO_1377 | HLAVVEYVED | YNFYKLTE- | -DESRVN-NY | MEFFQPELNH | KMRAILVDWL | | 212 |
| SEQ_ID_NO_1379 | ELAVVEYVED | IYKFYKLTE- | -GESRVH-DY | MDFSQPEINS | KMRSILIDWL | | 217 |
| SEQ_ID_NO_1380 | PLAVVDYVDD | IYNVYRRVE- | -ASSCVHPDY | MS-NQFDIND | KMRAILIDWL | | 189 |
| SEQ_ID_NO_1383 | PLAVTQYVND | YQYWYKVE- | -PDTRVSETY | ML-IQGDINY | KMRAILIDWL | | 139 |

| | | | | | | | |
|---|---|---|---|---|---|---|---|
| SEQ_ID_NO_1363 | VEVSEEYRLV | PETLYLTVNY | IDRYLSGNV | SRQKLQLLGV | ACMMIAA-KY | | 247 |
| SEQ_ID_NO_1373 | VEVTEEYKLV | SDTLYLAVSY | IDRFLSSHVL | AVEKLQLLGV | SCMLVAS-KY | | 203 |
| SEQ_ID_NO_1342 | VEVAEEYKLV | ADTLYLTISY | VDRFLSVNAL | GRDKLQLLGV | ASMLIAA-KF | | 167 |
| SEQ_ID_NO_1381 | VEVADEYKLV | ADTLYLAVSY | LDRYLSAHPL | RRNRLQLLGV | GAMLIAA-KY | | 207 |
| SEQ_ID_NO_1382 | VEVADEYKLV | ADTLYLAVSY | LDRYLSAHPL | RRNRLQLLGV | GAMLIAA-KY | | 207 |
| SEQ_ID_NO_1371 | VEVSLEYKLL | PETLYLAISY | VDRYLSVNVL | NRQKLQLLGV | SSFLIAS-KY | | 166 |
| SEQ_ID_NO_1366 | VEVAEEYKLV | SDTLYFSVAY | IDRFLSLNIL | SRQRLQLLGV | ASMLIAS-KY | | 184 |
| SEQ_ID_NO_1370 | VEVAEEYKLV | ADTLYFSVSY | IDRFLSLNDL | SRQKLQLLGV | SSMLIAS-KY | | 174 |
| SEQ_ID_NO_1346 | VEVAEEYKLV | SETLYLTVSY | VDRFLSFNVL | SRQRLQLLGV | SSMLLAS-KY | | 184 |
| SEQ_ID_NO_1372 | VEVAEEYKLL | PDTLYLTVSY | IDRFLSMNAL | SRQKLQLLGV | SSMLIAS-KY | | 196 |
| SEQ_ID_NO_1374 | VEVAEEYKLL | SDTLYLAVSY | DRFLSTNV | TROKLQLLGV | SSMLISA-KY | | 205 |
| SEQ_ID_NO_1355 | VEVAEEYKLL | SDTLYLAVSY | DRFLSLKTV | NKQRLQLLGV | TSMLIAS-KY | | 177 |
| SEQ_ID_NO_1364 | VEVAEEYKLV | SDTLYLTVSY | VDRFLSAKPL | NRQRLQLVGV | SAMLIASRKY | | 186 |
| SEQ_ID_NO_1378 | VQVHYKFELS | PETLYLTIN | VDRYLASKTT | SRRELQLLGM | SSMLIAS-KY | | 277 |
| SEQ_ID_NO_1377 | LEVHRKFELM | PESLYLTIN | LDRFLSMKTV | PRKELQLVGI | SAMLIAC-KY | | 261 |
| SEQ_ID_NO_1379 | TEVHRKFELM | PETLYLTIN | VDRYLSMNAV | PRRELQLVGI | SSMLIAC-KY | | 266 |
| SEQ_ID_NO_1380 | VEVHYKFELM | EETLYLTVN | DRFLSRQAV | VRKKLQLVGV | TAMLLAC-KY | | 238 |
| SEQ_ID_NO_1383 | VEVHLKFKLM | PETLFLTTNL | DRFLELKTV | TRRNLQLVGV | TAMLVAS-KY | | 188 |

Figure 45 (continued)

| | | | | | | | |
|---|---|---|---|---|---|---|---|
| SEQ_ID_NO_1363 | EEVCAPQVEE | FCYITDNTYL | KDEVLDMESA | VLNYLKFEMS | APTVKCFLRR | 297 |
| SEQ_ID_NO_1373 | EEISPPHVED | FCYITDNTYT | REEVVNMERD | LLSFLNFEIS | SPTTITFLRI | 253 |
| SEQ_ID_NO_1342 | EEISPPHPED | FCYITDNTYT | KEELLKMESD | LKLLKFELG | NPTIKTFLRR | 217 |
| SEQ_ID_NO_1381 | EEISPPHVED | FCYITDNTYT | RQEVVKMESD | LKLLEFEMG | NPTIKTFLRR | 257 |
| SEQ_ID_NO_1382 | EEISPPHVED | FCYITDNTYT | RQEVVKMESD | LKLLEFEMG | NPTIKTFLRR | 257 |
| SEQ_ID_NO_1371 | EEIKPKNVAD | FVDTDNTYS | QQEVVKMEAD | LLKTLKFEMG | SPTVKTFL-G | 215 |
| SEQ_ID_NO_1365 | EEIKPPEVED | FCYITDNTYS | KEEVVNMEAE | LKALKFELG | GPTVKTFLRR | 234 |
| SEQ_ID_NO_1370 | EEIKPPEVED | FCYITDNTYS | KEEVLSMEAE | LKTLKFELG | GPTIKTFLRR | 224 |
| SEQ_ID_NO_1346 | EEINPPHVED | FCYITDNTYT | KEEVVKMEAD | LKSLKFEMG | NPTIKTFLRR | 234 |
| SEQ_ID_NO_1372 | EEISPPHVED | FCYITDNTYK | KEEVVKMEAD | VLKFLKFEMG | NPTIKTFLRR | 246 |
| SEQ_ID_NO_1374 | EEISPPHVED | FCYITDNTYT | KEEVVKMEAD | VLKTLNFEMG | NPTVKTFLRR | 255 |
| SEQ_ID_NO_1355 | EEITPPNVDD | FCYITDNTYT | KQEIVKMEAD | LLALQFELG | NPTSNTFLRR | 227 |
| SEQ_ID_NO_1364 | EEISPPKVED | FMYITDNTFT | RQDVVSMEAD | LLALQFELG | CPTIKTFLRR | 236 |
| SEQ_ID_NO_1378 | EEIWAPEVND | LVCSDGSYS | NFQVLRMEKK | LGALEWYLT | VPTPYVFLVR | 327 |
| SEQ_ID_NO_1377 | EEIWAPEVND | FMHISDNWYT | RDHLQMEKA | LGKLEWYLT | VPTPYVFLVR | 311 |
| SEQ_ID_NO_1379 | EEIWAPEVSD | FIVSDNAYV | REQILIMEKA | LGKLEWYLT | VPTPYVFLVR | 316 |
| SEQ_ID_NO_1380 | EEVSVPNVDD | LVTSDRAYT | RKEVLDMEKS | IVKTLQFNTS | VPTPFVFLRR | 288 |
| SEQ_ID_NO_1383 | EEIWAPEVRD | FMYISDRAYT | RQQILEMEKQ | MLNTLGFHLT | VPTPYCFLNR | 238 |

| | | | | | | | |
|---|---|---|---|---|---|---|---|
| SEQ_ID_NO_1363 | LF-SGCPRVH | EAPCMQLECM | ASYIAELSLL | EY-TMLSHPP | SLVAASAIFL | 345 |
| SEQ_ID_NO_1373 | FL-KAAQDNL | SFLTLQFEFL | SCYLAELSLL | DY-SCVRFLP | SMTAASAIFL | 301 |
| SEQ_ID_NO_1342 | FI-RSAHEDK | KGSILLMEFL | GSYLAELSLL | DY-GCLRFLP | SVVAASVMFV | 265 |
| SEQ_ID_NO_1381 | FT-RSCQEDK | KRSSLLLEFM | GSYLAELSLL | DY-SCLRFLP | SVVAASVVFV | 305 |
| SEQ_ID_NO_1382 | FT-RSCQEDK | KRSSLLLEFM | GSYLAELSLL | DY-GCLRFLP | SVVAASVVFV | 305 |
| SEQ_ID_NO_1371 | FI-RAVQENP | DVPKLKFEFL | ANYLAELSLL | DY-GCLEFVP | SLIAASVTFL | 263 |
| SEQ_ID_NO_1366 | FS-RVGQEGV | DTSDLQFEFL | SCYLAELSLL | DY-NCIKFLP | SLVAASVVFL | 282 |
| SEQ_ID_NO_1370 | FITKVGQEGV | DASELQFEFL | CCYLAELSLL | DY-NCVKFLP | SMVAASVVFL | 273 |
| SEQ_ID_NO_1346 | FT-RVALEDY | KTSNLQLEFL | GFYLAELSLL | DY-NCVKFLP | SLVAASVIFL | 282 |
| SEQ_ID_NO_1372 | LT-RVVQDGD | KNPNLQFEFL | GYYLAELSLL | DY-GCVKFLP | SLIASSVIFL | 294 |
| SEQ_ID_NO_1374 | FT-GVAQEDY | KTPNLQLEFL | GYYLAELSIL | DY-SCVKYVP | SLLAAAVVFL | 303 |
| SEQ_ID_NO_1355 | FT-RVAQEDF | EMSHLQMEFL | CSYLSELSML | DY-QSVKFLP | STVAASAVFL | 275 |
| SEQ_ID_NO_1364 | FT-RVAQEDF | NESLLQIECL | CCYLSELSLL | DY-SCVKFLP | SMLAASAVFL | 284 |
| SEQ_ID_NO_1378 | FI-KASLPDS | D----VEKNM | VYFLAELGMM | NYATIMYCP | SMIAAAAVYA | 372 |
| SEQ_ID_NO_1377 | YI-KAAMPSD | DQ---EIQNM | AFFAELGLM | NYTTISYCP | SMLAASAVYA | 357 |
| SEQ_ID_NO_1379 | FI-KASVPSN | DHRE-EMENM | VFFLAELGLM | HYPTILYCP | SMIAASAVYA | 364 |
| SEQ_ID_NO_1380 | FL-KAAGSEK | K----LELL | SSFIELSLV | EY-QMLKFQP | SLLAAAAYT | 331 |
| SEQ_ID_NO_1383 | FF-KAAGGDR | Q----FQLY | ASYAVECALP | EY-GMLKYSG | STLAAAGVYI | 281 |

Figure 45 (continued)

| | | | | | | | |
|---|---|---|---|---|---|---|---|
| SEQ_ID_NO_1363 | AKYTLDP TRR | PWNSTLRHYT | QYEAMELRGC | VMDLQRLCSN | AHV- - - | STLP | 392 |
| SEQ_ID_NO_1373 | SRFTVLPEVC | PWTLALQQCT | GYKPSELKDC | VLVIHELQSS | LME- - - | ATGR | 348 |
| SEQ_ID_NO_1342 | ARLTIDPNTN | PWNTKLQKWT | GYKVSELKDC | VAIHDLQLN | RKC- - - | PSLT | 312 |
| SEQ_ID_NO_1381 | AKLNIDPYTN | PWSKKMQKLT | GYKVSELKDC | LAIHDLQLR | KKC- - - | SNLT | 352 |
| SEQ_ID_NO_1382 | AKLNIDPYTN | PWSKKMQKLT | GYKVSELKDC | LAIHDLQLR | KKC- - - | SNLT | 352 |
| SEQ_ID_NO_1371 | ARFTIRPNVN | PWSIALQKCS | GYKSKDLKEC | VLLLHDLQMG | RRG- - - | GSLS | 310 |
| SEQ_ID_NO_1366 | ARFMFSTKTH | PWNSALHQLT | RYKPADLKEC | VLNLHDLYLS | RRG- - - | ASLQ | 329 |
| SEQ_ID_NO_1370 | ARFMLNPKSR | PWNSAICQFT | SYKPADLKEC | VLNMHDLYLS | RKG- - - | ATLQ | 320 |
| SEQ_ID_NO_1346 | TRFLMRPKTN | PWSSTLQQYT | GYKAADLREC | VLIIHDLYLS | RRG- - - | GGLQ | 329 |
| SEQ_ID_NO_1372 | SRFTLDPKVH | PWNSLLQHNS | GYKPADLKEC | VLIIHDLQLS | KRG- - - | SSLV | 341 |
| SEQ_ID_NO_1374 | SRFTLQPNTH | PWSLALQQYS | GYKAADLKEC | LILHDLQLS | RRG- - - | GSLA | 350 |
| SEQ_ID_NO_1355 | ARFIIRPKQH | PWNYMLEEYT | RYKAGDLKEC | VAMIHDLYLS | RKC- - - | GALE | 322 |
| SEQ_ID_NO_1364 | ARFIIRPKQR | PWNQMLEEYT | KYKASDLGQP | VGIIHDLYLS | RRG- - - | NSLE | 331 |
| SEQ_ID_NO_1378 | ARCTLNKMPI | -WNETLRWHT | GFSEVQLMDC | AKLLIDFHGG | STD- - - | QKLQ | 418 |
| SEQ_ID_NO_1377 | ARGTLNKGPL | -WTPTLQHHT | GYSEEQLMEC | TKQLVSYHKG | AAE- - - | SKLK | 403 |
| SEQ_ID_NO_1379 | ARCTLNSNPL | -WTETLKIHT | GYSEDOLGDC | AKMLARFHSD | GGGVEKSKLK | | 413 |
| SEQ_ID_NO_1380 | AQCSLKGFKF | -WTRTCEQYT | MYTEDQLLEC | SKMMVGFHRN | AGS- - - | GKLT | 377 |
| SEQ_ID_NO_1383 | AIRGLQTGS- | -WNHTMEAHT | RLSESEVYPC | ACDMAELMRK | APT- - - | ATLT | 326 |

| | | | | | |
|---|---|---|---|---|---|
| SEQ_ID_NO_1363 | AVRDKYSQHK | YKFVAKKFCP | SIIPPDFFK- | ---NSLY- | 425 |
| SEQ_ID_NO_1373 | ALREKYMNHK | YKCVAALHPP | -DIPSCFFD- | ---DA- - - | 378 |
| SEQ_ID_NO_1342 | AIRDKYKQHK | FKCVSLILVP | VVIPTSYFE- | ---DLAE- | 345 |
| SEQ_ID_NO_1381 | AIRDKYKQHK | FKCVSTLLPP | VDIPASYLQ- | ---DLTE- | 385 |
| SEQ_ID_NO_1382 | AIRDKYKQHK | FKCVSTLLPP | VDIPASYLQ- | ---DLTE- | 385 |
| SEQ_ID_NO_1371 | AVRDKYKKHK | FKCVSTLSPA | PEIPESIFN- | ---DVI- - | 341 |
| SEQ_ID_NO_1366 | AVREKYKQHK | FKCVATTPSP | PEIPLSFFEF | EGQILRQL | 367 |
| SEQ_ID_NO_1370 | AVRDKYKQHK | FKCVATTPSP | PEISLSFFEF | RGADP- - - | 355 |
| SEQ_ID_NO_1346 | AVREKYKQHK | FKCVANMPSP | PELPALYFE- | ---EVI- - | 360 |
| SEQ_ID_NO_1372 | AVRDKYKQHK | FKCVSTLTAP | PSIPDEFFE- | ---DII- - | 372 |
| SEQ_ID_NO_1374 | AVRDKYKQHK | FKCVSSLISP | VEIPASFFE- | ---DNRQL | 384 |
| SEQ_ID_NO_1355 | AIREKYKQHK | FKCVATMPVS | PELPLTNFE- | ---DVNI- | 355 |
| SEQ_ID_NO_1364 | AVRNKYKQHK | FKCVATMPVS | PELPQAFFE- | ---DVTIR | 365 |
| SEQ_ID_NO_1378 | GIYRKYSRLE | KGAVALLPQP | LLA- - - - - | - - - - - - | 441 |
| SEQ_ID_NO_1377 | AIYRKFSSPD | RGAVALFPPA | RNLLPTTTT- | ---TTTSS | 437 |
| SEQ_ID_NO_1379 | AVYKKFSSSD | RSSVALFPPA | RSLLLVL- - - | - - - - - - | 440 |
| SEQ_ID_NO_1380 | GVHRKYSTSK | FGFAGKSYPA | LFLLDNRL- - | - - - - - - | 405 |
| SEQ_ID_NO_1383 | AVYKKYSSEK | FMKIATLPVP | HDLRL- - - - | - - - - - - | 351 |

Figure 46

| | | | | | | | |
|---|---|---|---|---|---|---|---|
| SEQ_ID_NO_1404 | -MA------ | ---SEWSKEE | NKLFEQAIAY | YGEGAPDLWH | KVSRAMGGTK | | 39 |
| SEQ_ID_NO_1401 | -MSGSRSSSP | NSKSEWSRKE | NKMFEEALAY | YGEDTPNRWD | KVASAMGGLK | | 49 |
| SEQ_ID_NO_1400 | -MAGSOSSSP | NSNSTWSLKE | NKMFEEALAY | YGESTPNLWD | KVSSAIGGLK | | 49 |
| SEQ_ID_NO_1385 | -MSASRSSSP | NSISQWSQKE | NKMFEEALAY | YGEGTSNRWD | KVSRAMGGLK | | 49 |
| SEQ_ID_NO_1407 | -MSASRSSSP | NSMSKWSPKE | NKMFEQALAY | YGESTPNRWD | KVSSAMGGLK | | 49 |
| SEQ_ID_NO_1387 | -MSSHQTPR | NSSSWTPRE | NKLFEKALAL | FDKDTPDRWQ | NIAKAVGGVK | | 49 |
| SEQ_ID_NO_1393 | MASSSLSKQK | ASDSSWTPKQ | NKLFEKALAK | YDKDTPDRWQ | NVAKAYGG-K | | 49 |
| SEQ_ID_NO_1390 | MASSSMSSQ- | -SSGSWTAKQ | NKAFEQALAT | YDQDTPNRWQ | NVAKVVGG-K | | 47 |
| SEQ_ID_NO_1395 | --MSSMSSQH | GSSGSWTAKQ | NKAFEKALAV | YDKETRDRWS | NVAKAVGG-K | | 47 |
| SEQ_ID_NO_1398 | MASGSMS--- | ---SSWTAKE | NKMFEKALAV | YDRDTPDRWH | KIARAIGG-K | | 43 |
| SEQ_ID_NO_1396 | -MASTRGSG- | ---RPWSAKE | NKAFERALAV | YDKDTPDRWA | NVARAVEG-R | | 44 |
| SEQ_ID_NO_1394 | MASSSMSAS- | ---GSWSVKE | NKAFERALAV | YDKDTPDRWY | NVAHAVGG-K | | 45 |

| | | | | | | | |
|---|---|---|---|---|---|---|---|
| SEQ_ID_NO_1404 | TADEVRLHFE | LVDDIKLLE | ARRVPFPKYN | TOGAIN---- | ---------- | | 75 |
| SEQ_ID_NO_1401 | SAEEIRCHYE | DLTDDVKTIE | SGRVDFPKYK | TQGYWT---- | ---------- | | 85 |
| SEQ_ID_NO_1400 | SAEEVRCHYE | DLVDDVKMIE | SGRVIYPKYK | TQGFWTRG-- | ---------- | | 87 |
| SEQ_ID_NO_1385 | SAEEVRCHYE | DLDYDVKMIE | SGHVPYPKYK | THGFWT---- | ---------- | | 85 |
| SEQ_ID_NO_1407 | SAEEVRCHYE | DLDYDVKMIE | SGHVPYPQYK | TQGFWTRGSL | MPTNYVGSNP | | 99 |
| SEQ_ID_NO_1387 | SAEEMKRHYE | FLIEDLKHIE | SGRVPIPNIYK | SSRSYSNTNE | EER------- | | 92 |
| SEQ_ID_NO_1393 | SADEVKRHYE | ILEDLRHIE | SGHVPLPKYK | STGSSTNVEE | EERLLKYLKL | | 99 |
| SEQ_ID_NO_1390 | TTEEVKRHYE | LLVQDINSIE | NGHVPFPNYR | TSGGCTNGRL | SQEEKRYVLS | | 97 |
| SEQ_ID_NO_1395 | TAEEVKRHYE | LLRDVFFID | NGMVPFPKYK | TTGGSHNSTS | Q--------- | | 88 |
| SEQ_ID_NO_1398 | TADEVKRYYD | LLVEDVRRIE | AGQMPYANYR | SSNGRG---- | ---------- | | 79 |
| SEQ_ID_NO_1396 | TPEEVKKHYE | LVEDIKYIE | SGKVPFPNYR | TTGGNMKTDE | KRFRNLKIR- | | 93 |
| SEQ_ID_NO_1394 | TPEEVKKHYE | LLVEDIKHIE | SGKVPFPNYK | KISVSHEEKR | MRNMSLH--- | | 92 |

| | | |
|---|---|---|
| SEQ_ID_NO_1404 | ---------- | 75 |
| SEQ_ID_NO_1401 | ---------- | 85 |
| SEQ_ID_NO_1400 | ---------- | 87 |
| SEQ_ID_NO_1385 | ---------- | 85 |
| SEQ_ID_NO_1407 | SIMTKISYFQ | 109 |
| SEQ_ID_NO_1387 | ---------- | 92 |
| SEQ_ID_NO_1393 | N--------- | 100 |
| SEQ_ID_NO_1390 | ---------- | 97 |
| SEQ_ID_NO_1395 | ---------- | 88 |
| SEQ_ID_NO_1398 | ---------- | 79 |
| SEQ_ID_NO_1396 | ---------- | 93 |
| SEQ_ID_NO_1394 | ---------- | 92 |

Figure 47

| | | |
|---|---|---|
| SEQ_ID_NO_1419 | ---------- ----- MSFYL F---------- ---------- --FLFITMPL | 14 |
| SEQ_ID_NO_1421 | ---------- -----MAC-- F---------- ---------- --RSRSRAAA | 12 |
| SEQ_ID_NO_1409 | ---------- -----MGQRR F---------- ---------- --EDERAALA | 14 |
| SEQ_ID_NO_1425 | ---------- -----MADC- ---------- ---------- ---TTMRLAS | 11 |
| SEQ_ID_NO_1424 | MEPWRWQICL VTPRSFLFQA FVRTGFRAMR VSSASSTPPP PAFAAAAMAV | 50 |
| SEQ_ID_NO_1413 | ---------- -----MNRRF L--------- ---------- --FVLSSLSF | 14 |
| SEQ_ID_NO_1418 | ---------- -----MRMEH I--------- ---------- --YKFQHWLF | 14 |
| SEQ_ID_NO_1415 | MEGELKMRGG DLIRPGRFCI L--------- ---------- --SVATISS | 29 |

| | | |
|---|---|---|
| SEQ_ID_NO_1419 | IVFCDF---- ---------- --EMPSGSST QFHSFHE--- ---------- | 36 |
| SEQ_ID_NO_1421 | VVVVTM---- ---------- -LLLDACSEV SASSSPQF-- ----RKM--- | 38 |
| SEQ_ID_NO_1409 | TVASLL---- ---------- -LILTTAQAA AAASGRH--- ---LSLPT-  | 42 |
| SEQ_ID_NO_1425 | SMTLIL---- ---------- -LLLVASQAL VVSGESSS-- ----SAM--- | 37 |
| SEQ_ID_NO_1424 | VLLAML---- -------RSD VALAAAASGN DDTGLSPLMP PPPPLAAPVP | 89 |
| SEQ_ID_NO_1413 | AVLFLF---- ---------- LVALFSGDGK NINGSFGL-- ----KLLR-- | 42 |
| SEQ_ID_NO_1418 | FIGLGV---- ---------L LSLSLSVKAN DFEGSNDR-- ----RSIALK | 45 |
| SEQ_ID_NO_1415 | LLAVFFEDIY HSSMHASSLV SLLLNPVDTQ SLTELFHL-- ----KAVSEI | 73 |

| | | |
|---|---|---|
| SEQ_ID_NO_1419 | -------DKN GSLTVSEKVE HAH------- ---------- --------YTPR | 56 |
| SEQ_ID_NO_1421 | ---------- -LVSYNASSM SSS------- ---------- -GG-GGHSAE | 58 |
| SEQ_ID_NO_1409 | --QKAAAARM NDTSSSDMQV ITP------- ---------- -APLAISTAA | 72 |
| SEQ_ID_NO_1425 | --QSKTLNMN KLLNISED-- HSP------- ---------- -NG-GRHWMQ | 64 |
| SEQ_ID_NO_1424 | AAVSPAPATP PAVLSPRKLL RPPGADVVGV GFVSGSGGGG GGGGGGDGVR | 139 |
| SEQ_ID_NO_1413 | --LRINQGNH TLLTPHRKLL RTA------- ---------- -------LAEPN | 68 |
| SEQ_ID_NO_1418 | A-RSFVSINE NRTALSRKLL LSP------- ---------- -DI--GDGTN | 74 |
| SEQ_ID_NO_1415 | GSKKPVFYKE NNTNFARKLL QLP------- ---------- -DA---GSTN | 102 |

| | | |
|---|---|---|
| SEQ_ID_NO_1419 | KFWFHGSCTK -RDISISDSK GST--SGIPQ YLYQIVNTCV SG-------  | 95 |
| SEQ_ID_NO_1421 | PLE-LEECSK -DLLEVFQNN APSMAGGMPT YSVEITNTCI -D-------  | 97 |
| SEQ_ID_NO_1409 | RMG-PDGCSG -EDVAVYQSS ANPLPSGIPA YTVRINVCS GG--------  | 112 |
| SEQ_ID_NO_1425 | RMQ-PDSCSE -QNVVVYQNN AEHLPSGIPT YSVEIINVCT -A-------  | 103 |
| SEQ_ID_NO_1424 | TRRVDDGCAG ADDIAIYQGR ATPLPSGVPA YTVDVMNRCA GGGGGGGDEE | 189 |
| SEQ_ID_NO_1413 | RIW-GEKCSK -ADIVLNQGP TAPLPSGIPT YTVEILNVCV SG-------  | 108 |
| SEQ_ID_NO_1418 | RIG-QDCSK -DDIVLFQGS TNPLPSGVPS YTVEIFNSCV SD-------  | 113 |
| SEQ_ID_NO_1415 | RIG--AACSK -DGIDIVQGS TAPLPNGIPS YTYQILNVCV SG-------  | 141 |

Figure 47 (continued)

| | | | | | | | |
|---|---|---|---|---|---|---|---|
| SEQ_ID_NO_1419 | CAPYDIHLHC | GWFASARIIN | PKLFKRLSYD | DCLVHGGKPL | TSNQIRFTY | | 145 |
| SEQ_ID_NO_1421 | CAVCDVHIAC | SDFASNDVID | PDKFRRLGFN | DCLVNGGGSI | EPSFPVSFQY | | 147 |
| SEQ_ID_NO_1409 | CTVYDVHVSC | SDFASTELVD | PAKFQRVGFN | DCVVKGGGAL | EPSETVSFQY | | 162 |
| SEQ_ID_NO_1425 | CTVYDVHISC | SEFASAELVD | PSQFQRIGFN | DCLVKGGGRL | GPSEAVSFQY | | 153 |
| SEQ_ID_NO_1424 | CAIAGIHVRC | GWFSSVSLVD | PRVFRRLGHD | DCLLNDGRPL | LAGETVSFEY | | 239 |
| SEQ_ID_NO_1413 | CDISGIHLTC | GWFSSARLIN | PKIFKRLRYN | DCLVNDGKPL | INGGTLSFQY | | 158 |
| SEQ_ID_NO_1418 | CNIAEIHVSC | GWFSSVRLVN | PRVFRRLDYD | DCLVNDGQPL | GPGQSLSFQY | | 163 |
| SEQ_ID_NO_1415 | CSISNIHVSC | GWFSSAKLIN | PSVFRRIYYD | DCLVNDGEPL | GPGETLSFQY | | 191 |

| | | | | | | | |
|---|---|---|---|---|---|---|---|
| SEQ_ID_NO_1419 | SNSFMYPLAF | KSARFC | ---------- | ---------- | ---------- | ---------- | 161 |
| SEQ_ID_NO_1421 | GNSFPYPMTV | ASASCDCN | ---------- | ---------- | ---------- | ---------- | 165 |
| SEQ_ID_NO_1409 | SNSFSYHLSV | ASVACR | ---------- | ---------- | ---------- | ---------- | 178 |
| SEQ_ID_NO_1425 | SNSFAYPLAV | ANVACFHYSI | VWASMIPCLP | EHACHTASSV | KGLGPRPHA | | 202 |
| SEQ_ID_NO_1424 | TNSFPYKLSV | SVATCVVDPA | AP-------- | ---------- | ---------- | ---------- | 261 |
| SEQ_ID_NO_1413 | ANTFLYPLSV | SRVVCS | ---------- | ---------- | ---------- | ---------- | 174 |
| SEQ_ID_NO_1418 | ANSFSYPLSV | ASVSCF | ---------- | ---------- | ---------- | ---------- | 179 |
| SEQ_ID_NO_1415 | ANSFLYPLSV | SSVACC | ---------- | ---------- | ---------- | ---------- | 207 |

Figure 48

```
SEQ_ID_NO_1436   ..............MTRPARFL ETAATPPQPS EQ.............ML A   23
SEQ_ID_NO_1444   ..........M GVHARAMSWY TSPPGSPAPG SAAEA-QHAL SSSPRGGDTS   40
SEQ_ID_NO_1452   ..........M GVHGRSMGWY LGPPGSPAPG SAVAEAQHAL SSSPGGGDAS   41
SEQ_ID_NO_1428   ............MHRL--LL ESHGGGNETS GSGGG-----DGYTRDMN   29
SEQ_ID_NO_1430   MMQAKTAMVT TLYHRPHRLL DTQPNASPS LPNGS---R TRNAFANEAN   46
SEQ_ID_NO_1432   ............MHR--RM DTVPLDVAPA NGN----R THDSYINETN   30
SEQ_ID_NO_1439   ..................MPP SVGG-...N TSDTFISDAN   19
SEQ_ID_NO_1442   ............MRRLSDAG EATPLVTPA AAAAAGGTLA SPAAAGSNAN   37
SEQ_ID_NO_1453   ............MRRLGDVV EAPALVLTPA SMQQA----..GGRGSSGA   31
SEQ_ID_NO_1457   ............MRRLVDVV EAPALVLTPA WAATA---S MQQAGGSSGA   34

SEQ_ID_NO_1436   AESDMVVILS ALLCALICVA GLAAVVRCAL -MRRFTTGE NSPSANK--   68
SEQ_ID_NO_1444   FDTNMVVVLA ALLFALLFAL GINSLARCLI RWARRAPAAE GGGG------   84
SEQ_ID_NO_1452   FDTNMVIILA ALLFALLFAL GLNQLARCLI RWARRASEGE AGARGG----   87
SEQ_ID_NO_1428   FDANMVIILA ALLCALILAL GLNSILRCAM RCGFGLSSSA AAGTVADRAL   78
SEQ_ID_NO_1430   FDTNMVIILA ALLCALICAL GLNSIMRCTF RCGRRFGLDA TEETAARLAA   96
SEQ_ID_NO_1432   FDTNMVIILA ALLCALIGAL GLNSIVRCLL RCSSRFALET TEEAAARLAA   80
SEQ_ID_NO_1439   FDTNMVIILA ALLCALICAL GLNSIARCAL RCGRPFGNET AEDAAARLAS   69
SEQ_ID_NO_1442   FDANMVIILA ALLCVLIFAL GLNSVIRCVL HCGRRLAPSS SLAASATTAR   87
SEQ_ID_NO_1453   LDASMVVILA ALLCVVICAL GLTSLIRCAL HCARGLSPTT ATPTPSVSTA   81
SEQ_ID_NO_1457   LDANMVIVLA ALLCVVICSL GLSSLIRCAL HCARGLSPSP AMATPAAATT   84

SEQ_ID_NO_1436   ........G LKKKALQSLP RSTF TAAEST SGTAAEDG---GDSTECAI   105
SEQ_ID_NO_1444   ........G FEKRVLRSMP VEVY------GAAAV----TVADVCAI   112
SEQ_ID_NO_1452   ........G LKRRALRSIP VEVY------GACGADGAA A-VAADVCAI   120
SEQ_ID_NO_1428   ........G LKKRELKKFP VAEY------GSGEVK---AATECAI   107
SEQ_ID_NO_1430   AT------G LKKSALRRLP VAVY------GSGMD----WATECPI   126
SEQ_ID_NO_1432   T-------G LKKRDLRQIP VAIY------GAGGS----SATECPI   109
SEQ_ID_NO_1439   T-------G LKRRELSRIP VAVY------GAAGENT---PATECPI   100
SEQ_ID_NO_1442   TTTSVHVQAG LKRKALRKIP VEVY------GGAKSSGGA LPATATECAX   130
SEQ_ID_NO_1453   AT------AG LKKTELRRIP VEVY------GAKQAG---VPDGECAI   113
SEQ_ID_NO_1457   TG------G LKKKELRRIT VEVY------GAKQAG---VPDAECAI   115
```

Figure 48 (continued)

| | | | | | | | |
|---|---|---|---|---|---|---|---|
| SEQ_ID_NO_1436 | CLSDFADGEE | IRVLPLCGHS | FHVECIDKML | VSRSSCPXCR | XILRPV- -X | 152 |
| SEQ_ID_NO_1444 | CLGEFADGEK | VRVLPRCTHG | FHVRCVDTWL | LSHDSCPTCR | ASVLDG- - - - | 158 |
| SEQ_ID_NO_1452 | CLGEFADGEK | VRVLPRCAHG | FHVRCVDTWL | LSHDSCPTCR | GTVLEAAAPG | 170 |
| SEQ_ID_NO_1428 | CLGEFADGER | VRVLPPCNHS | FHMSCIDTWL | VSHSSCPNCR | HSLIEV- - - | 153 |
| SEQ_ID_NO_1430 | CLGEFMGGEK | VRVLPKCNHG | FHVRCIDTWL | LSHSSCPTCR | QSLLDQA- -T | 174 |
| SEQ_ID_NO_1432 | CLGEFVDGEK | VRVLPKCNHG | FHVRCIDTWL | LSHSSCPNCR | HSLLEH- - -T | 156 |
| SEQ_ID_NO_1439 | CLGEFEKGDR | VRMLPKCNHG | FHVRCIDTWL | LSHSSCPNCR | HSLLEK- - - - | 146 |
| SEQ_ID_NO_1442 | CLGEFADGEK | VRVLPRCHHG | FHVRCIDMML | ATHTSCPNCR | ASLAED- - - - | 176 |
| SEQ_ID_NO_1453 | CLGDFADGDK | VRVLPRCHHG | FHVRCIDTWL | AAHTSCPTCR | DSILSV- - - | 159 |
| SEQ_ID_NO_1457 | CLGDFADGDK | VRVLPRCHHG | FHVGCIDTWL | AAHTSCPTCR | DSILSV- - - | 161 |

| | | | | | | |
|---|---|---|---|---|---|---|
| SEQ_ID_NO_1436 | CDRCGHASXA | GSQMKDHQHX | QHXSQLTSXX | XTFXP | | 187 |
| SEQ_ID_NO_1444 | - -AKAATPAG | GGSRMQGSEA | AAIAVVIR- - | - - - - - | | 184 |
| SEQ_ID_NO_1452 | KDKAAASAPA | GGSRRQGSEA | AAIAVVIG- - | - - - - - | | 198 |
| SEQ_ID_NO_1428 | - - - - - - -HVA | GSE- - - - - | - - - - - - - - - - | - - - - - | | 159 |
| SEQ_ID_NO_1430 | SSSDGAVEIE | NGIRPHGNSS | GGDQADVPVP | ADEVG | | 209 |
| SEQ_ID_NO_1432 | TDSGAAQEVT | GAARPGENDP | GRQARGWP- | -EHGG | | 188 |
| SEQ_ID_NO_1439 | - - -PAAAPES | GSGRRSEVVV | VVEQAS- - - | - - - - - | | 169 |
| SEQ_ID_NO_1442 | - - - -GAAAAN | GGGR- - - - - | - - - - - - - - - - | - - - - - | | 186 |
| SEQ_ID_NO_1453 | - - - - -HGVVA | GGQT- - - - - | - - - - - - - - - - | - - - - - | | 168 |
| SEQ_ID_NO_1457 | - - - - -HAGVT | GGQT- - - - - | - - - - - - - - - - | - - - - - | | 170 |

Figure 49

```
SEQ_ID_NO_1473   ----------   ---MKLVWCP ETASQAFIAG VSALSDAEHG PAGSAG-VAE    36
SEQ_ID_NO_1474   ----------   ----------  -MASKAYIDG VRALAG--HD LAGAAADVAE    27
SEQ_ID_NO_1476   MAPPPPPAAQ   VVRMKLVWCP EMASKAYIDG VRALAG--HD LAGAAADVAE    48
SEQ_ID_NO_1471   ----------   ---MKLAWSP ERASKAYIDT VQSCQV--FR ESG---VAE     31
SEQ_ID_NO_1463   ----------   ---MKLVWSP ETASDAYIDT VKSCKS--DK ESG---VAE     31
SEQ_ID_NO_1465   ----------   ---MKLVWTP DTALKAYVCI VKTCED--FK ESS---VAE     31

SEQ_ID_NO_1473   LVSAMVGGWN AQLVVEAPEV SAPDSATMSL ALAAAAGRTG GRYARVLPDE    86
SEQ_ID_NO_1474   LVSAMAGGWN ARLVVEAPDS AAPAAAATSL ALAAVARRTG GRYALVLPDR    77
SEQ_ID_NO_1476   LVSAMAGGWN ARLIVEAPDS AAPAAAATSL ALAAAARRTG GRYALVLPDR    98
SEQ_ID_NO_1471   FISAMAAGWN SQLIVETWSQ GGL---ATSV GLALARSHTC GRHVCVVPDE    79
SEQ_ID_NO_1463   FLSATAAGWN ARLIVETWSR GDP--TTSV GLAVAATHTG GRHVCIVPDE    79
SEQ_ID_NO_1465   LLSAMAAGWN AKLIVESWSK AGP--ATSI GLAVAAKHTC GRHVCVVPDE    79

SEQ_ID_NO_1473   DA--------   ---------- -----DRAMA ELEGVDFLVV DARRRDGAAV  113
SEQ_ID_NO_1474   DAAASAAET ------AEV VVGEADEAMA GLHGVDLLVV DARRRDAAAV  120
SEQ_ID_NO_1476   DAAASAAET ------AEV VVGEADEAMA GLHGVDLLVV DARRRDAAAV  141
SEQ_ID_NO_1471   RARSEYAERM GEAGVT-AEI VVGEPEENME GLVGVDFLVV DSRRKDFTRV  128
SEQ_ID_NO_1463   QSKLEYVLAM RGFVTTEVVV VGESVFNTME EFPGVDFLVV DSKRREFVRT  129
SEQ_ID_NO_1465   GSRSEYVKAM HGAGMRETEV LVGEAEEVMA GLVGVDFLVA DCRRRDFVRV  129

SEQ_ID_NO_1473   LAAARPGPRG MVVV-RHGDE RRPGTKALEA SMAAGT-RV VRSVYLPVDK  160
SEQ_ID_NO_1474   LRAARPGARG MVVV-RHGDG RORGAKDLAA SMAAGT-RV VRSVYLPIGK  167
SEQ_ID_NO_1476   LRAARPGARG MVVV-RHGDG RORGAKDLAA SMAAGT-RV VRSVYLPIGK  188
SEQ_ID_NO_1471   LRIAKLSNKG AVLLCKNANS NSKGFIARS LVAKGSRRV VRSAFLPVGK  177
SEQ_ID_NO_1463   LRFAKLSNKG AVLVCKNAMH RAISGFKMD VLKRGT-RV VRSVFLPVGS  177
SEQ_ID_NO_1465   LRFAKLSHKG AVLACKNAFQ QSVSGFKMHG VLERGT-RV VKTAYLPVGQ  177

SEQ_ID_NO_1473   GVEVLHVGV- GKGPSLQCRR SRSASSRWIR HVDHKTGEEH LFRRP         204
SEQ_ID_NO_1474   GVEVLHVGV- GKGPSLQNHR DRRSTSRWIR HVDHDTGEEH VFRRQ         211
SEQ_ID_NO_1476   GVEVLHVGV- GKGPSLQNHR DRRSTSRWIR HVDHDTGEEH VFRRQ         232
SEQ_ID_NO_1471   GLDMAHVSAS G-G----N- -NSSGHRWIK HVDQHSGDVH FIRR-         213
SEQ_ID_NO_1463   GLDIVHVGAT GRG-----D SRNLRSRWIR HVDHLSGEEH LFRR-         215
SEQ_ID_NO_1465   GLDMAHIGSN G-G----DKR SRGGPSRWIK HIDRKSGEEH VFRE-         216
```

Figure 50

| | | | | | | | |
|---|---|---|---|---|---|---|---|
| SEQ_ID_NO_1493 | MTFLMPSPEV | ---STAFAKI | FSNPT-PRHK | FLKSCAISKN | DDEKVWSKTN | | 46 |
| SEQ_ID_NO_1503 | MAFLLPKLTT | ---PSCKLPP | S--PL-LKPQ | LAQPVHGGGK | IQGSVFGSVA | | 44 |
| SEQ_ID_NO_1508 | MAFLLPKLTT | PSGPSCKLPP | S--PL-LKPQ | LAQPGHSGGK | IQGSVSGAGA | | 47 |
| SEQ_ID_NO_1501 | MAFLLPKLTT | ---PPCRSPP | P--SP-LKPQ | LGLPSHGGGR | ----LHGAGS | | 40 |
| SEQ_ID_NO_1504 | MAFLLPKLTT | ---PSCKSPP | S--PL-LKSQ | LGLPGGGKLQ | ---------P | | 34 |
| SEQ_ID_NO_1505 | MAFLLPKLTT | ---PSCKSPP | S--PL-LKSQ | LGLPGGGKLQ | ---------P | | 34 |
| SEQ_ID_NO_1495 | MAFLLPNLSL | ---PSLLINS | KSFKDREKPV | LYQTQTLPSH | ---------- | | 35 |
| SEQ_ID_NO_1499 | MAFLLPNLSL | ---PSFLLQT | GKSLK-EKPI | STHSLSISSS | -----SSSSN | | 40 |
| SEQ_ID_NO_1491 | MAFLLSNLSS | ---PSIHLQT | GKYPN-LKPI | FSQSLSSSSS | ---------V | | 37 |

| | | | | | | | |
|---|---|---|---|---|---|---|---|
| SEQ_ID_NO_1493 | ARVGVKDVGS | TVSGLSQNLR | LYVQFSAPVK | -------RGS | KSSKEEEEKQ | | 89 |
| SEQ_ID_NO_1503 | AQVAAPGHLS | LLLLSASQQ | AAAPL-AAKST | ATKNR----- | GKGGGDPQRS | | 89 |
| SEQ_ID_NO_1508 | AQVAAPGHLS | LLLLSAPQQ | AADPL-ASKST | ATKNR----- | GKGGGDPQRS | | 91 |
| SEQ_ID_NO_1501 | AQAAAPTHLN | LPLLSASQQ | EAPL-TAKSA | ETRNRAASGG | GGGGGDPRRS | | 88 |
| SEQ_ID_NO_1504 | AQAVAPSHLN | LLLLLGASQQ | EAAAVPTPKS | RSKNGGGRSG | GGGGEDPRRS | | 84 |
| SEQ_ID_NO_1505 | AQAVAPSHLN | LLLLLGASQQ | EAAAVPTPKS | RSKNGGGRSG | GGGGEDPRRS | | 84 |
| SEQ_ID_NO_1495 | -YQTTTTTTS | TTTKKPTNTN | SSMPPPLQVK | T------PPG | AQDKEQHQRD | | 79 |
| SEQ_ID_NO_1499 | SYEFEEGSLS | LLSLPVQAP- | -----PAPGA | QVKTM--PSE | QDKHQQHGKD | | 82 |
| SEQ_ID_NO_1491 | SYEFVEENLS | TLSLLSIQS- | ----PLPLKDT | QVQTR--HSS | QDKHNNHDRD | | 80 |

| | | | | | | | |
|---|---|---|---|---|---|---|---|
| SEQ_ID_NO_1493 | DYYVNMGYAI | RTLRKELPDI | FYRELSFDIY | RDDIVFKDPL | NTFLSIDNYK | | 139 |
| SEQ_ID_NO_1503 | DFYLNLGTAV | RTLRDDLPDV | FVREPNYDIY | REDITFVDPL | NTFHGIDNYK | | 138 |
| SEQ_ID_NO_1508 | DFYLNLGTAV | RTLRDDLPDV | FDREPNYDIY | REDITFVDPL | NTFHGIDNYK | | 141 |
| SEQ_ID_NO_1501 | DFYLNLGAAV | RALRDDLPAV | FLREPNYDIY | REDITFVDPL | NTFHGIDNYK | | 138 |
| SEQ_ID_NO_1504 | DYYLNLGTAV | RTLRDDLPAV | FVREPNYDIY | REDITFVDPL | NTFHGIDNYK | | 134 |
| SEQ_ID_NO_1505 | DYYLNLGTAV | RTLRDDLPAV | FVREPNYDIY | REDITFVDPL | NTFHGIDNYK | | 134 |
| SEQ_ID_NO_1495 | EFYVNLGLAV | RTLREDLPVL | FTEDLNYDIY | RDDITFIDPL | NTFTGIDNYK | | 129 |
| SEQ_ID_NO_1499 | EFYINLGLAI | RTLREDLPLL | FSKDLNYDIY | RDDITLVDPA | NTFSGIENYK | | 132 |
| SEQ_ID_NO_1491 | EFYINLGVAV | RTLREDLPLL | FTRDLNYDIY | RDDITFVDPM | NTFTGMDNYK | | 130 |

| | | | | | | | |
|---|---|---|---|---|---|---|---|
| SEQ_ID_NO_1493 | SFFSAPRFHG | RIFFKALNLD | VSVWQPMEN | VLMVRWIHG | IPRVPWESHG | | 189 |
| SEQ_ID_NO_1503 | TIFWALRFHG | RLLFREIGLD | VSRIWQLTEN | SIVVRWELWG | TPRVPWESYG | | 188 |
| SEQ_ID_NO_1508 | TIFWALRFHG | RLLFREIGLD | VSRIWQLTET | SIVVRWELWG | TPRVPWESYG | | 191 |
| SEQ_ID_NO_1501 | TIFWALRFHG | RLLFSEIGLD | VSRIWQLTET | SIVVRWELWG | TPRVPWESYG | | 188 |
| SEQ_ID_NO_1504 | TIFWALRFHG | RLLFREIGLD | ISRIWQLTEN | SIVVRWELWG | TPRVPWESYG | | 184 |
| SEQ_ID_NO_1505 | TIFWALRFHG | RLLFREIGLD | ISRIWQLTEN | SIVVRWELWG | TPRVPWESYG | | 184 |
| SEQ_ID_NO_1495 | LIFWALRFHG | KMLFREISLE | VYRIWQPSEN | VLLIRWNLKG | VPRVPWEAKG | | 179 |
| SEQ_ID_NO_1499 | LIFWALRFHG | KILFRDXXXE | XYRVWQPSEN | MLLIRWNXKG | VPRVPWEAKG | | 182 |
| SEQ_ID_NO_1491 | IIFWALRFHG | KILFRDISLE | IFRVWQPSEN | MLLIRWNLKG | VPRVPWEAKG | | 180 |

Figure 50 (continued)

| | | | | | | | | |
|---|---|---|---|---|---|---|---|---|
| SEQ_ID_NO_1493 | RFDGTSEYKL | DKKGKIYEHR | VDNTALNSPP | KF-HMLAVED | LIRSVGCPST | | | 238 |
| SEQ_ID_NO_1503 | CFSGTSRYKV | DRNGKIYEHK | VDNLALDFPR | SVAKVGSIAD | MV-VATP--S | | | 235 |
| SEQ_ID_NO_1508 | CFSGTSRYKV | DRNGKIYEHK | VDNLALDFPR | SVAKVGSIAD | MV-VATP--S | | | 238 |
| SEQ_ID_NO_1501 | CFSGTSRYKV | DRNGKIYEHK | VDNLALDFPR | PAVKVSSITN | LV-VAAYPPS | | | 237 |
| SEQ_ID_NO_1504 | CFSGTSRYKV | DRNGKIYEHK | VDNLALDFPR | PAAKVGSIAD | IV-VATCPPS | | | 233 |
| SEQ_ID_NO_1505 | CFSGTSRYKV | DRNGKIYEHK | VDNLALDFPR | PAAKVGSIAD | IV-VASCPPS | | | 233 |
| SEQ_ID_NO_1495 | EFQGTSRYKL | DRNGKIYEHK | VDNLAFNFPQ | QLKPAASVLD | LV--AACPAS | | | 227 |
| SEQ_ID_NO_1499 | EFQGTSRYKL | DRNGKIYEHK | VDNLAFNFPH | QLKPATSVLD | LV--TACPAS | | | 230 |
| SEQ_ID_NO_1491 | EFQGTSRYKL | DRNGKIYEHK | VDNLAFNFPQ | QLKPAASVLD | LVTASPASS | | | 229 |

| | | | | | | | |
|---|---|---|---|---|---|---|---|
| SEQ_ID_NO_1493 | PRPTY----- | ---------- | ---------F | ELSSASPPEK | NI-----IKP | 259 |
| SEQ_ID_NO_1503 | PNLTF-MNVV | G-TGDGCSWT | KLYEAVLEAV | EREEHSSTGI | GVGALGPVGC | 283 |
| SEQ_ID_NO_1508 | PNLTF-MNVV | G-PGDGCSWT | KLYEAVVEAV | EREEHGSTGI | GVGGL-PVPC | 285 |
| SEQ_ID_NO_1501 | PNPTF-MDVV | G-TGDGCSWT | KLYRAVLETV | EREGDIPAGI | CMEGL--LTC | 283 |
| SEQ_ID_NO_1504 | PNLTF-MDMV | GSTGDGCSWA | NLYQAVVETV | EQEGNDPAGI | AIEGL--LTC | 280 |
| SEQ_ID_NO_1505 | PNLTF-MDMV | GSTGDGCSWA | NLYQAVVETV | EREGNDPAGI | AIEGL--LTC | 280 |
| SEQ_ID_NO_1495 | PNPTFLGPA | D--VYSSSW | EFYRAVRETL | DXEN---STN | CFCKM-ATC | 270 |
| SEQ_ID_NO_1499 | PNPTFVFGS- | ---SYSSSW | EFYQAVQRTL | DKQQDQI--M | MQDRF--VLC | 272 |
| SEQ_ID_NO_1491 | PNPTFFSPV | D--SYSSSW | KFYQAVRGIL | ETEDMFVTTD | CL----VTC | 272 |

| | | |
|---|---|---|
| SEQ_ID_NO_1493 | P-------- | 260 |
| SEQ_ID_NO_1503 | G----CGCSF | 289 |
| SEQ_ID_NO_1508 | SFGCGCGSSF | 295 |
| SEQ_ID_NO_1501 | S-------- | 284 |
| SEQ_ID_NO_1504 | S-------- | 281 |
| SEQ_ID_NO_1505 | S-------- | 281 |
| SEQ_ID_NO_1495 | S-------- | 271 |
| SEQ_ID_NO_1499 | L-------- | 273 |
| SEQ_ID_NO_1491 | S-------- | 273 |

Figure 51

```
SEQ_ID_NO_1520   MDSLPKLR---------- -HPSPFPTPL SSSLSFRSLP PPHFPSSSFR   37
SEQ_ID_NO_1510   MESLGKLQLH HQPFHLSFTH TSSSTFPKNL -----FKSSI QPSSL---LK   42
SEQ_ID_NO_1512   MESLTKLHCR LQPLHLSFNH QRPSFAKPI  SSSVSFRTSL ---SSSSPFK   45
SEQ_ID_NO_1516   MESVAKLHCR HQPFNLSLNP HRPSFPKPI  -ISLSFKTPP PSSSSPFKLS   48

SEQ_ID_NO_1520   LPSIRASSSP SQNDPAFRTP RNTPSLPPLL QTLTSFLSPL LETTCIVILA   86
SEQ_ID_NO_1510   SASIKASSSK FQNS---TP  LPK------- ST---PFRL  FKSTCITLTT   78
SEQ_ID_NO_1512   LTSIRALSSS SSS---SVP  LHQTPKPSLL QT---LAPL  LKTTCITITA   87
SEQ_ID_NO_1516   STSIRASSSS SSR----TP  LN-------- KN----LGTI KITSITLTA   82

SEQ_ID_NO_1520   AAAFFFMRFH HT-PAVIAAP LTSPAAETDT -----AFTQE EAERLLEERL   130
SEQ_ID_NO_1510   AAALLLANLH LKSPAIAAPI APPPSVESKE -----NVTLE EEERALDEHL   123
SEQ_ID_NO_1512   GAALLFMRFH QK-PALAATP TVTPTVEPAQ TDSL-NVSLE DOEKTIEEHL   134
SEQ_ID_NO_1516   AAALFFTRLN IK-PAIASPL TASSTVDPTE ESSKENVSYE EQERALQDYL   131

SEQ_ID_NO_1520   STNPRDTEAL HALMEVKIKA RKMDEAFEVL NRLIELEPEE QEWPLLKANM   180
SEQ_ID_NO_1510   ITHPSDVDAL RSLMEVKIKS RKLTEAVEVI DRLIKLEPEE KEWPVLKANI   173
SEQ_ID_NO_1512   TQYPNDVEAL QSLMEVRIKS RKLPQAIEVI DRLIQLEPED TEWPMLRAQI   184
SEQ_ID_NO_1516   SQNPNDIEAL RSLMEVRIKS KKLVEAIEVV DRLIELEPNE QEWPLLKSQI   181

SEQ_ID_NO_1520   HLYNDDHASA RKLFEEILKK DPLRVEAFHG LVMATAQSNE PLKSLLKRVE   230
SEQ_ID_NO_1510   FTYSGDLDLA KTGFEEILAK DPLRVEAYHG LLMAYSDAGL DLKEVESRIE   223
SEQ_ID_NO_1512   HSYSGDFALA KNEFEEILAK DPVRVEAFHG LVMASSESGQ KLKELEKRIE   234
SEQ_ID_NO_1516   YTYSGDFESA KDGFEAILKK DPLRVEAYHG LVMANSESGG SLEVVLKRIE   231

SEQ_ID_NO_1520   EAIEVCKKQK KDSDVRDFRL LIAQIKVMEG DYTEALKAYQ ELVKEEPRDF   280
SEQ_ID_NO_1510   EAMLKCKKEN NQNDFRDFKL LVAQIRVIEG KHSEALKLYQ ELVKEEPRDF   273
SEQ_ID_NO_1512   GAMEKCKKEK KNKDFRDFKL LIAQIRVIEG DHLEALKVYE GLVKEEPRDF   284
SEQ_ID_NO_1516   SAMDKCKKEK KTSDLRDFKL LVAQVRVMEE KYLDALKVYE ELVKEEPRDF   281

SEQ_ID_NO_1520   RPYLCQGIIY TLLRKKDEAD KQFNKFRRLV PKDHPYKDYF EDNMFATKFF   330
SEQ_ID_NO_1510   RPYLCQGIIY TLLKKKDKAE EQFDNFRKLV PKNHPYREYF MDNMIATKLF   323
SEQ_ID_NO_1512   RPYLCMGIIY SLMKKKDEAE KHFEKVRKLV PRNHPYREYF VDNMVATKLF   334
SEQ_ID_NO_1516   RPYLCQGIIY TLLRKKDEAE KKFEQFKKLV PKNHPYREYL VDNMFATKFF   331
```

Figure 51 (continued)

| | | |
|---|---|---|
| SEQ_ID_NO_1520 | SQKLEREGA ···GARG | 343 |
| SEQ_ID_NO_1510 | SEKAQREMAE EMAGSTS | 340 |
| SEQ_ID_NO_1512 | SERAEREGA ------- | 343 |
| SEQ_ID_NO_1516 | SDKVERERS ------- | 340 |

Figure 52

| | | | | | | |
|---|---|---|---|---|---|---|
| SEQ_ID_NO_1525 | ---------- | MAFPQRKRTP | SFSSSVLDSV | YRSIDESDG | LQSDLKGS N | 39 |
| SEQ_ID_NO_1535 | ---------- | MALPQRQRTQ | SFSSSYLDSI | YRSIDESDG | LQSDLRGT N | 39 |
| SEQ_ID_NO_1527 | MYKKERSSRE | STFHPRRRTP | SFSSTLLDSI | YRSIDESNG | -EEQHVLGIK | 48 |
| SEQ_ID_NO_1534 | MHERSMKEAA | GTCPQRRRTP | SFSSSLLDAI | YRSIDESKSN | LHDDQLGLH | 50 |

| | | | | | | |
|---|---|---|---|---|---|---|
| SEQ_ID_NO_1525 | EN----VSS | SSSSPSPNKK | DDKLTTLRRA | MDEEHWLYA | RSS------ | 77 |
| SEQ_ID_NO_1535 | SNNNENVSSS | SSSSPSPNKK | DDKLTTLRRA | MDEEHWLYG | RSS---TTT | 85 |
| SEQ_ID_NO_1527 | KQSCNSVSTT | RRDTSFLEEE | KEVSTTLRRA | VR-TESWMEK | KST-RGSMQ | 95 |
| SEQ_ID_NO_1534 | HHD---QTT | HSFTSEKGGK | KERMNLRRA | VMLEDWMEK | HGSHSLNAQL | 94 |

| | | | | | | |
|---|---|---|---|---|---|---|
| SEQ_ID_NO_1525 | -TTTTNSSDS | SS-------- | --FSSSEAES | -----YRTKR | RLRKLAEQGK | 111 |
| SEQ_ID_NO_1535 | TTTTTNSSDS | SAL------- | --FSSSEAES | -----FRTKR | RLRKLAEQGN | 120 |
| SEQ_ID_NO_1527 | YNSTSSSSDS | SSAGGGGSGG | GVFSSSENES | ------SVR | GNSSSCQQRT | 138 |
| SEQ_ID_NO_1534 | LNSSSSSSED | SSA------G | GIFSSSETDT | TTTLTLKKQR | PARLTSEKKK | 138 |

| | | | | | | |
|---|---|---|---|---|---|---|
| SEQ_ID_NO_1525 | RSGDERQRTK | RTVMDNDSRL | FSKSDDDKKP | KAVKILEEL | KRSKQPVSPG | 160 |
| SEQ_ID_NO_1535 | RLGEERQRT | ---------- | --KSDDDIKV | KAVKMFEEL | KRSKQPVSPG | 156 |
| SEQ_ID_NO_1527 | KPLSDKPHQK | PKCEG----- | --GGFHKTKL | RALKIYGEL | KKVKQPISPG | 180 |
| SEQ_ID_NO_1534 | KKQDRIMSSE | KQNKE----- | --SGFTRTKL | RALKIYGELN | QRVKQPISPG | 181 |

| | | | | | | |
|---|---|---|---|---|---|---|
| SEQ_ID_NO_1525 | ARLTSFLNSI | FQSN-AKKV | KLCSVGKTTD | VK------- | -------SSS | 193 |
| SEQ_ID_NO_1535 | ARLTSFLNSI | FQSN-AKKV | KFCSVGKTTD | VK------- | -------SSSS | 190 |
| SEQ_ID_NO_1527 | GRIASFLNSI | FNSASAAKKV | KMCSIGAMDD | VSFERKSKSA | CSSA-TSFS | 228 |
| SEQ_ID_NO_1534 | SRIASFLSSI | FNSDN-VKKA | KMCYAGAVED | VSFEHKSNGP | CFSSPSSFS | 230 |

| | | | | | | |
|---|---|---|---|---|---|---|
| SEQ_ID_NO_1525 | SKSCFSRTRN | KTDNNNNNC- | --KKLERSIR | FYPVRVTIDG | DCRDYAQKH | 239 |
| SEQ_ID_NO_1535 | SRSCFSRTRN | KTNNNNNNAN | NFKKLERSIR | FYPVRVTIDG | DCRDYAHKN | 239 |
| SEQ_ID_NO_1527 | -RSCLSKTPP | PRGKPSNG-- | ----TKRSVR | FYPVGVIVDE | DSRPCGHKS- | 270 |
| SEQ_ID_NO_1534 | RRSCMSKTPS | SAKKSNNNE- | ----VKRSVR | FYPVSVILGE | DSEPDSSYHK | 275 |

| | | | | | | |
|---|---|---|---|---|---|---|
| SEQ_ID_NO_1525 | ---TRVRK- | --PIPEFTAK | -KSVKE---- | EIKTNDHHTE | FTCITRNI- | 276 |
| SEQ_ID_NO_1535 | ---TR---- | --PIPTKVHQ | TELMKE---- | EIKTVHDTE | LTCITRK- | 274 |
| SEQ_ID_NO_1527 | ---YEDDPG | LMPTPRKVVK | SSSVKELEVA | KGAAADYLRS | YH-QRKNV- | 314 |
| SEQ_ID_NO_1534 | CNILYE--- | --SEPNLGVR | SSSIKELKKN | TARGNENGAE | EAAARGFVKG | 319 |

Figure 52 (continued)

```
SEQ_ID_NO_1525       ------GLKD FVRSNKY EG KEEEGDAWSH SSSDLFELDS YRI GMGRYLK    319
SEQ_ID_NO_1535       ------GLKD YVRSSNI DEG KEEEDDVWSY SSSDLFELDH YRI GMGRYLK    318
SEQ_ID_NO_1527       ------SEFD FRGFHNYVAD DSDSDDEF SC TSSDLFELDH LF GI GRYRE     356
SEQ_ID_NO_1534       YRNSGQGEFD FRGF--YDDD DEDDDDDVSC SSSDLFELDH LF GAARYDE      366

SEQ_ID_NO_1525       ELPVYETTDF KTNQAI ARSL LL    341
SEQ_ID_NO_1535       ELPVYETTDF KFNQAI ARGL LL    340
SEQ_ID_NO_1527       ELPVYETTNF KTNQAI ANGF FP    378
SEQ_ID_NO_1534       ELPVYETTNL ETNKAI ASGL CL    388
```

Figure 53

| | | | | | | |
|---|---|---|---|---|---|---|
| SEQ_ID_NO_1550 | MDMNESSEKG | ME----GNGS | SGPGGGI PVE | MQSQFS---G | GGFS-A--- | 38 |
| SEQ_ID_NO_1552 | MYSGQQSDQC | PS----ANS- | ---------- | ---------G | REFSEA--- | 22 |
| SEQ_ID_NO_1537 | MLEGLVSQES | LSLNS-MDMS | VLER----LK | WVQQQQQLQ | QVVSHS--- | 41 |
| SEQ_ID_NO_1543 | MLESLVSLES | MSLSS-MDVS | VLER----LK | WLQQQ----Q | QQVLST--- | 37 |
| SEQ_ID_NO_1545 | MLGYANPSGN | LAVD--GDMT | VLERQRARMK | WQEEQEYFSG | NSFNGV--- | 44 |
| SEQ_ID_NO_1539 | MLHC------ | ------TDIT | VLERQRACIK | WQQEQQDQQQ | VQLQQQEISY | 38 |
| SEQ_ID_NO_1548 | MLHCLNTSGN | LVGGIISDMT | VLERQRARKK | FQHEHDD-Q | QFFMVG--- | 45 |
| | | | | | | |
| SEQ_ID_NO_1550 | HQHQQHPHMM | DSFGSGMWS- | --------AA | SQHGAGFLAP | VPGFLPPPGL | 79 |
| SEQ_ID_NO_1552 | NRNTVTMHQK | MGYNSG---- | ---------- | ---------- | ------PYGF | 42 |
| SEQ_ID_NO_1537 | SNNSPELLQI | LQFHGSN--- | --------ND | ELLESSFSQF | Q---WLGSGF | 77 |
| SEQ_ID_NO_1543 | TNASPELLQF | HGTN------ | --------ND | ELLQNTFSHF | Q---WLRSGF | 70 |
| SEQ_ID_NO_1545 | FSSSSSLHVP | DSIMVAADS- | --------G | CALAEVVAQA | QPRSINKPSA | 84 |
| SEQ_ID_NO_1539 | FTELTGVFQQ | AGFHEGGLSE | VVTRSVKPDP | GLMDNGMNND | H---VVGLGV | 85 |
| SEQ_ID_NO_1548 | CDSALGEVVA | NSMKPG---- | ---------- | ---------- | ---------- | 61 |
| | | | | | | |
| SEQ_ID_NO_1550 | GGHFPVDSG- | -FIE----RA | ARSSCFVGPG | AGGGMWGAGA | FGGAGDQQMG | 123 |
| SEQ_ID_NO_1552 | GP---YNMG | -LEE----RP | GLYQSSSGTF | SQNIQM---- | ---------S | 70 |
| SEQ_ID_NO_1537 | GPNYNMGFGP | PHES----IS | RTSSCHMEPV | DTMEVL---- | ------LKTG | 113 |
| SEQ_ID_NO_1543 | GPNYSMGFGP | SHEAMDGC-S | ITNSCQMDQA | DTVGVM---- | ------LKNS | 110 |
| SEQ_ID_NO_1545 | AP-----G | -LHANSSS-S | RTFSCPPALV | DPEPKPT--- | ---------D | 114 |
| SEQ_ID_NO_1539 | GPLYDNGSG- | -FELNYGA-S | RISSCPPAAV | AAVAAATVKG | SESVVSDK-S | 133 |
| SEQ_ID_NO_1548 | ------DLG | -FEN------ | ---------- | ---------- | ---------- | 87 |
| | | | | | | |
| SEQ_ID_NO_1550 | SAFGEGYLDH | RRKEGGDKAE | PELAGSGGVP | SSEAAGGDCS | SKGSDSKKRR | 173 |
| SEQ_ID_NO_1552 | DEHSGGVKKR | KGMD------ | ---------- | ------DCV | AMLQNAGDQQ | 97 |
| SEQ_ID_NO_1537 | EETRAVALKN | KRKP------ | ---------- | ------EVK | TREEQKTEKK | 140 |
| SEQ_ID_NO_1543 | EENITISLKN | KRKS------ | ---------- | ------EVK | TREEEKTEKK | 137 |
| SEQ_ID_NO_1545 | SSIGKDSFKK | RKTD------ | ---------- | --KPHN-PKV | VAENENKDKR | 145 |
| SEQ_ID_NO_1539 | SGVGRESSKK | RKVD------ | ---------- | --NKQNNSKV | DAEEDTRDKR | 165 |
| SEQ_ID_NO_1548 | ---VEFTVKK | RKAD------ | ---------- | --------H | KVDMKSKDKR | 89 |

Figure 53 (continued)

| | | | | | | |
|---|---|---|---|---|---|---|
| SEQ_ID_NO_1550 | RPSEVMGGDD | VQSSNVAADS | ANESAQSKDK | GEESSPATGT | TTGGKSKGKG | 223 |
| SEQ_ID_NO_1552 | ----TEGSSQ | PE-------- | ----RNSLEG | NRKISPKMQS | ---KEDSSDG | 128 |
| SEQ_ID_NO_1537 | ----IKVEAE | TESSMK---- | ----GKSNMG | NTEASSDTSK | ---ETSKGAS | 175 |
| SEQ_ID_NO_1543 | ----IKVEAE | TELNMK---- | ----VKSNLS | NTEASSETSK | ---QKSKAAS | 172 |
| SEQ_ID_NO_1545 | ----IKVGAD | DGESKITKCN | T---INTNTN | NKETCTDTSN | ---SKQNSKA | 185 |
| SEQ_ID_NO_1539 | ----KGCAE | EGESKITEKN | NNKNSRNNNT | NKNNNSNKES | SA-GNSKDNS | 210 |
| SEQ_ID_NO_1548 | ----IKVSVE | EGESKITEQI | KGN-KNTKLK | NRENCDDVGS | ----KENSKG | 130 |
| | | | | | | |
| SEQ_ID_NO_1550 | AKESSEKEDY | HVRARRGQA | TNSHSLAERL | RREKISERMK | LLQDLVPGCS | 273 |
| SEQ_ID_NO_1552 | DG---TKEDY | VHVRAKQGQA | TNSHSLAERL | RRKKISERMK | LLQDLVPGCS | 175 |
| SEQ_ID_NO_1537 | EN---QKLDY | IHVRARRGQA | TDRHSLAERA | RREKISKKMK | YLQDIVPGCN | 222 |
| SEQ_ID_NO_1543 | EN---QKLDY | HVRARRGQA | TDRHSLAERA | RREKISKKMK | YLQDLVPGCN | 219 |
| SEQ_ID_NO_1545 | S----EKPDY | HVRARRGQA | TDSHSLAERV | RREKISERMN | YLQDLVPGCN | 231 |
| SEQ_ID_NO_1539 | KVTEVQKPDY | HVRARRGQA | TDSHSLAERV | RREKISERMK | YLQDLVPGCN | 260 |
| SEQ_ID_NO_1548 | SEIQNHKPDY | HVRARRGQA | TDSHSLAERV | RREKISERMK | YLQDLVPGCN | 180 |
| | | | | | | |
| SEQ_ID_NO_1550 | KVTGKAVMLD | EIINYVQSLQ | RQVEFLSMKL | ATVNPRLDLN | IEGLLSKDLL | 323 |
| SEQ_ID_NO_1552 | KITGKAVMLD | EIINYVQSLQ | RQVEFLSMKL | ATVNPELGFD | IEDLSKQMM | 225 |
| SEQ_ID_NO_1537 | KVTGKAGMLD | EIINYVQCLQ | RQVEFLSMKL | AVLNPELELA | VEDVSVKQAY | 272 |
| SEQ_ID_NO_1543 | KVTGRAGMLD | EIINYVQSLQ | RQVEFLSMKL | AVLNPELELA | MEDLSVKQLF | 268 |
| SEQ_ID_NO_1545 | KVTGKAGMLD | EIINYVQSLQ | RQVEFLSMKL | AAVNPRLDFS | MDDLFDKDVF | 281 |
| SEQ_ID_NO_1539 | KITGKAGMLD | EIINYVQSLQ | RQVEFLSMKL | AAVNPRLDFN | FDNLFAREAF | 310 |
| SEQ_ID_NO_1548 | KIAGKAGMLD | EIINYVQSLQ | RQVEFLSMKL | AAVNPRLDFN | IDELFAKEVF | 230 |
| | | | | | | |
| SEQ_ID_NO_1550 | RF-------- | ---PGVSSSS | MGFSPEMMHP | QLQLSQPGLM | QGGARAMANS | 362 |
| SEQ_ID_NO_1552 | LSQDRHFAFY | GVDPGSSSLA | SQFSDGIMQP | QM-------- | --MCNISNPA | 265 |
| SEQ_ID_NO_1537 | FTNV------ | --------VA | SKQSIMVDVP | LFPLDQQGSL | --DLSAINPN | 306 |
| SEQ_ID_NO_1543 | QAYFTNLPVV | --------VA | SKPSLMVDAP | LFPLDQQGSL | --DLSVINPN | 308 |
| SEQ_ID_NO_1545 | PTCAANFPNI | GMSSTSSDIT | NPAYLPFNSP | QQIFQYDGL- | --DTGINPSD | 328 |
| SEQ_ID_NO_1539 | PACSVNFPTI | GM---SSDMT | NPAYLDFNPA | QQQLVTCCGL | --DMGTDPPD | 355 |
| SEQ_ID_NO_1548 | TQNFQMM--- | -----QSEMS | NPAYLDFNSA | QDQVSCCGGL | INNMGILPPE | 272 |

Figure 53 (continued)

| | | |
|---|---|---|
| SEQ_ID_NO_1550 | DVFRRIMDAD·········□GAKDCSHSQM AHALNGPFSD HVAQMAYPSM | 403 |
| SEQ_ID_NO_1552 | DVLQGTIHDV············STMNQI PAMAEG-LQN -LPQNNFNPG | 299 |
| SEQ_ID_NO_1537 | QT······················TSIEAP SGSWETQSQS -LYN····· | 327 |
| SEQ_ID_NO_1543 | QA······················TTIEAP SASWETQSQS -LYN····· | 329 |
| SEQ_ID_NO_1545 | YGLRRTISAP VS--MPETYL QSSCFTQMLP SSTWEGDFQN -LCNFDVDQA | 375 |
| SEQ_ID_NO_1539 | MGLKRTTSSP ES--IPETFL DSSCFTQAHP PPAWDADLQN -LYNVAFDQG | 402 |
| SEQ_ID_NO_1548 | IGVRRNINAP ASASLPEIFL DPSCFTHILP SSTWEGDFQN -LHSVDFDQG | 321 |

| | | |
|---|---|---|
| SEQ_ID_NO_1550 | GSSHSHSQDL S········□ RPSQDAYQM | 424 |
| SEQ_ID_NO_1552 | VAADSSANN············ -SGSMKIED | 316 |
| SEQ_ID_NO_1537 | ····················· -TSSLGFHY | 335 |
| SEQ_ID_NO_1543 | ····················· -TSSLGFDY | 337 |
| SEQ_ID_NO_1545 | RATSFPSQLL SGL······V EASNLKMEM | 398 |
| SEQ_ID_NO_1539 | RQTSFPTQPF TGKIKLSCS EASNLKMEM | 431 |
| SEQ_ID_NO_1548 | RSTSFPSQPF TGM······□ EASNLKMEM | 344 |

Figure 54

```
SEQ_ID_NO_1571    MAVEAVS-- ------GNGG EAVAPAPA-- ---------- ----------    19
SEQ_ID_NO_1567    MAEEPQ--- ------PQAA AAPAAAAT-- ---------- -EVVAEKAP    27
SEQ_ID_NO_1572    MAEEPQ--- ------PEAA PAAVAATT-- ---------- -EVAAEKAP    27
SEQ_ID_NO_1574    MAEEPQ--- ------PEAA PAAVAATT-- ---------- -EVAAEKAP    27
SEQ_ID_NO_1555    MAEETDK--- ------PAAA EAPTSTQP-- ---------- -VPEEPAVVPP   29
SEQ_ID_NO_1563    MSQEQDVVVV TDV---PQAE KTAPVPPT-- ---------- MPVVEKEPP    35
SEQ_ID_NO_1575    MAEEPQK--- ------PTEQ VATTPATS--- ---------- -ETTLEKTPP    28
SEQ_ID_NO_1554    MAEEPTTTTL VTPEKLPSPS LTPSEVSEST QDALPTETET LEKVTETNPP    50
SEQ_ID_NO_1565    MAQNDSN--- ------PTPP PEPHVAAE--- ---------- ---------P    20

SEQ_ID_NO_1571    ---------- ---------- PV KEVSAK--- ---------- ----VEAKEA    33
SEQ_ID_NO_1567    --AEVEKKAE E------PA AEAEAE--- ---------- -ETAAVADDG    53
SEQ_ID_NO_1572    VEAEKEKKVE EET----PA VEAEAK--- --EEKKDEAA ---AAGGDEA    63
SEQ_ID_NO_1574    VEAEKEKKVE EET----PA VEAEAK--- --EEKKDEAA AAAAGGDEA    66
SEQ_ID_NO_1555    PVPAAEIQLP DSAPAPPQPE ASPAKP---- --DSVAEVAE DEKPKASEEF    73
SEQ_ID_NO_1563    V--------- ---------PV PETEEEPMKP KQVEEGAVET QVLKPSGGDD    68
SEQ_ID_NO_1575    PQAEEVVAAA DADAVVVPPV VAEETE---- --KPAEDVKP ADETAAATDK    72
SEQ_ID_NO_1554    ETADTTTKPE EETAAEHHPP TVTETETAST EKQEVKDEAS QKEVAEEKKS    100
SEQ_ID_NO_1565    ITEDLVQDKE EEDDSSKIVI PVPESE---- ---------- ----------    46

SEQ_ID_NO_1571    AAVTKNASFR EESNFLDDLK ESERKALAEL RDKVEAATLE GKLFDDGKPE    83
SEQ_ID_NO_1567    GAVEATGSFK EESNLVADLP DPEKKALDEF KELIVAALAA GEFNLPPPPP    103
SEQ_ID_NO_1572    GAIEGTGSFK EESNLVADLP DPEKKALDEF KQLIAAALAA CEFNLPPPPP    113
SEQ_ID_NO_1574    GAIEGTGSFK EESNLVADLP DPEKKALDEF KQLIAAALAA CEFNLPPPPP    116
SEQ_ID_NO_1555    EKISQSVSFK EESNVVGELP ESQRKALADL KVLIQEALNK HEFTAPPAPL    123
SEQ_ID_NO_1563    EKMPQLVSFK EESTKVADLL DSEKKALQEF KQLVQEALN- ----------    107
SEQ_ID_NO_1575    KILQ-SVSFK EETNVVSELP ESQKKALDEL KQLIQEALNK HEFTAPPPPP    121
SEQ_ID_NO_1554    MIPQNLGSFK EESSKLSDLS NSEKKSLDEL KHLVREALDN HQFTN-----    145
SEQ_ID_NO_1565    ----SLSLK EDSNRVSD-- -SEKNAIDEL KKLLKEELED ----------    78

SEQ_ID_NO_1571    ---------- ---------- VKEKREAKKK AEKAPEEKKE EEEEGKKEPE    113
SEQ_ID_NO_1567    PPKAKTEAAA EETKTEAPAK EEAKTEEPAK AEEPAKEEPK AEEPAKAEAA    153
SEQ_ID_NO_1572    PPKAKVEAAV EETKA----- EESKAEEEPK AEEPAKEEEP KAEVAAAAAA    158
SEQ_ID_NO_1574    PPKAKVEAAV EETKA----- EETKAEEEPK AEEPAKEEEP KAEVAAAAAA    161
SEQ_ID_NO_1555    PPK-----E EEKPA----- EEKKEDTEKP AEQPQIDE-P AKEPVIEEPP    161
SEQ_ID_NO_1563    ---------- ---------- ---------- ---------- ----------    107
SEQ_ID_NO_1575    PTKAVAEVAE EKKPE----- EEEKKTEEVV AEEKKVEEVV AEEKKVEEAV    166
SEQ_ID_NO_1554    ---------- ---------- ---------- ---------- ----------    145
SEQ_ID_NO_1565    ---------- ---------- ---------- ---------- ----------    78
```

Figure 54 (continued)

| | | | | | | |
|---|---|---|---|---|---|---|
| SEQ_ID_NO_1571 | AVEKKGEEDD | KKEAEVEGKE | EEEESKKEAE | KEMEDEE--- | ---------- | 150 |
| SEQ_ID_NO_1567 | AAEPAAEEPK | AVVA------ | ----AEAAAE | EPAKEEPK-- | ---AEEAKPA | 188 |
| SEQ_ID_NO_1572 | PPEAGTEEPK | AEASSEEAKT | EEPKAEAAAD | EPAKDESKAE | AAPAEEAKPA | 208 |
| SEQ_ID_NO_1574 | PPEAGTEEPK | AEASSEEAKT | EEPKAEAAAD | EPAKEESKAE | AAPAEEAKPA | 211 |
| SEQ_ID_NO_1555 | KTEAEPEPVT | ETVTVKVEET | ITPHPAPETS | LAPEADEKAA | EPSTVVEKVA | 211 |
| SEQ_ID_NO_1563 | ---------- | ---------- | ---------- | ---------- | ---------- | 107 |
| SEQ_ID_NO_1575 | AEEKKVEEVE | KKEEEKGSSS | EEPKTEAKIE | AEPEAKKEET | VLEVVEKIAT | 216 |
| SEQ_ID_NO_1554 | ---------- | ---------- | ---------- | ---------- | ---------- | 145 |
| SEQ_ID_NO_1565 | ---------- | ---------- | ---------- | ---------- | ---------- | 78 |

| | | | | | | |
|---|---|---|---|---|---|---|
| SEQ_ID_NO_1571 | ---------- | ---------- | ---------- | --AGEAEKVA | AAAEEKPAET | 168 |
| SEQ_ID_NO_1567 | EPKKEEEAVV | VAEE--GTKT | ------AEPV | EEAAAAATTT | EQAAAPEPEA | 230 |
| SEQ_ID_NO_1572 | EPEPEEKTVV | VTEEEAATKT | VEAIEETVVP | AAAAPAAAAT | EEAAAPEPEV | 258 |
| SEQ_ID_NO_1574 | EPEPGGED-- | ---------- | ------RRGH | RGRGGHQDGG | SDRGNRRARC | 243 |
| SEQ_ID_NO_1555 | VIDEDGAKTV | EAIEESVVAV | ------STPP | PEESAPSKEE | AEVEVEAAEA | 255 |
| SEQ_ID_NO_1563 | ---------- | ---------- | ---------- | ---------- | ---------- | 107 |
| SEQ_ID_NO_1575 | STEEDGAKTV | EAIQESIVSV | ------TVTD | GEQPVTETVG | EAVAVAEVEE | 259 |
| SEQ_ID_NO_1554 | ---------- | ---------- | ---------- | ---------- | ---------- | 145 |
| SEQ_ID_NO_1565 | ---------- | ---------- | ---------- | ---------- | ---------- | 78 |

| | | | | | | |
|---|---|---|---|---|---|---|
| SEQ_ID_NO_1571 | AAVVVDKDIA | LWGVPLLPSK | GDE-ATDVVL | LKFLRARDFK | AGAAFEMLRR | 217 |
| SEQ_ID_NO_1567 | E-AAAAPEPVF | IWGVPLV--- | GDDERTDAVL | LKFLRAREFK | VKEAMAMLRS | 276 |
| SEQ_ID_NO_1572 | QAAAAPEPVL | IWGVPLV--- | GDDERTDIVL | LKFLRAREFK | VKEAMAMLRS | 305 |
| SEQ_ID_NO_1574 | CCACCRRHGG | SRGAGTG--- | GDDERTDIVL | LKFLRAREFK | VKEAMAMLRS | 290 |
| SEQ_ID_NO_1555 | VPPPPPEEVF | IWGIPLL--- | GDE-RSDVIL | LKFLRARDFK | VKDAFTMIKN | 301 |
| SEQ_ID_NO_1563 | ---------- | ---------- | ---KSDVIL | LKFLRARDFK | VKDAFTMLKS | 133 |
| SEQ_ID_NO_1575 | VTPTTPEEVE | IWGIPLL--- | ADE-RSDVIL | LKFLRARDFK | VKEAYTMIKD | 305 |
| SEQ_ID_NO_1554 | ----TPEEVK | IWGIPLL--- | EDD-RSDVVL | LKFLRAREFK | VKDSFAMLKN | 187 |
| SEQ_ID_NO_1565 | ------EEVS | IWGVPLF--- | KDD-RTDVIL | LKFLRARELK | VKDALVMFQN | 118 |

| | | | | | | |
|---|---|---|---|---|---|---|
| SEQ_ID_NO_1571 | TLRWRRDWPG | FDADADADLP | -EELAGACVL | DGADREGHPV | CYNALRVFAD | 266 |
| SEQ_ID_NO_1567 | AVLWRKRF-G | IESLLEADLA | FPELEKVVFY | RGADREGHPV | CYNVYGEFQD | 325 |
| SEQ_ID_NO_1572 | AVLWRKRF-G | IESLLDADLA | LPELDSVVFY | RGADREGHPV | CYNVYGEFQD | 354 |
| SEQ_ID_NO_1574 | AVLWRKRF-G | IESLLDADLA | LPELDSVVFY | RGADREGHPV | CYNVYGEFQD | 339 |
| SEQ_ID_NO_1555 | TVRWRKQF-D | IEALLDEDLG | -NQMDKYVFS | HGVDREGHPV | CYNVFGEFEN | 349 |
| SEQ_ID_NO_1563 | TIRWRKEF-G | IDELLEQDLG | FDDLGKVVFM | HGLDKEGHPV | CYNVYGEFQN | 182 |
| SEQ_ID_NO_1575 | TVLWRKEF-G | IEALLQEDLG | -TDMDKYVFT | DGYDKEGHPV | YYNVFGEFEN | 353 |
| SEQ_ID_NO_1554 | TIKWRKEF-K | IDEL-VEEDLV | -DDLDKVVFM | HGHDREGHPV | CYNVYGEFQN | 235 |
| SEQ_ID_NO_1565 | TLRWRKDF-N | IDALLDEDLG | -DHLEKVVFM | HGHGREGHPV | CYNVYGEFQN | 166 |

Figure 54 (continued)

| SEQ_ID_NO_1571 | DAVYKKALGT EEGKARFLRW RVRAMERHV- AELDLKP-GG AASLLQVTDL | 314 |
|---|---|---|
| SEQ_ID_NO_1567 | KEVYEKAFGD EEKRERFLKW RICLLERGL SQLDFAP-SG ICSMVQVTDL | 374 |
| SEQ_ID_NO_1572 | KDLYEKAFGD EEKRERFLKW RICLLERGL SQLDFSP-SG ICSMVQVTDL | 403 |
| SEQ_ID_NO_1574 | KDLYEKAFGD EEKRERFLKW RICLLERGL SQLDFSP-SG ICSMVQVTDL | 388 |
| SEQ_ID_NO_1555 | KDLYQITFSD DEKSLKFLRW RVQFLEKSI- RKLDFSP-NG ISTIVQVNDL | 397 |
| SEQ_ID_NO_1563 | KELYKNSFSD EEKRQRFLRW RIQFLEKSI- RTLDFSP-GG ISTIVQVNDL | 230 |
| SEQ_ID_NO_1575 | KELYQNTFSD DEKRTKFIRW RICSLEKSI- RKLDFTP-SG ISTIVQVNDL | 401 |
| SEQ_ID_NO_1554 | KELYNKTFSD EEKRKHFLRT RIQFLERSI- RKLDFSS-GG VSTIFQVNDM | 283 |
| SEQ_ID_NO_1565 | KDLYHKAFSS QDNRNKFLRW RICLLERSI- RHLDFTPSSG INTIFQVNDL | 215 |

| SEQ_ID_NO_1571 | KNSPGPAKKD FRVAVKQMLD LFQDNYPELV ARNILJ NVPF WYYAFSTLFY | 364 |
|---|---|---|
| SEQ_ID_NO_1567 | KNSPPMLGKH -RAVTRQAVA LLQDNYPEFI AKKVFINVPW WYLAANKMMS | 423 |
| SEQ_ID_NO_1572 | KNSPPMLGKH -RAVTRQAVA LLQDNYPEFI AKKVFINVPW WYLAANKMMS | 452 |
| SEQ_ID_NO_1574 | KNSPPMLGKH -RAVTRQAVA LLQDNYPEFI AKKVFINVPW WYLAANKMMS | 437 |
| SEQ_ID_NO_1555 | KNSPGLTKME LRNATKRALQ LFQDNYPEFA AKQVFINVPW WYLAVNRMIS | 447 |
| SEQ_ID_NO_1563 | KNSPGPAKRE LRQATRQALQ LLQDNYPEFV AKQIFINVPW WYLTVNRMIS | 280 |
| SEQ_ID_NO_1575 | KNSPGLGKKE LRQATNKALQ LLQDNYPEFV AKQVFINVPW WYLAFSRFLS | 451 |
| SEQ_ID_NO_1554 | KNSPGLGKKE LRSATKQAVE LLQDNYPEFV FKQAFINVPW WYLVFYTVIG | 333 |
| SEQ_ID_NO_1565 | KNSPGPAKRE LRLATKQALQ LLQDNYPEFV AKQVFINVPW WYLAFYTMIN | 265 |

| SEQ_ID_NO_1571 | PFLTQRTKSK FVLARPSKVT ETLLKYIPIE AIPVKYGGLK RDD---DTEF | 411 |
|---|---|---|
| SEQ_ID_NO_1567 | PFLTQRTKSK FVFASQAKSP ETLFRYIAPE QVPVQFGGLF KED---DPDF | 470 |
| SEQ_ID_NO_1572 | PFLTQRTKSK FIFASPAKSA ETLFRYIAPE QVPVQFGGLF KED---DPEF | 499 |
| SEQ_ID_NO_1574 | PFLTQRTKSK FIFASPAKSA ETLFRYIAPE QVPVQFGGLF KED---DPEF | 484 |
| SEQ_ID_NO_1555 | PFFTQRTKSK FVFAGPSKTA ETLFKYVTPE QVPVQYGGLS REG---EQEF | 494 |
| SEQ_ID_NO_1563 | PFLTQRTRSK FVFVGPSKSA ETLLRYIAAE QIPVKYGGLS KDG----EF | 325 |
| SEQ_ID_NO_1575 | AFLTQRTKSK FVFAGPSKSA DTLFKYIAPE QVPVQYGGLS REG---EQEF | 498 |
| SEQ_ID_NO_1554 | PFMTPRSKSK LVFAGPSRSA ETLFKYISPE QVPVQYGGLS VDPCDCNPDF | 383 |
| SEQ_ID_NO_1565 | PFLTSRTKSK FVFAGPSKSP DTLFKYIFPE QVPVQYGGLS VDFCDCNPDF | 315 |

| SEQ_ID_NO_1571 | SSADDGEVAE LTVKGSSTET IEIEAAEADA TLTMDLIVLG MEVNYKEEFV | 461 |
|---|---|---|
| SEQ_ID_NO_1567 | TTSD--SVTE LTIKASSKET IEIPVTE-NS TIVWELRVLG MEVSHGAEFT | 517 |
| SEQ_ID_NO_1572 | TTSD--AVTE LTIKPSSKET VEIPVTE-NS TIGMELRVLG MEVSYGAEFT | 546 |
| SEQ_ID_NO_1574 | TTSD--AVTE LTIKPSSKET VEIPVTE-NS TIGMELRVLG MEVSYGAEFT | 531 |
| SEQ_ID_NO_1555 | SIDD--PVTE VAIKAATKHT VEFPISE-PS LLVWELRVVG MDVSYGAEFL | 541 |
| SEQ_ID_NO_1563 | GSAD--AVTE ITVKPAAKHT VEFPVTE-TC LLTMEVRVAG MDVSYSAEFV | 372 |
| SEQ_ID_NO_1575 | TTAD--PATE VTIKPATKHA VEFPISE-KS TLVWEVRVVD NSVNYGAEFV | 545 |
| SEQ_ID_NO_1554 | SLED--SASE ITVKPGTKQT VEIIYE KC ELVWEIRVTG MEVSYKAEFV | 430 |
| SEQ_ID_NO_1565 | TMSD--PVTE IPLKPTTKQT VEIALYE KC IFVWELRVVG MEVSYNAEFK | 362 |

Figure 54 (continued)

| | | | | | | | | |
|---|---|---|---|---|---|---|---|---|
| SEQ_ID_NO_1571 | PADEGSYTII | VRKGKKMGAG | EEAVLRNSFR | AGEPGKVVLT | VENTSH-KKK | | | 509 |
| SEQ_ID_NO_1567 | PDAEGAYTVI | VQKTRKVPAN | EEPIMKGSFK | AGEAGKIVLT | VSNAAS-KKK | | | 566 |
| SEQ_ID_NO_1572 | PDAEGGYTVI | VQKTRKVPAN | EEPIMKGSFK | VGEPGKIVLT | INNPAS-KKK | | | 595 |
| SEQ_ID_NO_1574 | PDAEGGYTVI | VQKTRKVPAN | EEPIMKGSFK | VGEPGKIVLT | INNPAS-KKK | | | 580 |
| SEQ_ID_NO_1555 | PSAEGGYTVI | VQKTAKLGPA | DEPVISNSYR | VGEAGKIVLT | IDNLSSKKKK | | | 591 |
| SEQ_ID_NO_1563 | PSAEDSYTVI | IQKARKVAAT | EEPVVCNSFK | IGEPGKVVLT | IDNSTSKKKK | | | 422 |
| SEQ_ID_NO_1575 | PSAEDGYTVI | IQKNRKVAPA | DETIISNTFK | IGEPGKVILT | IDNQSS-KKK | | | 594 |
| SEQ_ID_NO_1554 | PEEKDAYTVV | IQKPRKMRPS | DEPVLTHSFK | VNELGKVLLT | VDNPTS-KKK | | | 479 |
| SEQ_ID_NO_1565 | PDVEDAYTVI | IQKATKMSPT | DEPVVSNSFK | VVELGKLLLT | IDNPTL-KKK | | | 411 |

| | | | |
|---|---|---|---|
| SEQ_ID_NO_1571 | KVLFRHKSKS | AFAKKC------ | 525 |
| SEQ_ID_NO_1567 | KLLYRSKVKC | STGESVEADI P | 587 |
| SEQ_ID_NO_1572 | KLLYRSKVKS | TSESV------- | 610 |
| SEQ_ID_NO_1574 | KLLYRSKVKS | TSESV------- | 595 |
| SEQ_ID_NO_1555 | ILLYRSKTKP | ISD--------- | 604 |
| SEQ_ID_NO_1563 | KLLYRLKTKP | ASSD-------- | 436 |
| SEQ_ID_NO_1575 | KLLYRSKTIP | ISE--------- | 607 |
| SEQ_ID_NO_1554 | KLVYRFNVKP | L----------- | 490 |
| SEQ_ID_NO_1565 | RLLYRFKIKP | YSD--------- | 424 |

Figure 55

| | | | | | | |
|---|---|---|---|---|---|---|
| SEQ_ID_NO_1578 | ---------- | ---------- | ---------- | ---------- | -MSFYRGTAS | 9 |
| SEQ_ID_NO_1607 | MADNKDGVTP | KSSAAFPLR- | --------N | PNVTLNERNF | AAFTNRSAAA | 40 |
| SEQ_ID_NO_1440 | MDEEMNAVAE | MNAVASKVKE | EY-------R | RAPKLNQRII | SSMSRRSVAA | 43 |
| SEQ_ID_NO_1648 | ----MSEEAA | TETGSSSVK- | ---------R | TTPKLNERIL | SSLSRRSVAA | 36 |
| SEQ_ID_NO_1651 | ---MSQENGA | TNGHLAEEQQ | DVWMEVEPKR | RAPRLNERIL | SSLSRRSVAA | 47 |
| SEQ_ID_NO_1487 | MSSENGENGH | GAADEVVEPY | QQTP-----R | PGPKLNERIL | SSLSRRSVAA | 45 |
| SEQ_ID_NO_1040 | --MSQEDSTS | AAAAQQPTS- | ---------R | PAPKLNERIL | SSLSRRGGGA | 38 |
| SEQ_ID_NO_1465 | ---MSEEDTN | AAAGQP---- | ---------R | RAPKLNERIL | SSLSRRSVAA | 34 |
| SEQ_ID_NO_1580 | ----MSEEDK | NEAKVLETP- | ---------R | KPPRLNERIL | SSMSRRSVAA | 36 |
| SEQ_ID_NO_1623 | --------MS | NENDDLSPQ- | ---------R | RAPRLNERIL | SSISRRSVAA | 32 |
| SEQ_ID_NO_1622 | MSEHDDEVQE | VQENVQEIH- | ---------R | PVPRLNERIL | SSLSRRSVAA | 40 |
| SEQ_ID_NO_1041 | ----MSDVTK | TQENEVETK- | ---------H | QAPRLNERIL | SSLSRRTVAA | 36 |
| SEQ_ID_NO_1590 | ---MSDETKT | QENEVVEAK- | ---------R | QAPRLNERIL | SSLSRRTVAA | 37 |
| SEQ_ID_NO_1577 | ---MNGEEVK | TSQPQKKLQ- | ---------N | PTPRLNERIL | SSLSKRSVAA | 37 |
| SEQ_ID_NO_1611 | ---MSEEVKE | NQSDKLQ--- | ---------R | TAPRLNERIL | SSLSRKSVAA | 35 |
| SEQ_ID_NO_1637 | ---MSEEVKE | NQSGKLQ--- | ---------K | PTPRLNERIL | SSLSKRSVAA | 35 |
| SEQ_ID_NO_1627 | -MAPSQEVAA | ATKEPSTNGN | GTQAAAAPKT | KTPALNERIL | SSITRRSVAA | 49 |
| SEQ_ID_NO_1608 | MAPPIETVQK | VQPPPNAIEP | HVTYHHQH-S | SHPPLNERIL | SSMTRRSIAA | 49 |
| SEQ_ID_NO_1609 | ---MSPPLES | PAKVAITQH- | ---------S | KPPPLNERII | SSMTRRSVAA | 37 |

| | | | | | | |
|---|---|---|---|---|---|---|
| SEQ_ID_NO_1578 | HPWHDLHPGN | DAPNFVSCVI | EIPRGSKVKY | ELDKDTGLCF | VDRILYSSVV | 59 |
| SEQ_ID_NO_1607 | HPWHDLEIGP | EAPAVFNCVV | EISKGGKVKY | ELDKNSGLIK | VDRVLYSSIV | 90 |
| SEQ_ID_NO_1440 | HPWHDLEIGP | NAPEICNCVV | EIPKGSKVKY | ELDKKTGLIM | VDRILYSSVV | 93 |
| SEQ_ID_NO_1648 | HPWHDLEIGP | GAPSVVNAVV | EITKGSKVKY | ELDKKTGMIK | VDRVLYSSVV | 86 |
| SEQ_ID_NO_1651 | HPWHDLEIGP | EAPAVFNVVV | EITKGSKVKY | ELDKKTGLIK | VDRVLYSSVV | 97 |
| SEQ_ID_NO_1487 | HPWHDLEIGP | DAPAVFNVVV | EITKGSKVKY | ELDKKTGLIK | VDRILYSSVV | 95 |
| SEQ_ID_NO_1040 | HPWHDLEIGP | GAPAVFNVVV | EITKGSKVKY | ELDKKTGLIK | VDRVLYSSVV | 88 |
| SEQ_ID_NO_1465 | HPWHDLEIGP | GAPAVFNVVV | EITKGSKVKY | ELDKKTGLIK | VDRVLYSSVV | 84 |
| SEQ_ID_NO_1580 | HPWHDLEIGP | GAPAIFNCVV | EIPKGSKVKY | ELDKKTGLIK | VDRVLYSSVV | 86 |
| SEQ_ID_NO_1623 | HPWHDLEIGP | EAPSVFNVVI | EISKGSKVKY | ELDKKTGLIK | VDRILYSSVV | 82 |
| SEQ_ID_NO_1622 | HPWHDLEIGP | GAPHIFNCVV | EITKGSKVKY | ELDKKTGLIK | VDRILYSSVV | 90 |
| SEQ_ID_NO_1041 | HPWHDLEIGP | GAPHIFNVVV | EITKGSKVKY | ELDKKTGLIK | VDRILYSSVV | 86 |
| SEQ_ID_NO_1590 | HPWHDLEIGP | GAPHIFNVVV | EITKGSKVKY | ELDKKTGLIK | VDRILYSSVV | 87 |
| SEQ_ID_NO_1577 | HPWHDLEIGP | GAPVIFNVVI | EISKGSKVKY | ELDKKTGLIK | VDRILYSSVV | 87 |
| SEQ_ID_NO_1611 | HPWHDLEIGP | GAPSIFNVVI | EISKGSKVKY | ELDKKTGLIK | VDRILYSSVV | 85 |
| SEQ_ID_NO_1637 | HPWHDLEIGP | GAPVIFNVVV | EISKGSKVKY | ELDKKTGLIK | VDRILYSSVV | 85 |
| SEQ_ID_NO_1627 | HPWHDLEIGP | DAPTIFNCVI | EIPKGSKVKY | ELDKKTGLIK | VDRVLYSSVV | 99 |
| SEQ_ID_NO_1608 | HPWHDLEIGP | GAPKIFNCVI | EIPKGSKVKY | ELDKKTGLIK | GDRILDSSVV | 99 |
| SEQ_ID_NO_1609 | HPWHDLEIGP | EAPKIFNCVV | EIGKGSKVKY | ELDKKTGLIK | VDRVLYSSVV | 67 |

Figure 55 (continued)

| | | | | | | |
|---|---|---|---|---|---|---|
| SEQ_ID_NO_1578 | YPHNYGFVPK | TLCEDGDPLD | VLVLMQEPVV | PMCFLRAKPI | GVMQMLDQGE | 109 |
| SEQ_ID_NO_1607 | YPHNYGFIPR | TICEDSDPID | VLVLMQEPVL | TGSFLRARAI | GLMPMIDQGE | 140 |
| SEQ_ID_NO_1440 | YPHNYGFIPR | TLCEDGDPMD | VLVLMQEPVV | PGRFLRARAI | GLMPMIDQGE | 143 |
| SEQ_ID_NO_1648 | YPHNYGFIPR | TLCEDNDPLD | VLILMQEPVL | PGCFLRRAI | GLMPMIDQGE | 136 |
| SEQ_ID_NO_1651 | YPHNYGFIPR | SLCEDNDPMD | VLVLMQEPVL | PGAFLRARAI | GLMPMIDQGE | 147 |
| SEQ_ID_NO_1487 | YPHNYGFIPR | TLCEDNDPMD | VLVLMQEPVL | PGSFLRARAI | GLMPMIDQGE | 145 |
| SEQ_ID_NO_1040 | YPHNYGFIPR | TLCEDNDPMD | VLVLMQEPVI | PGSFLRARAI | GLMPMIDQGE | 138 |
| SEQ_ID_NO_1485 | YPHNYGFIPR | TLCEDNDPMD | VLVLMQEPVI | PGSFLRARAI | GLMPMIDQGE | 134 |
| SEQ_ID_NO_1580 | YPHNYGFIPR | TLCEDNDPLD | CLVIMQEPVL | PGCFLRARAL | GLMPMIDQGE | 136 |
| SEQ_ID_NO_1623 | YPQNYGFIPR | TLCEDNDPMD | VLVLMQEPVL | PGCFLRARAI | GLMPMIDQGE | 132 |
| SEQ_ID_NO_1622 | YPHNYGFIPR | TLCEDNDPID | VLVLMQEPVL | PGCFLRARAI | GLMPMIDQGE | 140 |
| SEQ_ID_NO_1041 | YPHNYGFIPR | TLCEDNDPLD | VLVLMQEPVL | PGCFLRARAI | GLMPMIDQGE | 136 |
| SEQ_ID_NO_1590 | YPHNYGFIPR | TLCEDNDPLD | VLVLMQEPVL | PGCFLRARAI | GLMPMIDQGE | 137 |
| SEQ_ID_NO_1577 | YPHNYGFVPR | TLCEDNDPID | VLVIMQEPVL | PGCFLRARAI | GLMPMIDQGE | 137 |
| SEQ_ID_NO_1611 | YPHNYGFIPR | TLCEDNDPLD | VLVIMQEPVL | PGCFLRARAI | GLMPMIDQGE | 135 |
| SEQ_ID_NO_1637 | YPHNYGFIPR | TLCEDNDPLD | VLVIMQEPVL | PGCFLRARAI | GLMPMIDQGE | 135 |
| SEQ_ID_NO_1627 | YPHNYGFIPR | TLCDDSDPID | VLVIMQEPVV | PGCFLRAKAI | GLMPMIDQGE | 149 |
| SEQ_ID_NO_1608 | YPHNYGFIPR | TLCEDNDPLS | CLDIMQEPVV | PGCFLRAKAI | GLMPMIDQGE | 149 |
| SEQ_ID_NO_1609 | YPHNYGFIPR | TICEDSDPMD | VLVIMQEPVL | PGCFLRAKAI | GLMPMIDQGE | 137 |

| | | | | | | |
|---|---|---|---|---|---|---|
| SEQ_ID_NO_1578 | RDDKLIAVHA | DDPEYKGFTD | ISQLPPHRLA | EIKRFFEDYK | KNEHKEVVVD | 159 |
| SEQ_ID_NO_1607 | KDDKIIAVCA | DDPEFRHYRD | IKELPPHRLA | EIRRFFEDYK | KNENKKVAVE | 190 |
| SEQ_ID_NO_1440 | KDDKIIAVCA | DDPEVRHYTD | INQLPPHRLA | EIRRFFEDYK | KNENKEVAVN | 193 |
| SEQ_ID_NO_1648 | KDDKIIAVCA | DDPEYRHYTD | IKQLAPHRLA | EIRRFFEDYK | KNENKEVAVN | 186 |
| SEQ_ID_NO_1651 | KDDKIIAVCA | DDPEYRHYND | ISELSPHRLQ | EIRRFFEDYK | KNENKEVAVN | 197 |
| SEQ_ID_NO_1487 | KDDKIIAVCA | DDPEYRHFNN | LSELSPHRLQ | EIRRFFEDYK | KNENKEVAVN | 195 |
| SEQ_ID_NO_1040 | KDDKIIAVCA | DDPEYRHYSI | SVSLPFRLQ | EIKRFLEDYK | KNENKEVAVD | 186 |
| SEQ_ID_NO_1485 | KDDKIIAVCA | DDPEYRHYND | IN·······K | | KNENKEVAVD | 167 |
| SEQ_ID_NO_1580 | KDDKIIAVCV | DDPEYKHYTD | IKDLPPHRLT | EIRRFFEDYK | KNENKEVAVD | 186 |
| SEQ_ID_NO_1623 | KDDKIIAVCA | DDPEYRHYTD | IKQLPPHRLA | EIRRFFEDYK | KNENKDVAVD | 182 |
| SEQ_ID_NO_1622 | KDDKIIAVCA | DDPEYKHFTD | YKELAPHRIM | EIRRFFEDYK | KNENKEVAVN | 190 |
| SEQ_ID_NO_1041 | KDDKIIAVCA | DDPEYKHYTD | IKELAPHRLS | EIRRFFEDYK | KNENKEVAVN | 186 |
| SEQ_ID_NO_1590 | KDDKIIAVCA | DDPEYKHYTD | IRELAPHRLS | EIRRFFEDYK | KNENKEVAVN | 187 |
| SEQ_ID_NO_1577 | KDDKIIAVCV | DDPEYKHITN | INELPPHRLS | EIRRFFEDYK | KNENKEVAVN | 187 |
| SEQ_ID_NO_1611 | KDDKIIAVCV | DDPEYKHYTD | IKELPPHRLS | EIRRFFEDYK | KNENKEVAVN | 185 |
| SEQ_ID_NO_1637 | KDDKIIAVCV | DDPEYKHYTD | IKELPPHRLT | EIRRFFEDYK | KNENKEVAVN | 185 |
| SEQ_ID_NO_1627 | ADDKIIAVCA | DDPEYRHFND | IKELPPHRLA | EIRRFFEDYK | KNENKEVAVN | 199 |
| SEQ_ID_NO_1608 | KDDQIIAVCA | DDPEYRHYND | IKELPPHRLA | EIRRFFEDYK | KNENKEVAVD | 199 |
| SEQ_ID_NO_1609 | KDDKIIAVCA | DDPEYRHYND | IKELPPHRLA | EIRRFFEDYK | KNENKEVEVH | 187 |

Figure 55 (continued)

| | | | | | |
|---|---|---|---|---|---|
| SEQ_ID_NO_1578 | DFLGAEEAKK | VVKDSLNMYQ | EHYVPRKLRN | VYE | 192 |
| SEQ_ID_NO_1607 | GFLPAQAAID | AIKDSMDLYA | A-YIKAGLQR | --- | 219 |
| SEQ_ID_NO_1440 | EFLPAQIAHD | AIQHSMDLYA | E-YILQTLRR | --- | 222 |
| SEQ_ID_NO_1648 | DFLPSATAHE | AIQYSMDLYA | E-YIMMSLRR | --- | 215 |
| SEQ_ID_NO_1651 | EFLPAEAARE | AIQYSMDLYG | Q-YIMQTLRR | --- | 226 |
| SEQ_ID_NO_1487 | DFLPAPTARE | AIQYSMDLYA | Q-YILQSLKR | --- | 224 |
| SEQ_ID_NO_1040 | AFLPATTARE | AIQYSMDLYA | Q-YILQSLRQ | --- | 215 |
| SEQ_ID_NO_1485 | AFLPANTARD | AIQYSMDLYA | Q-YILQSLRQ | --- | 196 |
| SEQ_ID_NO_1580 | KFLPATAAVE | AVQYSMDLYA | E-YIMQTLRR | --- | 215 |
| SEQ_ID_NO_1623 | DFLPPNSAVN | AIQYSMDLYA | E-YILHSLRK | --- | 211 |
| SEQ_ID_NO_1622 | DFLPPSTAVE | AIQYSMDLYA | E-YILHTLRR | --- | 219 |
| SEQ_ID_NO_1041 | DFLPSNTAVE | AIQYSMDLYA | E-YILHTLRR | --- | 215 |
| SEQ_ID_NO_1590 | DFLPSNSAVE | AIQYSMDLYA | E-YILHTLRR | --- | 216 |
| SEQ_ID_NO_1577 | DFLQPGPAIE | AIQYSMDLYA | E-YILHTLRR | --- | 216 |
| SEQ_ID_NO_1611 | DFLPNGPAVE | AIQYSMDLYA | E-YILHTLRR | --- | 214 |
| SEQ_ID_NO_1637 | DFLPNGPAVE | AIQYSMDLYA | E-YILHTLRR | --- | 214 |
| SEQ_ID_NO_1627 | DFLPSEDAYE | AIQHSMDLYA | T-YICEGLRR | --- | 228 |
| SEQ_ID_NO_1608 | DFLPASTAFD | AIQHSMNLYA | D-YIVESLRR | --- | 228 |
| SEQ_ID_NO_1609 | DFLLATTAMR | AIKHSMTLYA | D-YIVESLRR | --- | 216 |

Figure 56

| | | | | | | | | |
|---|---|---|---|---|---|---|---|---|
| SEQ_ID_NO_361 | --MNGGI GDA | LMQP- | -QHVQ | V-MSS | ---- | ---------- | S | LPMVASTFVA | 31 |
| SEQ_ID_NO_443 | MDDPGASADP | AARHH | LSPQQ | LGGQP | ---- | ---------- | P | VPRSPTPLDL | 36 |
| SEQ_ID_NO_212 | -MDDPGAADP | GARP- | -HHLS | PGQPP | ---- | ---------- | V | VPRSPTPLDL | 33 |
| SEQ_ID_NO_421 | ---------- | ----- | ----- | ----- | ---- | ---------- | - | ---------- | 0 |
| SEQ_ID_NO_1437 | MGGGSDTTDT | NMMQR | VNSSS | GTSSS | ---- | ---------- | S | PKHNLHLNP | 36 |
| SEQ_ID_NO_740 | -MGDTEEANS | EMI QR | LQSSF | GTTQS | SSTTM | AKQPFSLINQ | DVSDLSLNP | 49 |
| SEQ_ID_NO_173 | -MEDTEAASS | FKMN- | -NHME | QLTI P | ---- | ---------- | Q | FNASSQSQMR | 33 |
| SEQ_ID_NO_1461 | -MEDTEAASS | FKMN- | -NHME | QLTI P | ---- | ---------- | Q | FNASSQSQMR | 33 |

| | | | | | | | | |
|---|---|---|---|---|---|---|---|---|
| SEQ_ID_NO_361 | EPAAAAAA- | ----- | ---------- | ---------- | -ANKP- | RAAG | ---- | LPPTP | 52 |
| SEQ_ID_NO_443 | ASAAAASG-- | -YRRL | SPS- | ---LRPPAHP | QARLP- | SPYG | ---- | QI PSP | 72 |
| SEQ_ID_NO_212 | SSAAAAAAA | SYRRL | SPS- | ---LRPPAHP | QARLP- | SPYP | ---- | QI PSSS | 73 |
| SEQ_ID_NO_421 | ---------- | ----- | ----- | -----MADS | NSKPPMSSQN | ---------- | 14 |
| SEQ_ID_NO_1437 | ALI RSHHH- | ----- | FRH-- | ---PFTGAPP | PPI PPI SPYS | ---- | QI PAFL | 69 |
| SEQ_ID_NO_740 | TQMRARHFTN | FSQNF | SGDSN | KRVGFPPSHP | NQI PPI SPYS | ---- | QI PVSR | 95 |
| SEQ_ID_NO_173 | TVTRNHHH- | ---NQRGG- | ---GI PPSHP | HQI PPI SPYS | HMNNQI PVSR | 73 |
| SEQ_ID_NO_1461 | TVTRNHHH- | ---NQRGG- | ---GI PPSHP | HQI PPI SPYS | HMNNQI PVSR | 73 |

| | | | | | | | | |
|---|---|---|---|---|---|---|---|---|
| SEQ_ID_NO_361 | ---------- | ----- | ---------- | ----P- | QVFA | AQRAAAAA- | ---------- | 65 |
| SEQ_ID_NO_443 | ---------- | -GAGA- | HHAR | SLSQP- | LFFS | LDSLPPPP- | ---------- | 97 |
| SEQ_ID_NO_212 | S------APA | AGSSG- | HHAR | SLSQP- | LFFS | LDSLPPLP- | ---------- | 103 |
| SEQ_ID_NO_421 | ---------- | FGVGAVSHVR | SLSQS- | SIFS | NSCLPPLSPF | PPSEPGMVSG | 53 |
| SEQ_ID_NO_1437 | ---------- | --LQP- | RHSR | SMSQPSSFFS | FDSLPPLNPS | APL------- | 98 |
| SEQ_ID_NO_740 | PVNQQMGPQB | FSLGP- | THSR | SLSQPSSFFS | LDSLPPLSPA | PFRDSSSPSV | 144 |
| SEQ_ID_NO_173 | P---QMPSHS | TSPTP- | SHTR | SLSQP- | SFFS | LDSLPPLSPC | TFRESSSTSD | 118 |
| SEQ_ID_NO_1461 | P---QMPSHS | TSPTP- | SHTR | SLSQP- | SFFS | LDSLPPLSPC | TFRESSSTSD | 118 |

| | | | | | | | | |
|---|---|---|---|---|---|---|---|---|
| SEQ_ID_NO_361 | ----GGDVCM | EESAQGGGG | ---------- | ---------- | --GLPPRKA- | 87 |
| SEQ_ID_NO_443 | ----YADL- | ------GAAP | AVPPSPPP-- | --STSDPPPL | --GLPPRRAG | 129 |
| SEQ_ID_NO_212 | ----YADL- | ------AAPP | AI PPSPPS- | --SSSDPPPP | --GLPPRKGG | 135 |
| SEQ_ID_NO_421 | RSS-LKDI SM | EEADVNSQGV | GVVSS- | ---- | --FTRD- | --GLPPRKG- | 88 |
| SEQ_ID_NO_1437 | ----SVSVSV | EEKTGAGFSP | SLPPSPFTMC | HSSSSRNAGD | GENLPPRKS- | 143 |
| SEQ_ID_NO_740 | SDPI STDVFM | EEKDGGSHSL | -LPPSPF--- | --NRGNAPRN | VESLPPRKA- | 187 |
| SEQ_ID_NO_173 | ----HADVSM | EDRDVTSHSP | -LPP------ | --FAARNP- | --SLPPRKS- | 150 |
| SEQ_ID_NO_1461 | ----HADVSM | EDRDVTSHSP | -LPP------ | --FAARNP- | --SLPPRKS- | 150 |

Figure 56 (continued)

| | | | | | | |
|---|---|---|---|---|---|---|
| SEQ_ID_NO_361 | HRRSSSDVPF | GYL-----A | GQHQLLPP- | ---------- | ---------- | 109 |
| SEQ_ID_NO_443 | HRRSQSDIPF | GFA-----Q | LSPPLPPP- | ---------- | ---------- | 151 |
| SEQ_ID_NO_212 | HRRSQSDIPF | GFS-----H | LSPPLPPP- | ---------- | ---------- | 157 |
| SEQ_ID_NO_421 | HRRSNSDVPL | GFSAMI--Q | SSPQLMPI- | ---------- | --------S | 114 |
| SEQ_ID_NO_1437 | HRRSNSDVTF | GFSSMMSQNQ | KSPPLSSLER | SISGEDT--- | --------SD | 182 |
| SEQ_ID_NO_740 | HRRSNSDIPF | GLANVL--Q | CSPPLIPS-R | GSSGLERSMS | GRENLGMAKP | 233 |
| SEQ_ID_NO_173 | HRRSNSDIPF | GFSTVL--Q | SSPPLIPL-R | GREGV----- | --------KP | 183 |
| SEQ_ID_NO_1461 | HRRSNSDIPF | GFSTVL--Q | SSPPLIPL-R | GREGV----- | --------KP | 183 |

| | | | | | | |
|---|---|---|---|---|---|---|
| SEQ_ID_NO_361 | -----KVEAG | A-----GHL | GACA----GG | AAAADDLFNA | YLNLDGLDGL | 144 |
| SEQ_ID_NO_443 | --APVKREVT | A-----AAD | GCRSDGGGGD | DAALYDLVNA | YMDLDGLDPL | 193 |
| SEQ_ID_NO_212 | --APVKREAA | T-----AAE | GCRSD---GD | DFALYDLVNS | YMDLDGMEAL | 196 |
| SEQ_ID_NO_421 | GDKVLGRAVS | LG-----DSN | GKIDERKPKG | ELVTDELLFS | YMNLENIETL | 158 |
| SEQ_ID_NO_1437 | WSNLVKKE-- | -------PRE | GFYKGRKPEV | EAAMDDVFTA | YMNLDNIDVL | 223 |
| SEQ_ID_NO_740 | ADSVKK---E | WERGCDSNAE | GMGERKS-EG | ELVVDDLFSA | YMNLDNIDVL | 278 |
| SEQ_ID_NO_173 | NSSVVKRETN | WEHG--NVE | GSGEKKSPEG | ELVVDDLFSA | YMNLDSFDTL | 229 |
| SEQ_ID_NO_1461 | NSSVVKRETN | WEHG--NVE | EKIKSLSPEG | ELVVDDLFSA | YMNLDNIDAI | 228 |

| | | | | | | |
|---|---|---|---|---|---|---|
| SEQ_ID_NO_361 | NSSDDRH-DE | GD------- | SRGSSI-KTN | GADSSENESE | ECADDTRGGI | 184 |
| SEQ_ID_NO_443 | NSSEDRH-DD | RD------- | SRASGTRAGS | AAESSENEAE | S--------- | 225 |
| SEQ_ID_NO_212 | NSSEERH-ED | RD------- | SRASGTRTGS | VADSSENEAE | S--------- | 228 |
| SEQ_ID_NO_421 | NGSGTKD-RD | KD------- | SIVSGT-KVT | GSESSNNEAE | SVNKGNNVS- | 197 |
| SEQ_ID_NO_1437 | NSFGGEDGKN | GNENVFEMES | SRGSGTKKTN | GGDSSDSEGD | SSASGNVK-- | 271 |
| SEQ_ID_NO_740 | NSSGTDD-KN | GNENREDLD- | SRASGT-KTN | GGDSSDNEAE | SSVNESGGNL | 325 |
| SEQ_ID_NO_173 | NSSGTDD-KN | GENRDDLD- | SRADGT-KTN | GGDSSDNEAE | SSVNESGH-- | 274 |
| SEQ_ID_NO_1461 | NDDKNAATDD | ---------- | SRASGT-KTN | GGDSSDNEAE | SSVNESG--- | 264 |

| | | | | | | |
|---|---|---|---|---|---|---|
| SEQ_ID_NO_361 | RLWS-ADGGE | RREGVKRNAA | GEPATAPLAR | HARSLSMDS- | LIGKFNFTAG | 232 |
| SEQ_ID_NO_443 | ---------- | QSTSADRKDG | GK-----BR | HCRSLSIDS- | FMGKLSFAAG | 258 |
| SEQ_ID_NO_212 | ---------- | HSTPVERKDG | GG-----KSR | HCRSLSVDS- | FIEKLNF--- | 259 |
| SEQ_ID_NO_421 | -----IQPTN | LREGTKRSAD | AN---APAAR | HFRSLSMDS- | AIGNFHY-G | 237 |
| SEQ_ID_NO_1437 | -----VALSS | SSSGVKRRAG | GD--APTGR | HYRSVSMDSC | FMGKLNF-G | 312 |
| SEQ_ID_NO_740 | PRAGLSSSTE | KREGIKRSAG | GD--APTTR | HYRSVSMDS- | FMGKLNF-G | 370 |
| SEQ_ID_NO_173 | ------GGSE | KREGMKRSAG | GE--APTTR | HYRSVSMDS- | FIGKLNF-G | 313 |
| SEQ_ID_NO_1461 | ------DSMQ | RREGNKRSAG | GD--APTTR | HYRSVSMDS- | FIGKLNF-N | 303 |

Figure 56 (continued)

| | | | | | | | |
|---|---|---|---|---|---|---|---|
| SEQ_ID_NO_361 | TA------- | AAAGNGVALG | PN------- | RFSLEFGSGE | FTPSEMKKIM | 266 |
| SEQ_ID_NO_443 | EESPKLPLP | SPGGSLTRSG | SGSLEGGAVA | LFNMEFTNGE | FTDSEKKKIM | 307 |
| SEQ_ID_NO_212 | DESPKLPLP | SPSGGLSRSG | SGSLDGGAAS | LFSAEFANGE | FTEAEKKKIM | 308 |
| SEQ_ID_NO_421 | DESPNLPT | SLMMRSGQLS | PSNSGNESSS | KHNLDFGNSE | FSEAEMKKIM | 285 |
| SEQ_ID_NO_1437 | DESSLKLPP | SSSA---KVS | PTNSGEGNSS | AYSVEFGNSE | FTAAEMKKIA | 358 |
| SEQ_ID_NO_740 | NESPKLPP | SPGTRPGQLS | PTDSIDGN-- | AFSLDFGNGE | FSGAELKKIM | 416 |
| SEQ_ID_NO_173 | DESPKLPP | SPGDRGRLMS | PAGGDGNSA | AFSLEFGSGE | FSGPELKKIM | 361 |
| SEQ_ID_NO_1461 | DESL-KMPP | SPGG---LMS | PGNSGDGNNA | AFSLEFGNGE | FSGPELKKIM | 348 |

| | | | | | | | |
|---|---|---|---|---|---|---|---|
| SEQ_ID_NO_361 | ADEKLAEMAL | ADPKRVKRVL | ANRQSAARSK | ERKMRYIAEL | EQKVQLQSE | 316 |
| SEQ_ID_NO_443 | ANERLAEIAL | TDPKRVKRIL | ANRQSAARSK | ERKMRYIQEL | EHKVQVLQTE | 357 |
| SEQ_ID_NO_212 | ANERLAEIAL | TDPKRVKRIL | ANRQSAARSK | ERKMRYIQEL | EHKVQVLQTE | 358 |
| SEQ_ID_NO_421 | ADERLAEIAV | LDPKRAKRIL | ANRLSAARSK | ERKTRYISEL | EHKVQKLQTE | 335 |
| SEQ_ID_NO_1437 | ADEKLAEIVM | ADPKRVKRIL | ANRVSAARSK | ERKTRYMAEL | EHKVQTLQTE | 408 |
| SEQ_ID_NO_740 | ANEKLAEIAL | ADPKRAKRIL | ANRQSAARSK | ERKMRYISEL | EHKVQTLQTE | 466 |
| SEQ_ID_NO_173 | ANEKLAEIAL | TDPKRAKRIL | ANRQSAARSK | ERKMRYISEL | EHKVQTLQTE | 411 |
| SEQ_ID_NO_1461 | ANEKLAEIAM | ADPKRAKRIL | ANRQSAARSK | ERKMRYISEL | EHKVQTLQTE | 398 |

| | | | | | | | |
|---|---|---|---|---|---|---|---|
| SEQ_ID_NO_361 | ATNLSAQLTM | MQRDSAGLAT | QNNELKFRLH | AMEQQAQLRD | ALNEALTTFV | 366 |
| SEQ_ID_NO_443 | ATTLSAQLTM | LQRDSAGLAT | QNNELKIRLQ | AMEQQAQLRD | ALNEALTAEV | 407 |
| SEQ_ID_NO_212 | ATTLSAQLTM | LQRDSTGLAT | QNNELKIRLQ | AMEQQAQLRD | ALNEALTAEV | 408 |
| SEQ_ID_NO_421 | TTTLSTQVTI | LQKNFVESS | LNSELKFRIQ | AMEQQAQLRD | ALHEALTAEV | 385 |
| SEQ_ID_NO_1437 | ATTLSAQLTH | LQRDSMGLTN | QNSELKFRLQ | AMEQQAQLRD | ALSEKLNEFV | 458 |
| SEQ_ID_NO_740 | ATTLSAQLTL | LQRDSVGLTN | QNNELKFRIQ | AMEQQAQLRD | ALNEALTAEV | 516 |
| SEQ_ID_NO_173 | ATTLSAQLTL | LQRDSAGLTN | QNSELKFRLQ | SMEQQAKLRD | ALNEALTAEV | 461 |
| SEQ_ID_NO_1461 | ATTLSAQLTL | LQRDSVGLTN | QNSELKFRLQ | SMEQQAKLRD | ALNEALTAEV | 448 |

| | | | | | | | |
|---|---|---|---|---|---|---|---|
| SEQ_ID_NO_361 | QRLKLATAEL | GDSCSSSSLA | QQLQLNAQNQ | MFQL------ | -------QQQ | 403 |
| SEQ_ID_NO_443 | QRLKLATGEV | TDGRMPKGL | QQQM---NSQ | MLQL------ | ------QQL | 440 |
| SEQ_ID_NO_212 | QRLKLATGEI | TDGRMSKGL | QQQM---NSQ | LIQL------ | ---------- | 438 |
| SEQ_ID_NO_421 | QRLKLAAGEH | REEGRLPNNM | TQQT-PVKHN | FQM------ | ---------- | 418 |
| SEQ_ID_NO_1437 | QRLKLVIGEP | NRRQSGSSSS | ESKMSLNPE | MFQQ------ | ---------L | 492 |
| SEQ_ID_NO_740 | RRLKIATAEQ | GDSDPSKSM | VQQQLSINPQ | MYLQQPRPSQ | LGMHQLQQS | 566 |
| SEQ_ID_NO_173 | QRLKIATAEL | SSDSHGSSCL | POHSVNPL | MFQQ------ | ------QPP | 497 |
| SEQ_ID_NO_1461 | QRLKIVTAEL | NGESLPSNCM | POHSVNPM | MFQQ------ | ---------- | 481 |

Figure 56 (continued)

| | | | | | | | |
|---|---|---|---|---|---|---|---|
| SEQ_ID_NO_361 | QAT Q PFYQ | QQSQ- - - - - | - - - - - - - - - Q | NGAAKNNESK | E | 429 |
| SEQ_ID_NO_443 | QVQQQAPQAQ | QQGQ- - - - - | - - - - - - - - - - | RQQQQQPQKS | A | 465 |
| SEQ_ID_NO_212 | - - QQLQIQQQ | QSSQ- - - - - | - - - - - - - - - - | - - - - TTQQDR | L | 457 |
| SEQ_ID_NO_421 | - - QRQQPSQM | QQLS- - - - - | - - - - - - - VGK | ASAASATPAS | A | 444 |
| SEQ_ID_NO_1437 | SISQLQHQQM | QHSN- - - - - | - - - - - - - QC | STMKAKHTSN | D | 519 |
| SEQ_ID_NO_740 | SASQFNMHQR | QRQQQQQQQQ | QSSQPQPQQN | GNTTPKPDSN | Q | 607 |
| SEQ_ID_NO_173 | SASQQNIHLQ | QQQH- - - - - | - - - - - - - RQN | GNANSNSDLK | Q | 525 |
| SEQ_ID_NO_1461 | - - - QHQHQQH | QQQQ- - - - - | - - - - - - - QQN | GNANSKNELK | Q | 506 |

Figure 57

| | | | | | | |
|---|---|---|---|---|---|---|
| SEQ_ID_NO_97 | ----MGMKSP | NIAAFMLPLL | LILFTLSSCL | KVVESTGRKL | -AWGFSSTPI | 46 |
| SEQ_ID_NO_2013 | MKKKMGSKSP | NGAFVLPLL | LILFTLSSQA | RLIESTGRKL | AAWGFGGAPI | 50 |
| SEQ_ID_NO_2015 | ----MGSKSP | NIAALVLPLL | LILFSLSSQA | RLVESSGRKL | AAWGFGGAPI | 46 |

| | | | | | | |
|---|---|---|---|---|---|---|
| SEQ_ID_NO_97 | VYTPPSRSCG | TSPAVFTSKW | RRPRPCRLPP | GEY PHSDQS | P | 86 |
| SEQ_ID_NO_2013 | WTPPSNSCG | ASPAVWYPKP | TKRGPCRGPP | GIGIPTSYQS | P | 91 |
| SEQ_ID_NO_2015 | STPSSNSCG | ASPAVWYPKP | TKPRPCRRTP | GIGIPTSHQS | P | 87 |

NUCLEOTIDE SEQUENCES AND CORRESPONDING POLYPEPTIDES CONFERRING MODIFIED PHENOTYPE CHARACTERISTICS IN PLANTS

CROSS REFERENCES TO RELATED APPLICATIONS

This application is a divisional of co-pending application Ser. No. 13/644,359, filed Oct. 4, 2012 (pending), which application is a Continuation-in-Part of application Ser. No. 13/465,846 filed on May 7, 2012 (abandoned), and for which priority is claimed under 35 U.S.C. § 120. Application Ser. No. 13/465,846 is a Division of application Ser. No. 10/572,827, now U.S. Pat. No. 8,193,409, filed on Mar. 7, 2007. Application Ser. No. 10/572,827 is a national phase under 35 U.S.C. § 371 of PCT International Application No. PCT/US2003/025997 which has the International filing date of Aug. 18, 2003, which designated the United States of America. The entire contents of each of which are hereby incorporated by reference, including their sequence listings.

This application is a Continuation-in-Part of co-pending application Ser. No. 11/779,266 filed on Jul. 17, 2007 and for which priority is claimed under 35 U.S.C. § 120. Application Ser. No. 11/779,266 is a Continuation-in-Part of application Ser. No. 11/778,060, now abandoned, filed Jul. 15, 2007. Application Ser. No. 11/778,060 is a Continuation-in-Part of application Ser. No. 11/248,547, now U.S. Pat. No. 7,244,879, filed Oct. 12, 2005. The entire contents of each of which are hereby incorporated by reference, including their sequence listings.

This application is a Continuation-in-Part of co-pending application Ser. No. 12/514,991 filed on Jan. 8, 2010 and for which priority is claimed under 35 U.S.C. § 120. Application Ser. No. 12/514,991 is a national phase under 35 U.S.C. § 371 of PCT International Application No. PCT/US2007/085007 which has the International filing date of Nov. 16, 2007, which designated the United States of America, and which claims priority under 35 U.S.C. § 119(e) of U.S. Provisional Application No. 60/859,467, filed Nov. 16, 2006. The entire contents of each of which are hereby incorporated by reference, including their sequence listings.

This application is a Continuation-in-Part of co-pending application Ser. No. 12/445,005 filed on Jul. 13, 2011 and for which priority is claimed under 35 U.S.C. § 120. Application Ser. No. 12/445,005 is a national phase under 35 U.S.C. § 371 of PCT International Application No. PCT/US2007/081301 which has the International filing date of Oct. 12, 2007, which designated the United States of America, and which claims priority under 35 U.S.C. § 119(e) of U.S. Provisional Application No. 60/851,585, filed Oct. 12, 2006. The entire contents of each of which are hereby incorporated by reference, including their sequence listings.

This application is a Continuation-in-Part of co-pending application Ser. No. 12/515,707 filed on Dec. 16, 2009 and for which priority is claimed under 35 U.S.C. § 120. Application Ser. No. 12/515,707 is a national phase under 35 U.S.C. § 371 of PCT International Application No. PCT/US2007/085439 which has the International filing date of Nov. 21, 2007, which designated the United States of America, and which claims priority under 35 U.S.C. § 119(e) of U.S. Provisional Application No. 60/860,296, filed Nov. 21, 2006. The entire contents of each of which are hereby incorporated by reference, including their sequence listings.

This application is a Continuation-in-Part of co-pending application Ser. No. 12/615,920 filed on Nov. 10, 2009 and for which priority is claimed under 35 U.S.C. § 120. Application Ser. No. 12/615,920 is a Continuation of application Ser. No. 11/114,963, now U.S. Pat. No. 7,696,409, filed on Apr. 25, 2005. Application Ser. No. 11/114,963 claims priority under 35 U.S.C. § 119(e) of U.S. Provisional Application No. 60/564,659, filed Apr. 23, 2004. The entire contents of each of which are hereby incorporated by reference, including their sequence listings.

This application is a Continuation-in-Part of co-pending application Ser. No. 12/605,261 filed on Oct. 23, 2009 and for which priority is claimed under 35 U.S.C. § 120. Application Ser. No. 12/605,261 is a Division of application Ser. No. 11/298,391, now U.S. Pat. No. 7,663,027, filed on Dec. 8, 2005. Application Ser. No. 11/298,391 claims priority under 35 U.S.C. § 119(e) of U.S. Provisional Application Nos. 60/635,115, filed Dec. 8, 2004 and 60/635,140, filed on Dec. 8, 2004. The entire contents of each of which are hereby incorporated by reference, including their sequence listings.

This application is a Continuation-in-Part of co-pending application Ser. No. 12/377,106 filed on Aug. 13, 2010 and for which priority is claimed under 35 U.S.C. § 120. Application Ser. No. 12/377,106 is a national phase under 35 U.S.C. § 371 of PCT International Application No. PCT/US2007/075747 which has the International filing date of Aug. 10, 2007, which designated the United States of America, and which claims priority under 35 U.S.C. § 119(e) of U.S. Provisional Application No. 60/837,434, filed Aug. 11, 2006. The entire contents of each of which are hereby incorporated by reference, including their sequence listings.

This application is a Continuation-in-Part of co-pending application Ser. No. 12/541,607 filed on Aug. 14, 2009 and for which priority is claimed under 35 U.S.C. § 120. Application Ser. No. 12/541,607 is a Continuation of application Ser. No. 11/140,347, now U.S. Pat. No. 7,576,260, filed on May 27, 2005. Application Ser. No. 11/140,347 claims priority under 35 U.S.C. § 119(e) of U.S. Provisional Application No. 60/575,309, filed May 27, 2004. The entire contents of each of which are hereby incorporated by reference, including their sequence listings.

This application is a Continuation-in-Part of co-pending application Ser. No. 13/184,361 filed on Jul. 15, 2011 and for which priority is claimed under 35 U.S.C. § 120. Application Ser. No. 13/184,361 is a Division of application Ser. No. 11/140,450, now U.S. Pat. No. 8,022,273, filed on May 27, 2005. Application Ser. No. 11/140,450 claims priority under 35 U.S.C. § 119(e) of U.S. Provisional Application No. 60/575,253, filed May 27, 2004. The entire contents of each of which are hereby incorporated by reference, including their sequence listings.

This application is a Continuation-in-Part of co-pending application Ser. No. 11/654,357 filed on Jan. 16, 2007 and for which priority is claimed under 35 U.S.C. § 120. Application Ser. No. 11/654,357 is a Non-Provisional which claims priority under 35 U.S.C. § 119(e) of U.S. Provisional Application Nos. 60/778,568, filed Mar. 1, 2006 and 60/758,831, filed on Jan. 13, 2006. The entire contents of each of which are hereby incorporated by reference, including their sequence listings.

This application is a Continuation-in-Part of co-pending application Ser. No. 13/465,841 filed on May 7, 2012 and for which priority is claimed under 35 U.S.C. § 120. Application Ser. No. 13/465,841 is a Division of application Ser. No. 11/858,117, now abandoned, filed on Sep. 19, 2007. Application Ser. No. 11/858,117 is a Continuation-in-Part of Application No. PCT/US2007/06544 which has the International filing date of Mar. 14, 2007, and which claims priority under 35 U.S.C. § 119(e) of U.S. Provisional Application No. 60/782,735, filed Mar. 14, 2006. The entire contents of each of which are hereby incorporated by reference, including their sequence listings.

This application is a Continuation-in-Part of co-pending application Ser. No. 12/918,309 filed on Nov. 22, 2010 and for which priority is claimed under 35 U.S.C. § 120. Application Ser. No. 12/918,309 is a national phase under 35 U.S.C. § 371 of PCT International Application No. PCT/US2009/034638 which has the International filing date of Feb. 20, 2009, which designated the United States of America, and which claims priority under 35 U.S.C. § 119(e) of U.S. Provisional Application No. 61/030,152, filed Feb. 20, 2008. The entire contents of each of which are hereby incorporated by reference, including their sequence listings.

This application is a Continuation-in-Part of co-pending application Ser. No. 12/922,143 filed on Feb. 1, 2011 and for which priority is claimed under 35 U.S.C. § 120. Application Ser. No. 12/922,143 is a national phase under 35 U.S.C. § 371 of PCT International Application No. PCT/US2009/037025 which has the International filing date of Mar. 12, 2009, which designated the United States of America, and which claims priority under 35 U.S.C. § 119(e) of U.S. Provisional Application No. 61/036,396, filed Mar. 13, 2008. The entire contents of each of which are hereby incorporated by reference, including their sequence listings.

This application is a Continuation-in-Part of co-pending application Ser. No. 11/241,685 filed on Sep. 30, 2005 and for which priority is claimed under 35 U.S.C. § 120. Application Ser. No. 11/241,685 is a Non-provisional which claims priority under 35 U.S.C. § 119(e) of U.S. Provisional Application No. 60/615,080, filed on Sep. 30, 2004. The entire contents of each of which are hereby incorporated by reference, including their sequence listings.

This application is a Continuation-in-Part of co-pending application Ser. No. 12/863,773 filed on Nov. 23, 2010 and for which priority is claimed under 35 U.S.C. § 120. Application Ser. No. 12/863,773 is a national phase under 35 U.S.C. § 371 of PCT International Application No. PCT/US2009/031609 which has the International filing date of Jan. 21, 2009, which designated the United States of America, and which claims priority under 35 U.S.C. § 119(e) of U.S. Provisional Application No. 61/022,786, filed Jan. 22, 2008. The entire contents of each of which are hereby incorporated by reference, including their sequence listings.

This application is a Continuation-in-Part of co-pending application Ser. No. 12/282,342 filed on Nov. 17, 2008 and for which priority is claimed under 35 U.S.C. § 120. Application Ser. No. 12/282,342 is a national phase under 35 U.S.C. § 371 of PCT International Application No. PCT/US2007/06544 which has the International filing date of Mar. 14, 2007, which designated the United States of America, and which claims priority under 35 U.S.C. § 119(e) of U.S. Provisional Application No. 60/782,735, filed Mar. 14, 2006. The entire contents of each of which are hereby incorporated by reference, including their sequence listings.

This application is a Continuation-in-Part of co-pending application Ser. No. 12/776,319 filed on May 7, 2010 and for which priority is claimed under 35 U.S.C. § 120. Application Ser. No. 12/776,319 is a Division of application Ser. No. 11/324,093, now U.S. Pat. No. 7,803,983, filed on Dec. 29, 2005. Application Ser. No. 11/324,093 is a Continuation-in-Part of application Ser. No. 11/172,740, now U.S. Pat. No. 7,396,979, filed on Jun. 30, 2005. Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

This application is a Continuation-in-Part of co-pending application Ser. No. 12/911,698 filed on Oct. 25, 2010 and for which priority is claimed under 35 U.S.C. § 120. Application Ser. No. 12/911,698 is a Division of application Ser. No. 11/324,098, now U.S. Pat. No. 7,884,261, filed on Dec. 29, 2005. Application Ser. No. 11/324,098 is a Continuation-in-Part of application Ser. No. 11/172,740, now U.S. Pat. No. 7,396,979, filed on Jun. 30, 2005. Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

This application is a Continuation-in-Part of co-pending application Ser. No. 13/609,176 filed on Sep. 10, 2012 and for which priority is claimed under 35 U.S.C. § 120. Application Ser. No. 13/609,176 is a Division of application Ser. No. 12/139,269, pending, filed on Jun. 13, 2008. Application Ser. No. 12/139,269 is a Division of application Ser. No. 11/172,740, now U.S. Pat. No. 7,396,979, filed on Jun. 30, 2005. Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

TECHNICAL FIELD the present invention relates to methods and materials involved in tolerance of a plant to limiting exogenous nitrogen sources. For example, this document provides plants having increased low-nitrogen tolerance levels as well as materials and methods for making plants and plant products having increased low-nitrogen tolerance levels.

BACKGROUND

Nitrogen is often the rate-limiting element in plant growth, and all field crops have a fundamental dependence on exogenous nitrogen sources.

According to a recent study published in Field Crops Research (Volume 100, Issues 2-3, 1 Feb. 2007, Pages 210-217), Nitrogenous fertilizer, which is usually supplied as ammonium nitrate, potassium nitrate, or urea, typically accounts for 40% of the costs associated with crops, such as corn and wheat in intensive agriculture.

Improving nitrogen use efficiency of crop plants is an important goal towards reducing input costs and reducing the environmental consequences of intensive nitrogen fertilization on the environment. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively.

Plants have a number of means to cope with nutrient deficiencies, such as poor nitrogen availability. One important mechanism senses nitrogen availability in the soil and respond accordingly by modulating gene expression while a second mechanism is to sequester or store nitrogen in times of abundance to be used later. The nitrogen sensing mechanism relies on regulated gene expression and enables rapid physiological and metabolic responses to changes in the supply of inorganic nitrogen in the soil by adjusting nitrogen uptake, reduction, partitioning, remobilization and transport in response to changing environmental conditions. Nitrate acts as a signal to initiate a number of responses that serve to reprogram plant metabolism, physiology and development (Redinbaugh et al. (1991) *Physiol. Plant.* 82, 640-650; Forde (2002) *Annual Review of Plant Biology* 53, 203-224). Nitrogen-inducible gene expression has been characterized for a number of genes in some detail. These include nitrate reductase, nitrite reductase, 6-phosphoglucante dehydrogenase, and nitrate and ammonium transporters (Redinbaugh et al. (1991) *Physiol. Plant.* 82, 640-650; Huber et al. (1994) *Plant Physiol* 106, 1667-1674; Hwang et al. (1997) *Plant Physiol.* 113, 853-862; Redinbaugh et al. (1998) *Plant Science* 134, 129-140; Gazzarrini et al. (1999) *Plant Cell* 11, 937-948; Glass et al. (2002) *J. Exp. Bot.* 53, 855-864; Okamoto et al. (2003) *Plant Cell Physiol.* 44, 304-317).

In the fields of agriculture and forestry, efforts are constantly being made to produce plants with an increased growth potential in order to feed the ever-increasing world population and to guarantee the supply of reproducible raw materials. There is a need for methods of increasing nitrogen use efficiency in plants, which leads to better growth potential and more biomass. This is done conventionally through plant breeding. The breeding process is, however, both time-consuming and labor-intensive. Furthermore, appropriate breeding programs must be performed for each relevant plant species. In addition, although great progresses that have been made about nitrogen utilization and the components involved in nitrogen use efficiency, such as nitrogen uptake, nitrogen assimilation and nitrogen partitioning or remobilization, much is still unknown about many of these complex interactions. Therefore, there is a continuing need for generally applicable processes that improve forest or agricultural plant growth to suit particular needs depending on specific environmental conditions. For example, genes that confer tolerance to growth on low nitrogen supply are valuable product prototypes for manipulating nitrogen use efficiency in plants (Good et al., 2004). One strategy to achieve such desirable traits involves genetic manipulation of plant characteristics through the introduction of exogenous nucleic acids conferring increased efficiency of nitrogen use by plants, which in turn should enable the production of higher yields with existing fertilizer inputs and/or enable existing yields of crops to be obtained with lower fertilizer input, or better yields on soils of poorer quality. Such approaches have the advantage of not usually being limited to one plant species, but instead being transferable among plant species. The present invention relates to a method for increasing growth potential, and/or increasing levels of nitrogen use efficiency in plants, characterized by expression of recombinant DNA molecules stably integrated into the plant genome

SUMMARY

The present invention provides methods and materials related to plants having modulated levels of low-nitrogen tolerance. For example, the present invention provides transgenic plants and plant cells having increased levels of low-nitrogen tolerance, nucleic acids (i.e. isolated polynucleotides), polypeptides encoded thereby used to generate transgenic plants and plant cells having increased levels of low-nitrogen tolerance, and methods for making plants and plant cells having increased levels of low-nitrogen tolerance. Such plants and plant cells can be grown under limiting exogenous nitrogen without stunted growth and diminished yields. Plants having increased low-nitrogen tolerance levels may be useful to produce biomass which may be converted to a liquid fuel or other chemicals and/or to produce food and feed on land that is currently marginally productive, resulting in an overall expansion of arable land.

Methods of producing a plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-57. The tissue has a difference in the level of low-nitrogen tolerance as compared to the corresponding level in tissue of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577. A plant and/or plant tissues produced from the plant cell has a difference in the level of low-nitrogen tolerance as compared to the corresponding level of low-nitrogen tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. A plant and/or plant tissues produced from the plant cell has a difference in the level of low-nitrogen tolerance as compared to the corresponding level low-nitrogen tolerance of a control plant that does not comprise the exogenous nucleic acid.

In another aspect, the invention provides a method of producing a plant, the method comprising growing a plant cell comprising an exogenous nucleic acid that is effective for downregulating an endogenous nucleic acid in the plant cell, wherein the endogenous nucleic acid encodes a polypeptide, and wherein the HMM bit score of the amino acid sequence of the polypeptide is greater than about 20, said HMM based on the amino acid sequences depicted in one of FIGS. 1-57

Methods of modulating the level of low-nitrogen tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-57. A plant and/or plant tissue produced from the plant cell has a difference in the level of low-nitrogen tolerance as compared to the corresponding level of low-nitrogen tolerance of a control plant that does not comprise the exogenous nucleic acid.

In certain embodiments, the HMM bit score of the amino acid sequence of the polypeptide is greater than about 40, using an HMM generated from the amino acid sequences depicted in one of FIGS. 1-57, wherein the polypeptide comprises a Pfam domain having 70 percent or greater sequence identity to a Pfam domain of any one of the polypeptides in the sequence listing.

In another aspect, a method comprises modulating the level of low-nitrogen tolerance in a plant by introducing into a plant cell an exogenous nucleic acid that comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

In another aspect, a method comprises modulating the level of low-nitrogen tolerance in a plant by introducing into a plant cell an exogenous nucleic acid, that comprises a regulatory region operably linked to a nucleotide sequence having 80 percent or greater sequence identity to a nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-57. The plant has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. A plant and/or plant tissue produced from the plant cell has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, or a fragment thereof. A plant and/or plant tissue of a plant produced from the plant cell has a difference in the level of low-nitrogen tolerance as compared to the corresponding level of low-nitrogen tolerance of a control plant that does not comprise the exogenous nucleic acid. A transgenic plant comprising such a plant cell is also provided.

Isolated nucleic acids are also provided. In one aspect, an isolated nucleic acid comprises a nucleotide sequence having 80% or greater sequence identity to the nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. In another aspect, an isolated nucleic acid comprises a nucleotide sequence encoding a polypeptide having 80% or greater sequence identity to the amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577.

In another aspect, methods of identifying a genetic polymorphism associated with variation in the level of low-nitrogen tolerance are provided. The methods include providing a population of plants, and determining whether one or more genetic polymorphisms in the population are genetically linked to the locus for a polypeptide selected from the group consisting of the polypeptides depicted in FIGS. 1-57, SEQ ID NO:556, SEQ ID NO:853, SEQ ID NO:1157, and functional homologs thereof, such as those in the Sequence Listing. The correlation between variation in the level of low-nitrogen tolerance in a tissue in plants of the population and the presence of the one or more genetic polymorphisms in plants of the population is measured, thereby permitting identification of whether or not the one or more genetic polymorphisms are associated with such variation.

In another aspect, the invention provides a method of making a plant line, said method comprising:

a) determining whether one or more genetic polymorphisms in a population of plants is associated with the locus for a polypeptide selected from the group consisting of the polypeptides depicted in FIGS. 1-57, SEQ ID NO: 556, SEQ ID NO: 853, and SEQ ID NO: 1157 and functional homologs thereof;

b) identifying one or more plants in said population in which the presence of at least one allele at said one or more genetic polymorphisms is associated with variation in a trait;

c) crossing each said one or more identified plants with itself or a different plant to produce seed;

d) crossing at least one progeny plant grown from said seed with itself or a different plant; and e) repeating steps c) and d) for an additional 0-5 generations to make said plant line, wherein said at least one allele is present in said plant line.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of Ceres SEEDLINE No. ME00919 (SEQ ID NO:3) with homologous and/or orthologous amino acid sequences GI No. 5921925 (SEQ ID NO:4), CeresClone:1929222 (SEQ ID NO:6), CeresAnnot: 1471370 (SEQ ID NO:10), GI No. 84380741 (SEQ ID NO:21), GI No. 5921926 (SEQ ID NO:22), GI No. 84514161 (SEQ ID NO:25), CeresClone:779234 (SEQ ID NO:27), CeresClone:1600726 (SEQ ID NO:29), GI No. 78183420 (SEQ ID NO:36), CeresClone:1877346 (SEQ ID NO:38), GI No. 125562440 (SEQ ID NO:39), GI No. 115477665 (SEQ ID NO:40), GI No. 1173624 (SEQ ID NO:46), and GI No. 84468276 (SEQ ID NO:47). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of ME01312 (SEQ ID NO:49) with homologous and/or orthologous amino acid sequences CeresClone:1869410 (SEQ ID NO:51), CeresAnnot: 1540549 (SEQ ID NO:53), CeresClone:978708 (SEQ ID NO:58), CeresClone:1623097 (SEQ ID NO:60), GI No. 92873064 (SEQ ID NO:63), GI No. 37051131 (SEQ ID NO:64), GI No. 3341468 (SEQ ID NO:65), CeresClone: 937560 (SEQ ID NO:67), CeresClone:456844 (SEQ ID NO:69), GI No. 125564100 (SEQ ID NO:70), GI No. 52077334 (SEQ ID NO:71), GI No. 113205234 (SEQ ID NO:73), and CeresAnnot:6100272 (SEQ ID NO:75).

FIG. 3 is an alignment of ME01463 (SEQ ID NO:77) with homologous and/or orthologous amino acid sequences GI No. 2811029 (SEQ ID NO:78), CeresClone:1853284 (SEQ ID NO:80), CeresAnnot:1476446 (SEQ ID NO:82), CeresClone:527024 (SEQ ID NO:87), GI No. 27527063 (SEQ ID NO:88), CeresClone:913632 (SEQ ID NO:90), CeresClone: 1386710 (SEQ ID NO:92), GI No. 115461885 (SEQ ID NO:93), and CeresAnnot:6054519 (SEQ ID NO:95)

FIG. 4 is an alignment of ME01910 (SEQ ID NO:100) with homologous and/or orthologous amino acid sequences GI No. 585238 (SEQ ID NO:101), GI No. 90704789 (SEQ ID NO:102), CeresClone:1895729 (SEQ ID NO:104), CeresAnnot:1442808 (SEQ ID NO:108), CeresClone:1104700 (SEQ ID NO:113), GI No. 32966575 (SEQ ID NO:116), GI No. 4996567 (SEQ ID NO:117), GI No. 62286644 (SEQ ID NO:118), GI No. 2623960 (SEQ ID NO:119), GI No. 585241 (SEQ ID NO:120), GI No. 790929 (SEQ ID NO:122), CeresClone:579112 (SEQ ID NO:125), CeresClone:244199 (SEQ ID NO:137), CeresClone:1725848 (SEQ ID NO:144), GI No. 6474950 (SEQ ID NO:145), GI No. 125546057 (SEQ ID NO:146), GI No. 115455945 (SEQ ID NO:147), GI No. 2641211 (SEQ ID NO:149), and GI No. 30024108 (SEQ ID NO:150).

FIG. 5 is an alignment of ME02538 (SEQ ID NO:152) with homologous and/or orthologous amino acid sequences CeresClone:1843642 (SEQ ID NO:154), CeresAnnot: 1459112 (SEQ ID NO:158), CeresClone:953633 (SEQ ID NO:162), and CeresClone:587957 (SEQ ID NO:164).

FIG. 6 is an alignment of ME02603 (SEQ ID NO:166) with homologous and/or orthologous amino acid sequences CeresClone:1857256 (SEQ ID NO:168), CeresAnnot: 1442042 (SEQ ID NO:170), GI No. 89257469 (SEQ ID NO:174), CeresClone:389818 (SEQ ID NO:177), CeresClone:2019147 (SEQ ID NO:181), GI No. 125537720 (SEQ ID NO:182), GI No. 115443697 (SEQ ID NO:183), and GI No. 20340241 (SEQ ID NO:184).

FIG. 7 is an alignment of ME02613 (SEQ ID NO:186) with homologous and/or orthologous amino acid sequences CeresAnnot:1490274 (SEQ ID NO:188), CeresClone: 873093 (SEQ ID NO:193), GI No. 6635384 (SEQ ID NO:194), CeresClone:663726 (SEQ ID NO:196), GI No. 92881411 (SEQ ID NO:197), CeresClone:686525 (SEQ ID NO:199), CeresClone:1524364 (SEQ ID NO:201), CeresClone:1742159 (SEQ ID NO:203), and GI No. 125543535 (SEQ ID NO:204).

FIG. 8 is an alignment of ME02801 (SEQ ID NO:208) with homologous and/or orthologous amino acid sequences CeresClone:981621 (SEQ ID NO:214) and CeresClone: 564714 (SEQ ID NO:216).

FIG. 9 is an alignment of ME03123 (SEQ ID NO:218) with homologous and/or orthologous amino acid sequences CeresClone:1899168 (SEQ ID NO:220), CeresAnnot: 1494669 (SEQ ID NO:222), CeresClone:1017441 (SEQ ID NO:225), CeresClone:1065937 (SEQ ID NO:227), CeresClone:1822919 (SEQ ID NO:229), GI No. 125553329 (SEQ ID NO:230), GI No. 115439053 (SEQ ID NO:231), and CeresAnnot:6040744 (SEQ ID NO:1052).

FIG. 10 is an alignment of ME04204 (SEQ ID NO:234) with homologous and/or orthologous amino acid sequences CeresAnnot:1519952 (SEQ ID NO:236), CeresClone: 234768 (SEQ ID NO:241), GI No. 108707052 (SEQ ID NO:242), and GI No. 55978030 (SEQ ID NO:244).

FIG. 11 s an alignment of ME04477 (SEQ ID NO:246) with homologous and/or orthologous amino acid sequences CeresClone:1620215 (SEQ ID NO:248), GI No. 38016527 (SEQ ID NO:249), CeresClone:1798756 (SEQ ID NO:251), CeresAnnot:1460527 (SEQ ID NO:255), GI No. 119720772 (SEQ ID NO:260), CeresClone:708446 (SEQ ID NO:262), GI No. 92896423 (SEQ ID NO:265), GI No. 113196593 (SEQ ID NO:267), GI No. 75133829 (SEQ ID NO:268), CeresClone:1030374 (SEQ ID NO:270), CeresClone: 1387149 (SEQ ID NO:274), GI No. 5031281 (SEQ ID NO:277), CeresClone:1775820 (SEQ ID NO:279), GI No. 35187687 (SEQ ID NO:286), GI No. 115468934 (SEQ ID NO:290), GI No. 118424243 (SEQ ID NO:296), and CeresAnnot:6063957 (SEQ ID NO:298).

FIG. 12 is an alignment of ME04507 (SEQ ID NO:300) with homologous and/or orthologous amino acid sequences CeresAnnot:1513514 (SEQ ID NO:302), CeresClone: 923483 (SEQ ID NO:310), CeresClone:304357 (SEQ ID NO:312), CeresClone:1902716 (SEQ ID NO:316), GI No. 116309713 (SEQ ID NO:319), GI No. 38345408 (SEQ ID NO:321), and CeresAnnot:6017635 (SEQ ID NO:325).

FIG. 13 is an alignment of ME04587 (SEQ ID NO:332) with homologous and/or orthologous amino acid sequences Ceres ANNOT ID no. 1474882 (SEQ ID NO:334), Ceres ANNOT ID no. 553243 (SEQ ID NO:338), Public GI ID no. 5514645 (SEQ ID NO:339), Ceres CLONE ID no. 464376 (SEQ ID NO:341), Public GI ID no. 1345643 (SEQ ID NO:346), Public GI ID no. 5832707 (SEQ ID NO:347), Public GI ID no. 81157968 (SEQ ID NO:348), Public GI ID no. 6118407 (SEQ ID NO:349), Public GI ID no. 5081817 (SEQ ID NO:351), Public GI ID no. 125556057 (SEQ ID NO:353), Public GI ID no. 115468946 (SEQ ID NO:354), Public GI ID no. 5915860 (SEQ ID NO:356), Public GI ID no. 6979544 (SEQ ID NO:358), Public GI ID no. 5832709 (SEQ ID NO:359), Public GI ID no. 6979542 (SEQ ID NO:360), Public GI ID no. 14278923 (SEQ ID NO:364), Public GI ID no. 81157970 (SEQ ID NO:365), Public GI ID no. 81157972 (SEQ ID NO:366), Public GI ID no. 169793907 (SEQ ID NO:2541), Public GI ID no. 84514153

(SEQ ID NO:2543), Public GI ID no. 184202209 (SEQ ID NO:2544), Ceres ANNOT ID no. 8459850 (SEQ ID NO:2546), Ceres ANNOT ID no. 8743452 (SEQ ID NO:2548), Public GI ID no. 157327290 (SEQ ID NO:2549), Public GI ID no. 148839039 (SEQ ID NO:2550), Public GI ID no. 197209782 (SEQ ID NO:2551), Public GI ID no. 171906244 (SEQ ID NO:2553).

FIG. 14 is an alignment of ME04753 (SEQ ID NO:368) with homologous and/or orthologous amino acid sequences GI No. 21388658 (SEQ ID NO:369), GI No. 4704605 (SEQ ID NO:371), GI No. 90704785 (SEQ ID NO:372), GI No. 115529229 (SEQ ID NO:373), GI No. 20152613 (SEQ ID NO:374), CeresClone:1916226 (SEQ ID NO:376), CeresAnnot:1460836 (SEQ ID NO:392), GI No. 83032218 (SEQ ID NO:420), GI No. 1346180 (SEQ ID NO:422), CeresClone:621487 (SEQ ID NO:425), GI No. 6273331 (SEQ ID NO:433), GI No. 92874469 (SEQ ID NO:434), GI No. 1778374 (SEQ ID NO:436), GI No. 18076086 (SEQ ID NO:437), GI No. 2674201 (SEQ ID NO:438), GI No. 2267567 (SEQ ID NO:440), GI No. 544426 (SEQ ID NO:441), GI No. 6911144 (SEQ ID NO:444), GI No. 469071 (SEQ ID NO:447), GI No. 1934994 (SEQ ID NO:450), GI No. 82623423 (SEQ ID NO:451), GI No. 90265701 (SEQ ID NO:454), GI No. 544423 (SEQ ID NO:455), CeresClone:1320097 (SEQ ID NO:458), CeresClone:1469740 (SEQ ID NO:465), CeresClone:1740834 (SEQ ID NO:473), GI No. 2226370 (SEQ ID NO:474), GI No. 27527723 (SEQ ID NO:475), CeresClone:1762613 (SEQ ID NO:477), GI No. 125545195 (SEQ ID NO:488), GI No. 108710322 (SEQ ID NO:494), GI No. 34851124 (SEQ ID NO:504), GI No. 111162637 (SEQ ID NO:505), GI No. 7024451 (SEQ ID NO:506), and GI No. 1229138 (SEQ ID NO:507).

FIG. 15 is an alignment of ME04772 (SEQ ID NO:510) with homologous and/or orthologous amino acid sequences GI No. 38016521 (SEQ ID NO:511), CeresClone:1895044 (SEQ ID NO:513), CeresAnnot:1512198 (SEQ ID NO:517), CeresClone:682503 (SEQ ID NO:521), CeresClone:685324 (SEQ ID NO:523), CeresClone:1384414 (SEQ ID NO:525), CeresClone:1739919 (SEQ ID NO:527), CeresClone:2002832 (SEQ ID NO:529), GI No. 125531563 (SEQ ID NO:530), and GI No. 115478344 (SEQ ID NO:531).

FIG. 16 is an alignment of ME04909 (SEQ ID NO:533) with homologous and/or orthologous amino acid sequences CeresClone:1839156 (SEQ ID NO:535), GI No. 56605378 (SEQ ID NO:536), CeresAnnot:1467946 (SEQ ID NO:538), GI No. 110931704 (SEQ ID NO:539), GI No. 92869601 (SEQ ID NO:542), GI No. 12005328 (SEQ ID NO:543), GI No. 119331596 (SEQ ID NO:546), GI No. 7705206 (SEQ ID NO:547), GI No. 18874263 (SEQ ID NO:548), CeresClone:753605 (SEQ ID NO:550), CeresClone:291733 (SEQ ID NO:552), and GI No. 21902114 (SEQ ID NO:553).

Figure 17:
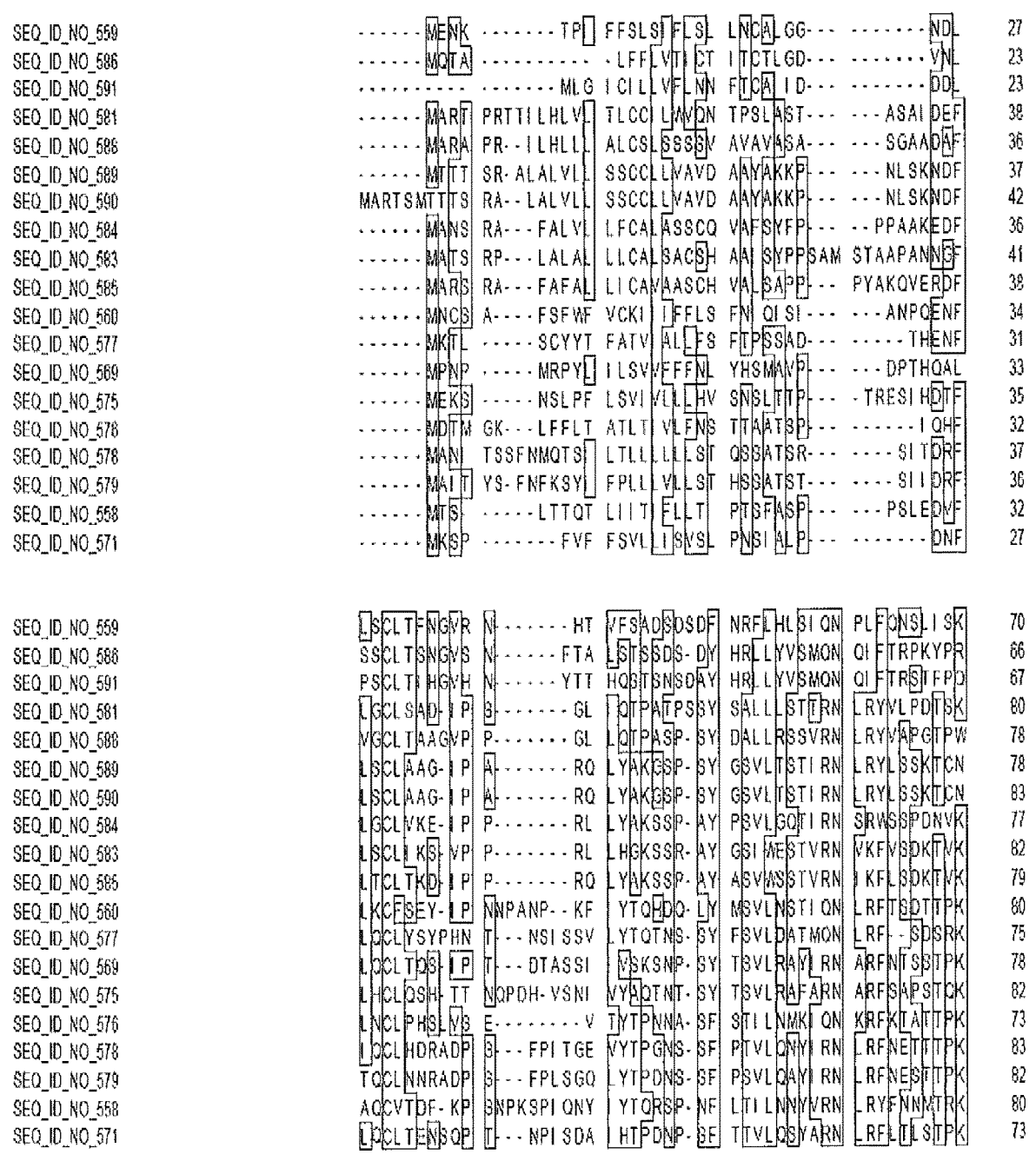

FIG. 17 is an alignment of ME05194 (SEQ ID NO:558) with homologous and/or orthologous amino acid sequences GI No. 400972 (SEQ ID NO:559), GI No. 81158002 (SEQ ID NO:560), CeresClone:1834135 (SEQ ID NO:569), CeresAnnot:1467218 (SEQ ID NO:571), CeresClone:1104143 (SEQ ID NO:575), GI No. 87240745 (SEQ ID NO:576), GI No. 13161397 (SEQ ID NO:577), GI No. 18652400 (SEQ ID NO:578), GI No. 18652398 (SEQ ID NO:579), CeresClone:778892 (SEQ ID NO:581), CeresClone:222523 (SEQ ID NO:583), GI No. 82492267 (SEQ ID NO:584), GI No. 41393750 (SEQ ID NO:585), GI No. 4335857 (SEQ ID NO:586), CeresClone:1776394 (SEQ ID NO:588), GI No. 125555681 (SEQ ID NO:589), GI No. 115468460 (SEQ ID NO:590), and GI No. 51980210 (SEQ ID NO:591).

FIG. 18 is an alignment of ME05267 (SEQ ID NO:593) with homologous and/or orthologous amino acid sequences CeresAnnot:1511954 (SEQ ID NO:595), CeresClone:560687 (SEQ ID NO:599), CeresClone:579724 (SEQ ID NO:603), CeresClone:286197 (SEQ ID NO:605), and GI No. 115489090 (SEQ ID NO:610).

FIG. 19 is an alignment of ME05300 (SEQ ID NO:613) with homologous and/or orthologous amino acid sequences CeresAnnot:6431448 (SEQ ID NO:615), CeresClone:969084 (SEQ ID NO:620), CeresClone:471052 (SEQ ID NO:622), CeresClone:733048 (SEQ ID NO:624), CeresClone:1062332 (SEQ ID NO:626), CeresClone:1743166 (SEQ ID NO:634), CeresClone:1778589 (SEQ ID NO:638), GI No. 125548354 (SEQ ID NO:643), and GI No. 115458464 (SEQ ID NO:644).

FIG. 20 is an alignment of ME05341 (SEQ ID NO:646) with homologous and/or orthologous amino acid sequences CeresClone:1808421 (SEQ ID NO:648), CeresAnnot:1452653 (SEQ ID NO:656), CeresClone:1660955 (SEQ ID NO:660), CeresClone:1287179 (SEQ ID NO:668), CeresClone:1770929 (SEQ ID NO:676), GI No. 125542421 (SEQ ID NO:679), GI No. 115450741 (SEQ ID NO:681), and CeresAnnot:6063505 (SEQ ID NO:685).

FIG. 21 is an alignment of ME05392 (SEQ ID NO:687) with homologous and/or orthologous amino acid sequences CeresClone:1841531 (SEQ ID NO:689), CeresAnnot:1507382 (SEQ ID NO:691), CeresClone:978410 (SEQ ID NO:699), CeresClone:527314 (SEQ ID NO:703), GI No. 92893019 (SEQ ID NO:706), CeresClone:638935 (SEQ ID NO:708), CeresClone:1437744 (SEQ ID NO:712), CeresClone:1728293 (SEQ ID NO:718), GI No. 125526460 (SEQ ID NO:721), GI No. 115463325 (SEQ ID NO:724), and GI No. 40642817 (SEQ ID NO:728).

FIG. 22 is an alignment of ME05429 (SEQ ID NO:730) with homologous and/or orthologous amino acid sequences CeresAnnot:1539629 (SEQ ID NO:732), CeresClone:682471 (SEQ ID NO:735), CeresClone:729869 (SEQ ID NO:737), GI No. 115459766 (SEQ ID NO:738), and CeresAnnot: 6026765 (SEQ ID NO:742).

FIG. 23 is an alignment of ME05493 (SEQ ID NO:746) with homologous and/or orthologous amino acid sequences CeresAnnot:1455092 (SEQ ID NO:748), GI No. 15229284 (SEQ ID NO:751), CeresClone:961796 (SEQ ID NO:753), CeresClone:706956 (SEQ ID NO:755), GI No. 87162911 (SEQ ID NO:758), CeresClone:1061446 (SEQ ID NO:760), GI No. 125540686 (SEQ ID NO:761), GI No. 115447931 (SEQ ID NO:762), GI No. 20152976 (SEQ ID NO:763), and CeresAnnot:6007280 (SEQ ID NO:765).

FIG. 24 is an alignment of ME05885 (SEQ ID NO:769) with homologous and/or orthologous amino acid sequences CeresClone:1808741 (SEQ ID NO:771), CeresAnnot:1437729 (SEQ ID NO:773), CeresClone:952789 (SEQ ID NO:777), CeresClone:724313 (SEQ ID NO:779), CeresClone:791239 (SEQ ID NO:783), CeresClone:208975 (SEQ ID NO:785), CeresClone:1727075 (SEQ ID NO:789), and GI No. 115475611 (SEQ ID NO:790).

FIG. 25 is an alignment of ME07344 (SEQ ID NO:792) with homologous and/or orthologous amino acid sequences CeresClone:1843695 (SEQ ID NO:794), GI No. 56605376 (SEQ ID NO:799), CeresAnnot:1508502 (SEQ ID NO:801), CeresClone:1239229 (SEQ ID NO:805), GI No. 92893962 (SEQ ID NO:808), CeresClone:327364 (SEQ ID NO:810), CeresClone:1820378 (SEQ ID NO:816), GI No. 125524748 (SEQ ID NO:819), and GI No. 115435036 (SEQ ID NO:821).

FIG. 26 is an alignment of ME07859 (SEQ ID NO:824) with homologous amino acid sequence Fragment_of_Ceres ANNOT ID no. 6007357 (SEQ ID NO:826), Fragment_of_Ceres CLONE ID no. 771707 (SEQ ID NO:1708), and Fragment_of_Ceres CLONE ID no. 1790436 (SEQ ID NO:1713).

FIG. 27 is an alignment of ME08464 (SEQ ID NO:828) with homologous and/or orthologous amino acid sequences CeresAnnot:1499777 (SEQ ID NO:832), GI No. 22328730 (SEQ ID NO:837), GI No. 92886131 (SEQ ID NO:839), GI No. 559921 (SEQ ID NO:840), CeresClone:910787 (SEQ ID NO:842), CeresClone:1797432 (SEQ ID NO:844), GI No. 116310135 (SEQ ID NO:845), GI No. 38345464 (SEQ ID NO:847), and GI No. 90657544 (SEQ ID NO:850).

FIG. 28 is an alignment of ME11735 (SEQ ID NO:855) with homologous and/or orthologous amino acid sequences GI No. 35187445 (SEQ ID NO:856), CeresClone:1798230 (SEQ ID NO:858), CeresAnnot:1500963 (SEQ ID NO:862), CeresClone:567542 (SEQ ID NO:868), CeresClone:702251 (SEQ ID NO:870), CeresClone:1606777 (SEQ ID NO:876), CeresClone:1789146 (SEQ ID NO:878), GI No. 116309500 (SEQ ID NO:885), and GI No. 115446281 (SEQ ID NO:886).

Figure 29:
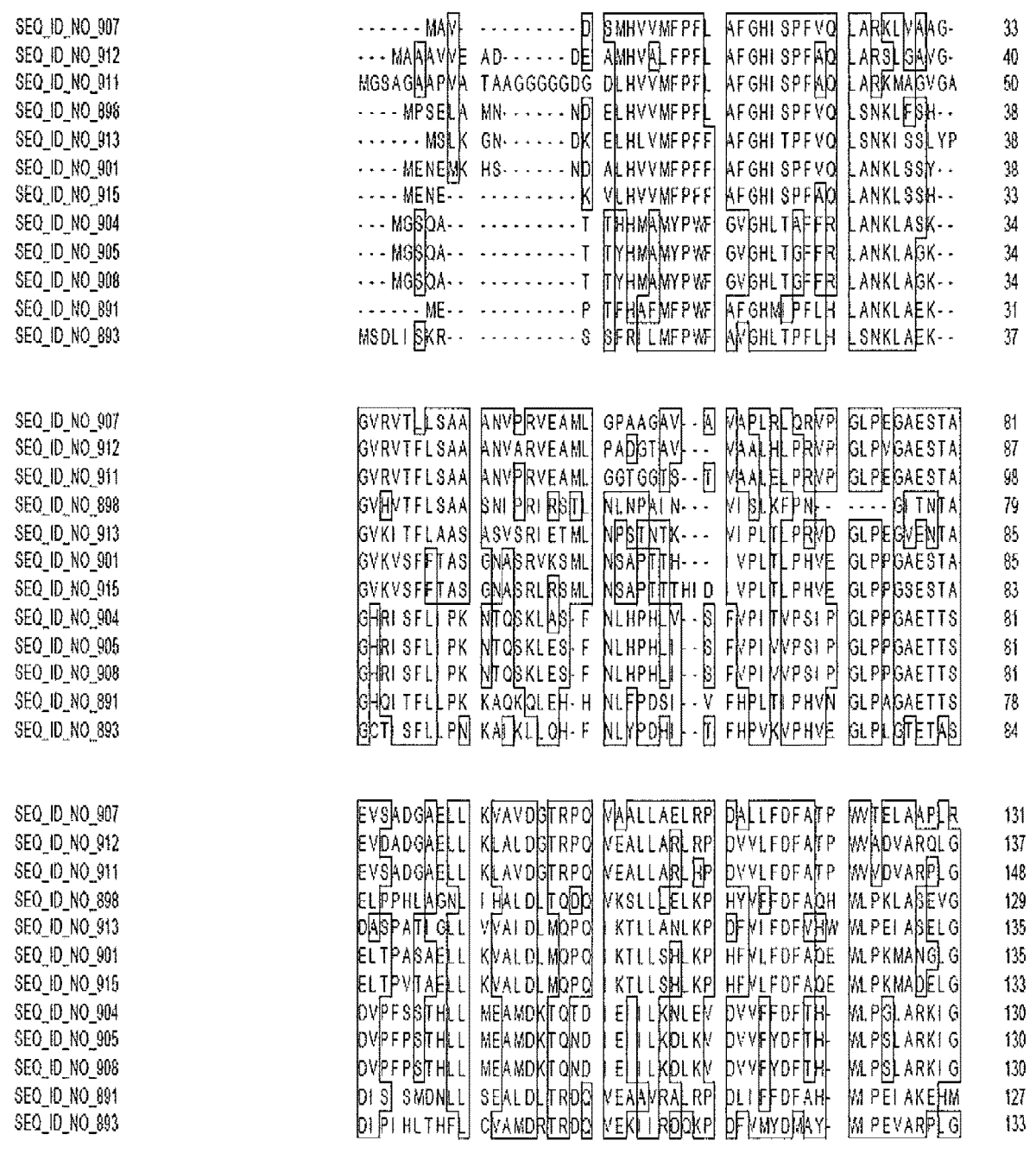

FIG. 29 is an alignment of ME12910 (SEQ ID NO:891) with homologous and/or orthologous amino acid sequences CeresAnnot:1466353 (SEQ ID NO:893), CeresClone:519143 (SEQ ID NO:898), GI No. 2501497 (SEQ ID NO:901), GI No. 119394507 (SEQ ID NO:904), GI No. 62857206 (SEQ ID NO:905), CeresClone:766529 (SEQ ID NO:907), GI No. 62857204 (SEQ ID NO:908), GI No. 125534279 (SEQ ID NO:911), GI No. 115485437 (SEQ ID NO:912), GI No. 23955910 (SEQ ID NO:913), and GI No. 22759895 (SEQ ID NO:915).

FIG. 30 is an alignment of ME12927 (SEQ ID NO:917) with homologous and/or orthologous amino acid sequences CeresAnnot:1503548 (SEQ ID NO:919), CeresClone:37778 (SEQ ID NO:921), CeresClone:681297 (SEQ ID NO:923), CeresClone:575835 (SEQ ID NO:925), CeresClone:1714750 (SEQ ID NO:935), CeresClone:1721907 (SEQ ID NO:937), and GI No. 115451923 (SEQ ID NO:940).

FIG. 31 is an alignment of ME12929 (SEQ ID NO:944) with homologous and/or orthologous amino acid sequences CeresAnnot:1447562 (SEQ ID NO:946), GI No. 98962139 (SEQ ID NO:947), CeresClone:641607 (SEQ ID NO:950), CeresClone:1715150 (SEQ ID NO:962), CeresClone:1873767 (SEQ ID NO:964), GI No. 115468306 (SEQ ID NO:967), and CeresAnnot:6059980 (SEQ ID NO:972).

FIG. 32 is an alignment of ME12954 (SEQ ID NO:976) with homologous and/or orthologous amino acid sequences CeresClone:957229 (SEQ ID NO:978) and CeresAnnot:1496202 (SEQ ID NO:980).

FIG. 33 is an alignment of ME12970 (SEQ ID NO:982) with homologous and/or orthologous amino acid sequences CeresClone:1935438 (SEQ ID NO:984), GI No. 117573664 (SEQ ID NO:985), GI No. 68349002 (SEQ ID NO:991), GI No. 68348998 (SEQ ID NO:992), CeresAnnot:1497170 (SEQ ID NO:995), GI No. 15221718 (SEQ ID NO:996), GI No. 3860331 (SEQ ID NO:1001), CeresClone:1075911 (SEQ ID NO:1003), GI No. 2920839 (SEQ ID NO:1008), CeresClone:698452 (SEQ ID NO:1011), CeresClone:2019456 (SEQ ID NO:1023), GI No. 90399071 (SEQ ID NO:1026), GI No. 115459588 (SEQ ID NO:1028), and GI No. 68349016 (SEQ ID NO:1032).

FIG. 34 is an alignment of ME13021 (SEQ ID NO:1054) with homologous and/or orthologous amino acid sequences GI No. 2493647 (SEQ ID NO:1055), CeresClone:1924252 (SEQ ID NO:1057), GI No. 461736 (SEQ ID NO:1058), CeresAnnot:1542060 (SEQ ID NO:1061), GI No. 15226314 (SEQ ID NO:1068), GI No. 464727 (SEQ ID NO:1072), CeresClone:480644 (SEQ ID NO:1074), GI No. 124301264 (SEQ ID NO:1075), GI No. 1710807 (SEQ ID NO:1076), GI No. 110349923 (SEQ ID NO:1077), GI No. 1762130 (SEQ ID NO:1078), CeresClone:706098 (SEQ ID NO:1080), GI No. 3790441 (SEQ ID NO:1083), CeresClone:1795282 (SEQ ID NO:1085), GI No. 125546535 (SEQ ID NO:1086), GI No. 115488160 (SEQ ID NO:1088), GI No. 84468456 (SEQ ID NO:1092), GI No. 116060917 (SEQ ID NO:1095), and CeresAnnot:6039555 (SEQ ID NO:1097).

FIG. 35 is an alignment of ME13064 (SEQ ID NO:1099) with homologous and/or orthologous amino acid sequences CeresAnnot:1528508 (SEQ ID NO:1101), CeresClone:9248 (SEQ ID NO:1103), GI No. 87240560 (SEQ ID NO:1105), GI No. 19453 (SEQ ID NO:1106), CeresClone:1795329 (SEQ ID NO:1108), and GI No. 108862979 (SEQ ID NO:1109).

FIG. 36 is an alignment of ME13071 (SEQ ID NO:1112) with homologous and/or orthologous amino acid sequences GI No. 125541485 (SEQ ID NO:1113), and GI No. 115449245 (SEQ ID NO:1114).

FIG. 37 is an alignment of ME13087 (SEQ ID NO:1116) with homologous and/or orthologous amino acid sequences CeresClone:100062822 (SEQ ID NO:1118), CeresAnnot:1440025 (SEQ ID NO:1120), GI No. 15238538 (SEQ ID NO:1123), GI No. 69111473 (SEQ ID NO:1129), GI No. 92873711 (SEQ ID NO:1132), GI No. 55734106 (SEQ ID NO:1133), GI No. 2346974 (SEQ ID NO:1134), CeresClone:569852 (SEQ ID NO:1136), CeresClone:1715326 (SEQ ID NO:1138), CeresClone:1608104 (SEQ ID NO:1140), GI No. 115456237 (SEQ ID NO:1141), GI No. 68655289 (SEQ ID NO:1143), GI No. 81022807 (SEQ ID NO:1144), GI No. 75706704 (SEQ ID NO:1145), and CeresAnnot:6016055 (SEQ ID NO:1147).

FIG. 38 is an alignment of ME13107 (SEQ ID NO:1159) with homologous and/or orthologous amino acid sequences CeresClone:1371824 (SEQ ID NO:1161), GI No. 22585 (SEQ ID NO:1162), GI No. 22208482 (SEQ ID NO:1163), and GI No. 16073 (SEQ ID NO:1164).

FIG. 39 is an alignment of ME13108 (SEQ ID NO:1166) with homologous and/or orthologous amino acid sequences GI No. 99109436 (SEQ ID NO:1167), CeresClone:1627939 (SEQ ID NO:1169), CeresClone:1840433 (SEQ ID NO:1171), CeresAnnot:1524198 (SEQ ID NO:1173), CeresClone:1650 (SEQ ID NO:1175), CeresClone:691979 (SEQ ID NO:1177), GI No. 92876897 (SEQ ID NO:1180), CeresClone:1774130 (SEQ ID NO:1182), and GI No. 115450018 (SEQ ID NO:1183).

FIG. 40 is an alignment of ME13110 (SEQ ID NO:1185) with homologous and/or orthologous amino acid sequences CeresClone:737317 (SEQ ID NO:1187), CeresClone:1880853 (SEQ ID NO:1189), GI No. 125558381 (SEQ ID NO:1190), and GI No. 115472157 (SEQ ID NO:1191).

FIG. 41 is an alignment of ME13125 (SEQ ID NO:1194) with homologous and/or orthologous amino acid sequences CeresClone:1938817 (SEQ ID NO:1196), CeresAnnot:1457245 (SEQ ID NO:1200), CeresClone:577910 (SEQ ID NO:1202), Public PUBLICCLONE ID no. 100736184 (SEQ ID NO:1203), GI No. 125553355 (SEQ ID NO:1204), and GI No. 5091600 (SEQ ID NO:1205).

FIG. 42 is an alignment of ME13149 (SEQ ID NO:1210) with homologous and/or orthologous amino acid sequences GI No. 1703374 (SEQ ID NO:1211), CeresClone:1846330 (SEQ ID NO:1213), GI No. 29124979 (SEQ ID NO:1216), CeresAnnot:1531725 (SEQ ID NO:1218), GI No. 3334321 (SEQ ID NO:1229), CeresClone:571410 (SEQ ID NO:1232), GI No. 39653273 (SEQ ID NO:1233), GI No.

92875403 (SEQ ID NO:1234), GI No. 11131026 (SEQ ID NO:1235), GI No. 77812440 (SEQ ID NO:1236), GI No. 89475524 (SEQ ID NO:1238), GI No. 3182919 (SEQ ID NO:1239), GI No. 7643794 (SEQ ID NO:1240), GI No. 1710851 (SEQ ID NO:1241), GI No. 115501471 (SEQ ID NO:1242), GI No. 77999251 (SEQ ID NO:1243), GI No. 3450893 (SEQ ID NO:1249), CeresClone:704589 (SEQ ID NO:1251), CeresClone:1384151 (SEQ ID NO:1253), CeresClone:1713894 (SEQ ID NO:1259), GI No. 125560752 (SEQ ID NO:1264), GI No. 115475543 (SEQ ID NO:1265), GI No. 3182922 (SEQ ID NO:1267), GI No. 145353078 (SEQ ID NO:1268), GI No. 11131023 (SEQ ID NO:1269), GI No. 47026845 (SEQ ID NO:1270), and GI No. 38353642 (SEQ ID NO:1272).

FIG. 43 is an alignment of ME13151 (SEQ ID NO:1274) with homologous and/or orthologous amino acid sequences CeresClone:1884601 (SEQ ID NO:1276), CeresAnnot:1445717 (SEQ ID NO:1280), CeresClone:527903 (SEQ ID NO:1284), GI No. 92891722 (SEQ ID NO:1285), CeresClone:790881 (SEQ ID NO:1287), CeresClone:299417 (SEQ ID NO:1289), CeresClone:1993894 (SEQ ID NO:1291), GI No. 125539547 (SEQ ID NO:1294), GI No. 48716424 (SEQ ID NO:1295), GI No. 84468278 (SEQ ID NO:1297), and CeresAnnot:6036303 (SEQ ID NO:1300).

FIG. 44 is an alignment of ME13153 (SEQ ID NO:1302) with homologous and/or orthologous amino acid sequences GI No. 70609690 (SEQ ID NO:1303), CeresClone:1927524 (SEQ ID NO:1305), CeresAnnot:1467310 (SEQ ID NO:1311), GI No. 45935270 (SEQ ID NO:1313), CeresClone:718446 (SEQ ID NO:1317), GI No. 92875133 (SEQ ID NO:1318), GI No. 1706318 (SEQ ID NO:1319), GI No. 3252856 (SEQ ID NO:1320), GI No. 1169238 (SEQ ID NO:1326), GI No. 31296711 (SEQ ID NO:1327), CeresClone:1468893 (SEQ ID NO:1330), GI No. 51587340 (SEQ ID NO:1331), CeresClone:1796201 (SEQ ID NO:1333), GI No. 125543034 (SEQ ID NO:1334), GI No. 115476804 (SEQ ID NO:1336), GI No. 75268060 (SEQ ID NO:1339), and GI No. 75268007 (SEQ ID NO:1340).

FIG. 45 is an alignment of ME13177 (SEQ ID NO:1342) with homologous and/or orthologous amino acid sequences CeresAnnot:1443786 (SEQ ID NO:1346), GI No. 15239172 (SEQ ID NO:1355), GI No. 562190 (SEQ ID NO:1363), GI No. 83032266 (SEQ ID NO:1364), CeresClone:602910 (SEQ ID NO:1366), GI No. 7242793 (SEQ ID NO:1370), GI No. 116167 (SEQ ID NO:1371), GI No. 2190259 (SEQ ID NO:1372), GI No. 5420278 (SEQ ID NO:1373), GI No. 1064931 (SEQ ID NO:1374), GI No. 6093215 (SEQ ID NO:1377), GI No. 461726 (SEQ ID NO:1378), GI No. 89111295 (SEQ ID NO:1379), GI No. 82949283 (SEQ ID NO:1380), GI No. 125537180 (SEQ ID NO:1381), GI No. 115489300 (SEQ ID NO:1382), and GI No. 55978000 (SEQ ID NO:1383).

FIG. 46 is an alignment of ME13200 (SEQ ID NO:1385) with homologous and/or orthologous amino acid sequences CeresAnnot:1503394 (SEQ ID NO:1387), GI No. 4914437 (SEQ ID NO:1390), CeresClone:638126 (SEQ ID NO:1393), GI No. 124360540 (SEQ ID NO:1394), GI No. 7981380 (SEQ ID NO:1395), GI No. 118137433 (SEQ ID NO:1396), CeresClone:1723374 (SEQ ID NO:1398), CeresClone:1785379 (SEQ ID NO:1400), GI No. 125553354 (SEQ ID NO:1401), GI No. 115471859 (SEQ ID NO:1404), and CeresAnnot:6040771 (SEQ ID NO:1407).

FIG. 47 is an alignment of ME13204 (SEQ ID NO:1409) with homologous and/or orthologous amino acid sequences CeresClone:1939206 (SEQ ID NO:1413), CeresAnnot:1453316 (SEQ ID NO:1415), GI No. 79319075 (SEQ ID NO:1418), GI No. 124359953 (SEQ ID NO:1419), CeresClone:891431 (SEQ ID NO:1421), GI No. 125536578 (SEQ ID NO:1424), and GI No. 20270065 (SEQ ID NO:1425).

FIG. 48 is an alignment of ME14649 (SEQ ID NO:1428) with homologous and/or orthologous amino acid sequences CeresClone:1978733 (SEQ ID NO:1430), CeresAnnot:1476165 (SEQ ID NO:1432), CeresClone:871529 (SEQ ID NO:1436), CeresClone:1043344 (SEQ ID NO:1439), CeresClone:786542 (SEQ ID NO:1442), CeresClone:346115 (SEQ ID NO:1444), CeresClone:1821683 (SEQ ID NO:1452), GI No. 125533171 (SEQ ID NO:1453), and GI No. 77553492 (SEQ ID NO:1457)

FIG. 49 is an alignment of ME16546 (SEQ ID NO:1463) with homologous and/or orthologous amino acid sequences CeresAnnot:1444102 (SEQ ID NO:1465), CeresClone:582439 (SEQ ID NO:1471), CeresClone:579953 (SEQ ID NO:1473), GI No. 125539335 (SEQ ID NO:1474), and GI No. 115445987 (SEQ ID NO:1476).

FIG. 50 is an alignment of ME17567 (SEQ ID NO:1491) with homologous and/or orthologous amino acid sequences CeresClone:1895876 (SEQ ID NO:1493), CeresAnnot:1464522 (SEQ ID NO:1495), CeresClone:968434 (SEQ ID NO:1499), CeresClone:686479 (SEQ ID NO:1501), CeresClone:1564962 (SEQ ID NO:1503), GI No. 125549699 (SEQ ID NO:1504), GI No. 125591612 (SEQ ID NO:1505), and CeresAnnot:6006969 (SEQ ID NO:1508).

FIG. 51 is an alignment of ME17932 (SEQ ID NO:1510) with homologous and/or orthologous amino acid sequences CeresClone:1842178 (SEQ ID NO:1512), CeresAnnot:1475265 (SEQ ID NO:1516) and CeresClone:1044646 (SEQ ID NO:1520).

FIG. 52 is an alignment of ME17936 (SEQ ID NO:1525) with homologous and/or orthologous amino acid sequences CeresAnnot:1454324 (SEQ ID NO:1527), CeresClone:1652842 (SEQ ID NO:1534), and GI No. 75214620 (SEQ ID NO:1535).

FIG. 53 is an alignment of ME18275 (SEQ ID NO:1537) with homologous and/or orthologous amino acid sequences CeresAnnot:1514086 (SEQ ID NO:1539), CeresClone:1087909 (SEQ ID NO:1543), CeresClone:1359070 (SEQ ID NO:1545), GI No. 92880913 (SEQ ID NO:1548), CeresClone:932449 (SEQ ID NO:1550), and CeresClone:1788695 (SEQ ID NO:1552).

FIG. 54 is an alignment of ME18924 (SEQ ID NO:1554) with homologous and/or orthologous amino acid sequences GI No. 82469976 (SEQ ID NO:1555), CeresAnnot:1533704 (SEQ ID NO:1563), CeresClone:524404 (SEQ ID NO:1565), CeresClone:846541 (SEQ ID NO:1567), CeresClone:1769321 (SEQ ID NO:1571), GI No. 125528559 (SEQ ID NO:1572), GI No. 125572823 (SEQ ID NO:1574), and GI No. 84453208 (SEQ ID NO:1575).

FIG. 55 is an alignment of ME19182 (SEQ ID NO:1577) with homologous and/or orthologous amino acid sequences GI No. 4033417 (SEQ ID NO:1040), GI No. 5669924 (SEQ ID NO:1041), GI No. 40642617 (SEQ ID NO:1440), GI No. 90399018 (SEQ ID NO:1485), GI No. 115464117 (SEQ ID NO:1487), GI No. 75164812 (SEQ ID NO:1578), CeresClone:1794223 (SEQ ID NO:1580), CeresAnnot:1471422 (SEQ ID NO:1590), CeresClone:968096 (SEQ ID NO:1607), GI No. 6752884 (SEQ ID NO:1608), GI No. 47775656 (SEQ ID NO:1609), CeresClone:1020799 (SEQ ID NO:1611), GI No. 87240865 (SEQ ID NO:1622), GI No. 2500047 (SEQ ID NO:1623), CeresClone:705340 (SEQ ID NO:1627), CeresClone:1430456 (SEQ ID NO:1637), GI No. 84619270 (SEQ ID NO:1648), and CeresClone:1821143 (SEQ ID NO:1651).

FIG. 56 is an alignment of ME20628 (SEQ ID NO:1437) with homologous and/or orthologous amino acid sequences GI No. 113367236 (SEQ ID NO:173), GI No. 115477615 (SEQ ID NO:212), GI No. 125542223 (SEQ ID NO:361), GI No. 1838976 (SEQ ID NO:421), CeresClone:1547185 (SEQ ID NO:443), CeresAnnot:1450452 (SEQ ID NO:740), and GI No. 92870675 (SEQ ID NO:1461).

FIG. 57 is an alignment of ME01821 (SEQ ID NO:97) with homologous and/or orthologous amino acid sequences Public GI ID no. 167480754 (SEQ ID NO:2013) and Public GI ID no. 83830869 (SEQ ID NO:2015).

DETAILED DESCRIPTION

The invention provides methods and materials related to modulating low-nitrogen tolerance levels in plants. In some embodiments, the plants may also have modulated levels of low-nitrogen tolerance. The methods can include transforming a plant cell with a nucleic acid encoding a low nitrogen tolerance-modulating polypeptide, wherein expression of the polypeptide results in a modulated level of low-nitrogen tolerance. Plant cells produced using such methods can be grown to produce plants having an increased tolerance to conditions with limiting exogenous nitrogen sources. Such plants can be used for the production of higher yields and biomasses with existing fertilizer inputs, and/or enable existing yields and biomass of crops to be obtained with lower fertilizer input, or better yields and biomasses on soils of poorer quality.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic Panicum virgatum plant transformed with and expressing the coding sequence for a nitrogen transporter polypeptide from a Zea mays plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Low Nitrogen Conditions" as used herein refers to nitrogen concentrations which lead to nitrogen deficiency symptoms such as pale green leaf color, chlorosis and reduced growth and vigor. Typically, low nitrogen conditions lead to a reduction of at least 20%, 25%, 30%, 35%, 40%, 45%, 50%, 60%, 70%, 80% or 90% in growth and/or vigor.

"Modulation" of the level of low-nitrogen tolerance refers to the change in the level of tolerance of a plant to limiting exogenous nitrogen sources that is observed as a result of expression of, or transcription from, an exogenous nucleic acid in a plant cell. The change in low-nitrogen tolerance level is measured by changes in plant size and greenness as well as greater photosynthesis efficiency, relative to the corresponding level in control plants in an environment with limiting nitrogen supply.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line.

Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *The Plant Cell,* 1:977-984.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include low nitrogen tolerance-modulating polypeptides. Low nitrogen tolerance-modulating polypeptides can be effective to modulate low-nitrogen tolerance levels when expressed in a plant or plant cell. Such polypeptides typically contain at least one domain indicative of low nitrogen tolerance-modulating polypeptides, as described in more detail herein. Low nitrogen tolerance-modulating polypeptides typically have an HMM bit score that is greater than 20, as described in more detail herein. In some embodiments, low nitrogen tolerance-modulating polypeptides have greater than 80% identity to SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, as described in more detail herein.

A. Domains Indicative of Low Nitrogen Tolerance-Modulating Polypeptides

A low nitrogen tolerance-modulating polypeptide can contain a P450 domain, which is characteristic of polypeptides belonging to the Cytochrome P450 superfamily. Cytochrome P450s are haem-thiolate proteins involved in the oxidative degradation of various compounds. They are particularly well known for their role in the degradation of environmental toxins and mutagens. In plants, these proteins are important for the biosynthesis of several compounds such as hormones, defensive compounds and fatty acids. Sequence conservation is relatively low within the family—there are only 3 absolutely conserved residues—but their general topography and structural fold are highly conserved. The conserved core is composed of a coil termed the 'meander', a four-helix bundle, helices J and K, and two sets of beta-sheets. These constitute the haem-binding loop, the proton-transfer groove and the conserved EXXR motif in helix K. While prokaryotic P450s are soluble proteins, most eukaryotic P450s are associated with microsomal membranes. Their general enzymatic function is to catalyse regiospecific and stereospecific oxidation of non-activated hydrocarbons at physiological temperatures. SEQ ID NO:3 and SEQ ID NO:332 set forth the amino acid sequence of *Arabidopsis* clones, identified herein as ME00919 (SEQ ID NO:3) and ME04587 (SEQ ID NO:332) respectively, that are predicted to encode polypeptides containing a Cytochrome P450 domain.

A low nitrogen tolerance-modulating polypeptide can contain a zf-Dof domain, which is conserved in several DNA-binding proteins of higher plants. Dof domain is a zinc finger DNA-binding domain that shows resemblance to the Cys2 zinc finger, although it has a longer putative loop where an extra Cys residue is typically conserved. The motif is also present in SEQ ID NO:49, which sets forth the amino acid sequence of an *Arabidopsis* clone, identified herein as Ceres ME01312 (SEQ ID NO:49), that is predicted to encode a polypeptide containing a zf-Dof domain.

A low nitrogen tolerance-modulating polypeptide can contain an Aminotran_3 domain characteristic of polypeptides belonging to the aminotransferase Class-III family. Aminotransferases share certain mechanistic features with other pyridoxalphosphate-dependent enzymes, such as the covalent binding of the pyridoxalphosphate group to a lysine residue. Class-III aminotransferases include acetylornithine aminotransferase, which catalyzes the transfer of an amino group from acetylornithine to alpha-ketoglutarate, yielding N-acetyl-glutamic-5-semi-aldehyde and glutamic acid; ornithine aminotransferase, which catalyzes the transfer of an amino group from ornithine to alpha-ketoglutarate, yielding glutamic-5-semi-aldehyde and glutamic acid; omega-amino acid—pyruvate aminotransferase, which catalyzes transamination between a variety of omega-amino acids, mono- and diamines, and pyruvate; 4-aminobutyrate aminotransferase; GABA transaminase, which catalyzes the transfer of an amino group from GABA to alpha-ketoglutarate, yielding succinate semialdehyde and glutamic acid; DAPA aminotransferase, a bacterial enzyme (bioA), which catalyzes an intermediate step in the biosynthesis of biotin, the transamination of 7-keto-8-aminopelargonic acid to form 7,8-diaminopelargonic acid; 2,2-dialkylglycine decarboxylase, a *Burkholderia cepacia* (*Pseudomonas cepacia*) enzyme (dgdA) that catalyzes the decarboxylating amino transfer of 2,2-dialkylglycine and pyruvate to dialkyl ketone, alanine and carbon dioxide; glutamate-1-semialdehyde aminotransferase (GSA); *Bacillus subtilis* aminotransferases yhxA and yodT; *Haemophilus influenzae* aminotransferase HI0949; and *Caenorhabditis elegans* aminotransferase. On the basis of sequence similarity, these various enzymes can be grouped into subfamilies. The aminotran_3 domain is also present in SEQ ID NO:77, which set forth the amino acid sequences of *Arabidopsis* clone, identified herein as Ceres ME01463 (SEQ ID NO:77), that is predicted to encode polypeptides containing an aminotran_3 domain.

A low nitrogen tolerance-modulating polypeptide can contain a linker histone domain characteristic of polypeptides belonging to the linker histone H1 and H5 family. Linker histone H1 is an essential component of chromatin structure. H1 links nucleosomes into higher order structures. Histone H5 performs the same function as histone H1, and replaces H1 in certain cells. The structure of GH5, the globular domain of the linker histone H5 fold is similar to the DNA-binding domain of the catabolite gene activator protein, CAP, thus providing a possible model for the binding of GH5 to DNA. The domain is also present in SEQ ID NO:100, which sets forth the amino acid sequence of an *Arabidopsis* clone, identified herein as Ceres ME01910 (SEQ ID NO:100), that is predicted to encode a polypeptide containing a linker histone domain.

A low nitrogen tolerance-modulating polypeptide can contain a zf-C3HC4 domain, which is predicted to be characteristic of proteins belonging to the C3HC4 type zinc-finger (RING finger) protein family. The C3HC4 type zinc-finger (RING finger) is a cysteine-rich domain of approximately 40 to 60 residues that coordinates two zinc ions, and is probably involved in mediating protein-protein interactions. Members of the C3HC4 type zinc-finger (RING finger) protein family contain the loosely conserved sequence: C-X2-C-X(9-39)-C-X(1-3)-H-X(2-3)-C-X2-C-X(4-48)-C-X2-C where X is any amino acid. The domain is also present in SEQ ID NOs: 166, 746, 976, 1428, which set forth the amino acid sequences of *Arabidopsis* clones, identified herein as Ceres ME02603 (SEQ ID NO:166), ME05493 (SEQ ID NO:746), ME12954 (SEQ ID NO:976), ME14649 (SEQ ID NO:1428) respectively, that are predicted to encode polypeptides containing a zf-C3HC4 domain.

A low nitrogen tolerance-modulating polypeptide can contain a Gal_Lectin domain characteristic of a galactose binding lectin domain protein. SEQ ID NO:208 sets forth the amino acid sequence of an *Arabidopsis* clone, identified herein as Ceres ME02801 (SEQ ID NO:208), that is predicted to encode a polypeptide containing a galactose binding lectin domain.

A low nitrogen tolerance-modulating polypeptide can contain a TRP_1 domain characteristic of tetratricopeptide repeat (TPR) domain protein. The tetratricopeptide repeat is a structural motif present in a wide range of proteins identified in various different organisms, ranging from bacteria to humans. It mediates protein-protein interactions and the assembly of multiprotein complexes. Sequence alignment of the TPR domains reveals a consensus sequence defined by a pattern of small and large amino acids. Proteins containing TPRs are involved in a variety of biological processes, such as cell cycle regulation, transcriptional control, mitochondrial and peroxisomal protein transport, neurogenesis and protein folding. The X-ray structure of a domain containing three TPRs from protein phosphatase 5 revealed that TPR adopts a helixturnhelix arrangement, with adjacent TPR motifs packing in a parallel fashion, resulting in a spiral of repeating anti-parallel alpha-helices. The two helices are denoted helix A and helix B. The packing angle between helix A and helix B is ~24° within a single TPR and generates a right-handed superhelical shape. Helix A interacts with helix B and with helix A' of the next TPR. Two protein surfaces are generated: the inner concave surface is contributed to mainly by residue on helices A, and the other surface presents residues from both helices A and B.

A low nitrogen tolerance-modulating polypeptide can contain a TRP_2 tetratricopeptide repeat domain, which is predicted to be characteristic of scaffold-proteins in multiprotein complexes. The TPR_2 domain consists of approximately 34-amino-acid motif with a loose consensus and is present, usually as multiple tandem repeats, in proteins with many cellular functions, including mitosis, transcription, protein transport, and development. Structural analysis of the TPR-2 domain demonstrates that it forms two α-helical regions separated by a turn, such that apposed bulky and small side chains form a "knob and hole" structure. In general, the hydrophobic surface of this structure mediates protein-protein interactions between TPR- and non-TPR-containing proteins.

SEQ ID NO:234 sets forth the amino acid sequence of *Arabidopsis* clone, identified herein as Ceres ME04204 (SEQ ID NO:234), that is predicted to encode a polypeptide containing a TRP_1 tetratricopeptide repeat domain and a TRP_2 tetratricopeptide repeat domain. SEQ ID NO:1510 sets forth the amino acid sequence of *Arabidopsis* clone, identified herein as Ceres ME17932 (SEQ ID NO:1510), that is predicted to encode a polypeptide containing a TRP_2 tetratricopeptide repeat domain.

A low nitrogen tolerance-modulating polypeptide can contain a zf-AN1 domain characteristic of polypeptides belonging to the AN1-like Zinc finger domain protein family. The AN1-like Zinc finger domain was first identified as a zinc finger at the C-terminus of An1a ubiquitin-like protein in *Xenopus laevis*. The following pattern describes the zinc finger: C-X2-C-X(9-12)-C-X(1-2)-C-X4-C-X2-H-X5-H-X-C, where X can be any amino acid, and numbers in brackets indicate the number of residues.

A low nitrogen tolerance-modulating polypeptide can contain a zf-A20 domain, which is characteristic of A20— (an inhibitor of cell death)-like zinc fingers. In animals, A20-like zinc fingers are believed to mediate self-association in A20. These fingers also mediate IL-1-induced NF-kappa B activation. SEQ ID NO: 246 sets forth the amino acid sequence of *Arabidopsis* clone, identified herein as Ceres ME04477 (SEQ ID NO:246), that is predicted to encode a polypeptide containing an AN1-like Zinc finger domain and zf-A20 domain.

A low nitrogen tolerance-modulating polypeptide can contain an Aa_trans domain, or transmembrane amino acid transporter domain, which is predicted to be characteristic of amino acid transporters and amino acid permeases. The domain is also present in SEQ ID NO:300, which sets forth the amino acid sequence of an *Arabidopsis* clone, identified herein as Ceres ME04507 (SEQ ID NO:300), that is predicted to encode a polypeptide containing an transmembrane amino acid transporter domain.

A low nitrogen tolerance-modulating polypeptide can contain an RNA recognition motif (as known as RRM_1, RRM, RBD, or RNP domain), which is characteristic of polypeptides belonging to the single strand RNA-binding protein superfamily. RRM proteins have a variety of RNA binding preferences and functions, and include heterogeneous nuclear ribonucleoproteins (hnRNPs), proteins implicated in regulation of alternative splicing, protein components of small nuclear ribonucleoproteins, and proteins that regulate RNA stability and translation. The RRM in heterodimeric splicing factor U2 snRNP auxiliary factor (U2AF) appears to have two RRM-like domains with specialized features for protein recognition. The motif also appears in a few single stranded DNA binding proteins. The typical RRM consists of four anti-parallel beta-strands and two alpha-helices arranged in a beta-alpha-beta-beta-alpha-beta fold with side chains that stack with RNA bases. Specificity of RNA binding is determined by multiple contacts with surrounding amino acids. A third helix is present during RNA binding in some cases. The motif is also present in SEQ ID NO:368 and SEQ ID NO:1274, which set forth the amino acid sequences of *Arabidopsis* clones, identified herein as Ceres ME04753 (SEQ ID NO:368) and ME13151 (SEQ ID NO:1274) respectively, that are predicted to encode polypeptides containing an RNA recognition motif.

A low nitrogen tolerance-modulating polypeptide can contain an NTF2 domain characteristic of a nuclear transport factor 2 (NTF2) polypeptide. NTF2 is a homodimer of approximately 14 kDa subunits which stimulates efficient nuclear import of a cargo protein. NTF2 binds to both RanGDP and FxFG repeat-containing nucleoporins. NTF2 binds to RanGDP sufficiently strongly for the complex to remain intact during transport through nucleopore complexes (NPCs), but the interaction between NTF2 and FxFG nucleoporins is much more transient, which would enable NTF2 to move through the NPC by hopping from one repeat to another. NTF2 folds into a cone with a deep hydrophobic cavity, the opening of which is surrounded by several negatively charged residues. RanGDP binds to NTF2 by inserting a conserved phenylalanine residue into the hydrophobic pocket of NTF2 and making electrostatic interactions with the conserved negatively charged residues that surround the cavity. A structurally similar domain appears in other nuclear import proteins. SEQ ID NO:1274, which sets forth the amino acid sequence of an *Arabidopsis* clone, identified herein as Ceres ME13151 (SEQ ID NO:1274), that is predicted to encode a polypeptide containing a NTF2 domain.

A low nitrogen tolerance-modulating polypeptide can contain a DUF1218 domain. SEQ ID NO:1274, which sets forth the amino acid sequence of an *Arabidopsis* clone, identified herein as Ceres ME04772 (SEQ ID NO:510), that is predicted to encode a polypeptide containing a DUF1218 domain.

A low nitrogen tolerance-modulating polypeptide can contain a Myb-like DNA-binding domain characteristic of polypeptides belonging to a protein family whose members contain the DNA binding domains from Myb proteins, as well as the SANT domain family. SEQ ID NO:533, which sets forth the amino acid sequence of an *Arabidopsis* clone, identified herein as Ceres ME04909 (SEQ ID NO:533), that is predicted to encode a polypeptide containing a Myb-like DNA-binding domain.

A low nitrogen tolerance-modulating polypeptide can contain a FAD_binding_4 domain. This domain is predicted to be characteristic of polypeptides belonging to a family of enzymes that use FAD (flavin adenine dinucleotide) as a co-factor, most of the enzymes are similar to oxygen oxidoreductase, containing a covalently bound FAD group which is attached to a histidine via an 8-alpha-(N3-histidyl)-riboflavin linkage.

A low nitrogen tolerance-modulating polypeptide can contain a BBE domain, which is predicted to be characteristic of a berberine bridge and berberine bridge-like enzyme. BBE enzymes are typically involved in the biosynthesis of numerous isoquinoline alkaloids. They catalyse the transformation of the N-methyl group of (S)-reticuline into the C-8 berberine bridge carbon of (S)-scoulerine. SEQ ID NO:558 sets forth the amino acid sequence of an *Arabidopsis* clone, identified herein as Ceres ME05194 (SEQ ID NO:558), that is predicted to encode a polypeptide containing an FAD_binding_4 domain and a BBE domain.

A low nitrogen tolerance-modulating polypeptide can contain a prefoldin (PFD) domain characteristic of polypeptides belonging to the prefoldin subunit family. Prefoldin (PFD) is a chaperone that typically interacts with type II chaperonins, hetero-oligomers lacking an obligate co-chaperonin that are found in eukaryotes (chaperonin-containing T-complex polypeptide-1 (CCT)) and archaea. Eukaryotic PFD can typically bind both actin and tubulin co-translationally. The chaperone can then delivers the target protein to CCT, interacting with the chaperonin through the tips of the coiled coils. SEQ ID NO:593 sets forth the amino acid sequence of an *Arabidopsis* clone, identified herein as Ceres ME05267 (SEQ ID NO:593), that is predicted to encode a polypeptide containing a prefoldin domain.

A low nitrogen tolerance-modulating polypeptide can contain an HR-lesion domain characteristic of polypeptides belonging to a family of plant proteins can be associated with the hypersensitive response (HR) pathway of defense against plant pathogens. The domain is also present in SEQ ID NO: 646, which sets forth the amino acid sequence of an *Arabidopsis* clone, identified herein as Ceres ME05341 (SEQ ID NO: 646), that is predicted to encode a polypeptide containing an HR-lesion domain.

A low nitrogen tolerance-modulating polypeptide can contain a DUF538 domain. SEQ ID NO:687 sets forth the amino acid sequence of an *Arabidopsis* clone, identified herein as Ceres ME05392 (SEQ ID NO:687), that is predicted to encode a polypeptide containing a DUF538 domain.

A low nitrogen tolerance-modulating polypeptide can contain a zinc finger C-x8-C-x5-C-x3-H type domain (zf-CCCH), which is characteristic of polypeptides belonging to the zinc finger protein superfamily. Members of zinc finger domains proteins are thought to be involved in DNA-binding, and exist as different types. Proteins containing zinc finger domains of the C-x8-C-x5-C-x3-H type include zinc finger proteins from eukaryotes involved in cell cycle or growth phase-related regulation. It has been shown that different CCCH zinc finger proteins interact with the 3' untranslated region of various mRNA. SEQ ID NO:792 sets forth the amino acid sequence of an *Arabidopsis* clone, identified herein as Ceres ME07344 (SEQ ID NO:792), that is predicted to encode a polypeptide containing a zf-CCCH domain.

A low nitrogen tolerance-modulating polypeptide can contain a DUF246 domain. SEQ ID NO:828 sets forth the amino acid sequence of an *Arabidopsis* clone, identified herein as Ceres ME08464 (SEQ ID NO:828), that is predicted to encode a polypeptide containing a DUF246 domain.

A low nitrogen tolerance-modulating polypeptide can contain a C2 domain. The C2 domain is a Ca2+-dependent membrane-targeting module found in many cellular proteins involved in signal transduction or membrane trafficking. C2 domains are unique among membrane targeting domains in that they typically show wide range of lipid selectivity for the major components of cell membranes, including phosphatidylserine and phosphatidylcholine. SEQ ID NO:982 sets forth the amino acid sequence of an *Arabidopsis* clone, identified herein as Ceres ME12970 (SEQ ID NO:982), that is predicted to encode a polypeptide containing an C2 domain.

A low nitrogen tolerance-modulating polypeptide can contain a Cpn60_TCP1 domain characteristic of polypeptides belonging to the TCP-1/cpn60 chaperonin family. This family includes members from the HSP60 chaperone family and the TCP-1 (T-complex protein) family. Chaperonins, a subfamily of molecular chaperones, are typically essential for the correct folding and assembly of polypeptides into oligomeric structures. Chaperonins are typically found in abundance in prokaryotes, chloroplasts and mitochondria. They are typically required for normal cell growth, and are stress-induced, acting to stabilize or protect disassembled polypeptides under heat-shock conditions. SEQ ID NO: 1054 sets forth the amino acid sequence of an *Arabidopsis* clone, identified herein as Ceres ME13021 (SEQ ID NO: 1054), that is predicted to encode a polypeptide containing a Cpn60_TCP1 domain.

A low nitrogen tolerance-modulating polypeptide can contain a zf-C2H2 domain characteristic of a C2H2 zinc finger domain polypeptide. Zinc finger domains are nucleic acid-binding protein structures composed of 25 to 30 amino-acid residues including 2 conserved Cys and 2 conserved His residues in a C-2-C-12-H-3-H type motif. The 12 residues separating the second Cys and the first His are mainly polar and basic, implicating this region in particular in nucleic acid binding. They have the ability to bind to both RNA and DNA, and it has been suggested that the zinc finger may thus represent the original nucleic acid binding protein. It has also been suggested that a Zn-centered domain could be used in a protein interaction, e.g. in protein kinase C. Many classes of zinc fingers are characterized according to the number and positions of the histidine and cysteine residues involved in the zinc atom coordination. In C2H2 zinc finger class, the first pair of zinc coordinating residues are cysteines, while the second pair are histidines. The motif is also present in SEQ ID NO:1116, which sets forth the amino acid sequence of an *Arabidopsis* clone, identified herein as Ceres ME13087 (SEQ ID NO:1116), that is predicted to encode a polypeptide containing a zf-C2H2 domain.

A low nitrogen tolerance-modulating polypeptide can contain a zein domain characteristic of polypeptides belonging to the zein family of seed storage proteins. SEQ ID NO:1159, which sets forth the amino acid sequence of an *Arabidopsis* clone, identified herein as Ceres ME13107 (SEQ ID NO: 1159), that is predicted to encode a polypeptide containing a zein domain.

A low nitrogen tolerance-modulating polypeptide can contain a snf7 domain characteristic of polypeptides belonging to a family of eukaryotic proteins related to yeast SNF7. SEQ ID NO:1185 sets forth the amino acid sequence of an *Arabidopsis* clone, identified herein as Ceres ME13110 (SEQ ID NO:1185), that is predicted to encode a polypeptide containing a snf7 domain.

A low nitrogen tolerance-modulating polypeptide can contain an HhH-GPD domain characteristic of polypeptides belonging to the HhH-GPD base excision DNA repair protein superfamily. Members of the HhH-GPD base excision DNA repair protein superfamily contain helix-hairpin-helix and Gly/Pro rich loop followed by a conserved aspartate. This domain is found in a diverse range of structurally related DNA repair proteins. The domain is also present in SEQ ID NO:1194 sets forth the amino acid sequence of an *Arabidopsis* clone, identified herein as Ceres ME13125 (SEQ ID NO:1194), that is predicted to encode a polypeptide containing an HhH-GPD domain.

A low nitrogen tolerance-modulating polypeptide can contain an Arf domain characteristic of polypeptides belonging to the ADP-ribosylation factor family. The small ADP ribosylation factor (Arf) GTP-binding proteins are major regulators of vesicle biogenesis in intracellular traffic. They are the founding members of a growing family that includes Arl (Arf-like), Arp (Arf-related proteins) and the remotely related Sar (Secretion-associated and Ras-related) proteins. Arf proteins cycle between inactive GDP-bound and active GTP-bound forms that bind selectively to effectors. The classical structural GDP/GTP switch is characterized by conformational changes at the so-called switch 1 and switch 2 regions, which bind tightly to the gamma-phosphate of GTP but poorly or not at all to the GDP nucleotide. Structural studies of Arf1 and Arf6 have revealed that although these proteins feature the switch 1 and 2 conformational changes, they depart from other small GTP-binding proteins in that they use an additional, unique switch to propagate structural information from one side of the protein to the other. The GDP/GTP structural cycles of human Arf1 and Arf6 feature a unique conformational change that affects the beta2beta3 strands connecting switch 1 and switch 2 (inter-switch) and also the amphipathic helical N-terminus. SEQ ID NO: 1210 sets forth the amino acid sequence of an *Arabidopsis* clone, identified herein as Ceres ME13149 (SEQ ID NO:1210), that is predicted to encode a polypeptide containing an Arf domain.

A low nitrogen tolerance-modulating polypeptide can contain a Pyridoxal_deC domain characteristic of pyridoxal-dependent decarboxylase polypeptide. Pyridoxal-dependent decarboxylases typically share regions of sequence similarity, particularly in the vicinity of a conserved lysine residue, which provides the attachment site for the pyridoxal-phosphate (PLP) group. Pyridoxal phosphate is the active form of vitamin B6 (pyridoxine or pyridoxal). PLP is a versatile catalyst, acting as a coenzyme in a multitude of reactions, including decarboxylation, deamination and transamination. PLP-dependent enzymes, including pyridoxal-dependent decarboxylases, are involved in the biosynthesis of amino acids and amino acid-derived metabolites, but they are also found in the biosynthetic pathways of amino sugars and in the synthesis or catabolism of neurotransmitter. SEQ ID NO:1302 sets forth the amino acid sequence of an *Arabidopsis* clone, identified herein as Ceres ME13153 (SEQ ID NO:1302), that is predicted to encode a polypeptide containing a Pyridoxal_deC domain.

A low nitrogen tolerance-modulating polypeptide can contain a Cyclin_C domain, which is characteristic to the C-terminal domain of polypeptides belonging to the Cyclin family. Cyclins are eukaryotic proteins that play an active role in controlling nuclear cell division cycles, and regulate cyclin dependent kinases (CDKs). Cyclins, together with the p34 (cdc2) or cdk2 kinases, form the Maturation Promoting Factor (MPF). There are two main groups of cyclins, G1/S cyclins, which play a role in the control of the cell cycle at the G1/S (start) transition, and G2/M cyclins, which play a role in the control of the cell cycle at the G2/M (mitosis) transition. G2/M cyclins accumulate steadily during G2 and are abruptly destroyed as cells exit from mitosis (at the end of the M-phase). Cyclins typically contain two domains of similar all-alpha fold, of which this family corresponds with the C-terminal domain.

A low nitrogen tolerance-modulating polypeptide can contain a Cyclin_N domain, which defines the N-terminal domain of polypeptides belonging to the Cyclin family. SEQ ID NO: 1342 sets forth the amino acid sequence of an *Arabidopsis* clone, identified herein as Ceres ME13177 (SEQ ID NO: 1342), that is predicted to encode a polypeptide containing a Cyclin_C domain and a Cyclin_N domain A low nitrogen tolerance-modulating polypeptide can contain a DUF1442 domain. SEQ ID NO:1463, which sets forth the amino acid sequence of an *Arabidopsis* clone, identified herein as Ceres ME16546 (SEQ ID NO:1463), that is predicted to encode a polypeptide containing a DUF1442 domain.

A low nitrogen tolerance-modulating polypeptide can contain an HLH domain characteristic of polypeptides belonging to the Helix-loop-helix DNA-binding domain superfamily. Basic helix-loop-helix proteins (bHLH) are a group of eukaryotic transcription factors that can exert a determinative influence in a variety of developmental pathways. These transcription factors are characterized by a conserved bHLH domain that mediates specific dimerization. They can facilitate the conversion of inactive monomers to trans-activating dimers at appropriate stages of development. Members of this superfamily can be classified into discrete categories according to dimerization, DNA binding and expression characteristics. SEQ ID NO:1537 sets forth the amino acid sequence of an *Arabidopsis* clone, identified herein as Ceres ME18275 (SEQ ID NO:1537), that is predicted to encode a polypeptide containing an HLH domain.

A low nitrogen tolerance-modulating polypeptide can contain a CRAL_TRIO domain characteristic of the C-terminal of retinaldehyde/retinal-binding protein family. In animals, retinaldehyde/retinal-binding proteins may be functional components of the visual cycle. Cellular retinaldehyde-binding protein (CRALBP) may function as a substrate carrier protein that modulates interaction of these retinoids with visual cycle enzymes. The multidomain protein Trio can bind the LAR transmembrane tyrosine phosphatase, contains a protein kinase domain, and has separate rac-specific and rho-specific guanine nucleotide exchange factor domains. Trio is a multifunctional protein that can integrate and amplify signals involved in coordinating actin remodeling, which is necessary for cell migration and growth. Other members of the family are transfer proteins that include, guanine nucleotide exchange factor that may function as an effector of RAC1, phosphatidylinositol/phosphatidylcholine transfer protein that is required for the transport of secretory proteins from the Golgi complex and alpha-tocopherol transfer protein that enhances the transfer of the ligand between separate membranes.

A low nitrogen tolerance-modulating polypeptide can contain a CRAL_TRIO_N which defines the N-terminal of retinaldehyde/retinal-binding protein family.

A low nitrogen tolerance-modulating polypeptide can contain an EMP24_GP25L domain characteristic of polypeptides belonging to the emp24/gp25L/p24 family/GOLD gene family. Members of this family are implicated in bringing cargo forward from the ER and binding to coat proteins by their cytoplasmic domains. This domain corresponds closely to the beta-strand rich GOLD domain. The GOLD domain is often found combined with lipid- or membrane-association domains. p24 proteins are major membrane components of COPI- and COPII-coated vesicles and are implicated in cargo selectivity of ER to Golgi transport. Multiple members of the p24 family are found in all eukaryotes, from yeast to mammals. Members of the p24 family are type I membrane proteins with a signal peptide at the amino terminus, a lumenal coiled-coil (extracytosolic) domain, a single transmembrane domain with conserved amino acids, and a short cytoplasmic tail. They may be grouped into at least three subfamilies based on primary sequence. One subfamily comprises yeast Emp24p and mammalian p24A. Another subfamily comprises yeast Erv25p and mammalian Tmp21, and the third subfamily comprises mammalian gp25L proteins. SEQ ID NO:1554 sets forth the amino acid sequence of an *Arabidopsis* clone, identified herein as Ceres ME18924 (SEQ ID NO:1554), that is predicted to encode a polypeptide containing a CRAL_TRIO domain, a CRAL_TRIO_N domain, and a EMP24_GP25L domain.

A low nitrogen tolerance-modulating polypeptide can contain a Pyrophosphatase domain, which is predicted to be characteristic of an inorganic pyrophosphatase (PPase). PPase is the enzyme responsible for the hydrolysis of pyrophosphate (PPi) which is formed principally as the product of the many biosynthetic reactions that utilize ATP. PPases may require the presence of divalent metal cations, with magnesium conferring the highest activity. Among other residues, a lysine has been postulated to be part of or close to the active site. The sequences of PPases share some regions of similarities, among which is a region that contains three conserved aspartates that are involved in the binding of cations. SEQ ID NO:1577 sets forth the amino acid sequence of an *Arabidopsis* clone, identified herein as Ceres ME19182 (SEQ ID NO:1577), that is predicted to encode a polypeptide containing a Pyrophosphatase domain.

A low nitrogen tolerance-modulating polypeptide can contain a bZIP_1 domain characteristic of polypeptides belonging to the superfamily of basic ZIP transcription factors. Members of the eukaryotic bZIP transcription factor superfamily contain a basic region mediating sequence-specific DNA-binding followed by a leucine zipper region required for dimerization. SEQ ID NO: 1437 sets forth the amino acid sequence of an *Arabidopsis* clone, identified herein as Ceres ME20628 (SEQ ID NO: 1437), that is predicted to encode a polypeptide containing a bZIP_1 domain.

B. Functional Homologs Identified by Reciprocal BLAST

In some embodiments, one or more functional homologs of a reference low nitrogen tolerance-modulating polypeptide defined by one or more of the Pfam descriptions indicated above are suitable for use as low nitrogen tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a low nitrogen tolerance-modulating polypeptide, or by combining domains from the coding sequences for different naturally-occurring low nitrogen tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of low nitrogen tolerance-modulating polypeptides. Sequence analysis can involve BLAST, Reciprocal BLAST, or PSI-BLAST analysis of nonredundant databases using a low nitrogen tolerance-modulating polypeptide amino acid sequence as the reference sequence Amino acid sequence is, in some instances, deduced from the nucleotide sequence. Those polypeptides in the database that have greater than 20% sequence identity are candidates for further evaluation for suitability as a low nitrogen tolerance-modulating polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in low nitrogen tolerance-modulating polypeptides, e.g., conserved functional domains.

Conserved regions can be identified by locating a region within the primary amino acid sequence of a low nitrogen tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al. (1998) *Nucl. Acids Res.,* 26:320-322; Sonnhammer et al. (1997) *Proteins,* 28:405-420; and Bateman et al. (1999) *Nucl. Acids Res.,* 27:260-262. Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 20% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
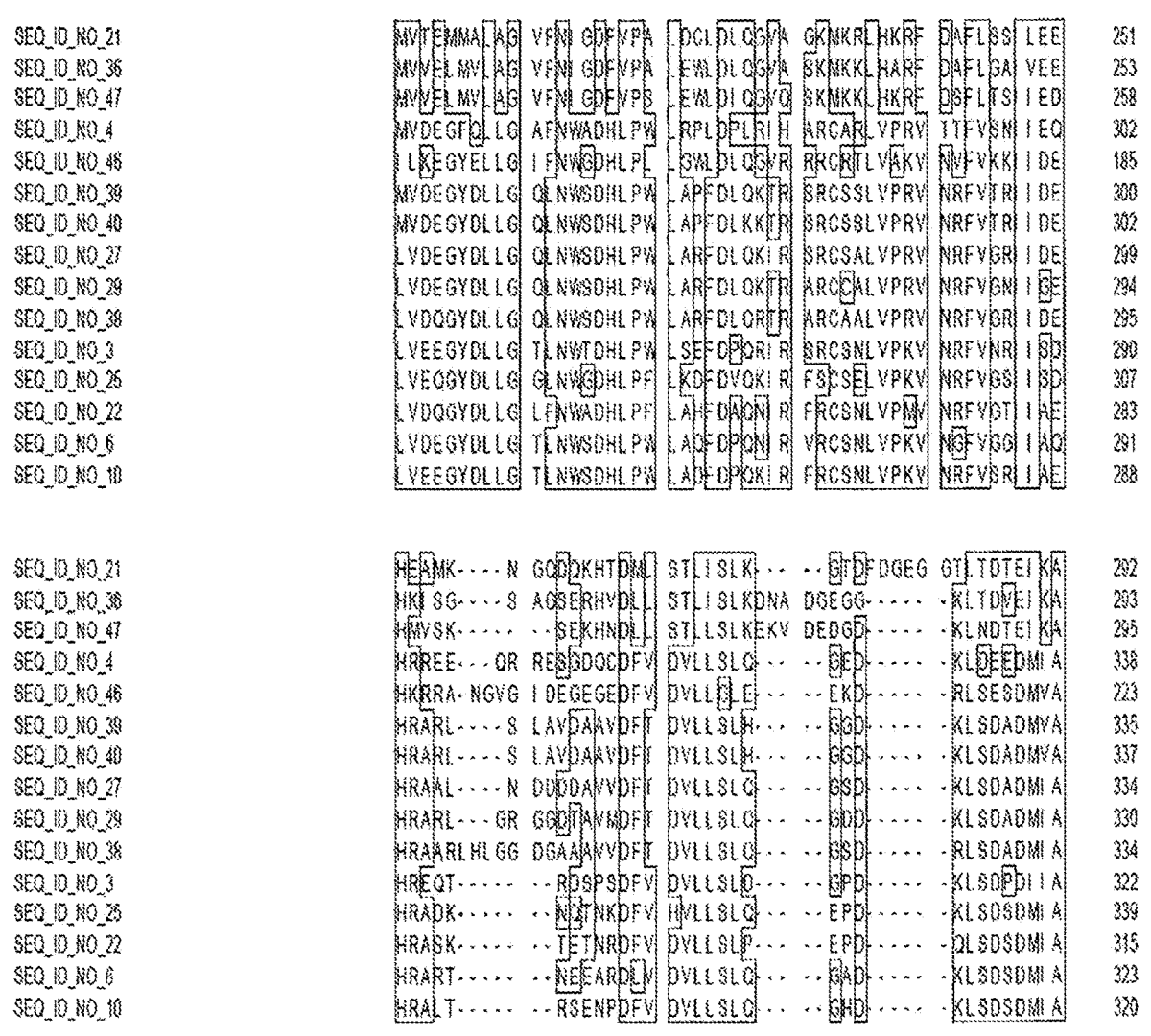

Examples of amino acid sequences of functional homologs of the polypeptide set forth in SEQ ID NO:3 are provided in FIG. 1 and in the Sequence Listing. Such functional homologs include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some cases, a functional homolog of SEQ ID NO:3 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Examples of amino acid sequences of functional homologs of the polypeptide set forth in SEQ ID NO:49 are provided in FIG. 2 and in the Sequence Listing. Such functional homologs include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75. In some cases, a functional homolog of SEQ ID NO:49 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49.

Examples of amino acid sequences of functional homologs of the polypeptide set forth in SEQ ID NO:77 are provided in FIG. 3 and in the Sequence Listing. Such functional homologs include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and CeresAnnot: 839064 (SEQ ID NO:1479). In some cases, a functional homolog of SEQ ID NO:77 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77.

Examples of amino acid sequences of functional homologs of the polypeptide set forth in SEQ ID NO:100 are provided in FIG. 4 and in the Sequence Listing. Such functional homologs include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150. In some cases, a functional homolog of SEQ ID NO:100 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100.

Examples of amino acid sequences of functional homologs of the polypeptide set forth in SEQ ID NO:152 are provided in FIG. 5 and in the Sequence Listing. Such functional homologs include SEQ ID NO:154, SEQ ID NO:156, SEQ ID NO:158, SEQ ID NO:160, SEQ ID NO:162, and SEQ ID NO:164. In some cases, a functional homolog of SEQ ID NO:152 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152.

Examples of amino acid sequences of functional homologs of the polypeptide set forth in SEQ ID NO:166 are provided in FIG. 6 and in the Sequence Listing. Such functional homologs include SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184. In some cases, a functional homolog of SEQ ID NO:166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166.

Examples of amino acid sequences of functional homologs of the polypeptide set forth in SEQ ID NO:186 are provided in FIG. 7 and in the Sequence Listing. Such functional homologs include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206. In some cases, a functional homolog of SEQ ID NO:186 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186.

Examples of amino acid sequences of functional homologs of the polypeptide set forth in SEQ ID NO:208 are provided in FIG. 8 and in the Sequence Listing. Such functional homologs include SEQ ID NO:209, SEQ ID NO:210, SEQ ID NO:214, and SEQ ID NO:216. In some cases, a functional homolog of SEQ ID NO:208 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208.

Examples of amino acid sequences of functional homologs of the polypeptide set forth in SEQ ID NO:218 are provided in FIG. 9 and in the Sequence Listing. Such functional homologs include SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052. In some cases, a functional homolog of SEQ ID NO:218 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218.

Examples of amino acid sequences of functional homologs of the polypeptide set forth in SEQ ID NO:234 are provided in FIG. 10 and in the Sequence Listing. Such functional homologs include SEQ ID NO:236, SEQ ID NO:238, SEQ ID NO:239, SEQ ID NO:241, SEQ ID NO:242, SEQ ID NO:243, and SEQ ID NO:244. In some cases, a functional homolog of SEQ ID NO:234 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234.

Examples of amino acid sequences of functional homologs of the polypeptide set forth in SEQ ID NO:246 are provided in FIG. 11 and in the Sequence Listing. Such functional homologs include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298. In some cases, a functional homolog of SEQ ID NO:246 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246.

Examples of amino acid sequences of functional homologs of the polypeptide set forth in SEQ ID NO:300 are provided in FIG. 12 and in the Sequence Listing. Such functional homologs include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329. In some cases, a functional homolog of SEQ ID NO:300 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300.

Examples of amino acid sequences of functional homologs of the polypeptide set forth in SEQ ID NO:332 are provided in FIG. 13 and in the Sequence Listing. Such functional homologs include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553. In some cases, a functional homolog of SEQ ID NO:332 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332.

Examples of amino acid sequences of functional homologs of the polypeptide set forth in SEQ ID NO:368 are provided in FIG. 14 and in the Sequence Listing. Such functional homologs include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508. In some cases, a functional homolog of SEQ ID NO:368 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368.

Examples of amino acid sequences of functional homologs of the polypeptide set forth in SEQ ID NO:510 are provided in FIG. 15 and in the Sequence Listing. Such functional homologs include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531. In some cases, a functional homolog of SEQ ID NO:510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510.

Examples of amino acid sequences of functional homologs of the polypeptide set forth in SEQ ID NO:533 are provided in FIG. 16 and in the Sequence Listing. Such functional homologs include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554. In some cases, a functional homolog of SEQ ID NO:533 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533.

Examples of amino acid sequences of functional homologs of the polypeptide set forth in SEQ ID NO:558 are provided in FIG. 17 and in the Sequence Listing. Such functional homologs include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591. In some cases, a functional homolog of SEQ ID NO:558 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558.

Examples of amino acid sequences of functional homologs of the polypeptide set forth in SEQ ID NO:593 are provided in FIG. 18 and in the Sequence Listing. Such functional homologs include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611. In some cases, a functional homolog of SEQ ID NO:593 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593.

Examples of amino acid sequences of functional homologs of the polypeptide set forth in SEQ ID NO:613 are provided in FIG. 19 and in the Sequence Listing. Such functional homologs include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644. In some cases, a functional homolog of SEQ ID NO:613 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613.

Examples of amino acid sequences of functional homologs of the polypeptide set forth in SEQ ID NO:646 are provided in FIG. 20 and in the Sequence Listing. Such functional homologs include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685. In some cases, a functional homolog of SEQ ID NO:646 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646.

Examples of amino acid sequences of functional homologs of the polypeptide set forth in SEQ ID NO:687 are provided in FIG. 21 and in the Sequence Listing. Such functional homologs include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728. In some cases, a functional homolog of SEQ ID NO:687 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687.

Examples of amino acid sequences of functional homologs of the polypeptide set forth in SEQ ID NO:730 are provided in FIG. 22 and in the Sequence Listing. Such functional homologs include SEQ ID NO:732, SEQ ID NO:733, SEQ ID NO:735, SEQ ID NO:737, SEQ ID NO:738, and SEQ ID NO:742. In some cases, a functional homolog of SEQ ID NO:730 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730.

Examples of amino acid sequences of functional homologs of the polypeptide set forth in SEQ ID NO:746 are provided in FIG. 23 and in the Sequence Listing. Such functional homologs include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767. In some cases, a functional homolog of SEQ ID NO:746 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746.

Examples of amino acid sequences of functional homologs of the polypeptide set forth in SEQ ID NO:769 are provided in FIG. 24 and in the Sequence Listing. Such functional homologs include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790. In some cases, a functional homolog of SEQ ID NO:769 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769.

Examples of amino acid sequences of functional homologs of the polypeptide set forth in SEQ ID NO:792 are provided in FIG. 25 and in the Sequence Listing. Such functional homologs include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822. In some cases, a functional homolog of SEQ ID NO:792 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792.

Examples of amino acid sequences of functional homologs of the polypeptide set forth in SEQ ID NO:824 are provided in FIG. 26 and in the Sequence Listing. Such functional homologs include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716. In some cases, a functional homolog of SEQ ID NO:824 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824.

Examples of amino acid sequences of functional homologs of the polypeptide set forth in SEQ ID NO:828 are provided in FIG. 27 and in the Sequence Listing. Such functional homologs include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851. In some cases, a functional homolog of SEQ ID NO:828 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828.

Examples of amino acid sequences of functional homologs of the polypeptide set forth in SEQ ID NO:855 are provided in FIG. 28 and in the Sequence Listing. Such functional homologs include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889. In some cases, a functional homolog of SEQ ID NO:855 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855.

Examples of amino acid sequences of functional homologs of the polypeptide set forth in SEQ ID NO:891 are provided in FIG. 29 and in the Sequence Listing. Such functional homologs include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915. In some cases, a functional homolog of SEQ ID NO:891 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891.

Examples of amino acid sequences of functional homologs of the polypeptide set forth in SEQ ID NO:917 are provided in FIG. 30 and in the Sequence Listing. Such functional homologs include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940. In some cases, a functional homolog of SEQ ID NO:917 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917.

Examples of amino acid sequences of functional homologs of the polypeptide set forth in SEQ ID NO:944 are provided in FIG. 31 and in the Sequence Listing. Such functional homologs include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974. In some cases, a functional homolog of SEQ ID NO:944 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944.

Examples of amino acid sequences of functional homologs of the polypeptide set forth in SEQ ID NO:976 are provided in FIG. 32 and in the Sequence Listing. Such functional homologs include, but not limited to, SEQ ID NO:978 and SEQ ID NO:980. In some cases, a functional homolog of SEQ ID NO:976 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976.

Examples of amino acid sequences of functional homologs of the polypeptide set forth in SEQ ID NO:982 are provided in FIG. 33 and in the Sequence Listing. Such functional homologs include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033. In some cases, a functional homolog of SEQ ID NO:982 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982.

Examples of amino acid sequences of functional homologs of the polypeptide set forth in SEQ ID NO:1054 are provided in FIG. 34 and in the Sequence Listing. Such functional homologs include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097. In some cases, a functional homolog of SEQ ID NO:1054 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054.

Examples of amino acid sequences of functional homologs of the polypeptide set forth in SEQ ID NO:1099 are provided in FIG. 35 and in the Sequence Listing. Such functional homologs include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110. In some cases, a functional homolog of SEQ ID NO:1099 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099.

Examples of amino acid sequences of functional homologs of the polypeptide set forth in SEQ ID NO:1112 are provided in FIG. 36 and in the Sequence Listing. Such functional homologs include SEQ ID NO:1113 and SEQ ID NO:1114. In some cases, a functional homolog of SEQ ID NO:1112 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112.

Examples of amino acid sequences of functional homologs of the polypeptide set forth in SEQ ID NO:1116 are provided in FIG. 37 and in the Sequence Listing. Such functional homologs include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155. In some cases, a functional homolog of SEQ ID NO:1116 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116.

Examples of amino acid sequences of functional homologs of the polypeptide set forth in SEQ ID NO:1159 are provided in FIG. 38 and in the Sequence Listing. Such functional homologs include SEQ ID NO:1161, SEQ ID NO:1162, SEQ ID NO:1163, and SEQ ID NO:1164. In some cases, a functional homolog of SEQ ID NO:1159 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159.

Examples of amino acid sequences of functional homologs of the polypeptide set forth in SEQ ID NO:1166 are provided in FIG. 39 and in the Sequence Listing. Such functional homologs include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183. In some cases, a functional homolog of SEQ ID NO:1166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166.

Examples of amino acid sequences of functional homologs of the polypeptide set forth in SEQ ID NO:1185 are provided in FIG. 40 and in the Sequence Listing. Such functional homologs include SEQ ID NO:1187, SEQ ID NO:1189, SEQ ID NO:1190, SEQ ID NO:1191, and SEQ ID NO:1192. In some cases, a functional homolog of SEQ ID NO:1185 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185.

Examples of amino acid sequences of functional homologs of the polypeptide set forth in SEQ ID NO:1194 are provided in FIG. 41 and in the Sequence Listing. Such functional homologs include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208. In some cases, a functional homolog of SEQ ID NO:1194 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194.

Examples of amino acid sequences of functional homologs of the polypeptide set forth in SEQ ID NO:1210 are provided in FIG. 42 and in the Sequence Listing. Such functional homologs include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272. In some cases, a functional homolog of SEQ ID NO:1210 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210.

Examples of amino acid sequences of functional homologs of the polypeptide set forth in SEQ ID NO:1274 are provided in FIG. 43 and in the Sequence Listing. Such functional homologs include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300. In some cases, a functional homolog of SEQ ID NO:1274 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274.

Examples of amino acid sequences of functional homologs of the polypeptide set forth in SEQ ID NO:1302 are provided in FIG. 44 and in the Sequence Listing. Such functional homologs include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340. In some cases, a functional homolog of SEQ ID NO:1302 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302.

Examples of amino acid sequences of functional homologs of the polypeptide set forth in SEQ ID NO:1342 are provided in FIG. 45 and in the Sequence Listing. Such functional homologs include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383. In some cases, a functional homolog of SEQ ID NO:1342 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342.

Examples of amino acid sequences of functional homologs of the polypeptide set forth in SEQ ID NO:1385 are provided in FIG. 46 and in the Sequence Listing. Such functional homologs include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407. In some cases, a functional homolog of SEQ ID NO:1385 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385.

Examples of amino acid sequences of functional homologs of the polypeptide set forth in SEQ ID NO:1409 are provided in FIG. 47 and in the Sequence Listing. Such functional homologs include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426. In some cases, a functional homolog of SEQ ID NO:1409 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409.

Examples of amino acid sequences of functional homologs of the polypeptide set forth in SEQ ID NO:1428 are provided in FIG. 48 and in the Sequence Listing. Such functional homologs include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459. In some cases, a functional homolog of SEQ ID NO:1428 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428.

Examples of amino acid sequences of functional homologs of the polypeptide set forth in SEQ ID NO:1463 are provided in FIG. 49 and in the Sequence Listing. Such functional homologs include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477. In some cases, a functional homolog of SEQ ID NO:1463 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463.

Examples of amino acid sequences of functional homologs of the polypeptide set forth in SEQ ID NO:1491 are provided in FIG. 50 and in the Sequence Listing. Such functional homologs include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508. In some cases, a functional homolog of SEQ ID NO:1491 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491.

Examples of amino acid sequences of functional homologs of the polypeptide set forth in SEQ ID NO:1510 are provided in FIG. 51 and in the Sequence Listing. Such functional homologs include SEQ ID NO:1512, SEQ ID NO:1514, SEQ ID NO:1516, SEQ ID NO:1518, SEQ ID NO:1520, SEQ ID NO:1522, and SEQ ID NO:1523. In some cases, a functional homolog of SEQ ID NO:1510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510.

Examples of amino acid sequences of functional homologs of the polypeptide set forth in SEQ ID NO:1525 are provided in FIG. 52 and in the Sequence Listing. Such functional homologs include SEQ ID NO:1527, SEQ ID NO:1529, SEQ ID NO:1530, SEQ ID NO:1532, SEQ ID NO:1534, and SEQ ID NO:1535. In some cases, a functional homolog of SEQ ID NO:1525 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525.

Examples of amino acid sequences of functional homologs of the polypeptide set forth in SEQ ID NO:1537 are provided in FIG. 53 and in the Sequence Listing. Such functional homologs include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392. In some cases, a functional homolog of SEQ ID NO:1537 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537.

Examples of amino acid sequences of functional homologs of the polypeptide set forth in SEQ ID NO:1554 are provided in FIG. 54 and in the Sequence Listing. Such functional homologs include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575. In some cases, a functional homolog of SEQ ID NO:1554 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554.

Examples of amino acid sequences of functional homologs of the polypeptide set forth in SEQ ID NO:1577 are provided in FIG. 55 and in the Sequence Listing. Such functional homologs include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653. In some cases, a functional homolog of SEQ ID NO:1577 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577.

Examples of amino acid sequences of functional homologs of the polypeptide set forth in SEQ ID NO:1437 are provided in FIG. 56 and in the Sequence Listing. Such functional homologs include SEQ ID NO:173, SEQ ID NO:212, SEQ ID NO:361, SEQ ID NO:421, SEQ ID NO:443, SEQ ID NO:740, SEQ ID NO:744, SEQ ID NO:942, and SEQ ID NO:1461. In some cases, a functional homolog of SEQ ID NO:1437 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437.

Examples of amino acid sequences of functional homologs of the polypeptide set forth in SEQ ID NO:97 are provided in FIG. 57 and in the Sequence Listing. Such functional homologs include SEQ ID NO:2010, SEQ ID NO:2011, SEQ ID NO:2013, SEQ ID NO:2015, SEQ ID NO:2017. In some cases, a functional homolog of SEQ ID NO:97 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97.

The identification of conserved regions in a low nitrogen tolerance-modulating polypeptide facilitates production of variants of low nitrogen tolerance-modulating polypeptides. Variants of low nitrogen tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1-57 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful low nitrogen tolerance-modulating polypeptides include those that fit a Hidden Markov Model based on the polypeptides set forth in any one of FIGS. 1-57. A Hidden Markov Model (HMM) is a statistical model of a consensus sequence for a group of functional homologs. See, Durbin et al. (1998) Biological Sequence Analysis: *Probabilistic Models of Proteins and Nucleic Acids*, Cambridge University Press, Cambridge, UK. An HMM is generated by the program HMMER 2.3.2 with default program parameters, using the sequences of the group of functional homologs as input. The multiple sequence alignment is generated by ProbCons (Do et al. (2005) Genome Res., 15(2):330-40) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer janelia.org; hmmer wustl.edu; and fr.com/hmmer232/. Hmmbuild outputs the model as a text file.

The HMM for a group of functional homologs can be used to determine the likelihood that a candidate low nitrogen tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The low nitrogen tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a low nitrogen tolerance-modulating polypeptide discussed below is about 50%, 60%, 70%, 80%, 90%, or 95% of the HMM bit score of a functional homolog provided the Sequence Listing of this application. In some embodiments, a low nitrogen tolerance-modulating polypeptide discussed below fits the indicated HMM with an HMM bit score greater than 20, and has a domain indicative of a low nitrogen tolerance-modulating polypeptide. In some embodiments, a low nitrogen tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-57.

Examples of polypeptides are shown in the sequence listing that have HMM bit scores greater than 800 when fitted to an HMM generated from the amino acid sequences set forth in FIG. 1 are identified in the Sequence Listing of this application. Such polypeptides include SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

Examples of polypeptides are shown in the sequence listing that have HMM bit scores greater than 150 when fitted to an HMM generated from the amino acid sequences set forth in FIG. 2 are identified in the Sequence Listing of this application. Such polypeptides include SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

Examples of polypeptides are shown in the sequence listing that have HMM bit scores greater than 540 when fitted to an HMM generated from the amino acid sequences set forth in FIG. 3 are identified in the Sequence Listing of this application. Such polypeptides include SEQ ID NO:77, SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and SEQ ID NO:1479.

Examples of polypeptides are shown in the sequence listing that have HMM bit scores greater than 210 when fitted to an HMM generated from the amino acid sequences set forth in FIG. 4 are identified in the Sequence Listing of this application. Such polypeptides include SEQ ID NO:100, SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

Examples of polypeptides are shown in the sequence listing that have HMM bit scores greater than 90 when fitted to an HMM generated from the amino acid sequences set forth in FIG. 5 are identified in the Sequence Listing of this application. Such polypeptides include SEQ ID NO:152, SEQ ID NO:154, SEQ ID NO:156, SEQ ID NO:158, SEQ ID NO:160, SEQ ID NO:162, and SEQ ID NO:164.

Examples of polypeptides are shown in the sequence listing that have HMM bit scores greater than 230 when fitted to an HMM generated from the amino acid sequences set forth in FIG. 6 are identified in the Sequence Listing of this application. Such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184.

Examples of polypeptides are shown in the sequence listing that have HMM bit scores greater than 90 when fitted to an HMM generated from the amino acid sequences set forth in FIG. 7 are identified in the Sequence Listing of this application. Such polypeptides include SEQ ID NO:186, SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

Examples of polypeptides are shown in the sequence listing that have HMM bit scores greater than 380 when fitted to an HMM generated from the amino acid sequences set forth in FIG. 8 are identified in the Sequence Listing of this application. Such polypeptides include SEQ ID NO:208, SEQ ID NO:209, SEQ ID NO:210, SEQ ID NO:214, and SEQ ID NO:216.

Examples of polypeptides are shown in the sequence listing that have HMM bit scores greater than 110 when fitted to an HMM generated from the amino acid sequences set forth in FIG. 9 are identified in the Sequence Listing of this application. Such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

Examples of polypeptides are shown in the sequence listing that have HMM bit scores greater than 220 when fitted to an HMM generated from the amino acid sequences set forth in FIG. 10 are identified in the Sequence Listing of this application. Such polypeptides include SEQ ID NO:234, SEQ ID NO:236, SEQ ID NO:238, SEQ ID NO:239, SEQ ID NO:241, SEQ ID NO:242, SEQ ID NO:243, and SEQ ID NO:244.

Examples of polypeptides are shown in the sequence listing that have HMM bit scores greater than 150 when fitted to an HMM generated from the amino acid sequences set forth in FIG. 11 are identified in the Sequence Listing of this application. Such polypeptides include SEQ ID NO:246, SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

Examples of polypeptides are shown in the sequence listing that have HMM bit scores greater than 950 when fitted to an HMM generated from the amino acid sequences set forth in FIG. 12 are identified in the Sequence Listing of this application. Such polypeptides include SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

Examples of polypeptides are shown in the sequence listing that have HMM bit scores greater than 460 when fitted to an HMM generated from the amino acid sequences set forth in FIG. 13 are identified in the Sequence Listing of this application. Such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

Examples of polypeptides are shown in the sequence listing that have HMM bit scores greater than 150 when fitted to an HMM generated from the amino acid sequences set forth in FIG. 14 are identified in the Sequence Listing of this application. Such polypeptides include SEQ ID NO:368, SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

Examples of polypeptides are shown in the sequence listing that have HMM bit scores greater than 410 when fitted to an HMM generated from the amino acid sequences set forth in FIG. 15 are identified in the Sequence Listing of this application. Such polypeptides include SEQ ID NO:510, SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

Examples of polypeptides are shown in the sequence listing that have HMM bit scores greater than 520 when fitted to an HMM generated from the amino acid sequences set forth in FIG. 16 are identified in the Sequence Listing of this application. Such polypeptides include SEQ ID NO:533, SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

Examples of polypeptides are shown in the sequence listing that have HMM bit scores greater than 1150 when fitted to an HMM generated from the amino acid sequences set forth in FIG. 17 are identified in the Sequence Listing of this application. Such polypeptides include SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

Examples of polypeptides are shown in the sequence listing that have HMM bit scores greater than 340 when fitted to an HMM generated from the amino acid sequences set forth in FIG. 18 are identified in the Sequence Listing of this application. Such polypeptides include SEQ ID NO:593, SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

Examples of polypeptides are shown in the sequence listing that have HMM bit scores greater than 140 when fitted to an HMM generated from the amino acid sequences set forth in FIG. 19 are identified in the Sequence Listing of this application. Such polypeptides include SEQ ID NO:613, SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

Examples of polypeptides are shown in the sequence listing that have HMM bit scores greater than 250 when fitted to an HMM generated from the amino acid sequences set forth in FIG. 20 are identified in the Sequence Listing of this application. Such polypeptides include SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

Examples of polypeptides are shown in the sequence listing that have HMM bit scores greater than 170 when fitted to an HMM generated from the amino acid sequences set forth in FIG. 21 are identified in the Sequence Listing of this application. Such polypeptides include SEQ ID NO:687, SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

Examples of polypeptides are shown in the sequence listing that have HMM bit scores greater than 210 when fitted to an HMM generated from the amino acid sequences set forth in FIG. 22 are identified in the Sequence Listing of this application. Such polypeptides include SEQ ID NO:730, SEQ ID NO:732, SEQ ID NO:733, SEQ ID NO:735, SEQ ID NO:737, SEQ ID NO:738, and SEQ ID NO:742.

Examples of polypeptides are shown in the sequence listing that have HMM bit scores greater than 230 when fitted to an HMM generated from the amino acid sequences set forth in FIG. 23 are identified in the Sequence Listing of this application. Such polypeptides include SEQ ID NO:746, SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

Examples of polypeptides are shown in the sequence listing that have HMM bit scores greater than 180 when fitted to an HMM generated from the amino acid sequences set forth in FIG. 24 are identified in the Sequence Listing of this application. Such polypeptides include SEQ ID NO:769, SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

Examples of polypeptides are shown in the sequence listing that have HMM bit scores greater than 300 when fitted to an HMM generated from the amino acid sequences set forth in FIG. 25 are identified in the Sequence Listing of this application. Such polypeptides include SEQ ID NO:792, SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

Examples of polypeptides are shown in the sequence listing that have HMM bit scores greater than 190 when fitted to an HMM generated from the amino acid sequences set forth in FIG. 26 are identified in the Sequence Listing of this application. Such polypeptides include SEQ ID NO:824, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

Examples of polypeptides are shown in the sequence listing that have HMM bit scores greater than 630 when fitted to an HMM generated from the amino acid sequences set forth in FIG. 27 are identified in the Sequence Listing of this application. Such polypeptides include SEQ ID NO:828, SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

Examples of polypeptides are shown in the sequence listing that have HMM bit scores greater than 95 when fitted to an HMM generated from the amino acid sequences set forth in FIG. 28 are identified in the Sequence Listing of this application. Such polypeptides include SEQ ID NO:855, SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

Examples of polypeptides are shown in the sequence listing that have HMM bit scores greater than 850 when fitted to an HMM generated from the amino acid sequences set forth in FIG. 29 are identified in the Sequence Listing of this application. Such polypeptides include SEQ ID NO:891, SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

Examples of polypeptides are shown in the sequence listing that have HMM bit scores greater than 300 when fitted to an HMM generated from the amino acid sequences set forth in FIG. 30 are identified in the Sequence Listing of this application. Such polypeptides include SEQ ID NO:917, SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

Examples of polypeptides are shown in the sequence listing that have HMM bit scores greater than 60 when fitted to an HMM generated from the amino acid sequences set forth in FIG. 31 are identified in the Sequence Listing of this application. Such polypeptides include SEQ ID NO:944, SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

Examples of polypeptides are shown in the sequence listing that have HMM bit scores greater than 340 when fitted to an HMM generated from the amino acid sequences set forth in FIG. 32 are identified in the Sequence Listing of this application. Such polypeptides include SEQ ID NO:976, SEQ ID NO:978, and SEQ ID NO:980.

Examples of polypeptides are shown in the sequence listing that have HMM bit scores greater than 180 when fitted to an HMM generated from the amino acid sequences set forth in FIG. 33 are identified in the Sequence Listing of this application. Such polypeptides include SEQ ID NO:982, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

Examples of polypeptides are shown in the sequence listing that have HMM bit scores greater than 1060 when fitted to an HMM generated from the amino acid sequences set forth in FIG. 34 are identified in the Sequence Listing of this application. Such polypeptides include SEQ ID NO:1054, SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

Examples of polypeptides are shown in the sequence listing that have HMM bit scores greater than 260 when fitted to an HMM generated from the amino acid sequences set forth in FIG. 35 are identified in the Sequence Listing of this application. Such polypeptides include SEQ ID NO:1099, SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

Examples of polypeptides are shown in the sequence listing that have HMM bit scores greater than 150 when fitted to an HMM generated from the amino acid sequences set forth in FIG. 36 are identified in the Sequence Listing of this application. Such polypeptides include SEQ ID NO:1112, SEQ ID NO:1113, and SEQ ID NO:1114.

Examples of polypeptides are shown in the sequence listing that have HMM bit scores greater than 40 when fitted to an HMM generated from the amino acid sequences set forth in FIG. 37 are identified in the Sequence Listing of this application. Such polypeptides include SEQ ID NO:1116, SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

Examples of polypeptides are shown in the sequence listing that have HMM bit scores greater than 450 when fitted to an HMM generated from the amino acid sequences set forth in FIG. 38 are identified in the Sequence Listing of this application. Such polypeptides include SEQ ID NO:1159, SEQ ID NO:1161, SEQ ID NO:1162, SEQ ID NO:1163, and SEQ ID NO:1164.

Examples of polypeptides are shown in the sequence listing that have HMM bit scores greater than 160 when fitted to an HMM generated from the amino acid sequences set forth in FIG. 39 are identified in the Sequence Listing of this application. Such polypeptides include SEQ ID NO:1166, SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

Examples of polypeptides are shown in the sequence listing that have HMM bit scores greater than 180 when fitted to an HMM generated from the amino acid sequences set forth in FIG. 40 are identified in the Sequence Listing of this application. Such polypeptides include SEQ ID NO:1185, SEQ ID NO:1187, SEQ ID NO:1189, SEQ ID NO:1190, SEQ ID NO:1191, and SEQ ID NO:1192.

Examples of polypeptides are shown in the sequence listing that have HMM bit scores greater than 670 when fitted to an HMM generated from the amino acid sequences set forth in FIG. 41 are identified in the Sequence Listing of this application. Such polypeptides include SEQ ID NO:1194, SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

Examples of polypeptides are shown in the sequence listing that have HMM bit scores greater than 280 when fitted to an HMM generated from the amino acid sequences set forth in FIG. 42 are identified in the Sequence Listing of this application. Such polypeptides include SEQ ID NO:1210, SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

Examples of polypeptides are shown in the sequence listing that have HMM bit scores greater than 700 when fitted to an HMM generated from the amino acid sequences set forth in FIG. 43 are identified in the Sequence Listing of this application. Such polypeptides include SEQ ID NO:1274, SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

Examples of polypeptides are shown in the sequence listing that have HMM bit scores greater than 920 when fitted to an HMM generated from the amino acid sequences set forth in FIG. 44 are identified in the Sequence Listing of this application. Such polypeptides include SEQ ID NO:1302, SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

Examples of polypeptides are shown in the sequence listing that have HMM bit scores greater than 510 when fitted to an HMM generated from the amino acid sequences set forth in FIG. 45 are identified in the Sequence Listing of this application. Such polypeptides include SEQ ID NO:1342, SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

Examples of polypeptides are shown in the sequence listing that have HMM bit scores greater than 140 when fitted to an HMM generated from the amino acid sequences set forth in FIG. 46 are identified in the Sequence Listing of this application. Such polypeptides include SEQ ID NO:1385, SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

Examples of polypeptides are shown in the sequence listing that have HMM bit scores greater than 150 when fitted to an HMM generated from the amino acid sequences set forth in FIG. 47 are identified in the Sequence Listing of this application. Such polypeptides include SEQ ID NO:1409, SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, SEQ ID NO:1426.

Examples of polypeptides are shown in the sequence listing that have HMM bit scores greater than 190 when fitted to an HMM generated from the amino acid sequences set forth in FIG. 48 are identified in the Sequence Listing of this application. Such polypeptides include SEQ ID NO:1428, SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

Examples of polypeptides are shown in the sequence listing that have HMM bit scores greater than 450 when fitted to an HMM generated from the amino acid sequences set forth in FIG. 49 are identified in the Sequence Listing of this application. Such polypeptides include SEQ ID NO:1463, SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

Examples of polypeptides are shown in the sequence listing that have HMM bit scores greater than 580 when fitted to an HMM generated from the amino acid sequences set forth in FIG. 50 are identified in the Sequence Listing of this application. Such polypeptides include SEQ ID NO:1491, SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

Examples of polypeptides are shown in the sequence listing that have HMM bit scores greater than 100 when fitted to an HMM generated from the amino acid sequences set forth in FIG. 51 are identified in the Sequence Listing of this application. Such polypeptides include SEQ ID NO:1510, SEQ ID NO:1512, SEQ ID NO:1514, SEQ ID NO:1516, SEQ ID NO:1518, SEQ ID NO:1520, SEQ ID NO:1522, and SEQ ID NO:1523.

Examples of polypeptides are shown in the sequence listing that have HMM bit scores greater than 800 when fitted to an HMM generated from the amino acid sequences set forth in FIG. 52 are identified in the Sequence Listing of this application. Such polypeptides include SEQ ID NO:1525, SEQ ID NO:1527, SEQ ID NO:1529, SEQ ID NO:1530, SEQ ID NO:1532, SEQ ID NO:1534, and SEQ ID NO:1535.

Examples of polypeptides are shown in the sequence listing that have HMM bit scores greater than 490 when fitted to an HMM generated from the amino acid sequences set forth in FIG. 53 are identified in the Sequence Listing of this application. Such polypeptides include SEQ ID NO:1537, SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

Examples of polypeptides are shown in the sequence listing that have HMM bit scores greater than 690 when fitted to an HMM generated from the amino acid sequences set forth in FIG. 54 are identified in the Sequence Listing of this application. Such polypeptides include SEQ ID NO:1554, SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

Examples of polypeptides are shown in the sequence listing that have HMM bit scores greater than 380 when fitted to an HMM generated from the amino acid sequences set forth in FIG. 55 are identified in the Sequence Listing of this application. Such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1577, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653.

Examples of polypeptides are shown in the sequence listing that have HMM bit scores greater than 870 when fitted to an HMM generated from the amino acid sequences set forth in FIG. 56 are identified in the Sequence Listing of this application. Such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1437, and SEQ ID NO:1461.

Examples of polypeptides are shown in the sequence listing that have HMM bit scores greater than 140 when fitted to an HMM generated from the amino acid sequences set forth in FIG. 57 are identified in the Sequence Listing of this application. Such polypeptides include SEQ ID NO:97, SEQ ID NO:2010, SEQ ID NO:2011, SEQ ID NO:2013, SEQ ID NO:2015, and SEQ ID NO:2017.

D. Percent Identity

In some embodiments, a low nitrogen tolerance-modulating polypeptide has an amino acid sequence with at least 20% sequence identity, e.g., at least 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Polypeptides having such a percent sequence identity often have a domain indicative of a low nitrogen tolerance-modulating polypeptide and/or have an HMM bit score that is greater than 20, as discussed above. Amino acid sequences of low nitrogen tolerance-modulating polypeptides having at least 20% sequence identity to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577 are provided in FIGS. 1-57 and in the Sequence Listing.

"Percent sequence identity" refers to the degree of sequence identity between any given reference sequence, e.g., SEQ ID NO:3, and a candidate low nitrogen tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al. (2003) *Nucleic Acids Res.*, 31(13): 3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a low nitrogen tolerance-modulating polypeptide has an amino acid sequence with sequence similarity to the amino acid sequence set forth in SEQ ID NO:3, and preferably has at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 3 Amino acid sequences of polypeptides having greater than 20% sequence identity to the polypeptide set forth in SEQ ID NO:3 are provided in FIG. 1 and in the Sequence Listing. Examples of such polypeptides include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

In some cases, a low nitrogen tolerance-modulating polypeptide has an amino acid sequence with sequence similarity to the amino acid sequence set forth in SEQ ID NO:49, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49 Amino acid sequences of polypeptides having greater than 45% sequence identity to the polypeptide set forth in SEQ ID NO:49 are provided in FIG. 2 and in the Sequence Listing. Examples of such polypeptides include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

In some cases, a low nitrogen tolerance-modulating polypeptide has an amino acid sequence with sequence similarity to the amino acid sequence set forth in SEQ ID NO:77, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77 Amino acid sequences of polypeptides having greater than 45% sequence identity to the polypeptide set forth in SEQ ID NO:77 are provided in FIG. 3 and in the Sequence Listing. Examples of such polypeptides include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, SEQ ID NO:1479.

In some cases, a low nitrogen tolerance-modulating polypeptide has an amino acid sequence with sequence similarity to the amino acid sequence set forth in SEQ ID NO:100, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100. Amino acid sequences of polypeptides having greater than 45% sequence identity to the polypeptide set forth in SEQ ID NO: 100 are provided in FIG. 4 and in the Sequence Listing. Examples of such polypeptides include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

In some cases, a low nitrogen tolerance-modulating polypeptide has an amino acid sequence with sequence similarity to the amino acid sequence set forth in SEQ ID NO:152, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152. Amino acid sequences of polypeptides having greater than 45% sequence identity to the polypeptide set forth in SEQ ID NO:152 are provided in FIG. 5 and in the Sequence Listing. Examples of such polypeptides include SEQ ID NO:154, SEQ ID NO:156, SEQ ID NO:158, SEQ ID NO:160, SEQ ID NO:162, and SEQ ID NO:164.

In some cases, a low nitrogen tolerance-modulating polypeptide has an amino acid sequence with sequence similarity to the amino acid sequence set forth in SEQ ID NO:166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166. Amino acid sequences of polypeptides having greater than 45% sequence identity to the polypeptide set forth in SEQ ID NO:166 are provided in FIG. 6 and in the Sequence Listing. Examples of such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, SEQ ID NO:184.

In some cases, a low nitrogen tolerance-modulating polypeptide has an amino acid sequence with sequence similarity to the amino acid sequence set forth in SEQ ID NO:186, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186. Amino acid sequences of polypeptides having greater than 45% sequence identity to the polypeptide set forth in SEQ ID NO:186 are provided in FIG. 7 and in the Sequence Listing. Examples of such polypeptides include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

In some cases, a low nitrogen tolerance-modulating polypeptide has an amino acid sequence with sequence similarity to the amino acid sequence set forth in SEQ ID NO:208, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208. Amino acid sequences of polypeptides having greater than 45% sequence identity to the polypeptide set forth in SEQ ID NO:208 are provided in FIG. 8 and in the Sequence Listing. Examples of such polypeptides include SEQ ID NO:209, SEQ ID NO:210, SEQ ID NO:214, and SEQ ID NO:216.

In some cases, a low nitrogen tolerance-modulating polypeptide has an amino acid sequence with sequence similarity to the amino acid sequence set forth in SEQ ID NO:218, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218. Amino acid sequences of polypeptides having greater than 45% sequence identity to the polypeptide set forth in SEQ ID NO:218 are provided in FIG. 9 and in the Sequence Listing. Examples of such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

In some cases, a low nitrogen tolerance-modulating polypeptide has an amino acid sequence with sequence similarity to the amino acid sequence set forth in SEQ ID NO:234, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234. Amino acid sequences of polypeptides having greater than 45% sequence identity to the polypeptide set forth in SEQ ID NO:234 are provided in FIG. 10 and in the Sequence Listing. Examples of such polypeptides include SEQ ID NO:236, SEQ ID NO:238, SEQ ID NO:239, SEQ ID NO:241, SEQ ID NO:242, SEQ ID NO:243, and SEQ ID NO:244.

In some cases, a low nitrogen tolerance-modulating polypeptide has an amino acid sequence with sequence similarity to the amino acid sequence set forth in SEQ ID NO:246, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246. Amino acid sequences of polypeptides having greater than 45% sequence identity to the polypeptide set forth in SEQ ID NO:246 are provided in FIG. 11 and in the Sequence Listing. Examples of such polypeptides include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

In some cases, a low nitrogen tolerance-modulating polypeptide has an amino acid sequence with sequence similarity to the amino acid sequence set forth in SEQ ID NO:300, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300. Amino acid sequences of polypeptides having greater than 45% sequence identity to the polypeptide set forth in SEQ ID NO:300 are provided in FIG. 12 and in the Sequence Listing. Examples of such polypeptides include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

In some cases, a low nitrogen tolerance-modulating polypeptide has an amino acid sequence with sequence similarity to the amino acid sequence set forth in SEQ ID NO:332, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332. Amino acid sequences of polypeptides having greater than 45% sequence identity to the polypeptide set forth in SEQ ID NO:332 are provided in FIG. 13 and in the Sequence Listing. Examples of such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

In some cases, a low nitrogen tolerance-modulating polypeptide has an amino acid sequence with sequence similarity to the amino acid sequence set forth in SEQ ID NO:368, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368. Amino acid sequences of polypeptides having greater than 45% sequence identity to the polypeptide set forth in SEQ ID NO:368 are provided in FIG. 14 and in the Sequence Listing. Examples of such polypeptides include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

In some cases, a low nitrogen tolerance-modulating polypeptide has an amino acid sequence with sequence similarity to the amino acid sequence set forth in SEQ ID NO:510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510. Amino acid sequences of polypeptides having greater than 45% sequence identity to the polypeptide set forth in SEQ ID NO:510 are provided in FIG. 15 and in the Sequence Listing. Examples of such polypeptides include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

In some cases, a low nitrogen tolerance-modulating polypeptide has an amino acid sequence with sequence similarity to the amino acid sequence set forth in SEQ ID NO:533, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533. Amino acid sequences of polypeptides having greater than 45% sequence identity to the polypeptide set forth in SEQ ID NO:533 are provided in FIG. 16 and in the Sequence Listing. Examples of such polypeptides include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

In some cases, a low nitrogen tolerance-modulating polypeptide has an amino acid sequence with sequence similarity to the amino acid sequence set forth in SEQ ID NO:558, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558. Amino acid sequences of polypeptides having greater than 45% sequence identity to the polypeptide set forth in SEQ ID NO:558 are provided in FIG. 17 and in the Sequence Listing. Examples of such polypeptides include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

In some cases, a low nitrogen tolerance-modulating polypeptide has an amino acid sequence with sequence similarity to the amino acid sequence set forth in SEQ ID NO:593, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593. Amino acid sequences of polypeptides having greater than 45% sequence identity to the polypeptide set forth in SEQ ID NO:593 are provided in FIG. 18 and in the Sequence Listing. Examples of such polypeptides include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

In some cases, a low nitrogen tolerance-modulating polypeptide has an amino acid sequence with sequence similarity to the amino acid sequence set forth in SEQ ID NO:613, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613. Amino acid sequences of polypeptides having greater than 45% sequence identity to the polypeptide set forth in SEQ ID NO:613 are provided in FIG. 19 and in the Sequence Listing. Examples of such polypeptides include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

In some cases, a low nitrogen tolerance-modulating polypeptide has an amino acid sequence with sequence similarity to the amino acid sequence set forth in SEQ ID NO:646, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646. Amino acid sequences of polypeptides having greater than 45% sequence identity to the polypeptide set forth in SEQ ID NO:646 are provided in FIG. 20 and in the Sequence Listing. Examples of such polypeptides include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

In some cases, a low nitrogen tolerance-modulating polypeptide has an amino acid sequence with sequence similarity to the amino acid sequence set forth in SEQ ID NO:687, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687. Amino acid sequences of polypeptides having greater than 45% sequence identity to the polypeptide set forth in SEQ ID NO:687 are provided in FIG. 21 and in the Sequence Listing. Examples of such polypeptides include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

In some cases, a low nitrogen tolerance-modulating polypeptide has an amino acid sequence with sequence similarity to the amino acid sequence set forth in SEQ ID NO:730, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730. Amino acid sequences of polypeptides having greater than 45% sequence identity to the polypeptide set forth in SEQ ID NO:730 are provided in FIG. 22 and in the Sequence Listing. Examples of such polypeptides include SEQ ID NO:732, SEQ ID NO:733, SEQ ID NO:735, SEQ ID NO:737, SEQ ID NO:738, and SEQ ID NO:742.

In some cases, a low nitrogen tolerance-modulating polypeptide has an amino acid sequence with sequence similarity to the amino acid sequence set forth in SEQ ID NO:746, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746. Amino acid sequences of polypeptides having greater than 45% sequence identity to the polypeptide set forth in SEQ ID NO:746 are provided in FIG. 23 and in the Sequence Listing. Examples of such polypeptides include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

In some cases, a low nitrogen tolerance-modulating polypeptide has an amino acid sequence with sequence similarity to the amino acid sequence set forth in SEQ ID NO:769, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769. Amino acid sequences of polypeptides having greater than 45% sequence identity to the polypeptide set forth in SEQ ID NO:769 are provided in FIG. 24 and in the Sequence Listing. Examples of such polypeptides include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

In some cases, a low nitrogen tolerance-modulating polypeptide has an amino acid sequence with sequence similarity to the amino acid sequence set forth in SEQ ID NO:792, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792. Amino acid sequences of polypeptides having greater than 20% sequence identity to the polypeptide set forth in SEQ ID NO:792 are provided in FIG. 25 and in the Sequence Listing. Examples of such polypeptides include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

In some cases, a low nitrogen tolerance-modulating polypeptide has an amino acid sequence with sequence similarity to the amino acid sequence set forth in SEQ ID NO:824, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824. Amino acid sequences of polypeptides having greater than 45% sequence identity to the polypeptide set forth in SEQ ID NO:824 are provided in FIG. 26 and in the Sequence Listing. Such polypeptides include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

In some cases, a low nitrogen tolerance-modulating polypeptide has an amino acid sequence with sequence similarity to the amino acid sequence set forth in SEQ ID NO:828, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828. Amino acid sequences of polypeptides having greater than 20% sequence identity to the polypeptide set forth in SEQ ID NO:828 are provided in FIG. 27 and in the Sequence Listing. Examples of such polypeptides include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

In some cases, a low nitrogen tolerance-modulating polypeptide has an amino acid sequence with sequence similarity to the amino acid sequence set forth in SEQ ID NO:855, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855. Amino acid sequences of polypeptides having greater than 20% sequence identity to the polypeptide set forth in SEQ ID NO:855 are provided in FIG. 28 and in the Sequence Listing. Examples of such polypeptides include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

In some cases, a low nitrogen tolerance-modulating polypeptide has an amino acid sequence with sequence similarity to the amino acid sequence set forth in SEQ ID NO:891, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891. Amino acid sequences of polypeptides having greater than 20% sequence identity to the polypeptide set forth in SEQ ID NO:891 are provided in FIG. 29 and in the Sequence Listing. Examples of such polypeptides include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

In some cases, a low nitrogen tolerance-modulating polypeptide has an amino acid sequence with sequence similarity to the amino acid sequence set forth in SEQ ID NO:917, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917. Amino acid sequences of polypeptides having greater than 20% sequence identity to the polypeptide set forth in SEQ ID NO:917 are provided in FIG. 30 and in the Sequence Listing. Examples of such polypeptides include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

In some cases, a low nitrogen tolerance-modulating polypeptide has an amino acid sequence with sequence similarity to the amino acid sequence set forth in SEQ ID NO:944, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944. Amino acid sequences of polypeptides having greater than 20% sequence identity to the polypeptide set forth in SEQ ID NO:944 are provided in FIG. 31 and in the Sequence Listing. Examples of such polypeptides include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

In some cases, a low nitrogen tolerance-modulating polypeptide has an amino acid sequence with sequence similarity to the amino acid sequence set forth in SEQ ID NO:976, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976. Amino acid sequences of polypeptides having greater than 45% sequence identity to the polypeptide set forth in SEQ ID NO:976 are provided in FIG. 32 and in the Sequence Listing. Examples of such polypeptides include SEQ ID NO:978 and SEQ ID NO:980.

In some cases, a low nitrogen tolerance-modulating polypeptide has an amino acid sequence with sequence similarity to the amino acid sequence set forth in SEQ ID NO:982, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982. Amino acid sequences of polypeptides having greater than 20% sequence identity to the polypeptide set forth in SEQ ID NO:982 are provided in FIG. 33 and in the Sequence Listing. Examples of such polypeptides include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

In some cases, a low nitrogen tolerance-modulating polypeptide has an amino acid sequence with sequence similarity to the amino acid sequence set forth in SEQ ID NO:1054, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054 Amino acid sequences of polypeptides having greater than 20% sequence identity to the polypeptide set forth in SEQ ID NO:1054 are provided in FIG. 34 and in the Sequence Listing. Examples of such polypeptides include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

In some cases, a low nitrogen tolerance-modulating polypeptide has an amino acid sequence with sequence similarity to the amino acid sequence set forth in SEQ ID NO:1099, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099 Amino acid sequences of polypeptides having greater than 20% sequence identity to the polypeptide set forth in SEQ ID NO:1099 are provided in FIG. 35 and in the Sequence Listing. Examples of such polypeptides include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

In some cases, a low nitrogen tolerance-modulating polypeptide has an amino acid sequence with sequence similarity to the amino acid sequence set forth in SEQ ID NO:1112, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112 Amino acid sequences of polypeptides having greater than 20% sequence identity to the polypeptide set forth in SEQ ID NO:1112 are provided in FIG. 36 and in the Sequence Listing. Examples of such polypeptides include SEQ ID NO:1113 and SEQ ID NO:1114.

In some cases, a low nitrogen tolerance-modulating polypeptide has an amino acid sequence with sequence similarity to the amino acid sequence set forth in SEQ ID NO:1116, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116 Amino acid sequences of polypeptides having greater than 20% sequence identity to the polypeptide set forth in SEQ ID NO:1116 are provided in FIG. 37 and in the Sequence Listing. Examples of such polypeptides include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

In some cases, a low nitrogen tolerance-modulating polypeptide has an amino acid sequence with sequence similarity to the amino acid sequence set forth in SEQ ID NO:1159, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159 Amino acid sequences of polypeptides having greater than 20% sequence identity to the polypeptide set forth in SEQ ID NO:1159 are provided in FIG. 38 and in the Sequence Listing. Examples of such polypeptides include SEQ ID NO:1161, SEQ ID NO:1162, SEQ ID NO:1163, and SEQ ID NO:1164.

In some cases, a low nitrogen tolerance-modulating polypeptide has an amino acid sequence with sequence similarity to the amino acid sequence set forth in SEQ ID NO:1166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166 Amino acid sequences of polypeptides having greater than 20% sequence identity to the polypeptide set forth in SEQ ID NO:1166 are provided in FIG. 39 and in the Sequence Listing. Examples of such polypeptides include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

In some cases, a low nitrogen tolerance-modulating polypeptide has an amino acid sequence with sequence similarity to the amino acid sequence set forth in SEQ ID NO:1185, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185 Amino acid sequences of polypeptides having greater than 20% sequence identity to the polypeptide set forth in SEQ ID NO:1185 are provided in FIG. 40 and in the Sequence Listing. Examples of such polypeptides include SEQ ID NO:1187, SEQ ID NO:1189, SEQ ID NO:1190, SEQ ID NO:1191, and SEQ ID NO:1192.

In some cases, a low nitrogen tolerance-modulating polypeptide has an amino acid sequence with sequence similarity to the amino acid sequence set forth in SEQ ID NO:1194, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194 Amino acid sequences of polypeptides having greater than 20% sequence identity to the polypeptide set forth in SEQ ID NO:1194 are provided in FIG. 41 and in the Sequence Listing. Examples of such polypeptides include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

In some cases, a low nitrogen tolerance-modulating polypeptide has an amino acid sequence with sequence similarity to the amino acid sequence set forth in SEQ ID NO:1210, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210 Amino acid sequences of polypeptides having greater than 20% sequence identity to the polypeptide set forth in SEQ ID NO:1210 are provided in FIG. 42 and in the Sequence Listing. Examples of such polypeptides include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

In some cases, a low nitrogen tolerance-modulating polypeptide has an amino acid sequence with sequence similarity to the amino acid sequence set forth in SEQ ID NO:1274, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274 Amino acid sequences of polypeptides having greater than 20% sequence identity to the polypeptide set forth in SEQ ID NO:1274 are provided in FIG. 43 and in the Sequence Listing. Examples of such polypeptides include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

In some cases, a low nitrogen tolerance-modulating polypeptide has an amino acid sequence with sequence similarity to the amino acid sequence set forth in SEQ ID NO:1302, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302 Amino acid sequences of polypeptides having greater than 20% sequence identity to the polypeptide set forth in SEQ ID NO:1302 are provided in FIG. 44 and in the Sequence Listing. Examples of such polypeptides include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

In some cases, a low nitrogen tolerance-modulating polypeptide has an amino acid sequence with sequence similarity to the amino acid sequence set forth in SEQ ID NO:1342, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342 Amino acid sequences of polypeptides having greater than 20% sequence identity to the polypeptide set forth in SEQ ID NO:1342 are provided in FIG. 45 and in the Sequence Listing. Examples of such polypeptides include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

In some cases, a low nitrogen tolerance-modulating polypeptide has an amino acid sequence with sequence similarity to the amino acid sequence set forth in SEQ ID NO:1385, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385 Amino acid sequences of polypeptides having greater than 20% sequence identity to the polypeptide set forth in SEQ ID NO:1385 are provided in FIG. 46 and in the Sequence Listing. Examples of such polypeptides include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

In some cases, a low nitrogen tolerance-modulating polypeptide has an amino acid sequence with sequence similarity to the amino acid sequence set forth in SEQ ID NO:1409, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409 Amino acid sequences of polypeptides having greater than 20% sequence identity to the polypeptide set forth in SEQ ID NO:1409 are provided in FIG. 47 and in the Sequence Listing. Examples of such polypeptides include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426.

In some cases, a low nitrogen tolerance-modulating polypeptide has an amino acid sequence with sequence similarity to the amino acid sequence set forth in SEQ ID NO:1428, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428 Amino acid sequences of polypeptides having greater than 20% sequence identity to the polypeptide set forth in SEQ ID NO:1428 are provided in FIG. 48 and in the Sequence Listing. Examples of such polypeptides include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

In some cases, a low nitrogen tolerance-modulating polypeptide has an amino acid sequence with sequence similarity to the amino acid sequence set forth in SEQ ID NO:1463, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463 Amino acid sequences of polypeptides having greater than 20% sequence identity to the polypeptide set forth in SEQ ID NO:1463 are provided in FIG. 49 and in the Sequence Listing. Examples of such polypeptides include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

In some cases, a low nitrogen tolerance-modulating polypeptide has an amino acid sequence with sequence similarity to the amino acid sequence set forth in SEQ ID NO:1491, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491 Amino acid sequences of polypeptides having greater than 20% sequence identity to the polypeptide set forth in SEQ ID NO:1491 are provided in FIG. 50 and in the Sequence Listing. Examples of such polypeptides include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

In some cases, a low nitrogen tolerance-modulating polypeptide has an amino acid sequence with sequence similarity to the amino acid sequence set forth in SEQ ID NO:1510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510 Amino acid sequences of polypeptides having greater than 20% sequence identity to the polypeptide set forth in SEQ ID NO:1510 are provided in FIG. 51 and in the Sequence Listing. Examples of such polypeptides include SEQ ID NO:1512, SEQ ID NO:1514, SEQ ID NO:1516, SEQ ID NO:1518, SEQ ID NO:1520, SEQ ID NO:1522, and SEQ ID NO:1523.

In some cases, a low nitrogen tolerance-modulating polypeptide has an amino acid sequence with sequence similarity to the amino acid sequence set forth in SEQ ID NO:1525, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525 Amino acid sequences of polypeptides having greater than 20% sequence identity to the polypeptide set forth in SEQ ID NO:1525 are provided in FIG. 52 and in the Sequence Listing. Examples of such polypeptides include SEQ ID NO:1527, SEQ ID NO:1529, SEQ ID NO:1530, SEQ ID NO:1532, SEQ ID NO:1534, and SEQ ID NO:1535.

In some cases, a low nitrogen tolerance-modulating polypeptide has an amino acid sequence with sequence similarity to the amino acid sequence set forth in SEQ ID NO:1537, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537 Amino acid sequences of polypeptides having greater than 20% sequence identity to the polypeptide set forth in SEQ ID NO:1537 are provided in FIG. 53 and in the Sequence Listing. Examples of such polypeptides include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

In some cases, a low nitrogen tolerance-modulating polypeptide has an amino acid sequence with sequence similarity to the amino acid sequence set forth in SEQ ID NO:1554, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554 Amino acid sequences of polypeptides having greater than 20% sequence identity to the polypeptide set forth in SEQ ID NO:1554 are provided in FIG. 54 and in the Sequence Listing. Examples of such polypeptides include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

In some cases, a low nitrogen tolerance-modulating polypeptide has an amino acid sequence with sequence similarity to the amino acid sequence set forth in SEQ ID NO:1577, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577 Amino acid sequences of polypeptides having greater than 20% sequence identity to the polypeptide set forth in SEQ ID NO:1577 are provided in FIG. 55 and in the Sequence Listing. Examples of such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, SEQ ID NO:1653.

In some cases, a low nitrogen tolerance-modulating polypeptide has an amino acid sequence with sequence similarity to the amino acid sequence set forth in SEQ ID NO:1437, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437 Amino acid sequences of polypeptides having greater than 20% sequence identity to the polypeptide set forth in SEQ ID NO:1437 are provided in FIG. 56 and in the Sequence Listing. Examples of such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1461.

In some cases, a low nitrogen tolerance-modulating polypeptide has an amino acid sequence with sequence similarity to the amino acid sequence set forth in SEQ ID NO:97, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97 Amino acid sequences of polypeptides having greater than 20% sequence identity to the polypeptide set forth in SEQ ID NO:1437 are provided in FIG. 57 and in the Sequence Listing. Examples of such polypeptides include SEQ ID NO:2010, SEQ ID NO:2011, SEQ ID NO:2013, SEQ ID NO:2015, and SEQ ID NO:2017

E. Other Sequences

It should be appreciated that a low nitrogen tolerance-modulating polypeptide can include additional amino acids that are not involved in low nitrogen tolerance-modulation, and thus such a polypeptide can be longer than would otherwise be the case. For example, a low nitrogen tolerance-modulating polypeptide can include a purification tag, a chloroplast transit peptide, a mitochondrial transit peptide, an amyloplast peptide, or a leader sequence added to the amino or carboxy terminus. In some embodiments, a low nitrogen tolerance-modulating polypeptide includes an amino acid sequence that functions as a reporter, e.g., a green fluorescent protein or yellow fluorescent protein.

III. Nucleic Acids

Nucleic acids described herein include nucleic acids that are effective to modulate low-nitrogen tolerance levels when transcribed in a plant or plant cell. Such nucleic acids include, without limitation, those that encode a low nitrogen tolerance-modulating polypeptide and those that can be used to inhibit expression of low nitrogen tolerance-modulating polypeptide via a nucleic acid based method.

A. Nucleic Acids Encoding Low Nitrogen Tolerance-Modulating Polypeptides

Nucleic acids encoding low nitrogen tolerance-modulating polypeptides are described herein. Examples of such nucleic acids include SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576.

A low nitrogen tolerance-modulating nucleic acid can comprise the nucleotide sequence set forth in SEQ ID NO:1. Alternatively, a low nitrogen tolerance-modulating nucleic acid can be a variant of the nucleic acid having the nucleotide sequence set forth in SEQ ID NO:2. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:2.

A low nitrogen tolerance-modulating nucleic acid can comprise the nucleotide sequence set forth in SEQ ID NO: 48. Alternatively, a low nitrogen tolerance-modulating nucleic acid can be a variant of the nucleic acid having the nucleotide sequence set forth in SEQ ID NO: 48. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 48.

A low nitrogen tolerance-modulating nucleic acid can comprise the nucleotide sequence set forth in SEQ ID NO:76. Alternatively, a low nitrogen tolerance-modulating nucleic acid can be a variant of the nucleic acid having the nucleotide sequence set forth in SEQ ID NO:76. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:76.

A low nitrogen tolerance-modulating nucleic acid can comprise the nucleotide sequence set forth in SEQ ID NO:96. Alternatively, a low nitrogen tolerance-modulating nucleic acid can be a variant of the nucleic acid having the nucleotide sequence set forth in SEQ ID NO:96. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:96.

A low nitrogen tolerance-modulating nucleic acid can comprise the nucleotide sequence set forth in SEQ ID NO:99. Alternatively, a low nitrogen tolerance-modulating nucleic acid can be a variant of the nucleic acid having the nucleotide sequence set forth in SEQ ID NO:99. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:99.

A low nitrogen tolerance-modulating nucleic acid can comprise the nucleotide sequence set forth in SEQ ID NO:151. Alternatively, a low nitrogen tolerance-modulating nucleic acid can be a variant of the nucleic acid having the nucleotide sequence set forth in SEQ ID NO:151. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:151.

A low nitrogen tolerance-modulating nucleic acid can comprise the nucleotide sequence set forth in SEQ ID NO:165. Alternatively, a low nitrogen tolerance-modulating nucleic acid can be a variant of the nucleic acid having the nucleotide sequence set forth in SEQ ID NO:165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:165.

A low nitrogen tolerance-modulating nucleic acid can comprise the nucleotide sequence set forth in SEQ ID NO:175. Alternatively, a low nitrogen tolerance-modulating nucleic acid can be a variant of the nucleic acid having the nucleotide sequence set forth in SEQ ID NO:175. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:175.

A low nitrogen tolerance-modulating nucleic acid can comprise the nucleotide sequence set forth in SEQ ID NO:185. Alternatively, a low nitrogen tolerance-modulating nucleic acid can be a variant of the nucleic acid having the nucleotide sequence set forth in SEQ ID NO:185. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:185.

A low nitrogen tolerance-modulating nucleic acid can comprise the nucleotide sequence set forth in SEQ ID NO:207. Alternatively, a low nitrogen tolerance-modulating nucleic acid can be a variant of the nucleic acid having the nucleotide sequence set forth in SEQ ID NO:207. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:207.

A low nitrogen tolerance-modulating nucleic acid can comprise the nucleotide sequence set forth in SEQ ID NO:217. Alternatively, a low nitrogen tolerance-modulating nucleic acid can be a variant of the nucleic acid having the nucleotide sequence set forth in SEQ ID NO:217. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:217.

A low nitrogen tolerance-modulating nucleic acid can comprise the nucleotide sequence set forth in SEQ ID NO:233. Alternatively, a low nitrogen tolerance-modulating nucleic acid can be a variant of the nucleic acid having the nucleotide sequence set forth in SEQ ID NO:233. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:233.

A low nitrogen tolerance-modulating nucleic acid can comprise the nucleotide sequence set forth in SEQ ID NO:245. Alternatively, a low nitrogen tolerance-modulating nucleic acid can be a variant of the nucleic acid having the nucleotide sequence set forth in SEQ ID NO:245. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:245.

A low nitrogen tolerance-modulating nucleic acid can comprise the nucleotide sequence set forth in SEQ ID NO:299. Alternatively, a low nitrogen tolerance-modulating nucleic acid can be a variant of the nucleic acid having the nucleotide sequence set forth in SEQ ID NO:299. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:299.

A low nitrogen tolerance-modulating nucleic acid can comprise the nucleotide sequence set forth in SEQ ID NO:331. Alternatively, a low nitrogen tolerance-modulating nucleic acid can be a variant of the nucleic acid having the nucleotide sequence set forth in SEQ ID NO:331. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:331.

A low nitrogen tolerance-modulating nucleic acid can comprise the nucleotide sequence set forth in SEQ ID NO:367. Alternatively, a low nitrogen tolerance-modulating nucleic acid can be a variant of the nucleic acid having the nucleotide sequence set forth in SEQ ID NO:367. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:367.

A low nitrogen tolerance-modulating nucleic acid can comprise the nucleotide sequence set forth in SEQ ID NO:509. Alternatively, a low nitrogen tolerance-modulating nucleic acid can be a variant of the nucleic acid having the nucleotide sequence set forth in SEQ ID NO:509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:509.

A low nitrogen tolerance-modulating nucleic acid can comprise the nucleotide sequence set forth in SEQ ID NO:532. Alternatively, a low nitrogen tolerance-modulating nucleic acid can be a variant of the nucleic acid having the nucleotide sequence set forth in SEQ ID NO:532. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:532.

A low nitrogen tolerance-modulating nucleic acid can comprise the nucleotide sequence set forth in SEQ ID NO:555. Alternatively, a low nitrogen tolerance-modulating nucleic acid can be a variant of the nucleic acid having the nucleotide sequence set forth in SEQ ID NO:555. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:555.

A low nitrogen tolerance-modulating nucleic acid can comprise the nucleotide sequence set forth in SEQ ID NO:557. Alternatively, a low nitrogen tolerance-modulating nucleic acid can be a variant of the nucleic acid having the nucleotide sequence set forth in SEQ ID NO:557. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:557.

A low nitrogen tolerance-modulating nucleic acid can comprise the nucleotide sequence set forth in SEQ ID NO:592. Alternatively, a low nitrogen tolerance-modulating nucleic acid can be a variant of the nucleic acid having the nucleotide sequence set forth in SEQ ID NO:592. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:592.

A low nitrogen tolerance-modulating nucleic acid can comprise the nucleotide sequence set forth in SEQ ID NO:612. Alternatively, a low nitrogen tolerance-modulating nucleic acid can be a variant of the nucleic acid having the nucleotide sequence set forth in SEQ ID NO:612. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:612.

A low nitrogen tolerance-modulating nucleic acid can comprise the nucleotide sequence set forth in SEQ ID NO:645. Alternatively, a low nitrogen tolerance-modulating nucleic acid can be a variant of the nucleic acid having the nucleotide sequence set forth in SEQ ID NO:645. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:645.

A low nitrogen tolerance-modulating nucleic acid can comprise the nucleotide sequence set forth in SEQ ID NO:686. Alternatively, a low nitrogen tolerance-modulating nucleic acid can be a variant of the nucleic acid having the nucleotide sequence set forth in SEQ ID NO:686. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:686.

A low nitrogen tolerance-modulating nucleic acid can comprise the nucleotide sequence set forth in SEQ ID NO:729. Alternatively, a low nitrogen tolerance-modulating nucleic acid can be a variant of the nucleic acid having the nucleotide sequence set forth in SEQ ID NO:729. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:729.

A low nitrogen tolerance-modulating nucleic acid can comprise the nucleotide sequence set forth in SEQ ID NO:745. Alternatively, a low nitrogen tolerance-modulating nucleic acid can be a variant of the nucleic acid having the nucleotide sequence set forth in SEQ ID NO:745. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:745.

A low nitrogen tolerance-modulating nucleic acid can comprise the nucleotide sequence set forth in SEQ ID NO:768. Alternatively, a low nitrogen tolerance-modulating nucleic acid can be a variant of the nucleic acid having the nucleotide sequence set forth in SEQ ID NO:768. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:768.

A low nitrogen tolerance-modulating nucleic acid can comprise the nucleotide sequence set forth in SEQ ID NO:791. Alternatively, a low nitrogen tolerance-modulating nucleic acid can be a variant of the nucleic acid having the nucleotide sequence set forth in SEQ ID NO:791. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:791.

A low nitrogen tolerance-modulating nucleic acid can comprise the nucleotide sequence set forth in SEQ ID NO:823. Alternatively, a low nitrogen tolerance-modulating nucleic acid can be a variant of the nucleic acid having the nucleotide sequence set forth in SEQ ID NO:823. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:823.

A low nitrogen tolerance-modulating nucleic acid can comprise the nucleotide sequence set forth in SEQ ID NO:827. Alternatively, a low nitrogen tolerance-modulating nucleic acid can be a variant of the nucleic acid having the nucleotide sequence set forth in SEQ ID NO:827. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:827.

A low nitrogen tolerance-modulating nucleic acid can comprise the nucleotide sequence set forth in SEQ ID NO:852. Alternatively, a low nitrogen tolerance-modulating nucleic acid can be a variant of the nucleic acid having the nucleotide sequence set forth in SEQ ID NO:852. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:852.

A low nitrogen tolerance-modulating nucleic acid can comprise the nucleotide sequence set forth in SEQ ID NO:854. Alternatively, a low nitrogen tolerance-modulating nucleic acid can be a variant of the nucleic acid having the nucleotide sequence set forth in SEQ ID NO:854. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:854.

A low nitrogen tolerance-modulating nucleic acid can comprise the nucleotide sequence set forth in SEQ ID NO:890. Alternatively, a low nitrogen tolerance-modulating nucleic acid can be a variant of the nucleic acid having the nucleotide sequence set forth in SEQ ID NO:890. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:890.

A low nitrogen tolerance-modulating nucleic acid can comprise the nucleotide sequence set forth in SEQ ID NO:916. Alternatively, a low nitrogen tolerance-modulating nucleic acid can be a variant of the nucleic acid having the nucleotide sequence set forth in SEQ ID NO:916. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:916.

A low nitrogen tolerance-modulating nucleic acid can comprise the nucleotide sequence set forth in SEQ ID NO:943. Alternatively, a low nitrogen tolerance-modulating nucleic acid can be a variant of the nucleic acid having the nucleotide sequence set forth in SEQ ID NO:943. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:943.

A low nitrogen tolerance-modulating nucleic acid can comprise the nucleotide sequence set forth in SEQ ID NO:975. Alternatively, a low nitrogen tolerance-modulating nucleic acid can be a variant of the nucleic acid having the nucleotide sequence set forth in SEQ ID NO:975. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:975.

A low nitrogen tolerance-modulating nucleic acid can comprise the nucleotide sequence set forth in SEQ ID NO:981. Alternatively, a low nitrogen tolerance-modulating nucleic acid can be a variant of the nucleic acid having the nucleotide sequence set forth in SEQ ID NO:981. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:981.

A low nitrogen tolerance-modulating nucleic acid can comprise the nucleotide sequence set forth in SEQ ID NO: 1034. Alternatively, a low nitrogen tolerance-modulating nucleic acid can be a variant of the nucleic acid having the nucleotide sequence set forth in SEQ ID NO: 1034. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1034.

A low nitrogen tolerance-modulating nucleic acid can comprise the nucleotide sequence set forth in SEQ ID NO:1053. Alternatively, a low nitrogen tolerance-modulating nucleic acid can be a variant of the nucleic acid having the nucleotide sequence set forth in SEQ ID NO:1053. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1053.

A low nitrogen tolerance-modulating nucleic acid can comprise the nucleotide sequence set forth in SEQ ID NO:1098. Alternatively, a low nitrogen tolerance-modulating nucleic acid can be a variant of the nucleic acid having the nucleotide sequence set forth in SEQ ID NO:1098. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1098.

A low nitrogen tolerance-modulating nucleic acid can comprise the nucleotide sequence set forth in SEQ ID NO:1111. Alternatively, a low nitrogen tolerance-modulating nucleic acid can be a variant of the nucleic acid having the nucleotide sequence set forth in SEQ ID NO:1111. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1111.

A low nitrogen tolerance-modulating nucleic acid can comprise the nucleotide sequence set forth in SEQ ID NO:1115. Alternatively, a low nitrogen tolerance-modulating nucleic acid can be a variant of the nucleic acid having the nucleotide sequence set forth in SEQ ID NO:1115. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1115.

A low nitrogen tolerance-modulating nucleic acid can comprise the nucleotide sequence set forth in SEQ ID NO:1156. Alternatively, a low nitrogen tolerance-modulating nucleic acid can be a variant of the nucleic acid having the nucleotide sequence set forth in SEQ ID NO:1156. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1156.

A low nitrogen tolerance-modulating nucleic acid can comprise the nucleotide sequence set forth in SEQ ID NO:1158. Alternatively, a low nitrogen tolerance-modulating nucleic acid can be a variant of the nucleic acid having the nucleotide sequence set forth in SEQ ID NO:1158. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1158.

A low nitrogen tolerance-modulating nucleic acid can comprise the nucleotide sequence set forth in SEQ ID NO:1165. Alternatively, a low nitrogen tolerance-modulating nucleic acid can be a variant of the nucleic acid having the nucleotide sequence set forth in SEQ ID NO:1165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1165.

A low nitrogen tolerance-modulating nucleic acid can comprise the nucleotide sequence set forth in SEQ ID NO:1184. Alternatively, a low nitrogen tolerance-modulating nucleic acid can be a variant of the nucleic acid having the nucleotide sequence set forth in SEQ ID NO:1184. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1184.

A low nitrogen tolerance-modulating nucleic acid can comprise the nucleotide sequence set forth in SEQ ID NO:1193. Alternatively, a low nitrogen tolerance-modulating nucleic acid can be a variant of the nucleic acid having the nucleotide sequence set forth in SEQ ID NO:1193. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1193.

A low nitrogen tolerance-modulating nucleic acid can comprise the nucleotide sequence set forth in SEQ ID NO: 1209. Alternatively, a low nitrogen tolerance-modulating nucleic acid can be a variant of the nucleic acid having the nucleotide sequence set forth in SEQ ID NO: 1209. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1209.

A low nitrogen tolerance-modulating nucleic acid can comprise the nucleotide sequence set forth in SEQ ID NO:1273. Alternatively, a low nitrogen tolerance-modulating nucleic acid can be a variant of the nucleic acid having the nucleotide sequence set forth in SEQ ID NO:1273. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1273.

A low nitrogen tolerance-modulating nucleic acid can comprise the nucleotide sequence set forth in SEQ ID NO:1301. Alternatively, a low nitrogen tolerance-modulating nucleic acid can be a variant of the nucleic acid having the nucleotide sequence set forth in SEQ ID NO:1301. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1301.

A low nitrogen tolerance-modulating nucleic acid can comprise the nucleotide sequence set forth in SEQ ID NO:1341. Alternatively, a low nitrogen tolerance-modulating nucleic acid can be a variant of the nucleic acid having the nucleotide sequence set forth in SEQ ID NO:1341. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1341.

A low nitrogen tolerance-modulating nucleic acid can comprise the nucleotide sequence set forth in SEQ ID NO:1384. Alternatively, a low nitrogen tolerance-modulating nucleic acid can be a variant of the nucleic acid having the nucleotide sequence set forth in SEQ ID NO:1384. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1384.

A low nitrogen tolerance-modulating nucleic acid can comprise the nucleotide sequence set forth in SEQ ID NO:1408. Alternatively, a low nitrogen tolerance-modulating nucleic acid can be a variant of the nucleic acid having the nucleotide sequence set forth in SEQ ID NO:1408. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1408.

A low nitrogen tolerance-modulating nucleic acid can comprise the nucleotide sequence set forth in SEQ ID NO:1427. Alternatively, a low nitrogen tolerance-modulating nucleic acid can be a variant of the nucleic acid having the nucleotide sequence set forth in SEQ ID NO:1427. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1427.

A low nitrogen tolerance-modulating nucleic acid can comprise the nucleotide sequence set forth in SEQ ID NO:1462. Alternatively, a low nitrogen tolerance-modulating nucleic acid can be a variant of the nucleic acid having the nucleotide sequence set forth in SEQ ID NO:1462. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1462.

A low nitrogen tolerance-modulating nucleic acid can comprise the nucleotide sequence set forth in SEQ ID NO:1490. Alternatively, a low nitrogen tolerance-modulating nucleic acid can be a variant of the nucleic acid having the nucleotide sequence set forth in SEQ ID NO:1490. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1490.

A low nitrogen tolerance-modulating nucleic acid can comprise the nucleotide sequence set forth in SEQ ID NO:1509. Alternatively, a low nitrogen tolerance-modulating nucleic acid can be a variant of the nucleic acid having the nucleotide sequence set forth in SEQ ID NO:1509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1509.

A low nitrogen tolerance-modulating nucleic acid can comprise the nucleotide sequence set forth in SEQ ID NO:1524. Alternatively, a low nitrogen tolerance-modulating nucleic acid can be a variant of the nucleic acid having the nucleotide sequence set forth in SEQ ID NO:1524. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1524.

A low nitrogen tolerance-modulating nucleic acid can comprise the nucleotide sequence set forth in SEQ ID NO:1536. Alternatively, a low nitrogen tolerance-modulating nucleic acid can be a variant of the nucleic acid having the nucleotide sequence set forth in SEQ ID NO:1536. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1536.

A low nitrogen tolerance-modulating nucleic acid can comprise the nucleotide sequence set forth in SEQ ID NO:1553. Alternatively, a low nitrogen tolerance-modulating nucleic acid can be a variant of the nucleic acid having the nucleotide sequence set forth in SEQ ID NO:1553. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1553.

A low nitrogen tolerance-modulating nucleic acid can comprise the nucleotide sequence set forth in SEQ ID NO:1576. Alternatively, a low nitrogen tolerance-modulating nucleic acid can be a variant of the nucleic acid having the nucleotide sequence set forth in SEQ ID NO:1576. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1576.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Low Nitrogen Tolerance-Modulating Polypeptide A nucleic acid encoding one of the low nitrogen tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular low nitrogen tolerance-modulating polypeptide; i.e., for many amino acids, there is more than one nucleotide triplet that serves as the codon for the amino acid. Thus, codons in the coding sequence for a given low nitrogen tolerance-modulating polypeptide can be modified such that optimal expression in a particular plant species is obtained, using appropriate codon bias tables for that species.

In some cases, expression of a low nitrogen tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Low Nitrogen Tolerance-Modulating Polypeptide

Polynucleotides and recombinant constructs described herein can be used to inhibit expression of a low nitrogen tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding low nitrogen tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P.C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a low nitrogen tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the low nitrogen tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a low nitrogen tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the low nitrogen tolerance-modulating polypeptide. In other embodiments, one strand of the stem portion of a double stranded RNA comprises a sequence that is similar or identical to the sequence of an intron, or a fragment thereof, in the pre-mRNA encoding a low nitrogen tolerance-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a low nitrogen tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a low nitrogen tolerance-modulating polypeptide, or a fragment of such sequences. In some embodiments, the sense or antisense sequence is identical or complementary to a sequence of the regulatory region that drives transcription of the gene encoding a low nitrogen tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a low nitrogen tolerance-modulating polypeptide described herein. The sense sequence complementary to the antisense sequence can be a sequence present within the mRNA of the low nitrogen tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.*, 7:187-195; Hyrup et al. (1996) *Bioorgan. Med. Chem.*, 4:5-23. In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate low-nitrogen tolerance levels. A recombinant nucleic acid construct can comprise a nucleic acid encoding a low nitrogen tolerance-modulating polypeptide as described herein, operably linked to a regulatory region suitable for expressing the low nitrogen tolerance-modulating polypeptide in the plant or cell. Thus, a nucleic acid can comprise a coding sequence that encodes any of the low nitrogen tolerance-modulating polypeptides as set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Examples of nucleic acids encoding low nitrogen tolerance-modulating polypeptides are set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576. The low nitrogen tolerance-modulating polypeptide encoded by a recombinant nucleic acid can be a native low nitrogen tolerance-modulating polypeptide, or can be heterologous to the cell. In some cases, the recombinant construct contains a nucleic acid that inhibits expression of a low nitrogen tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, 3-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al. (1989) *Plant Cell*, 1:855-866; Bustos et al. (1989) *Plant Cell*, 1:839-854; Green et al. (1988) *EMBO J.*, 7:4035-4044;

Meier et al. (1991) *Plant Cell*, 3:309-316; and Zhang et al. (1996) *Plant Physiology*, 110:1069-1079.

Examples of various classes of regulatory regions are described below. Some of the regulatory regions indicated below as well as additional regulatory regions are described in more detail in U.S. Patent Application Ser. Nos. 60/505, 689; 60/518,075; 60/544,771; 60/558,869; 60/583,691; 60/619,181; 60/637,140; 60/757,544; 60/776,307; 10/957, 569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/ 011105; PCT/US05/23639; PCT/US05/034308; PCT/US05/ 034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/ US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/ 62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA*, 86:7890-7894), root cell specific promoters reported by Conkling et al. (1990) *Plant Physiol.*, 93:1203-1211, and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al. (1989) *Plant Cell*, 1(9):839-853), the soybean trypsin inhibitor promoter (Riggs et al. (1989) *Plant Cell*, 1(6):609-621), the ACP promoter (Baerson et al. (1993) *Plant Mol. Biol.*, 22(2):255-267), the stearoyl-ACP desaturase promoter (Slocombe et al. (1994) *Plant Physiol.*, 104(4):167-176), the soybean a' subunit of β-conglycinin promoter (Chen et al. (1986) *Proc. Natl. Acad. Sci. USA*, 83:8560-8564), the oleosin promoter (Hong et al. (1997) *Plant Mol. Biol.*, 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.*, 13:5829-5842), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) Plant, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142:1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp 1) promoter (*Plant Cell* Rep (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.*, 35:773-778), the Cab-1 promoter from wheat (Fejes et al. (1990) *Plant Mol. Biol.*, 15:921-932), the CAB-1 promoter from spinach (Lubberstedt et al. (1994) *Plant Physiol.*, 104:997-1006), the cab1R promoter from rice (Luan et al. (1992) *Plant Cell*, 4:971-981), the pyruvate orthophosphate dikinase (PPDK) promoter from corn (Matsuoka et al. (1993) *Proc. Natl. Acad. Sci. USA*, 90:9586-9590), the tobacco Lhcb1*2 promoter (Cerdan et al. (1997) *Plant Mol. Biol.*, 33:245-255), the *Arabidopsis thaliana* SUC2 sucrose-H+ symporter promoter (Truernit et al. (1995) *Planta*, 196:564-570), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner (1991) *Plant Cell*, 3(10):1051-1061), the *Commelina* yellow mottle virus (CoYMV) promoter (Medberry et al. (1992) *Plant Cell*, 4(2):185-192), and the rice tungro bacilliform virus (RTBV) promoter (Dai et al. (2004) *Proc. Natl. Acad. Sci. USA*, 101(2):687-692).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a low nitrogen tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low nitrogen tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/selection

A population of transgenic plants can be screened and/or selected for those members of the population that have a trait or phenotype conferred by expression of the transgene. For example, a population of progeny of a single transformation event can be screened for those plants having a desired level of expression of a low nitrogen tolerance-modulating polypeptide or nucleic acid. Physical and biochemical methods can be used to identify expression levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of low-nitrogen tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in low nitrogen tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea*.

Suitable species include *Panicum* spp. or hybrid thereof, *Sorghum* spp. or hybrid thereof, sudangrass, *Miscanthus* spp. or hybrid thereof, *Saccharum* spp. or hybrid thereof, Erianthus spp., *Populus* spp., *Andropogon gerardii* (big bluestem), *Pennisetum purpureum* (elephant grass)) or hybrid thereof (e.g., *Pennisetum purpureum* x *Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrid thereof, *Secale cereale* (rye), *Salix* spp. (willow), *Eucalyptus* spp. (*eucalyptus*), Triticosecale (*triticum*—wheat X rye), Tripsicum *dactyloides* (Eastern gammagrass), *Leymus cinereus* (basin wildrye), *Leymus condensatus* (giant wildrye) and bamboo.

In some embodiments, a suitable species can be a wild, weedy, or cultivated *Sorghum* species such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum* x *almum*, *Sorghum* x sudangrass or *Sorghum* x *drummondii*.

Suitable species also include *Helianthus annuus* (sunflower), Carthamus tinctorius (safflower), Jatropha curcas (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), Musa paradisiaca (banana), *Solanum tuberosum* (potato), *Brassica oleracea* (broccoli, cauliflower, Brussels sprouts), *Camellia sinensis* (tea), Fragaria *ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina*, Rauwolfia spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include Rosa spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica*, Carthamus, *Glycine, Gossypium, Helianthus, Jatropha, Parthenium, Populus,* and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (*Sorghum*, sudangrass), *Miscanthus giganteus* (*Miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., *Saccharum* sp. X *Miscanthus* sp., *Panicum virgatum* x *Panicum amarum*,

*Panicum virgatum* x *Panicum amarulum*, and *Pennisetum purpureum* x *Pennisetum typhoidum*).

D. Transgenic Plant Phenotypes

In some embodiments, a plant in which expression of a low nitrogen tolerance-modulating polypeptide is modulated can have increased levels of photosynthetic efficiency in seedlings. For example, a low nitrogen tolerance-modulating polypeptide described herein can be expressed in a transgenic plant, resulting in increased levels of photosynthetic efficiency in growth conditions with low nitrogen sources. The level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic in a corresponding control plant that does not express the transgene.

In some embodiments, a plant in which expression of a low nitrogen tolerance-modulating polypeptide is modulated can have increased or decreased levels of photosynthetic efficiency in one or more green tissues, e.g., leaves, stems, bulbs, flowers, fruits, young seeds. For example, the level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency in one or more green tissues. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic efficiency in a corresponding control plant that does not express the transgene.

Increases in photosynthetic efficiency in low-nitrogen growth conditions in such plants can provide improved plant growth in geographic locales where plant's intake of nitrogenous fertilizers is often insufficient. Decreases in photosynthetic efficiency, and hence less tolerance to low-nitrogen growth conditions in such plants can be useful for removing weeds and such from the environment, by applying to weeds and such. For example, a plant capable of inducing the decrease in photosynthetic efficiency can be prepared to apply for land improvements and such.

Typically, a difference in the level of photosynthetic efficiency in a transgenic plant or cell relative to a control plant or cell is considered statistically significant at p≤0.05 with an appropriate parametric or non-parametric statistic, e.g., Chi-square test, Student's t-test, Mann-Whitney test, or F-test. In some embodiments, a difference in the level of photosynthetic is statistically significant at p<0.01, p<0.005, or p<0.001. A statistically significant difference in, for example, the level of photosynthetic efficiency in a transgenic plant compared to the amount in cells of a control plant indicates that the recombinant nucleic acid present in the transgenic plant results in altered levels of photosynthetic efficiency.

In some embodiments, a plant in which expression of a low nitrogen tolerance-modulating polypeptide is modulated can have increased growth rates in seedlings. For example, a low nitrogen tolerance-modulating polypeptide described herein can be expressed in a transgenic plant, resulting in increased growth rate in growth conditions of limiting nitrogen sources. The growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased growth rates. The growth rate can be decreased by at least 2 percent, e.g., 2, 3, 4, 5, 10, 15, 20, 25, 30, 35, or more than 35 percent, as compared to the growth rate in a corresponding control plant that does not express the transgene. Growth rate can be measured in seedlings, developing, or mature plants and measured for periods of time such as about 1 hour, 3 hours, 6 hours, 12 hours, 1 day, 3 days, 5 days, 10 days, 1 month, 3 months, 6 months, 12 months, or the entire lifespan of a plant.

In some embodiments, a plant in which expression of a low nitrogen tolerance-modulating polypeptide is modulated can have increased or decreased growth rates in one or more vegetative and reproductive tissues, e.g., leaves, stems, flowers, bulbs, fruits, young seeds. For example, the growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased levels of growth rate in one or more vegetative tissues. The growth rate can be decreased by at least 2 percent, e.g., 2, 3, 4, 5, 10, 15, 20, 25, 30, 35, or more than 35 percent, as compared to the growth rate in a corresponding control plant that does not express the transgene.

Increases in growth rate in low-nitrogen conditions in such plants can provide improved plant growth and initial establishment in geographic locales where plant's intake of nitrogenous fertilizers is often insufficient. Decreases in growth rate, and hence less tolerance to low-nitrogen growth conditions in such plants can be useful for engineering slow-growing plants, by applying to ornamentals and such. For example, a plant capable of inducing the decrease in growth rate can be prepared to apply for land improvements and such.

Typically, a difference in the growth rate of a transgenic plant or cell relative to a control plant or cell is considered statistically significant at p≤0.05 with an appropriate parametric or non-parametric statistic, e.g., Chi-square test, Student's t-test, Mann-Whitney test, or F-test. In some embodiments, a difference in the growth rate is statistically significant at p<0.01, p<0.005, or p<0.001. A statistically significant difference in, for example, the growth rate of a transgenic plant compared to the growth rate of a control plant indicates that the recombinant nucleic acid present in the transgenic plant results in altered growth rates.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Plant Breeding

Genetic polymorphisms are discrete allelic sequence differences in a population. Typically, an allele that is present at 1% or greater is considered to be a genetic polymorphism. The discovery that polypeptides disclosed herein can modulate photosynthetic efficiency and/or nitrogen content is useful in plant breeding, because genetic polymorphisms exhibiting a degree of linkage with loci for such polypeptides are more likely to be correlated with variation in a low-nitrogen tolerance trait. For example, genetic polymorphisms linked to the loci for such polypeptides are more likely to be useful in marker-assisted breeding programs to create lines having a desired modulation in the low-nitrogen tolerance trait.

Thus, one aspect of the invention includes methods of identifying whether one or more genetic polymorphisms are associated with variation in a low-nitrogen tolerance trait. Such methods involve determining whether genetic polymorphisms in a given population exhibit linkage with the locus for one of the polypeptides depicted in FIGS. 1-57, SEQ ID NO:556, SEQ ID NO:853, SEQ ID NO:1157 and/or a functional homolog thereof, such as, but not limited to those identified in the Sequence Listing of this application. The correlation is measured between variation in the low-nitrogen tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the low-nitrogen tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al. (1997) *Electrophoresis* 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), The Maize Handbook, c. 1994 by Springer-Verlag New York, Inc.: New York, N.Y., USA; Berlin Germany; Burr et al. (1998) *Genetics* 118: 519; and Gardiner, J. et al. (1993) *Genetics* 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the low-nitrogen tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought or limiting nitrogen sources. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the nitrogenous composition of the plant material. By providing higher yields at an equivalent or even decreased cost of production, the transgenic plants described herein improve profitability for farmers and processors as well as decrease costs to consumers$_{[RCL1]}$.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. EXAMPLES

Example 1—Transgenic *Arabidopsis* plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following is a list of nucleic acids that were isolated from *Arabidopsis thaliana* plants, CeresClone:29661 (SEQ ID NO:1), CeresClone:251343 (SEQ ID NO:48), Ceres-Clone:19586 (SEQ ID NO:76), CeresClone:25136 (SEQ ID NO:96), CeresClone:1820 (SEQ ID NO:99), CeresClone: 13102 (SEQ ID NO:151), CeresClone:15457 (SEQ ID NO:165), Ceres Annot:859276 (SEQ ID NO:175), Ceres-Clone:17883 (SEQ ID NO:185), CeresClone:251590 (SEQ ID NO:207), CeresClone:4898 (SEQ ID NO:217), Ceres-Clone:148977 (SEQ ID NO:233), CeresClone:24255 (SEQ ID NO:245), CeresClone:38432 (SEQ ID NO:299), Ceres Annot:553243 (SEQ ID NO:331), CeresClone:1011900 (SEQ ID NO:367), CeresClone:5232 (SEQ ID NO:509), CeresClone:29302 (SEQ ID NO:532), CeresClone:93971 (SEQ ID NO:555), Ceres Annot:12669619_cDNA (SEQ ID NO:557), CeresClone:21608 (SEQ ID NO:592), Ceres-Clone:2031 (SEQ ID NO:612), CeresClone:94503 (SEQ ID NO:645), CeresClone:21740 (SEQ ID NO:686), Ceres-Clone:5609 (SEQ ID NO:729), CeresClone:3137 (SEQ ID NO:745), CeresClone:32430 (SEQ ID NO:768), Ceres-Clone:101255 (SEQ ID NO:791), Ceres Annot:573161 (SEQ ID NO:854), Ceres Annot:552727 (SEQ ID NO:890), CeresClone:732 (SEQ ID NO:1193), CeresClone:2267 (SEQ ID NO:1209), CeresClone:39358 (SEQ ID NO:1273), CeresClone:115046 (SEQ ID NO:1301), Ceres Annot: 850581 (SEQ ID NO:1427), Ceres Annot:862321 (SEQ ID NO:1462), Ceres Annot:839064 (SEQ ID NO:1478), Ceres Annot:864666 (SEQ ID NO:1490), Ceres Annot:875012 (SEQ ID NO:1509), Ceres Annot:874016 (SEQ ID NO:1524), Ceres Annot:827304 (SEQ ID NO:1536), Ceres Annot:869192 (SEQ ID NO:1553), and Ceres Annot:876419 (SEQ ID NO:1576). The nucleic acid designated Ceres Clone: 968180 (SEQ ID NO:1115) was isolated from the species *Brassica napus*. The nucleic acid designated Ceres Clone: 1017441 (SEQ ID NO:224) was isolated from the species *Triticum* aesticum. The following is a list of nucleic acids that were isolated from *Zea mays* plants, CeresClone: 1387146 (SEQ ID NO:981), CeresClone:1408950 (SEQ ID NO:1098, CeresClone:208453 (SEQ ID NO:1111), Ceres-Clone:208995 (SEQ ID NO:943), CeresClone:225681 (SEQ ID NO:975), CeresClone:239806 (SEQ ID NO:916), Ceres-Clone:244306 (SEQ ID NO:1053), CeresClone:276809 (SEQ ID NO:823), CeresClone:324216 (SEQ ID NO:852), CeresClone:339439 (SEQ ID NO:1341), CeresClone: 424522 (SEQ ID NO:827), CeresClone:896483 (SEQ ID NO:1384), CeresClone:986438 (SEQ ID NO:1156), Ceres-Clone:988083 (SEQ ID NO:1184), CeresClone:995409 (SEQ ID NO:1408), CeresClone:996227 (SEQ ID NO:1158), and CeresClone:996263 (SEQ ID NO:1165).

With the exception of Ceres Clone:29661 (SEQ ID NO:1), each isolated nucleic acid described above was cloned into a Ti plasmid vector, CRS338, containing a phosphinothricin acetyltransferase gene which confers FINALE™ resistance to transformed plants. Constructs were made using CRS338 that contained SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, each operably linked to a 35S promoter. Ceres Clone:29661 (SEQ ID NO:1) was cloned into a Ti plasmid vector, CRS 311, containing a phosphinothricin acetyltransferase gene, which confers FINALE™ resistance to transformed plants. SEQ ID NO:1 was operably linked to a p32449 promoter in the constructs made using the CRS 331 vector. Wild-type *Arabidopsis thaliana* ecotype Wassilewskija (Ws) plants were transformed separately with each construct. The transformations were performed essentially as described in Bechtold et al. (1993) *C. R. Acad. Sci. Paris,* 316:1194-1199.

Transgenic *Arabidopsis* lines containing SEQ ID NO:1, SEQ ID NO:48, SEQ ID NO:76, SEQ ID NO:96, SEQ ID NO:99, SEQ ID NO:151, SEQ ID NO:165, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:224, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1478, SEQ ID NO:1490, SEQ ID NO:1509, SEQ ID NO:1524, SEQ ID NO:1536, SEQ ID NO:1553, SEQ ID NO:1576, or SEQ ID NO:175 were designated ME00919, ME01312, ME01463, ME01821, ME01910, ME02538, ME02603, ME02613, ME02801, ME03123, ME04204, ME04477, ME04507, ME04587, ME04753, ME04772, ME04909, ME05033, ME05194, ME05267, ME05300, ME05341, ME05392, ME05429, ME05493, ME05885, ME07344, ME07859, ME08464, ME09939, ME11735, ME12910, ME12927, ME12929, ME12954, ME12970, ME13006, ME13021, ME13064, ME13071, ME13087, ME13106, ME13107, ME13108, ME13110, ME13125, ME13149, ME13151, ME13153, ME13177, ME13200, ME13204, ME14649, ME16546, ME17457, ME17567, ME17932, ME17936, ME18275, ME18924, ME19182, or ME20628, respectively. The presence of each vector containing a nucleic acid described above in the respective transgenic *Arabidopsis* line transformed with the vector was confirmed by FINALE™ resistance, PCR amplification from green leaf tissue extract, and/or sequencing of PCR products. As controls, wild-type *Arabidopsis* ecotype Ws plants were transformed with the empty vector, either CRS338 or CRS311.

Example 2—Screening for Transgenic Plants Tolerant to Low-Nitrogen Growth Conditions A low-nitrogen tolerance screen was carried out on seedlings in order to identify transgenic lines that showed increased photosynthesis efficiency or seedling size or greenness under limiting nitrogen conditions relative to the internal control plants. The media used for the low-nitrogen tolerance assay contained 0.5% sucrose, 0.5×MS without nitrogen media (PhytoTech), 0.05% MES Hydrate, and 0.8% Phytagar. In addition, for low ammonium nitrate assay, 240 µM NH4NO3 was used as nitrogen source. For low nitrate assay, nitrogen source was 300 µM KNO3. pH of the media was adjusted to pH 5.7 using 10N KOH. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Screen the seedlings daily starting at 14 days. In this screen, seedlings that were larger or greener relative to the internal controls on low nitrogen growth media were selected. As they were found each day, candidate seedlings were aseptically transplanted to standard MS germination plates for recovery. This intermediate recovery step was necessary before transplanting to soil to minimize the overall candidate mortality rate. The scoring and transplanting of candidates were continued until all remaining plants were small and yellowed from nitrogen stress. On the very last day of scoring, each plate was scanned for photosynthetic efficiency (Fv/Fm) on the chlorophyll fluorescence (CF) imager and scored as candidates and transplanted any extreme outliers on the high end of Fv/Fm scores. Fv/Fm ratio typically provides an estimate of the photosystem II (PSII) maximum efficiency within dark-adapted material where Fv is variable fluorescence, i.e. difference between minimum (Fo) and maximum (Fm) fluorescence signal, from dark-adapted material. This could be done visually by looking at the false color image for each seedling using the CF image analysis software (plants with high end Fv/Fm scores appear red). This step was typically done at ~24 days after germination. Seven days after being transferred to MS recovery plates, candidates were transplanted to soil (standard Sunshine:vermiculite 3:2 mix; Osmocote; Marathon). Five days after being transplanted to soil, candidates were sprayed with FINALE® [5 mL FINALE®/48 oz. water] to eliminate non-transgenics from the population. Two days after spraying with FINALE®, cauline leaf tissue of each candidate was collected for genomic DNA extraction, PCR, and sequencing to determine the identity of the transgene for each candidate.

Example 3—Validation Plate Assay

This assay was designed to validate transgenic lines that showed increased photosynthesis or size under limiting nitrogen conditions relative to the internal control. The media used for the low-nitrogen tolerance assay contained 0.5% sucrose, 0.5×MS without nitrogen media (PhytoTech), 0.05% MES Hydrate, and 0.8% Phytagar. pH of the media was adjusted to pH 5.7 using 10N KOH. In addition, for low ammonium nitrate assay, 240 µM NH$_4$NO$_3$ was used as nitrogen source. For low nitrate assay, nitrogen source was 300 µM KNO$_3$. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Plates were scanned every other day using the CF Imager (after 45 minute of dark-acclimation) and were completed after all wild-type plants have completely yellowed. After the plates were scanned on the last day, they were sprayed with FINALE® (10 mL FINALE® into 48 oz. full-strength MS liquid media). Two days after spraying, each plate was dark-acclimated for 45 minutes and scanned for Fv/Fm on the CF imager and scored for each of the plants at each time point. For each separate time point, the data for all the T$_2$ transgenic plants across an event was pooled and a one-tailed t-test was used to compare both the Fv/Fm ratios and rosette areas relative to the pooled non-transgenics across the same plate. Whenever possible, this process was repeated for the T$_3$ generation plants. A low nitrogen tolerant candidate was confirmed when the transgenic Fv/Fm ratio and/or rosette area was greater than the wild-type segregants with a p-value≤0.05 in 2 or more events in both generations Example 4—Validation Soil Assay A Low, Medium, and High Nitrogen experiment on soil was carried out to assess phenotypic characteristics at a mature point in the life cycle of *Arabidopsis*, as compared to seedling screens. The lines to be tested were originally identified through superpool screens for low nitrate and low ammonium nitrate tolerance. These lines were later individually assayed as seedlings on low nitrate and low ammonium nitrate agar. For this assay, MetroMix200 soil was mixed with vermiculite and Marathon™ (MetroMix200:

vermiculite 3:2 mix; Osmocote; Marathon) autoclaved and cooled before use. Experimental plants and controls were randomized across the flats. Prior to sowing seed, each flat was watered with 3 L filtered water. Flats with 24 wells were filled with the following 3:2 ratios of MetroMix200 to Thermorock vermiculite. At the beginning of the experiment no nitrogen was provided until 2 weeks after germination when ¼ Hoaglands supplemented with $KNO_3$ at 25 ppm, 250 ppm, and 1500 ppm were used to water the flats from beneath.

Seeds were stratified on soil and in the dark at 4° C. for 3 days. After the cold treatment, flats were transferred to the growth chamber. Plants were grown for approximately 5 weeks, or until full grown/mature. Plants were then dark-acclimated for one hour. Chlorophyll fluorescence images were taken using a CF-Imager (Technologica, UK) according to the manufacturer's protocol to measure the performance and efficiency of photosystem II: 1) Fv/Fm, maximum photosystem II efficiency 2) Fq'/Fm', operating efficiency and 3) non-photochemical quenching (NPQ).

One week after watering with ¼ Hoaglands supplemented with various $KNO_3$ concentrations, plant rosette area measurements were taken using the WhinRhizo imaging software (Reagent Instruments, Canada). The plants were then collected in manila envelopes, placed in a 125° C. drying oven for 1-2 days and weighed.

Example 5—Analysis of ME00919 Events

ME00919 contains Ceres Clone:29661 (At3g61880, SEQ ID NO:1) from *Arabidopsis thaliana*, which encodes a 534 amino acid cytochrome P450 protein. Evaluation of low-nitrogen tolerance for ME00919 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -03, showed significantly increased photosynthetic efficiency relative to the internal controls in both generations at $p \le 0.05$ using a one-tailed t-test assuming unequal variance. A summary of photosynthetic efficiency of ME00919 seedlings on low ammonium nitrate-containing media are shown in Table 1. Events-01 and -03 segregated 15:1 and 3:1 (R:S), respectively, for FINALE™ resistance in the $T_2$ generation. ME00919 events were also tested for enhanced growth on the low ammonium nitrate media. No significant differences between the transgenics and the controls were observed.

Events-01 and -03 of ME00919 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 6—Analysis of ME01312 Events

ME01312 contains Ceres Clone:251343 (At3g21270, SEQ ID NO:48) from *Arabidopsis thaliana*, which encodes a 204 amino acid Dof zinc finger protein. Ceres Clone: 251343 shares approximately 40% amino acid identity to the corn Dof1 gene, which when overexpressed in *Arabidopsis*, has shown to confer tolerance to plants receiving low nitrogen stress (Yanagisawa et al., 2004). Evaluation of low-nitrogen tolerance for ME01312 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -11, showed significantly enhanced photosynthetic efficiency on either low nitrate or low ammonium nitrate-containing media after 16 and 17 days compared to the internal controls in both generations at $p \le 0.05$ using a one-tailed t-test assuming unequal variance. Event-03 had a slightly greater p-value than 0.05 in the $T_3$ generation for the low nitrate screen, significant at $p \le 0.10$. A summary of photosynthetic efficiency of ME01312 seedlings on either low nitrate or low ammonium nitrate-containing media is shown in Table 2. Events-03 and -11 segregated 3:1 (R:S), respectively, for FINALE™ resistance in the $T_2$ generation.

TABLE 1 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME00919 | ME00919-01 ($T_2$) | 0.65641304 | 46 | 0.595818 | 11 | $2.48 \times 10^{-2}$ |
| ME00919 | ME00919-01 ($T_3$) | 0.66348780 | 41 | 0.595818 | 11 | $1.55 \times 10^{-2}$ |
| ME00919 | ME00919-03 ($T_2$) | 0.67212195 | 41 | 0.634026 | 38 | $3.35 \times 10^{-3}$ |
| ME00919 | ME00919-03 ($T_3$) | 0.69278947 | 19 | 0.634026 | 38 | $2.39 \times 10^{-5}$ |

TABLE 2A

T-test comparison of photosynthetic efficiency between transgenic seedlings and pooled non-transgenic segregants after 16 days of growth on low nitrate.

| Line | Events | Transgenic Fv/Fm | n | Pooled Non-Transgenics Fv/Fm | n | t-test p-value |
|---|---|---|---|---|---|---|
| ME01312 | ME01312-03 ($T_2$) | 0.63 | 38 | 0.60 | 58 | 0.03 |
| ME01312 | ME01312-03 ($T_3$) | 0.63 | 38 | 0.60 | 58 | 0.07 |
| ME01312 | ME01312-11 ($T_2$) | 0.64 | 41 | 0.60 | 58 | 0.019 |
| ME01312 | ME01312-11 ($T_3$) | 0.64 | 47 | 0.60 | 58 | $9.89 \times 10^{-3}$ |

TABLE 2B

T-test comparison of photosynthetic efficiency between transgenic seedlings and pooled non-transgenic segregants after 17 days of growth on low ammonium nitrate.

| Line | Events | Transgenic Fv/Fm | n | Pooled Non-Transgenics Fv/Fm | n | t-test p-value |
|---|---|---|---|---|---|---|
| ME01312 | ME01312-03 ($T_2$) | 0.64 | 36 | 0.61 | 88 | $2.64 \times 10^{-3}$ |
| ME01312 | ME01312-03 ($T_3$) | 0.66 | 27 | 0.61 | 88 | $1.87 \times 10^{-5}$ |
| ME01312 | ME01312-11 ($T_2$) | 0.65 | 35 | 0.61 | 88 | $7.06 \times 10^{-4}$ |
| ME01312 | ME01312-11 ($T_3$) | 0.64 | 37 | 0.61 | 88 | 0.011 |

Events-03-11 of ME01312 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 7—Analysis of ME01463 Events

ME01463 contains Ceres Clone:19586 (At1g80600, SEQ ID NO:76) from *Arabidopsis thaliana*, which encodes a 457 acetylornithine aminotransferase, a member of the Class-III aminotransferase family. Evaluation of low-nitrogen tolerance for ME01463 in two generations was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -06, and -10, showed significantly increased photosynthetic efficiency on low ammonium nitrate containing-media relative to the internal controls in both generations at $p \leq 0.05$ using a one-tailed t-test assuming unequal variance. A summary of photosynthetic efficiency of ME01463 seedlings is shown in Table 3. Events-02, -06, and -10 segregated 2:1, 2:1 and 3:1 (R:S), respectively, for FINALE™ resistance in the $T_2$ generation. ME01463 events were also tested for enhanced growth on the low ammonium nitrate media. No significant differences between the transgenics and the controls were observed (data not shown).

TABLE 3

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01463 | ME01463-02 ($T_3$) | 0.6815 | 26 | 0.6376 | 122 | $2.47 \times 10^{-4}$ |
| ME01463 | ME01463-02 ($T_4$) | 0.6701 | 41 | 0.6376 | 122 | $1.57 \times 10^{-3}$ |
| ME01463 | ME01463-06 ($T_3$) | 0.6615 | 31 | 0.6376 | 122 | $2.37 \times 10^{-2}$ |
| ME01463 | ME01463-06 ($T_4$) | 0.6881 | 35 | 0.6376 | 122 | $5.85 \times 10^{-6}$ |
| ME01463 | ME01463-10 ($T_2$) | 0.6699 | 33 | 0.6376 | 122 | $2.25 \times 10^{-3}$ |
| ME01463 | ME01463-10 ($T_3$) | 0.6809 | 18 | 0.6376 | 122 | $4.60 \times 10^{-4}$ |

Events-02, -06, and -10 of ME01463 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 8—Analysis of ME01821 Events

ME01821 contains Ceres Clone:25136 (At1g65500, SEQ ID NO:96) from *Arabidopsis thaliana*, which encodes a 86 amino acid protein of unknown function. Evaluation of low-nitrogen tolerance for ME01821 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low nitrate-containing media relative to the internal controls in $T_2$ generation. Two events, -04 and -05, showed significantly increased photosynthetic efficiency on low ammonium nitrate-containing media relative to the internal controls in $T_2$ generation at $p \leq 0.05$ using a one-tailed t-test assuming unequal variance. A summary of photosynthetic efficiency of ME01821 seedlings is shown in Table 4.

TABLE 4A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME01821 | ME01821-01 ($T_2$) | 0.6745 | 15 | 0.6520 | 33 | $3.76 \times 10^{-2}$ |
| ME01821 | ME01821-04 ($T_2$) | 0.6826 | 17 | 0.6614 | 14 | $2.76 \times 10^{-2}$ |
| ME01821 | ME01821-05 ($T_2$) | 0.6826 | 20 | 0.6614 | 14 | $3.74 \times 10^{-2}$ |

TABLE 4B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01821 | ME01821-04 ($T_2$) | 0.7422 | 13 | 0.7166 | 21 | $5.20 \times 10^{-3}$ |
| ME01821 | ME01821-05 ($T_2$) | 0.7426 | 19 | 0.7166 | 21 | $6.07 \times 10^{-3}$ |

A summary of the enhanced growth of ME01812 events on either low nitrate- or low ammonium nitrate-containing media is shown in Table 5. For two events-01 and -05, transgenic seedlings were found significantly larger than the pooled non-transgenic segregants after 14 days of growth on low nitrate-containing media (Table 5A). Transgenic seedlings of two events-02 and -05 were found significantly larger than the pooled non-transgenic segregants after 14 days of growth on low ammonium nitrate-containing media (Table 5B). In this study, the seedling area for transgenic plants within an event was compared to the seedling area for non-transgenic segregants pooled across the same line.

TABLE 5A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME01821 | ME01821-01 ($T_2$) | 0.0608 | 15 | 0.0555 | 33 | $3.97 \times 10^{-2}$ |
| ME01821 | ME01821-05 ($T_2$) | 0.0666 | 20 | 0.0530 | 14 | $3.05 \times 10^{-6}$ |

TABLE 5B

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME01821 | ME01821-02 ($T_2$) | 0.0750 | 19 | 0.0567 | 21 | $8.94 \times 10^{-5}$ |
| ME01821 | ME01821-05 ($T_2$) | 0.0680 | 19 | 0.0567 | 21 | $7.89 \times 10^{-3}$ |

Example 9—Analysis of ME01910 Events

ME01910 contains Ceres Clone:1820 (At2g30620, SEQ ID NO:99) from *Arabidopsis thaliana*, which encodes a 273 amino acid linker histone H1 and H5 family protein. Evaluation of low-nitrogen tolerance for ME01910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency relative to the internal controls in both generations at $p \leq 0.05$ using a one-tailed t-test assuming unequal variance. A summary of photosynthetic efficiency of ME01910 seedlings is shown in Table 6. Events-01 and -02 segregated 3:1 (R:S) for FINALE™ resistance in the $T_2$ generation. ME01910 events were also tested for enhanced growth on the low ammonium nitrate media. No significant differences between the transgenics and the controls were observed.

TABLE 6 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01910 | ME01910-01 ($T_2$) | 0.60433 | 39 | 0.56396 | 27 | $2.03 \times 10^{-2}$ |
| ME01910 | ME01910-01 ($T_3$) | 0.61274 | 31 | 0.56396 | 27 | $9.23 \times 10^{-3}$ |
| ME01910 | ME01910-02 ($T_2$) | 0.62705 | 37 | 0.58083 | 29 | $7.39 \times 10^{-3}$ |
| ME01910 | ME01910-02 ($T_3$) | 0.64146 | 24 | 0.58083 | 29 | $9.23 \times 10^{-4}$ |

Events-01 and -02 of ME01910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 10—Analysis of ME02538 Events

ME02538 contains Ceres Clone:13102 (At1g67920, SEQ ID NO:151) from *Arabidopsis thaliana*, which encodes a 67 amino acid protein of unknown function. Evaluation of low-nitrogen tolerance for ME02538 in $T_2$ generation was conducted under the same conditions as described in Example 2. In this study, the seedling photosynthetic efficiency was measured as Fv/Fm comparing transgenic plants within an event to non-transgenic segregants pooled across the same plate. Two events, -04 and -05, showed significantly increased photosynthetic efficiency relative to the internal controls in $T_2$ generation on both low nitrate-containing and ammonium nitrate-containing media at $p \leq 0.05$ using a one-tailed t-test assuming unequal variance. A summary of photosynthetic efficiency of ME01821 seedlings is shown in Table 7.

TABLE 7A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02538 | ME02538-04 ($T_2$) | 0.6686 | 15 | 0.6171 | 24 | $1.92 \times 10^{-4}$ |
| ME02538 | ME02538-05 ($T_2$) | 0.6420 | 20 | 0.6171 | 24 | $4.84 \times 10^{-2}$ |

TABLE 7B

T-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME02538 | ME02538-04 ($T_2$) | 0.7345 | 13 | 0.7080 | 22 | $4.45 \times 10^{-3}$ |
| ME02538 | ME02538-05 ($T_2$) | 0.7356 | 20 | 0.7080 | 22 | $5.93 \times 10^{-3}$ |

ME02538 events were also tested for enhanced growth on the low ammonium nitrate media. A summary of the growth assay performed on ME01812 events is shown in Table 8. Transgenic seedlings of two events-01 and -02 were found significantly larger than the pooled non-transgenic segregants on both low nitrate—(Table 8A) and low ammonium nitrate-containing media (Table 8B).

TABLE 8A

T-test comparison of seedling area between transgenic seedlings and pooled non-transgenic segregants after 14 days of growth on low nitrate.

| Line | Events | Transgenic | | Pooled Non-Transgenics | | t-test |
|---|---|---|---|---|---|---|
| | | Area | n | Area | n | p-value |
| ME02538 | ME02538-01 ($T_2$) | 0.0655 | 16 | 0.0558 | 36 | $2.80 \times 10^{-4}$ |
| ME02538 | ME02538-02 ($T_2$) | 0.0651 | 13 | 0.0601 | 20 | $1.32 \times 10^{-2}$ |

TABLE 8B

T-test comparison of seedling area between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Area | n | Area | n | p-value |
| ME02538 | ME02538-01 ($T_2$) | 0.0856 | 15 | 0.0737 | 39 | $8.60 \times 10^{-3}$ |
| ME02538 | ME02538-02 ($T_2$) | 0.0864 | 14 | 0.0776 | 22 | $3.13 \times 10^{-2}$ |

Example 11—Analysis of ME02603 Events

ME02603 contains Ceres Clone:15457 (At5g47610, SEQ ID NO:165) from *Arabidopsis thaliana*, which encodes a 166 amino acid zinc ion binding protein. Evaluation of low-nitrogen tolerance for ME02603 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME02603 seedlings is shown in Table 9. Events-01 and -04 segregated 3:1 (R:S) for FINALE™ resistance in the $T_2$ generation. Transgenic plants of two events-01 and -04—were also tested for enhanced photosynthetic efficiency on the low nitrate media. No significant differences between the transgenics and the controls were observed.

TABLE 9

T-test comparison of photosynthetic efficiency between transgenic seedlings and pooled non-transgenic segregants after 17 days (21 days for the $T_2$ generation of ME02603-01) of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME02603 | ME02603-01 ($T_2$) | 0.61 | 10 | 0.54 | 32 | $9.00 \times 10^{-4}$ |
| ME02603 | ME02603-01 ($T_3$) | 0.67 | 28 | 0.65 | 62 | $6.11 \times 10^{-3}$ |
| ME02603 | ME02603-04 ($T_2$) | 0.69 | 25 | 0.65 | 62 | $4.45 \times 10^{-5}$ |
| ME02603 | ME02603-04 ($T_3$) | 0.68 | 24 | 0.65 | 62 | $7.53 \times 10^{-3}$ |

Events-01 and -04 of ME02603 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 12—Analysis of ME02613 Events

ME02613 contains Ceres Clone:17883 (At3g13910, SEQ ID NO:185) from *Arabidopsis thaliana*, which encodes a 102 amino acid protein of unknown function. Evaluation of low-nitrogen tolerance for ME02613 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. In $T_2$ generation, two events, -01 and -04, showed significantly increased photosynthetic efficiency on low nitrate containing-media relative to the internal controls in $T_2$ generation at $p \leq 0.05$ using a one-tailed t-test assuming unequal variance. Two events, -03 and -04, showed significantly increased photosynthetic efficiency on low ammonium nitrate containing-media relative to the internal controls in $T_2$ generation at $p \leq 0.05$ using a one-tailed t-test assuming unequal variance. A summary of photosynthetic efficiency of ME02613 seedlings is shown in Table 10.

TABLE 10A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME02613 | ME02613-01 ($T_2$) | 0.6979 | 16 | 0.6630 | 21 | $1.45 \times 10^{-2}$ |
| ME02613 | ME02613-04 ($T_2$) | 0.7046 | 13 | 0.6630 | 21 | $5.73 \times 10^{-4}$ |

TABLE 10B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME02613 | ME02613-03 ($T_2$) | 0.7270 | 9 | 0.7068 | 29 | $4.34 \times 10^{-2}$ |
| ME02613 | ME02613-04 ($T_2$) | 0.7485 | 15 | 0.7068 | 29 | $7.09 \times 10^{-5}$ |

A summary of the enhanced growth of ME02613 events on either low nitrate- or low ammonium nitrate-containing media is shown in Table 11. For two events-01 and -03, transgenic seedlings were found significantly larger than the pooled non-transgenic segregants after 14 days of growth on low nitrate-containing media (Table 11A). Transgenic seedlings of two events-02 and -03 were found significantly larger than the pooled non-transgenic segregants after 14 days of growth on low ammonium nitrate-containing media (Table 11B.

TABLE 11A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME02613 | ME02613-01 ($T_2$) | 0.05706 | 16 | 0.05259 | 31 | $4.71 \times 10^{-2}$ |
| ME02613 | ME02613-03 ($T_2$) | 0.06236 | 12 | 0.05789 | 29 | $2.39 \times 10^{-2}$ |

TABLE 1

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME02613 | ME02613-02 ($T_2$) | 0.08324 | 14 | 0.07018 | 29 | $2.72 \times 10^{-4}$ |
| ME02613 | ME02613-03 ($T_2$) | 0.08273 | 9 | 0.07018 | 29 | $1.41 \times 10^{-2}$ |

Example 13—Analysis of ME02801 Events

ME02801 contains Ceres Clone:251590 (At3g53080, SEQ ID NO:207) from *Arabidopsis thaliana*, which encodes a 155 amino acid protein of unknown function. Evaluation of low-nitrogen tolerance for ME02801 in $T_2$ and $T_3$ was conducted under the same conditions as described in Example 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME02801 seedlings is shown in Table 12. Events-02 and -04 segregated 3:1 (R:S) for FINALE™ resistance in the $T_2$ generation. ME02801 events were also tested for enhanced growth on the low nitrate media and enhanced photosynthetic efficiency and growth on low ammonium nitrate media. No significant differences between the transgenics and the controls were observed.

days to flowering; there was no observable or statistical differences between transgenics and controls in the size of the rosette area 7 days post-bolting; and there was no observable or statistical differences between transgenics and controls in fertility (silique number and seed fill).

Example 14—Analysis of ME03123 Events

ME03123 contains Ceres Clone:4898 (At1g29970, SEQ ID NO:217) from *Arabidopsis thaliana*, which encodes a 158 amino acid protein of unknown function. Evaluation of low-nitrogen tolerance for ME03123 in $T_2$ and/or $T_3$ was conducted under the same conditions as described in Examples 2 and 3. In this study, the seedling photosynthetic efficiency was measured as Fv/Fm comparing transgenic plants within an event to non-transgenic segregants pooled across the same plate. A summary of photosynthetic efficiency of ME03123 seedlings is shown in Table 13. Two

TABLE 12 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02801 | ME02801-02 ($T_2$) | 0.536385 | 39 | 0.465903 | 113 | $5.49 \times 10^{-7}$ |
| ME02801 | ME02801-02 ($T_3$) | 0.536465 | 43 | 0.465903 | 113 | $5.11 \times 10^{-7}$ |
| ME02801 | ME02801-04 ($T_2$) | 0.532419 | 31 | 0.465903 | 113 | $1.28 \times 10^{-5}$ |
| ME02801 | ME02801-04 ($T_3$) | 0.510406 | 32 | 0.465903 | 113 | $1.74 \times 10^{-2}$ |

Events-02 and -04 of ME02801 exhibited no statistically relevant negative phenotypes. That is, there was no detectable reduction in germination rate, the transgenic plants appeared wild type in all instances; there was no observable or statistical differences between transgenics and controls in events, -01 and -10, showed significantly increased photosynthetic efficiency on low nitrate- or low ammonium nitrate-containing media relative to the internal controls in $T_2$ or $T_3$ generation at p≤0.05 using a one-tailed t-test assuming unequal variance.

TABLE 13A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME03123 | ME03123-01 ($T_2$) | 0.6282 | 15 | 0.5732 | 26 | $6.60 \times 10^{-5}$ |
| ME03123 | ME03123-10 ($T_3$) | 0.6069 | 12 | 0.5732 | 26 | $1.05 \times 10^{-2}$ |

TABLE 13B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME03123 | ME03123-01 ($T_2$) | 0.6736 | 17 | 0.6315 | 16 | $1.74 \times 10^{-2}$ |
| ME03123 | ME03123-10 ($T_3$) | 0.6699 | 20 | 0.6315 | 16 | $1.60 \times 10^{-2}$ |

ME03123 events were also tested for enhanced growth on the low ammonium nitrate media. In this assay, transgenic seedlings of ME03123-02 and ME03123-04 ($T_2$) were significantly larger than the pooled non-transgenic segregants after 14 days of growth on low nitrate (Table 14).

TABLE 14

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME03123 | ME03123-02 ($T_2$) | 0.07235 | 19 | 0.05623 | 20 | $1.41 \times 10^{-6}$ |
| ME03123 | ME03123-04 ($T_3$) | 0.06571 | 7 | 0.05729 | 41 | $7.74 \times 10^{-3}$ |

Example 15—Analysis of ME04204 Events

ME04204 contains Ceres Clone:148977 (At1g78770, SEQ ID NO:233) from *Arabidopsis thaliana*, which encodes a 159 amino acid anaphase promoting complex/cyclosome subunit protein. However, it is also possible that this is natural variant transcript produced by the plant, because multiple annotations for locus At1g78770 were found in public domain. Evaluation of low-nitrogen tolerance for ME04204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency relative to the internal controls in both generations at p≤0.05 using a one-tailed t-test assuming unequal variance. A summary of photosynthetic efficiency of ME04204 seedlings is shown in Table 15. Events-01 and -05 segregated 3:1 (R:S) for FINALE™ resistance in the $T_2$ generation. ME04204 events were also tested for enhanced growth on the low nitrate media. No significant differences between the transgenics and the controls were observed.

Events-01 and -05 of ME04204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 16—Analysis of ME04477 Events

ME04477 contains Ceres Clone:24255 (At2g36320, SEQ ID NO:245) from *Arabidopsis thaliana*, which encodes a 161 amino acid DNA binding/zinc ion binding protein. Evaluation of low-nitrogen tolerance for ME04477 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME04477 seedlings is shown in Table 16. Events-01 and -05 segregated 3:1 (R:S) for FINALE™ resistance in the

TABLE 15

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

$T_2$ generation. ME04477 events were also tested for enhanced growth on the low nitrate media. No significant differences between the transgenics and the controls were observed.

TABLE 16

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events-01 and -05 of ME04477 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 17—Analysis of ME04507 Events

ME04507 contains Ceres Clone:38432 (At4g38250, SEQ ID NO:299) from *Arabidopsis thaliana*, which encodes a 436 amino acid transmembrane amino acid transporter protein. Evaluation of low-nitrogen tolerance for ME04507 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME04507 seedlings is shown in Table 17. Events-03 and -04 segregated 15:1 and 3:1 (R:S), respectively, for FINALE™ resistance in the $T_2$ generation. ME04507 events were also tested for enhanced growth on the low nitrate media. No significant differences between the transgenics and the controls were observed.

Events-03 and -04 of ME04507 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 18—Analysis of ME04587 Events

ME04587 contains Ceres Annot: 553243 (At2g27010, SEQ ID NO:331) from *Arabidopsis thaliana*, which encodes a 516 amino acid cytochrome P450 protein. Evaluation of low-nitrogen tolerance for ME04587 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME04587 seedlings is shown in Table 18. In $T_2$ generation, events-01 and -02 segregated 1:1 and 47:1 respectively (R:S) for FINALE™ resistance. These two events segregated 2:1 and 7:1 respectively (R:S) for FINALE® resistance in the $T_3$ generation.

TABLE 17

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04507 | ME04507-03 ($T_2$) | 0.57753 | 40 | 0.53084 | 103 | $4.90 \times 10^{-4}$ |
| ME04507 | ME04507-03 ($T_3$) | 0.56318 | 39 | 0.53084 | 103 | $2.64 \times 10^{-2}$ |
| ME04507 | ME04507-04 ($T_2$) | 0.57708 | 38 | 0.53084 | 103 | $6.12 \times 10^{-3}$ |
| ME04507 | ME04507-04 ($T_3$) | 0.57277 | 22 | 0.53084 | 103 | $2.35 \times 10^{-2}$ |

TABLE 18

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME04587 | ME04587-01 ($T_2$) | 0.6424 | 10 | 0.5437 | 30 | $2.48 \times 10^{-3}$ |
| ME04587 | ME04587-01 ($T_3$) | 0.6165 | 25 | 0.5437 | 30 | $1.24 \times 10^{-2}$ |
| ME04587 | ME04587-02 ($T_2$) | 0.6022 | 47 | 0.5437 | 30 | $3.08 \times 10^{-2}$ |
| ME04587 | ME04587-02 ($T_3$) | 0.6310 | 43 | 0.5437 | 30 | $3.68 \times 10^{-3}$ |

ME04587 events were also tested for enhanced growth on the low ammonium nitrate media. In addition, these events were tested on low nitrate media for increased seedling area and photosynthetic efficiency. No statistically significant differences between the transgenics and the controls were observed.

Events-01 and -02 of ME04587 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 19—Analysis of ME04753 Events

ME04753 contains Ceres Clone:1011900 (At2g21660, SEQ ID NO:367) from *Arabidopsis thaliana*, which encodes a 130 amino acid glycine-rich RNA binding protein. Evaluation of low-nitrogen tolerance for ME04753 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low nitrate-containing media relative to the internal controls in both generations at p≤0.05 using a one-tailed t-test assuming unequal variance. A summary of photosynthetic efficiency of ME04753 seedlings is shown in Table 19. Events-01 and -02 segregated 3:1 and 2:1 respectively (R:S) for FINALE™ resistance in the $T_2$ generation. ME04753 events were also tested for enhanced growth on the low nitrate media. No significant differences between the transgenics and the controls were observed.

Events-01 and -02 of ME04753 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 20—Analysis of ME04772 Events

ME04772 contains Ceres Clone:5232 (At1g13380, SEQ ID NO:509) from *Arabidopsis thaliana*, which encodes a 188 amino acid protein of unknown function. Evaluation of low-nitrogen tolerance for ME04772 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME04772 seedlings is shown in Table 20. Events-02 and -04 segregated 2:1 and 3:1 respectively (R:S) for FINALE™ resistance in the $T_2$ generation. ME04772 events were also tested for enhanced growth on the low nitrate media. No significant differences between the transgenics and the controls were observed.

TABLE 19

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04753 | ME04753-01 ($T_2$) | 0.49323 | 39 | 0.45917 | 66 | $3.17 \times 10^{-2}$ |
| ME04753 | ME04753-01 ($T_3$) | 0.50942 | 26 | 0.45917 | 66 | $1.80 \times 10^{-2}$ |
| ME04753 | ME04753-02 ($T_2$) | 0.49856 | 34 | 0.45917 | 66 | $2.43 \times 10^{-2}$ |
| ME04753 | ME04753-02 ($T_3$) | 0.51274 | 27 | 0.45917 | 66 | $1.15 \times 10^{-2}$ |

TABLE 20

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04772 | ME04772-02 ($T_2$) | 0.53708 | 25 | 0.46204 | 53 | $3.36 \times 10^{-5}$ |
| ME04772 | ME04772-02 ($T_3$) | 0.53121 | 34 | 0.46204 | 53 | $1.27 \times 10^{-4}$ |
| ME04772 | ME04772-04 ($T_2$) | 0.52921 | 34 | 0.46204 | 53 | $3.71 \times 10^{-4}$ |
| ME04772 | ME04772-04 ($T_3$) | 0.50272 | 36 | 0.46204 | 53 | $2.73 \times 10^{-2}$ |

Events-02 and -04 of ME04772 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 21—Analysis of ME04772 Events

ME04909 contains Ceres Clone:29302 (At1g49010, SEQ ID NO:532) from *Arabidopsis thaliana*, which encodes a 314 amino acid Myb-like DNA-binding domain protein. Evaluation of low-nitrogen tolerance for ME04909 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at $p \leq 0.05$ using a one-tailed t-test assuming unequal variance. A summary of photosynthetic efficiency of ME04909 seedlings is shown in Table 21. Events-01 and -03 segregated 15:1 (R:S) for FINALE™ resistance in the $T_2$ generation. ME04909 events were also tested for enhanced growth on the low nitrate media. No significant differences between the transgenics and the controls were observed.

Events-01 and -03 of ME04909 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 22—Analysis of ME05033 Events

ME05033 contains Ceres Clone:93971 (At4g19095, SEQ ID NO:555) from *Arabidopsis thaliana*, which encodes a 188 amino acid protein of unknown function. Evaluation of low-nitrogen tolerance for ME05033 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME05033 seedlings is shown in Table 22. Events-03 and -05 segregated 15:1 and 2:1 respectively (R:S) for FINALE™ resistance in the $T_2$ generation. ME05033 events were also tested for enhanced growth on the low nitrate media. No significant differences between the transgenics and the controls were observed.

TABLE 21 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME04909 | ME04909-01 ($T_2$) | 0.587774 | 31 | 0.550342 | 111 | $1.36 \times 10^{-2}$ |
| ME04909 | ME04909-01 ($T_3$) | 0.607452 | 31 | 0.550342 | 111 | $1.28 \times 10^{-3}$ |
| ME04909 | ME04909-03 ($T_2$) | 0.581537 | 41 | 0.550342 | 111 | $1.8 \times 10^{-2}$ |
| ME04909 | ME04909-03 ($T_3$) | 0.609806 | 31 | 0.550342 | 111 | $4.3 \times 10^{-5}$ |

TABLE 22

T-test comparison of seedling photosynthetic efficiency between transgenic seedlings and pooled non-transgenic segregants after 14 days of growth on low nitrate media.

| Line | Events | Transgenic | | Pooled Non-Transgenics | | t-test |
|---|---|---|---|---|---|---|
| | | Fv/Fm | n | Fv/Fm | n | p-value |
| ME05033 | ME05033-03 ($T_2$) | 0.65717 | 46 | 0.62621 | 132 | $9.20 \times 10^{-5}$ |
| ME05033 | ME05033-03 ($T_3$) | 0.64956 | 39 | 0.62621 | 132 | $4.52 \times 10^{-3}$ |
| ME05033 | ME05033-05 ($T_2$) | 0.64448 | 29 | 0.62621 | 132 | $3.46 \times 10^{-2}$ |
| ME05033 | ME05033-05 ($T_3$) | 0.65537 | 30 | 0.62621 | 132 | $2.38 \times 10^{-4}$ |

Events-03 and -05 of ME05033 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 23—Analysis of ME05194 Events

ME05194 contains Ceres cDNA:12669619 (At1g30710, SEQ ID NO:557) from *Arabidopsis thaliana*, which encodes a 531 amino acid electron carrier protein. Evaluation of low-nitrogen tolerance for ME05194 in $T_2$ and $T_3$ was conducted under the same conditions as described in Examples 2 and 3. Two events, -03 and -05, showed significantly enhanced growth on low nitrate-containing media relative to the internal controls in both generations at p≤0.05 using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 23. Events-03 and -05 segregated 1:1 (R:S) for FINALE™ resistance in the $T_2$ generation. ME05194 events were also tested for increased photosynthetic efficiency on the low nitrate media. No significant differences between the transgenics and the controls were observed.

Events-03 and -05 of ME05194 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 24—Analysis of ME05267 Events

ME05267 contains Ceres Clone:21608 (At5g49510, SEQ ID NO:592) from *Arabidopsis thaliana*, which encodes a 195 amino acid von Hippel-Lindau binding protein. Evaluation of low-nitrogen tolerance for ME05267 in $T_2$ and $T_3$ was conducted under the same conditions as described in Examples 2 and 3. Two events, -01 and -04, showed significantly enhanced growth on low nitrate-containing media relative to the internal controls in both generations at p≤0.05 using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 24. Events-01 and -04 segregated 15:1 (R:S) for FINALE™ resistance in the $T_2$ generation. ME05267 events were also tested for increased photosynthetic efficiency on the low nitrate media. No significant differences between the transgenics and the controls were observed.

TABLE 23 t-test comparison of seedling area between transgenic seedlings and pooled non-transgenic segregants after 14 days of growth on low nitrate.

| Line | Events | Transgenic | | Pooled Non-Transgenics | | t-test |
|---|---|---|---|---|---|---|
| | | Area | n | Area | n | p-value |
| ME05194 | ME05194-03 ($T_2$) | 0.051216 | 38 | 0.040874 | 82 | $2.54 \times 10^{-5}$ |
| ME05194 | ME05194-03 ($T_3$) | 0.047042 | 45 | 0.040874 | 82 | $2.61 \times 10^{-2}$ |
| ME05194 | ME05194-05 ($T_2$) | 0.048746 | 26 | 0.040874 | 82 | $6.15 \times 10^{-3}$ |
| ME05194 | ME05194-05 ($T_3$) | 0.048457 | 14 | 0.040874 | 82 | $3.03 \times 10^{-2}$ |

TABLE 24 t-test comparison of seedling area between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME05267 | ME05267-01 ($T_2$) | 0.053263 | 46 | 0.0450197 | 122 | $4.4 \times 10^{-5}$ |
| ME05267 | ME05267-01 ($T_3$) | 0.051135 | 26 | 0.0450197 | 122 | $5.0 \times 10^{-2}$ |
| ME05267 | ME05267-04 ($T_2$) | 0.049977 | 44 | 0.0450197 | 122 | $6.4 \times 10^{-3}$ |
| ME05267 | ME05267-04 ($T_3$) | 0.053084 | 38 | 0.0450197 | 122 | $8.4 \times 10^{-4}$ |

Events-01 and -04 of ME05267 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 25—Analysis of ME05300 Events

ME05300 contains Ceres Clone:2031 (At1g72020, SEQ ID NO:612) from *Arabidopsis thaliana*, which encodes a 97 amino acid protein of unknown function. Evaluation of low-nitrogen tolerance for ME05300 in $T_2$ generation was conducted under the same conditions as described in Examples 2 and 3. A summary of photosynthetic efficiency of ME05300 seedlings is shown in Table 25. Two events, -04 and -05, showed significantly increased photosynthetic efficiency on low nitrate- and low ammonium nitrate-containing media relative to the internal controls in $T_2$ generation at $p \le 0.05$ using a one-tailed t-test assuming unequal variance. In this study, the seedling photosynthetic efficiency was measured as Fv/Fm comparing transgenic plants within an event to non-transgenic segregants pooled across the same plate. In addition, two events, -01 and -05, showed significantly enhanced growth on low nitrate- and low ammonium nitrate-containing media relative to the internal controls in $T_2$ generation at $p \le 0.05$ using a one-tailed t-test assuming unequal variance. In this study, the seedling area for transgenic plants within an event was compared to the seedling area for non-transgenic segregants pooled across the same line. A summary of enhanced growth under low nitrate and low ammonium nitrate growth conditions of ME05300 seedlings is shown in Table 26.

TABLE 25A

T-test comparison of seedling photosynthetic efficiency between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME05300 | ME05300-04 ($T_2$) | 0.6867 | 7 | 0.6488 | 27 | $1.65 \times 10^{-2}$ |
| ME05300 | ME05300-05 ($T_2$) | 0.6839 | 16 | 0.6488 | 27 | $2.50 \times 10^{-3}$ |

TABLE 25B

T-test comparison of seedling photosynthetic efficiency between transgenic seedlings and pooled non-transgenic segregants after 18 days of growth on low ammonium

| Line | Events | Transgenic | | Pooled Non-Transgenics | | t-test |
| --- | --- | --- | --- | --- | --- | --- |
| | | Fv/Fm | n | Fv/Fm | n | p-value |
| ME05300 | ME05300-04 ($T_2$) | 0.6767 | 6 | 0.6323 | 32 | $1.68 \times 10^{-2}$ |
| ME05300 | ME05300-05 ($T_2$) | 0.6934 | 11 | 0.6323 | 32 | $7.04 \times 10^{-4}$ |

TABLE 26A

T-test comparison of seedling area between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME05300 | ME05300-01 ($T_2$) | 0.0737 | 18 | 0.0588 | 21 | $3.80 \times 10^{-3}$ |
| ME05300 | ME05300-05 ($T_2$) | 0.0655 | 16 | 0.0570 | 27 | $1.59 \times 10^{-2}$ |

TABLE 26B t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0987 | 17 | 0.0776 | 29 | $3.89 \times 10^{-3}$ |
| ME05300 | ME05300-05 ($T_2$) | 0.1082 | 11 | 0.0776 | 29 | $1.57 \times 10^{-3}$ |

Example 26—Analysis of ME05341 Events

ME05341 contains Ceres Clone:94503 (At4g14420, SEQ ID NO:645) from *Arabidopsis thaliana*, which encodes a 158 amino acid elicitor-like protein. Evaluation of low-nitrogen tolerance for ME05341 in $T_2$ and $T_3$ was conducted under the same conditions as described in Examples 2 and 3. Two events, -01 and -02, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of photosynthetic efficiency of ME05341 seedlings is shown in Table 27. Events-01 and -02 segregated 15:1 (R:S) for FINALE™ resistance in the $T_2$ generation. ME05341 events were also tested for increased photosynthetic efficiency on the low nitrate media. No significant differences between the transgenics and the controls were observed.

TABLE 27 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05341 | ME05341-01 ($T_2$) | 0.06253 | 46 | 0.04988 | 143 | $4.17 \times 10^{-10}$ |
| ME05341 | ME05341-01 ($T_3$) | 0.05876 | 38 | 0.04988 | 143 | $4.13 \times 10^{-4}$ |
| ME05341 | ME05341-02 ($T_2$) | 0.06152 | 46 | 0.04988 | 143 | $2.91 \times 10^{-7}$ |
| ME05341 | ME05341-02 ($T_3$) | 0.05572 | 48 | 0.04988 | 143 | $2.90 \times 10^{-3}$ |

Events-01 and -02 of ME05341 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 27—Analysis of ME05392 Events

ME05392 contains Ceres Clone:21740 (At5g01610, SEQ ID NO:686) from *Arabidopsis thaliana*, which encodes a 170 amino acid protein of unknown function. Evaluation of low-nitrogen tolerance for ME05392 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at $p \leq 0.05$ using a one-tailed t-test assuming unequal variance. A summary of photosynthetic efficiency of ME05392 seedlings is shown in Table 20. Events-01 and -03 segregated 2:1 (R:S) for FINALE™ resistance in the $T_2$ generation. ME05392 events were also tested for enhanced growth on the low nitrate media. No significant differences between the transgenics and the controls were observed.

TABLE 28

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05392 | ME05392-01 ($T_2$) | 0.61759 | 32 | 0.60093 | 107 | $3.70 \times 10^{-2}$ |
| ME05392 | ME05392-01 ($T_3$) | 0.63388 | 40 | 0.60093 | 107 | $5.05 \times 10^{-5}$ |
| ME05392 | ME05392-03 ($T_2$) | 0.64335 | 23 | 0.60093 | 107 | $5.81 \times 10^{-5}$ |
| ME05392 | ME05392-03 ($T_3$) | 0.63397 | 36 | 0.60093 | 107 | $4.30 \times 10^{-5}$ |

Events-01 and -03 of ME05392 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 28—Analysis of ME05429 Events

ME05429 contains Ceres Clone:5609 (At3g60480, SEQ ID NO:729) from *Arabidopsis thaliana*, which encodes a 188 amino acid protein of unknown function. Evaluation of low-nitrogen tolerance for ME05429 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -06 and -08, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME05429 seedlings is shown in Table 29. Events-06 and -08 segregated 3:1 and 2:1 respectively (R:S) for FINALE™ resistance in the $T_2$ generation. ME05429 events were tested for enhanced growth on the low ammonium nitrate media. In addition, these events were also tested for enhanced growth and photosynthetic efficiency on low nitrate media. No significant differences between the transgenics and the controls were observed.

TABLE 29 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME05429 | ME05429-06 ($T_2$) | 0.62521 | 28 | 0.59991 | 78 | $2.85 \times 10^{-2}$ |
| ME05429 | ME05429-06 ($T_3$) | 0.63031 | 39 | 0.59991 | 78 | $8.49 \times 10^{-3}$ |
| ME05429 | ME05429-08 ($T_2$) | 0.64526 | 23 | 0.59991 | 78 | $1.67 \times 10^{-3}$ |
| ME05429 | ME05429-08 ($T_3$) | 0.65076 | 17 | 0.59991 | 78 | $2.76 \times 10^{-4}$ |

Events-06 and -08 of ME05429 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 29—Analysis of ME05493 Events

ME05493 contains Ceres Clone:3137 (At3g43430, SEQ ID NO:745) from *Arabidopsis thaliana*, which encodes a 169 amino acid zinc finger family protein. Evaluation of low-nitrogen tolerance for ME05493 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME05493 seedlings is shown in Table 30. Events-01 and -05 segregated 15:1 (R:S) for FINALE™ resistance in the $T_2$ generation. ME05493 events were also tested for enhanced growth on the low nitrate media. No significant differences between the transgenics and the controls were observed.

TABLE 30 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05493 | ME05493-01 ($T_2$) | 0.64121 | 32 | 0.61097 | 92 | $1.13 \times 10^{-3}$ |
| ME05493 | ME05493-01 ($T_3$) | 0.64250 | 46 | 0.61097 | 92 | $3.03 \times 10^{-4}$ |
| ME05493 | ME05493-05 ($T_2$) | 0.62865 | 43 | 0.61097 | 92 | $1.75 \times 10^{-2}$ |
| ME05493 | ME05493-05 ($T_3$) | 0.63936 | 42 | 0.61097 | 92 | $1.21 \times 10^{-4}$ |

Events-01 and -05 of ME05493 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 30—Analysis of ME05885 Events

ME05885 contains Ceres Clone:32430 (At1g16170, SEQ ID NO:768) from *Arabidopsis thaliana*, which encodes a 92 amino acid protein of unknown function. Evaluation of low-nitrogen tolerance for ME05885 in $T_3$ generation was conducted under the same conditions as described in Examples 2 and 3. A summary of photosynthetic efficiency of ME05885 seedlings is shown in Table 31. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media and low ammonium nitrate-containing media relative to the internal controls in $T_3$ generation at $p \leq 0.05$ using a one-tailed t-test assuming unequal variance.

TABLE 31A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME05885 | ME05885-01 ($T_3$) | 0.6759 | 12 | 0.6533 | 28 | $4.32 \times 10^{-2}$ |
| ME05885 | ME05885-05 ($T_3$) | 0.6831 | 7 | 0.6530 | 52 | $3.68 \times 10^{-6}$ |

TABLE 31B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05885 | ME05885-01 ($T_3$) | 0.6490 | 13 | 0.6135 | 30 | $3.06 \times 10^{-2}$ |
| ME05885 | ME05885-05 ($T_3$) | 0.6810 | 9 | 0.6133 | 43 | $6.77 \times 10^{-5}$ |

ME05885 events were also tested for enhanced growth on the low nitrate and low ammonium nitrate media. A summary of enhanced growth under low nitrate and low ammonium nitrate growth conditions of ME05885 seedlings in $T_3$ generation is shown in Table 32. Two events, -03 and -05, showed significantly enhanced growth on low nitrate-containing media. Two events, -02 and -05, showed significantly enhanced growth on low ammonium nitrate-containing media relative to the internal controls at $p \leq 0.05$ using a one-tailed t-test assuming unequal variance. In this study, the seedling area for transgenic plants within an event was compared to the seedling area for non-transgenic segregants pooled across the same line.

TABLE 32A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05885 | ME05885-03 ($T_3$) | 0.06245 | 6 | 0.05286 | 14 | $1.42 \times 10^{-2}$ |
| ME05885 | ME05885-05 ($T_3$) | 0.05893 | 7 | 0.04725 | 12 | $5.61 \times 10^{-3}$ |

TABLE 32B

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME05885 | ME05885-02 ($T_3$) | 0.0744 | 14 | 0.05595 | 6 | $3.28 \times 10^{-5}$ |
| ME05885 | ME05885-05 ($T_3$) | 0.0753 | 9 | 0.06179 | 11 | $5.08 \times 10^{-3}$ |

Example 31—Analysis of ME07344 Events

ME07344 contains Ceres Clone:101255 (At2g19810, SEQ ID NO:791) from *Arabidopsis thaliana*, which encodes a 359 amino acid CCCH-type zinc finger protein. Evaluation of low-nitrogen tolerance for ME07344 in $T_2$ and $T_3$ was conducted under the same conditions as described in Example 4. In this study, the $4^{th}$ true leaf from each plant was collected on day 38 and analyzed on the CF imager for its Fv/Fm value. Transgenic plants within an event were compared to all non-transgenic plants, including the non-transgenic segregants and external controls. Two events, -02 and -03, showed significantly increased photosynthetic efficiency relative to the internal controls in both generations at $p \leq 0.05$ using a one-tailed t-test assuming unequal variance. A summary of photosynthetic efficiency of ME07344 seedlings is shown in Table 33. Events-02 and -03 segregated 3:1 (R:S) for FINALE™ resistance in the $T_2$ generation. ME07344 events were also tested for enhanced growth on the low nitrate media. No significant differences between the transgenics and the controls were observed.

Events-02 and -03 of ME07344 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 32—Analysis of ME07859 Events

ME07859 contains Ceres Clone:276809 (SEQ ID NO:823) from *Zea mays*, which encodes a 135 amino acid sterol desaturase protein. Evaluation of low-nitrogen tolerance for ME07859 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME07859 seedlings is shown in Table 34. Events-02 and -04 segregated 1:1 and 2:1 respectively (R:S) for FINALE™ resistance in the $T_2$ generation. ME07859 events were also tested for enhanced growth on the low nitrate media as well as for enhanced growth and photosynthetic efficiency on low ammonium nitrate media. No significant differences between the transgenics and the controls were observed.

TABLE 33

T-test comparison of photosynthetic efficiency between transgenic plants and non-transgenic controls after 38 days of growth on nitrogen-depleted soil.

| Line | Events | Transgenic Fv/Fm | n | Non-Transgenic Controls Fv/Fm | n | t-test p-value |
|---|---|---|---|---|---|---|
| ME07344 | ME07344-02 ($T_2$) | 0.752 | 17 | 0.729 | 50 | $2.86 \times 10^{-4}$ |
| ME07344 | ME07344-02 ($T_3$) | 0.750 | 16 | 0.729 | 50 | $1.11 \times 10^{-4}$ |
| ME07344 | ME07344-03 ($T_2$) | 0.741 | 13 | 0.729 | 50 | 0.018 |
| ME07344 | ME07344-03 ($T_3$) | 0.754 | 17 | 0.729 | 50 | $4.62 \times 10^{-6}$ |

TABLE 34 t-test comparison of seedling photosynthetic efficiency between transgenic seedlings and pooled non-transgenic segregants after 14 days of growth on low nitrate media.

| Line | Events | Transgenic | | Pooled Non-Transgenics | | t-test |
|---|---|---|---|---|---|---|
| | | Fv/Fm | n | Fv/Fm | n | p-value |
| ME07859 | ME07859-02 ($T_2$) | 0.6598 | 24 | 0.6378 | 127 | 0.03 |
| ME07859 | ME07859-02 ($T_3$) | 0.6825 | 14 | 0.6378 | 127 | $1.3 \times 10^{-3}$ |
| ME07859 | ME07859-04 ($T_2$) | 0.6539 | 33 | 0.6378 | 127 | 0.05 |
| ME07859 | ME07859-04 ($T_3$) | 0.6601 | 17 | 0.6378 | 127 | 0.05 |

Events-02 and -04 of ME07859 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 33—Analysis of ME08464 Events

ME08464 contains Ceres Clone:424522 (SEQ ID NO:827) from *Zea mays*, which encodes a 500 amino acid unknown protein. Evaluation of low-nitrogen tolerance for ME08464 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME07859 seedlings is shown in Table 35. Events-02 and -03 segregated 3:1 (R:S) for FINALE™ resistance in the $T_2$ generation. ME08464 events were also tested for increased photosynthetic efficiency on the low nitrate media. No significant differences between the transgenics and the controls were observed.

Events-02 and -03 of ME08464 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 34—Analysis of ME09939 Events

ME09939 contains Ceres Clone:324216 (SEQ ID NO:852) from *Zea mays*, which encodes a 38 amino acid protein of unknown function. Evaluation of low-nitrogen tolerance for ME09939 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME09939 seedlings is shown in Table 36. Events-04 and -05 segregated 15:1 and 3:1 respectively (R:S) for FINALE™ resistance in the $T_2$ generation. ME09939 events were also tested for enhanced growth on the low ammonium nitrate media. No significant differences between the transgenics and the controls were observed.

TABLE 35

T-test comparison of photosynthetic efficiency between transgenic seedlings and pooled non-transgenic segregants after 15 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME08464 | ME08464-02 ($T_2$) | 0.65 | 41 | 0.62 | 40 | 0.015 |
| ME08464 | ME08464-02 ($T_3$) | 0.67 | 32 | 0.62 | 40 | $2.32 \times 10^{-4}$ |
| ME08464 | ME08464-03 ($T_2$) | 0.65 | 43 | 0.62 | 40 | 0.013 |
| ME08464 | ME08464-03 ($T_3$) | 0.65 | 42 | 0.62 | 40 | $6.85 \times 10^{-3}$ |

TABLE 36

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME09939 | ME09939-04 ($T_2$) | 0.49285 | 40 | 0.38571 | 7 | 0.05 |
| ME09939 | ME09939-04 ($T_3$) | 0.50697 | 34 | 0.38571 | 7 | $3.50 \times 10^{-2}$ |
| ME09939 | ME09939-05 ($T_2$) | 0.53487 | 39 | 0.47492 | 24 | $1.19 \times 10^{-2}$ |
| ME09939 | ME09939-05 ($T_3$) | 0.55341 | 32 | 0.47492 | 24 | $1.82 \times 10^{-3}$ |

Events-04 and -05 of ME09939 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 35—Analysis of ME11735 Events

ME11735 contains Ceres Annot:573161 (At5g43260, SEQ ID NO:854) from *Arabidopsis thaliana*, which encodes a 97 amino acid DnaJ-related chaperone protein. Evaluation of low-nitrogen tolerance for ME11735 in $T_2$ and $T_3$ was conducted under the same conditions as described in Example 2 and 3. A summary of the enhanced growth of ME11735 events on low nitrate-containing media is shown in Table 37. In this study, the seedling area for transgenic plants within an event was compared to the seedling area for non-transgenic segregants pooled across the same line. Two events, -04 and -05, were found significantly larger than the pooled non-transgenic segregants after 14 days of growth on low nitrate-containing media relative to the internal controls in both generations at p≤0.05 using a one-tailed t-test assuming unequal variance. ME11735 events were also tested for increased photosynthetic efficiency on the low nitrate media. No significant differences between the transgenics and the controls were observed. Events-04 and -05 segregated 40:1 and 4:1 respectively (R:S) for FINALE™ resistance in the $T_2$ generation.

Events-04 and -05 of ME11735 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 36—Analysis of ME12910 Events

ME12910 contains Ceres Annot:552727 (At2g22930, SEQ ID NO:890) from *Arabidopsis thaliana*, which encodes a 442 amino acid UDP-glucoronosyl and UDP-glucosyl transferase family protein. Evaluation of low-nitrogen tolerance for ME12910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME12910 seedlings is shown in Table 38. ME12910 events were also tested for enhanced growth on the low ammonium nitrate media. No significant differences between the transgenics and the controls were observed.

TABLE 37 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME11735 | ME11735-04 ($T_2$) | 0.05820 | 41 | 0.04994 | 127 | $5.91 \times 10^{-5}$ |
| ME11735 | ME11735-04 ($T_3$) | 0.05553 | 42 | 0.04994 | 127 | $1.26 \times 10^{-2}$ |
| ME11735 | ME11735-05 ($T_2$) | 0.05788 | 37 | 0.04994 | 127 | $1.59 \times 10^{-3}$ |
| ME11735 | ME11735-05 ($T_3$) | 0.06011 | 13 | 0.04994 | 127 | $1.64 \times 10^{-2}$ |

TABLE 38 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12910 | ME12910-03 ($T_2$) | 0.5851 | 39 | 0.5191 | 29 | $1.54 \times 10^{-3}$ |
| ME12910 | ME12910-03 ($T_3$) | 0.5861 | 22 | 0.5191 | 29 | $2.17 \times 10^{-3}$ |
| ME12910 | ME12910-05 ($T_2$) | 0.5523 | 44 | 0.4251 | 7 | $1.23 \times 10^{-2}$ |
| ME12910 | ME12910-05 ($T_3$) | 0.5600 | 42 | 0.4251 | 7 | $9.62 \times 10^{-3}$ |

Events-03 and -05 segregated 3:1 and 15:1 respectively (R:S) for FINALE™ resistance in the $T_2$ generation.

Events-03 and -05 of ME12910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 37—Analysis of ME12927 Events

ME12927 contains Ceres Clone:239806 (SEQ ID NO:916) from Zea mays, which encodes a 201 amino acid lipoprotein amino terminal region. Evaluation of low-nitrogen tolerance for ME12927 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -03 and -05, showed significantly increased photosynthetic efficiency on low ammonium nitrate-containing media relative to the internal controls in both generations at p≤0.05, using a one-tailed t-test assuming unequal variance. A summary of photosynthetic efficiency of ME12927 seedlings is shown in Table 39.

TABLE 39 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12927 | ME12927-02 ($T_2$) | 0.60843 | 44 | 0.47813 | 8 | $4.88 \times 10^{-3}$ |
| ME12927 | ME12927-02 ($T_3$) | 0.60867 | 36 | 0.47813 | 8 | $5.23 \times 10^{-3}$ |
| ME12927 | ME12927-03 ($T_2$) | 0.61906 | 32 | 0.57929 | 38 | $8.96 \times 10^{-3}$ |
| ME12927 | ME12927-03 ($T_3$) | 0.63437 | 19 | 0.57929 | 38 | $5.35 \times 10^{-4}$ |
| ME12927 | ME12927-05 ($T_2$) | 0.60581 | 43 | 0.53982 | 22 | $7.26 \times 10^{-3}$ |
| ME12927 | ME12927-05 ($T_3$) | 0.63145 | 29 | 0.53982 | 22 | $5.83 \times 10^{-4}$ |

ME12927 events were also tested for enhanced growth on the low ammonium nitrate media. A summary of the enhanced growth of ME11735 events on low ammonium nitrate-containing media is shown in Table 40. In this study, the seedling area for transgenic plants within an event was compared to the seedling area for non-transgenic segregants pooled across the same line. Three events, -02, -03 and -05, were found significantly larger than the pooled non-transgenic segregants after 18 days of growth on low ammonium nitrate-containing media relative to the internal controls in both generations at p≤0.05, using a one-tailed t-test assuming unequal variance.

TABLE 40 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12927 | ME12927-02 ($T_2$) | 0.066920 | 44 | 0.056585 | 117 | $1.65 \times 10^{-4}$ |
| ME12927 | ME12927-02 ($T_3$) | 0.062119 | 36 | 0.056585 | 117 | $3.51 \times 10^{-2}$ |
| ME12927 | ME12927-03 ($T_2$) | 0.068972 | 32 | 0.056585 | 117 | $1.18 \times 10^{-5}$ |
| ME12927 | ME12927-03 ($T_3$) | 0.063716 | 19 | 0.056585 | 117 | $1.98 \times 10^{-2}$ |
| ME12927 | ME12927-05 ($T_2$) | 0.069972 | 43 | 0.056585 | 117 | $4.25 \times 10^{-6}$ |
| ME12927 | ME12927-05 ($T_3$) | 0.064014 | 29 | 0.056585 | 117 | $8.49 \times 10^{-3}$ |

Events 02, -03 and -05 segregated 15:1, 2:1 and 15:1 respectively (R:S) for FINALE™ resistance in the $T_2$ generation.

Events 02, -03 and -05 of ME12927 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in $T_1$ generation.

Example 38—Analysis of ME12929 Events

ME12929 contains Ceres Clone:208995 (SEQ ID NO:943) from Zea mays, which encodes a 94 amino acid protein of unknown function. Evaluation of low-nitrogen tolerance for ME12929 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME12929 seedlings is shown in Table 41. ME12929 events were also tested for enhanced growth on the low ammonium nitrate media. No significant differences between the transgenics and the controls were observed. Events-03 and -04 segregated 1:1 and 3:1 respectively (R:S) for FINALE™ resistance in the $T_2$ generation.

Events-03 and -04 of ME12929 exhibited no statistically relevant negative phenotypes. That is, there was no detectable reduction in germination rate, the transgenic

TABLE 41 t-test comparison of seedling photosynthetic efficiency between transgenic seedlings and pooled non-transgenic segregants after 14 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME12929 | ME12929-03 ($T_2$) | 0.6410 | 33 | 0.5736 | 24 | $9.44 \times 10^{-4}$ |
| ME12929 | ME12929-03 ($T_3$) | 0.6610 | 41 | 0.5736 | 24 | $4.38 \times 10^{-5}$ |
| ME12929 | ME12929-04 ($T_2$) | 0.6544 | 47 | 0.5790 | 9 | $3.68 \times 10^{-2}$ |
| ME12929 | ME12929-04 ($T_3$) | 0.6663 | 43 | 0.5790 | 9 | $2.15 \times 10^{-2}$ | plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 39—Analysis of ME12954 Events

ME12954 contains Ceres Clone:225681 (SEQ ID NO:975) from Zea mays, which encodes a 286 amino acid protein of unknown function. Evaluation of low-nitrogen tolerance for ME12954 in $T_2$ and $T_3$ was conducted under the same conditions as described in Examples 2 and 3. Two events, -04 and -05, showed significantly increased photosynthetic efficiency on low ammonium nitrate-containing media relative to the internal controls in both generations at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12954 seedlings is shown in Table 42.

TABLE 42 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME12954 | ME12954-04 ($T_2$) | 0.6236 | 40 | 0.5973 | 152 | $6.61 \times 10^{-3}$ |
| ME12954 | ME12954-04 ($T_3$) | 0.6200 | 39 | 0.5973 | 152 | $1.97 \times 10^{-2}$ |

TABLE 42-continued t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12954 | ME12954-05 ($T_2$) | 0.6280 | 45 | 0.5973 | 152 | $1.79 \times 10^{-2}$ |
| ME12954 | ME12954-05 ($T_3$) | 0.6315 | 35 | 0.5973 | 152 | $2.85 \times 10^{-2}$ |

ME12954 events were also tested for enhanced growth on the low ammonium nitrate media. A summary of the enhanced growth of ME12954 events on low ammonium nitrate-containing media is shown in Table 43. In this study, the seedling area for transgenic plants within an event was compared to the seedling area for non-transgenic segregants pooled across the same line. Two events, -02 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 43 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12954 | ME12954-02 ($T_2$) | 0.06883 | 31 | 0.05579 | 152 | $1.86 \times 10^{-5}$ |
| ME12954 | ME12954-02 ($T_3$) | 0.06604 | 26 | 0.05579 | 152 | $1.48 \times 10^{-3}$ |
| ME12954 | ME12954-04 ($T_2$) | 0.06469 | 40 | 0.05579 | 152 | $1.95 \times 10^{-4}$ |
| ME12954 | ME12954-04 ($T_3$) | 0.06301 | 39 | 0.05579 | 152 | $3.32 \times 10^{-3}$ |

Events-02, -04 and -05 segregated 2:1, 3:1 and 15:1 respectively (R:S) for FINALE™ resistance in the T2 generation.

Events-02, -04 and -05 of ME12954 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 40—Analysis of ME12970 Events

ME12970 contains Ceres Clone:1387146 (SEQ ID NO:981) from *Zea mays*, which encodes a 147 amino acid C2 domain-containing protein. Evaluation of low-nitrogen tolerance for ME12970 in $T_2$ and $T_3$ was conducted under the same conditions as described in Examples 2 and 3. Two events, -02 and -03, showed significantly increased photosynthetic efficiency on low ammonium nitrate-containing media relative to the internal controls in both generations at p≤0.05 using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12970 seedlings is shown in Table 44. ME12970 events were also tested for enhanced growth on the low ammonium nitrate media. No significant differences between the transgenics and the controls were observed.

TABLE 44 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12970 | ME12970-02 ($T_2$) | 0.55136 | 44 | 0.52401 | 108 | $3.78 \times 10^{-2}$ |
| ME12970 | ME12970-02 ($T_3$) | 0.58305 | 43 | 0.52401 | 108 | $1.89 \times 10^{-5}$ |
| ME12970 | ME12970-03 ($T_2$) | 0.58759 | 37 | 0.52401 | 108 | $2.14 \times 10^{-6}$ |
| ME12970 | ME12970-03 ($T_3$) | 0.59131 | 29 | 0.52401 | 108 | $3.05 \times 10^{-6}$ |

Events-02 and -03 segregated 15:1 and 3:1 respectively (R:S) for FINALE™ resistance in the T2 generation.

Events-02 and -03 of ME12970 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 41—Analysis of ME13006 Events

ME13006 contains Ceres Clone:1017441 (SEQ ID NO:224) from *Triticum aestivum*, which encodes a 143 amino acid polypeptide, predicted to be a homolog of Ceres Clone:4898 (ME03123, SEQ ID NO:217). Evaluation of low-nitrogen tolerance for ME13006 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13006 seedlings is shown in Table 45. ME13006 events were also tested for enhanced growth on the low nitrate media. No significant differences between the transgenics and the controls were observed.

TABLE 45 t-test comparison of seedling area between transgenic seedlings and pooled non-transgenic segregants after 14 days of growth on low ammonium nitrate.

| Line | Events | Transgenic Area | n | Pooled Non-Transgenics Area | n | t-test p-value |
|---|---|---|---|---|---|---|
| ME13006 | ME13006-01 ($T_2$) | 0.0777 | 42 | 0.0648 | 7 | $3.29 \times 10^{-2}$ |
| ME13006 | ME13006-01 ($T_3$) | 0.0660 | 28 | 0.0540 | 19 | $1.49 \times 10^{-3}$ |
| ME13006 | ME13006-03 ($T_2$) | 0.0706 | 21 | 0.0601 | 29 | $4.83 \times 10^{-3}$ |
| ME13006 | ME13006-03 ($T_3$) | 0.0758 | 14 | 0.0617 | 33 | $2.60 \times 10^{-3}$ |

Events-01 and -03 segregated 3:1 and 1:1 respectively (R:S) for FINALE™ resistance in the $T_2$ generation.

Events-01 and -03 of ME13006 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 42—Analysis of ME13021 Events

ME13021 contains Ceres Clone:244306 (SEQ ID NO:1053) from *Zea mays*, which encodes a 572 amino acid TCP-1/cpn60 chaperonin family protein. Evaluation of low-nitrogen tolerance for ME13021 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13021 seedlings is shown in Table 46. ME13021 events were also tested for enhanced growth on the low ammonium nitrate media. No significant differences between the transgenics and the controls were observed.

TABLE 46 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13021 | ME13021-04 ($T_2$) | 0.56697 | 39 | 0.49440 | 10 | $2.47 \times 10^{-2}$ |
| ME13021 | ME13021-04 ($T_3$) | 0.59916 | 37 | 0.48685 | 13 | $1.54 \times 10^{-3}$ |
| ME13021 | ME13021-05 ($T_2$) | 0.60575 | 32 | 0.50344 | 18 | $6.05 \times 10^{-4}$ |
| ME13021 | ME13021-05 ($T_3$) | 0.64400 | 23 | 0.55638 | 26 | $3.86 \times 10^{-6}$ |

Events-04 and -05 segregated 3:1 and 2:1 respectively (R:S) for FINALE™ resistance in the T2 generation.

Events-04 and -05 of ME13021 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 43—Analysis of ME13064 Events

ME13064 contains Ceres Clone:1408950 (SEQ ID NO:1098) from *Zea mays*, which encodes a 152 amino acid protein of unknown function. Evaluation of low-nitrogen tolerance for ME13064 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13064 seedlings is shown in Table 47. ME13064 events were also tested for enhanced growth on the low ammonium nitrate media. No significant differences between the transgenics and the controls were observed.

Example 44—Analysis of ME13071 Events

ME13071 contains Ceres Clone:208453 (SEQ ID NO:1111) from *Zea mays*, which encodes a 74 amino acid protein of unknown function. Evaluation of low-nitrogen tolerance for ME13071 in $T_2$ and $T_3$ was conducted under the same conditions as described in Examples 2 and 3. Two events, -03 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 48. ME13071 events were also tested for photosynthetic efficiency on the low ammonium nitrate media. No significant differences between the transgenics and the controls were observed.

TABLE 47 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13064 | ME13064-03 ($T_2$) | 0.59444 | 27 | 0.54793 | 28 | $5.84 \times 10^{-3}$ |
| ME13064 | ME13064-03 ($T_3$) | 0.59676 | 29 | 0.54793 | 28 | $1.25 \times 10^{-2}$ |
| ME13064 | ME13064-04 ($T_2$) | 0.58577 | 31 | 0.51053 | 40 | $2.05 \times 10^{-3}$ |
| ME13064 | ME13064-04 ($T_3$) | 0.59128 | 25 | 0.51053 | 40 | $8.93 \times 10^{-4}$ |

Events-03 and -04 segregated 2:1 (R:S) for FINALE™ resistance in the T2 generation.

Events-03 and -04 of ME13064 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

TABLE 48 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME13071 | ME13071-03 ($T_2$) | 0.06694 | 26 | 0.05915 | 19 | $3.55 \times 10^{-3}$ |
| ME13071 | ME13071-03 ($T_3$) | 0.07787 | 24 | 0.07040 | 22 | $3.65 \times 10^{-2}$ |
| ME13071 | ME13071-05 ($T_2$) | 0.06232 | 32 | 0.05491 | 16 | $2.07 \times 10^{-3}$ |
| ME13071 | ME13071-05 ($T_3$) | 0.06335 | 22 | 0.05626 | 28 | $1.09 \times 10^{-2}$ |

Events-03 and -05 segregated 1:1 and 2:1 respectively (R:S) for FINALE™ resistance in the T2 generation.

Events-03 and -05 of ME13071 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 45—Analysis of ME13087 Events

ME13087 contains Ceres Clone:968180 (SEQ ID NO:1115) from *Brassica napus*, which encodes a 159 amino acid zinc finger protein. Evaluation of low-nitrogen tolerance for ME13087 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13087 seedlings is shown in Table 49. ME13087 events were also tested for enhanced growth on the low ammonium nitrate media. No significant differences between the transgenics and the controls were observed.

statistical differences between transgenics and controls in the size of the rosette area 7 days post-bolting; and there was no observable or statistical differences between transgenics and controls in fertility (silique number and seed fill) in T1 generation.

Example 46—Analysis of ME13106 Events

ME13106 contains Ceres Clone:986438 (SEQ ID NO:1156) from *Zea mays*, which encodes a 188 amino acid protein of unknown function. Evaluation of low-nitrogen tolerance for ME13106 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13106 seedlings is shown in Table 50. ME13106 events were also tested for enhanced growth on the low ammonium nitrate media. No significant differences between the transgenics and the controls were observed.

TABLE 49 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13087 | ME13087-01 ($T_2$) | 0.59761 | 23 | 0.56163 | 38 | $9.61 \times 10^{-3}$ |
| ME13087 | ME13087-01 ($T_3$) | 0.61247 | 15 | 0.56163 | 38 | $5.99 \times 10^{-4}$ |
| ME13087 | ME13087-02 ($T_2$) | 0.63400 | 39 | 0.58532 | 34 | $9.30 \times 10^{-3}$ |
| ME13087 | ME13087-02 ($T_3$) | 0.63442 | 26 | 0.58532 | 34 | $1.22 \times 10^{-2}$ |
| ME13087 | ME13087-03 ($T_2$) | 0.61429 | 38 | 0.55533 | 24 | $5.04 \times 10^{-3}$ |
| ME13087 | ME13087-03 ($T_3$) | 0.62283 | 35 | 0.55533 | 24 | $3.31 \times 10^{-3}$ |
| ME13087 | ME13087-04 ($T_2$) | 0.62714 | 28 | 0.60068 | 56 | $3.02 \times 10^{-2}$ |
| ME13087 | ME13087-04 ($T_3$) | 0.64543 | 7 | 0.60068 | 56 | $9.04 \times 10^{-3}$ |

Events-01, -02, -03 and -04 segregated 2:1, 3:1, 3:1 and 2:1 respectively (R:S) for FINALE™ resistance in the T2 generation.

Events-01, -02, -03 and -04 of ME13087 exhibited no statistically relevant negative phenotypes. That is, there was no detectable reduction in germination rate, the transgenic plants appeared wild type in all instances; there was no observable or statistical differences between transgenics and controls in days to flowering; there was no observable or

TABLE 50 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13106 | ME13106-03 ($T_2$) | 0.62726 | 27 | 0.58600 | 43 | $1.50 \times 10^{-2}$ |
| ME13106 | ME13106-03 ($T_3$) | 0.65163 | 30 | 0.58600 | 43 | $1.69 \times 10^{-4}$ |
| ME13106 | ME13106-04 ($T_2$) | 0.60836 | 36 | 0.55876 | 25 | $2.62 \times 10^{-2}$ |
| ME13106 | ME13106-04 ($T_3$) | 0.64250 | 38 | 0.55876 | 25 | $5.01 \times 10^{-4}$ |

Events-03 and -04 segregated 1:1 and 3:1 respectively (R:S) for FINALE™ resistance in the $T_2$ generation.

Events-03 and -04 of ME13106 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 47—Analysis of ME13107 Events

ME13107 contains Ceres Clone:996227 (SEQ ID NO:1158) from *Zea mays*, which encodes a 240 amino acid zein seed storage protein. Evaluation of low-nitrogen tolerance for ME13107 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13107 seedlings is shown in Table 51.

TABLE 51 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13107 | ME13107-02 ($T_2$) | 0.63122 | 37 | 0.56643 | 21 | $1.07 \times 10^{-2}$ |
| ME13107 | ME13107-02 ($T_3$) | 0.63848 | 29 | 0.56643 | 21 | $6.03 \times 10^{-3}$ |
| ME13107 | ME13107-04 ($T_2$) | 0.62948 | 27 | 0.55918 | 50 | $2.07 \times 10^{-5}$ |
| ME13107 | ME13107-04 ($T_3$) | 0.63019 | 21 | 0.55918 | 50 | $6.72 \times 10^{-5}$ |
| ME13107 | ME13107-05 ($T_2$) | 0.61952 | 29 | 0.54440 | 48 | $7.85 \times 10^{-5}$ |
| ME13107 | ME13107-05 ($T_3$) | 0.62185 | 20 | 0.54440 | 48 | $4.02 \times 10^{-5}$ |

ME13107 events were also tested for enhanced growth on the low ammonium nitrate media. Two events, -02 and -04, showed significantly enhanced growth on low ammonium nitrate-containing media relative to the internal controls in $T_2$ generation at p≤0.05 using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 52.

TABLE 2 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME13107 | ME13107-02 ($T_2$) | 0.07738 | 37 | 0.06919 | 203 | $3.63 \times 10^{-2}$ |
| ME13107 | ME13107-02 ($T_3$) | 0.07688 | 29 | 0.06919 | 203 | $4.60 \times 10^{-2}$ |
| ME13107 | ME13107-04 ($T_2$) | 0.07514 | 27 | 0.06919 | 203 | $3.18 \times 10^{-2}$ |
| ME13107 | ME13107-04 ($T_3$) | 0.07585 | 21 | 0.06919 | 203 | $2.27 \times 10^{-2}$ |

Events-02, -04 and -05 segregated 3:1, 1:1 and 2:1 respectively (R:S) for FINALE™ resistance in the $T_2$ generation.

Events-02, -04 and -05 of ME13107 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 48—Analysis of ME13108 Events

ME13108 contains Ceres Clone:996263 (SEQ ID NO:1165) from *Zea mays*, which encodes an 84 amino acid BRICK1 protein. Evaluation of low-nitrogen tolerance for ME13108 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13108 seedlings is shown in Table 53. ME13108 events were also tested for enhanced growth on the low ammonium nitrate media. No significant differences between the transgenics and the controls were observed.

TABLE 53 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13108 | ME13108-01 ($T_2$) | 0.56703 | 36 | 0.53932 | 195 | $1.97 \times 10^{-2}$ |
| ME13108 | ME13108-01 ($T_3$) | 0.59250 | 26 | 0.53932 | 195 | $3.64 \times 10^{-4}$ |
| ME13108 | ME13108-04 ($T_2$) | 0.60032 | 37 | 0.53932 | 195 | $3.37 \times 10^{-7}$ |
| ME13108 | ME13108-04 ($T_3$) | 0.60463 | 30 | 0.53932 | 195 | $4.10 \times 10^{-5}$ |
| ME13108 | ME13108-05 ($T_2$) | 0.60727 | 30 | 0.53932 | 195 | $4.97 \times 10^{-9}$ |
| ME13108 | ME13108-05 ($T_3$) | 0.61850 | 32 | 0.53932 | 195 | $2.35 \times 10^{-9}$ |

Events-01, -04 and -05 segregated 3:1 (R:S) for FINALE™ resistance in the $T_2$ generation.

Events-01, -04 and -05 of ME13108 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 49—Analysis of ME13110 Events

ME13110 contains Ceres Clone:988083 (SEQ ID NO:1184) from *Zea mays*, which encodes a 188 amino acid protein of unknown function. Evaluation of low-nitrogen tolerance for ME13110 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -03, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13110 seedlings is shown in Table 54. ME13110 events were also tested for enhanced growth on the low ammonium nitrate media. No significant differences between the transgenics and the controls were observed.

TABLE 54 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13110 | ME13110-03 ($T_2$) | 0.5721 | 34 | 0.3948 | 16 | $8.92 \times 10^{-3}$ |
| ME13110 | ME13110-03 ($T_3$) | 0.5773 | 24 | 0.4583 | 26 | $4.58 \times 10^{-4}$ |
| ME13110 | ME13110-04 ($T_2$) | 0.5651 | 35 | 0.4243 | 15 | $4.34 \times 10^{-2}$ |
| ME13110 | ME13110-04 ($T_3$) | 0.6000 | 10 | 0.4594 | 40 | $3.29 \times 10^{-3}$ |
| ME13110 | ME13110-05 ($T_2$) | 0.5143 | 28 | 0.3809 | 22 | $2.24 \times 10^{-2}$ |
| ME13110 | ME13110-05 ($T_3$) | 0.5278 | 28 | 0.3688 | 21 | $1.28 \times 10^{-2}$ |

Events-03, -04 and -05 segregated 3:1, 1:1 and 3:1 respectively (R:S) for FINALE™ resistance in the $T_2$ generation.

Events-03, -04 and -05 of ME13110 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 50—Analysis of ME13125 Events

ME13125 contains Ceres Clone:732 (At3g50880, SEQ ID NO:1193) from *Arabidopsis thaliana*, which encodes a 188 amino acid protein of unknown function. Evaluation of low-nitrogen tolerance for ME13125 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -03 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13125 seedlings is shown in Table 55. ME13125 events were also tested for enhanced growth on the low ammonium nitrate media. No significant differences between the transgenics and the controls were observed.

TABLE 55 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13125 | ME13125-01 ($T_2$) | 0.61129 | 42 | 0.53829 | 125 | $4.82 \times 10^{-7}$ |
| ME13125 | ME13125-01 ($T_3$) | 0.61929 | 38 | 0.53829 | 125 | $1.96 \times 10^{-7}$ |
| ME13125 | ME13125-03 ($T_2$) | 0.63360 | 45 | 0.53829 | 125 | $3.05 \times 10^{-13}$ |
| ME13125 | ME13125-03 ($T_3$) | 0.62218 | 44 | 0.53829 | 125 | $3.81 \times 10^{-9}$ |
| ME13125 | ME13125-05 ($T_2$) | 0.61565 | 31 | 0.53829 | 125 | $4.12 \times 10^{-8}$ |
| ME13125 | ME13125-05 ($T_3$) | 0.58469 | 16 | 0.53829 | 125 | 0.05 |

Events-01, -03 and -05 segregated 3:1, 15:1 and 2:1 respectively (R:S) for FINALE™ resistance in the $T_2$ generation.

Events-01, -03 and -05 of ME13125 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 51—Analysis of ME13149 Events

ME13149 contains Ceres Clone:2267 (At2g24765, SEQ ID NO:1209) from *Arabidopsis thaliana*, which encodes a 182 amino acid ADP-ribosylation factor 3 protein. Evaluation of low-nitrogen tolerance for ME13149 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13149 seedlings is shown in Table 56. ME13149 events were also tested for enhanced growth on the low ammonium nitrate media. No significant differences between the transgenics and the controls were observed.

TABLE 56 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13149 | ME13149-02 ($T_2$) | 0.55623 | 30 | 0.51138 | 55 | $2.29 \times 10^{-2}$ |
| ME13149 | ME13149-02 ($T_3$) | 0.54818 | 17 | 0.51138 | 55 | $4.56 \times 10^{-2}$ |
| ME13149 | ME13149-03 ($T_2$) | 0.55998 | 42 | 0.51138 | 55 | $5.11 \times 10^{-3}$ |
| ME13149 | ME13149-03 ($T_3$) | 0.58450 | 24 | 0.51138 | 55 | $2.77 \times 10^{-4}$ |

Events-02 and -03 segregated 2:1 and 15:1 respectively (R:S) for FINALE™ resistance in the $T_2$ generation.

Events-02 and -03 of ME13149 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 52—Analysis of ME13151 Events

ME13151 contains Ceres Clone:39358 (At3g25150, SEQ ID NO:1273) from *Arabidopsis thaliana*, which encodes a 488 amino acid nuclear transport factor 2 (NTF2) domain protein. Evaluation of low-nitrogen tolerance for ME13151 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME13151 seedlings is shown in Table 57. ME13151 events were also tested for enhanced growth on the low ammonium nitrate media. No significant differences between the transgenics and the controls were observed.

Events-01 and -02 segregated 9:1 and 6:1 respectively (R:S) for FINALE™ resistance in the T2 generation.

Events-01 and -02 of ME13151 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 53—Analysis of ME13153 Events

ME13153 contains Ceres Clone:115046 (At3g17760, SEQ ID NO:1301) from *Arabidopsis thaliana*, which encodes a 494 amino acid glutamate decarboxylase. Evaluation of low-nitrogen tolerance for ME13153 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13153 seedlings is shown in Table 58. ME13153 events were also tested for increased photosynthetic efficiency on the low nitrate media. No significant differences between the transgenics and the controls were observed.

TABLE 57

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13151 | ME13151-01 ($T_2$) | 0.62593 | 44 | 0.53141 | 17 | $8.58 \times 10^{-4}$ |
| ME13151 | ME13151-01 ($T_3$) | 0.59936 | 33 | 0.53141 | 17 | $1.21 \times 10^{-2}$ |
| ME13151 | ME13151-02 ($T_2$) | 0.59879 | 39 | 0.46956 | 16 | $3.08 \times 10^{-5}$ |
| ME13151 | ME13151-02 ($T_3$) | 0.59566 | 32 | 0.46956 | 16 | $4.28 \times 10^{-5}$ |

TABLE 58

T-test comparison of seedling photosynthetic efficiency between transgenic seedlings and non-transgenic segregants after 14 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME13153 | ME13153-03 ($T_2$) | 0.62 | 34 | 0.56 | 16 | $3.0 \times 10^{-2}$ |
| ME13153 | ME13153-03 ($T_3$) | 0.60 | 19 | 0.54 | 22 | $2.9 \times 10^{-2}$ |
| ME13153 | ME13153-04 ($T_2$) | 0.57 | 32 | 0.50 | 18 | $4.3 \times 10^{-2}$ |
| ME13153 | ME13153-04 ($T_3$) | 0.61 | 24 | 0.55 | 24 | $2.1 \times 10^{-2}$ |

Events-03 and -04 segregated 3:1 (R:S) for FINALE™ resistance in the $T_2$ generation.

Events-03 and -04 of ME13153 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting. Events-03 and -04 yielded slightly less seed per plant compared to the controls, but these differences are not significant at $p \leq 0.10$.

Example 54—Analysis of ME13177 Events

ME13177 contains Ceres Clone:339439 (SEQ ID NO:1341) from *Zea mays*, which encodes a 345 amino acid cyclin C-terminal domain protein. Evaluation of low-nitrogen tolerance for ME13177 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13177 seedlings is shown in Table 59. ME13177 events were also tested for enhanced growth on the low ammonium nitrate media. No significant differences between the transgenics and the controls were observed.

Events-01 and -02 segregated 2:1 and 3:1 respectively (R:S) for FINALE™ resistance in the $T_2$ generation.

Events-01 and -02 of ME13177 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 55—Analysis of ME13200 Events

ME13200 contains Ceres Clone:896483 (SEQ ID NO:1384) from *Zea mays*, which encodes an 85 amino acid myb family transcription factor. Evaluation of low-nitrogen tolerance for ME13200 in $T_2$ and $T_3$ was conducted under the same conditions as described in Examples 2 and 3. A summary of the enhanced growth of ME13200 events on low ammonium nitrate-containing media is shown in Table 60. In this study, the seedling area for transgenic plants within an event was compared to the seedling area for non-transgenic segregants pooled across the same line. Two events, -03 and -04, were found significantly larger than the pooled non-transgenic segregants after 18 days of growth on low ammonium nitrate-containing media relative to the internal controls in both generations at $p \leq 0.05$ using a one-tailed t-test assuming unequal variance. ME13200 events were also tested for increased photosynthetic efficiency on the low ammonium nitrate media as well as for enhanced photosynthesis and growth on low nitrate media. No significant differences between the transgenics and the controls were observed.

TABLE 59 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME13177 | ME13177-01 ($T_2$) | 0.6315 | 32 | 0.6112 | 175 | $2.43 \times 10^{-2}$ |
| ME13177 | ME13177-01 ($T_3$) | 0.6407 | 29 | 0.6112 | 175 | $7.33 \times 10^{-3}$ |
| ME13177 | ME13177-02 ($T_2$) | 0.6400 | 41 | 0.6112 | 175 | $1.23 \times 10^{-3}$ |
| ME13177 | ME13177-02 ($T_3$) | 0.6499 | 20 | 0.6112 | 175 | $6.47 \times 10^{-3}$ |

TABLE 60

T-test comparison of seedling area between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Area | n | Area | n | p-value |
| ME13200 | ME13200-03 ($T_2$) | 0.07366 | 43 | 0.06342 | 35 | $4.09 \times 10^{-4}$ |
| ME13200 | ME13200-03 ($T_3$) | 0.08193 | 34 | 0.06342 | 35 | $2.37 \times 10^{-5}$ |
| ME13200 | ME13200-04 ($T_2$) | 0.07377 | 48 | 0.06342 | 35 | $4.87 \times 10^{-4}$ |
| ME13200 | ME13200-04 ($T_3$) | 0.07530 | 47 | 0.06342 | 35 | $1.88 \times 10^{-4}$ |

Events-03 and -04 segregated 3:1 and 15:1 respectively respectively (R:S) for FINALE™ resistance in the $T_2$ generation.

Events-03 and -04 of ME13200 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 56—Analysis of ME13204 Events

ME13204 contains Ceres Clone:995409 (SEQ ID NO:1408) from *Zea mays*, which encodes a 178 amino acid protein of unknown function. Evaluation of low-nitrogen tolerance for ME13204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME13204 seedlings is shown in Table 61. ME13204 events were also tested for enhanced growth on the low nitrate media as well as for enhanced growth and photosynthetic efficiency on low ammonium nitrate media. No significant differences between the transgenics and the controls were observed.

Events-01 and -05 segregated 9:1 and 3:1 respectively (R:S) for FINALE™ resistance in the $T_2$ generation.

Events-01 and -05 of ME13204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 57—Analysis of ME14649 Events

ME14649 contains Ceres Annot:850581 (At5g01880, SEQ ID NO:1427) from *Arabidopsis thaliana*, which encodes a 159 amino acid zinc finger protein. Evaluation of low-nitrogen tolerance for ME14649 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME14649 seedlings is shown in Table 62. ME14649 events were also tested for enhanced growth on the low ammonium nitrate media. No significant differences between the transgenics and the controls were observed.

TABLE 61

T-test comparison of seedling photosynthetic efficiency between transgenic seedlings and pooled non-transgenic segregants after 14 days of growth on low nitrate media.

| Line | Events | Transgenic | | Pooled Non-Transgenics | | t-test |
|---|---|---|---|---|---|---|
| | | Fv/Fm | n | Fv/Fm | n | p-value |
| ME13204 | ME13204-01 ($T_2$) | 0.5874 | 45 | 0.5354 | 46 | $1.41 \times 10^{-2}$ |
| ME13204 | ME13204-01 ($T_3$) | 0.5932 | 36 | 0.5354 | 46 | $9.85 \times 10^{-3}$ |
| ME13204 | ME13204-05 ($T_2$) | 0.5855 | 34 | 0.5354 | 46 | $2.00 \times 10^{-2}$ |
| ME13204 | ME13204-05 ($T_3$) | 0.5998 | 20 | 0.5354 | 46 | $5.58 \times 10^{-3}$ |

TABLE 62 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME14649 | ME14649-02 ($T_2$) | 0.59789 | 35 | 0.54533 | 30 | $1.54 \times 10^{-4}$ |
| ME14649 | ME14649-02 ($T_3$) | 0.58154 | 26 | 0.54533 | 30 | $3.42 \times 10^{-2}$ |
| ME14649 | ME14649-03 ($T_2$) | 0.61875 | 28 | 0.56539 | 33 | $2.03 \times 10^{-3}$ |
| ME14649 | ME14649-03 ($T_3$) | 0.62630 | 27 | 0.56539 | 33 | $9.18 \times 10^{-4}$ |

Events-02 and -03 segregated 3:1 and 2:1 respectively (R:S) for FINALE™ resistance in the $T_2$ generation.

Events-02 and -03 of ME14649 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 58—Analysis of ME16546 Events

ME16546 contains Ceres Annot:862321 (At2g45360, SEQ ID NO:1462) from *Arabidopsis thaliana*, which encodes a 215 amino acid protein of unknown function. Evaluation of low-nitrogen tolerance for ME16546 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME16546 seedlings is shown in Table 63. ME16546 events were also tested for enhanced growth on the low ammonium nitrate media. No significant differences between the transgenics and the controls were observed.

Events-04 and -05 segregated 2:1 and 3:1 respectively (R:S) for FINALE™ resistance in the $T_2$ generation.

Events-04 and -05 of ME16546 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 59—Analysis of ME17457 Events

ME17457 contains Ceres Annot:839064 (At1g80600, SEQ ID NO:1478) from *Arabidopsis thaliana*, which encodes a 457 acetylornithine aminotransferase, a member of the Class-III aminotransferase family. This is a homolog of Ceres Clone:19586 (ME01463, SEQ ID NO:76). Evaluation of low-nitrogen tolerance for ME17457 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -02, -03, -05 and -06, showed significantly increased photosynthetic efficiency on low ammonium nitrate-containing media relative to the internal controls in both generations at p≤0.05 using a one-tailed t-test assuming unequal variance. A summary of photosynthetic efficiency of ME17457 seedlings is shown in Table 64. ME17457 events were also tested for enhanced growth on the low ammonium nitrate media. No significant differences between the transgenics and the controls were observed.

TABLE 63 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME16546 | ME16546-04 ($T_2$) | 0.59891 | 33 | 0.56124 | 130 | $2.21 \times 10^{-4}$ |
| ME16546 | ME16546-04 ($T_3$) | 0.57924 | 41 | 0.56124 | 130 | $3.77 \times 10^{-2}$ |
| ME16546 | ME16546-05 ($T_2$) | 0.58861 | 36 | 0.56124 | 130 | $7.17 \times 10^{-3}$ |
| ME16546 | ME16546-05 ($T_3$) | 0.61763 | 27 | 0.56124 | 130 | $3.25 \times 10^{-6}$ |

TABLE 64 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17457 | ME17457-02 ($T_2$) | 0.60800 | 21 | 0.50878 | 46 | $6.99 \times 10^{-4}$ |
| ME17457 | ME17457-02 ($T_3$) | 0.59539 | 18 | 0.50878 | 46 | $9.02 \times 10^{-3}$ |
| ME17457 | ME17457-03 ($T_2$) | 0.55164 | 11 | 0.49673 | 45 | $3.45 \times 10^{-2}$ |
| ME17457 | ME17457-03 ($T_3$) | 0.57356 | 18 | 0.49673 | 45 | $2.49 \times 10^{-3}$ |
| ME17457 | ME17457-05 ($T_2$) | 0.52928 | 18 | 0.42672 | 32 | $2.23 \times 10^{-3}$ |
| ME17457 | ME17457-05 ($T_3$) | 0.56660 | 25 | 0.42672 | 32 | $5.97 \times 10^{-5}$ |
| ME17457 | ME17457-06 ($T_2$) | 0.54088 | 33 | 0.47350 | 30 | $3.59 \times 10^{-4}$ |
| ME17457 | ME17457-06 ($T_3$) | 0.52210 | 21 | 0.47350 | 30 | $2.03 \times 10^{-2}$ |

Events-02, -03 and -05 segregated 1:1, and Event-06 segregated 3:1 (R:S) for FINALE™ resistance in the $T_2$ generation.

Events-02, -03, -05 and -06 of ME17457 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 60—Analysis of ME17567 Events

ME17567 contains Ceres Annot:864666 (At1g16320, SEQ ID NO:1490) from *Arabidopsis thaliana*, which encodes a 273 amino acid protein of unknown function. Evaluation of low-nitrogen tolerance for ME17567 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low nitrate-containing media relative to the internal controls in both generations at p≤0.05 using a one-tailed t-test assuming unequal variance. A summary of photosynthetic efficiency of ME17567 seedlings is shown in Table 65. ME17567 events were also tested for enhanced growth on the low nitrate media as well as enhanced photosynthetic efficiency and growth on low ammonium nitrate media. No significant differences between the transgenics and the controls were observed.

Events-01 and -04 segregated 2:1 and 3:1 respectively (R:S) for FINALE™ resistance in the $T_2$ generation.

Events-01 and -04 of ME17567 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 61—Analysis of ME17932 Events

ME17932 contains Ceres Annot:875012 (At3g53560, SEQ ID NO:1509) from *Arabidopsis thaliana*, which encodes a 340 amino acid chloroplast lumen common family protein. Evaluation of low-nitrogen tolerance for ME17932 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME17932 seedlings is shown in Table 66. ME17932 events were also tested for enhanced growth on the low ammonium nitrate media. No significant differences between the transgenics and the controls were observed.

TABLE 65 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME17567 | ME17567-01 ($T_2$) | 0.605455 | 33 | 0.474791 | 67 | $9.69 \times 10^{-10}$ |
| ME17567 | ME17567-01 ($T_3$) | 0.6244 | 20 | 0.474791 | 67 | $6.79 \times 10^{-13}$ |
| ME17567 | ME17567-04 ($T_2$) | 0.57727 | 37 | 0.474791 | 67 | $1.22 \times 10^{-7}$ |
| ME17567 | ME17567-04 ($T_3$) | 0.615143 | 35 | 0.474791 | 67 | $5.95 \times 10^{-13}$ |

TABLE 66 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17932 | ME17932-01 ($T_2$) | 0.6292 | 36 | 0.6094 | 194 | 0.050 |
| ME17932 | ME17932-01 ($T_3$) | 0.6640 | 22 | 0.6094 | 194 | $2.82 \times 10^{-6}$ |
| ME17932 | ME17932-02 ($T_2$) | 0.6351 | 32 | 0.6094 | 194 | $1.05 \times 10^{-2}$ |
| ME17932 | ME17932-02 ($T_3$) | 0.6373 | 20 | 0.6094 | 194 | $2.82 \times 10^{-2}$ |
| ME17932 | ME17932-03 ($T_2$) | 0.6504 | 45 | 0.6094 | 194 | $1.80 \times 10^{-5}$ |
| ME17932 | ME17932-03 ($T_3$) | 0.6708 | 20 | 0.6094 | 194 | $8.38 \times 10^{-4}$ |
| ME17932 | ME17932-05 ($T_2$) | 0.6349 | 24 | 0.6094 | 194 | $3.23 \times 10^{-2}$ |
| ME17932 | ME17932-05 ($T_3$) | 0.6615 | 11 | 0.6094 | 194 | $1.16 \times 10^{-3}$ |

Events-01, -02, -03 and -05 segregated 3:1, 2:1, 15:1 and 1:1 respectively (R:S) for FINALE™ resistance in the $T_2$ generation.

Events-01, -02, -03 and -05 of ME17932 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 62—Analysis of ME17936 Events

ME17936 contains Ceres Annot:874016 (At3g42800, SEQ ID NO:1524) from *Arabidopsis thaliana*, which encodes a 341 amino acid protein of unknown function. Evaluation of low-nitrogen tolerance for ME17936 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME17936 seedlings is shown in Table 67. ME17936 events were also tested for for enhanced growth on the low nitrate media as well as for increased photosynthetic efficiency and enhanced growth on low ammonium nitrate media. No significant differences between the transgenics and the controls were observed.

Events-01 and -05 segregated 3:1 (R:S) for FINALE™ resistance in the $T_2$ generation.

Events-01 and -05 of ME17936 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 63—Analysis of ME18275 Events

ME18275 contains Ceres Annot:827304 (At2g18300, SEQ ID NO:1536) from *Arabidopsis thaliana*, which encodes a 335 amino acid helix-loop-helix DNA-binding domain. Evaluation of low-nitrogen tolerance for ME18275 in $T_2$ and $T_3$ was conducted under the same conditions as described in Examples 2 and 3. A summary of the enhanced growth of ME18275 events on low nitrate-containing media is shown in Table 68. In this study, the seedling area for transgenic plants within an event was compared to the seedling area for non-transgenic segregants pooled across the same line. Three events, -01, -02 and -03, were found significantly larger than the pooled non-transgenic segregants after 14 days of growth on low nitrate-containing media relative to the internal controls in both generations at p≤0.05, using a one-tailed t-test assuming unequal variance. ME18275 events were also tested for photosynthetic efficiency on the low nitrate media as well as for increased photosynthetic efficiency and enhanced growth on low ammonium nitrate media. No significant differences between the transgenics and the controls were observed.

TABLE 67 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME17936 | ME17936-01 ($T_2$) | 0.64778 | 36 | 0.61762 | 39 | $4.68 \times 10^{-3}$ |
| ME17936 | ME17936-01 ($T_3$) | 0.66081 | 21 | 0.61762 | 39 | $4.33 \times 10^{-5}$ |
| ME17936 | ME17936-05 ($T_2$) | 0.63189 | 35 | 0.61444 | 50 | $2.73 \times 10^{-2}$ |
| ME17936 | ME17936-05 ($T_3$) | 0.64257 | 14 | 0.61444 | 50 | $2.56 \times 10^{-2}$ |

TABLE 68 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME18275 | ME18275-01 ($T_2$) | 0.09574 | 40 | 0.05961 | 10 | $3.24 \times 10^{-10}$ |
| ME18275 | ME18275-01 ($T_3$) | 0.07807 | 32 | 0.05142 | 15 | $3.71 \times 10^{-4}$ |
| ME18275 | ME18275-02 ($T_2$) | 0.11903 | 33 | 0.05884 | 16 | $6.21 \times 10^{-14}$ |
| ME18275 | ME18275-02 ($T_3$) | 0.08552 | 22 | 0.04208 | 24 | $2.82 \times 10^{-5}$ |
| ME18275 | ME18275-03 ($T_2$) | 0.10281 | 39 | 0.06789 | 9 | $9.48 \times 10^{-8}$ |
| ME18275 | ME18275-03 ($T_3$) | 0.09136 | 20 | 0.05646 | 26 | $9.46 \times 10^{-4}$ |

Events-01, -02 and -03 segregated 3:1 (R:S) for FINALE™ resistance in the $T_2$ generation.

Events-01, -02 and -03 of ME18275 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 64—Analysis of ME18924 Events

ME18924 contains Ceres Annot:869192 (At1g72160, SEQ ID NO:1553) from *Arabidopsis thaliana*, which encodes a 490 amino acid emp24/gp25L/p24 family protein. Evaluation of low-nitrogen tolerance for ME18924 in $T_2$ and $T_3$ was conducted under the same conditions as described in Examples 2 and 3. A summary of photosynthetic efficiency of ME18924 seedlings is shown in Table 69. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05, using a one-tailed t-test assuming unequal variance.

TABLE 69 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME18924 | ME18924-02 ($T_2$) | 0.6515 | 46 | 0.6223 | 138 | $6.43 \times 10^{-3}$ |
| ME18924 | ME18924-02 ($T_3$) | 0.6639 | 45 | 0.6223 | 138 | $1.52 \times 10^{-4}$ |
| ME18924 | ME18924-04 ($T_2$) | 0.6489 | 33 | 0.6223 | 138 | $2.72 \times 10^{-3}$ |
| ME18924 | ME18924-04 ($T_3$) | 0.6517 | 21 | 0.6223 | 138 | $1.58 \times 10^{-2}$ |
| ME18924 | ME18924-05 ($T_2$) | 0.6602 | 35 | 0.6223 | 138 | $5.55 \times 10^{-5}$ |
| ME18924 | ME18924-05 ($T_3$) | 0.6488 | 31 | 0.6223 | 138 | $4.25 \times 10^{-2}$ |

ME18924 events were also tested for enhanced growth on the low ammonium nitrate media. A summary of the enhanced growth of ME18924 events on low nitrate-containing media is shown in Table 70. In this study, the seedling area for transgenic plants within an event was compared to the seedling area for non-transgenic segregants pooled across the same line. Two events, -01 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 70 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME18924 | ME18924-01 ($T_2$) | 0.06881 | 37 | 0.06311 | 138 | $1.31 \times 10^{-2}$ |
| ME18924 | ME18924-01 ($T_3$) | 0.07164 | 34 | 0.06311 | 138 | $7.43 \times 10^{-3}$ |
| ME18924 | ME18924-04 ($T_2$) | 0.08401 | 33 | 0.06311 | 138 | $5.64 \times 10^{-8}$ |
| ME18924 | ME18924-04 ($T_3$) | 0.07365 | 21 | 0.06311 | 138 | $3.82 \times 10^{-2}$ |

Events-01, -02, -04 and -05 segregated 3:1, 15:1, 2:1 and 2:1 respectively (R:S) for FINALE™ resistance in the $T_2$ generation.

Events-01, -02, -04 and -05 of ME18924 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 65—Analysis of ME19182 Events

ME19182 contains Ceres Annot:876419 (At4g01480, SEQ ID NO:1576) from *Arabidopsis thaliana*, which encodes a 216 amino acid inorganic pyrophosphatase protein. Evaluation of low-nitrogen tolerance for ME19182 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME19182 seedlings is shown in Table 71. ME19182 events were also tested for enhanced growth on the low ammonium nitrate media. No significant differences between the transgenics and the controls were observed.

TABLE 71 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME19182 | ME19182-01 ($T_2$) | 0.64938 | 24 | 0.61988 | 154 | $2.47 \times 10^{-2}$ |
| ME19182 | ME19182-01 ($T_3$) | 0.65546 | 13 | 0.61988 | 154 | $1.08 \times 10^{-2}$ |
| ME19182 | ME19182-03 ($T_2$) | 0.64797 | 37 | 0.61988 | 154 | $3.84 \times 10^{-3}$ |
| ME19182 | ME19182-03 ($T_3$) | 0.65388 | 26 | 0.61988 | 154 | $3.15 \times 10^{-3}$ |

Events-01 and -03 segregated 2:1 and 3:1 respectively (R:S) for FINALE™ resistance in the T2 generation.

Events-01 and -03 of ME19182 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 66—Analysis of ME20628 Events

ME20628 contains Ceres Annot:859276 (At2g21230, SEQ ID NO:175) from *Arabidopsis thaliana*, which encodes a 188 amino acid protein of unknown function. Evaluation of low-nitrogen tolerance for ME20628 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME20628 seedlings is shown in Table 72. ME20628 events were also tested for enhanced growth on the low nitrate media as well as for increased photosynthetic efficiency and enhanced growth on low ammonium nitrate media. No significant differences between the transgenics and the controls were observed.

TABLE 72 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME20628 | ME20628-03 ($T_2$) | 0.62771 | 42 | 0.58957 | 7 | $9.94 \times 10^{-3}$ |
| ME20628 | ME20628-03 ($T_3$) | 0.64375 | 20 | 0.61914 | 28 | $2.97 \times 10^{-2}$ |
| ME20628 | ME20628-04 ($T_2$) | 0.62439 | 38 | 0.59667 | 12 | $4.78 \times 10^{-2}$ |
| ME20628 | ME20628-04 ($T_3$) | 0.64768 | 22 | 0.61360 | 25 | $9.93 \times 10^{-4}$ |

Events-03 and -04 segregated 3:1 (R:S) for FINALE™ resistance in the $T_2$ generation.

Events-03 and -04 of ME20628 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 67—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al. (1998) *Proc. Natl. Acad. Sci. USA,* 95:6239-6244) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:49, SEQ ID NO:77, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1463, SEQ ID NO:1491, SEQ ID NO:1510, SEQ ID NO:1525, SEQ ID NO:1537, SEQ ID NO:1554, SEQ ID NO:1577, and SEQ ID NO:1437 are shown in FIGS. 1-57, respectively. Additional exemplary homologs are correlated to certain Figures in the Sequence Listing.

Example 68—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-57, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10815494B2). An electronic copy of the "Sequence Listing" will also be available from the USPTO upon request and payment of the fee set forth in 37 CFR 1.19(b)(3).

What is claimed is:

1. A method of producing a plant, said method comprising growing a plant cell comprising an exogenous nucleic acid molecule, said exogenous nucleic acid molecule comprising a regulatory region operably linked to a polynucleotide comprising a nucleic acid sequence having 95 percent or greater sequence identity to the nucleic acid sequence of SEQ ID NO:96, producing a plant from said plant cell, and selecting a plant for an increased level of low-nitrogen tolerance as compared to the level of low-nitrogen tolerance of a control plant that does not comprise said nucleic acid molecule.

2. The method of claim 1, wherein the polynucleotide comprises the nucleotide sequence of SEQ ID NO:96.

3. A method of increasing a level of low-nitrogen tolerance in a plant, said method comprising introducing into a plant cell an exogenous nucleic acid molecule, said exogenous nucleic acid molecule comprising a regulatory region operably linked to a polynucleotide comprising a nucleic acid sequence having 95 percent or greater sequence identity to the nucleic acid sequence of SEQ ID NO:96, producing a plant from said plant cell, and selecting a plant comprising a tissue that has an increased level of low-nitrogen tolerance as compared to the level of low-nitrogen tolerance of a control plant that does not comprise said nucleic acid molecule.

4. The method claim 1, wherein said polynucleotide comprises a nucleic acid sequence having 97 percent or greater sequence identity to the nucleic acid sequence of SEQ ID NO:96.

5. The method of claim 3, wherein the polynucleotide comprises a nucleic acid sequence that has 97 percent or greater sequence identity to the nucleic acid sequence of SEQ ID NO:96.

6. A plant cell comprising an exogenous nucleic acid molecule said exogenous nucleic acid molecule comprising regulatory region operably linked to a polynucleotide comprising a nucleic acid sequence having 95 percent or greater sequence identity to the nucleic acid sequence of SEQ ID NO:96, wherein a plant comprising said plant cell has an increased level of low-nitrogen tolerance as compared to the level of low-nitrogen tolerance of a control plant that does not comprise said nucleic acid molecule.

7. The plant cell of claim 6, wherein the polynucleotide comprises a nucleotide sequence that has 97 percent or greater sequence identity to the nucleic acid sequence of SEQ ID NO:96.

8. A transgenic plant comprising the plant cell of claim 6.

9. The transgenic plant of claim 8, wherein said plant is a member of a species selected from the group consisting of Panicum virgatum (switchgrass), Sorghum bicolor (Sorghum, sudangrass), Miscanthus giganteus (Miscanthus), Saccharum sp. (energycane), Populus balsamifera (poplar), Zea mays (corn), Glycine max (soybean), Brassica napus (canola), Triticum aestivum (wheat), Gossypium hirsutum (cotton), Oryza sativa (rice), Helianthus annuus (sunflower), Medicago sativa (alfalfa), Beta vulgaris (sugarbeet), and Pennisetum glaucum (pearl millet).

10. A product comprising plant tissue from the transgenic plant according to claim 9.

11. A transgenic plant or a progeny thereof, wherein the transgenic plant is produced by the method of claim 1, and wherein the progeny comprises the exogenous nucleic acid molecule.

* * * * *